(12) United States Patent
Mogi et al.

(10) Patent No.: US 8,012,972 B2
(45) Date of Patent: Sep. 6, 2011

(54) PYRIDINECARBOXYLIC ACID (2-AMINOPHENYL) AMIDE DERIVATIVE HAVING UREA STRUCTURE

(75) Inventors: Hiroyuki Mogi, Ikoma (JP); Hisashi Tajima, Ikoma (JP); Noriko Mishina, Ikoma (JP); Yusuke Yamazaki, Ikoma (JP); Shinji Yoneda, Ikoma (JP); Katsuhiko Watanabe, Ikoma (JP); Junko Fujikawa, Ikoma (JP); Minoru Yamamoto, Ikoma (JP)

(73) Assignee: Santen Pharmaceutical Co., Ltd., Osaka-Shi, Osaka (JP)

( * ) Notice: Subject to any disclaimer, the term of this patent is extended or adjusted under 35 U.S.C. 154(b) by 0 days.

(21) Appl. No.: 12/450,387
(22) PCT Filed: Mar. 28, 2008
(86) PCT No.: PCT/JP2008/056012
§ 371 (c)(1), (2), (4) Date: Sep. 23, 2009
(87) PCT Pub. No.: WO2008/117862
PCT Pub. Date: Oct. 2, 2008

(65) Prior Publication Data
US 2010/0063045 A1    Mar. 11, 2010

(30) Foreign Application Priority Data
Mar. 28, 2007   (JP) .................. 2007-084258

(51) Int. Cl.
A61K 31/5377 (2006.01)
A61K 31/44 (2006.01)
C07D 413/12 (2006.01)
C07D 213/81 (2006.01)

(52) U.S. Cl. ............ 514/237.2; 514/354; 544/124; 546/323

(58) Field of Classification Search .......... 514/232.2, 514/354, 237.2, 342, 338, 253.13, 332, 318; 546/328, 270.1, 273.4, 283.7, 282.4, 262, 546/194; 544/131, 365, 82
See application file for complete search history.

(56) References Cited

U.S. PATENT DOCUMENTS
6,897,220 B2   5/2005   Delorme et al.
7,465,719 B2  12/2008   Finn et al.
2004/0138270 A1  7/2004   Fertig et al.

FOREIGN PATENT DOCUMENTS
| JP | 11-302173 A | 11/1999 |
| JP | 2005-272419 A | 10/2005 |
| JP | 2007-191398 A | 8/2007 |
| WO | WO 97/24328 A1 | 7/1997 |
| WO | WO 97/30701 A2 | 8/1997 |
| WO | WO 00/09162 A1 | 2/2000 |
| WO | WO 2004/043348 A2 | 5/2004 |
| WO | WO 2004/052838 A1 | 6/2004 |

OTHER PUBLICATIONS

"Protein, Nucleic Acid and Enzyme", vol. 51, No. 14, title page & pp. 2069-2075 (2006) (translation of relevant portion, p. 2069, left column, lines 1-11 only).

L.S. Cousens et al, "Different Accessibilities in Chromatin to Histone Acetylase", *J. Biol., Chem.*, vol. 254, No. 5, pp. 1716-1723 (1979).
M. Yoshida et al, "Effects of Trichostatins on Differentiation of Murine Erythroleukemia Cells", *Cancer Res.*, 47, pp. 3688-3691 (1987).
M. Yoshida et al, "Reversible Arrest of Proliferation of Rat 3Y1 Fribroblasts in Both the G1 and G2 Phases by Trichstatin A", *Exp. Cell Res.*, 177, pp. 122-131 (1988).
M. Yoshida et al, "Potent and Specific Inhibition of Mammalian Histone Deacetylase Both in Vivo and in Vitro by Tichostatin A", *J. Biol. Chem.*, vol. 265, No. 28, pp. 17174-17179 (1990). H. Itazaki et al, "Isolation and Structural Elucidation of New Cyclotetrapeptides, Trapoxins A and B, Having Detransformation Activities as Antitumor Agents", *J. Antibiotics*, 43, pp. 1524-1532 (1990).
M. Kijima et al, "Trapoxin, an Antitumor Cyclic Tetrapeptide, Is an Irreversible Inhibitor of Mammalian Histon Deacetylase", *J. Biol. Chem.*, vol. 268, No. 30, pp. 22429-224435 (1993).
U.S. Appl. No. 12/450,388, filed Sep. 23, 2009, Confirmation No. 3071.
D.C. Coffey et al., "The Histone Deacetylase Inhibitor, CBHA, Inhibits Growth of Human Neuroblastoma Xenografts in Vivo, Alon and Synergistically with *All-Trans* Retinoic Acid,"*Cancer Research*, vol. 61, No. 9, pp. 3591-3594, (2001).
Noriyuki Takai et al., "M344 is a novel synthesized histone deacetylase Inhibitor that induces growth inhibition, cell cycle arrest, and apoptosis in human endometrial cancer and ovarian cancer cells," *Gynecologic Oncology*, vol. 101, pp. 108-113, (2006).
Claude Monneret, "Histone deacetylase inhibitors," *European Journal of Medicinal Chemistry*, vol. 40, pp. 1-13, (2005).

*Primary Examiner* — Kamal Saeed
*Assistant Examiner* — Kristin Bianchi
(74) *Attorney, Agent, or Firm* — Holtz, Holtz, Goodman & Chick, P.C.

(57) ABSTRACT

Objects of the present invention are to study the synthesis of a novel pyridinecarboxylic acid (2-aminophenyl)amide derivative having a novel urea structure and to find a pharmacological effect of the derivative. The invention provides a compound represented by the formula (1) or a salt thereof. In the formula, $R^1$ and $R^2$ represent a hydrogen atom, a lower alkyl group or the like; $R^3$ represents a hydroxy group, a lower alkoxy group, a lower cycloalkyloxy group, an aryloxy group, a carboxy group, a lower alkoxycarbonyl group, —OCON-$R^aR^b$, —NR$^c$R$^d$ or the like; $R^4$ and $R^5$ represent a halogen atom, a lower alkyl group, a hydroxy group, a lower alkoxy group or the like; $R^a$ and $R^b$ represent a hydrogen atom, a lower alkyl group, a lower cycloalkyl group, an aryl group, a heterocyclic group or the like; $R^c$ and $R^d$ represent a hydrogen atom, a lower alkyl group, a lower cycloalkyl group, an aryl group or the like; X represents a lower alkylene group; Y represents a single bond, a lower alkylene group; $W^1$-$W^2$ represents N—C or C—N; and l and m represent 0, 1, 2 or 3.

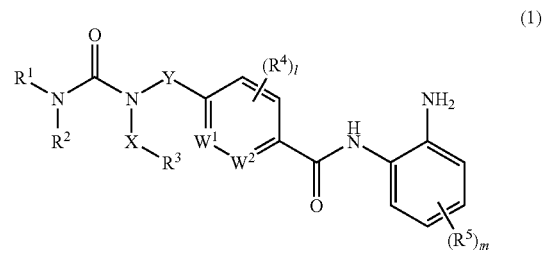

(1)

11 Claims, No Drawings

PYRIDINECARBOXYLIC ACID (2-AMINOPHENYL) AMIDE DERIVATIVE HAVING UREA STRUCTURE

This application is the United States national phase application of International Application PCT/JP2008/056012 filed Mar. 28, 2009.

TECHNICAL FIELD

The present invention relates to a novel pyridinecarboxylic acid (2-aminophenyl)amide derivative having a urea structure or a salt thereof which is useful as a pharmaceutical. The derivative or a salt thereof has a histone deacetylase inhibitory activity and is therefore expected as a preventive and/or therapeutic agent for a disease against which a histone deacetylase inhibitor is considered to be effective.

BACKGROUND ART

Eukaryotic chromosomal DNA wraps around core histone proteins, histones H2A, H2B, H3 and H4, etc. to form a basic structure called nucleosome. Further, the nucleosome structures assemble to form a chromatin structure. Post-translational modifications of histones are closely related to the constitution of the chromatin structure, and as the post-translational modification, acetylation, methylation, phosphorylation, ubiquitylation and the like are known.

For example, it is thought that histone acetylation is related to gene transcriptional induction, replication, repair and the like.

The histone acetylation is reversibly regulated by a histone acetyltransferase (hereinafter referred to as "HAT") and a histone deacetylase (hereinafter referred to as "HDAC").

It is thought that if HDAC is inhibited, histone acetylation by HAT is enhanced and subsequent gene transcriptional induction, replication, repair and the like are activated, and therefore, various diseases considered to be associated with cell proliferation, senescence and the like. Such as cancer, autoimmune diseases, neurodegenerative diseases and infectious diseases can be prevented and/or treated (Protein, Nucleic Acid and Enzyme, Vol. 51. No. 14 (2006), JP-A-2005-272419 and JP-T-2006-517532).

As typical examples of an HDAC inhibitor, butyric acid which has an effect of cell cycle arrest, an effect of normalization and differentiation of transformed cells and the like (J. Biol. Chem., 254, 1716-1723 (1979)), trichostatin A which is a microbial metabolite and has an effect of cell cycle arrest, an effect of induction of differentiation and the like (Cancer Res., 47, 3688-3691 (1987), Exp. Cell Res., 177, 122-131 (1988) and J. Biol. Chem., 265, 17174-17179 (1990)), trapoxin which is a microbial metabolite and has an inhibitory effect of cell proliferation (J. Antibiotics, 43, 1524-1532 (1990) and J. Biol. Chem., 268, 22429-22435 (1993)) and the like are known.

On the other hand, a compound having an arylenecarboxylic acid (2-aminophenyl)amide structure is disclosed as an inhibitor of tumor cell proliferation in WO 2004/052838. However, there is no specific description regarding a novel pyridinecarboxylic acid (2-aminophenyl)amide derivative having a urea structure.

DISCLOSURE OF THE INVENTION

Problems to be Solved

It is a very interesting subject to study the synthesis of a novel pyridinecarboxylic acid (2-aminophenyl)amide derivative having a urea structure or a salt thereof and to study its pharmacological effects.

Means for Solving the Problems

The present inventors conducted studies of the synthesis of a novel pyridinecarboxylic acid (2-aminophenyl)amide derivative having a novel chemical structure or a salt thereof and succeeded in creating a large number of novel compounds.

Further, as a result of studies of a pharmacological effect of the derivative or a salt thereof, the present inventors found that the derivative or a salt thereof has an HDAC inhibitory activity and therefore is useful as a preventive and/or therapeutic agent for a disease against which an HDAC inhibitor is considered to be effective, and has an effect of morphological change on trabecular meshwork cells and an effect of intraocular pressure reduction and therefore is useful as a preventive and/or therapeutic agent for a disease considered to be associated with circulation of aqueous humor and/or intraocular pressure, and thus, the present invention has been completed.

That is, the invention relates to a compound represented by the following general formula (1) or a salt thereof (hereinafter referred to as "the present compound") and a pharmaceutical composition containing the same.

Further, a preferred invention of the medical use thereof is an invention relating to a preventive and/or therapeutic agent for a diseases against which an HDAC inhibitor is considered to be useful in treating, for example, cancer, autoimmune diseases, inflammatory diseases, neurodegenerative diseases, infectious diseases, hematopoietic disorders, fibrosis, cardiovascular disorders, diseases associated with angiogenesis, and the like. Further, since the present compound has an effect of morphological change on trabecular meshwork cells and an effect of intraocular pressure reduction, it is an invention relating to a preventive and/or therapeutic agent for a disease considered to be associated with circulation of aqueous humor and/or intraocular pressure such as glaucoma or ocular hypertension.

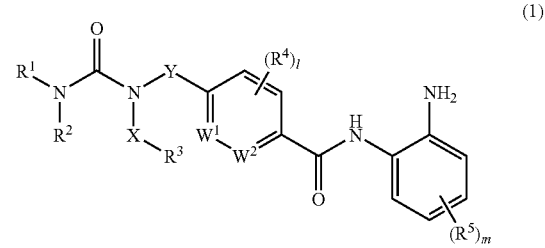

[$R^1$ and $R^2$ are the same or different and represent a hydrogen atom, a lower alkyl group which may have a substituent, a lower alkenyl group which may have a substituent, a lower alkynyl group which may have a substituent or a group represented by the following general formula (2);

(2)

$R^3$ represents a hydroxy group, a lower alkoxy group which may have a substituent, a lower cycloalkyloxy group which may have a substituent, an aryloxy group which may have a substituent, a carboxy group, a lower alkoxycarbonyl group which may have a substituent, —OCONR$^a$R$^b$, —NR$^c$R$^d$ or a group represented by the following general formula (3);

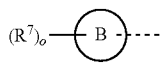
(3)

$R^4$ and $R^5$ are the same or different and represent a halogen atom, a lower alkyl group which may have a substituent, a hydroxy group, or a lower alkoxy group which may have a substituent;

$R^6$ represents a halogen atom, a lower alkyl group which may have a substituent, a lower cycloalkyl group which may have a substituent, an aryl group which may have a substituent, a heterocyclic group which may have a substituent, a hydroxy group, a lower alkoxy group which may have a substituent, a lower cycloalkyloxy group which may have a substituent, an aryloxy group which may have a substituent, a mercapto group, a lower alkylthio group which may have a substituent, a formyl group, a lower cycloalkylthio group which may have a substituent, an arylthio group which may have a substituent, a lower alkylcarbonyl group which may have a substituent, a carboxy group, a lower alkoxycarbonyl group which may have a substituent, a nitro group, a cyano group or —NR$^e$R$^f$;

$R^7$ represents a lower alkyl group which may have a substituent, a lower cycloalkyl group which may have a substituent, an aryl group which may have a substituent, a hydroxy group, a lower alkoxy group which may have a substituent, a lower cycloalkyloxy group which may have a substituent or an aryloxy group which may have a substituent;

$R^a$ and $R^b$ are the same or different and represent a hydrogen atom, a lower alkyl group which may have a substituent, a lower cycloalkyl group which may have a substituent, an aryl group which may have a substituent or a heterocyclic group which may have a substituent;

$R^c$, $R^d$, $R^e$ and $R^f$ are the same or different and represent a hydrogen atom, a lower alkyl group which may have a substituent, a lower cycloalkyl group which may have a substituent or an aryl group which may have a substituent;

the ring A represents a cyclic hydrocarbon or a heterocyclic ring;

the ring B represents a heterocyclic ring having one or plural heteroatoms selected from the group consisting of a nitrogen atom and an oxygen atom in the ring;

X represents a lower alkylene group which may have a substituent;

Y and Z are the same or different and represent a single bond or a lower alkylene group which may have a substituent;

$W^1$-$W^2$ represents N—C or C—N; and l, m, n and o are the same or different and represent 0, 1, 2 or 3. The same shall apply hereinafter.]

Advantageous Effects of the Invention

The invention provides a novel pyridinecarboxylic acid (2-aminophenyl)amide derivative having a urea structure or a salt thereof which is useful as a pharmaceutical. The present compound has an HDAC inhibitory activity, and is therefore useful as a preventive and/or therapeutic agent for a disease against which an HDAC inhibitor is considered to be effective, and is particularly expected as a preventive and/or therapeutic agent for cancer, an autoimmune diseases, an inflammatory diseases, a neurodegenerative diseases, an infectious diseases, hematopoietic disorders, fibrosis, a cardiovascular diseases or a diseases considered to be associated with angiogenesis. Further, since the present compound has an effect of morphological change on trabecular meshwork cells and an effect of intraocular pressure reduction, it is also an invention relating to a preventive and/or therapeutic agent for a disease considered to be associated with circulation of aqueous humor and/or intraocular pressure such as glaucoma or ocular hypertension.

BEST MODE FOR CARRYING OUT THE INVENTION

Hereinafter, definitions of terms and phrases (atoms, groups, rings and the like) to be used in this specification will be described in detail.

The "halogen atom" refers to a fluorine, chlorine, bromine or iodine atom.

The "lower alkyl group" refers to a straight-chain or branched alkyl group having 1 to 8, preferably 1 to 6 carbon atoms. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups.

The "lower alkenyl group" refers to a straight-chain or branched alkenyl group having 2 to 8, preferably 2 to 6 carbon atoms. Specific examples thereof include vinyl, propenyl, butenyl, pentenyl, hexenyl, heptenyl, octenyl, isopropenyl, 2-methyl-1-propenyl and 2-methyl-2-butenyl groups.

The "lower alkynyl group" refers to a straight-chain or branched alkynyl group having 2 to 8, preferably 2 to 6 carbon atoms. Specific examples thereof include ethynyl, propynyl, butynyl, pentynyl, hexynyl, heptynyl, octynyl isobutynyl and isopentynyl groups.

The "lower cycloalkyl group" refers to a cycloalkyl group having 3 to 8, preferably 3 to 6 carbon atoms. Specific examples thereof include cyclopropyl, cyclobutyl, cyclopentyl, cyclohexyl, cycloheptyl and cyclooctyl groups.

The "aryl group" refers to a residue formed by removing one hydrogen atom from a monocyclic aromatic hydrocarbon group, or a bicyclic or tricyclic condensed polycyclic aromatic hydrocarbon having 6 to 14 carbon atoms. Specific examples thereof include phenyl, naphthyl, anthryl and phenanthryl groups.

The "lower alkoxy group" refers to a group formed by substituting the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentyloxy groups.

The "lower cycloalkyloxy group" refers to a group formed by substituting the hydrogen atom of a hydroxy group with a lower cycloalkyl group. Specific examples thereof include cyclopropyloxy, cyclobutyloxy, cyclopentyloxy, cyclohexyloxy, cycloheptyloxy and cyclooctyloxy groups.

The "aryloxy group" refers to a group formed by substituting the hydrogen atom of a hydroxy group with an aryl group. Specific examples thereof include phenoxy, naphthoxy, anthryloxy and phenanthryloxy groups.

The "lower alkylthio group" refers to a group formed by substituting the hydrogen atom of a mercapto group with a lower alkyl group. Specific examples thereof include methylthio, ethylthio, n-propylthio, n-butylthio, n-pentylthio, n-hexylthio, n-heptylthio, n-octylthio, isopropylthio, isobutylthio, sec-butylthio, tert-butylthio and isopentylthio groups.

The "lower cycloalkylthio group" refers to a group formed by substituting the hydrogen atom of a mercapto group with a lower cycloalkyl group. Specific examples thereof include cyclopropylthio, cyclobutylthio, cyclopentylthio, cyclohexylthio, cycloheptylthio and cyclooctylthio groups.

The "arylthio group" refers to a group formed by substituting the hydrogen atom of a mercapto group with an aryl group. Specific examples thereof include phenylthio, naphthylthio, anthrylthio and phenanthrylthio groups.

The "lower alkylcarbonyl group" refers to a group formed by substituting the hydrogen atom of a formyl group with a lower alkyl group. Specific examples thereof include methylcarbonyl, ethylcarbonyl, n-propylcarbonyl, n-butylcarbonyl, n-pentylcarbonyl, n-hexylcarbonyl, n-heptylcarbonyl, n-octylcarbonyl, isopropylcarbonyl, isobutylcarbonyl, sec-butylcarbonyl, tert-butylcarbonyl and isopentylcarbonyl groups.

The "lower alkoxycarbonyl group" refers to a group formed by substituting the hydrogen atom of a formyl group with a lower alkoxy group. Specific examples thereof include methoxycarbonyl, ethoxycarbonyl, n-propoxycarbonyl, n-butoxycarbonyl, n-pentoxycarbonyl, n-hexyloxycarbonyl, n-heptyloxycarbonyl, n-octyloxycarbonyl, isopropoxycarbonyl, isobutoxycarbonyl, sec-butoxycarbonyl, tert-butoxycarbonyl and isopentyloxycarbonyl groups.

The "heterocyclic ring" refers to a saturated or unsaturated monocyclic heterocyclic ring, or bicyclic or tricyclic condensed polycyclic heterocyclic ring having one or plural heteroatoms selected from a nitrogen atom, an oxygen atom and a sulfur atom in the ring.

Specific examples of the saturated monocyclic heterocyclic ring include aziridine, azetidine, pyrrolidine, pyrazolidine, imidazolidine, triazolidine, piperidine, hexahydropyridazine, hexahydropyrimidine, piperazine, homopiperidine and homopiperazine, having a nitrogen atom in the ring; tetrahydrofuran, tetrahydropyran, 1,4-dioxane and 1,2-dioxirane, having an oxygen atom in the ring; tetrahydrothiophene and tetrahydrothiopyran, having a sulfur atom in the ring; oxazolidine, isoxazolidine and morpholine, having a nitrogen atom and an oxygen atom in the ring; and thiazolidine, isothiazolidine and thiomorpholine, having a nitrogen atom and a sulfur atom in the ring.

Further, such a saturated monocyclic heterocyclic ring may be condensed with a benzene ring or the like to form a bicyclic or tricyclic condensed polycyclic heterocyclic ring such as dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chroman, isochroman, benzo[1,3]dioxole, 2,3-dihydrobenzo[1,4]dioxin, dihydrobenzothiophene, dihydroisobenzothiophene, thiochroman, isothiochroman, dihydrobenzoxazole, dihydrobenzisoxazole, dihydrobenzoxazine, dihydrobenzothiazole, dihydrobenzoisothiazole, dihydrobenzothiazine, xanthene, 4a-carbazole or perimidine.

Specific examples of the unsaturated monocyclic heterocyclic ring include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine, having a nitrogen atom in the ring; dihydrofuran, furan, dihydropyran and pyran, having an oxygen atom in the ring; dihydrothiophene, thiophene, dihydrothiopyran and thiopyran, having a sulfur atom in the ring; dihydrooxazole, oxazole, dihydroisoxazole, isoxazole, dihydrooxazine and oxazine, having a nitrogen atom and an oxygen atom in the ring; dihydrothiazole, thiazole, dihydroisothiazole, isothiazole, dihydrothiazine and thiazine, having a nitrogen atom and a sulfur atom in the ring.

Further, such an unsaturated monocyclic heterocyclic ring may be condensed with a benzene ring or the like to form a bicyclic or tricyclic condensed polycyclic heterocyclic ring such as indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromen, isochromen, benzothiophene, isobenzothiophene, thiochromen, isothiochromen, benzoxazole, benzisoxazole, benzoxazine, benzothiazole, tetrahydrobenzothiazole, benzoisothiazole, benzothiazine, phenoxanthine, carbazole, β-carboline, phenanthridine, acridine, phenanthroline, phenazine, phenothiazine or phenoxazine.

Further, among these heterocyclic rings, in the case of a heterocyclic ring having two hydrogen atoms on the same carbon atom, these hydrogen atoms may be substituted with an oxo group to form a heterocyclic ketone such as 2-pyrrolidone, 4-piperidone, 4-thiazolidone, pyran-4-(4H)-one or pyrazin-2-(3H)-one, and these heterocyclic ketones are also included in the scope of the heterocyclic ring of the invention.

The "heterocyclic ring having one or plural heteroatoms selected from the group consisting of a nitrogen atom and an oxygen atom in the ring" refers to a heterocyclic ring having one or plural nitrogen atoms and/or oxygen atoms in the ring among the above-mentioned heterocyclic rings.

The "heterocyclic group" refers to a residue formed by removing one hydrogen atom from a heterocyclic ring.

The "cyclic hydrocarbon" refers to a saturated or unsaturated monocyclic hydrocarbon, or bicyclic or tricyclic hydrocarbon having 3 to 10 carbon atoms.

Specific examples of the saturated monocyclic hydrocarbon include cyclopropane, cyclobutane, cyclopentane, cyclohexane, cycloheptane and cyclooctane.

Specific examples of the saturated bicyclic hydrocarbon include octahydropentalene, octahydroindene and decahydronaphthalene.

Specific examples of the saturated tricyclic hydrocarbon include bicyclo[2.2.1]heptane.

Specific examples of the unsaturated monocyclic hydrocarbon include cyclopentene, cyclohexene, cyclopentadiene, cyclohexadiene and benzene.

Specific examples of the unsaturated bicyclic hydrocarbon include indan, 1,2,3,4-tetrahydronaphthalene and naphthalene.

The "lower alkylene group" refers to a straight or branched alkylene group having 1 to 8, preferably 1 to 6 carbon atoms. Specific examples thereof include methylene, ethylene, trimethylene, tetramethylene, pentamethylene, hexamethylene, heptamethylene, octamethylene, methylmethylene and ethylmethylene.

The "lower alkyl group which may have a substituent", "lower alkenyl group which may have a substituent", "lower alkynyl group which may have a substituent", "lower alkoxy group which may have a substituent", "lower alkylthio group which may have a substituent", "lower alkylcarbonyl group which may have a substituent", "lower alkoxycarbonyl group which may have a substituent" and/or "lower alkylene group which may have a substituent" refers to a "lower alkyl group", a "lower alkenyl group", a "lower alkynyl group", a "lower alkoxy group", a "lower alkylthio group", a "lower alkylcarbonyl group", a "lower alkoxycarbonyl group" and/or a "lower alkylene group" which may have one or plural substituents selected from the group consisting of a halogen atom, a lower cycloalkyl group, an aryl group, a heterocyclic group, a nitro group, a cyano group, an oxo group, —OR$^p$, —SR$^q$, —COR$^r$, —COOR$^s$, —CONR$^t$R$^u$ and —NR$^v$R$^w$.

The "lower cycloalkyl group which may have a substituent", "aryl group which may have a substituent", "heterocyclic group which may have a substituent", "lower cycloalkyloxy group which may have a substituent" and/or "aryloxy group which may have a substituent" refers to a "lower cycloalkyl group", an "aryl group", a "heterocyclic group", a "lower cycloalkyloxy group" and/or an "aryloxy group" which may have one or plural substituents selected from the group consisting of a halogen atom, a lower alkyl group, a lower alkenyl group, a lower alkynyl group, a lower cycloalkyl group, an aryl group, a heterocyclic group, a nitro group, a cyano group, an oxo group, —OR$^p$, —SR$^q$, —COR$^r$, —COOR$^s$, —CONR$^t$R$^u$ and —NR$^v$R$^w$.

Here, R$^p$, R$^q$, R$^r$, R$^s$, R$^t$, R$^u$, R$^v$ and R$^w$ are the same or different and represent a group selected from the group consisting of a hydrogen atom, a lower alkyl group, a lower alkenyl group, a lower alkynyl group, a lower cycloalkyl group, an aryl group and a heterocyclic group.

With regard to the term "plural groups" as used herein, the respective groups may be the same or different, and the number of the groups is preferably 2 or 3, particularly preferably 2. Further, a hydrogen atom and a halogen atom are also included in the concept of the "group".

In the invention, when "l", "m", "n" and/or "o" represents 2 or 3, the respective plural groups represented by R$^4$, R$^5$, R$^6$ or R$^7$ may be the same or different. Incidentally, when "l", "m", "n" and/or "o" represents 0, the respective groups represented by R$^4$, R$^5$, R$^6$ and/or R$^7$ do not exist. That is, it shows that the compound does not have the substituents.

The "HDAC inhibitor" as used herein refers to a pharmaceutical composition which inhibits HDAC thereby enhancing acetylation of histones and the like to exhibit a pharmaceutical effect.

The "disease against which an HDAC inhibitor is considered to be effective" as used herein refers to a disease on which it is known that an HDAC inhibitor is expected to have a therapeutic effect and/or a preventive effect. Specific examples thereof include cancer, autoimmune diseases, inflammatory diseases, neurodegenerative diseases, infectious diseases, hematopoietic disorder, fibrosis and cardiovascular diseases.

More specific examples thereof include cancer such as acute leukemia, chronic leukemia, malignant lymphoma, multiple myeloma, colon cancer, brain tumor, head and neck cancer, breast cancer, lung cancer, esophageal cancer, stomach cancer, liver cancer, gallbladder cancer, bile duct cancer, pancreatic cancer, islet cell carcinoma, renal cell carcinoma, adrenal cortical carcinoma, bladder cancer, prostate cancer, testicular tumor, ovarian cancer, uterine cancer, choriocarcinoma, thyroid cancer, malignant carcinoid tumor, skin cancer, malignant melanoma, osteosarcoma, soft tissue sarcoma, neuroblastoma, Wilms' tumor and retinoblastoma; autoimmune diseases and/or inflammatory diseases such as rheumatoid arthritis, nephritis, diabetes, systemic lupus erythematosus, human autoimmune lymphoproliferative lymphadenopathy, immunoblastic lymphadenopathy, Crohn's disease, ulcerative colitis, multiple sclerosis, inflammatory bowel diseases, psoriasis, osteoarthropathy, juvenile chronic arthritis, graft-versus-host rejection, asthma, alcoholic hepatitis, Sjogren's syndrome, ankylosing spondylitis, membranous glomerulonephritis, intervertebral disk pain, atopic dermatitis, allergic rhinitis, allergic conjunctivitis, keratitis, conjunctivitis, uveitis, age-related macular degeneration, diabetic retinopathy and diabetic macular edema; neurodegenerative diseases such as Alzheimer's disease, Parkinson's disease, Huntington's disease, amyotrophic lateral sclerosis, spinocerebellar degeneration, polyglutamine diseases, striatonigral degeneration, progressive supranuclear palsy, torsion dystonia, cervical dystonia, familial tremor, Gilles de la Tourette syndrome, diffuse Lewy body disease, Pick's disease, intracerebral hemorrhage, primary lateral sclerosis, spinal muscular atrophy, amyotrophic lateral sclerosis, hypertrophic interstitial neuropathy, retinitis pigmentosa, hereditary optic atrophy, hereditary spastic paraplegia, progressive ataxia and Shy-Drager syndrome; infectious diseases such as fungal infection (such as candidal fungus), bacterial infection, viral infection (including herpes simplex), protozoan infection (such as malaria), toxoplasmosis and coccidiosis; hematopoietic disorder such as anemia, sickle cell anemia and thalassemia; fibrosis such as hepatic fibrosis, cystic fibrosis, and vascular fibrosis; cardiovascular diseases such as heart failure, restenosis, arteriosclerosis and cardiac hypertrophy; and diseases considered to be associated with angiogenesis such as the above-mentioned cancer, rheumatoid arthritis, psoriasis, age-related macular degeneration and diabetic retinopathy.

Incidentally, the above-mentioned specific diseases are described for the purpose of understanding the invention better and are not meant to limit the scope of the invention, and there is no particular limitation as long as it is a disease against which an HDAC inhibitor is considered to be effective.

Further, in the case where there are families and/or subtypes in HDAC in the invention, these families and/or subtypes are also included in the scope of HDAC of the invention.

The "disease considered to be associated with aqueous humor circulation and/or intraocular pressure" as used herein is not particularly limited as long as it is a disease considered to be associated with aqueous humor circulation and/or intraocular pressure, preferred examples thereof include glaucoma and ocular hypertension.

The "salt" of the present compound is not particularly limited as long as it is a pharmaceutically acceptable salt, and examples thereof include salts with an inorganic acid such as hydrochloric acid, hydrobromic acid, hydroiodic acid, nitric acid, sulfuric acid or phosphoric acid; salts with an organic acid such as acetic acid, fumaric acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid or sulfosalicylic acid; quaternary ammonium salts with methyl bromide, methyl iodide or the like; salts with a halogen ion such as a bromine ion, a chlorine ion or an iodine ion; salts with an alkali metal such as lithium, sodium or potassium; salts with an alkaline earth metal such as calcium or magnesium; salts with a metal such as iron or zinc; salts with ammonia; and salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine or N,N-bis(phenylmethyl)-1,2-ethanediamine.

In the case where there are geometric isomers or optical isomers in the present compound, these isomers are also included in the scope of the invention.

Further, the present compound may be in the form of a hydrate or a solvate.

Further, in the case where there is proton tautomerism in the present compound, the tautomeric isomers thereof are also included in the invention.

In the case where there are crystalline polymorphisms and crystalline polymorphism groups (crystalline polymorphism systems) in the present compound, these crystalline polymorphisms and crystalline polymorphism groups (crystalline polymorphism systems) are also included in the invention. Here, the crystalline polymorphism groups (crystalline polymorphism systems) mean individual crystal forms in respective stages when the crystal forms are changed by conditions for the production, crystallization, storage or the like of these crystals and/or states thereof (the states also include a formulated state) and/or all the processes thereof.

(a) Preferred examples of the present compound include compounds in which the respective groups are as defined below and salts thereof in the compounds represented by the general formula (1) and salts thereof:

(a1) $R^1$ and $R^2$ are the same or different and represent a hydrogen atom, a lower alkyl group, a lower alkyl group having a halogen atom as a substituent, a lower alkyl group having a methoxy group as a substituent, a lower alkyl group having a methylthio group as a substituent, a lower alkyl group having a cyano group as a substituent, a lower alkyl group having a methylaminocarbonyl group as a substituent, a lower alkyl group having a diisopropylamino group as a substituent, a lower alkenyl group, a lower alkynyl group or a group represented by the following general formula (2); and/or

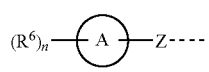

(2)

(a2) $R^3$ represents a hydroxy group, a lower alkoxy group, a lower cycloalkyloxy group, an aryloxy group, a carboxy group, a lower alkoxycarbonyl group, —OCONR$^a$R$^b$, —NR$^c$R$^d$ or a group represented by the following general formula (3); and/or

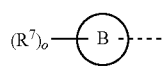

(3)

(a3) $R^4$ and $R^5$ are the same or different and represent a halogen atom, a lower alkyl group, a hydroxy group or a lower alkoxy group; and/or (a4) $R^6$ represents a halogen atom, a lower alkyl group, a lower alkyl group having a halogen atom as a substituent, a lower alkyl group having a cyano group as a substituent, a lower cycloalkyl group, an aryl group, a heterocyclic group, a hydroxy group, a lower alkoxy group, a lower alkoxy group having a halogen atom as a substituent, a lower alkoxy group having an aryl group as a substituent, a lower cycloalkyloxy group, an aryloxy group, a mercapto group, a lower alkylthio group, a lower cycloalkylthio group, an arylthio group, a formyl group, a lower alkylcarbonyl group, a carboxy group, a lower alkoxycarbonyl group, a nitro group, a cyano group or —NR$^e$R$^f$; and/or (a5) $R^7$ represents a lower alkyl group, a lower cycloalkyl group, an aryl group, a hydroxy group, a lower alkoxy group, a lower cycloalkyloxy group or an aryloxy group; and/or (a6) $R^a$ and $R^b$ are the same or different and represent a hydrogen atom, a lower alkyl group, a lower cycloalkyl group, an aryl group or a heterocyclic group; and/or (a7) $R^c$, $R^d$, $R^e$ and $R^f$ are the same or different and represent a hydrogen atom, a lower alkyl group, a lower cycloalkyl group or an aryl group; and/or (a8) the ring A represents a cyclic hydrocarbon or a heterocyclic ring; and/or (a9) the ring B represents a heterocyclic ring having one or plural heteroatoms selected from the group consisting of a nitrogen atom and an oxygen atom in the ring; and/or (a10) X represents a lower alkylene group; and/or (a11) Y and Z are the same or different and represent a single bond, a lower alkylene group or a lower alkylene group having an oxo group as a substituent; and/or (a12) $W^1$-$W^2$ represents N—C or C—N; and/or (a13) l, m, n and o are the same or different and represent 0, 1, 2 or 3.

That is, preferred examples of the present compound include, in the compounds represented by the general formula (1), compounds which comprise one or a combination of two or more selected from the group consisting of the above-mentioned (a1), (a2), (a3), (a4), (a5), (a6), (a7), (a8), (a9), (a10), (a11), (a12) and (a13) and salts thereof.

(b) More preferred examples of the present compound include compounds in which the respective groups are as defined below and salts thereof in the compounds represented by the general formula (1) and salts thereof:

(b1) $R^1$ represents a lower alkyl group, a lower alkyl group having a halogen atom as a substituent, a lower alkyl group having a methoxy group as a substituent, a lower alkyl group having a methylthio group as a substituent, a lower alkyl group having a cyano group as a substituent, a lower alkyl group having a methylaminocarbonyl group as a substituent, a lower alkyl group having a diisopropylamino group as a substituent, a lower alkynyl group or a group represented by the following general formula (2); and/or

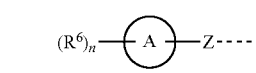

(2)

(b2) $R^2$ represents a hydrogen atom; and/or (b3) $R^3$ represents a hydroxy group, a carboxy group, a lower alkoxycarbonyl group, —OCONR$^a$R$^b$, —NR$^c$R$^d$ or a group represented by the following general formula (3); and/or

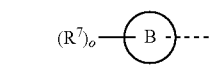

(3)

(b4) $R^6$ represents a halogen atom, a lower alkyl group, a lower alkyl group having a halogen atom as a substituent, a lower alkyl group having a cyano group as a substituent, an aryl group, a morpholino group, a hydroxy group, a lower alkoxy group, a lower alkoxy group having a halogen atom as a substituent, a lower alkoxy group having an aryl group as a substituent, a lower alkylthio group, a lower alkylcarbonyl group, a nitro group, a cyano group or —NR$^e$R$^f$; and/or (b5) R$^7$ represents a lower alkyl group or a lower alkoxy group; and/or (b6) R$^a$ and R$^b$ are the same or different and represent a hydrogen atom or a heterocyclic group; and/or (b7) R$^c$, R$^d$, R$^e$ and R$^f$ represent a lower alkyl group; and/or (b8) the ring A represents a cyclic hydrocarbon or a heterocyclic ring; and/or (b9) the ring B represents a heterocyclic ring having plural heteroatoms selected from the group consisting of a nitrogen atom and an oxygen atom in the ring; and/or (b10) X and Y represent a lower alkylene group; and/or (b11) Z represents a single bond, a lower alkylene group or a lower alkylene group substituted with an oxo group; and/or (b12) W$^1$-W$^2$ represents C—N or N—C; and/or (b13) l and m represent 0; and/or (b14) o represents 0 or 1; and/or (b15) n represents 0, 1 or 2.

That is, more preferred examples of the present compound include, in the compounds represented by the general formula (1), compounds which comprise one or a combination of two or more selected from the group consisting of the above-mentioned (b1), (b2), (b3), (b4), (b5), (b6), (b7), (b8), (b9), (b10), (b11), (b12), (b13), (b14) and (b15) and salts thereof.

(c) Preferred examples of the ring A include the following rings.

The ring A represents benzene, indan, thiophene, benzo[1,3]dioxole, 2,3-dihydrobenzofuran, 1H-benzimidazole, isoxazole, thiazole, benzothiazole, 2,3-dihydrobenzo[1,4]dioxin or pyridine.

Further, compounds which have the ring A and satisfy the requirements of the above-mentioned (a), (b), and/or the following (d) or salts thereof are particularly preferred.

(d) Other preferred examples of the ring B include the following rings.

The ring B represents pyrrolidine or morpholine.

Further, compounds which have the ring B and satisfy the requirements of the above-mentioned (a), (b), and/or (c) or salts thereof are particularly preferred.

(e) Particularly preferred specific examples of the present compound include the following compounds and salts thereof.

N-(2-Aminophenyl)-5-[3-(2,3-dihydrobenzo[1,4]dioxin-6-yl)-1-(3-dimethylaminopropyl)ureidomethyl]pyridine-2-carboxylic acid amide, N-(2-Aminophenyl)-5-[3-(4-dimethylaminophenyl)-1-(3-(morpholin-4-yl)propyl)ureidomethyl]pyridine-2-carboxylic acid amide, N-(2-Aminophenyl)-5-[1-(3-(morpholin-4-yl)propyl)-3-phenethylureidomethyl]pyridine-2-carboxylic acid amide, N-(2-Aminophenyl)-5-[3-(3,4-difluorophenyl)-1-(3-dimethylaminopropyl)ureidomethyl]pyridine-2-carboxylic acid amide, N-(2-Aminophenyl)-5-[1-(3-dimethylaminopropyl)-3-(4-methoxyphenyl)ureidomethyl]pyridine-2-carboxylic acid amide, N-(2-Aminophenyl)-5-[3-(4-diethylaminophenyl)-1-(3-dimethylaminopropyl)ureidomethyl]pyridine-2-carboxylic acid amide, N-(2-Aminophenyl)-5-[1-(3-dimethylaminopropyl)-3-(3-fluorophenyl)ureidomethyl]pyridine-2-carboxylic acid amide, N-(2-Aminophenyl)-5-[1-(3-dimethylaminopropyl)-3-(3-fluoro-4-methylphenyl)ureidomethyl]pyridine-2-carboxylic acid amide, N-(2-Aminophenyl)-5-[1-(3-dimethylaminopropyl)-3-(4-fluoro-3-methylphenyl)ureidomethyl]pyridine-2-carboxylic acid amide, N-(2-Aminophenyl)-5-[3-(4-cyanophenyl)-1-(3-dimethylaminopropyl)ureidomethyl]pyridine-2-carboxylic acid amide, N-(2-Aminophenyl)-5-[1-(3-dimethylaminopropyl)-3-(4-trifluoromethoxyphenyl)ureidomethyl]pyridine-2-carboxylic acid amide, N-(2-Aminophenyl)-5-[3-(benzo[1,3]dioxol-5-yl)-1-(3-hydroxypropyl)ureidomethyl]pyridine-2-carboxylic acid amide, N-(2-Aminophenyl)-5-[3-(4-dimethylaminophenyl)-1-(2-ethoxycarbonylethyl)ureidomethyl]pyridine-2-carboxylic acid amide, N-(2-Aminophenyl)-5-[3-(1,3-benzothiazol-2-yl)-1-(3-dimethylaminopropyl)ureidomethyl]pyridine-2-carboxylic acid amide, N-(2-Aminophenyl)-5-[3-(1H-benzoimidazol-2-yl)-1-(3-dimethylaminopropyl)ureidomethyl]pyridine-2-carboxylic acid amide, N-(2-Aminophenyl)-5-[3-(2,3-dihydro-1-benzofuran-5-yl)-1-(3-(morpholin-4-yl)propyl)ureidomethyl]pyridine-2-carboxylic acid amide, N-(2-Aminophenyl)-5-[3-(2,3-dihydrobenzo[1,4]dioxin-6-yl)-1-(2-hydroxyethyl)ureidomethyl]pyridine-2-carboxylic acid amide, N-(2-Aminophenyl)-5-[1-(3-dimethylaminopropyl)-3-(phenylcarbonylmethyl)ureidomethyl]pyridine-2-carboxylic acid amide, N-(2-Aminophenyl)-5-[1-(3-dimethylaminopropyl)-3-(1,3-thiazol-2-yl)ureidomethyl]pyridine-2-carboxylic acid amide, N-(2-Aminophenyl)-5-[1-(3-dimethylaminopropyl)-3-(6-methoxy-1,3-benzothiazol-2-yl)ureidomethyl]pyridine-2-carboxylic acid amide, N-(2-Aminophenyl)-5-[1-(3-dimethylaminopropyl)-3-(6-fluoro-1,3-benzothiazol-2-yl)ureidomethyl]pyridine-2-carboxylic acid amide, N-(2-Aminophenyl)-5-[1-(3-diethylaminopropyl)-3-(3,4-difluorophenyl)ureidomethyl]pyridine-2-carboxylic acid amide, N-(2-Aminophenyl)-5-[1-(3-(morpholin-4-yl)propyl)-3-(pyridin-3-yl)ureidomethyl]pyridine-2-carboxylic acid amide, N-(2-Aminophenyl)-5-[1-(3-dimethylaminopropyl)-3-(thiophen-3-yl)ureidomethyl]pyridine-2-carboxylic acid amide, N-(2-Aminophenyl)-5-[1-(3-dimethylaminopropyl)-3-(3-fluoro-4-methoxyphenyl)ureidomethyl]pyridine-2-carboxylic acid amide, N-(2-Aminophenyl)-5-[3-(3-chloro-4-fluorophenyl)-1-(3-diethylaminopropyl)ureidomethyl]pyridine-2-carboxylic acid amide, N-(2-Aminophenyl)-5-[1-(3-diethylaminopropyl)-3-(4-fluoro-3-nitrophenyl)ureidomethyl]pyridine-2-carboxylic acid amide, N-(2-Aminophenyl)-5-[3-(2,3-dihydrobenzo[1,4]dioxin-6-yl)-1-(2-dimethylaminoethyl)ureidomethyl]pyridine-2-carboxylic acid amide, N-(2-Aminophenyl)-5-[1-(2-dimethylaminoethyl)-3-(3-methoxyphenyl)ureidomethyl]pyridine-2-carboxylic acid amide, N-(2-Aminophenyl)-5-[1-(2-dimethylaminoethyl)-3-(3-fluorophenyl)ureidomethyl]pyridine-2-carboxylic acid amide, N-(2-Aminophenyl)-5-[1-(2-dimethylaminoethyl)-3-(thiophen-3-yl)ureidomethyl]pyridine-2-carboxylic acid amide, N-(2-Aminophenyl)-5-[3-(pyridin-3-yl)-1-[3-(pyrrolidin-1-yl)propyl]ureidomethyl]pyridine-2-carboxylic acid amide, N-(2-Aminophenyl)-5-[1-(3-(morpholin-4-yl)propyl)-3-(phenylcarbonylmethyl)ureidomethyl]pyridine-2-carboxylic acid amide, N-(2-Aminophenyl)-5-[3-(3-chlorophenyl)-1-(3-(morpholin-4-yl)propyl)ureidomethyl]pyridine-2-carboxylic acid amide, N-(2-Aminophenyl)-5-[3-(4-fluorophenethyl)-1-(3-(morpholin-4-yl)propyl)ureidomethyl]pyridine-2-carboxylic acid amide, N-(2-Aminophenyl)-5-[3-(4-cyanophenyl)-1-(3-hydroxypropyl)ureidomethyl]pyridine-2-carboxylic acid amide, N-(2-Aminophenyl)-5-[3-(3-fluorophenyl)-1-[2-(4-methylpiperazin-1-yl)ethyl]ureidomethyl]pyridine-2-carboxylic acid amide, N-(2-Aminophenyl)-5-[3-(2,3-dihydrobenzo[1,4]dioxin-6-yl)-1-[3-(4-methylpiperazin-1-yl)propyl]ureidomethyl]pyridine-2-carboxylic acid amide, N-(2-Aminophenyl)-5-[1-(2-dimethylaminoethyl)-3-(3-methylphenyl)ureidomethyl]pyridine-2-carboxylic acid amide, N-(2-Aminophenyl)-5-[3-(2,3-dihydrobenzo[1,4]dioxin-6-yl)-1-[4-(morpholin-4-yl)butyl]ureidomethyl]pyridine-2-carboxylic acid amide, N-(2-Aminophenyl)-5-[1-(2-dimethylaminoethyl)-3-(1,3-thiazol-2-yl)ureidomethyl]pyridine-2-carboxylic acid amide, N-(2-Aminophenyl)-5-[3-(2-methoxyphenyl)-1-[4-(morpholin-4-yl)butyl]ureidomethyl]pyridine-2-carboxylic acid amide, N-(2-Aminophenyl)-5-[3-(3-methylphenyl)-1-[3-(4-methylpiperidin-1-yl)propyl]ureidomethyl]pyridine-2-carboxylic acid amide; and N-(2-Aminophenyl)-5-[3-cyclopentyl-1-[5-(morpholin-4-yl)pentyl]ureidomethyl]pyridine-2-carboxylic acid amide.

The present compounds can be prepared according to the following methods. Each specific process for preparing the present compounds are described in detail in the following examples (section of Production Examples). Additionally, the term "Boc" used in the following synthetic routes represents a tert-butoxycarbonyl group. In the case that an oxygen atom, a nitrogen atom, a sulfur atom, and so on are contained in $R^1$, $R^2$, $R^3$, $R^4$, $R^5$ of the following scheme, they will be able to be protected or deprotected by generally used methods.

The processes for preparing the compounds of the present invention are divided roughly into the methods described below, and the suitable method can be chosen according to the kind of substituents.

1) The present compound (I) can be synthesized according to the synthetic route 1. Namely, the compound (I) can be given by the treatment of the compound (II) in an organic solvent such as methanol in the presence of an acid such as hydrogen chloride-ethyl acetate solution at 0° C. to room temperature for 30 minutes to 24 hours.

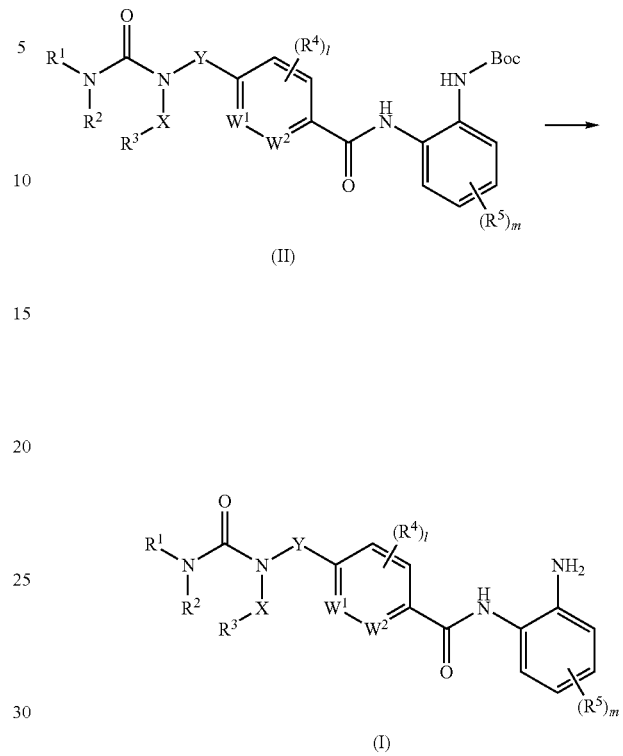

The compound (IIa, $R^2$=H) can be synthesized according to the synthetic route 1-1. Namely, it can be given by the reaction of the compound (III) with an isocyanate (IV) in an organic solvent such as dichloromethane at 0° C. to room temperature for 30 minutes to 24 hours.

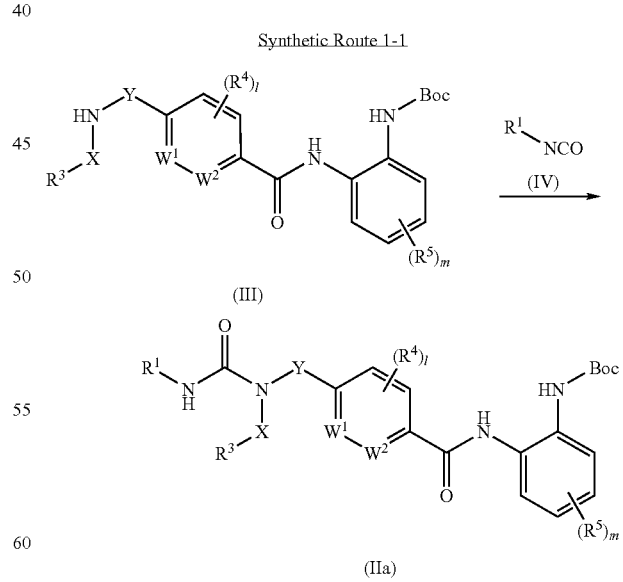

The compound (III) can be synthesized according to the synthetic route 1-2. Namely, it can be given by the reaction of the sulfonate (V) with an amine (VI) at 0° C. to room temperature for 30 minutes to 24 hours.

Synthetic Route 1-2

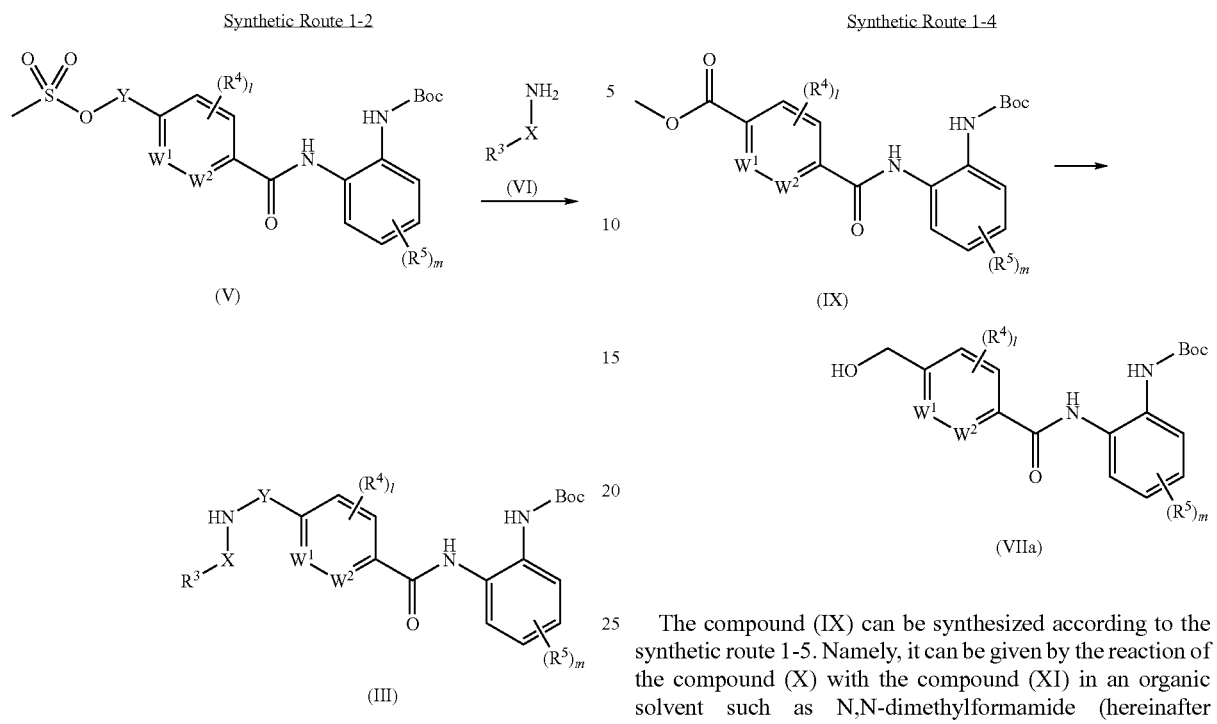

(V)

(III)

The compound (V) can be synthesized according to the synthetic route 1-3. Namely, it can be given by the reaction of the compound (VII) with methanesulfonyl chloride (VIII) in an organic solvent such as dichloromethane in the presence of a base such as triethylamine at 0° C. to room temperature for 30 minutes to 3 hours.

Synthetic Route 1-3

(VII)

(V)

The compound (VIIa, Y=$CH_2$) can be synthesized according to the synthetic route 1-4. Namely, it can be given by the treatment of the compound (IX) in an organic solvent such as tetrahydrofuran (hereinafter referred to as THF) in the presence of a reducing reagent such as lithium borohydride at 0° C. to room temperature for 30 minutes to 24 hours.

Synthetic Route 1-4

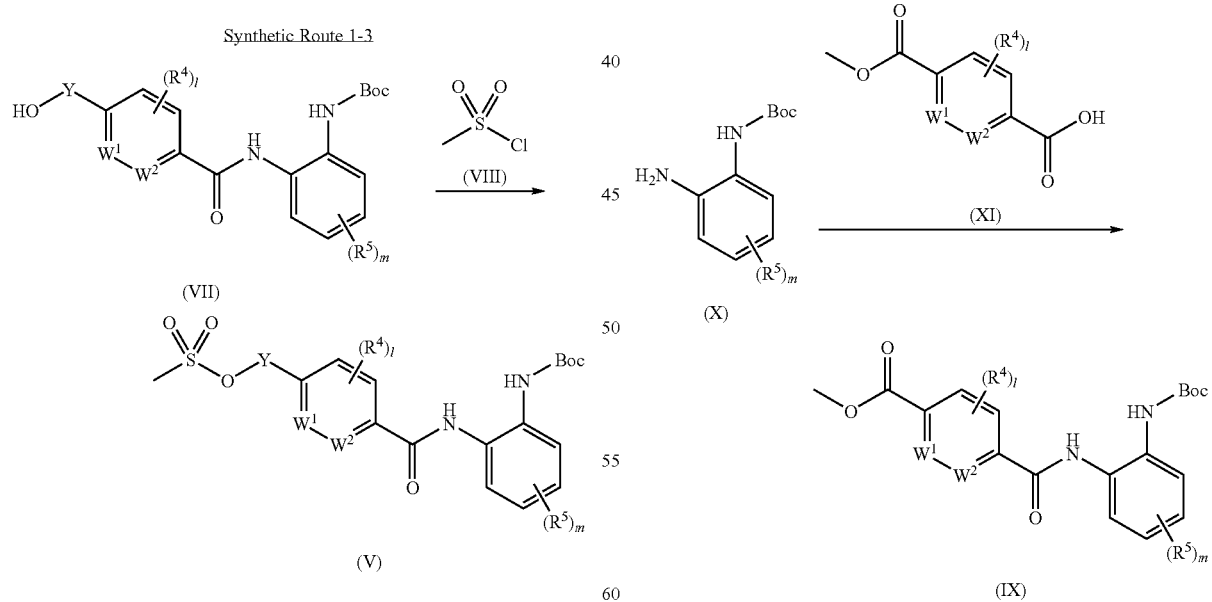

(IX)

(VIIa)

The compound (IX) can be synthesized according to the synthetic route 1-5. Namely, it can be given by the reaction of the compound (X) with the compound (XI) in an organic solvent such as N,N-dimethylformamide (hereinafter referred to as DMF) in the presence of a condensing reagent such as O-(7-azabenzotriazol-1-yl)-1,1,3,3-tetramethyluronium hexafluorophosphate (hereinafter referred to as HATU) and a base such as N,N-diisopropylethylamine at room temperature for 1 hour to 24 hours.

Synthetic Route 1-5

(X)     (XI)

(IX)

The compound (X) can be synthesized according to the synthetic route 1-6. Namely, it can be given by the reaction of the compound (XII) with di-tert-butyl dicarbonate (XIII) in an organic solvent such as THF in the presence of a base such as triethylamine at room temperature for 1 hour to 24 hours.

Synthetic Route 1-6

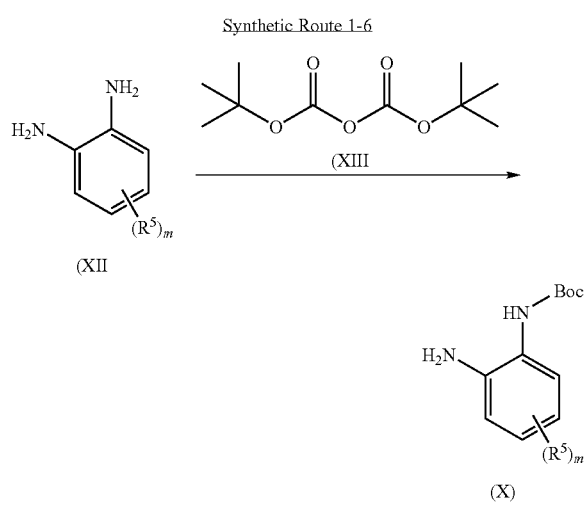

2) The compound (II) can be synthesized according to the synthetic route 2. Namely, it can be given by the reaction of the compound (III) with an amine (XIV) in an organic solvent such as THF in the presence of a reagent for urea formation such as 1,1'-carbonyldiimidazole at 0° C. to 60° C. for 30 minutes to 24 hours.

Synthetic Route 2

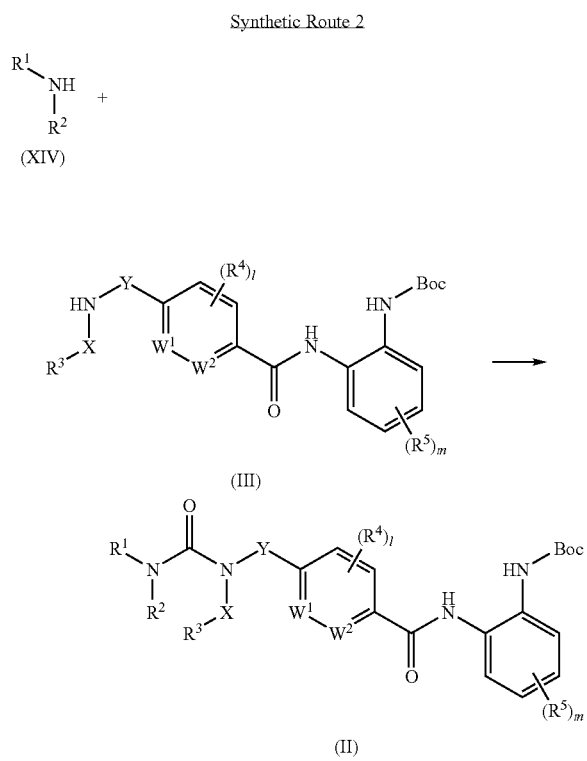

A pharmacological activity of the present compound will be described in detail in the following Examples under the item of "Pharmacological Tests", as a result of studying an HDAC inhibitory activity of the present compound using HDAC Fluorimetric Assay/Drug Discovery Kit (manufactured by BIOMOL, Inc.) according to the protocol of the kit, it was found that the present compound has an excellent HDAC inhibitory activity. That is, the present compound is useful as a preventive and/or therapeutic agent for a disease against which an HDAC inhibitor is considered to be effective, and is particularly expected as a preventive and/or therapeutic agent for cancer, an autoimmune disease, an inflammatory disease, a neurodegenerative disease, an infectious disease, hematopoietic disorder, fibrosis, a cardiovascular disease, a disease considered to be associated with angiogenesis or the like.

Further, as a result of studying an effect of morphological change of the present compound on trabecular meshwork cells, i.e., an effect of morphological change of the present compound on trabecular meshwork cells in an evaluation system using the cell shape index (hereinafter referred to as "CSI") reported in The Journal of Clinical Investigation, 103, 1141-1150 (1999) as an index, it was found the present compound has an excellent effect of morphological change on trabecular meshwork cells.

Further, as a result of studying an effect of intraocular pressure reduction of the present compound through intracameral administration using male Japanese white rabbits in order to confirm an actual effect of intraocular pressure reduction of the present compound, it was confirmed that the present compound has an effect of intraocular pressure reduction. That is, the present compound has an effect of morphological change on trabecular meshwork cells and an effect of intraocular pressure reduction and therefore is expected as a preventive and/or therapeutic agent for a disease considered to be associated with aqueous humor circulation and/or intraocular pressure such as glaucoma or ocular hypertension.

The present compound can be administered either orally or parenterally. Examples of the dosage form include a tablet, a capsule, a granule, a powder, an injection and an eye drop, and such a preparation can be prepared by a widely used technique.

For example, an oral preparation such as a tablet, a capsule, a granule or a powder can be prepared by optionally adding a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl parahydroxybenzoate or benzyl alcohol; a corrigent such as a sweetener, a sour agent or a flavor; or the like.

Further, a parenteral preparation such as an injection or an eye drop can be prepared by optionally adding a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polysorbate 80, polyoxy 40 stearate or polyoxyethylene hydrogenated castor oil 60; a stabilizer such as sodium citrate or sodium edetate; a preservative such as benzalkonium chloride, paraben, benzethonium chloride, parahydroxybenzoate ester, sodium benzoate, chlorobutanol or sorbic acid; a pH adjusting agent such as hydrochloric acid, citric acid, phosphoric acid, glacial acetic acid, sodium hydroxide, sodium carbonate or sodium hydrogen carbonate; a soothing agent such as benzyl alcohol; or the like.

The invention also relates to a method for inhibiting histone deacetylase comprising administering an effective amount of the present compound to a patient, and a method for preventing or treating a disease, against which a histone deacetylase inhibitor is considered to be effective, comprising administering an effective amount of the present compound to a patient.

The dose of the present compound can be properly selected depending on the symptoms, age, dosage form or the like. For example, in the case of an oral preparation, it can be administered in an amount of generally from 0.01 to 1000 mg, preferably from 1 to 100 mg per day in a single dose or several divided doses. Further, in the case of an eye drop, a preparation containing the present compound at a concentration of generally from 0.0001 to 10% (w/v), preferably from 0.01 to 5% (w/v) can be administered in a single dose or several divided doses per day.

Hereinafter, Production Examples, Preparation Examples and results of Pharmacological Tests of the present compound will be described. However, these examples are described for the purpose of understanding the invention better and are not meant to limit the scope of the invention.

PRODUCTION EXAMPLES

Reference Example 1

2-Aminophenylcarbamic acid t-butyl ester (Reference Compound No. 1-1)

A solution of di-t-butyl dicarbonate (44 g, 200 mmol) in THF (50 mL) was added dropwise to a solution of o-phenylenediamine (22 g, 200 mmol) and triethylamine (30 mL, 210 mmol) in THF (150 mL), and then the mixture was stirred

Reference Example 2

N-(2-t-Butoxycarbonylaminophenyl)-5-methoxycarbonylpyridine-2-carboxylic acid amide (Reference Compound No. 2-1)

HATU (21 g, 55 mmol) was added to a solution of 2-aminophenylcarbamic acid t-butyl ester (Reference Compound No. 1-1, 10 g, 50 mmol), 5-methoxycarbonylpyridine-2-carboxylic acid (10 g, 55 mmol), and N-methylmorpholine (11 mL, 100 mmol) in DMF (100 mL), and then the reaction mixture was stirred at room temperature for 20 hours. Water (300 mL) was added thereto, and then the whole was extracted with ethyl acetate (300 mL) three times. The organic layer was washed with brine (200 mL), and then dried over anhydrous magnesium sulfate. The solvent was evaporated under reduced pressure, and then the obtained solid was collected by filtration to give 15 g of the title reference compound as a pale brown solid. (Yield 79%)

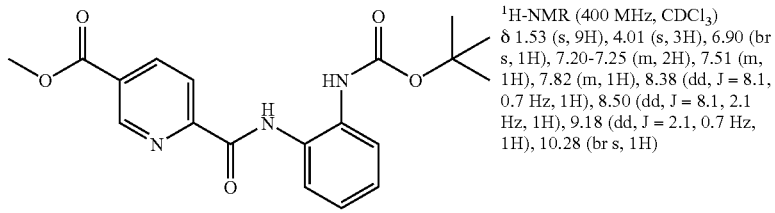

$^1$H-NMR (400 MHz, CDCl$_3$)
δ 1.53 (s, 9H), 4.01 (s, 3H), 6.90 (br s, 1H), 7.20-7.25 (m, 2H), 7.51 (m, 1H), 7.82 (m, 1H), 8.38 (dd, J = 8.1, 0.7 Hz, 1H), 8.50 (dd, J = 8.1, 2.1 Hz, 1H), 9.18 (dd, J = 2.1, 0.7 Hz, 1H), 10.28 (br s, 1H)

at room temperature for 15 hours. The reaction mixture was concentrated, the obtained solid was filtered with ethyl acetate, and then the solid was dried under reduced pressure to give 21 g of the title reference compound as a white solid. Additionally, another solid which was obtained by concentration of the filtrate was collected by filtration with ethyl acetate, and then the solid was dried under reduced pressure to give 11 g of the title reference compound as a white solid. (Yield 76%)

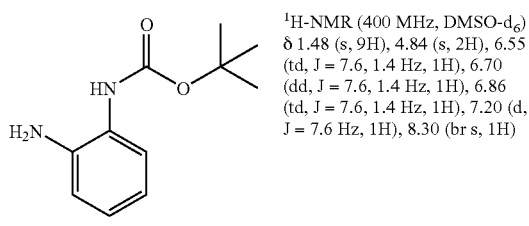

$^1$H-NMR (400 MHz, DMSO-d$_6$)
δ 1.48 (s, 9H), 4.84 (s, 2H), 6.55 (td, J = 7.6, 1.4 Hz, 1H), 6.70 (dd, J = 7.6, 1.4 Hz, 1H), 6.86 (td, J = 7.6, 1.4 Hz, 1H), 7.20 (d, J = 7.6 Hz, 1H), 8.30 (br s, 1H)

Reference Example 3

N-(2-t-Butoxycarbonylaminophenyl)-5-hydroxymethylpyridine-2-carboxylic acid amide (Reference Compound No. 3-1)

Under ice cooling, lithium tetrahydroborate (2.1 g, 100 mmol) was added to a solution of N-(2-t-butoxycarbonylaminophenyl)-5-methoxycarbonylpyridine-2-carboxylic acid amide (Reference Compound No. 2-1, 38 g, 100 mmol) in THF (400 mL), and then the reaction mixture was stirred for 3 hours. Under ice cooling, water (200 mL) and 1.0 M aqueous hydrochloric acid (300 mL) were added thereto, the whole was extracted with ethyl acetate (300 mL), and then the organic layer was washed with water (500 mL) and brine (400 mL). After the organic layer was dried over anhydrous magnesium sulfate, the solvent was evaporated under reduced pressure. Ethyl acetate (20 mL) and hexane (30 mL) were added to the residue, and then the resulting solid was collected by filtration to give 18 g of the title reference compound as a white solid. (Yield 53%)

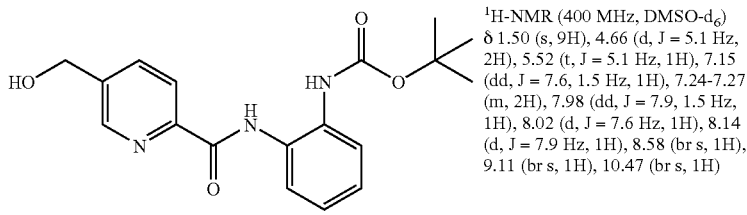

¹H-NMR (400 MHz, DMSO-d₆) δ 1.50 (s, 9H), 4.66 (d, J = 5.1 Hz, 2H), 5.52 (t, J = 5.1 Hz, 1H), 7.15 (dd, J = 7.6, 1.5 Hz, 1H), 7.24-7.27 (m, 2H), 7.98 (dd, J = 7.9, 1.5 Hz, 1H), 8.02 (d, J = 7.6 Hz, 1H), 8.14 (d, J = 7.9 Hz, 1H), 8.58 (br s, 1H), 9.11 (br s, 1H), 10.47 (br s, 1H)

Reference Example 4

N-(2-t-Butoxycarbonylaminophenyl)-5-methanesulfonyloxymethylpyridine-2-carboxylic acid amide (Reference Compound No. 4-1)

Under ice cooling, methanesulfonyl chloride (4.2 mL, 54 mmol) was added to a solution of N-(2-t-butoxycarbonylaminophenyl)-5-hydroxymethylpyridine-2-carboxylic acid amide (Reference Compound No. 3-1, 16 g, 45 mmol) and triethylamine (16 mL, 110 mmol) in dichloromethane (150 mL), and then the reaction mixture was stirred for 1 hour. Water (400 mL) was added thereto, and then the whole was extracted with ethyl acetate (500 mL) five times. The organic layer was washed with water (500 mL), dried over anhydrous magnesium sulfate, and then the solvent was evaporated under reduced pressure. The resulting solid was collected by filtration with hexane (80 mL) and ethyl acetate (20 mL) to give 18 g of the title reference compound as a white solid. (Yield 94%)

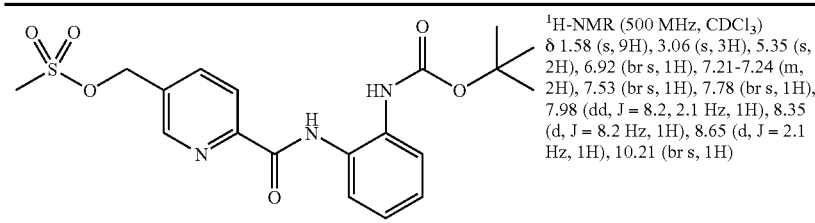

¹H-NMR (500 MHz, CDCl₃) δ 1.58 (s, 9H), 3.06 (s, 3H), 5.35 (s, 2H), 6.92 (br s, 1H), 7.21-7.24 (m, 2H), 7.53 (br s, 1H), 7.78 (br s, 1H), 7.98 (dd, J = 8.2, 2.1 Hz, 1H), 8.35 (d, J = 8.2 Hz, 1H), 8.65 (d, J = 2.1 Hz, 1H), 10.21 (br s, 1H)

Reference Example 5

N-(2-t-Butoxycarbonylaminophenyl)-5-(3-dimethylaminopropylaminomethyl)pyridine-2-carboxylic acid amide (Reference Compound No. 5-1)

N-(2-t-Butoxycarbonylaminophenyl)-5-methanesulfonyloxy methylpyridine-2-carboxylic acid amide (Reference Compound No. 4-1, 4.9 g, 12 mmol) was added to a suspension of N,N-dimethyl-1,3-propanediamine (3.0 mL, 24 mmol) and potassium carbonate (3.3 g, 24 mmol) in DMF (40 mL), and then the reaction mixture was stirred at room temperature for 6 hours. Saturated aqueous sodium hydrogen carbonate (100 mL) was added thereto, and then the whole was extracted with ethyl acetate (100 mL) twice. The organic layer was washed with water (100 mL) three times, dried over anhydrous magnesium sulfate, and then the solvent was evaporated under reduced pressure. The residue was purified by silica gel column chromatography (chloroform-methanol) to give 1.9 g of the title reference compound as a yellow amorphous product. (Yield 38%)

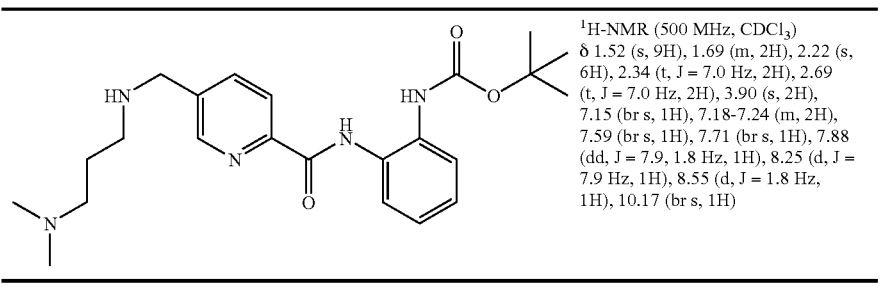

¹H-NMR (500 MHz, CDCl₃)
δ 1.52 (s, 9H), 1.69 (m, 2H), 2.22 (s, 6H), 2.34 (t, J = 7.0 Hz, 2H), 2.69 (t, J = 7.0 Hz, 2H), 3.90 (s, 2H), 7.15 (br s, 1H), 7.18-7.24 (m, 2H), 7.59 (br s, 1H), 7.71 (br s, 1H), 7.88 (dd, J = 7.9, 1.8 Hz, 1H), 8.25 (d, J = 7.9 Hz, 1H), 8.55 (d, J = 1.8 Hz, 1H), 10.17 (br s, 1H)

By using any compounds selected from Reference Compound No. 4-1 and commercially available compounds, the following Reference Compounds No. 5-2~5-19 were obtained by a method similar to that of Reference Compound No. 5-1. Additionally, by using any compounds selected from Reference Compound No. 11-1 and commercially available compounds, the following Reference Compound No. 5-20 was obtained by a method similar to that of Reference Compounds No. 4-1 and No. 5-1.

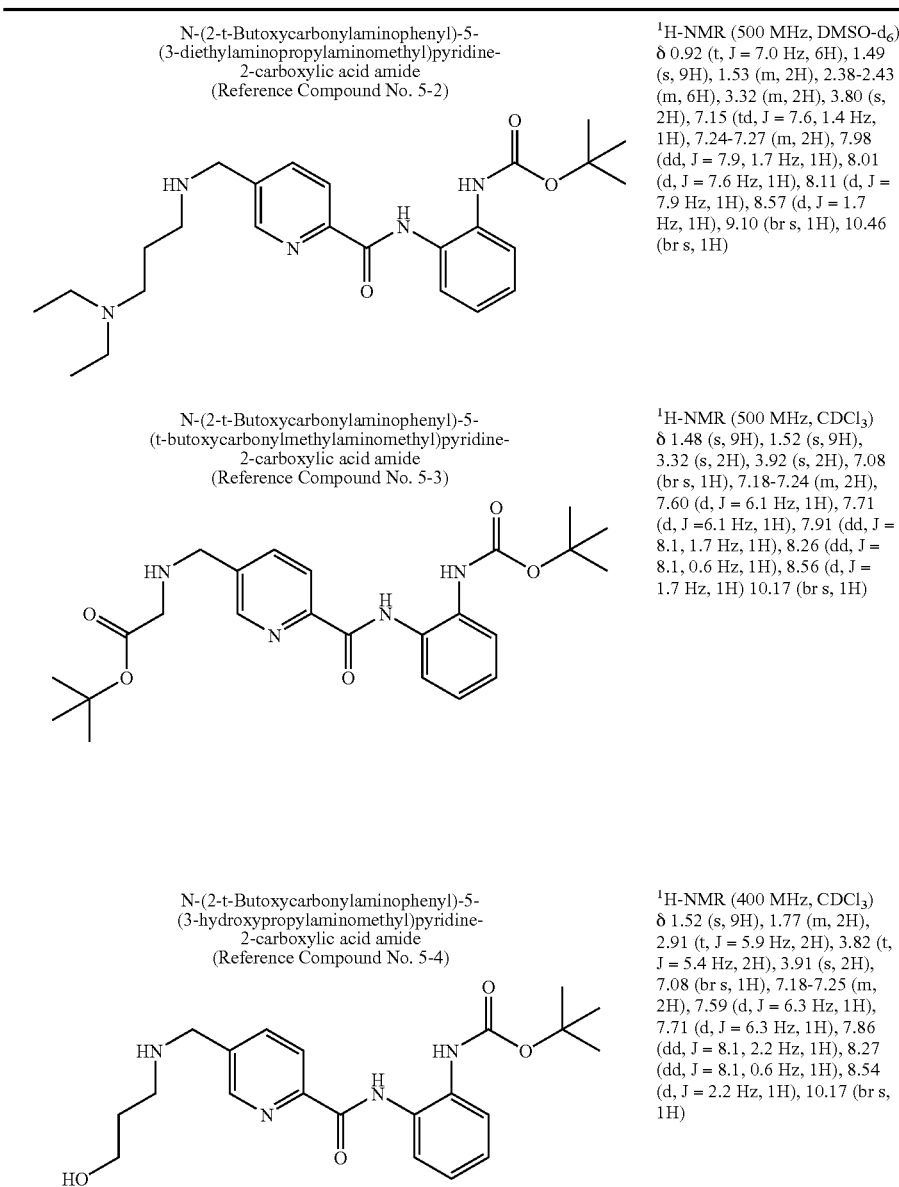

N-(2-t-Butoxycarbonylaminophenyl)-5-(3-diethylaminopropylaminomethyl)pyridine-2-carboxylic acid amide
(Reference Compound No. 5-2)

¹H-NMR (500 MHz, DMSO-d₆)
δ 0.92 (t, J = 7.0 Hz, 6H), 1.49 (s, 9H), 1.53 (m, 2H), 2.38-2.43 (m, 6H), 3.32 (m, 2H), 3.80 (s, 2H), 7.15 (td, J = 7.6, 1.4 Hz, 1H), 7.24-7.27 (m, 2H), 7.98 (dd, J = 7.9, 1.7 Hz, 1H), 8.01 (d, J = 7.6 Hz, 1H), 8.11 (d, J = 7.9 Hz, 1H), 8.57 (d, J = 1.7 Hz, 1H), 9.10 (br s, 1H), 10.46 (br s, 1H)

N-(2-t-Butoxycarbonylaminophenyl)-5-(t-butoxycarbonylmethylaminomethyl)pyridine-2-carboxylic acid amide
(Reference Compound No. 5-3)

¹H-NMR (500 MHz, CDCl₃)
δ 1.48 (s, 9H), 1.52 (s, 9H), 3.32 (s, 2H), 3.92 (s, 2H), 7.08 (br s, 1H), 7.18-7.24 (m, 2H), 7.60 (d, J = 6.1 Hz, 1H), 7.71 (d, J = 6.1 Hz, 1H), 7.91 (dd, J = 8.1, 1.7 Hz, 1H), 8.26 (dd, J = 8.1, 0.6 Hz, 1H), 8.56 (d, J = 1.7 Hz, 1H) 10.17 (br s, 1H)

N-(2-t-Butoxycarbonylaminophenyl)-5-(3-hydroxypropylaminomethyl)pyridine-2-carboxylic acid amide
(Reference Compound No. 5-4)

¹H-NMR (400 MHz, CDCl₃)
δ 1.52 (s, 9H), 1.77 (m, 2H), 2.91 (t, J = 5.9 Hz, 2H), 3.82 (t, J = 5.4 Hz, 2H), 3.91 (s, 2H), 7.08 (br s, 1H), 7.18-7.25 (m, 2H), 7.59 (d, J = 6.3 Hz, 1H), 7.71 (d, J = 6.3 Hz, 1H), 7.86 (dd, J = 8.1, 2.2 Hz, 1H), 8.27 (dd, J = 8.1, 0.6 Hz, 1H), 8.54 (d, J = 2.2 Hz, 1H), 10.17 (br s, 1H)

| Compound | NMR |
|---|---|
| N-(2-t-Butoxycarbonylaminophenyl)-5-(2-ethoxycarbonylethylaminomethyl)pyridine-2-carboxylic acid amide (Reference Compound No. 5-5) 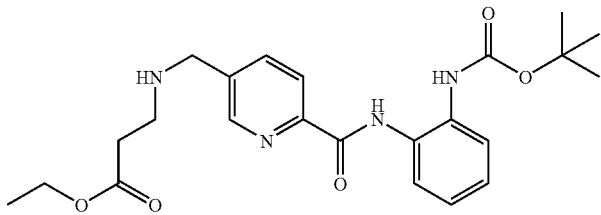 | $^1$H-NMR (400 MHz, DMSO-d$_6$) δ 1.18 (t, J = 7.1 Hz, 3H), 1.49 (s, 9H), 2.45 (t, J = 6.7 Hz, 2H), 2.72 (m, 2H), 3.83 (s, 2H), 4.05 (q, J = 7.1 Hz, 2H), 7.15 (td, J = 7.5, 1.7 Hz, 1H), 7.24-7.27 (m, 2H) 7.98 (dd, J = 8.1, 1.7 Hz, 1H), 8.02 (d, J = 7.5 Hz, 1H), 8.12 (d, J = 8.1 Hz, 1H), 8.57 (d, d = 1.7 Hz, 1H), 9.11 (br s, 1H), 10.47 (br s, 1H) |
| N-(2-t-Butoxycarbonylaminophenyl)-5-(2-hydroxyethylaminomethyl)pyridine-2-carboxylic acid amide (Reference Compound No. 5-6) 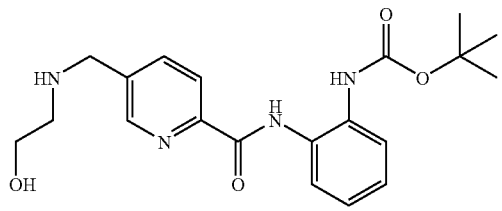 | $^1$H-NMR (400 MHz, CDCl$_3$) δ 1.51 (s, 9H), 2.83 (m, 2H), 3.70 (m, 2H), 3.93 (s, 2H), 7.14 (br s, 1H), 7.18-7.24 (m, 2H), 7.58 (d, J = 6.6 Hz, 1H), 7.72 (d, J = 6.1 Hz, 1H), 7.87 (dd, J = 8.1, 2.2 Hz, 1H), 8.24 (dd, J = 8.1, 0.7 Hz ,1H), 8.54 (dd, J = 2.2, 0.7 Hz, 1H), 10.18 (br s, 1H) |
| N-(2-t-Butoxycarbonylaminophenyl)-5-(2-dimethylaminoethylaminomethyl)pyridine-2-carboxylic acid amide (Reference Compound No. 5-7) 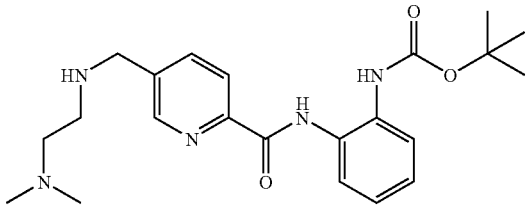 | $^1$H-NMR (400 MHz, CDCl$_3$) δ 1.51 (s, 9H), 1.94 (s, 1H), 2.23 (s, 6H), 2.44 (t, J = 5.9 Hz, 2H), 2.66 (t, J = 5.9 Hz, 2H), 3.91 (s, 2H), 7.15 (br s, 1H), 7.16-7.22 (m, 2H), 7.58 (s, 1H), 7.70 (s, 1H), 7.89 (dd, J = 7.8, 2.1 Hz, 1H), 8.24 (d, J = 7.8 Hz, 1H), 8.55 (d, J = 2.1 Hz, 1H), 10.17 (s, 1H) |
| N-(2-t-Butoxycarbonylaminophenyl)-5-[3-(pyrrolidin-1-yl)propylaminomethyl]pyridine-2-carboxylic acid amide (Reference Compound No. 5-8) 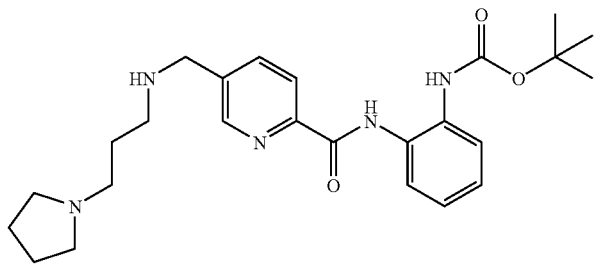 | $^1$H-NMR (500 MHz, CDCl$_3$) δ 1.52 (s, 9H), 1.72-1.80 (m, 6H), 2.48-2.55 (m, 6H), 2.70 (t, J = 6.9 Hz, 2H), 3.90 (s, 2H), 7.18-7.27 (m, 3H), 7.59 (br s, 1H), 7.71 (br s, 1H), 7.88 (dd, J = 7.9, 1.8 Hz, 1H), 8.25 (d, J= 7.9 Hz, 1H), 8.54 (d, J = 1.8 Hz, 1H), 10.17 (br s, 1H) |

| | |
|---|---|
| N-(2-t-Butoxycarbonylaminophenyl)-5-(2-t-butoxycarbonylethylaminomethyl)pyridine-2-carboxylic acid amide (Reference Compound No. 5-9) 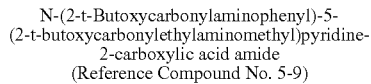 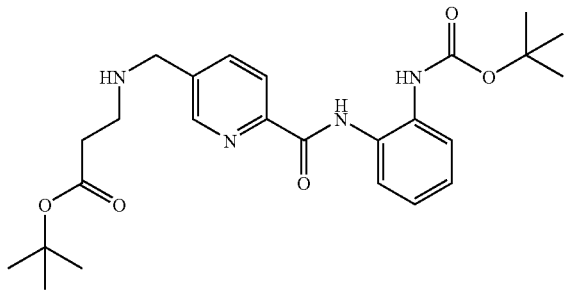 | $^1$H-NMR (500 MHz, CDCl$_3$) δ 1.46 (s, 9H), 1.52 (s, 9H), 2.46 (t, J = 6.4 Hz, 2H), 2.86 (t, J = 6.4 Hz, 2H), 3.92 (s, 2H), 7.09 (br s, 1H), 7.18-7.24 (m, 2H), 7.61 (d, J = 6.1 Hz, 1H), 7.70 (d, J = 6.1 Hz, 1H), 7.89 (dd, J = 7.9, 1.8 Hz, 1H), 8.26 (dd, J = 7.9, 0.6 Hz, 1H), 8.56 (d, J = 1.8 Hz, 1H), 10.16 (br s, 1H) |
| N-(2-t-Butoxycarbonylaminophenyl)-5-[3-(morpholin-4-yl)propylaminomethyl)]pyridine-2-carboxylic acid amide (Reference Compound No. 5-10) 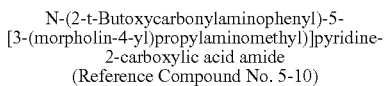 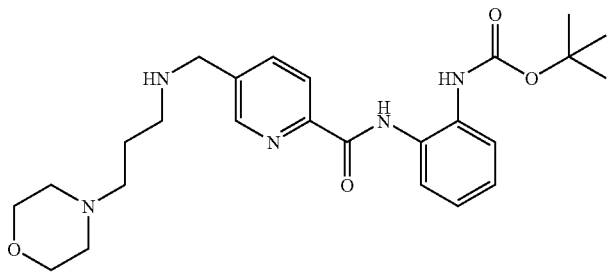 | $^1$H-NMR (400 MHz, CDCl$_3$) δ 1.52 (s, 9H), 1.72 (m, 2H), 2.40-2.44 (m, 6H), 2.70 (t, J = 6.8 Hz, 2H), 3.70 (m, 4H), 3.91 (s, 2H), 7.11 (br s, 1H), 7.18-7.25 (m, 2H), 7.59 (br s, 1H), 7.71 (br s, 1H), 7.88 (dd, J = 8.1, 2.2 Hz, 1H), 8.26 (dd J = 8.1, 0.7 Hz, 1H), 8.55 (dd, J = 2.2, 0.7 Hz, 1H), 10.17 (br s, 1H) |
| N-(2-t-Butoxycarbonylaminophenyl)-5-[2-(4-methylpiperazin-1-yl)ethylaminomethyl]pyridine-2-carboxylic acid amide (Reference Compound No. 5-11) 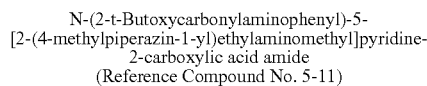 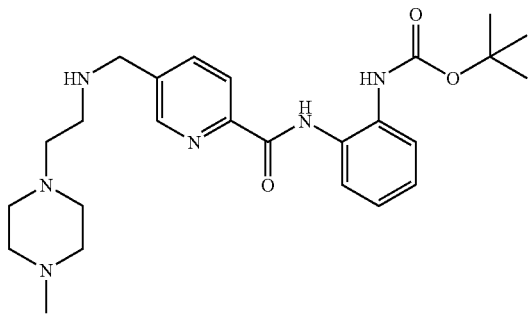 | $^1$H-NMR (400 MHz, CDCl$_3$) δ 1.52 (s, 9H), 2.29 (s, 3H), 2.46 (br s, 8H), 2.52 (t, J = 6.0 Hz, 2H), 2.71 (t, J = 6.0 Hz, 2H), 3.92 (s, 2H), 7.09 (br s, 1H), 7.17-7.25 (m, 2H), 7.60 (d, J = 7.3 Hz, 1H), 7.70 (d, J = 7.1 Hz, 1H), 7.89 (dd, J = 7.9, 2.2 Hz, 1H), 8.26 (d, J = 7.9 Hz, 1H), 8.55 (d, J = 2.2 Hz, 1H), 10.16 (s, 1H) |
| N-(2-t-Butoxycarbonylaminophenyl)-5-([3-(4-methylpiperazin-1-yl)propylaminomethyl]pyridine-2-carboxylic acid amide (Reference Compound No. 5-12) 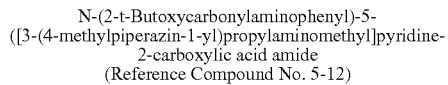 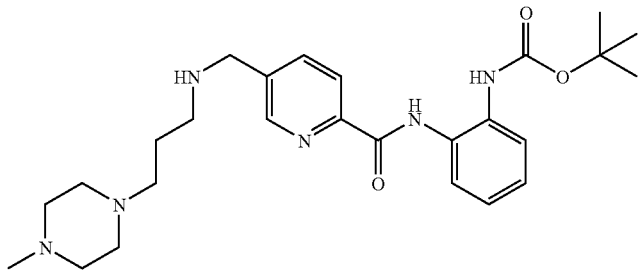 | $^1$H-NMR (400 MHz, CDCl$_3$) δ 1.52 (s, 9H), 1.72 (m, 2H), 2.28 (s, 3H), 2.43 (t, J = 6.9 Hz, 2H), 2.46 (br s, 8H), 2.69 (t, J = 6.9 Hz, 2H), 3.90 (s, 2H), 7.09 (br s, 1H), 7.17-7.25 (m, 2H), 7.60 (d, J = 6.6 Hz, 1H), 7.70 (d, J = 6.6 Hz, 1H), 7.88 (dd, J = 7.9, 2.0 Hz, 1H), 8.26 (d, J = 7.9 Hz, 1H), 8.55 (d, J = 2.0 Hz, 1H), 10.16 (s, 1H) |

| | |
|---|---|
| N-(2-t-Butoxycarbonylaminophenyl)-5-[4-(pyrrolidin-1-yl)butylaminomethyl]pyridine-2-carboxylic acid amide (Reference Compound No. 5-13)<br>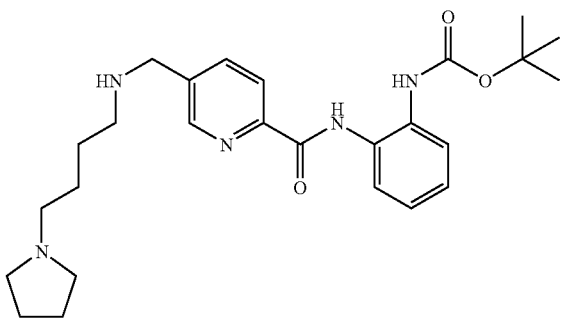 | $^1$H-NMR (500 MHz, CDCl$_3$) δ 1.52 (s, 9H), 1.55-1.65 (m, 4H), 1.80-1.86 (m, 4H), 2.54 (t, J = 7.4 Hz, 2H), 2.59-2.64 (m, 4H), 2.67 (t, J = 6.8 Hz, 2H), 3.90 (s, 2H), 7.13 (br s, 1H), 7.18-7.25 (m, 2H), 7.59 (d, J = 5.5 Hz, 1H), 7.71 (d, J = 6.1 Hz, 1H), 7.90 (dd, J = 7.9, 1.8 Hz, 1H), 8.25 (d, J = 7.9 Hz, 1H), 8.55 (d, J = 1.8 Hz, 1H), 10.17 (s, 1H) |
| N-(2-t-Butoxycarbonylaminophenyl)-5-(2-diethylaminoethylaminomethyl)pyridine-2-carboxylic acid amide (Reference Compound No. 5-14)<br>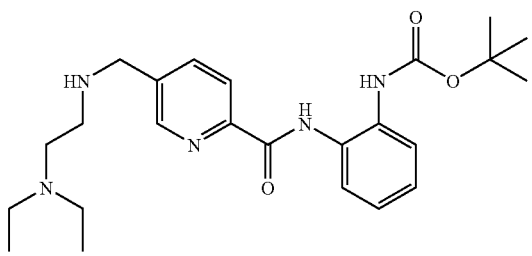 | $^1$H-NMR (400 MHz, CDCl$_3$) δ 1.01 (t, J = 7.2 Hz, 6H), 1.52 (s, 9H), 2.52 (q, J = 7.2 Hz, 4H), 2.58 (t, J = 5.7 Hz, 2H), 2.68 (t, J = 5.7 Hz, 2H), 3.92 (s, 2H), 7.09 (br s, 1H), 7.18-7.23 (m, 2H), 7.60 (d, J = 6.6 Hz, 1H), 7.70 (d, J = 6.3 Hz, 1H), 7.89 (dd, J = 8.1, 2.2 Hz, 1H), 8.26 (dd, J = 8.1, 0.6 Hz, 1H), 8.56 (dd, J = 2.2, 0.6 Hz, 1H), 10.17 (s, 1H) |
| N-(2-t-Butoxycarbonylaminophenyl)-5-(4-dimethylaminobutylaminomethyl)pyridine-2-carboxylic acid amide (Reference Compound No. 5-15)<br>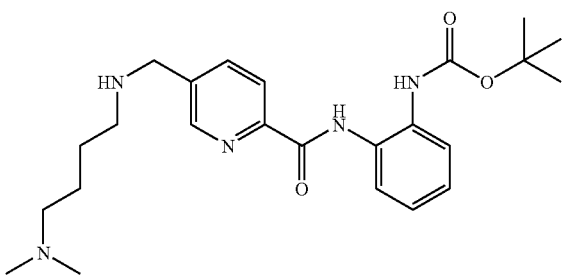 | $^1$H-NMR (400 MHz, CDCl$_3$) δ 1.52 (s, 9H), 1.63-1.69 (m, 4H), 2.36 (s, 6H), 2.51 (m, 2H), 2.71 (t, J = 6.5 Hz, 2H), 3.94 (s, 2H), 7.10 (br s, 1H), 7.18-7.25 (m, 2H), 7.60 (m, 1H), 7.71 (m, 1H), 7.97 (dd, J = 7.9, 2.2 Hz, 1H), 8.27 (dd, J = 7.9, 1.1 Hz, 1H), 8.59 (d, J = 2.2, 1.1 Hz, 1H), 10.17 (s, 1H) |
| N-(2-t-Butoxycarbonylaminophenyl)-5-[4-(morpholin-4-yl)butylaminomethyl]pyridine-2-carboxylic acid amide (Reference Compound No. 5-16)<br>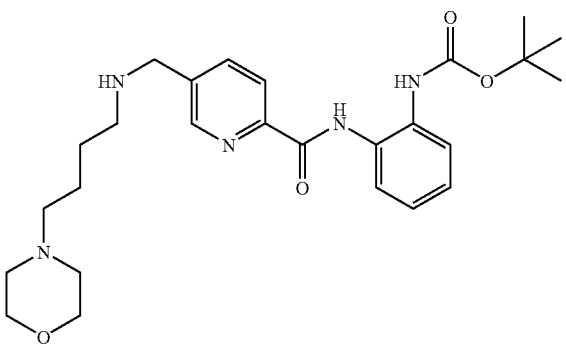 | $^1$H-NMR (500 MHz, CDCl$_3$) δ 1.52 (s, 9H), 1.54-1.60 (m, 4H), 2.35 (t, J = 7.0 Hz, 2H), 2.43 (br s, 4H), 2.66 (t, J = 6.7 Hz, 2H), 3.71 (t, J = 4.7 Hz, 4H), 3.91 (s, 2H), 7.08 (br s, 1H), 7.18-7.24 (m, 2H), 7.60 (d, J = 6.3 Hz, 1H), 7.70 (d, J = 6.3 Hz, 1H), 7.89 (dd, J = 7.9, 2.1 Hz, 1H), 8.26 (d, J = 7.9 Hz, 1H), 8.56 (d, J = 1.5 Hz, 1H), 10.16 (s, 1H) |

N-(2-t-Butoxycarbonylaminophenyl)-5-(5-dimethylaminopentylaminomethyl)pyridine-2-carboxylic acid amide
(Reference Compound No. 5-17)

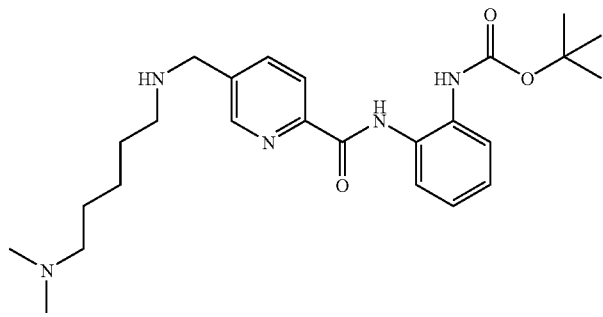

$^1$H-NMR (400 MHz, CDCl$_3$)
δ 1.38 (m, 2H), 1.52 (s, 9H), 1.52-1.59 (m, 4H), 2.31 (s, 6H), 2.37 (t, J = 7.6 Hz, 2H), 2.65 (t, J = 7.1 Hz, 2H), 3.90 (s, 2H), 7.11 (br s, 1H), 7.17-7.24 (m, 2H), 7.60 (d, J = 5.8 Hz, 1H), 7.70 (d, J = 5.8 Hz, 1H), 7.89 (dd, J = 7.9, 2.1 Hz, 1H), 8.26 (dd, J = 7.9, 0.7 Hz, 1H), 8.56 (dd, J = 2.1, 0.7 Hz, 1H), 10.17 (s, 1H)

N-(2-t-Butoxycarbonylaminophenyl)-5-[3-(4-methylpiperidin-1-yl)propylaminomethyl]pyridine-2-carboxylic acid amide
(Reference Compound No. 5-18)

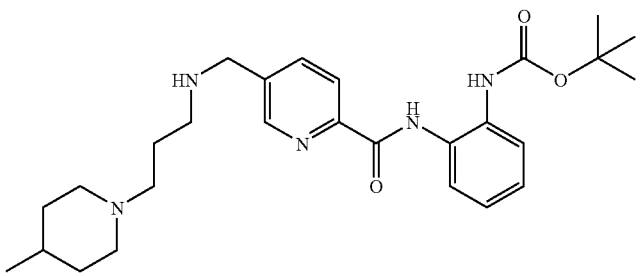

$^1$H-NMR (500 MHz, CDCl$_3$)
δ 0.91 (d, J = 6.4 Hz, 3H), 1.21 (m, 2H), 1.35 (m, 1H), 1.52 (s, 9H), 1.62 (m, 2H), 1.73 (m, 2H), 1.89 (m, 2H), 2.39 (t, J = 7.3 Hz, 2H), 2.68 (t, J = 6.7 Hz, 2H), 2.90 (d, J = 11.6 Hz, 2H), 3.90 (s, 2H), 7.10 (br s, 1H), 7.18-7.24 (m, 2H), 7.61 (d, J = 6.1 Hz, 1H), 7.70 (d, J = 6.4 Hz, 1H), 7.88 (dd, J = 7.9, 2.1 Hz, 1H), 8.26 (d, J = 7.9 Hz, 1H), 8.55 (d, J = 2.1 Hz, 1H), 10.16 (s, 1H)

N-(2-t-Butoxycarbonylaminophenyl)-5-[5-(morpholin-4-yl)pentylaminomethyl]pyridine-2-carboxylic acid amide
(Reference Compound No. 5-19)

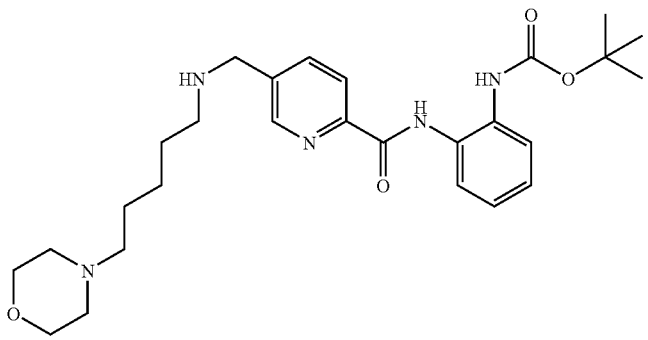

$^1$H-NMR (400 MHz, CDCl$_3$)
δ 1.36 (m, 2H), 1.47-1.56 (m, 4H), 1.52 (s, 9H), 2.33 (t, J = 7.5 Hz, 2H), 2.43 (br s, 4H), 2.64 (t, J = 7.1 Hz, 2H), 3.71 (t, J = 4.8 Hz, 4H), 3.90 (s, 2H), 7.09 (br s, 1H), 7.18-7.25 (m, 2H), 7.60 (d, J = 6.6 Hz, 1H), 7.71 (d, J = 6.3 Hz, 1H), 7.88 (dd, J = 8.1, 2.2 Hz, 1H), 8.26 (d, J = 8.1 Hz, 1H), 8.55 (d, J = 2.2 Hz, 1H), 10.17 (s, 1H)

N-(2-t-Butoxycarbonylaminophenyl)-6-(2-dimethylaminoethylaminomethyl)pyridine-3-carboxylic acid amide
(Reference Compound No. 5-20)

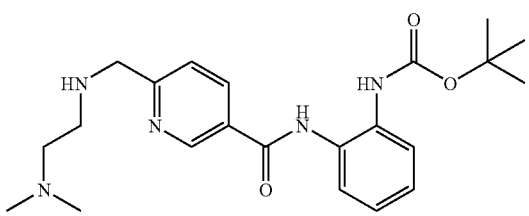

$^1$H-NMR (400 MHz, CDCl$_3$)
δ 1.52 (s, 9H), 2.23 (s, 6H), 2.35 (t, J = 6.2 Hz, 2H), 2.76 (m, 2H), 4.01 (s, 2H), 7.02 (s, 1H), 7.18 (td, J = 7.8, 1.5 Hz, 1H), 7.22-7.25 (m, 2H), 7.44 (d, J = 8.2 Hz, 1H), 7.82 (d, J = 7.8 Hz, 1H), 8.20 (dd, J = 8.2, 2.1 Hz, 1H), 9.12 (d, J = 2.1 Hz, 1H), 9.51 (s, 1H)

Reference Example 6

N-(2-t-Butoxycarbonylaminophenyl)-5-[1-(3-dimethylaminopropyl)-3-phenethylureidomethyl]pyridine-2-carboxylic acid amide (Reference Compound No. 6-1)

Phenethylisocyanate (15 μL, 0.11 mmol) was added to a solution of N-(2-t-butoxycarbonylaminophenyl)-5-(3-dimethylaminopropylaminomethyl)pyridine-2-carboxylic acid amide (Reference Compound No. 5-1, 27 mg, 0.060 mmol) in dichloromethane (1.0 mL), and then the mixture was stirred at room temperature for 2 hours. The reaction mixture was concentrated, and then the residue was purified by silica gel column chromatography (chloroform-methanol) to give 32 mg of the title reference compound as a colorless amorphous product. (Yield 88%)

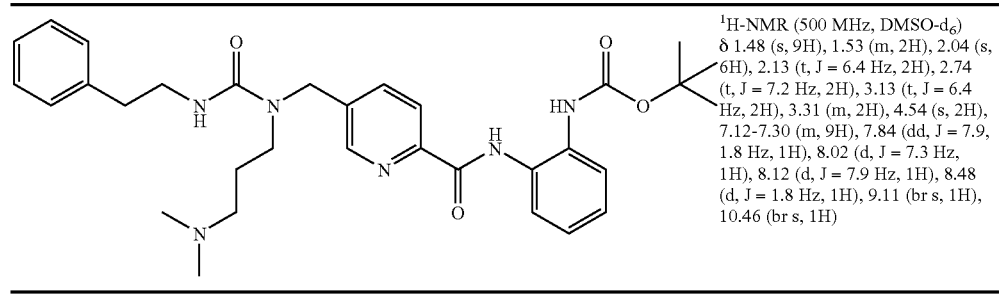

$^1$H-NMR (500 MHz, DMSO-$d_6$)
δ 1.48 (s, 9H), 1.53 (m, 2H), 2.04 (s, 6H), 2.13 (t, J = 6.4 Hz, 2H), 2.74 (t, J = 7.2 Hz, 2H), 3.13 (t, J = 6.4 Hz, 2H), 3.31 (m, 2H), 4.54 (s, 2H), 7.12-7.30 (m, 9H), 7.84 (dd, J = 7.9, 1.8 Hz, 1H), 8.02 (d, J = 7.3 Hz, 1H), 8.12 (d, J = 7.9 Hz, 1H), 8.48 (d, J = 1.8 Hz, 1H), 9.11 (br s, 1H), 10.46 (br s, 1H)

By using any compounds selected from Reference Compounds No. 5-1~5-20, commercially available compounds, and known compounds, the following Reference Compounds No. 6-2~6-141 were obtained by a method similar to that of Reference Compound No. 6-1.

N-(2-t-Butoxycarbonylaminophenyl)-5-[3-(2,3-dihydrobenzo[1,4]dioxin-6-yl)-1-(3-dimethylaminopropyl)ureidomethyl]pyridine-2-carboxylic acid amide (Reference Compound No. 6-2)

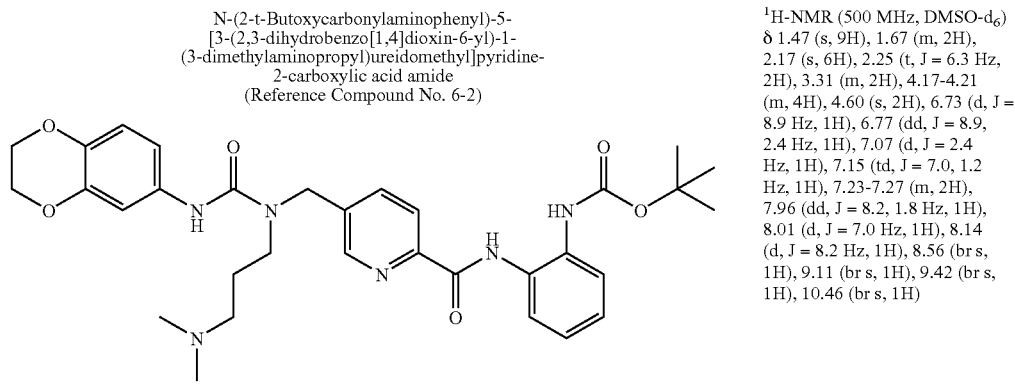

$^1$H-NMR (500 MHz, DMSO-$d_6$)
δ 1.47 (s, 9H), 1.67 (m, 2H), 2.17 (s, 6H), 2.25 (t, J = 6.3 Hz, 2H), 3.31 (m, 2H), 4.17-4.21 (m, 4H), 4.60 (s, 2H), 6.73 (d, J = 8.9 Hz, 1H), 6.77 (dd, J = 8.9, 2.4 Hz, 1H), 7.07 (d, J = 2.4 Hz, 1H), 7.15 (td, J = 7.0, 1.2 Hz, 1H), 7.23-7.27 (m, 2H), 7.96 (dd, J = 8.2, 1.8 Hz, 1H), 8.01 (d, J = 7.0 Hz, 1H), 8.14 (d, J = 8.2 Hz, 1H), 8.56 (br s, 1H), 9.11 (br s, 1H), 9.42 (br s, 1H), 10.46 (br s, 1H)

| | |
|---|---|
| N-(2-t-Butoxycarbonylaminophenyl)-5-[3-(3,4-difluorophenyl)-1-(3-dimethylaminopropyl)ureidomethyl]pyridine-2-carboxylic acid amide (Reference Compound No. 6-3)<br>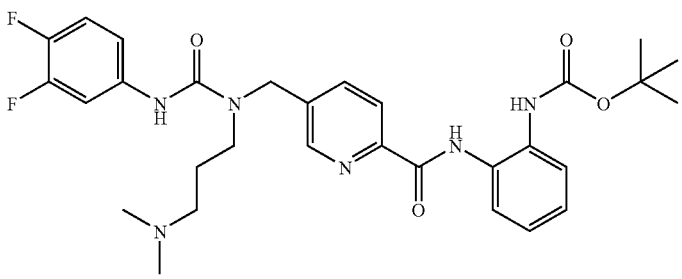 | $^1$H-NMR (500 MHz, DMSO-d$_6$) δ 1.47 (s, 9H), 1.70 (m, 2H), 2.19 (s, 6H), 2.26 (t, J = 6.3 Hz, 2H), 3.35 (m, 2H), 4.63 (s, 2H), 7.07 (m, 1H), 7.15 (td, J = 7.3, 1.5 Hz, 1H), 7.23-7.27 (m, 2H), 7.34 (dd, J = 19.7, 9.3 Hz, 1H), 7.68 (ddd, J = 13.7, 7.6, 2.4 Hz, 1H), 7.98 (dd, J = 7.9, 1.8 Hz, 1H), 8.01 (d, J = 7.3 Hz, 1H), 8.14 (d, J = 7.9 Hz, 1H), 8.58 (d, J = 1.8 Hz, 1H), 9.12 (br s, 1H), 9.43 (br s, 1H), 10.02 (br s, 1H) |
| 5-[3-(Benzo[1,3]dioxol-5-yl)-1-(3-dimethylaminopropyl)ureidomethyl]-N-(2-t-butoxycarbonylaminophenyl)pyridine-2-carboxylic acid amide (Reference Compound No. 6-4)<br>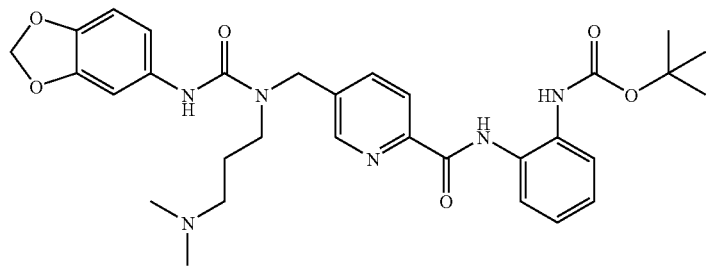 | $^1$H-NMR (500 MHz, DMSO-d$_6$) δ 1.47 (s, 9H), 1.68 (m, 2H), 2.18 (s, 6H), 2.25 (t, J = 6.3 Hz, 2H), 3.32 (m, 2H), 4.63 (s, 2H), 5.95 (s, 2H), 6.72 (dd, J = 8.2, 2.1 Hz, 1H), 6.80 (d, J = 8.2 Hz, 1H), 7.15 (td, J = 7.6, 1.5 Hz, 1H), 7.18 (d, J = 2.1 Hz, 1H), 7.23-7.27 (m, 2H), 7.97 (dd, J = 7.9, 1.8 Hz, 1H), 8.01 (d, J = 7.6 Hz, 1H), 8.14 (d, J = 7.9 Hz, 1H), 8.57 (d, J = 1.8 Hz, 1H), 9.11 (br s, 1H), 9.51 (br s, 1H), 10.47 (br s, 1H) |
| N-(2-t-Butoxycarbonylaminophenyl)-5-[1-(3-dimethylaminopropyl)-3-(4-methoxyphenyl)ureidomethyl]pyridine-2-carboxylic acid amide (Reference Compound No. 6-5)<br>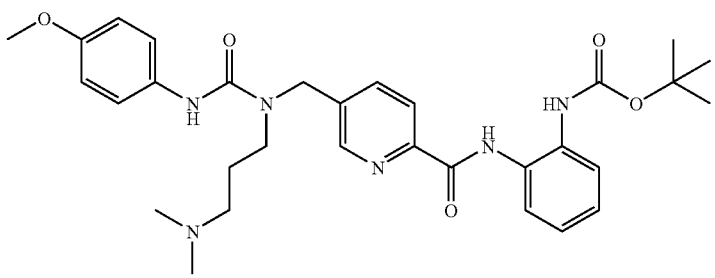 | $^1$H-NMR (400 MHz, DMSO-d$_6$) δ 1.47 (s, 9H), 1.68 (m, 2H), 2.18 (s, 6H), 2.26 (t, J = 6.3 Hz, 2H), 3.33 (m, 2H), 3.70 (s, 3H), 4.62 (s, 2H), 6.80 (d, J = 9.0 Hz, 2H), 7.15 (td, J = 8.3, 1.5 Hz, 1H), 7.23-7.27 (m, 2H), 7.33 (d, J = 9.0 Hz, 2H), 7.97 (dd, J = 8.1, 1.8 Hz, 1H), 8.01 (d, J = 8.3 Hz, 1H), 8.14 (d, J = 8.1 Hz, 1H), 8.57 (d, J = 1.8 Hz, 1H), 9.12 (br s, 1H), 9.42 (br s, 1H), 10.47 (br s, 1H) |
| 5-[3-(Benzo[1,3]dioxol-5-yl)-1-(3-diethylaminopropyl)ureidomethyl]-N-(2-t-butoxycarbonylaminophenyl)pyridine-2-carboxylic acid amide (Reference Compound No. 6-6)<br>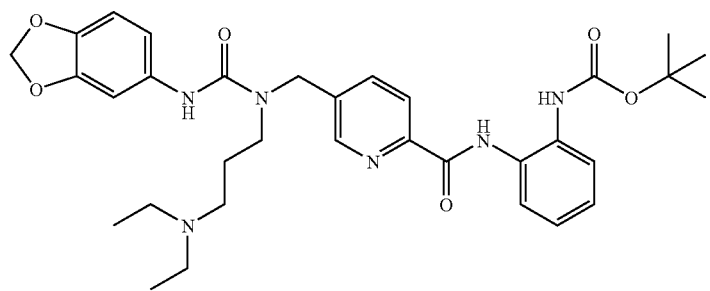 | $^1$H-NMR (500 MHz, CDCl$_3$) δ 1.02 (t, J = 7.2 Hz, 6H), 1.51 (s, 9H), 1.74 (m, 2H), 2.51 (t, J = 6.0 Hz, 2H), 2.62 (q, J = 7.2 Hz, 4H), 3.37 (t, J = 5.7 Hz, 2H), 4.61 (s, 2H), 5.92 (s, 2H), 6.71-6.72 (m, 2H), 7.06 (br s, 1H), 7.14 (s, 1H), 7.17-7.24 (m, 2H), 7.60 (d, J = 7.2 Hz, 1H), 7.69 (d, J = 7.2 Hz, 1H), 7.93 (dd, J = 7.9, 2.0 Hz, 1H), 8.25 (d, J = 7.9 Hz, 1H), 8.58 (d, J = 2.0 Hz, 1H), 9.69 (s, 1H), 10.15 (s, 1H) |

N-(2-t-Butoxycarbonylaminophenyl)-5-
[1-(3-dimethylaminopropyl)-3-
(2-fluorophenyl)ureidomethyl]pyridine-
2-carboxylic acid amide
(Reference Compound No. 6-7)

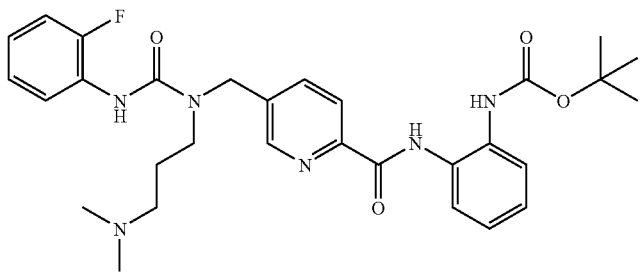

¹H-NMR (500 MHz, DMSO-d₆)
δ 1.47 (s, 9H), 1.75 (m, 2H),
2.16 (s, 6H), 2.28 (t, J = 6.1 Hz,
2H), 3.36 (t, J = 5.6 Hz, 2H),
4.63 (s, 2H), 7.04 (m, 1H), 7.11
(m, 1H), 7.14-7.21 (m, 2H),
7.24 (d, J = 7.7 Hz, 1H), 7.26
(m, 1H), 7.88 (t, d = 7.7 Hz,
1H), 7.99 (dd, J = 7.7, 1.5 Hz,
1H), 8.02 (d, J = 7.1 Hz, 1H),
8.14 (d, J = 7.7 Hz, 1H), 8.59
(d, J = 1.5 Hz, 1H), 9.10 (s,
1H), 9.87 (s, 1H), 10.47 (s, 1H)

N-(2-t-Butoxycarbonylaminophenyl)-5-
[1-(3-dimethylaminopropyl)-3-
(3-fluorophenyl)ureidomethyl]pyridine-
2-carboxylic acid amide
(Reference Compound No. 6-8)

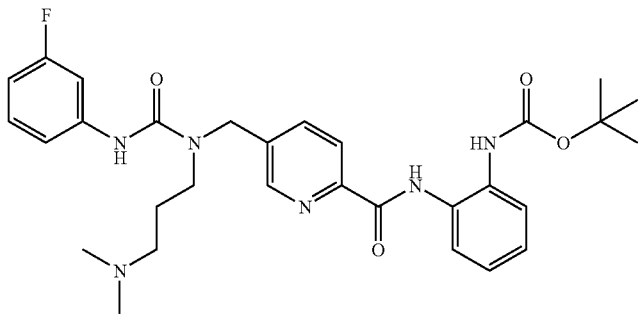

¹H-NMR (500 MHz, DMSO-d₆)
δ 1.46 (s, 9H), 1.71 (m, 2H),
2.20 (s, 6H), 2.28 (t, J = 6.3 Hz,
2H), 3.36 (t, J = 6.3 Hz, 2H),
4.63 (s, 2H), 6.75 (td, J = 8.2,
2.3 Hz, 1H), 7.07 (dd, J = 8.2,
1.2 Hz, 1H), 7.15 (td, J = 8.2,
1.5 Hz, 1H), 7.23-7.30 (m, 3H),
7.49 (ddd, J = 12.2, 2.3, 1.5 Hz,
1H), 7.98 (dd, J = 8.2, 2.3 Hz,
1H), 8.02 (d, J = 8.2 Hz, 1H),
8.14 (d, J = 8.2 Hz, 1H), 8.59
(d, J = 2.3 Hz, 1H), 9.11 (s,
1H), 10.00 (s, 1H), 10.47 (s, 1H)

N-(2-t-Butoxycarbonylaminophenyl)-5-
[3-(2,5-difluorophenyl)-1-
(3-dimethylaminopropyl)ureidomethyl]pyridine-
2-carboxylic acid amide
(Reference Compound No. 6-9)

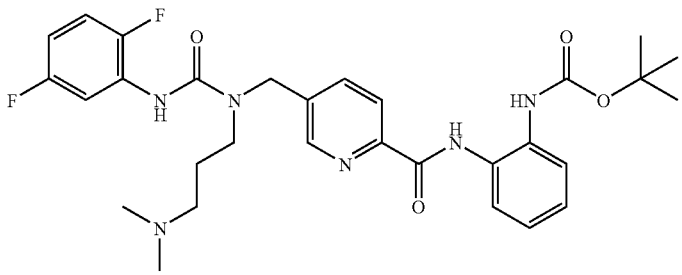

¹H-NMR (500 MHz, DMSO-d₆)
δ 1.46 (s, 9H), 1.75 (m, 2H),
2.15 (s, 6H), 2.28 (t, J = 6.1 Hz,
2H), 3.43 (t, J = 6.1 Hz, 2H),
4.62 (s, 2H), 6.81 (m, 1H), 7.15
(td, J = 7.7, 1.5 Hz, 1H),
7.22-7.28 (m, 3H), 7.93 (m,
1H), 7.99-8.02 (m, 2H), 8.14
(dd, J = 7.7, 0.6 Hz, 1H), 8.60
(d, J = 1.5 Hz, 1H), 9.11 (s,
1H), 10.42 (s, 1H), 10.48 (s, 1H)

N-(2-t-Butoxycarbonylaminophenyl)-5-
[3-(3,5-difluorophenyl)-1-
(3-dimethylaminopropyl)ureidomethyl]pyridine-
2-carboxylic acid amide
(Reference Compound No. 6-10)

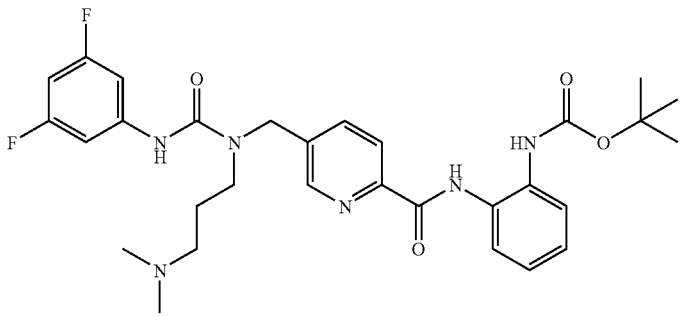

¹H-NMR (500 MHz, DMSO-d₆)
δ 1.47 (s, 9H), 1.71 (m, 2H),
2.20 (s, 6H), 2.27 (t, J = 6.4 Hz,
2H), 3.36 (t, J = 6.1 Hz, 2H),
4.64 (s, 2H), 6.76 (tt, J = 9.2,
2.2 Hz, 1H), 7.14-7.17 (m, 3H),
7.23-7.27 (m, 2H), 7.98 (dd, J =
7.9, 2.2 Hz, 1H), 8.01 (d, J =
7.9 Hz, 1H), 8.14 (d, J = 7.9
Hz, 1H), 8.58 (s, 1H), 9.11 (s,
1H), 10.13 (s, 1H), 10.47 (s, 1H)

N-(2-t-Butoxycarbonylaminophenyl)-5-
[1-(3-dimethylaminopropyl)-3-
(3-fluoro-4-methylphenyl)ureidomethyl]pyridine-
2-carboxylic acid amide
(Reference Compound No. 6-11)

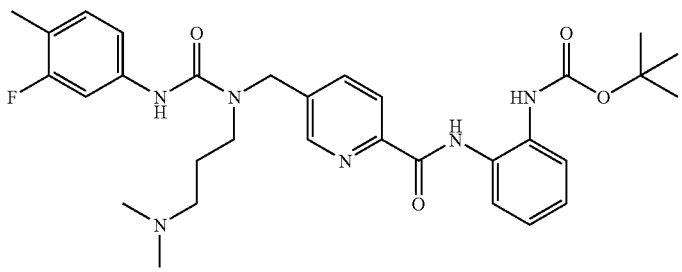

$^1$H-NMR (500 MHz, DMSO-$d_6$)
δ 1.47 (s, 9H), 1.70 (m, 2H),
2.15 (s, 3H), 2.20 (s, 6H), 2.26
(t, J = 6.4 Hz, 2H), 3.35 (t, J =
6.1 Hz, 2H), 4.62 (s, 2H), 6.98
(dd, J = 8.1, 2.1 Hz, 1H),
7.11-7.17 (m, 2H), 7.23-7.27
(m, 2H), 7.43 (dd, J = 12.8, 2.1
Hz, 1H), 7.98 (dd, J = 8.1, 2.1
Hz, 1H), 8.01 (d, J = 8.1 Hz,
1H), 8.14 (d, J = 8.1 Hz, 1H),
8.58 (d, J = 2.1 Hz, 1H), 9.11
(s, 1H), 9.82 (s, 1H), 10.47 (s, 1H)

N-(2-t-Butoxycarbonylaminophenyl)-5-
[1-(3-dimethylaminopropyl)-3-
(4-fluoro-3-methylphenyl)ureidomethyl]pyridine-
2-carboxylic acid amide
(Reference Compound No. 6-12)

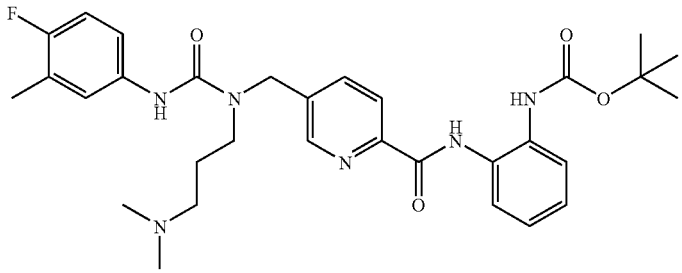

$^1$H-NMR (500 MHz, DMSO-$d_6$)
δ 1.47 (s, 9H), 1.69 (m, 2H),
2.18 (s, 6H), 2.20 (s, 3H), 2.26
(t, J = 6.4 Hz, 2H), 3.35 (t, J =
6.1 Hz, 2H), 4.62 (s, 2H), 7.01
(t, J = 9.2 Hz, 1H), 7.15 (td, J =
7.7, 1.5, 1H), 7.20-7.28 (m,
3H), 7.34 (dd, J = 7.0, 2.4 Hz,
1H), 7.97 (dd, J = 8.1, 2.0 Hz,
1H), 8.01 (d, J = 7.0 Hz, 1H),
8.14 (d, J = 8.1 Hz, 1H), 8.57
(s, 1H), 9.11 (s, 1H), 9.55 (s,
1H), 10.47 (s, 1H)

N-(2-t-Butoxycarbonylaminophenyl)-5-
[1-(t-butoxycarbonylmethyl)-3-
(4-dimethylaminophenyl)ureidomethyl]pyridine-
2-carboxylic acid amide
(Reference Compound No. 6-13)

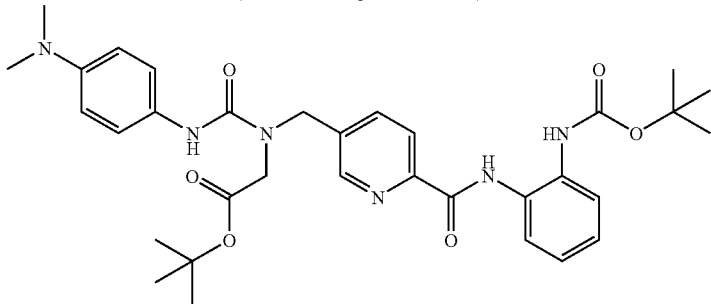

$^1$H-NMR (400 MHz, DMSO-$d_6$)
δ 1.34 (s, 9H), 1.48 (s, 9H),
2.82 (s, 6H), 4.11 (s, 2H), 4.70
(s, 2H), 6.66 (d, J = 9.3 Hz,
2H), 7.13-7.27 (m, 5H), 7.99
(dd, J = 8.1, 2.0 Hz, 1H), 8.01
(m, 1H), 8.13 (d, J = 8.1 Hz,
1H), 8.30 (br s, 1H), 8.60 (d, J =
2.0 Hz, 1H), 9.11 (br s, 1H),
10.48 (br s, 1H)

5-[3-(Benzo[1,3]dioxol-5-yl)-1-
(2-t-butoxycarbonylethyl)ureidomethyl]-N-
(2-t-butoxycarbonylaminophenyl)pyridine-
2-carboxylic acid amide
(Reference Compound No. 6-14)

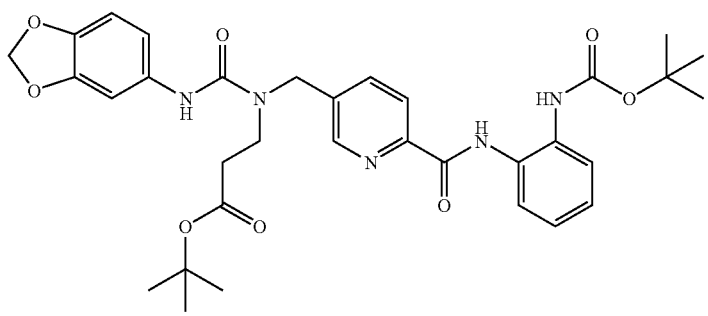

$^1$H-NMR (500 MHz, DMSO-$d_6$)
δ 1.38 (s, 9H), 1.47 (s, 9H),
2.52 (m, 2H), 3.55 (t, J = 7.0
Hz, 2H), 4.70 (s, 2H), 5.95 (s,
2H), 6.81 (m, 2H), 7.12 (m,
1H), 7.15 (td, J = 7.6, 1.5 Hz,
1H), 7.23-7.27 (m, 2H), 7.93
(dd, J = 8.2, 1.8 Hz, 1H), 8.01
(d, J = 7.6 Hz, 1H), 8.15 (d, J =
8.2 Hz, 1H), 8.47 (br s, 1H),
8.52 (d, J = 1.8 Hz, 1H), 9.12
(br s, 1H), 10.47 (br s, 1H)

| Compound | NMR |
|---|---|
| N-(2-t-Butoxycarbonylaminophenyl)-5-[1-(3-dimethylaminopropyl)-3-(indan-5-yl)ureidomethyl]pyridine-2-carboxylic acid amide (Reference Compound No. 6-15) 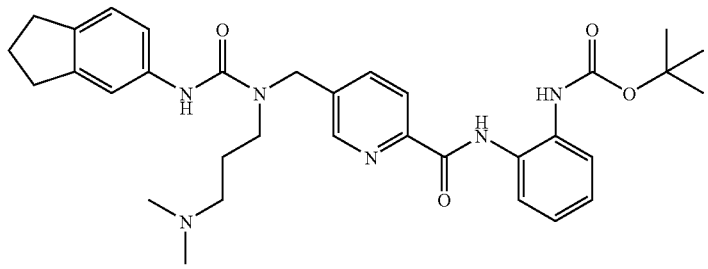 | $^1$H-NMR (400 MHz, DMSO-d$_6$) δ 1.47 (s, 9H), 1.69 (br s, 2H), 1.99 (m, 2H), 2.19 (s, 6H), 2.27 (t, J = 6.2 Hz, 2H), 2.76-2.83 (m, 4H), 3.36 (m, 2H), 4.61 (s, 2H), 7.08 (s, 1H), 7.09 (d, J = 7.6 Hz, 1H), 7.15 (td, J = 7.6, 1.6 Hz, 1H), 7.24 (d, J = 7.6 Hz, 1H), 7.25 (m, 1H), 7.37 (m, 1H), 7.97 (dd, J = 8.1, 1.8 Hz, 1H), 8.01 (d, J = 7.6 Hz, 1H), 8.14 (d, J = 8.1 Hz, 1H), 8.58 (d, J = 1.8 Hz, 1H), 9.13 (br s, 1H), 9.51 (br s, 1H), 10.47 (br s, 1H) |
| 5-[3-(Biphenyl-4-yl)-1-(3-dimethylaminopropyl)ureidomethyl]-N-(2-t-butoxycarbonylaminophenyl)pyridine-2-carboxylic acid amide (Reference Compound No. 6-16) 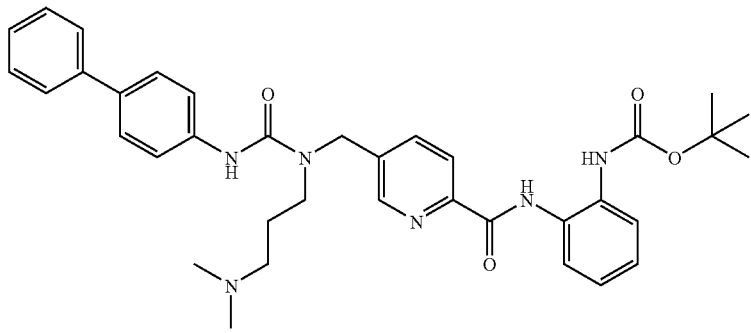 | $^1$H-NMR (500 MHz, DMSO-d$_6$) δ 1.47 (s, 9H), 1.72 (m, 2H), 2.23 (s, 6H), 2.29 (t, J = 6.3 Hz, 2H), 3.37 (t, J = 6.3 Hz, 2H), 4.65 (s, 2H), 7.15 (td, J = 7.6, 1.4 Hz, 1H), 7.25 (m, 1H), 7.31 (m, 1H), 7.43 (t, J = 7.6 Hz, 2H), 7.52-7.56 (m, 3H), 7.57-7.60 (m, 2H), 7.62-7.65 (m, 2H), 7.99-8.02 (m, 2H), 8.15 (d, J = 7.9 Hz, 1H), 8.60 (d, J = 1.7 Hz, 1H), 9.11 (br s, 1H), 9.84 (br s, 1H), 10.47 (br s, 1H) |
| N-(2-t-Butoxycarbonylaminophenyl)-5-[1-(3-dimethylaminopropyl)-3-(4-trifluoromethylphenyl)ureidomethyl]pyridine-2-carboxylic acid amide (Reference Compound No. 6-17) 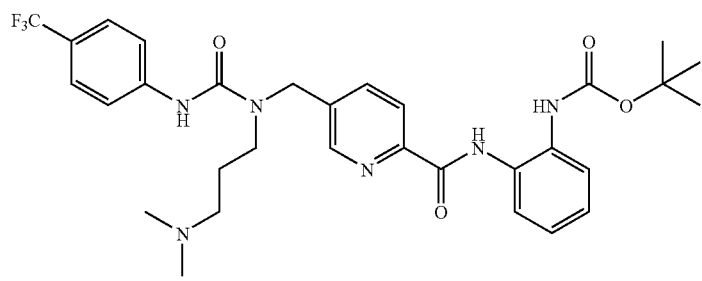 | $^1$H-NMR (500 MHz, DMSO-d$_6$) δ 1.47 (s, 9H), 1.71 (m, 2H), 2.06 (s, 6H), 2.28 (t, J = 6.1 Hz, 2H), 3.36 (t, J = 6.1 Hz, 2H), 4.65 (s, 2H), 7.15 (td, J = 7.9, 1.5 Hz, 1H), 7.25 (m, 1H), 7.39 (td, J = 7.9, 1.5 Hz, 1H), 7.65-7.72 (m, 4H), 7.95 (dd, J = 8.1, 1.8 Hz, 1H), 8.03 (dd, J = 7.9, 1.5 Hz, 1H), 8.14 (d, J = 8.1 Hz, 1H), 8.52 (d, J = 1.8 Hz, 1H), 9.12 (br s, 1H), 9.61 (br s, 1H), 10.46 (br s, 1H) |
| N-(2-t-Butoxycarbonylaminophenyl)-5-[3-(4-cyanophenyl)-1-(3-dimethylaminopropyl)ureidomethyl]pyridine-2-carboxylic acid amide (Reference Compound No. 6-18) 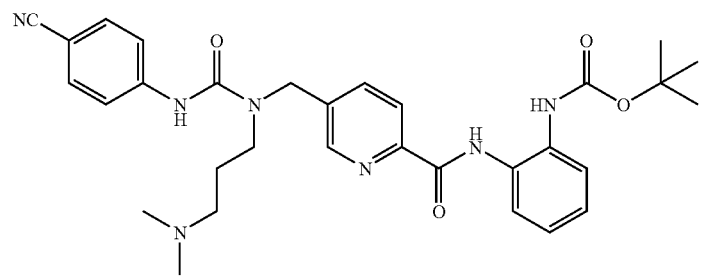 | $^1$H-NMR (400 MHz, DMSO-d$_6$) δ 1.46 (s, 9H), 1.72 (m, 2H), 2.21 (s, 6H), 2.28 (t, J = 6.0 Hz, 2H), 3.37 (t, J = 6.0 Hz, 2H), 4.64 (s, 2H), 7.15 (td, J = 7.6, 1.7 Hz, 1H), 7.23-7.28 (m, 2H), 7.61 (m, 2H), 7.72 (m, 2H), 7.98-8.02 (m, 2H), 8.15 (d, J = 8.1 Hz, 1H), 8.59 (d, J = 1.8 Hz, 1H), 9.12 (br s, 1H), 10.17 (br s, 1H), 10.47 (br s, 1H) |

N-(2-t-Butoxycarbonylaminophenyl)-5-
[1-(3-dimethylaminopropyl)-3-
(4-trifluoromethoxyphenyl)ureidomethyl]pyridine-
2-carboxylic acid amide
(Reference Compound No. 6-19)

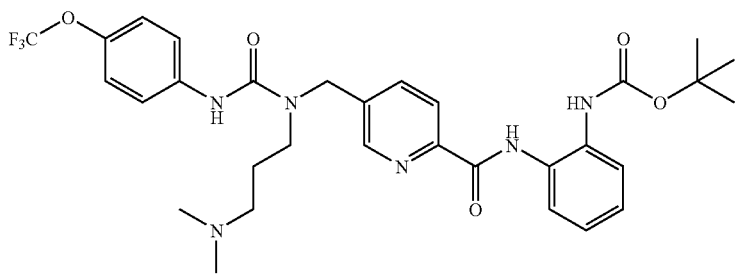

$^1$H-NMR (400 MHz, DMSO-$d_6$)
δ 1.46 (s, 9H), 1.71 (m, 2H),
2.20 (s, 6H), 2.27 (t, J = 6.1 Hz,
2H), 3.37 (t, J = 6.1 Hz, 2H),
4.64 (s, 2H), 7.15 (td, J = 7.6,
1.6 Hz, 1H), 7.23-7.30 (m, 3H),
7.51-7.56 (m, 3H), 7.98 (dd, J =
8.1, 1.8 Hz, 1H), 8.01 (d, J =
7.6 Hz, 1H), 8.14 (d, J = 8.1
Hz, 1H), 8.58 (d, J = 1.8 Hz,
1H), 9.13 (br s, 1H), 9.83 (br s,
1H), 10.47 (br s, 1H)

N-(2-t-Butoxycarbonylaminophenyl)-5-
[3-(4-dimethylaminophenyl)-1-
(3-hydroxypropyl)ureidomethyl]pyridine-
2-carboxylic acid amide
(Reference Compound No. 6-20)

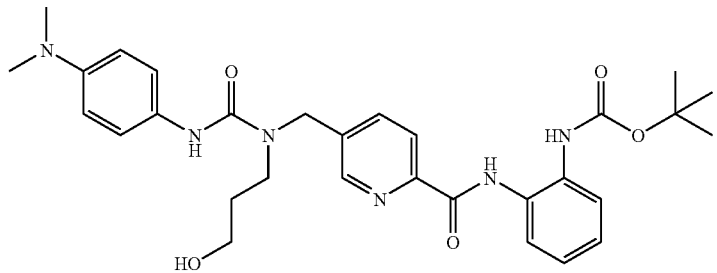

$^1$H-NMR (400 MHz, DMSO-$d_6$)
δ 1.47 (s, 9H), 1.67 (m, 2H),
2.82 (s, 6H), 3.39 (t, J = 6.5 Hz,
2H), 3.46 (m, 2H), 4.66 (s, 2H),
4.85 (br s, 1H), 6.66 (d, J = 9.0
Hz, 2H), 7.15 (td, J = 7.6, 1.6
Hz, 1H), 7.20-7.27 (m, 4H),
7.94 (dd, J = 8.1, 1.8 Hz, 1H),
8.01 (d, J = 7.6 Hz, 1H), 8.14
(d, J = 8.1 Hz, 1H), 8.31 (br s,
1H), 8.54 (d, J = 1.8 Hz, 1H),
9.12 (br s, 1H), 10.47 (br s, 1H)

N-(2-t-Butoxycarbonylaminophenyl)-5-
[3-(2,3-dihydrobenzo[1,4]dioxin-6-yl)-1-
(3-hydroxypropyl)ureidomethyl]pyridine-
2-carboxylic acid amide
(Reference Compound No. 6-21)

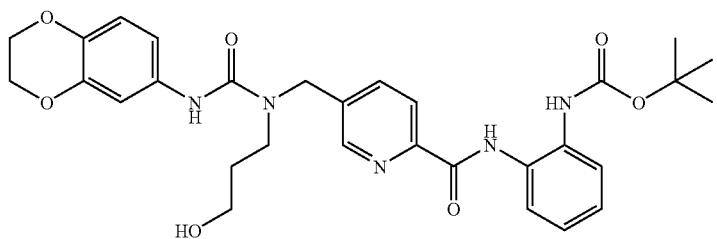

$^1$H-NMR (400 MHz, DMSO-$d_6$)
δ 1.47 (s, 9H), 1.66 (m, 2H), 3.38 (t,
J = 6.4 Hz, 2H), 3.46
(m, 2H), 4.16-4.21 (m, 4H),
4.65 (s, 2H), 4.91 (br s, 1H),
6.72 (d, J = 8.8 Hz, 1H), 6.84
(dd, J = 8.8, 2.4 Hz, 1H), 7.03
(d, J = 2.4 Hz, 1H), 7.15 (td, J =
7.7, 1.7 Hz, 1H), 7.23-7.27
(m, 2H), 7.94 (dd, J = 8.1, 1.7
Hz, 1H), 8.01 (d, J = 7.7 Hz,
1H), 8.14 (d, J = 8.1 Hz, 1H),
8.45 (br s, 1H), 8.54 (d, J = 1.7
Hz, 1H), 9.12 (br s, 1H), 10.47
(br s, 1H)

N-(2-t-Butoxycarbonylaminophenyl)-5-
[3-(4-cyanophenyl)-1-
(3-hydroxypropyl)ureidomethyl]pyridine-
2-carboxylic acid amide
(Reference Compound No. 6-22)

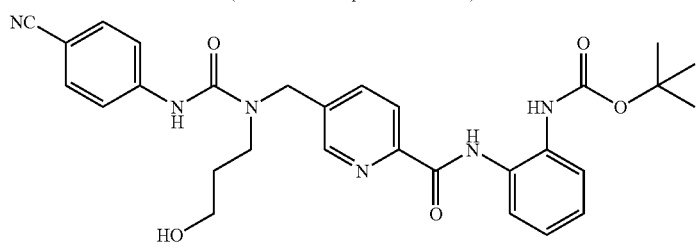

$^1$H-NMR (400 MHz, DMSO-$d_6$)
δ 1.46 (s, 9H), 1.69 (m, 2H),
3.33 (br s, 2H), 3.45 (m, 2H),
4.70 (s, 2H), 5.03 (br s, 1H),
7.15 (td, J = 7.7, 1.7 Hz, 1H),
7.23-7.27 (m, 2H), 7.65 (d, J =
9.0 Hz, 2H), 7.71 (d, J = 9.0
Hz, 2H), 7.97 (dd, J = 8.1, 1.7
Hz, 1H), 8.00 (d, J = 7.7 Hz,
1H), 8.14 (d, J = 8.1 Hz, 1H),
8.56 (d, J = 1.7 Hz, 1H), 9.13
(br s, 1H), 9.15 (br s, 1H),
10.47 (br s, 1H)

5-[3-(Benzo[1,3]dioxol-5-yl)-1-
(3-hydroxypropyl)ureidomethyl]-N-
(2-t-butoxycarbonylaminophenyl)pyridine-
2-carboxylic acid amide
(Reference Compound No. 6-23)

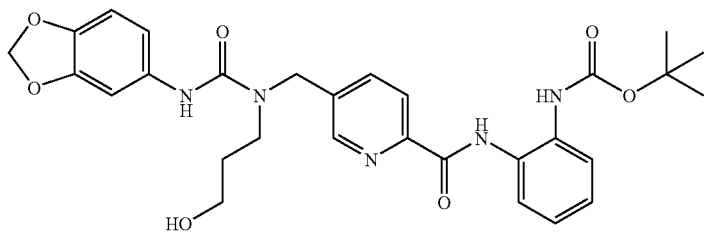

$^1$H-NMR (400 MHz, DMSO-$d_6$)
δ 1.47 (s, 9H), 1.67 (m, 2H),
3.39 (t, J = 6.6 Hz, 2H), 3.47
(m, 2H), 4.66 (s, 2H), 4.92 (br
s, 1H), 5.95 (s, 2H), 6.79-6.82
(m, 2H), 7.12 (m, 1H), 7.15 (td,
J = 7.8, 1.6 Hz, 1H), 7.23-7.27
(m, 2H), 7.95 (dd, J = 8.1, 2.0
Hz, 1H), 8.01 (d, J = 7.8 Hz,
1H), 8.15 (d, J = 8.1 Hz, 1H),
8.53 (br s, 1H), 8.56 (d, J = 2.0
Hz, 1H), 9.13 (br s, 1H), 10.47
(br s, 1H)

N-(2-t-Butoxycarbonylaminophenyl)-5-
[1-(3-hydroxypropyl)-3-
(4-methyoxyphenyl)ureidomethyl]pyridine-
2-carboxylic acid amide
(Reference Compound No. 6-24)

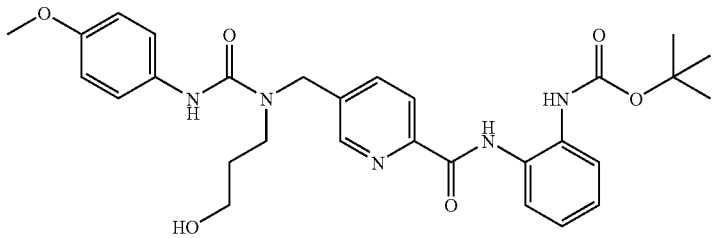

$^1$H-NMR (400 MHz, DMSO-$d_6$)
δ 1.47 (s, 9H), 1.68 (m, 2H),
3.40 (t, J = 6.6 Hz, 2H), 3.47
(m, 2H), 3.71 (s, 3H), 4.66 (s,
2H), 4.89 (br s, 1H), 6.84 (d, J =
9.3 Hz, 2H), 7.15 (td, J = 7.7,
1.6 Hz, 1H), 7.23-7.27 (m, 2H),
7.32 (d, J = 9.3 Hz, 2H), 7.95
(dd, J = 8.1, 1.8 Hz, 1H), 8.01
(d, J = 7.7 Hz, 1H), 8.15 (d, J =
8.1 Hz, 1H), 8.47 (br s, 1H),
8.55 (d, J = 1.8 Hz, 1H), 9.13
(br s, 1H), 10.47 (br s, 1H)

N-(2-t-Butoxycarbonylaminophenyl)-5-
[3-(4-dimethylaminophenyl)-1-
(2-ethoxycarbonylethyl)ureidomethyl]pyridine-
2-carboxylic acid amide
(Reference Compound No. 6-25)

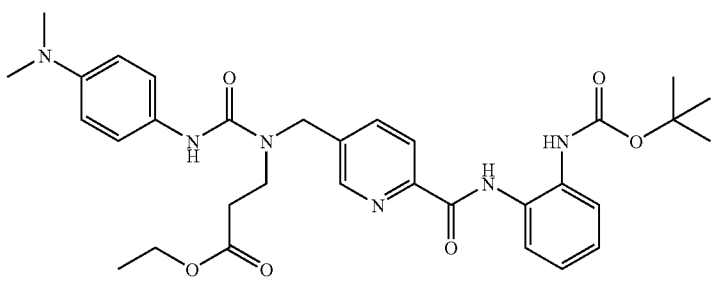

$^1$H-NMR (400 MHz, DMSO-$d_6$)
δ 1.16 (m, 3H), 1.47 (s, 9H),
2.60 (t, J = 7.1 Hz, 2H), 2.82 (s,
6H), 3.58 (t, J = 7.1 Hz, 2H),
4.03 (q, J = 7.1 Hz, 2H), 4.70
(s, 2H), 6.66 (d, J = 9.0 Hz,
2H), 7.15 (td, J = 7.8, 1.6 Hz,
1H), 7.21-7.27 (m, 4H), 7.93
(dd, J = 8.1, 1.7 Hz, 1H), 8.01
(d, J = 7.8 Hz, 1H), 8.15 (d, J =
8.1 Hz, 1H), 8.30 (br s, 1H),
8.52 (d, J = 1.7 Hz, 1H), 9.12
(br s, 1H), 10.47 (br s, 1H)

5-[3-(Benzo[1,3]dioxol-5-yl)-1-
(2-ethoxycarbonylethyl)ureidomethyl]-N-
(2-t-butoxycarbonylaminophenyl)pyridine-
2-carboxylic acid amide
(Reference Compound No. 6-26)

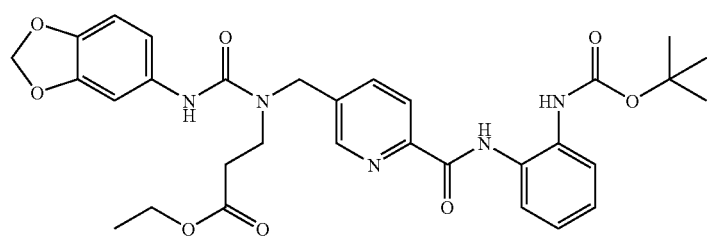

$^1$H-NMR (400 MHz, DMSO-$d_6$)
δ 1.16 (m, 3H), 1.47 (s, 9H),
2.60 (t, J = 7.1 Hz, 2H), 3.59 (t,
J = 7.1 Hz, 2H), 4.03 (q, J = 7.1
Hz, 2H), 4.71 (s, 2H), 5.95 (s,
2H), 6.81 (m, 2H), 7.12 (m,
1H), 7.15 (td, J = 7.6, 1.6 Hz,
1H), 7.23-7.27 (m, 2H), 7.93
(dd, J = 8.1, 1.8 Hz, 1H), 8.01
(d, J = 7.6 Hz, 1H), 8.15 (d, J =
8.1 Hz, 1H), 8.48 (br s, 1H),
8.52 (d, J = 1.8 Hz, 1H), 9.13
(br s, 1H), 10.47 (br s, 1H)

| Compound | NMR |
|---|---|
| N-(2-t-Butoxycarbonylaminophenyl)-5-[1-(2-ethoxycarbonylethyl)-3-(4-methoxyphenyl)ureidomethyl]pyridine-2-carboxylic acid amide (Reference Compound No. 6-27) 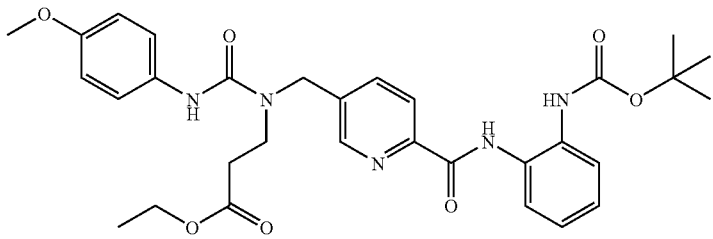 | $^1$H-NMR (400 MHz, DMSO-d$_6$) δ 1.16 (m, 3H), 1.47 (s, 9H), 2.61 (t, J = 7.1 Hz, 2H), 3.59 (t, J = 7.1 Hz, 2H), 3.71 (s, 3H), 4.03 (q, J = 7.2 Hz, 2H), 4.71 (s, 2H), 6.84 (d, J = 9.0 Hz, 2H), 7.15 (td, J = 7.6, 1.3 Hz, 1H), 7.23-7.27 (m, 2H), 7.33 (d, J = 9.0 Hz, 2H), 7.93 (dd, J = 8.1, 1.8 Hz, 1H), 8.01 (d, J = 7.6 Hz, 1H), 8.15 (d, J = 8.1 Hz, 1H), 8.44 (br s, 1H), 8.52 (d, J = 1.8 Hz, 1H), 9.12 (br s, 1H), 10.47 (br s, 1H) |
| N-(2-t-Butoxycarbonylaminophenyl)-5-[1-(3-dimethylaminopropyl)-3-(thiophen-2-yl)ureidomethyl]pyridine-2-carboxylic acid amide (Reference Compound No. 6-28) 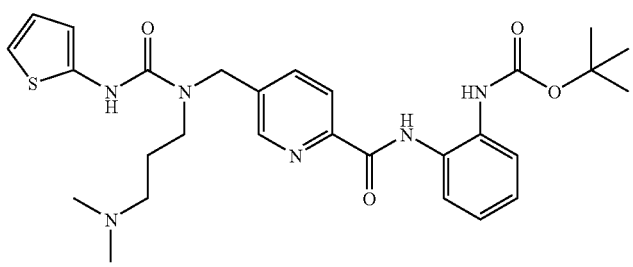 | $^1$H-NMR (400 MHz, DMSO-d$_6$) δ 1.47 (s, 9H), 1.68 (m, 2H), 2.21 (br s, 6H), 2.27 (t, J = 6.1 Hz, 2H), 3.32 (m, 2H), 4.64 (s, 2H), 6.52 (dd, J = 3.4, 1.7 Hz, 1H), 6.78-6.82 (m, 2H), 7.15 (m, 1H), 7.23-7.27 (m, 2H), 7.96 (dd, J = 8.1, 1.8 Hz, 1H), 8.01 (d, J = 7.8 Hz, 1H), 8.15 (d, J = 8.1 Hz, 1H), 8.57 (d, J = 1.8 Hz, 1H), 9.12 (br s, 1H), 10.47 (br s, 1H), 11.09 (br s, 1H) |
| N-(2-t-Butoxycarbonylaminophenyl)-5-[1-(3-dimethylaminopropyl)-3-(thiophen-3-yl)ureidomethyl]pyridine-2-carboxylic acid amide (Reference Compound No. 6-29) 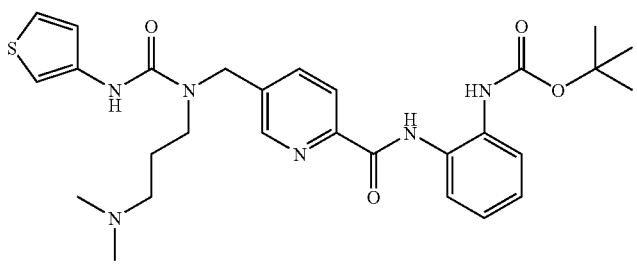 | $^1$H-NMR (400 MHz, DMSO-d$_6$) δ 1.47 (s, 9H), 1.68 (m, 2H), 2.19 (s, 6H), 2.25 (t, J = 6.1 Hz, 2H), 3.33 (m, 2H), 4.63 (s, 2H), 7.04 (dd, J = 5.1, 1.2 Hz, 1H), 7.15 (td, J = 7.7, 1.3 Hz, 1H), 7.23-7.28 (m, 3H), 7.40 (dd, J = 5.1, 3.2 Hz, 1H), 7.96 (dd, J = 8.1, 1.3 Hz, 1H), 8.01 (d, J = 7.7 Hz, 1H), 8.14 (d, J = 8.1 Hz, 1H), 8.57 (d, J = 1.3 Hz, 1H), 9.12 (br s, 1H), 10.07 (br s, 1H), 10.47 (br s, 1H) |
| N-(2-t-Butoxycarbonylaminophenyl)-5-[3-(2,3-dihydrobenzo[1,4]dioxin-6-yl)-1-[3-(morpholin-4-yl)propyl]ureidomethyl]pyridine-2-carboxylic acid amide (Reference Compound No. 6-30) 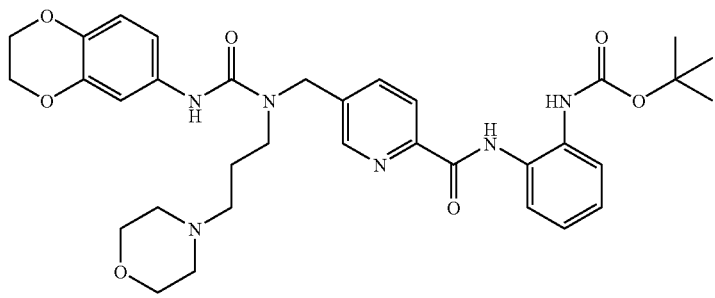 | $^1$H-NMR (400 MHz, DMSO-d$_6$) δ 1.47 (s, 9H), 1.68 (m, 2H), 2.26-2.30 (m, 6H), 3.34 (m, 2H), 3.53-3.55 (m, 4H), 4.17-4.22 (m, 4H), 4.67 (s, 2H), 6.72-6.78 (m, 2H), 6.87 (dd, J = 8.6, 2.6 Hz, 1H), 7.05 (m, 1H), 7.15 (dd, J = 7.6, 1.6 Hz, 1H), 7.24 (m, 1H), 7.94 (dd, J = 8.1, 1.7 Hz, 1H), 8.01 (d, J = 7.6 Hz, 1H), 8.14 (d, J = 8.1 Hz, 1H), 8.48 (br s, 1H), 8.54 (d, J = 1.7 Hz, 1H), 9.12 (br s, 1H), 10.47 (br s, 1H) |

5-[3-(Benzo[1,3]dioxol-5-yl)-1-
[3-(morpholin-4-yl)propyl]ureidomethyl]-
N-(2-t-butoxycarbonylaminophenyl)pyridine-
2-carboxylic acid amide
(Reference Compound No. 6-31)

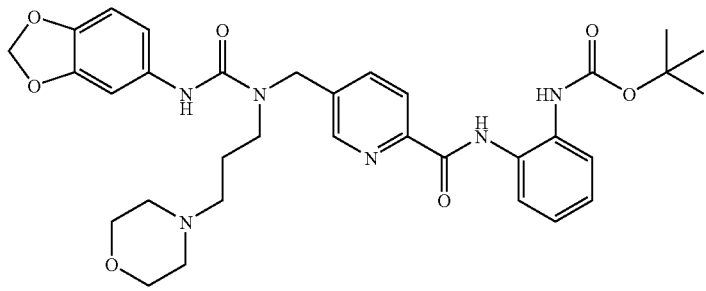

¹H-NMR (400 MHz, DMSO-d₆)
δ 1.47 (s, 9H), 1.68 (m, 2H), 2.26-2.30 (m, 6H), 3.35 (m, 2H), 3.52-3.54 (m, 4H), 4.67 (s, 2H), 5.95 (s, 2H), 6.82 (m, 2H), 7.14-7.19 (m, 2H), 7.23-7.27 (m, 2H), 7.95 (dd, J = 8.1, 1.6 Hz, 1H), 8.01 (d, J = 7.6 Hz, 1H), 8.15 (d, J = 8.1 Hz, 1H), 8.54 (d, J = 1.6 Hz, 1H), 8.57 (br s, 1H), 9.13 (br s, 1H), 10.47 (br s, 1H)

N-(2-t-Butoxycarbonylaminophenyl)-5-
[3-(4-methoxyphenyl)-1-
[3-(morpholin-4-yl)propyl]ureidomethyl]pyridine-
2-carboxylic acid amide
(Reference Compound No. 6-32)

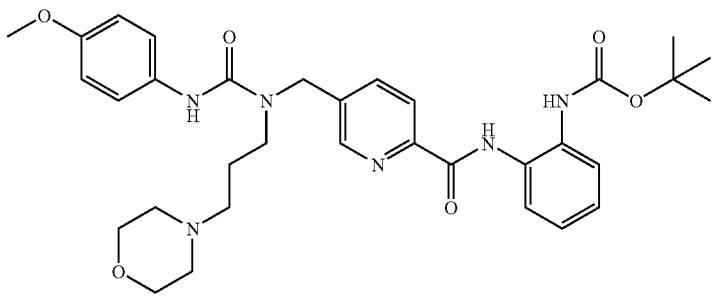

¹H-NMR (400 MHz, DMSO-d₆)
δ 1.47 (s, 9H), 1.69 (m, 2H), 2.27-2.30 (m, 6H), 3.36 (m, 2H), 3.52-3.54 (m, 4H), 3.71 (s, 3H), 4.68 (s, 2H), 6.85 (d, J = 9.1 Hz, 2H), 7.15 (td, J = 7.6, 1.6 Hz, 1H), 7.24 (d, J = 7.6 Hz, 1H), 7.25 (m, 1H), 7.34 (d, J = 9.1 Hz, 2H), 7.95 (dd, J = 8.1, 1.6 Hz, 1H), 8.01 (d, J = 7.6 Hz, 1H), 8.15 (d, J = 8.1 Hz, 1H), 8.54 (d, J = 1.6 Hz, 1H), 8.55 (br s, 1H), 9.12 (br s, 1H), 10.47 (br s, 1H)

N-(2-t-Butoxycarbonylaminophenyl)-5-
[3-(2,3-dihydro-1-benzofuran-5-yl)-1-
(3-dimethylaminopropyl)ureidomethyl]pyridine-
2-carboxylic acid amide
(Reference Compound No. 6-33)

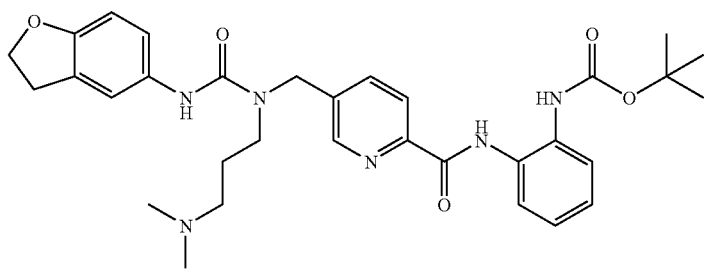

¹H-NMR (400 MHz, DMSO-d₆)
δ 1.48 (s, 9H), 1.68 (m, 2H), 2.17 (s, 6H), 2.25 (t, J = 6.3 Hz, 2H), 2.50 (m, 2H), 3.14 (t, J = 8.7 Hz, 2H), 4.47 (t, J = 8.7 Hz, 2H), 4.61 (s, 2H), 6.64 (d, J = 8.4 Hz, 1H), 7.01 (dd, J = 8.4, 2.1 Hz, 1H), 7.15 (td, J = 7.7, 1.6 Hz, 1H), 7.23-7.27 (m, 2H), 7.35 (d, J = 2.1 Hz, 1H), 7.96 (dd, d = 8.1, 2.0 Hz, 1H), 8.01 (d, J = 7.7 Hz, 1H), 8.14 (dd, J = 8.1, 0.5 Hz, 1H), 8.57 (d, J = 2.0 Hz, 1H), 9.13 (br s, 1H), 9.32 (br s, 1H), 10.47 (br s, 1H)

N-(2-t-Butoxycarbonylaminophenyl)-5-
[3-(2,3-dihydro-1-benzofuran-5-yl)-1-
[3-(morpholin-4-yl)propyl]ureidomethyl]pyridine-
2-carboxylic acid amide
(Reference Compound No. 6-34)

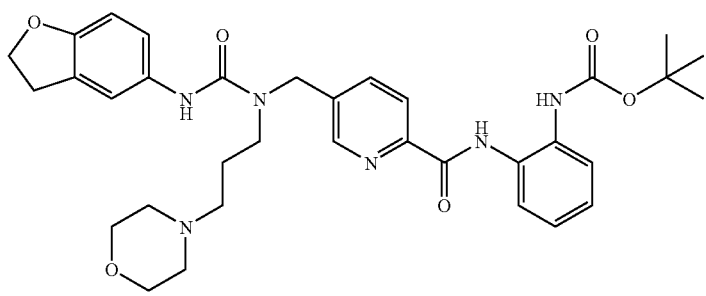

¹H-NMR (400 MHz, DMSO-d₆)
δ 1.48 (s, 9H), 1.68 (m, 2H), 2.27-2.32 (m, 6H), 3.14 (t, J = 8.5 Hz, 2H), 3.33 (m, 2H), 3.52-3.54 (m, 4H), 4.48 (t, J = 8.5 Hz, 2H), 4.67 (s, 2H), 6.65 (d, J = 8.5 Hz, 1H), 7.04 (dd, J = 8.5, 2.0 Hz, 1H), 7.15 (td, J = 7.6, 1.3 Hz, 1H), 7.23-7.27 (m, 2H), 7.32 (d, J = 2.0 Hz, 1H), 7.95 (dd, J = 8.1, 1.5 Hz, 1H), 8.01 (d, J = 7.6 Hz, 1H), 8.15 (d, J = 8.1 Hz, 1H), 8.50 (br s, 1H), 8.55 (d, J = 1.5 Hz, 1H), 9.13 (br s, 1H), 10.47 (br s, 1H)

| | |
|---|---|
| N-(2-t-Butoxycarbonylaminophenyl)-5-[1-(3-diethylaminopropyl)-3-(4-fluorophenyl)ureidomethyl]pyridine-2-carboxylic acid amide (Reference Compound No. 6-35)<br />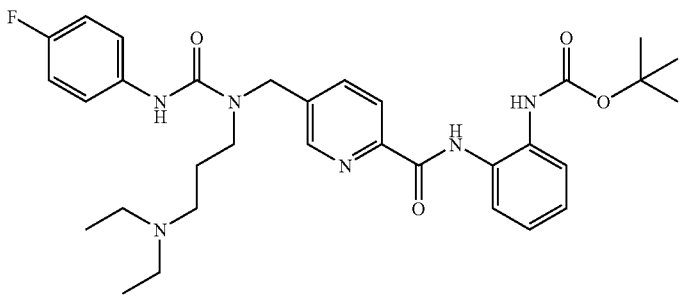 | ¹H-NMR (400 MHz, DMSO-d₆) δ 0.92 (t, J = 7.1 Hz, 6H), 1.47 (s, 9H), 1.67 (m, 2H), 2.37 (t, J = 6.3 Hz, 2H), 2.47 (m, 4H), 3.35 (m, 2H), 4.66 (s, 2H), 7.10 (t, J = 8.9 Hz, 2H), 7.15 (td, J = 7.5, 1.5 Hz, 1H), 7.23-7.27 (m, 2H), 7.43 (m, 2H), 7.95 (dd, J = 8.1, 1.6 Hz, 1H), 8.01 (d, J = 7.5 Hz, 1H), 8.15 (d, J = 8.1 Hz, 1H), 8.56 (d, J = 1.6 Hz, 1H), 9.11 (br s, 1H), 10.47 (br s, 1H) |
| N-(2-t-Butoxycarbonylaminophenyl)-5-[1-(3-diethylaminopropyl)-3-(3,4-difluorophenyl)ureidomethyl]pyridine-2-carboxylic acid amide (Reference Compound No. 6-36)<br />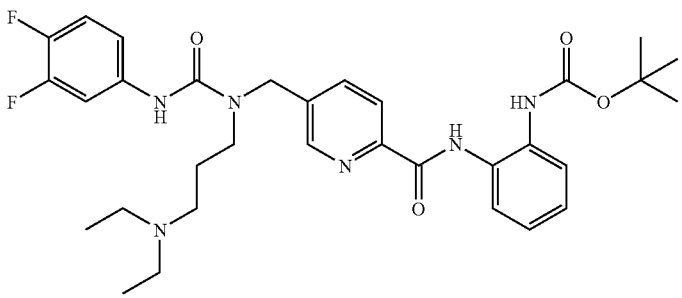 | ¹H-NMR (400 MHz, DMSO-d₆) δ 0.92 (t, J = 7.1 Hz, 6H), 1.46 (s, 9H), 1.67 (m, 2H), 2.36 (t, J = 6.3 Hz, 2H), 2.46 (m, 4H), 3.35 (m, 2H), 4.67 (s, 2H), 7.13-7.17 (m, 2H), 7.23-7.28 (m, 2H), 7.33 (dd, J = 19.7, 9.2 Hz, 1H), 7.65 (ddd, J = 13.7, 7.6, 2.4 Hz, 1H), 7.97 (dd, J = 8.1, 2.0 Hz, 1H), 8.01 (dd, J = 8.1, 1.2 Hz, 1H), 8.15 (d, J = 8.1 Hz, 1H), 8.56 (d, J = 2.0 Hz, 1H), 9.13 (br s, 1H), 9.30 (br s, 1H), 10.47 (br s, 1H) |
| N-(2-t-Butoxycarbonylaminophenyl)-5-[1-(3-diethylaminopropyl)-3-(3,5-difluorophenyl)ureidomethyl]pyridine-2-carboxylic acid amide (Reference Compound No. 6-37)<br />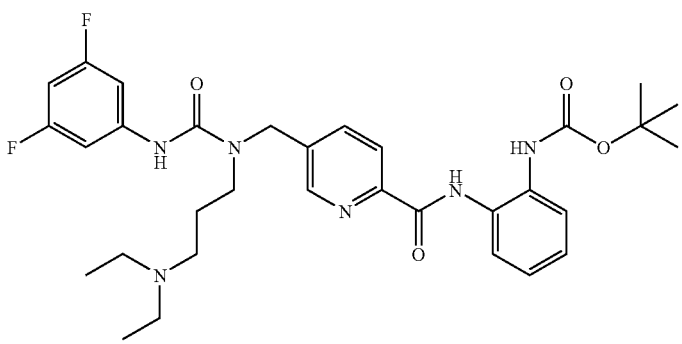 | ¹H-NMR (400 MHz, DMSO-d₆) δ 0.93 (t, J = 7.1 Hz, 6H), 1.46 (s, 9H), 1.67 (m, 2H), 2.36 (t, J = 6.6 Hz, 2H), 2.48 (m, 4H), 3.36 (t, J = 6.6 Hz, 2H), 4.68 (s, 2H), 6.77 (tt, J = 9.3, 2.4 Hz, 1H), 7.13-7.28 (m, 5H), 7.97 (dd, J = 8.1, 1.7 Hz, 1H), 8.01 (dd, J = 8.2, 1.7 Hz, 1H), 8.15 (d, J = 8.1 Hz, 1H), 8.57 (d, J = 1.7 Hz, 1H), 9.13 (br s, 1H), 9.47 (br s, 1H), 10.47 (br s, 1H) |

| | |
|---|---|
| N-(2-t-Butoxycarbonylaminophenyl)-5-[3-(3-chloro-4-fluorophenyl)-1-(3-diethylaminopropyl)ureidomethyl]pyridine-2-carboxylic acid amide (Reference Compound No. 6-38)<br>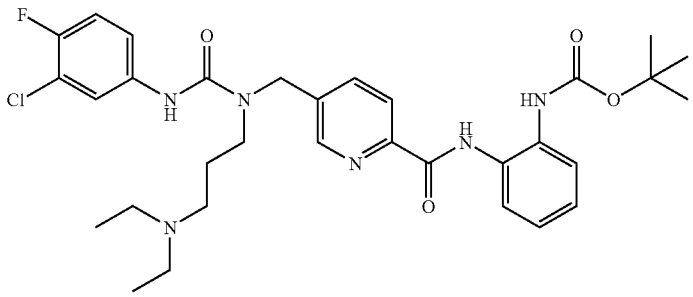 | ¹H-NMR (400 MHz, DMSO-d₆) δ 0.92 (t, J = 7.1 Hz, 6H), 1.46 (s, 9H), 1.67 (m, 2H), 2.36 (t, J = 6.7 Hz, 2H), 2.47 (m, 4H), 3.36 (t, J = 6.7 Hz, 2H), 4.67 (s, 2H), 7.15 (td, J = 7.6, 1.5 Hz, 1H), 7.22-7.28 (m, 2H), 7.31-7.35 (m, 2H), 7.78 (m, 1H), 7.97 (dd, J = 8.1, 1.7 Hz, 1H), 8.01 (d, J = 7.6, 1.5 Hz, 1H), 8.15 (d, J = 8.1 Hz, 1H), 8.56 (d, J = 1.7 Hz, 1H), 9.12 (br s, 1H), 9.25 (br s, 1H), 10.47 (br s, 1H) |
| N-(2-t-Butoxycarbonylaminophenyl)-5-[1-(3-diethylaminopropyl)-3-(3-fluorophenyl)ureidomethyl]pyridine-2-carboxylic acid amide (Reference Compound No. 6-39)<br>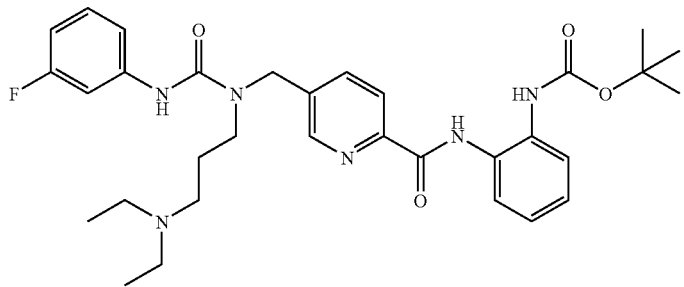 | ¹H-NMR (400 MHz, DMSO-d₆) δ 0.94 (t, J = 7.2 Hz, 6H), 1.46 (s, 9H), 1.68 (m, 2H), 2.37 (t, J = 6.5 Hz, 2H), 2.48 (m, 4H), 3.36 (t, J = 6.5 Hz, 2H), 4.67 (s, 2H), 6.77 (m, 1H), 7.12-7.17 (m, 2H), 7.23-7.32 (m, 3H), 7.46 (m, 1H), 7.98 (dd, J = 8.2, 2.0 Hz, 1H), 8.01 (dd, J = 8.1, 1.0 Hz, 1H), 8.15 (d, J = 8.2 Hz, 1H), 8.57 (d, J = 2.0 Hz, 1H), 9.12 (br s, 1H), 9.36 (br s, 1H), 10.47 (br s, 1H) |
| N-(2-t-Butoxycarbonylaminophenyl)-5-[1-(3-diethylaminopropyl)-3-(4-fluoro-3-methylphenyl)ureidomethyl]pyridine-2-carboxylic acid amide (Reference Compound No. 6-40)<br>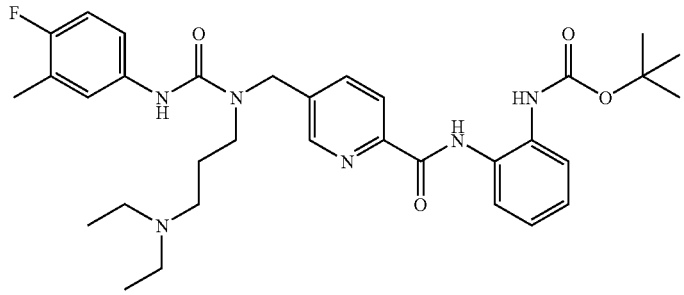 | ¹H-NMR (400 MHz, CDCl₃) δ 1.03 (t, J = 7.2 Hz, 6H), 1.51 (s, 9H), 1.76 (m, 2H), 2.25 (d, J = 2.0 Hz, 3H), 2.51 (t, J = 6.1 Hz, 2H), 2.63 (q, J = 7.2 Hz, 4H), 3.38 (t, J = 5.9 Hz, 2H), 4.62 (s, 2H), 6.91 (t, J = 9.0 Hz, 1H), 7.05 (br s, 1H), 7.10 (m, 1H), 7.17-7.25 (m, 2H), 7.34 (m, 1H), 7.60 (d, J = 7.3 Hz, 1H), 7.69 (d, J = 7.3 Hz, 1H), 7.93 (dd, J = 8.1, 2.2 Hz, 1H), 8.26 (d, J = 8.1 Hz, 1H), 8.58 (d, J = 2.2 Hz, 1H), 9.73 (s, 1H), 10.15 (s, 1H) |
| N-(2-t-Butoxycarbonylaminophenyl)-5-[1-(3-diethylaminopropyl)-3-(4-fluoro-3-nitrophenyl)ureidomethyl]pyridine-2-carboxylic acid amide (Reference Compound No. 6-41)<br>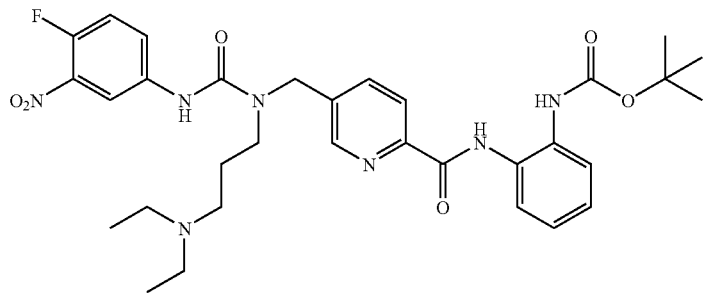 | ¹H-NMR (500 MHz, CDCl₃) δ 1.08 (t, J = 7.2 Hz, 6H), 1.52 (s, 9H), 1.80 (m, 2H), 2.54 (t, J = 6.1 Hz, 2H), 2.68 (q, J = 7.2 Hz, 4H), 3.40 (t, J = 5.7 Hz, 2H), 4.63 (s, 2H), 7.02 (br s, 1H), 7.18-7.24 (m, 2H), 7.58 (d, J = 6.4 Hz, 1H), 7.62-7.76 (m, 1H), 7.71 (d, J = 6.4 Hz, 1H), 7.88-7.93 (m, 2H), 8.03 (dd, J = 6.4, 2.7 Hz, 1H), 8.24 (d, J = 7.9 Hz, 1H), 8.59 (d, J = 1.5 Hz, 1H), 10.16 (s, 1H), 10.53 (s, 1H) |

| Compound | NMR |
|---|---|
| N-(2-t-Butoxycarbonylaminophenyl)-5-[1-(3-diethylaminopropyl)-3-(3-ethoxyphenyl)ureidomethyl]pyridine-2-carboxylic acid amide (Reference Compound No. 6-42)<br />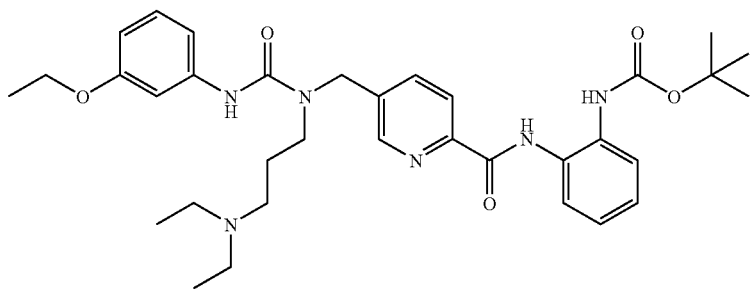 | $^1$H-NMR (400 MHz, CDCl$_3$) δ 1.06 (t, J = 7.2 Hz, 6H), 1.40 (t, J = 7.0 Hz, 3H), 1.51 (s, 9H), 1.76 (m, 2H), 2.51 (t, J = 6.1 Hz, 2H), 2.66 (q, J = 7.2 Hz, 4H), 3.38 (t, J = 5.6 Hz, 2H), 4.03 (q, J = 7.0 Hz, 2H), 4.63 (s, 2H), 6.56 (m, 1H), 6.90 (m, 1H), 7.05 (br s, 1H), 7.15 (t, J = 8.2 Hz, 1H), 7.19-7.23 (m, 3H), 7.60 (d, J = 6.9 Hz, 1H), 7.69 (d, J = 6.9 Hz, 1H), 7.93 (dd, J = 8.1, 2.2 Hz, 1H), 8.26 (d, J = 8.1 Hz, 1H), 8.58 (d, J = 2.2 Hz, 1H), 9.79 (s, 1H), 10.15 (s, 1H) |
| N-(2-t-Butoxycarbonylaminophenyl)-5-[3-(2,3-dihydrobenzo[1,4]dioxin-6-yl)-1-(2-dimethylaminoethyl)ureidomethyl]pyridine-2-carboxylic acid amide (Reference Compound No. 6-43)<br />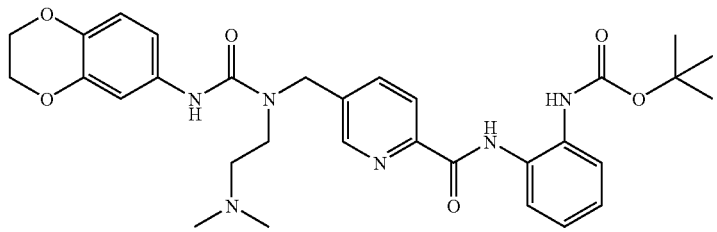 | $^1$H-NMR (400 MHz, CDCl$_3$) δ 1.52 (s, 9H), 2.38 (s, 6H), 2.51 (t, J = 4.3 Hz, 2H), 3.31 (t, J = 4.3 Hz, 2H), 4.21-4.25 (m, 4H), 4.64 (s, 2H), 6.76-6.82 (m, 2H), 6.93 (d, J = 2.0 Hz, 1H), 7.08 (br s, 1H), 7.18-7.23 (m, 2H), 7.58 (br s, 1H), 7.72 (br s, 1H), 7.91 (dd, J = 8.1, 2.2 Hz, 1H), 8.26 (d, J = 8.1 Hz, 1H), 8.56 (d, J = 2.2 Hz, 1H), 10.16 (s, 1H), 10.85 (s, 1H) |
| N-(2-t-Butoxycarbonylaminophenyl)-5-[1-(2-dimethylaminoethyl)-3-(3-methoxyphenyl)ureidomethyl]pyridine-2-carboxylic acid amide (Reference Compound No. 6-44)<br />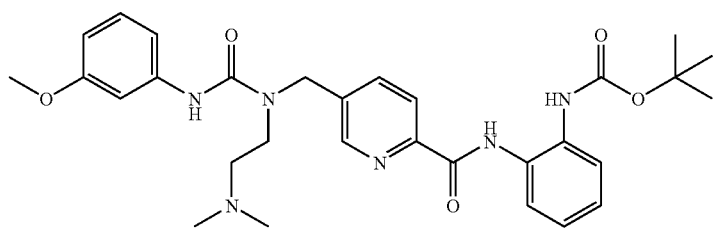 | $^1$H-NMR (400 MHz, CDCl$_3$) δ 1.51 (s, 9H), 2.40 (s, 6H), 2.53 (t, J = 4.3 Hz, 2H), 3.33 (t, J = 4.3 Hz, 2H), 3.81 (s, 3H), 4.66 (s, 2H), 6.56 (ddd, J = 7.8, 2.7, 0.8 Hz, 1H), 6.84 (dd, J = 7.8, 1.2 Hz, 1H), 7.07 (s, 1H), 7.14-7.22 (m, 4H), 7.58 (br s, 1H), 7.73 (br s, 1H), 7.91 (dd, J = 7.8, 2.1 Hz, 1H), 8.26 (d, J = 7.8 Hz, 1H), 8.57 (d, J = 2.1 Hz, 1H), 10.17 (s, 1H), 11.12 (s, 1H) |
| N-(2-t-Butoxycarbonylaminophenyl)-5-[1-(2-dimethylaminoethyl)-3-(3-fluorophenyl)ureidomethyl]pyridine-2-carboxylic acid amide (Reference Compound No. 6-45)<br />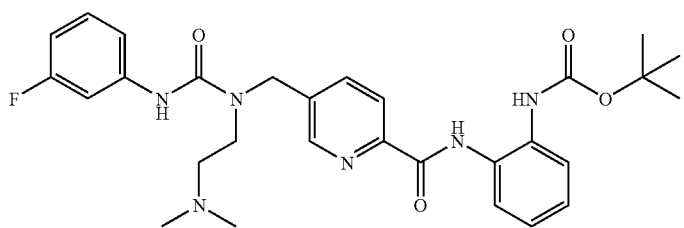 | $^1$H-NMR (400 MHz, CDCl$_3$) δ 1.52 (s, 9H), 2.41 (s, 6H), 2.55 (t, J = 4.3 Hz, 2H), 3.33 (t, J = 4.3 Hz, 2H), 4.66 (s, 2H), 6.68 (td, J = 8.4, 1.6 Hz, 1H), 6.98-7.07 (m, 2H), 7.18-7.29 (m, 4H), 7.58 (br s, 1H), 7.73 (br s, 1H), 7.91 (dd, J = 8.1, 2.2 Hz, 1H), 8.28 (d, J = 8.1 Hz, 1H), 8.58 (d, J = 2.2 Hz, 1H), 10.17 (s, 1H), 11.33 (s, 1H) |

N-(2-t-Butoxycarbonylaminophenyl)-5-
[1-(2-dimethylaminoethyl)-3-
(3-thiophen-3-yl)ureidomethyl]pyridine-
2-carboxylic acid amide
(Reference Compound No. 6-46)

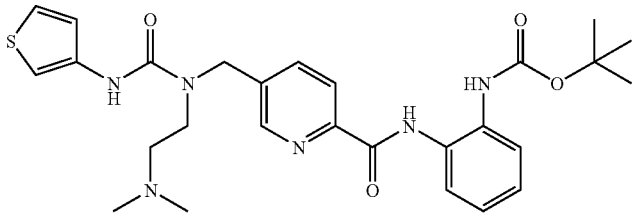

$^1$H-NMR (400 MHz, CDCl$_3$)
δ 1.51 (s, 9H), 2.39 (s, 6H),
2.53 (t, J = 4.3 Hz, 2H), 3.31 (t,
J = 4.3 Hz, 2H), 4.67 (s, 2H),
6.87 (dd, J = 5.1, 1.2 Hz, 1H),
7.00 (s, 1H), 7.18-7.22 (m, 3H),
7.30 (dd, J = 5.1, 1.3 Hz, 1H),
7.58 (br s, 1H), 7.71 (br s, 1H),
7.91 (dd, J = 7.9, 2.2 Hz, 1H),
8.26 (d, J = 7.9 Hz, 1H), 8.56
(d, J = 2.2 Hz, 1H), 10.16 (s,
1H), 11.49 (s, 1H)

N-(2-t-Butoxycarbonylaminophenyl)-5-
[3-(3,4-diflurorphenyl)-1-
[3-(pyrrolidin-1-yl)propyl]ureidomethyl]pyridine-
2-carboxylic acid amide
(Reference Compound No. 6-47)

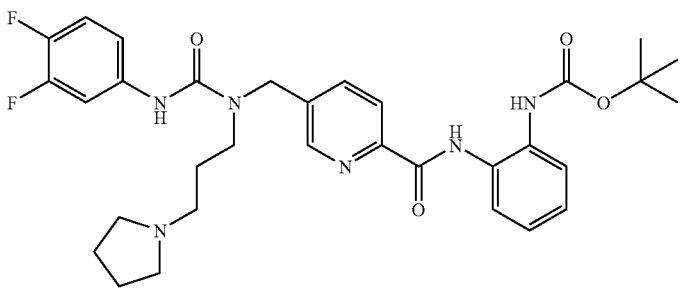

$^1$H-NMR (400 MHz, DMSO-d$_6$)
δ 1.47 (s, 9H), 1.69-1.74 (m,
6H), 2.40-2.44 (m, 6H), 3.40 (t,
J = 6.2 Hz, 2H), 4.65 (s, 2H),
7.10 (m, 1H), 7.15 (td, J = 7.6,
1.5 Hz, 1H), 7.23-7.27 (m, 2H),
7.35 (dd, J = 19.8, 9.3 Hz, 1H),
7.65 (ddd, J = 13.7, 7.6, 2.4 Hz,
1H), 7.97 (dd, J = 8.1, 1.8 Hz,
1H), 8.01 (d, J = 8.1 Hz, 1H),
8.14 (dd, J = 8.1, 0.5 Hz, 1H),
8.57 (d, J = 1.8 Hz, 1H), 9.12
(br s, 1H), 9.55 (br s, 1H),
10.47 (br s, 1H)

N-(2-t-Butoxycarbonylaminophenyl)-5-
[3-(pyridin-3-yl)-1-
[3-(pyrrolidin-1-yl)propyl]ureidomethyl]pyridine-
2-carboxylic acid amide
(Reference Compound No. 6-48)

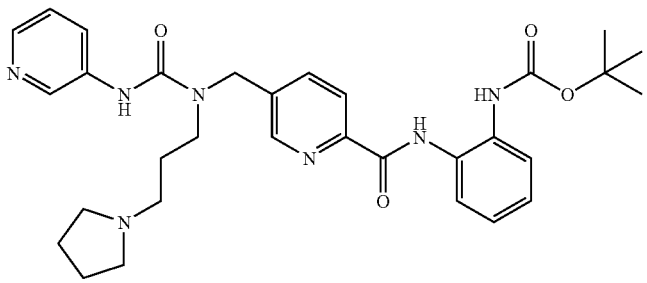

$^1$H-NMR (500 MHz, DMSO-d$_6$)
δ 1.47 (s, 9H), 1.72-1.74 (m,
6H), 2.42-2.46 (m, 6H), 3.43 (t,
J = 6.3 Hz, 2H), 4.67 (s, 2H),
7.15 (td, J = 7.5, 1.5 Hz, 1H),
7.24-7.27 (m, 2H), 7.30 (dd, J =
8.2, 4.7 Hz, 1H), 7.89 (ddd, J =
8.2, 2.4, 1.5 Hz, 1H), 7.98 (dd,
J = 7.9, 1.7 Hz, 1H), 8.01 (d, J =
7.5 Hz, 1H), 8.14 (d, J = 7.9
Hz, 1H), 8.18 (dd, J = 4.7, 1.5
Hz, 1H), 8.56 (d, J = 2.4 Hz,
1H), 8.57 (d, J = 1.7 Hz, 1H),
9.11 (br s, 1H), 9.58 (br s, 1H),
10.47 (br s, 1H)

N-(2-t-Butoxycarbonylaminophenyl)-5-
[3-(3-chlorophenyl)-1-
[3-(morpholin-4-yl)propyl]ureidomethyl]pyridine-
2-carboxylic acid amide
(Reference Compound No. 6-49)

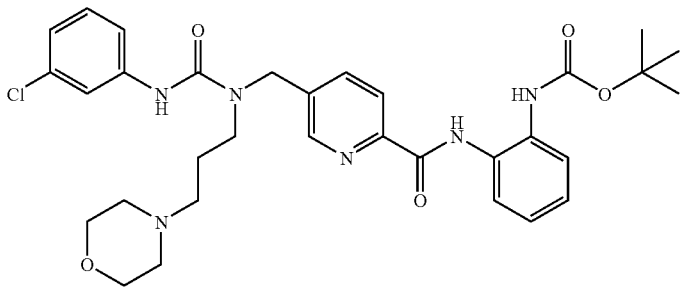

$^1$H-NMR (500 MHz, CDCl$_3$)
δ 1.52 (s, 9H), 1.80 (m, 2H),
2.45-2.52 (m, 6H), 3.39 (t, J =
5.7 Hz, 2H), 3.69-3.74 (m, 4H),
4.64 (s, 2H), 7.02 (br s, 1H),
7.09 (d, J = 8.1 Hz, 1H),
7.18-7.25 (m, 3H), 7.31 (d, J =
8.1 Hz, 1H), 7.55-7.61 (m, 2H),
7.71 (d, J = 6.4 Hz, 1H), 7.91
(dd, J = 8.1, 1.8 Hz, 1H), 8.26
(d, J = 8.1 Hz, 1H), 8.58 (d, J =
1.8 Hz, 1H), 9.04 (s, 1H), 10.16
(s, 1H)

| | |
|---|---|
| N-(2-t-Butoxycarbonylaminophenyl)-5-[3-(2-fluorophenethyl)-1-[3-(morpholin-4-yl)propyl]ureidomethyl]pyridine-2-carboxylic acid amide (Reference Compound No. 6-50)<br>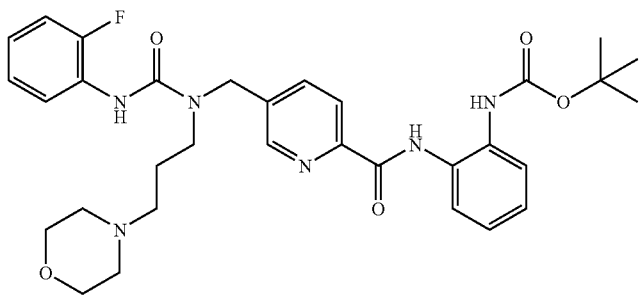 | $^1$H-NMR (400 MHz, CDCl$_3$) δ 1.52 (s, 9H), 1.62 (m, 2H), 2.27-2.36 (m, 6H), 2.92 (t, J = 6.6 Hz, 2H), 3.14 (t, J = 5.6 Hz, 2H), 3.49 (td, J = 6.6, 6.6 Hz, 2H), 3.56 (br s, 4H), 4.57 (s, 2H), 7.00-7.11 (m, 3H), 7.17-7.25 (m, 4H), 7.34 (br s, 1H), 7.61 (br s, 1H), 7.69 (br s, 1H), 7.78 (dd, J = 8.0, 1.8 Hz, 1H), 8.24 (dd, J = 8.0, 0.6 Hz, 1H), 8.50 (d, J = 1.8 Hz, 1H), 10.15 (s, 1H) |
| N-(2-t-Butoxycarbonylaminophenyl)-5-[3-(4-fluorophenethyl)-1-[3-(morpholin-4-yl)propyl]ureidomethyl]pyridine-2-carboxylic acid amide (Reference Compound No. 6-51)<br>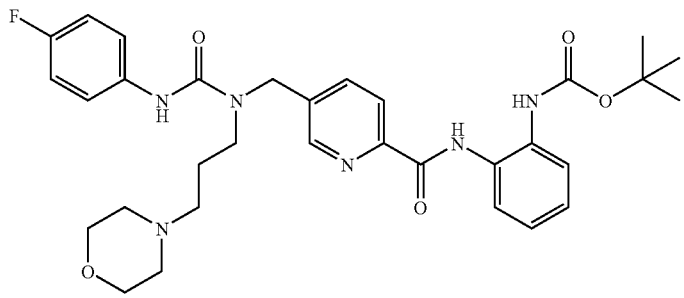 | $^1$H-NMR (500 MHz, CDCl$_3$) δ 1.51 (s, 9H), 1.63 (m, 2H), 2.27-2.35 (m, 6H), 2.84 (t, J = 6.8 Hz, 2H), 3.15 (t, J = 5.5 Hz, 2H), 3.45 (td, J = 6.8, 6.8 Hz, 2H), 3.57 (br s, 4H), 4.57 (s, 2H), 7.00 (t, J = 8.7 Hz, 2H), 7.08 (br s, 1H), 7.16 (dd, J = 8.7, 5.4 Hz, 2H), 7.19-7.25 (m, 3H), 7.62 (br s, 1H), 7.69 (br s, 1H), 7.82 (dd, J = 8.0, 1.8 Hz, 1H), 8.26 (dd, J = 8.0, 0.6 Hz, 1H), 8.47 (d, J = 1.8 Hz, 1H), 10.15 (s, 1H) |
| N-(2-t-Butoxycarbonylaminophenyl)-5-[1-[3-(morpholin-4)propyl]-3-phenethylureidomethyl]pyridine-2-carboxylic acid amide (Reference Compound No. 6-52)<br>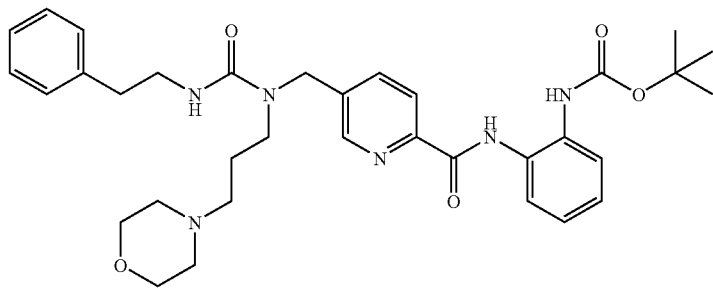 | $^1$H-NMR (400 MHz, CDCl$_3$) δ 1.53 (s, 9H), 1.61 (m, 2H), 2.27-2.32 (m, 6H), 2.86 (t, J = 6.7 Hz, 2H), 3.15 (t, J = 5.6 Hz, 2H), 3.45-3.52 (m, 6H), 4.58 (s, 2H), 7.14 (br s, 1H), 7.18-7.23 (m, 5H), 7.26-7.32 (m, 3H), 7.60 (br s, 1H), 7.69 (br s, 1H), 7.81 (dd, J = 8.2, 2.2 Hz, 1H), 8.25 (d, J = 8.2 Hz, 1H), 8.51 (d, J = 2.2 Hz, 1H), 10.15 (s, 1H) |

| | |
|---|---|
| N-(2-t-Butoxycarbonylaminophenyl)-5-[3-(3-fluorophenyl)-1-[2-(4-methylpiperazin-1-yl)ethyl]ureidomethyl]pyridine-2-carboxylic acid amide (Reference Compound No. 6-53)<br>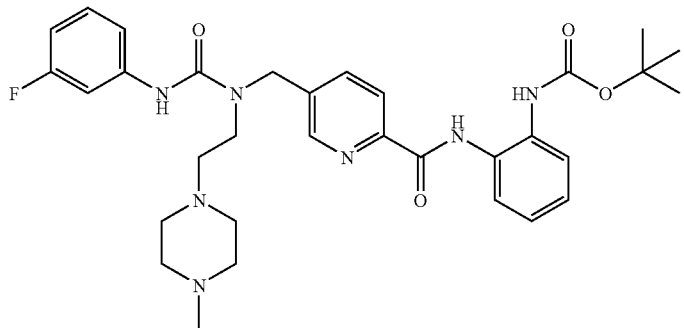 | $^1$H-NMR (400 MHz, CDCl$_3$) δ 1.52 (s, 9H), 2.33 (s, 3H), 2.54 (br s, 4H), 2.60 (t, J = 4.3 Hz, 2H), 2.68 (br s, 4H), 3.37 (t, J = 4.3 Hz, 2H), 4.65 (s, 2H), 6.74 (m, 1H), 7.03 (br s, 1H), 7.17-7.28 (m, 4H), 7.37 (m, 1H), 7.58 (d, J = 6.1 Hz, 1H), 7.72 (d, J = 6.1 Hz, 1H), 7.92 (dd, J = 8.1, 2.2 Hz, 1H), 8.27 (d, J = 8.1 Hz, 1H), 8.58 (d, J = 2.2 Hz, 1H), 10.17 (s, 1H), 10.19 (s, 1H) |
| N-(2-t-Butoxycarbonylaminophenyl)-5-[3-(3,4-difluorophenyl)-1-[2-(4-methylpiperazin-1-yl)ethyl]ureidomethyl]pyridine-2-carboxylic acid amide (Reference Compound No. 6-54)<br>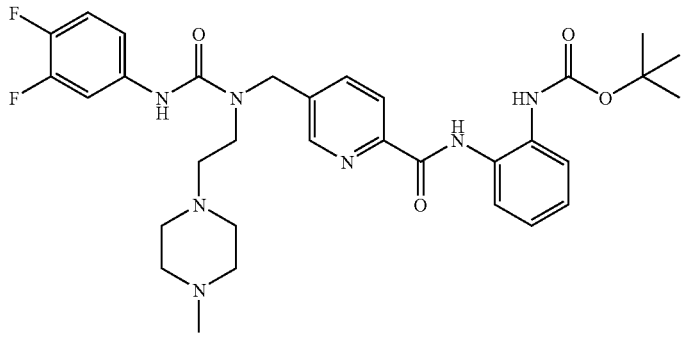 | $^1$H-NMR (400 MHz, CDCl$_3$) δ 1.52 (s, 9H), 2.32 (s, 3H), 2.51 (br s, 4H), 2.60 (t, J = 4.2 Hz, 2H), 2.67 (br s, 4H), 3.36 (t, J = 4.2 Hz, 2H), 4.64 (s, 2H), 7.02 (br s, 1H), 7.07-7.10 (m, 2H), 7.18-7.25 (m, 2H), 7.47 (m, 1H), 7.58 (d, J = 6.3 Hz, 1H), 7.72 (d, J = 6.3 Hz, 1H), 7.91 (dd, J = 8.1, 1.7 Hz, 1H), 8.28 (d, J = 8.1 Hz, 1H), 8.57 (d, J = 1.7 Hz, 1H), 10.17 (s, 1H), 10.23 (s, 1H) |
| N-(2-t-Butoxycarbonylaminophenyl)-5-[3-(2,3-dihydrobenzo[1,4]dioxin-6-yl)-1-[2-(4-methylpiperazin-1-yl)ethyl]ureidomethyl]pyridine-2-carboxylic acid amide (Reference Compound No. 6-55)<br>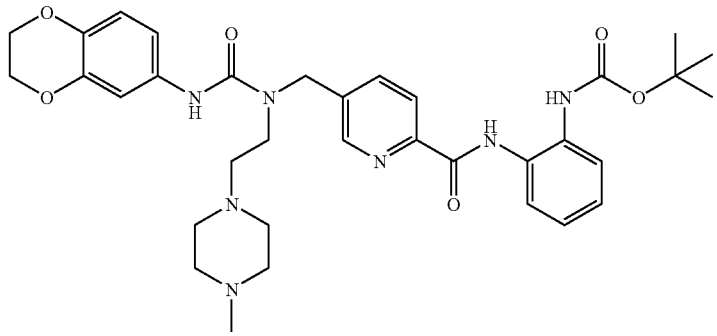 | $^1$H-NMR (400 MHz, CDCl$_3$) δ 1.52 (s, 9H), 2.31 (s, 3H), 2.52 (br s, 4H), 2.56 (t, J = 4.2 Hz, 2H), 2.64 (br s, 4H), 3.34 (t, J = 4.2 Hz, 2H), 4.22-4.26 (m, 4H), 4.64 (s, 2H), 6.80 (d, J = 8.7 Hz, 1H), 6.88 (dd, J = 8.7, 2.6 Hz, 1H), 7.03 (d, J = 2.6 Hz, 1H), 7.05 (br s, 1H), 7.18-7.25 (m, 2H), 7.59 (d, J = 6.8 Hz, 1H), 7.71 (d, J = 6.8 Hz, 1H), 7.92 (dd, J = 8.1, 2.1 Hz, 1H), 8.26 (d, J = 8.1 Hz, 1H), 8.56 (d, J = 2.1 Hz, 1H), 9.86 (s, 1H), 10.16 (s, 1H) |

| | |
|---|---|
| N-(2-t-Butoxycarbonylaminophenyl)-5-[3-(3-fluorophenyl)-1-[3-(4-methylpiperazin-1-yl)propyl]ureidomethyl]pyridine-2-carboxylic acid amide (Reference Compound No. 6-56)<br />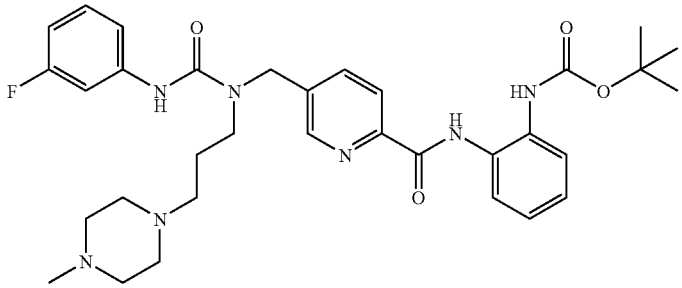 | $^1$H-NMR (400 MHz, CDCl$_3$) δ 1.51 (s, 9H), 1.79 (m, 2H), 2.29 (s, 3H), 2.46 (br s, 4H), 2.48 (t, J = 5.7 Hz, 2H), 2.52 (br s, 4H), 3.37 (t, J = 5.7 Hz, 2H), 4.64 (s, 2H), 6.78 (m, 1H), 7.04 (br s, 1H), 7.17-7.28 (m, 4H), 7.38 (m, 1H), 7.59 (d, J = 6.6 Hz, 1H), 7.70 (d, J = 6.6 Hz, 1H), 7.92 (dd, J = 8.1, 2.2 Hz, 1H), 8.25 (d, J = 8.1 Hz, 1H), 8.58 (d, J = 2.2 Hz, 1H), 9.20 (s, 1H), 10.16 (s, 1H) |
| N-(2-t-Butoxycarbonylaminophenyl)-5-[3-(3,4-difluorophenyl)-1-[3-(4-methylpiperazin-1-yl)propyl]ureidomethyl]pyridine-2-carboxylic acid amide (Reference Compound No. 6-57)<br />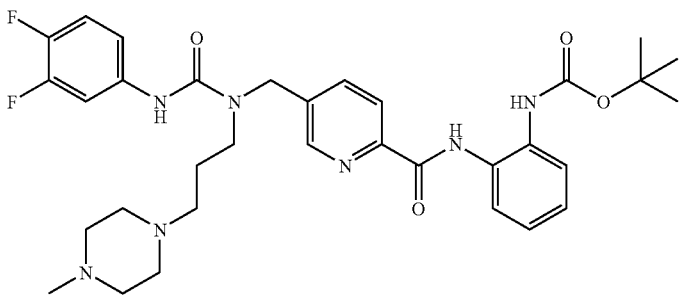 | $^1$H-NMR (500 MHz, CDCl$_3$) δ 1.51 (s, 9H), 1.79 (m, 2H), 2.26 (s, 3H), 2.40 (br s, 4H), 2.48 (t, J = 5.7 Hz, 2H), 2.49 (br s, 4H), 3.36 (t, J = 5.7 Hz, 2H), 4.62 (s, 2H), 7.03 (br s, 1H), 7.05-7.11 (m, 2H), 7.18-7.24 (m, 2H), 7.46 (m, 1H), 7.59 (d, J = 6.7 Hz, 1H), 7.70 (d, J = 6.7 Hz, 1H), 7.91 (dd, J = 7.9, 2.1 Hz, 1H), 8.25 (d, J = 7.9 Hz, 1H), 8.57 (d, J= 2.1 Hz, 1H), 9.31 (s, 1H), 10.15 (s, 1H) |
| N-(2-t-Butoxycarbonylaminophenyl)-5-[3-(2,3-dihydrobenzo[1,4]dioxin-6-yl)-1-[3-(4-methylpiperazin-1-yl)propyl]ureidomethyl]pyridine-2-carboxylic acid amide (Reference Compound No. 6-58)<br />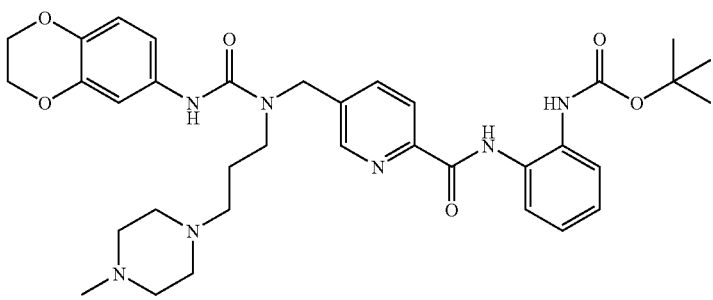 | $^1$H-NMR (400 MHz, CDCl$_3$) δ 1.51 (s, 9H), 1.76 (m, 2H), 2.24 (s, 3H), 2.39 (br s, 4H), 2.47 (t, J = 5.6 Hz, 2H), 2.48 (br s, 4H), 3.35 (t, J = 5.6 Hz, 2H), 4.24-4.25 (m, 4H), 4.62 (s, 2H), 6.78-6.86 (m, 2H), 7.02 (d, J = 2.2 Hz, 1H), 7.07 (br s, 1H), 7.17-7.24 (m, 2H), 7.60 (d, J = 6.6 Hz, 1H), 7.68 (d, J = 6.6 Hz, 1H), 7.93 (d, J = 8.1 Hz, 1H), 8.24 (d, J = 8.1 Hz, 1H), 8.56 (s, 1H), 9.06 (s, 1H), 10.14 (s, 1H) |
| N-(2-t-Butoxycarbonylaminophenyl)-5-[3-(3-fluorophenyl)-1-[4-(pyrrolidin-1-yl)butyl]ureidomethyl]pyridine-2-carboxylic acid amide (Reference Compound No. 6-59)<br />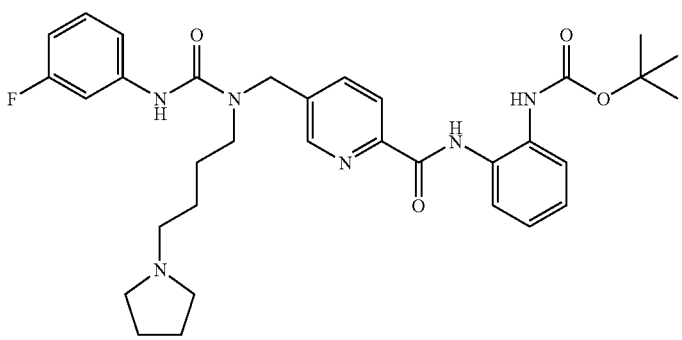 | $^1$H-NMR (400 MHz, CDCl$_3$) δ 1.51 (s, 9H), 1.56 (m, 2H), 1.71-1.78 (m, 6H), 2.49-2.53 (m, 6H), 3.30 (t, J = 8.3 Hz, 2H), 4.69 (s, 2H), 6.78 (m, 1H), 7.05 (m, 1H), 7.07 (br s, 1H), 7.19-7.28 (m, 4H), 7.34 (s, 1H), 7.59 (d, J = 6.8 Hz, 1H), 7.71 (d, J = 6.8 Hz, 1H), 7.89 (dd, J = 8.1, 2.2 Hz, 1H), 8.26 (d, J = 8.1 Hz, 1H), 8.57 (d, J = 2.2 Hz, 1H), 10.17 (s, 1H) |

N-(2-t-Butoxycarbonylaminophenyl)-5-[3-(3,4-difluorophenyl)-1-[4-(pyrrolidin-1-yl)butyl]ureidomethyl]pyridine-2-carboxylic acid amide
(Reference Compound No. 6-60)

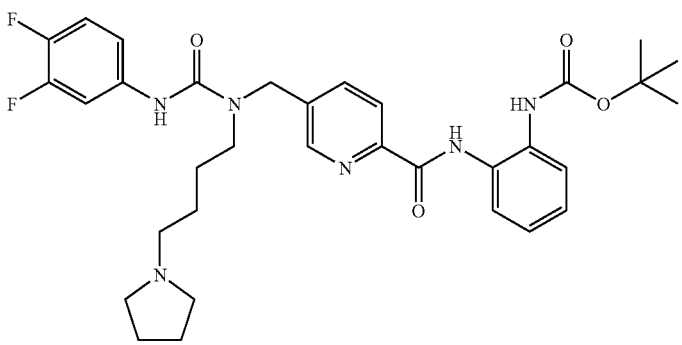

$^1$H-NMR (400 MHz, CDCl$_3$)
δ 1.51 (s, 9H), 1.55 (m, 2H), 1.66-1.77 (m, 6H), 2.48-2.54 (m, 6H), 3.28 (t, J = 8.2 Hz, 2H), 4.67 (s, 2H), 6.97 (m, 1H), 7.07 (m, 1H), 7.08 (br s, 1H), 7.18-7.25 (m, 2H), 7.34 (m, 1H), 7.55 (s, 1H), 7.58 (d, J = 7.0 Hz, 1H), 7.71 (d, J = 7.0 Hz, 1H), 7.88 (dd, J = 8.1, 2.1 Hz, 1H), 8.26 (d, J = 8.1 Hz, 1H), 8.56 (d, J = 2.1 Hz, 1H), 10.17 (s, 1H)

N-(2-t-Butoxycarbonylaminophenyl)-5-[3-(2,3-dihydrobenzo[1,4]dioxin-6-yl)-1-[4-(pyrrolidin-1-yl)butyl]ureidomethyl]pyridine-2-carboxylic acid amide
(Reference Compound No. 6-61)

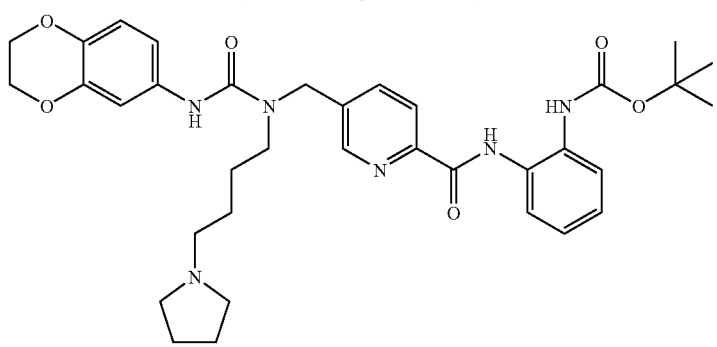

$^1$H-NMR (400 MHz, CDCl$_3$)
δ 1.52 (s, 9H), 1.53 (m, 2H), 1.64-1.68 (m, 4H), 1.72 (t, J = 8.3 Hz, 2H), 2.46-2.53 (m, 6H), 3.27 (t, J = 8.3 Hz, 2H), 4.23-4.24 (m, 4H), 4.67 (s, 2H), 6.75 (dd, J = 8.3, 2.2 Hz, 1H), 6.79 (d, J = 8.3 Hz, 1H), 6.89 (d, J = 2.2 Hz, 1H), 7.08 (br s, 1H), 7.17-7.25 (m, 2H), 7.37 (s, 1H), 7.60 (d, J = 7.1 Hz, 1H), 7.70 (d, J = 7.1 Hz, 1H), 7.89 (dd, J = 8.1, 2.0 Hz, 1H), 8.25 (d, J = 8.1 Hz, 1H), 8.56 (d, J = 2.0 Hz, 1H), 10.16 (s, 1H)

N-(2-t-Butoxycarbonylaminophenyl)-5-[1-(2-diethylaminoethyl)-3-(3-fluorophenyl)ureidomethyl]pyridine-2-carboxylic acid amide
(Reference Compound No. 6-62)

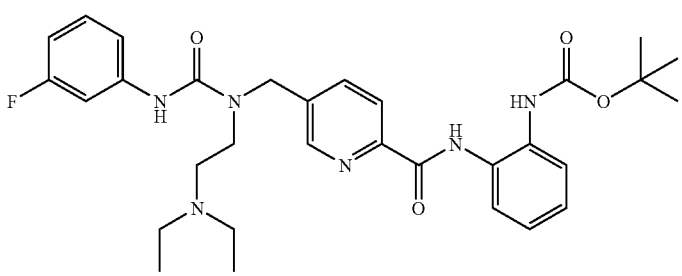

$^1$H-NMR (400 MHz, CDCl$_3$)
δ 1.10 (t, J = 7.2 Hz, 6H), 1.52 (s, 9H), 2.61 (t, J = 4.0 Hz, 2H), 2.68 (q, J = 7.2 Hz, 4H), 3.35 (t, J = 4.0 Hz, 2H), 4.66 (s, 2H), 6.69 (m, 1H), 7.02 (m, 1H), 7.02 (br s, 1H), 7.18-7.29 (m, 4H), 7.59 (d, J = 7.1 Hz, 1H), 7.72 (d, J = 7.1 Hz, 1H), 7.92 (dd, J = 8.1, 2.0 Hz, 1H), 8.27 (d, J = 8.1 Hz, 1H), 8.58 (d, J = 2.0 Hz, 1H), 10.17 (s, 1H), 11.23 (s, 1H)

N-(2-t-Butoxycarbonylaminophenyl)-5-
[1-(2-diethylaminoethyl)-3-
(3,4-difluorophenyl)ureidomethyl]pyridine-
2-carboxylic acid amide
(Reference Compound No. 6-63)

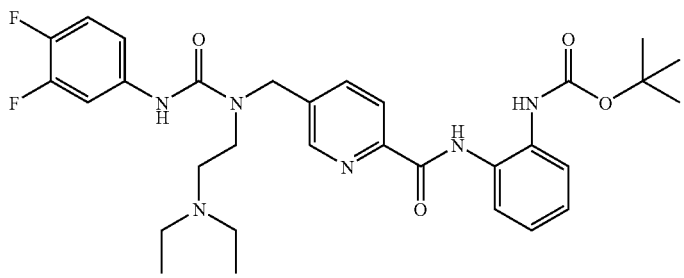

$^1$H-NMR (500 MHz, CDCl$_3$)
δ 1.09 (t, J = 7.1 Hz, 6H), 1.52
(s, 9H), 2.61 (t, J = 4.3 Hz, 2H),
2.67 (q, J = 7.1 Hz, 4H), 3.35
(t, J = 4.3 Hz, 2H), 4.65 (s, 2H),
6.92 (m, 1H), 7.03 (br s, 1H),
7.05 (m, 1H), 7.19-7.24 (m,
2H), 7.39 (m, 1H), 7.58 (d, J =
6.7 Hz, 1H), 7.72 (d, J = 6.7
Hz, 1H), 7.91 (dd, J = 7.9, 2.1
Hz, 1H), 8.28 (d, J = 7.9 Hz,
1H), 8.58 (d, J = 2.1 Hz, 1H),
10.17 (s, 1H), 11.23 (s, 1H)

N-(2-t-Butoxycarbonylaminophenyl)-5-
[1-(2-diethylaminoethyl)-3-
(2,3-dihydrobenzo[1,4]dioxin-6-yl)ureidomethyl]pyridine-
2-carboxylic acid amide
(Reference Compound No. 6-64)

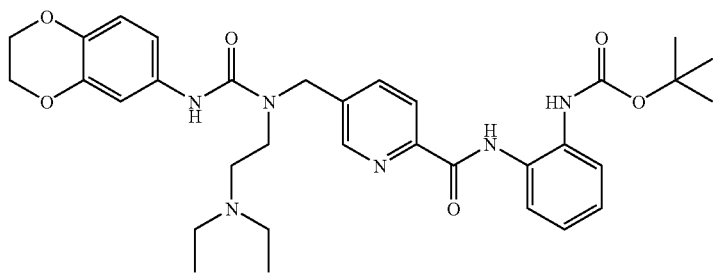

$^1$H-NMR (400 MHz, CDCl$_3$)
δ 1.08 (t, J = 7.2 Hz, 6H), 1.52
(s, 9H), 2.57 (t, J = 4.0 Hz, 2H),
2.64 (q, J = 7.2 Hz, 4H), 3.33
(t, J = 4.0 Hz, 2H), 4.21-4.25
(m, 4H), 4.65 (s, 2H), 6.80 (d, J =
8.5 Hz, 1H), 6.82 (dd, J = 8.5,
2.0 Hz, 1H), 6.93 (d, J = 2.0
Hz, 1H), 7.05 (br s, 1H),
7.17-7.25 (m, 2H), 7.60 (d, J =
6.8 Hz, 1H), 7.71 (d, J = 6.8
Hz, 1H), 7.93 (dd, J = 8.1, 2.2
Hz, 1H), 8.26 (d, J = 8.1 Hz,
1H), 8.57 (d, J = 2.2 Hz, 1H),
10.16 (s, 1H), 10.79 (s, 1H)

N-(2-t-Butoxycarbonylaminophenyl)-5-
[3-(2,3-dihydrobenzo[1,4]dioxin-6-yl)-1-
(4-dimethylaminobutyl)ureidomethyl]pyridine-
2-carboxylic acid amide
(Reference Compound No. 6-65)

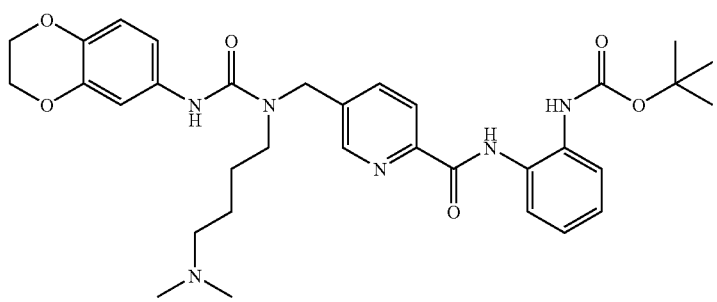

$^1$H-NMR (500 MHz, CDCl$_3$)
δ 1.52 (s, 9H), 1.54 (m, 2H),
1.69 (m, 2H), 2.21 (s, 6H), 2.35
(t, J = 6.4 Hz, 2H), 3.23 (t, J =
8.2 Hz, 2H), 4.23 (br s, 4H),
4.68 (s, 2H), 6.78 (d, J = 2.0
Hz, 1H), 6.79 (d, J = 0.8 Hz,
1H), 6.90 (dd, J = 2.0, 0.8 Hz,
1H), 7.08 (br s, 1H), 7.18-7.24
(m, 2H), 7.60 (d, J = 5.5 Hz,
1H), 7.70 (d, J = 6.2 Hz, 1H),
7.90 (dd, J = 8.2, 2.1 Hz, 1H),
8.25 (d, J = 8.2 Hz, 1H), 8.56
(d, J = 2.1 Hz, 1H), 10.16 (s, 1H)

N-(2-t-Butoxycarbonylaminophenyl)-5-
[1-(4-dimethylaminobutyl)-3-
(3-fluorophenyl)ureidomethyl]pyridine-
2-carboxylic acid amide
(Reference Compound No. 6-66)

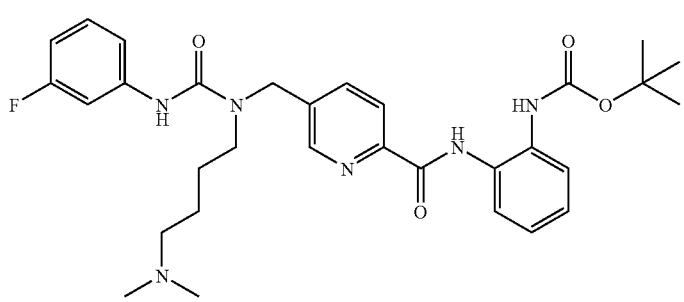

$^1$H-NMR (500 MHz, CDCl$_3$)
δ 1.52 (s, 9H), 1.55 (m, 2H),
1.72 (m, 2H), 2.24 (s, 6H), 2.36
(t, J = 6.5 Hz, 2H), 3.26 (t, J =
8.4 Hz, 2H), 4.69 (s, 2H), 6.77
(tdd, J = 8.4, 2.4, 0.8 Hz, 1H),
7.06 (d, J = 8.4 Hz, 1H), 7.07
(br s, 1H), 718-724 (m, 4H),
7.60 (d, J = 6.7 Hz, 1H), 7.70
(d, J = 6.1 Hz, 1H), 7.90 (dd, J =
8.1, 2.1 Hz, 1H), 7.99 (s, 1H),
8.26 (d, J = 8.1 Hz, 1H), 8.55
(d, J = 2.1 Hz, 1H), 10.17 (s, 1H)

N-(2-t-Butoxycarbonylaminophenyl)-5-
[1-(2-dimethylaminoethyl)-3-
(3-methylphenyl)ureidomethyl]pyridine-
2-carboxylic acid amide
(Reference Compound No. 6-67)

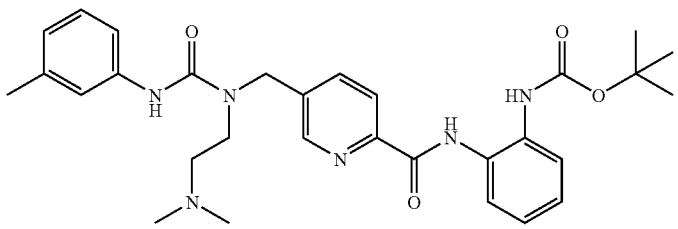

$^1$H-NMR (500 MHz, CDCl$_3$)
δ 1.52 (s, 9H), 2.34 (s, 3H),
2.40 (s, 6H), 2.53 (t, J = 4.4 Hz,
2H), 3.33 (t, J = 4.4 Hz, 2H),
4.66 (s, 2H), 6.82 (d, J = 7.3
Hz, 1H), 7.03 (br s, 1H), 7.05
(m, 1H), 7.15-7.24 (m, 3H),
7.29 (s, 1H), 7.59 (d, J = 6.7
Hz, 1H), 7.71 (d, J = 6.7 Hz,
1H), 7.92 (dd, J = 7.9, 2.1 Hz,
1H), 8.27 (d, J = 7.9 Hz, 1H),
8.57 (d, J = 2.1 Hz, 1H), 10.16
(s, 1H), 10.96 (s, 1H)

N-(2-t-Butoxycarbonylaminophenyl)-5-
[3-(3-chlorophenyl)-1-
(2-dimethylaminoethyl)ureidomethyl]pyridine-
2-carboxylic acid amide
(Reference Compound No. 6-68)

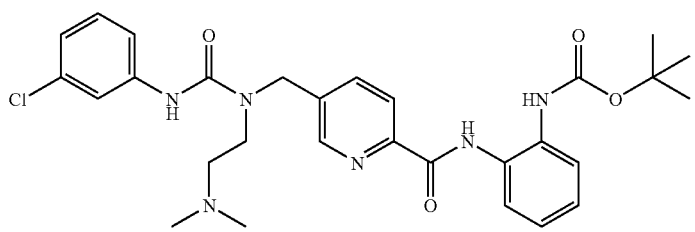

$^1$H-NMR (500 MHz, CDCl$_3$)
δ 1.52 (s, 9H), 2.41 (s, 6H),
2.55 (t, J = 4.3 Hz, 2H), 3.33 (t,
J = 4.3 Hz, 2H), 4.66 (s, 2H),
6.96 (dt, J = 7.3, 1.8 Hz, 1H),
7.02 (br s, 1H), 7.15-7.24 (m,
4H), 7.47 (t, J = 1.8 Hz, 1H),
7.58 (d, J = 5.8 Hz, 1H), 7.72
(d, J = 6.1 Hz, 1H), 7.91 (dd, J =
7.9, 2.1 Hz, 1H), 8.27 (d, J =
7.9 Hz, 1H), 8.58 (d, J = 2.1
Hz, 1H), 10.17 (s, 1H), 11.30
(s, 1H)

N-(2-t-Butoxycarbonylaminophenyl)-5-
[1-(2-dimethylaminoethyl)-3-
(pyridin-3-yl)ureidomethyl]pyridine-
2-carboxylic acid amide
(Reference Compound No. 6-69)

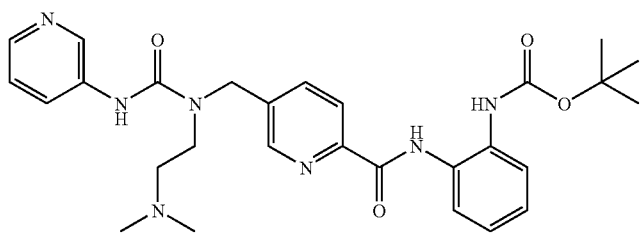

$^1$H-NMR (500 MHz, CDCl$_3$)
δ 1.52 (s, 9H), 2.42 (s, 6H),
2.58 (t, J = 4.3 Hz, 2H), 3.36 (t,
J = 4.3 Hz, 2H), 4.67 (s, 2H),
7.03 (br s, 1H), 7.19-7.26 (m,
3H), 7.58 (d, J = 6.4 Hz, 1H),
7.72 (d, J = 5.8 1H), 7.92
(dd, J = 7.9, 2.0 Hz, 1H), 8.09
(m, 1H), 8.23 (dd, J = 4.7, 1.4
Hz, 1H), 8.28 (d, J = 7.9 Hz,
1H), 8.32 (d, J = 2.4 Hz, 1H),
8.58 (d, J = 2.0 Hz, 1H), 10.17
(s, 1H), 11.53 (s, 1H)

N-(2-t-Butoxycarbonylaminophenyl)-5-
[3-(3-chlorophenyl)-1-
(3-dimethylaminopropyl)ureidomethyl]pyridine-
2-carboxylic acid amide
(Reference Compound No. 6-70)

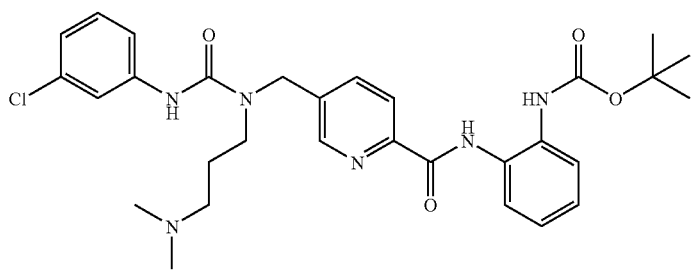

$^1$H-NMR (400 MHz, DMSO-d$_6$)
δ 1.47 (s, 9H), 1.71 (m, 2H),
2.20 (s, 6H), 2.27 (t, J = 6.3 Hz,
2H), 3.35 (m, 2H), 4.63 (s, 2H),
6.99 (ddd, J = 7.8, 2.0, 1.0 Hz,
1H), 7.15 (td, J = 8.1, 1.5 Hz,
1H), 7.19-7.30 (m, 4H), 7.73 (t,
J = 2.1 Hz, 1H), 7.98 (dd, J =
8.1, 1.8 Hz, 1H), 8.02 (dd, J =
8.1, 1.0 Hz, 1H), 8.14 (d, J =
8.1 Hz, 1H), 8.58 (d, J = 1.8
Hz, 1H), 9.13 (br s, 1H), 9.95
(br s, 1H), 10.48 (br s, 1H)

| | |
|---|---|
| N-(2-t-Butoxycarbonylaminophenyl)-5-[1-(3-dimethylaminopropyl)-3-(3-methylphenyl)ureidomethyl]pyridine-2-carboxylic acid amide (Reference Compound No. 6-71) 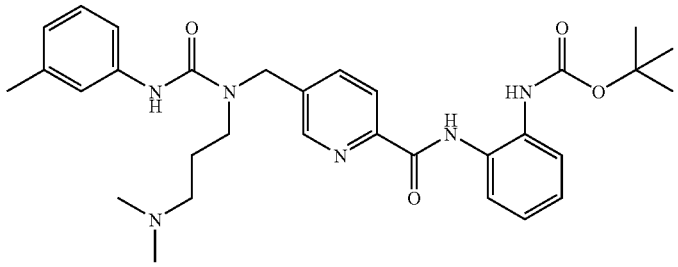 | $^1$H-NMR (400 MHz, DMSO-d$_6$) δ 1.47 (s, 9H), 1.70 (t, J = 6.1 Hz, 2H), 2.20 (s, 6H), 2.26 (s, 3H), 2.28 (m, 2H), 3.35 (m, 2H), 4.62 (s, 2H), 6.76 (d, J = 7.3 Hz, 1H), 7.11-7.28 (m, 6H), 7.98 (dd, J = 8.1, 1.8 Hz, 1H), 8.01 (dd, J = 8.1, 1.0 Hz, 1H), 8.14 (d, J = 8.0 Hz, 1H), 8.58 (d, J = 1.8 Hz, 1H), 9.12 (br s, 1H), 9.61 (br s, 1H), 10.47 (br s, 1H) |
| N-(2-t-Butoxycarbonylaminophenyl)-5-[3-(4-dimethylaminophenyl)-1-[4-(morpholin-4-yl)butyl]ureidomethyl]pyridine-2-carboxylic acid amide (Reference Compound No. 6-72) 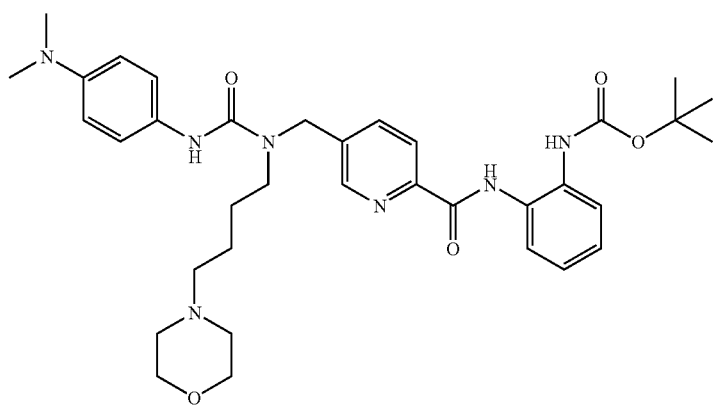 | $^1$H-NMR (500 MHz, CDCl$_3$) δ 1.52 (s, 9H), 1.54 (m, 2H), 1.70 (m, 2H), 2.39 (t, J = 6.9 Hz, 2H), 2.43 (m, 4H), 2.92 (s, 6H), 3.30 (t, J = 8.1 Hz, 2H), 3.63 (t, J = 4.3 Hz, 4H), 4.68 (s, 2H), 6.61 (s, 1H), 6.71 (d, J = 8.9 Hz, 2H), 7.06 (br s, 1H), 7.17 (d, J = 8.9 Hz, 2H), 7.19-7.22 (m, 2H), 7.59 (d, J = 5.8 Hz, 1H), 7.71 (d, J = 6.1 Hz, 1H), 7.90 (dd, 4 = 7.9, 1.8 Hz, 1H), 8.27 (d, J = 7.9 Hz, 1H), 8.56 (d, J = 1.8 Hz, 1H), 10.16 (s, 1H) |
| N-(2-t-Butoxycarbonylaminophenyl)-5-[3-(3-fluorophenyl)-1-[4-(morpholin-4-yl)butyl]ureidomethyl]pyridine-2-carboxylic acid amide (Reference Compound No. 6-73) 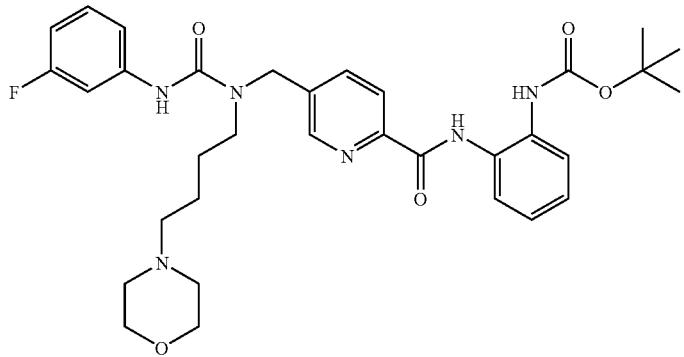 | $^1$H-NMR (500 MHz, CDCl$_3$) δ 1.52 (s, 9H), 1.55 (m, 2H), 1.71 (m, 2H), 2.39 (t, J = 7.0 Hz, 2H), 2.43 (m, 4H), 3.33 (t, J = 7.9 Hz, 2H), 3.67 (t, J = 4.7 Hz, 4H), 4.68 (s, 2H), 6.70 (s, 1H), 6.78 (td, J = 8.4, 2.4 Hz, 1H), 7.01 (dd, J = 7.9, 1.8 Hz, 1H), 7.05 (br s, 1H), 7.19-7.25 (m, 3H), 7.31 (dt, J = 10.8, 2.4 Hz, 1H), 7.56 (d, J = 6.1 Hz, 1H), 7.73 (d, J = 5.2 Hz, 1H), 7.87 (dd, J = 7.9, 2.1 Hz, 1H), 8.26 (d, J = 7.9 Hz, 1H), 8.55 (d, J = 2.1 Hz, 1H), 10.18 (s, 1H) |

| | |
|---|---|
| N-(2-t-Butoxycarbonylaminophenyl)-5-[1-[4-(morpholin-4-yl)butyl]-3-(thiophen-3-yl)ureidomethyl]pyridine-2-carboxylic acid amide (Reference Compound No. 6-74) 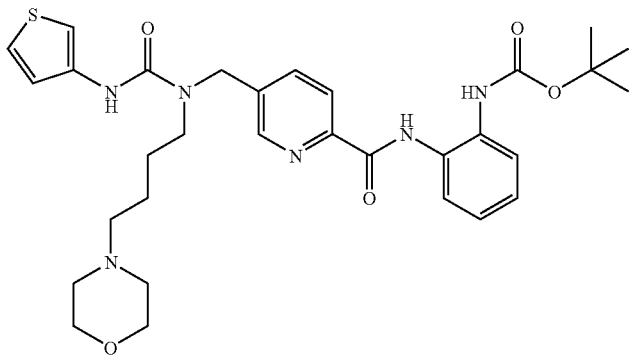 | $^1$H-NMR (500 MHz, CDCl$_3$) δ 1.51 (s, 9H), 1.54 (m, 2H), 1.70 (m, 2H), 2.38 (t, J = 7.0 Hz, 2H), 2.43 (t, J = 4.5 Hz, 4H), 3.31 (t, J = 7.9 Hz, 2H), 3.67 (t, J = 4.5 Hz, 4H), 4.69 (s, 2H), 6.86 (s, 1H), 6.98 (dd, J = 5.2, 1.5 Hz, 1H), 7.05 (br s, 1H), 7.20-7.25 (m, 3H), 7.27 (dd, J = 3.2, 1.5 Hz, 1H), 7.58 (d, J = 6.1 Hz, 1H), 7.72 (d, J = 6.4 Hz, 1H), 7.87 (dd, J = 7.9, 2.0 Hz, 1H), 8.26 (d, J = 7.9 Hz, 1H), 8.55 (d, J = 2.0 Hz, 1H), 10.16 (s, 1H) |
| N-(2-t-Butoxycarbonylaminophenyl)-5-[3-(2,3-dihydrobenzo[1,4]dioxin-6-yl)-1-[4-(morpholin-4-yl)butyl]ureidomethyl]pyridine-2-carboxylic acid amide (Reference Compound No. 6-75) 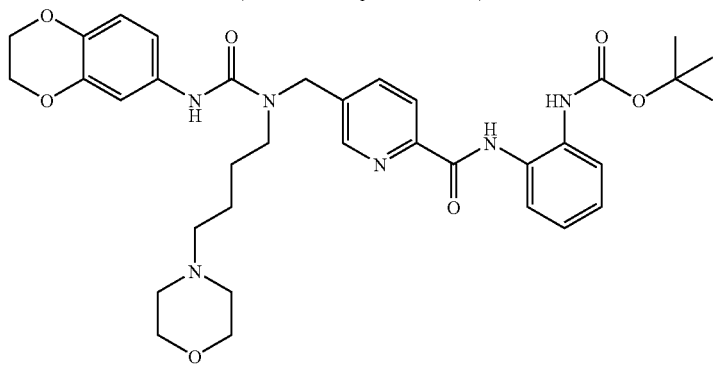 | $^1$H-NMR (500 MHz, CDCl$_3$) δ 1.52 (s, 9H), 1.54 (m, 2H), 1.70 (m, 2H), 2.39 (t, J = 7.0 Hz, 2H), 2.43 (m, 4H), 3.29 (t, J = 7.9 Hz, 2H), 3.64 (t, J = 4.6 Hz, 4H), 4.24 (br s, 4H), 4.67 (s, 2H), 6.61 (s, 1H), 6.75 (dd, J = 8.6, 2.4 Hz, 1H), 6.80 (d, J = 8.6 Hz, 1H), 6.92 (d, J = 2.4 Hz, 1H), 7.05 (br s, 1H), 7.19-7.24 (m, 2H), 7.59 (d, J = 6.1 Hz, 1H), 7.72 (d, J = 5.5 Hz, 1H), 7.89 (dd, J = 7.9, 1.8 Hz, 1H), 8.27 (d, J = 7.9 Hz, 1H), 8.56 (d, J = 1.8 Hz, 1H), 10.16 (s, 1H) |
| N-(2-t-Butoxycarbonylaminophenyl)-5-[1-[4-(morpholin-4-yl)butyl]-3-(pyridin-3-yl)ureidomethyl]pyridine-2-carboxylic acid amide (Reference Compound No. 6-76) 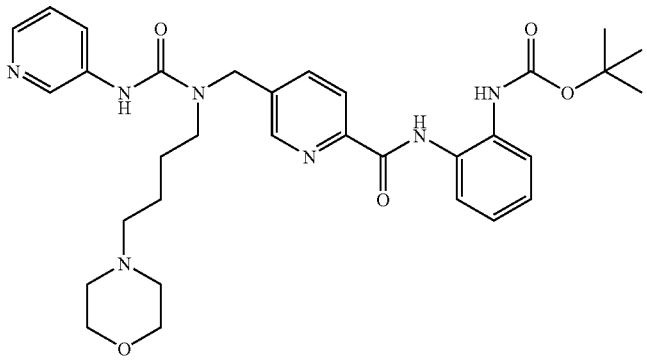 | $^1$H-NMR (500 MHz, CDCl$_3$) δ 1.51 (s, 9H), 1.57 (m, 2H), 1.74 (m, 2H), 2.41 (t, J = 7.0 Hz, 2H), 2.43 (t, J = 4.6 Hz, 4H), 3.36 (t, J = 8.1 Hz, 2H), 3.66 (t, J = 4.6 Hz, 4H), 4.70 (s, 2H), 6.86 (s, 1H), 7.05 (br s, 1H), 7.19-7.25 (m, 2H), 7.28 (dd, J = 8.7, 4.6 Hz, 1H), 7.55 (d, J = 6.4 Hz, 1H), 7.74 (d, J = 5.8 Hz, 1H), 7.87 (dd, J = 8.0, 2.0 Hz, 1H), 7.98 (ddd, J = 8.7, 2.4, 1.3 Hz, 1H), 8.26 (d, J = 8.0 Hz, 1H), 8.34 (dd, J = 4.6, 1.3 Hz, 1H), 8.45 (d, J = 2.4 Hz, 1H), 8.56 (d, J = 2.0 Hz, 1H), 10.19 (s, 1H) |

| | |
|---|---|
| N-(2-t-Butoxycarbonylaminophenyl)-5-[1-[4-(morpholin-4-yl)butyl]-3-phenethylureidomethyl]pyridine-2-carboxylic acid amide (Reference Compound No. 6-77) 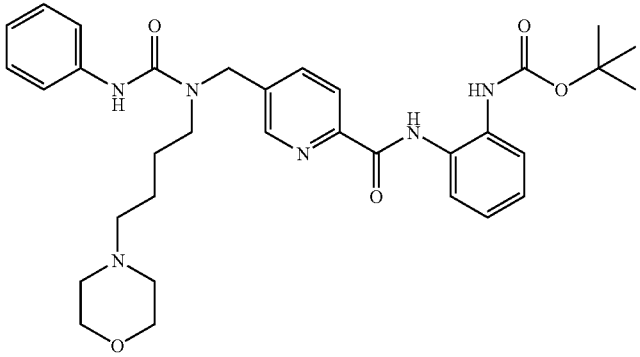 | $^1$H-NMR (500 MHz, CDCl$_3$) δ 1.40 (m, 2H), 1.49 (m, 2H), 1.52 (s, 9H), 2.25 (t, J = 7.0 Hz, 2H), 2.33 (m, 4H), 2.86 (t, J = 6.7 Hz, 2H), 3.09 (t, J = 7.9 Hz, 2H), 3.55 (td, J = 6.7, 5.7 Hz, 2H), 3.65 (t, J = 4.6 Hz, 4H), 4.58 (s, 2H), 4.75 (t, J = 5.7 Hz, 1H), 7.07 (br s, 1H), 7.17 (m, 2H), 7.19-7.25 (m, 3H), 7.27-7.30 (m, 2H), 7.59 (d, J = 6.7 Hz, 1H), 7.71 (d, J = 6.4 Hz, 1H), 7.76 (dd, J = 8.1, 1.8 Hz, 1H), 8.23 (d, J = 8.1 Hz, 1H), 8.47 (d, J = 1.8 Hz, 1H), 10.15 (s, 1H) |
| N-(2-t-Butoxycarbonylaminophenyl)-5-[3-(3-methoxyphenyl)-1-[4-(morpholin-4-yl)butyl]ureidomethyl]pyridine-2-carboxylic acid amide (Reference Compound No. 6-78) 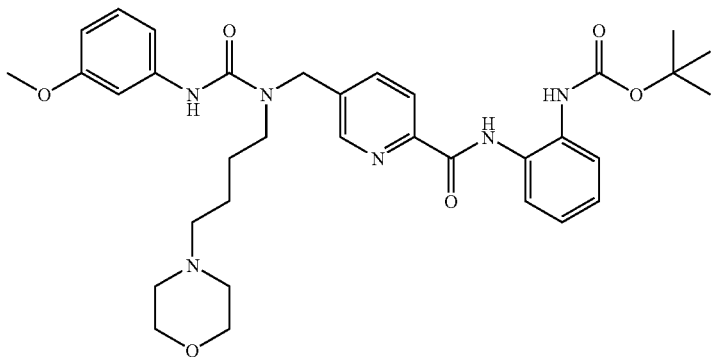 | $^1$H-NMR (500 MHz, CDCl$_3$) δ 1.51 (s, 9H), 1.54 (m, 2H), 1.71 (m, 2H), 2.38 (t, J = 7.0 Hz, 2H), 2.42 (m, 4H), 3.33 (t, J = 7.9 Hz, 2H), 3.67 (t, J = 4.6 Hz, 4H), 3.81 (s, 3H), 4.70 (s, 2H), 6.59 (s, 1H), 6.64 (dd, J = 8.0, 2.1 Hz, 1H), 6.84 (dd, J = 8.0, 2.1 Hz, 1H), 7.04 (br s, 1H), 7.11 (t, J = 2.1 Hz, 1H), 7.18-7.24 (m, 2H), 7.20 (t, J = 8.0 Hz, 1H), 7.58 (d, J = 6.1 Hz, 1H), 7.73 (d, J = 6.1 Hz, 1H), 7.89 (dd, J = 8.1, 2.0 Hz, 1H), 8.28 (d, J = 8.1 Hz, 1H), 8.57 (d, J = 2.0 Hz, 1H), 10.16 (s, 1H) |
| N-(2-t-Butoxycarbonylaminophenyl)-5-[3-(2,3-dihydrobenzo[1,4]dioxin-6-yl)-1-(5-dimethylaminopentyl)ureidomethyl]pyridine-2-carboxylic acid amide (Reference Compound No. 6-79) 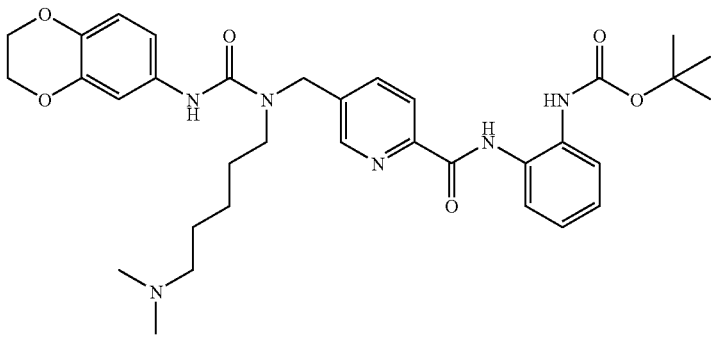 | $^1$H-NMR (500 MHz, CDCl$_3$) δ 1.38 (m, 2H), 1.50 (m, 2H), 1.52 (s, 9H), 1.67 (m, 2H), 2.20 (s, 6H), 2.25 (t, J = 7.0 Hz, 2H), 3.27 (t, J = 7.8 Hz, 2H), 4.21-4.27 (m, 4H), 4.67 (s, 2H), 6.53 (s, 1H), 6.74 (dd, J = 8.7, 2.4 Hz, 1H), 6.80 (d, J = 8.7 Hz, 1H), 6.95 (d, J = 2.4 Hz, 1H), 7.08 (br s, 1H), 7.18-7.24 (m, 2H), 7.59 (d, J = 6.1 Hz, 1H), 7.70 (d, J = 6.7 Hz, 1H), 7.87 (dd, J = 7.9, 2.1 Hz, 1H), 8.26 (d, J = 7.9 Hz, 1H), 8.55 (d, J = 2.1 Hz, 1H), 10.16 (s, 1H) |

| | |
|---|---|
| N-(2-t-Butoxycarbonylaminophenyl)-5-[1-(5-dimethylaminopentyl)-3-(fluorophenyl)ureidomethyl]pyridine-2-carboxylic acid amide (Reference Compound No. 6-80) 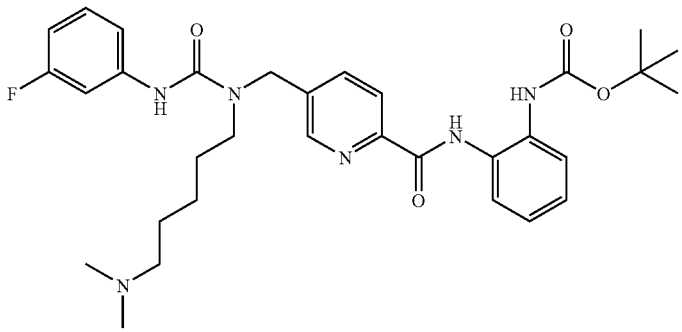 | $^1$H-NMR (500 MHz, CDCl$_3$) δ 1.40 (m, 2H), 1.50 (m, 2H), 1.52 (s, 9H), 1.68 (m, 2H), 2.20 (s, 6H), 2.26 (t, J = 7.0 Hz, 2H), 3.31 (t, J = 7.8 Hz, 2H), 4.69 (s, 2H), 6.73 (s, 1H), 6.78 (td, J = 8.4, 2.3 Hz, 1H), 7.02 (m, 1H), 7.06 (br s, 1H), 7.18-7.23 (m, 3H), 7.34 (dt, J = 11.1, 2.3 Hz, 1H), 7.56 (d, J = 6.1 Hz, 1H), 7.71 (d, J = 5.8 Hz, 1H), 7.87 (dd, J = 7.9, 1.8 Hz, 1H), 8.26 (d, J = 7.9 Hz, 1H), 8.56 (d, J = 1.8 Hz, 1H), 10.18 (s, 1H) |
| N-(2-t-Butoxycarbonylaminophenyl)-5-[1-(3-dimethylaminopropyl)-3-(pyridin-3-yl)ureidomethyl]pyridine-2-carboxylic acid amide (Reference Compound No. 6-81) 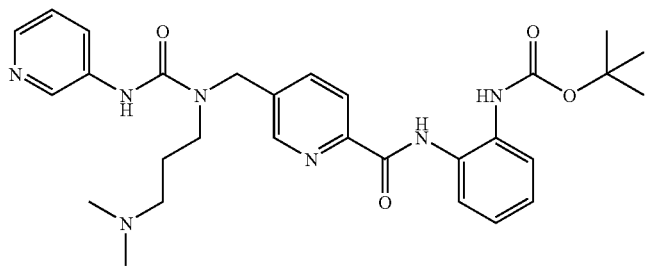 | $^1$H-NMR (500 MHz, DMSO-d$_6$) δ 1.47 (s, 9H), 1.71 (m, 2H), 2.20 (s, 6H), 2.28 (t, J = 6.3 Hz, 2H), 3.38 (t, J = 6.3 Hz, 2H), 4.65 (s, 2H), 7.15 (t, J = 8.1 Hz, 1H), 7.23-7.25 (m, 2H), 7.29 dd, J = 8.4, 4.7 Hz, 1H), 7.90 (ddd, J = 8.4, 2.6, 1.5 Hz, 1H), 7.99 (dd, J = 7.9, 2.0 Hz, 1H), 8.01 (d, J = 8.1 Hz, 1H), 8.15 (m, 1H), 8.16 (dd, J = 4.7, 1.5 Hz, 1H), 8.58 (d, J = 2.6 Hz, 1H), 8.59 (d, J = 2.0 Hz, 1H), 9.12 (br s, 1H), 9.93 (br s, 1H), 10.47 (br s, 1H) |
| N-(2-t-Butoxycarbonylaminophenyl)-5-[1-(3-dimethylaminopropyl)-3-(3-nitrophenyl)ureidomethyl]pyridine-2-carboxylic acid amide (Reference Compound No. 6-82) 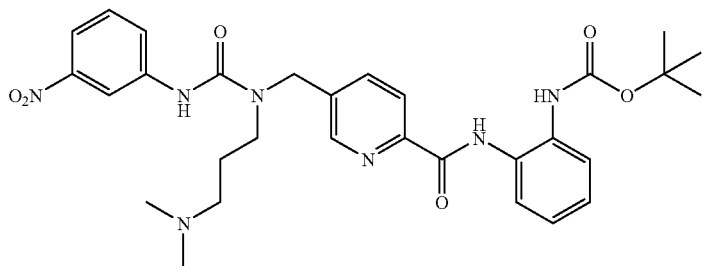 | $^1$H-NMR (400 MHz, DMSO-d$_6$) δ 1.46 (s, 9H), 1.73 (m, 2H), 2.21 (s, 6H), 2.29 (t, J = 6.2 Hz, 2H), 3.39 (t, J = 6.1 Hz, 2H), 4.67 (s, 2H), 7.15 (td, J = 7.8, 1.5 Hz, 1H), 7.23-7.29 (m, 2H), 7.55 (t, J = 8.2 Hz, 1H), 7.71 (dd, J = 7.8, 1.5 Hz, 1H), 7.81 (m, 1H), 7.99-8.02 (m, 2H), 8.15 (d, J = 8.1 Hz, 1H), 8.56 (m, 1H), 8.60 (d, J = 1.2 Hz, 1H), 9.13 (br s, 1H), 10.27 (br s, 1H), 10.48 (br s, 1H) |
| 5-[3-(3-Acetylphenyl)-1-(3-dimethylaminopropyl)ureidomethyl]-N-(2-t-butoxycarbonylaminophenyl)pyridine-2-carboxylic acid amide (Reference Compound No. 6-83) 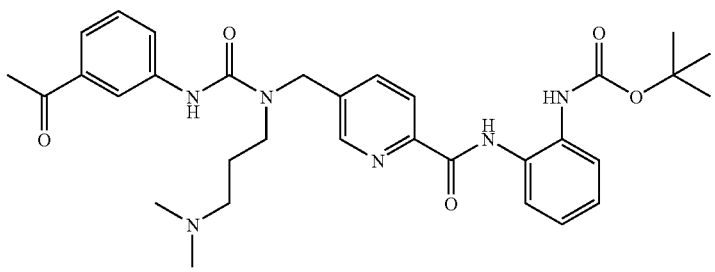 | $^1$H-NMR (400 MHz, DMSO-d$_6$) δ 1.46 (s, 9H), 1.71 (m, 2H), 2.21 (s, 6H), 2.28 (t, J = 6.2 Hz, 2H), 2.56 (s, 3H), 3.38 (t, J = 6.1 Hz, 2H), 4.65 (s, 2H), 7.15 (t, J = 7.6 Hz, 1H), 7.23-7.27 (m, 2H), 7.41 (t, J = 7.8 Hz, 1H), 7.57 (m, 1H), 7.70 (m, 1H), 7.98-8.03 (m, 3H), 8.15 (d, J = 7.8 Hz, 1H), 8.59 (d, J = 1.5 Hz, 1H), 9.12 (br s, 1H), 9.90 (br s, 1H), 10.48 (br s, 1H) |

N-(2-t-Butoxycarbonylaminophenyl)-5-
[1-(3-dimethylaminopropyl)-3-
(3-methylthiophenyl)ureidomethyl]pyridine-
2-carboxylic acid amide
(Reference Compound No. 6-84)

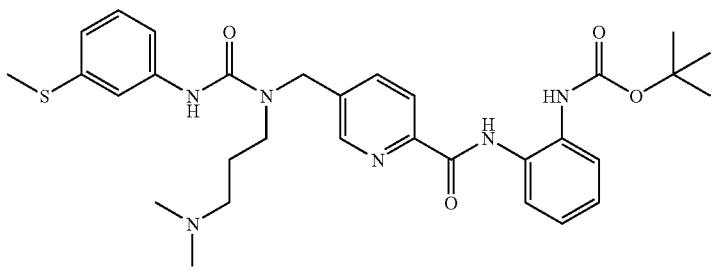

¹H-NMR (400 MHz, DMSO-d₆)
δ 1.47 (s, 9H), 1.70 (m, 2H),
2.20 (s, 6H), 2.27 (t, J = 6.2 Hz,
2H), 2.45 (s, 3H), 3.35 (m, 2H),
4.62 (s, 2H), 6.84 (ddd, J = 7.6,
1.8, 1.1 Hz, 1H), 7.12-7.28 (m,
5H), 7.45 (t, J = 1.8 Hz, 1H),
7.98 (dd, J = 8.1, 1.8 Hz, 1H),
8.01 (d, J = 7.1 Hz, 1H), 8.15
(d, J = 8.1 Hz, 1H), 8.58 (d, J =
1.8 Hz, 1H), 9.13 (br s, 1H),
9.75 (br s, 1H), 10.48 (br s, 1H)

N-(2-t-Butoxycarbonylaminophenyl)-5-
[3-(3-fluorophenyl)-1-
[3-morpholin-4-yl)propyl]ureidomethyl]pyridine-
2-carboxylic acid amide
(Reference Compound No. 6-85)

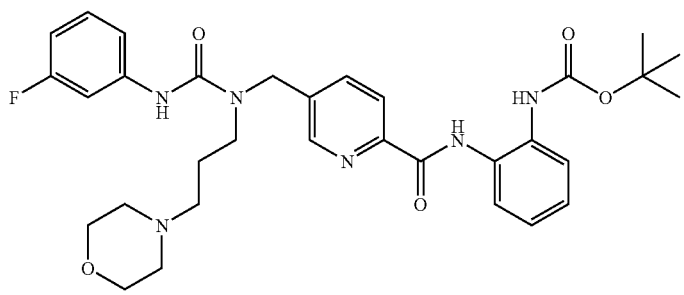

¹H-NMR (400 MHz, CDCl₃)
δ 1.51 (s, 9H), 1.80 (m, 2H),
2.43-2.54 (m, 6H), 3.39 (t, J =
5.6 Hz, 2H), 3.72 (t, J = 4.6 Hz,
4H), 4.65 (s, 2H), 6.79 (tdd, J =
8.4, 2.4, 0.8 Hz, 1H), 7.03 (br s,
1H), 7.13 (m, 1H), 7.17-7.30
(m, 3H), 7.42 (m, 1H), 7.59 (d,
J = 6.3 Hz, 1H), 7.70 (d, J = 7.3
Hz, 1H), 7.92 (dd, J = 8.1, 2.1
Hz, 1H), 8.26 (dd, J = 8.1, 0.5
Hz, 1H), 8.58 (dd, J = 2.1, 0.5
Hz, 1H), 9.05 (s, 1H), 10.16 (s,
1H)

N-(2-t-Butoxycarbonylaminophenyl)-5-
[3-(3-fluoro-4-methylphenyl)-1-
[3-morpholin-4-yl)propyl]ureidomethyl]pyridine-
2-carboxylic acid amide
(Reference Compound No. 6-86)

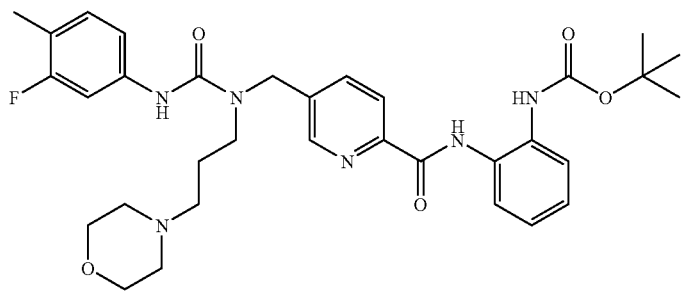

¹H-NMR (400 MHz, CDCl₃)
δ 1.51 (s, 9H), 1.79 (m, 2H),
2.23 (d, J = 1.7 Hz, 3H),
2.44-2.51 (m, 6H), 3.37 (t, J =
5.5 Hz, 2H), 3.69 (t, J = 4.5 Hz,
4H), 4.64 (s, 2H), 7.01 (dd, J =
8.1, 1.7 Hz, 1H), 7.04 (br s,
1H), 7.10 (t, J = 8.1 Hz, 1H),
7.17-7.25 (m, 2H), 7.31 (m,
1H), 7.59 (d, J = 6.1 Hz, 1H),
7.70 (d, J = 6.6 Hz, 1H), 7.92
(dd, J = 8.1, 2.2 Hz, 1H), 8.25
(dd, J = 8.1, 0.7 Hz, 1H), 8.57
(dd, J = 2.2, 0.7 Hz, 1H), 9.01
(s, 1H), 10.15 (s, 1H)

N-(2-t-Butoxycarbonylaminophenyl)-5-
[1-(3-morpholin-4-yl)propyl]-3-
(thiophen-3-yl)ureidomethyl]pyridine-
2-carboxylic acid amide
(Reference Compound No. 6-87)

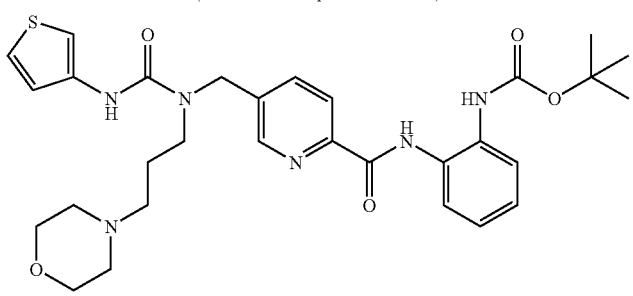

¹H-NMR (400 MHz, CDCl₃)
δ 1.51 (s, 9H), 1.78 (m, 2H),
2.41-2.52 (m, 6H), 3.36 (t, J =
5.6 Hz, 2H), 3.72 (t, J = 4.6 Hz,
4H), 4.65 (s, 2H), 7.05 (br s,
1H), 7.10 (dd, J = 5.1, 1.4 Hz,
1H), 7.17-7.25 (m, 2H), 7.25
(dd, J = 5.1, 3.4 Hz, 1H), 7.31
(dd, J = 3.4, 1.4 Hz, 1H), 7.60
(d, J = 7.1 Hz, 1H), 7.69 (d, J =
6.6 Hz, 1H), 7.92 (dd, J = 8.1,
2.2 Hz, 1H), 8.25 (dd, J = 8.1,
0.7 Hz, 1H), 8.57 (dd, J = 2.2,
0.7 Hz, 1H), 9.25 (s, 1H), 10.15
(s, 1H)

N-(2-t-Butoxycarbonylaminophenyl)-5-
[3-(4-methoxyphenyl)-1-
[4-(morpholin-4-yl)butyl]ureidomethyl]pyridine-
2-carboxylic acid amide
(Reference Compound No. 6-88)

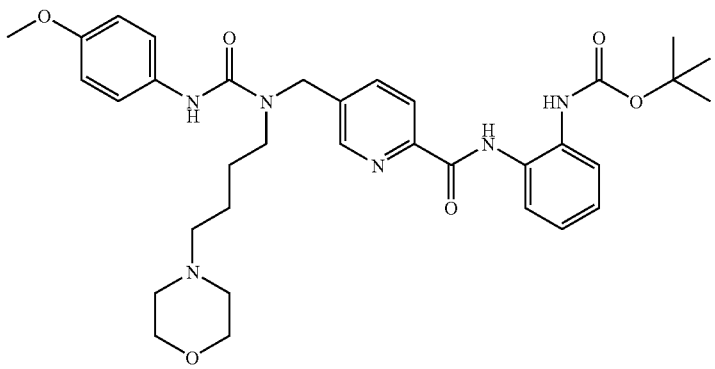

$^1$H-NMR (500 MHz, CDCl$_3$)
δ 1.52 (s, 9H), 1.55 (m, 2H),
1.72 (m, 2H), 2.39 (t, J = 6.9
Hz, 2H), 2.42 (m, 4H), 3.31 (t,
J = 7.9 Hz, 2H), 3.63 (t, J = 4.6
Hz, 4H), 3.80 (s, 3H), 4.68 (s,
2H), 6.68 (s, 1H), 6.87 (d, J = 9.2
Hz, 2H), 7.05 (br s, 1H),
7.18-7.24 (m, 2H), 7.23 (d, J =
9.2 Hz, 2H), 7.58 (d, J = 5.8
Hz, 1H), 7.72 (d, J = 6.1 Hz,
1H), 7.89 (dd, J = 7.9, 1.8 Hz,
1H), 8.27 (dd, J = 7.9, 0.6 Hz,
1H), 8.56 (dd, J = 1.8, 0.6 Hz,
1H), 10.16 (s, 1H)

N-(2-t-Butoxycarbonylaminophenyl)-5-
[3-(4-methylphenyl)-1-
[4-(morpholin-4-yl)butyl]ureidomethyl]pyridine-
2-carboxylic acid amide
(Reference Compound No. 6-89)

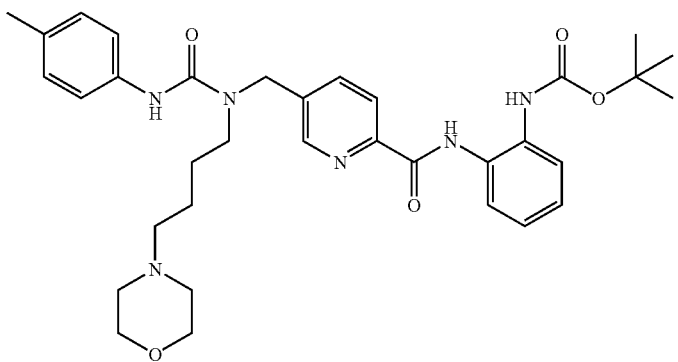

$^1$H-NMR (400 MHz, CDCl$_3$)
δ 1.51 (s, 9H), 1.56 (m, 2H),
1.71 (m, 2H), 2.31 (s, 3H), 2.38
(t, J = 7.0 Hz, 2H), 2.42 (t, J =
4.5 Hz, 4H), 3.32 (t, J = 7.9 Hz,
2H), 3.65 (t, J = 4.5 Hz, 4H),
4.68 (s, 2H), 6.62 (s, 1H), 7.06
(br s, 1H), 7.12 (d, J = 8.1 Hz,
2H), 7.20-7.25 (m, 2H), 7.22 (d,
J = 8.1 Hz, 2H), 7.58 (d, J = 6.6
Hz, 1H), 7.72 (d, J = 6.1 Hz,
1H), 7.89 (dd, J = 8.1, 2.2 Hz,
1H), 8.26 (dd, J = 8.1, 0.7 Hz,
1H), 8.56 (dd, J = 2.2, 0.7 Hz,
1H), 10.16 (s, 1H)

N-(2-t-Butoxycarbonylaminophenyl)-5-
[3-(3,4-dimethylphenyl)-1-
[4-(morpholin-4-yl)butyl]ureidomethyl]pyridine-
2-carboxylic acid amide
(Reference Compound No. 6-90)

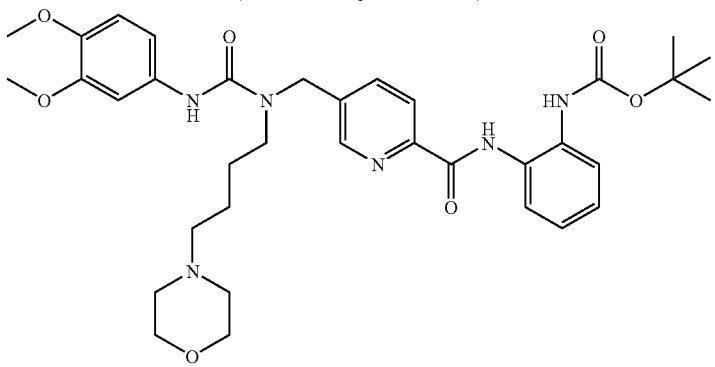

$^1$H-NMR (500 MHz, CDCl$_3$)
δ 1.51 (s, 9H), 1.53 (m, 2H),
1.71 (m, 2H), 2.39 (t, J = 7.0
Hz, 2H), 2.41 (m, 4H), 3.32 (t,
J = 7.9 Hz, 2H), 3.64 (t, J = 4.5
Hz, 4H), 3.86 (s, 3H), 3.90 (s,
3H), 4.70 (s, 2H), 6.64 (s, 1H),
6.71 (dd, J = 8.5, 2.4 Hz, 1H),
6.80 (d, J = 8.5 Hz, 1H), 7.04
(br s, 1H), 7.13 (d, J = 2.4 Hz,
1H), 7.19-7.25 (m, 2H), 7.58 (d,
J = 5.5 Hz, 1H), 7.72 (d, J = 6.1
Hz, 1H), 7.89 (dd, J = 7.9, 2.0
Hz, 1H), 8.28 (d, J = 7.9 Hz,
1H), 8.57 (d, J = 2.0 Hz, 1H),
10.16 (s, 1H)

| | |
|---|---|
| N-(2-t-Butoxycarbonylaminophenyl)-5-[3-(3-ethoxyphenyl)-1-[4-(morpholin-4-yl)butyl]ureidomethyl]pyridine-2-carboxylic acid amide (Reference Compound No. 6-91)<br />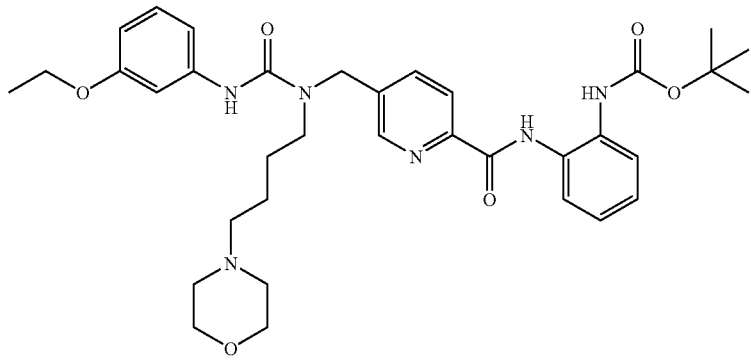 | $^1$H-NMR (400 MHz, CDCl$_3$) δ 1.40 (t, J = 7.0 Hz, 3H), 1.51 (s, 9H), 1.54 (m, 2H), 1.71 (m, 2H), 2.38 (t, J = 7.1 Hz, 2H), 2.42 (t, J = 4.4 Hz, 4H), 3.32 (t, J = 7.8 Hz, 2H), 3.67 (t, J = 4.4 Hz, 4H), 4.03 (q, J = 7.0 Hz, 2H), 4.69 (s, 2H), 6.60 (s, 1H), 6.63 (ddd, J = 8.2, 2.3, 0.9 Hz, 1H), 6.83 (ddd, J = 8.2, 2.3, 0.9 Hz, 1H), 7.06 (br s, 1H), 7.10 (t, J = 2.3 Hz, 1H), 7.17 (t, J = 8.2 Hz, 1H), 7.20-7.23 (m, 2H), 7.57 (d, J = 6.3 Hz, 1H), 7.73 (d, J = 6.3 Hz, 1H), 7.88 (dd, J = 8.1, 2.2 Hz, 1H), 8.26 (dd, J = 8.1, 0.7 Hz, 1H), 8.55 (dd, J = 2.2, 0.7 Hz, 1H), 10.17 (s, 1H) |
| N-(2-t-Butoxycarbonylaminophenyl)-5-[3-(3-methylphenyl)-1-[4-(morpholin-4-yl)butyl]ureidomethyl]pyridine-2-carboxylic acid amide (Reference Compound No. 6-92)<br />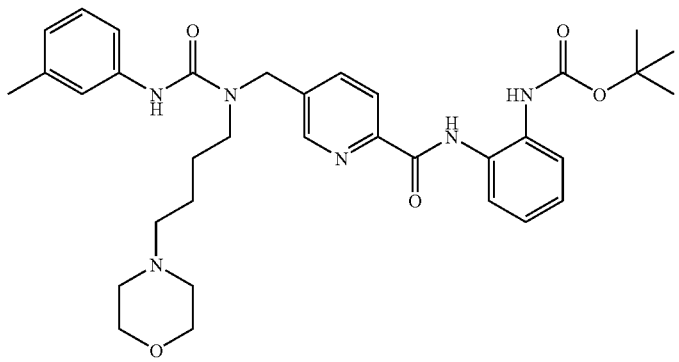 | $^1$H-NMR (500 MHz, CDCl$_3$) δ 1.52 (s, 9H), 1.54 (m, 2H), 1.72 (m, 2H), 2.34 (s, 3H), 2.39 (t, J = 7.0 Hz, 2H), 2.44 (t, J = 4.7 Hz, 4H), 3.33 (t, J = 7.9 Hz, 2H), 3.67 (t, J = 4.7 Hz, 4H), 4.69 (s, 2H), 6.57 (s, 1H), 6.91 (d, J = 7.8 Hz, 1H), 7.04 (br s, 1H), 7.12 (d, J = 7.8 Hz, 1H), 7.18-7.24 (m, 3H), 7.20 (t, J = 7.8 Hz, 1H), 7.58 (d, J = 5.8 Hz, 1H), 7.72 (d, J = 5.5 Hz, 1H), 7.89 (dd, J = 7.9, 2.1 Hz, 1H), 8.28 (dd, J = 7.9, 0.7 Hz, 1H), 8.57 (dd, J = 2.1, 0.7 Hz, 1H), 10.16 (s, 1H) |
| 5-[3-(3-Acetylphenyl)-1-[4-(morpholin-4-yl)butyl]ureidomethyl]-N-(2-t-butoxycarbonylaminophenyl)pyridine-2-carboxylic acid amide (Reference Compound No. 6-93)<br />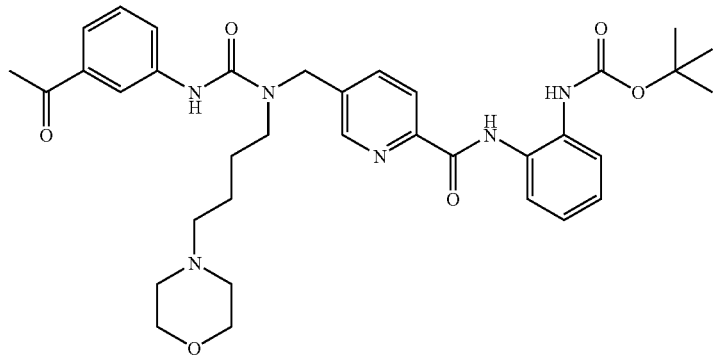 | $^1$H-NMR (400 MHz, CDCl$_3$) δ 1.51 (s, 9H), 1.55 (m, 2H), 1.74 (m, 2H), 2.41 (t, J = 7.0 Hz, 2H), 2.44 (t, J = 4.6 Hz, 4H), 2.61 (s, 3H), 3.35 (t, J = 7.9 Hz, 2H), 3.66 (t, J = 4.6 Hz, 4H), 4.70 (s, 2H), 6.83 (s, 1H), 7.05 (br s, 1H), 7.18-7.25 (m, 2H), 7.43 (t, J = 7.9 Hz, 1H), 7.55 (d, J = 6.3 Hz, 1H), 7.67 (ddd, J = 7.9, 1.8, 1.1 Hz, 1H), 7.72 (d, J = 6.8 Hz, 1H), 7.78 (ddd, J = 7.9, 1.8, 1.1 Hz, 1H), 7.82 (t, J = 1.8 Hz, 1H), 7.89 (dd, J = 8.0, 2.2 Hz, 1H), 8.28 (dd, J = 8.0, 0.6 Hz, 1H), 8.57 (dd, J = 2.2, 0.6 Hz, 1H), 10.17 (s, 1H) |

N-(2-t-Butoxycarbonylaminophenyl)-5-
[3-(2-methoxyphenyl)-1-
[4-(morpholin-4-yl)butyl]ureidomethyl]pyridine-
2-carboxylic acid amide
(Reference Compound No. 6-94)

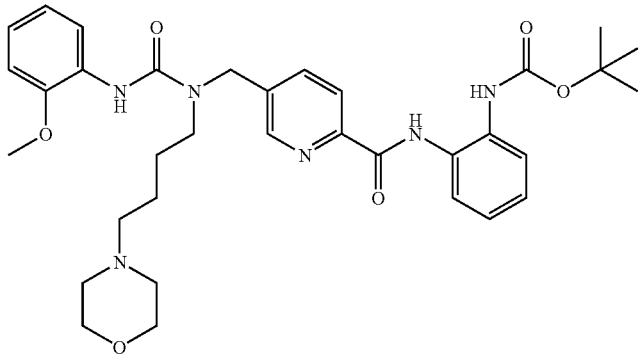

$^1$H-NMR (400 MHz, CDCl$_3$)
δ 1.51 (s, 9H), 1.56 (m, 2H), 1.73 (m, 2H), 2.37 (t, J = 7.3 Hz, 2H), 2.42 t, J = 4.6 Hz, 4H), 3.38 (t, J = 7.6 Hz, 2H), 3.69 (t, J = 4.6 Hz, 4H), 3.82 (s, 3H), 4.70 (s, 2H), 6.86 (dd, J = 7.2, 2.4 Hz, 1H), 6.98 (td, J = 7.2, 2.4 Hz, 1H), 7.01 (td, J = 7.2, 2.4 Hz, 1H), 7.05 (br s, 1H), 7.19-7.23 (m, 2H), 7.57 (d, J = 5.9 Hz, 1H), 7.73 (d, J = 5.6 Hz, 1H), 7.90 (dd, J = 8.1, 2.2 Hz, 1H), 8.13 (dd, J = 7.2, 2.4 Hz, 1H), 8.28 (dd, J = 8.1, 0.7 Hz, 1H), 8.57 (dd, J = 2.2, 0.7 Hz, 1H), 10.17 (s, 1H)

N-(2-t-Butoxycarbonylaminophenyl)-5-
[3-(3-methylphenyl)-1-
[3-(4-methylpiperidin-1-yl)propyl]ureidomethyl]pyridine-
2-carboxylic acid amide
(Reference Compound No. 6-95)

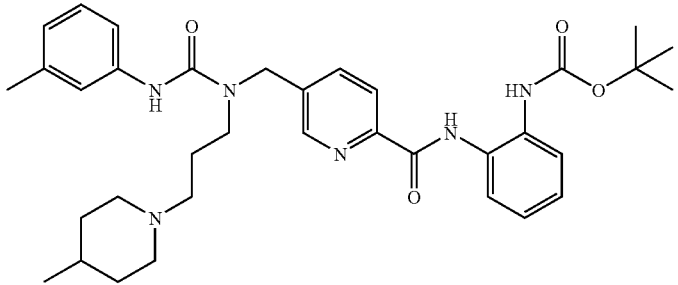

$^1$H-NMR (500 MHz, CDCl$_3$)
δ 0.90 (d, J = 6.4 Hz, 3H), 1.21 (m, 2H), 1.38 (m, 1H), 1.51 (s, 9H), 1.59 (m, 2H), 1.76 (m, 2H), 1.92 (m, 2H), 2.34 (s, 3H), 2.42 (t, J = 6.0 Hz, 2H), 2.88 (d, J = 11.6 Hz, 2H), 3.37 (t, J = 5.7 Hz, 2H), 4.63 (s, 2H), 6.89 (d, J = 7.6 Hz, 1H), 7.06 (s, 1H), 7.17-7.24 (m, 3H), 7.28-7.30 (m, 2H), 7.61 (d, J = 7.3 Hz, 1H), 7.68 (d, J = 7.0 Hz, 1H), 7.93 (dd, J = 7.9, 2.1 Hz, 1H), 8.24 (d, J = 7.9 Hz, 1H), 8.57 (d, J = 2.1 Hz, 1H), 9.34 (s, 1H), 10.14 (s, 1H)

N-(2-t-Butoxycarbonylaminophenyl)-5-
[3-(3,4-difluorophenyl)-1-
[3-(4-methylpiperidin-1-yl)propyl]ureidomethyl]pyridine-
2-carboxylic acid amide
(Reference Compound No. 6-96)

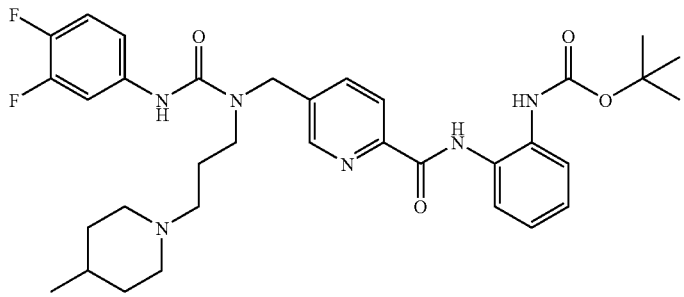

$^1$H-NMR (500 MHz, CDCl$_3$)
δ 0.90 (d, J = 6.4 Hz, 3H), 1.12 (m, 2H), 1.40 (m, 1H), 1.51 (s, 9H), 1.60 (m, 2H), 1.77 (m, 2H), 1.95 (m, 2H), 2.42 (t, J = 6.1 Hz, 2H), 2.86 (d, J = 11.6 Hz, 2H), 3.36 (t, J = 5.7 Hz, 2H), 4.61 (s, 2H), 7.03-7.10 (m, 3H), 7.18-7.24 (m, 2H), 7.45 (m, 1H), 7.59 (d, J = 6.4 Hz, 1H), 7.70 (d, J = 6.7 Hz, 1H), 7.91 (dd, J = 7.9, 2.1 Hz, 1H), 8.25 (d, J = 7.9 Hz, 1H), 8.57 (d, J = 2.1 Hz, 1H), 9.70 (s, 1H), 10.15 (s, 1H)

N-(2-t-Butoxycarbonylaminophenyl)-5-
[3-(2,3-dihydrobenzo[1,4]dioxin-6-yl)-1-
[3-(4-methylpiperidin-1-yl)propyl]ureidomethyl]pyridine-
2-carboxylic acid amide
(Reference Compound No. 6-97)

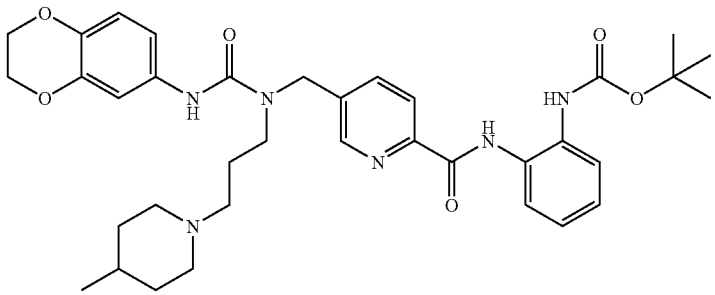

$^1$H-NMR (400 MHz, CDCl$_3$)
δ 0.87 (d, J = 6.3 Hz, 3H), 1.13 (m, 2H), 1.36 (m, 1H), 1.51 (s, 9H), 1.54 (m, 2H), 1.74 (m, 2H), 1.91 (m, 2H), 2.41 (t, J = 6.0 Hz, 2H), 2.85 (d, J = 11.5 Hz, 2H), 3.34 (t, J = 5.4 Hz, 2H), 4.23-4.24 (m, 4H), 4.61 (s, 2H), 6.79 (d, J = 8.7 Hz, 1H), 6.85 (dd, J = 8.7, 2.4 Hz, 1H), 7.01 (d, J = 2.4 Hz, 1H), 7.08 (br s, 1H), 7.17-7.24 (m, 2H), 7.61 (d, J = 7.1 Hz, 1H), 7.68 (d, J = 6.3 Hz, 1H), 7.93 (dd, J = 8.1, 2.2 Hz, 1H), 8.24 (d, J = 8.1 Hz, 1H), 8.56 (d, J = 2.2 Hz, 1H), 9.42 (s, 1H), 10.14 (s, 1H)

N-(2-t-Butoxycarbonylaminophenyl)-5-
[3-(4-fluorophenyl)-1-
[3-(morpholin-4-yl)propyl]ureidomethyl]pyridine-
2-carboxylic acid amide
(Reference Compound No. 6-98)

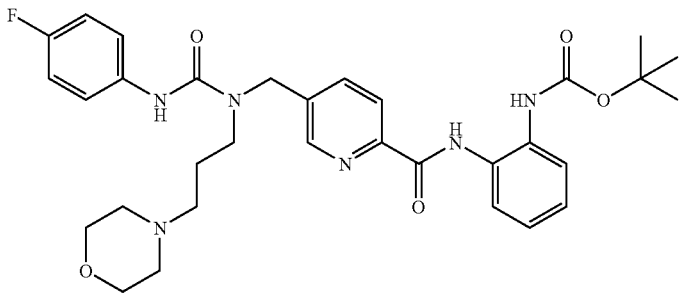

$^1$H-NMR (500 MHz, CDCl$_3$)
δ 1.51 (s, 9H), 1.79 (m, 2H), 2.45 (br s, 4H), 2.49 (t, J = 6.0 Hz, 2H), 3.39 (t, J = 5.5 Hz, 2H), 3.64 (t, J = 4.4 Hz, 4H), 4.64 (s, 2H), 7.03 (t, J = 8.7 Hz, 2H), 7.03 (br s, 1H), 7.18-7.24 (m, 2H), 7.38 (dd, J = 8.7, 4.9 Hz, 2H), 7.59 (d, J = 7.3 Hz, 1H), 7.69 (d, J = 7.0 Hz, 1H), 7.92 (dd, J = 8.1, 2.1 Hz, 1H), 8.25 (dd, J = 8.1, 0.6 Hz, 1H), 8.57 (dd, J = 2.1, 0.6 Hz, 1H), 9.08 (s, 1H), 10.14 (s, 1H)

N-(2-t-Butoxycarbonylaminophenyl)-5-
[3-(4-fluoro-3-methylphenyl)-1-
[3-(morpholin-4-yl)propyl]ureidomethyl]pyridine-
2-carboxylic acid amide
(Reference Compound No. 6-99)

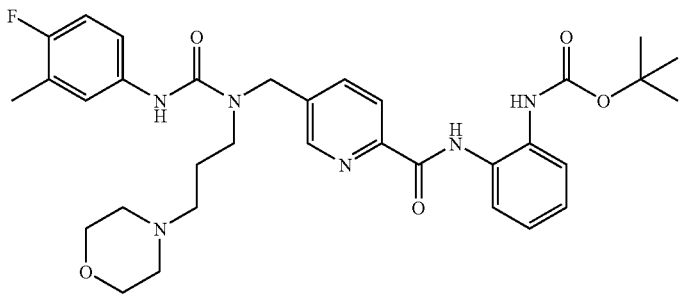

$^1$H-NMR (500 MHz, CDCl$_3$)
δ 1.51 (s, 9H), 1.79 (m, 2H), 2.27 (d, J = 1.8 Hz, 3H), 2.45 (br s, 4H), 2.49 (t, J = 6.0 Hz, 2H), 3.38 (t, J = 5.7 Hz, 2H), 3.64 (t, J = 4.6 Hz, 4H), 4.64 (s, 2H), 6.95 (t, J = 8.8 Hz, 1H), 7.05 (br s, 1H), 7.13 (ddd, J = 8.8, 4.3, 2.7 Hz, 1H), 7.18-7.24 (m, 2H), 7.30 (dd, J = 6.9, 2.7 Hz, 1H), 7.60 (d, J = 6.4 Hz, 1H), 7.69 (d, J = 7.3 Hz, 1H), 7.92 (dd, J = 7.9, 2.0 Hz, 1H), 8.25 (d, J = 7.9 Hz, 1H), 8.57 (d, J = 2.0 Hz, 1H), 9.00 (s, 1H), 10.14 (s, 1H)

N-(2-t-Butoxycarbonylaminophenyl)-5-
[3-(3,4-difluorophenyl)-1-
[3-(morpholin-4-yl)propyl]ureidomethyl]pyridine-
2-carboxylic acid amide
(Reference Compound No. 6-100)

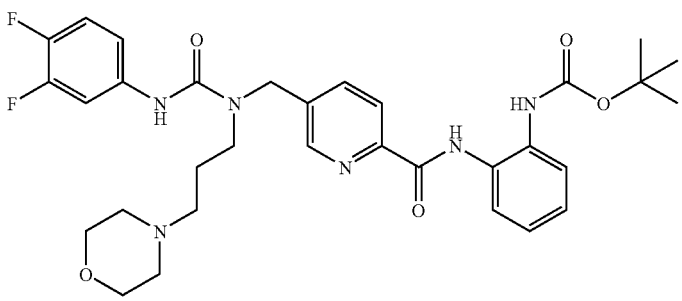

$^1$H-NMR (500 MHz, CDCl$_3$)
δ 1.51 (s, 9H), 1.80 (m, 2H), 2.46-2.50 (m, 6H), 3.38 (t, J = 5.7 Hz, 2H), 3.67 (t, J = 4.7 Hz, 4H), 4.63 (s, 2H), 6.95-7.06 (m, 2H), 7.10 (m, 1H), 7.17-7.25 (m, 2H), 7.50 (ddd, J = 12.2, 7.3, 2.4 Hz, 1H) 7.58 (d, J = 6.1 Hz, 1H), 7.71 (d, J = 5.8 Hz, 1H), 7.91 (dd, J = 7.9, 2.1 Hz, 1H), 8.26 (dd, J = 7.9, 0.6 Hz, 1H), 8.57 (dd, J = 2.1, 0.6 Hz, 1H), 9.15 (s, 1H), 10.15 (s, 1H)

| | |
|---|---|
| N-(2-t-Butoxycarbonylaminophenyl)-5-[3-(3-methylphenyl)-1-[3-(morpholin-4-yl)propyl]ureidomethyl]pyridine-2-carboxylic acid amide (Reference Compound No. 6-101)<br>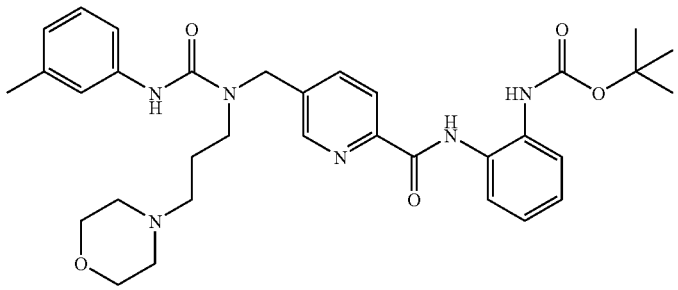 | $^1$H-NMR (500 MHz, CDCl$_3$) δ 1.51 (s, 9H), 1.79 (m, 2H), 2.35 (s, 3H), 2.46 (br s, 4H), 2.49 (t, J = 6.1 Hz, 2H), 3.39 (t, J = 5.7 Hz, 2H), 3.70 (t, J = 4.6 Hz, 4H), 4.65 (s, 2H), 6.91 (m, 1H), 7.05 (br s, 1H), 7.17-7.25 (m, 4H), 7.33 (s, 1H), 7.60 (d, J = 7.0 Hz, 1H), 7.69 (d, J = 6.7 Hz, 1H), 7.93 (dd, J = 8.2, 1.9 Hz, 1H), 8.25 (d, J = 8.2 Hz, 1H), 8.57 (d, J = 1.9 Hz, 1H), 8.86 (s, 1H), 10.15 (s, 1H) |
| 5-[3-(3-Acetylphenyl)-1-[3-(morpholin-4-yl)propyl]ureidomethyl]-N-(2-t-butoxycarbonylaminophenyl)pyridine-2-carboxylic acid amide (Reference Compound No. 6-102)<br>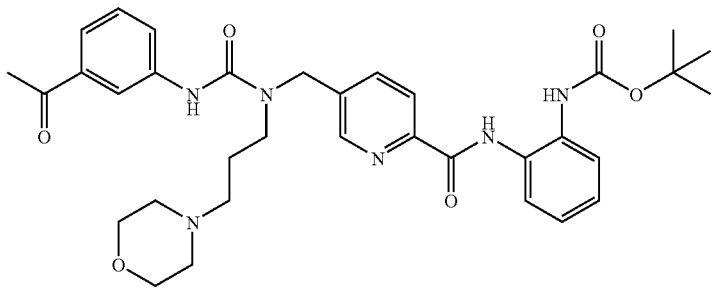 | $^1$H-NMR (500 MHz, CDCl$_3$) δ 1.51 (s, 9H), 1.83 (m, 2H), 2.49 (br s, 4H), 2.51 (t, J = 6.1 Hz, 2H), 2.62 (s, 3H), 3.42 (t, J = 5.5 Hz, 2H), 3.72 (t, J = 4.6 Hz, 4H), 4.66 (s, 2H), 7.03 (br s, 1H), 7.17-7.24 (m, 2H), 7.44 (t, J = 7.9 Hz, 1H), 7.59 (d, J = 6.1 Hz, 1H), 7.67 (d, J = 7.9 Hz, 1H), 7.70 (m, 1H), 7.80 (dd, J = 7.9, 1.8 Hz, 1H), 7.93 (dd, J = 8.0, 1.9 Hz, 1H), 7.99 (t, J = 1.8 Hz, 1H), 8.26 (d, J = 8.0 Hz, 1H), 8.58 (d, J = 1.9 Hz, 1H), 9.21 (s, 1H), 10.15 (s, 1H) |
| N-(2-t-Butoxycarbonylaminophenyl)-5-[3-(3-methylphenyl)-1-[5-(morpholin-4-yl)pentyl]ureidomethyl]pyridine-2-carboxylic acid amide (Reference Compound No. 6-103)<br>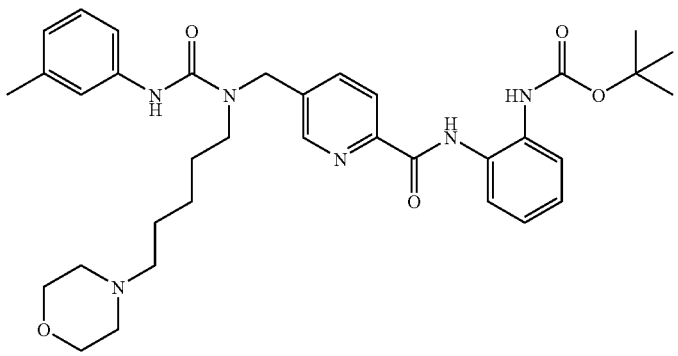 | $^1$H-NMR (500 MHz, CDCl$_3$) δ 1.38 (m, 2H), 1.50-1.56 (m, 4H), 1.51 (s, 9H), 1.68 (m, 2H), 2.32 (t, J = 7.6 Hz, 2H), 2.34 (s, 3H), 2.41 (br s, 4H), 3.31 (t, J = 7.6 Hz, 2H), 3.70 (t, J = 4.6 Hz, 4H), 4.69 (s, 2H), 6.89 (d, J = 7.6 Hz, 1H), 7.04 (br s, 1H), 7.12 (d, J = 8.6 Hz, 1H), 7.17-7.25 (m, 3H), 7.58 (d, J = 6.1 Hz, 1H), 7.72 (d, J = 6.1 Hz, 1H), 7.88 (dd, J = 7.9, 2.1 Hz, 1H), 8.28 (d, J = 7.9 Hz, 1H), 8.56 (d, J = 2.1 Hz, 1H), 10.17 (s, 1H) |

| | |
|---|---|
| N-(2-t-Butoxycarbonylaminophenyl)-5-[3-(3,4-difluorophenyl)-1-[5-(morpholin-4-yl)pentyl]ureidomethyl]pyridine-2-carboxylic acid amide (Reference Compound No. 6-104)<br>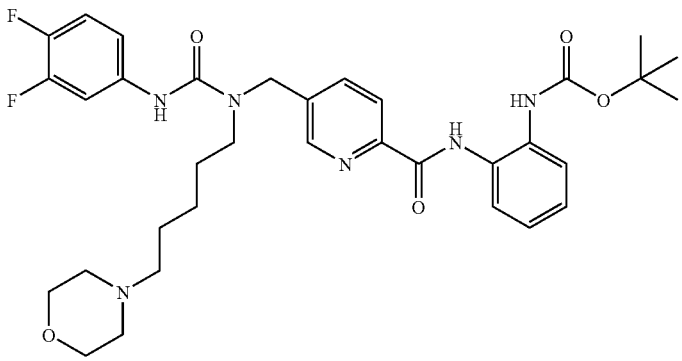 | $^1$H-NMR (500 MHz, CDCl$_3$) δ 1.37 (m, 2H), 1.51 (s, 9H), 1.53 (m, 2H), 1.67 (m, 2H), 2.32 (t, J = 7.6 Hz, 2H), 2.41 (br s, 4H), 3.30 (t, J = 7.6 Hz, 2H), 3.70 (t, J = 4.6 Hz, 4H), 4.67 (s, 2H), 6.41 (s, 1H), 6.94 (m, 1H), 7.04-7.10 (m, 2H), 7.19-7.24 (m, 2H), 7.46 (m, 1H), 7.56 (br s, 1H), 7.74 (br s, 1H), 7.85 (dd, J = 7.9, 2.1 Hz, 1H), 8.25 (d, J = 7.9 Hz, 1H), 8.54 (d, J = 2.1 Hz, 1H), 10.17 (s, 1H) |
| N-(2-t-Butoxycarbonylaminophenyl)-5-[3-(2,3-dihydrobenzo[1,4]dioxin-6-yl)-1-[5-(morpholin-4-yl)pentyl]ureidomethyl]pyridine-2-carboxylic acid amide (Reference Compound No. 6-105)<br>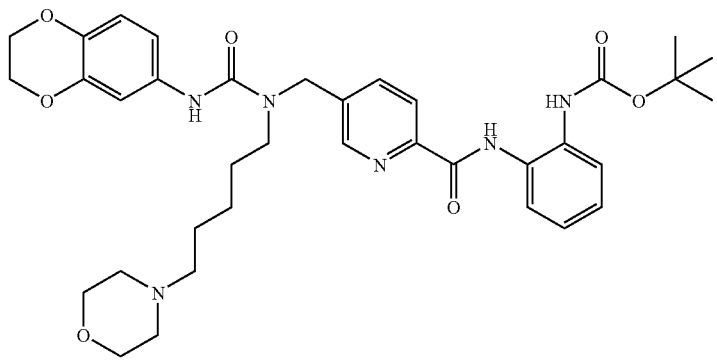 | $^1$H-NMR (500 MHz, CDCl$_3$) δ 1.37 (m, 2H), 1.52 (s, 9H), 1.53 (m, 2H), 1.66 (m, 2H), 2.31 (t, J = 7.5 Hz, 2H), 2.41 (br s, 4H), 3.28 (t, J =7.6 Hz, 2H), 3.70 (t, J = 4.6 Hz, 4H), 4.21-4.25 (m, 4H), 4.67 (s, 2H), 6.20 (s, 1H), 6.76 (dd, J = 8.6, 2.1 Hz, 1H), 6.79 (d, J = 8.6 Hz, 1H), 6.96 (d, J = 2.1 Hz, 1H), 7.07 (br s, 1H), 7.19-7.24 (m, 2H), 7.58 (d, J = 5.5 Hz, 1H), 7.72 (d, J = 5.2 Hz, 1H), 7.87 (dd, J = 7.9, 2.1 Hz, 1H), 8.26 (d, J = 7.9 Hz, 1H), 8.55 (d, J = 2.1 Hz, 1H), 10.16 (s, 1H) |
| N-(2-t-Butoxycarbonylaminophenyl)-5-[3-cyclopentyl-1-[3-(morpholin-4-yl)propyl]ureidomethyl]pyridine-2-carboxylic acid amide (Reference Compound No. 6-106)<br>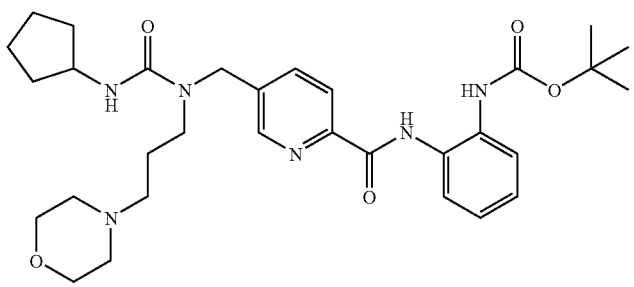 | $^1$H-NMR (400 MHz, CDCl$_3$) δ 1.35 (m, 2H), 1.52 (s, 9H), 1.62 (m, 2H), 1.69 (m, 4H), 2.06 (m, 2H), 2.37 (t, J = 6.1 Hz, 2H), 2.44 (t, J = 4.6 Hz, 4H), 3.21 (t, J = 6.0 Hz, 2H), 3.74 (t, J = 4.6 Hz, 4H), 4.11 (m, 1H), 4.58 (s, 2H), 5.92 (d, J = 7.3 Hz, 1H), 7.05 (br s, 1H), 7.18-7.24 (m, 2H), 7.59 (d, J = 7.1 Hz, 1H), 7.70 (d, J = 6.6 Hz, 1H), 7.85 (dd, d = 8.1, 2.2 Hz, 1H), 8.25 (dd, J = 8.1, 0.7 Hz, 1H), 8.52 (dd, J = 2.2, 0.7 Hz, 1H), 10.14 (s, 1H) |

5-[3-[2-(Benzo[1,3]dioxol-5-yl)ethyl]-1-[3-(morpholin-4-yl)propyl]ureidomethyl]-N-(2-t-butoxycarbonylaminophenyl)pyridine-2-carboxylic acid amide
(Reference Compound No. 6-107)

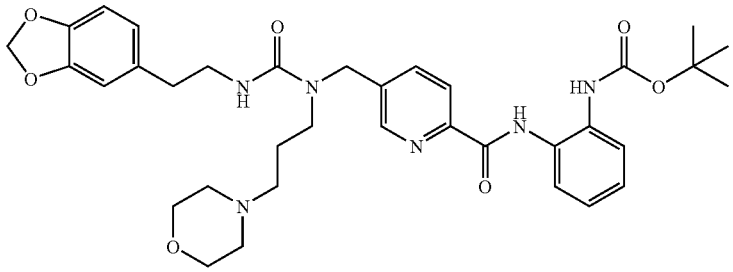

$^1$H-NMR (500 MHz, CDCl$_3$)
δ 1.51 (s, 9H), 1.63 (m, 2H), 2.33 (t, J = 5.8 Hz, 2H), 2.33 (m, 4H), 2.77 (t, J = 6.7 Hz, 2H), 3.17 (t, J = 5.7 Hz, 2H), 3.43 (q, J = 6.7 Hz, 2H), 3.60 (s, 4H), 4.57 (s, 2H), 5.92 (s, 2H), 6.64 (dd, J = 7.7, 1.5 Hz, 1H), 6.70 (d, J = 1.5 Hz, 1H), 6.75 (d, J = 7.7 Hz, 1H), 7.07 (m, 1H), 7.18-7.24 (m, 2H), 7.61 (d, J = 6.7 Hz, 1H), 7.69 (d, J = 6.4 Hz, 1H), 7.80 (dd, J = 8.0, 1.9 Hz, 1H), 8.25 (d, J = 8.0 Hz, 1H), 8.47 (d, J = 1.9 Hz, 1H), 10.15 (s, 1H)

N-(2-t-Butoxycarbonylaminophenyl)-5-[3-isopropyl-1-[3-(morpholin-4-yl)propyl]ureidomethyl]pyridine-2-carboxylic acid amide
(Reference Compound No. 6-108)

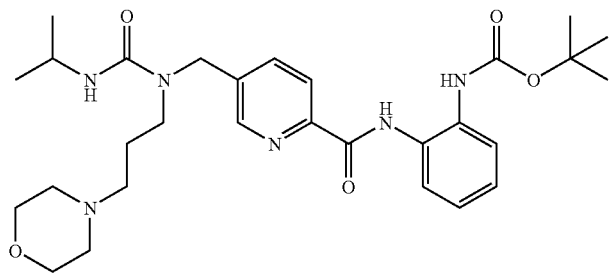

$^1$H-NMR (400 MHz, CDCl$_3$)
δ 1.20 (d, J = 6.6 Hz, 6H), 1.52 (s, 9H), 1.69 (m, 2H), 2.37 (t, J = 6.1 Hz, 2H), 2.45 (t, J = 4.5 Hz, 4H), 3.21 (t, J = 6.0 Hz, 2H), 3.76 (t, J = 4.5 Hz, 4H), 4.02 (m, 1H), 4.57 (s, 2H), 5.90 (d, J = 7.8 Hz, 1H), 7.06 (br s, 1H), 7.17-7.25 (m, 2H), 7.56 (d, J = 6.6 Hz, 1H), 7.70 (d, J = 6.1 Hz, 1H), 7.85 (dd, J = 8.1, 2.0 Hz, 1H), 8.24 (dd, J = 8.1, 0.7 Hz, 1H), 8.52 (dd, J = 2.0, 0.7 Hz, 1H), 10.15 (s, 1H)

N-(2-t-Butoxycarbonylaminophenyl)-5-[1-[3-(morpholin-4-yl)propyl]-3-propylureidomethyl]pyridine-2-carboxylic acid amide
(Reference Compound No. 6-109)

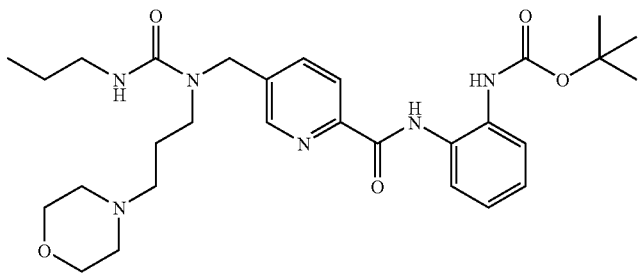

$^1$H-NMR (500 MHz, CDCl$_3$)
δ 0.95 (t, J = 7.5 Hz, 3H), 1.52 (s, 9H), 1.52 (m, 2H), 1.68 (m, 2H), 2.39 (t, J = 6.1 Hz, 2H), 2.45 (s, 4H), 3.19 (t, J = 6.3 Hz, 2H), 3.23 (t, J = 5.9 Hz, 2H), 3.74 (t, J = 4.4 Hz, 4H), 4.58 (s, 2H), 7.03 (t, J = 6.3 Hz, 1H), 7.05 (br s, 1H), 7.18-7.24 (m, 2H), 7.60 (d, J = 5.9 Hz, 1H), 7.68 (d, J = 7.6 Hz, 1H), 7.85 (dd, J = 7.9, 2.1 Hz, 1H), 8.24 (d, J = 7.9, 0.6 Hz, 1H), 8.52 (d, J = 2.1, 0.6 Hz, 1H), 10.14 (s, 1H)

N-(2-t-Butoxycarbonylaminophenyl)-5-[1-[4-(morpholin-4-yl)butyl]-3-propylureidomethyl]pyridine-2-carboxylic acid amide
(Reference Compound No. 6-110)

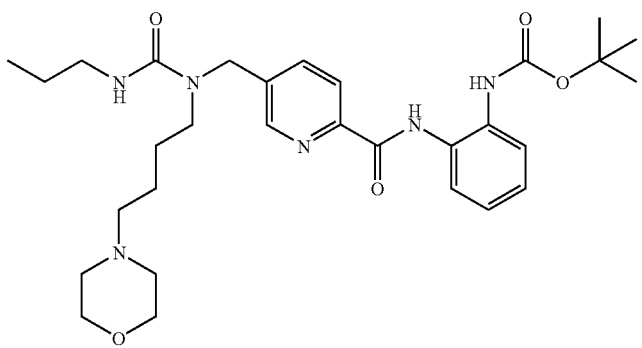

$^1$H-NMR (500 MHz, CDCl$_3$)
δ 0.92 (t, J = 7.3 Hz, 3H), 1.46-1.64 (m, 6H), 1.52 (s, 9H), 2.35 (t, J = 7.0 Hz, 2H), 2.41 (br s, 4H), 3.17 (t, J = 7.9 Hz, 2H), 3.25 (q, J = 5.7 Hz, 2H), 3.71 (t, J = 4.6 Hz, 4H), 4.61 (s, 2H), 4.78 (t, J = 5.7 Hz, 1H), 7.04 (br s, 1H), 7.18-7.24 (m, 2H), 7.59 (d, J = 6.7 Hz, 1H), 7.71 (d, J = 7.0 Hz, 1H), 7.82 (dd, J = 7.9, 2.1 Hz, 1H), 8.25 (d, J = 7.9 Hz, 1H), 8.51 (d, J = 2.1 Hz, 1H), 10.15 (s, 1H)

N-(2-t-Butoxycarbonylaminophenyl)-5-
[3-isopropyl-1-
[4-(morpholin-4-yl)butyl]ureidomethyl]pyridine-
2-carboxylic acid amide
(Reference Compound No. 6-111)

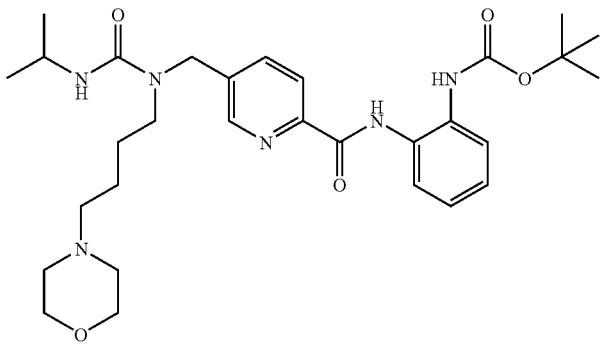

$^1$H-NMR (500 MHz, CDCl$_3$)
δ 1.17 (d, J = 6.4 Hz, 6H), 1.49 (m, 2H), 1.52 (s, 9H), 1.58 (m, 2H), 2.34 (t, J = 7.2 Hz, 2H), 2.41 (br s, 4H), 3.17 (t, J = 7.6 Hz, 2H), 3.71 (t, J = 4.6 Hz, 4H), 4.03 (m, 1H), 4.24 (d, J = 7.3 Hz, 1H), 4.59 (s, 2H), 7.04 (br s, 1H), 7.18-7.24 (m, 2H), 7.58 (d, J = 6.7 Hz, 1H), 7.72 (d, J = 6.7 Hz, 1H), 7.81 (dd, J = 7.9, 2.1 Hz, 1H), 8.26 (d, J = 7.9 Hz, 1H), 8.50 (d, J = 2.1 Hz, 1H), 10.15 (s, 1H)

N-(2-t-Butoxycarbonylaminophenyl)-5-
[3-cyclopentyl-1-
[4-(morpholin-4-yl)butyl]ureidomethyl]pyridine-
2-carboxylic acid amide
(Reference Compound No. 6-112)

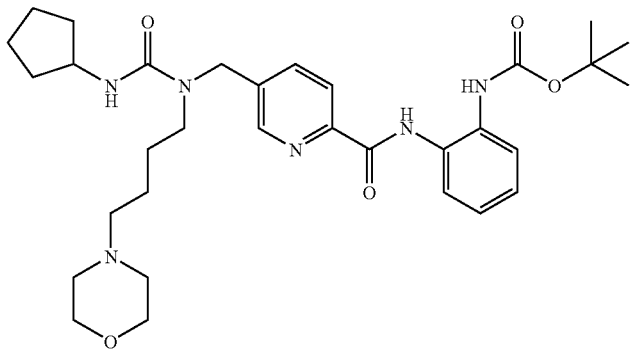

$^1$H-NMR (500 MHz, CDCl$_3$)
δ 1.34 (m, 2H), 1.45-1.66 (m, 8H), 1.52 (s, 9H), 2.01 (m, 2H), 2.33 (t, J = 7.2 Hz, 2H), 2.41 (br s, 4H), 3.17 (t, J = 7.8 Hz, 2H), 3.70 (t, J = 4.7 Hz, 4H), 4.15 (m, 1H), 4.35 (d, J = 7.0 Hz, 1H), 4.59 (s, 2H), 7.04 (br s, 1H), 7.18-7.24 (m, 2H), 7.59 (d, J = 6.7 Hz, 1H), 7.72 (d, J = 7.0 Hz, 1H), 7.82 (dd, J = 8.2, 2.1 Hz, 1H), 8.26 (d, J = 8.2 Hz, 1H), 8.50 (d, J = 2.1 Hz, 1H), 10.15 (s, 1H)

N-(2-t-Butoxycarbonylaminophenyl)-5-
[1-[5-(morpholin-4-yl)pentyl]-
3-propylureidomethyl]pyridine-
2-carboxylic acid amide
(Reference Compound No. 6-113)

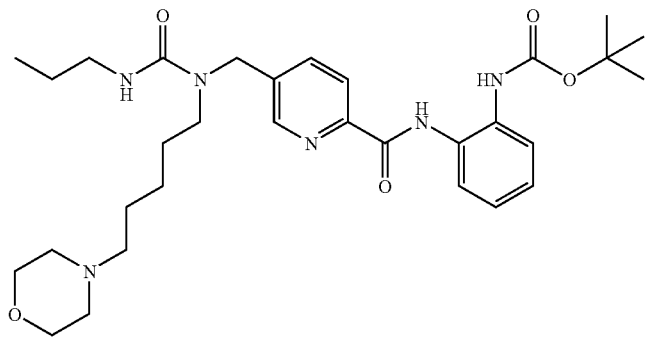

$^1$H-NMR (400 MHz, CDCl$_3$)
δ 0.92 (t, J = 7.3 Hz, 3H), 1.32 (m, 2H), 1.46-1.62 (m, 6H), 1.52 (s, 9H), 2.30 (t, J = 7.6 Hz, 2H), 2.41 (br s, 4H), 3.17 (t, J = 7.7 Hz, 2H), 3.24 (m, 2H), 3.70 (t, J = 4.6 Hz, 4H), 4.42 (t, J = 5.6 Hz, 1H), 4.60 (s, 2H), 7.05 (br s, 1H), 7.18-7.25 (m, 2H), 7.59 (d, J = 6.6 Hz, 1H), 7.72 (d, J = 7.3 Hz, 1H), 7.81 (dd, J = 8.0, 2.2 Hz, 1H), 8.26 (d, J = 8.0 Hz, 1H), 8.50 (d, J = 2.2 Hz, 1H), 10.15 (s, 1H)

| | |
|---|---|
| N-(2-t-Butoxycarbonylaminophenyl)-5-[3-isopropyl-1-[5-(morpholin-4-yl)pentyl]ureidomethyl]pyridine-2-carboxylic acid amide (Reference Compound No. 6-114)<br />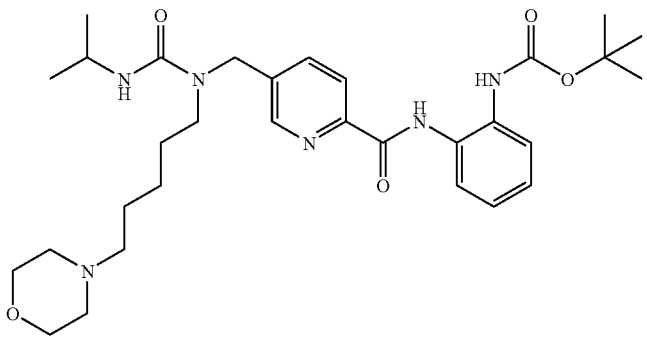 | $^1$H-NMR (400 MHz, CDCl$_3$) δ 1.17 (d, J = 6.3 Hz, 6H), 1.31 (m, 2H), 1.46-1.61 (m, 4H), 1.52 (s, 9H), 2.30 (t, J = 7.6 Hz, 2H), 2.41 (br s, 4H), 3.15 (t, J = 7.6 Hz, 2H), 3.70 (t, J = 4.6 Hz, 4H), 4.02 (m, 1H), 4.16 (d, J = 7.6 Hz, 1H), 4.59 (s, 2H), 7.05 (br s, 1H), 7.18-7.25 (m, 2H), 7.58 (d, J = 7.1 Hz, 1H), 7.72 (d, J = 6.8 Hz, 1H), 7.81 (dd, J = 8.0, 2.2 Hz, 1H), 8.26 (d, J = 8.0 Hz, 1H), 8.50 (d, J = 2.2 Hz, 1H), 10.16 (s, 1H) |
| N-(2-t-Butoxycarbonylaminophenyl)-5-[3-cyclopentyl-1-[5-(morpholin-4-yl)pentyl]ureidomethyl]pyridine-2-carboxylic acid amide (Reference Compound No. 6-115)<br />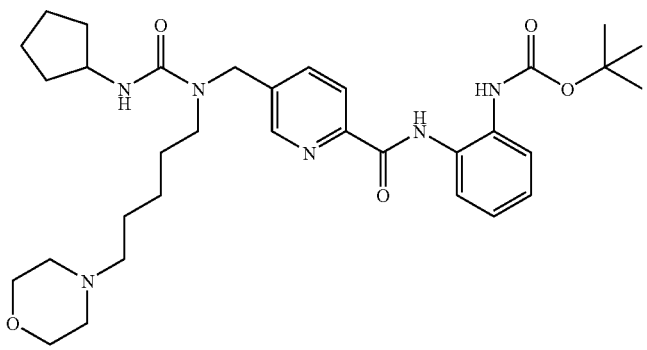 | $^1$H-NMR (400 MHz, CDCl$_3$) δ 1.27-1.38 (m, 4H), 1.46-1.65 (m, 8H), 1.52 (s, 9H), 2.01 (m, 2H), 2.30 (t, J = 7.6 Hz, 2H), 2.41 (br s, 4H), 3.15 (t, J = 7.7 Hz, 2H), 3.70 (t, J = 4.6 Hz, 4H), 4.14 (m, 1H), 4.29 (d, J = 6.8 Hz, 1H), 4.59 (s, 2H), 7.05 (br s, 1H), 7.18-7.25 (m, 2H), 7.58 (d, J = 7.1 Hz, 1H), 7.72 (d, J = 6.8 Hz, 1H), 7.81 (dd, J = 8.0, 2.2 Hz, 1H), 8.26 (d, J = 8.0 Hz, 1H), 8.50 (d, J = 2.2 Hz, 1H), 10.16 (s, 1H) |
| N-(2-t-Butoxycarbonylaminophenyl)-5-[1-(2-dimethylaminoethyl-3-propylureidomethyl]pyridine-2-carboxylic acid amide (Reference Compound No. 6-116)<br />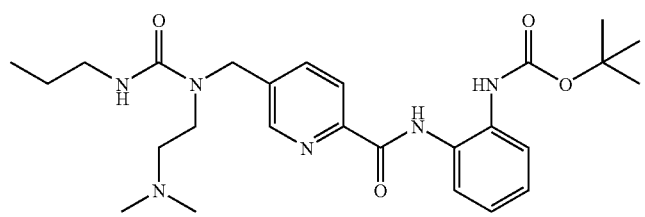 | $^1$H-NMR (400 MHz, CDCl$_3$) δ 0.95 (t, J = 7.5 1Hz, 3H), 1.52 (s, 9H), 1.53 (m, 2H), 2.26 (s, 6H), 2.41 (t, J = 4.6 Hz, 2H), 3.15-3.21 (m, 4H), 4.60 (s, 2H), 7.05 (s, 1H), 7.18-7.24 (m, 2H), 7.60 (d, J = 6.4 Hz, 1H), 7.69 (d, J = 7.0 Hz, 1H), 7.79 (t, J = 4.9 Hz, 1H), 7.86 (dd, J = 7.9, 2.1 Hz, 1H), 8.24 (d, J = 7.9 Hz, 1H), 8.51 (d, J = 2.1 Hz, 1H), 10.14 (s, 1H) |
| N-(2-t-Butoxycarbonylaminophenyl)-5-[1-(2-dimethylaminoethyl-3-isopropylureidomethyl]pyridine-2-carboxylic acid amide (Reference Compound No. 6-117)<br />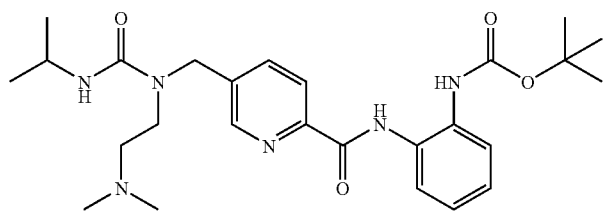 | $^1$H-NMR (500 MHz, CDCl$_3$) δ 1.15 (d, J = 6.7 Hz, 6H), 1.52 (s, 9H), 2.26 (s, 6H), 2.40 (t, J = 4.5 Hz, 2H), 3.18 (t, J = 4.5 Hz, 2H), 3.91 (m, 1H), 4.59 (s, 2H), 7.05 (br s, 1H), 7.18-7.24 (m, 2H), 7.59 (d, J = 6.7 Hz, 1H), 7.70 (d, J = 6.7 Hz, 1H), 7.85 (dd, J = 7.9, 2.0 Hz, 1H), 7.93 (d, J = 6.7 Hz, 1H), 8.24 (d, J = 7.9 Hz, 1H), 8.51 (d, J = 2.0 Hz, 1H), 10.15 (s, 1H) |

N-(2-t-Butoxycarbonylaminophenyl)-5-
[3-sec-butyl-1-
(2-dimethylaminoethyl)ureidomethyl]pyridine-
2-carboxylic acid amide
(Reference Compound No. 6-118)

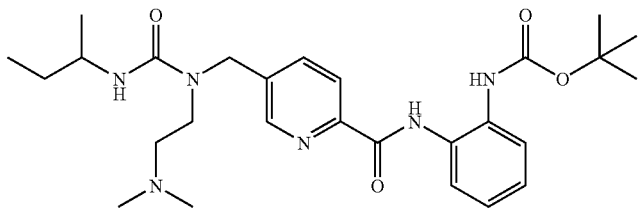

$^1$H-NMR (500 MHz, CDCl$_3$)
δ 0.93 (t, J = 7.3 Hz, 3H), 1.12
(d, J = 6.4 Hz, 3H), 1.47 (m,
2H), 1.52 (s, 9H), 2.25 (s, 6H),
2.40 (t, J = 4.6 Hz, 2H), 3.18 (t,
J = 4.6 Hz, 2H), 3.74 (m, 1H),
4.58 (d, J = 16.9 Hz, 1H), 4.62
(d, J = 16.9 Hz, 1H), 7.07 (br s,
1H), 7.17-7.24 (m, 2H), 7.59 (d,
J = 6.4 Hz, 1H), 7.71 (d, J = 6.7
Hz, 1H), 7.83 (d, J = 7.3 Hz,
1H), 7.85 (dd, J = 7.9, 2.0 Hz,
1H), 8.24 (d, J = 7.9 Hz, 1H),
8.51 (d, J = 2.0 Hz, 1H), 10.15
(s, 1H)

N-(2-t-Butoxycarbonylaminophenyl)-5-
[3-cyclopentyl-1-
(2-dimethylaminoethyl)ureidomethyl]pyridine-
2-carboxylic acid amide
(Reference Compound No. 6-119)

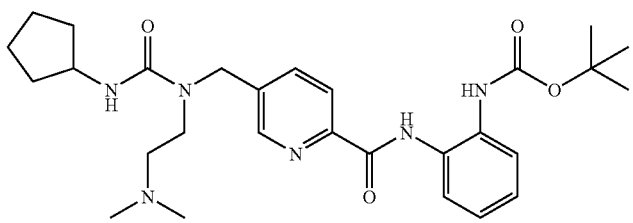

$^1$H-NMR (500 MHz, CDCl$_3$)
δ 1.36-1.41 (m, 2H), 1.52 (s,
9H), 1.61-1.68 (m, 4H),
1.93-1.99 (m, 2H), 2.25 (s, 6H),
2.40 (t, J = 4.4 Hz, 2H), 3.18 (t,
J = 4.4 Hz, 2H), 4.08 (m, 1H),
4.59 (s, 2H), 7.06 (br s, 1H),
7.18-7.24 (m, 2H), 7.60 (d, J =
7.0 Hz, 1H), 7.70 (d, J = 6.7
Hz, 1H), 7.86 (dd, J = 7.9, 2.1
Hz, 1H), 8.03 (d, J = 6.4 Hz,
1H), 8.24 (dd, J = 7.9, 0.6 Hz,
1H), 8.51 (dd, J = 2.1, 0.6 Hz,
1H), 10.15 (s, 1H)

N-(2-t-Butoxycarbonylaminophenyl)-5-
[1-(2-dimethylaminoethyl)-3-
hexylureidomethyl]pyridine-
2-carboxylic acid amide
(Reference Compound No. 6-120)

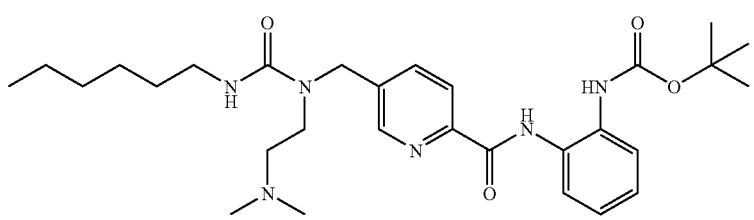

$^1$H-NMR (500 MHz, CDCl$_3$)
δ 0.89 (t, J = 7.0 Hz, 3H),
1.29-1.38 (m, 6H), 1.48 (m,
2H), 1.52 (s, 9H), 2.26 (s, 6H),
2.41 (t, J = 4.6 Hz, 2H), 3.19 (t,
J = 4.6 Hz, 2H), 3.21 (m, 2H),
4.60 (s, 2H), 7.06 (br s, 1H),
7.17-7.24 (m, 2H), 7.60 (d, J =
7.0 Hz, 1H), 7.68 (d, J = 6.7
Hz, 1H), 7.75 (t, J = 4.9 Hz,
1H), 7.86 (dd, J = 8.0, 1.9 Hz,
1H), 8.24 (d, J = 8.0 Hz, 1H),
8.51 (d, J = 1.9 Hz, 1H), 10.14
(s, 1H)

N-(2-t-Butoxycarbonylaminophenyl)-5-
[3-cyclohexyl-1-
(2-dimethylaminoethyl)ureidomethyl]pyridine-
2-carboxylic acid amide
(Reference Compound No. 6-121)

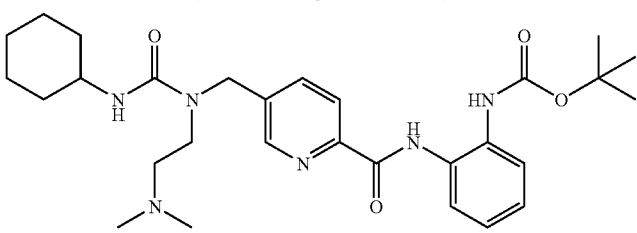

$^1$H-NMR (500 MHz, CDCl$_3$)
δ 1.06-1.19 (m, 4H), 1.38 (m,
2H), 1.52 (s, 9H), 1.70 (m, 2H),
1.94 (m, 2H), 2.25 (s, 6H), 2.40
(t, J = 4.7 Hz, 2H), 3.19 (t, J =
4.7 Hz, 2H), 3.59 (m, 1H), 4.59
(s, 2H), 7.05 (br s, 1H),
7.17-7.24 (m, 2H), 7.60 (d, J =
7.3 Hz, 1H), 7.69 (d, J = 7.3
Hz, 1H), 7.86 (dd, J = 8.2, 1.8
Hz, 1H), 7.89 (d, J = 6.7 Hz,
1H), 8.24 (d, J = 8.2 Hz, 1H),
8.51 (d, J = 1.8 Hz, 1H), 10.14
(s, 1H)

N-(2-t-Butoxycarbonylaminophenyl)-5-
[1-(2-dimethylaminoethyl)-3-
phenethylureidomethyl]pyridine-
2-carboxylic acid amide
(Reference Compound No. 6-122)

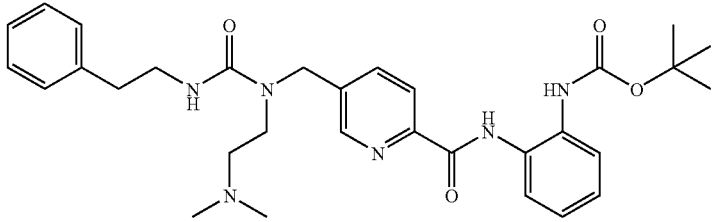

$^1$H-NMR (500 MHz, CDCl$_3$)
δ 1.52 (s, 9H), 2.04 (s, 6H),
2.31 (t, J = 4.7 Hz, 2H), 2.84 (t,
J = 6.9 Hz, 2H), 3.12 (t, J = 4.7
Hz, 2H), 3.53 (td, J = 6.9, 5.5
Hz, 2H), 4.59 (s, 2H), 7.06 (br
s, 1H), 7.17-7.24 (m, 4H) 7.29
(d, J = 7.6 Hz, 2H), 7.31 (m,
1H), 7.60 (d, J = 7.0 Hz, 1H),
7.69 (d, J = 5.6 Hz, 1H), 7.69
(m, 1H), 7.82 (dd, J = 7.9, 2.0
Hz, 1H), 8.24 (dd, J = 7.9, 0.6
Hz, 1H), 8.50 (dd, J = 2.0, 0.6
Hz, 1H), 10.14 (s, 1H)

N-(2-t-Butoxycarbonylaminophenyl)-5-
[1-(2-dimethylaminoethyl)-3-
[2-(thiophen-2-yl)ethyl]ureidomethyl]pyridine-
2-carboxylic acid amide
(Reference Compound No. 6-123)

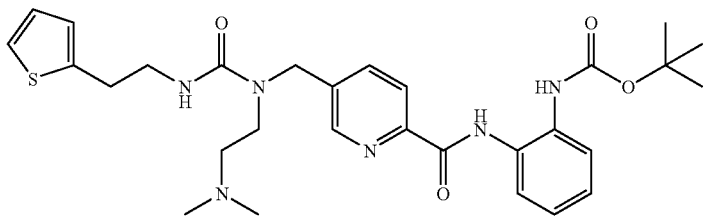

$^1$H-NMR (500 MHz, CDCl$_3$)
δ 1.51 (s, 9H), 2.09 (s, 6H),
2.33 (t, J = 4.7 Hz, 2H), 3.05 (t,
J = 6.5 Hz, 2H), 3.16 (t, J = 4.7
Hz, 2H), 3.53 (q, J = 6.5 Hz,
2H), 4.59 (s, 2H), 6.81 (dd, J =
3.4, 1.3 Hz, 1H), 6.93 (dd, J =
5.2, 3.4 Hz, 1H), 7.09 (br s,
1H), 7.14 (dd, J = 5.2, 1.3 Hz,
1H), 7.17-7.24 (m, 2H), 7.59 (d,
J = 6.4 Hz, 1H), 7.71 (d, J = 6.4
Hz, 1H), 7.83 (dd, J = 7.9, 2.1
Hz, 1H), 7.90 (br s, 1H), 8.23
(dd, J = 7.9, 0.6 Hz, 1H), 8.50
(dd, J = 2.1, 0.6 Hz, 1H), 10.15
(s, 1H)

N-(2-t-Butoxycarbonylaminophenyl)-5-
[3-isopropyl-1-[2-
(4-methylpiperazin-1-yl)ethyl]ureidomethyl]pyridine-
2-carboxylic acid amide
(Reference Compound No. 6-124)

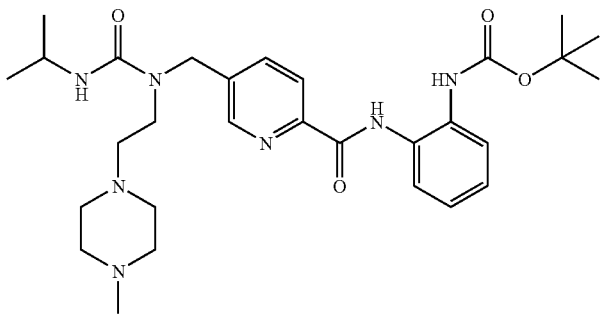

$^1$H-NMR (400 MHz, CDCl$_3$)
δ 1.22 (d, J = 6.6 Hz, 6H), 1.52
(s, 9H), 2.30 (s, 3H), 2.46 (t, J =
4.5 Hz, 2H), 2.54 (br s, 8H),
3.21 (t, J = 4.5 Hz, 2H), 3.99
(m, 1H), 4.59 (s, 2H), 7.02-7.07
(m, 2H), 7.17-7.25 (m, 2H),
7.60 (d, J = 6.6 Hz, 1H), 7.70
(d, J = 6.6 Hz, 1H), 7.85 (dd, J =
8.0, 2.2 Hz, 1H), 8.24 (d, J =
8.0 Hz, 1H), 8.51 (d, J = 2.2
Hz, 1H), 10.14 (s, 1H)

N-(2-t-Butoxycarbonylaminophenyl)-5-
[1-[2-(4-methylpiperazin-1-yl)ethyl]-
3-phenethylureidomethyl]pyridine-
2-carboxylic acid amide
(Reference Compound No. 6-125)

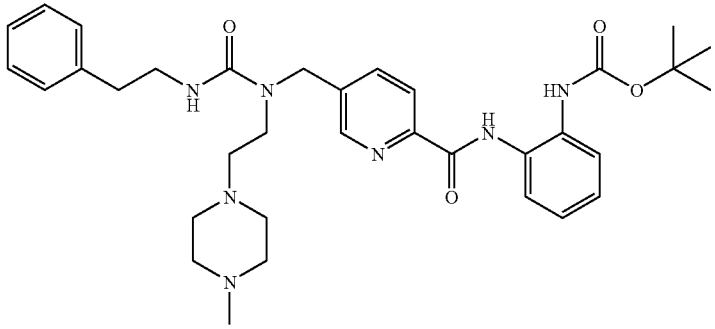

$^1$H-NMR (400 MHz, CDCl$_3$)
δ 1.51 (s, 9H), 2.24 (s, 3H),
2.32 (br s, 8H), 2.39 (t, J = 4.5
Hz, 2H), 2.87 (t, J = 7.0 Hz,
2H), 3.16 (t, J = 4.5 Hz, 2H),
3.49 (m, 2H), 4.60 (s, 2H), 7.06
(br s, 1H), 7.17-7.25 (m, 5H),
7.26-7.32 (m, 2H), 7.60 (d, J =
7.1 Hz, 1H), 7.69-7.75 (m, 2H),
7.82 (dd, J = 7.9, 2.1 Hz, 1H),
8.25 (d, J = 7.9 Hz, 1H), 8.50
(d, J = 2.1 Hz, 1H), 10.15 (s, 1H)

| | |
|---|---|
| N-(2-t-Butoxycarbonylaminophenyl)-5-[3-(4-methylphenyl)-1-[2-(4-methylpiperazin-1-yl)ethyl]ureidomethyl]pyridine-2-carboxylic acid amide (Reference Compound No. 6-126)<br>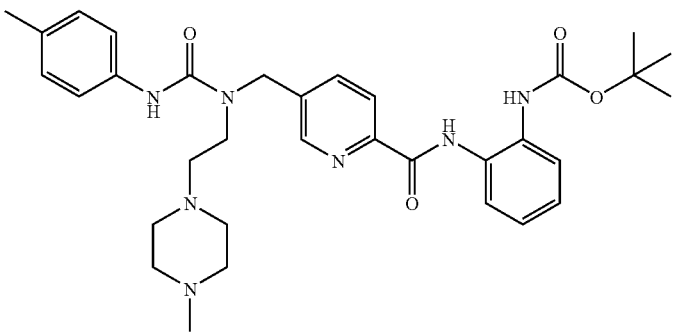 | $^1$H-NMR (400 MHz, CDCl$_3$) δ 1.52 (s, 9H), 2.31 (s, 3H), 2.32 (s, 3H), 2.53 (br s, 4H), 2.58 (t, J = 4.3 Hz, 2H), 2.65 (br s, 4H), 3.36 (t, J = 4.3 Hz, 2H), 4.65 (s, 2H), 7.04 (br s, 1H), 7.12 (d, J = 8.3 Hz, 2H), 7.18-7.25 (m, 2H), 7.34 (d, J = 8.3 Hz, 2H), 7.60 (d, J = 6.6 Hz, 1H), 7.71 (d, J = 6.6 Hz, 1H), 7.93 (dd, J = 7.9, 2.1 Hz, 1H), 8.27 (d, J = 7.9 Hz, 1H), 8.57 (d, J = 2.1 Hz, 1H), 9.88 (s, 1H), 10.16 (s, 1H) |
| N-(2-t-Butoxycarbonylaminophenyl)-5-[3-isopropyl-1-[3-(4-methylpiperazin-1-yl)propyl]ureidomethyl]pyridine-2-carboxylic acid amide (Reference Compound No. 6-127)<br>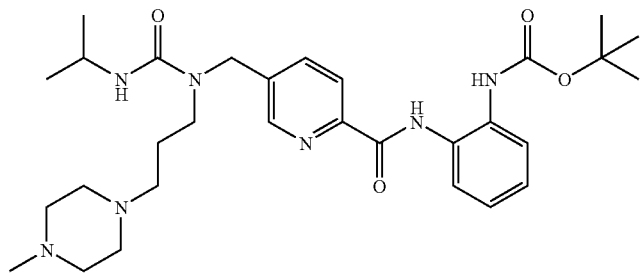 | $^1$H-NMR (400 MHz, CDCl$_3$) δ 1.21 (d, J = 6.6 Hz, 6H), 1.52 (s, 9H), 1.68 (m, 2H), 2.32 (s, 3H), 2.36 (t, J = 6.1 Hz, 2H), 2.48 (br s, 8H), 3.19 (t, J = 6.0 Hz, 2H), 4.01 (m, 1H), 4.57 (s, 2H), 6.04 (d, J = 8.3 Hz, 1H), 7.07 (br s, 1H), 7.17-7.25 (m, 2H), 7.61 (d, J = 7.1 Hz, 1H), 7.69 (d, J = 6.6 Hz, 1H), 7.85 (dd, J = 8.0, 2.2 Hz, 1H), 8.24 (d, J = 8.0 Hz, 1H), 8.52 (d, J = 2.2 Hz, 1H), 10.14 (s, 1H) |
| N-(2-t-Butoxycarbonylaminophenyl)-5-[1-[3-(4-methylpiperazin-1-yl)propyl]-3-phenethylureidomethyl]pyridine-2-carboxylic acid amide (Reference Compound No. 6-128)<br>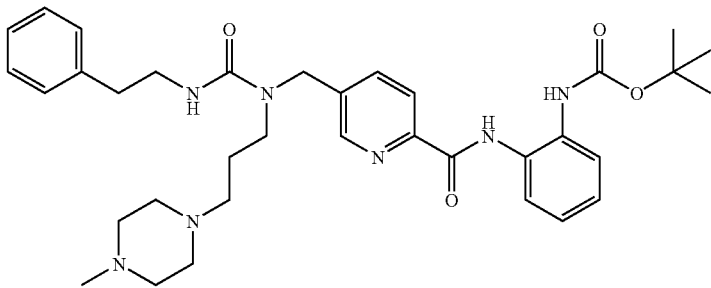 | $^1$H-NMR (400 MHz, CDCl$_3$) δ 1.51 (s, 9H), 1.62 (m, 2H), 2.27 (s, 3H), 2.30 (br s, 8H), 2.32 (t, J = 6.1 Hz, 2H), 2.87 (t, J = 7.0 Hz, 2H), 3.15 (t, J = 5.5 Hz, 2H), 3.49 (m, 2H), 4.58 (s, 2H), 7.07 (br s, 1H), 7.17-7.35 (m, 8H), 7.61 (d, J = 6.3 Hz, 1H), 7.69 (d, J = 6.6 Hz, 1H), 7.80 (dd, J = 8.0, 2.2 Hz, 1H), 8.25 (d, J = 8.0 Hz, 1H), 8.51 (d, J = 2.2 Hz, 1H), 10.15 (s, 1H) |
| N-(2-t-Butoxycarbonylaminophenyl)-5-[3-(4-methylphenyl)-1-[3-(4-methylpiperazin-1-yl)propyl]ureidomethyl]pyridine-2-carboxylic acid amide (Reference Compound No. 6-129)<br>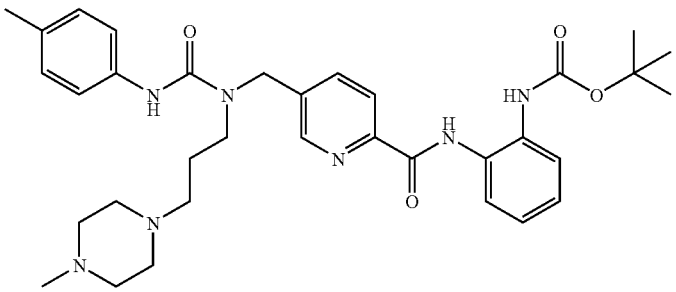 | $^1$H-NMR (400 MHz, CDCl$_3$) δ 1.51 (s, 9H), 1.77 (m, 2H), 2.25 (s, 3H), 2.32 (s, 3H), 2.41 (br s, 4H), 2.48 (t, J = 5.9 Hz, 2H), 2.49 (br s, 4H), 3.37 (t, J = 5.6 Hz, 2H), 4.64 (s, 2H), 7.06 (br s, 1H), 7.12 (d, J = 8.3 Hz, 2H), 7.17-7.24 (m, 2H), 7.33 (d, J = 8.3 Hz, 2H), 7.60 (d, J = 7.3 Hz, 1H), 7.68 (d, J = 7.1 Hz, 1H), 7.93 (dd, J = 8.0, 2.2 Hz, 1H), 8.24 (d, J = 8.0 Hz, 1H), 8.57 (d, J = 2.2 Hz, 1H), 8.99 (s, 1H), 10.14 (s, 1H) |

N-(2-t-Butoxycarbonylaminophenyl)-5-
[1-[3-(4-methylpiperidin-1-yl)propyl]-
[3-phenethylureidomethyl]pyridine-
2-carboxylic acid amide
(Reference Compound No. 6-130)

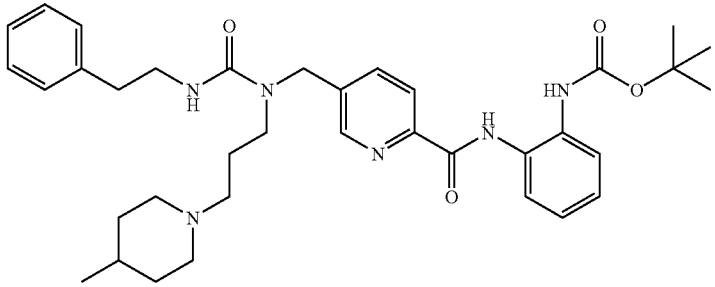

¹H-NMR (500 MHz, CDCl₃)
δ 0.92 (d, J = 6.7 Hz, 3H), 1.00 (m, 2H), 1.36 (m, 1H), 1.51 (s, 9H), 1.58-1.63 (m, 4H), 1.84 (t, J = 11.6 Hz, 2H), 2.28 (t, J = 6.1 Hz, 2H), 2.71 (d, J = 11.6 Hz, 2H), 2.85 (t, J = 7.0 Hz, 2H), 3.15 (t, J = 5.5 Hz, 2H), 3.47 (m, 2H), 4.57 (s, 2H), 7.08 (br s, 1H), 7.18-7.24 (m, 5H), 7.27-7.31 (m, 2H), 7.62 (d, J = 6.7 Hz, 1H), 7.66-7.70 (m, 2H), 7.79 (dd, J = 8.1, 2.0 Hz, 1H), 8.24 (d, J = 8.1 Hz, 1H), 8.50 (d, J = 2.0 Hz, 1H), 10.15 (s, 1H)

N-(2-t-Butoxycarbonylaminophenyl)-5-
[1-[5-(morpholin-4-yl)pentyl]-
3-phenethylureidomethyl]pyridine-
2-carboxylic acid amide
(Reference Compound No. 6-131)

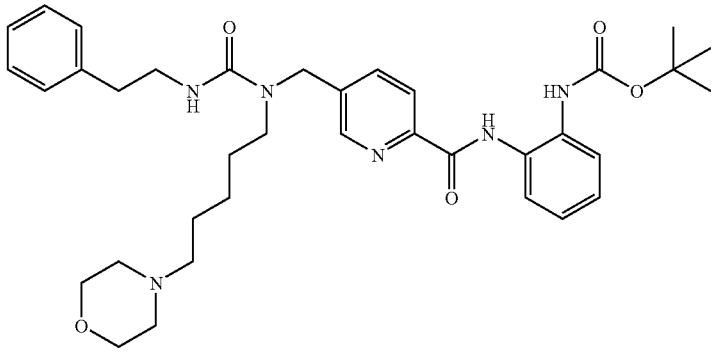

¹H-NMR (500 MHz, CDCl₃)
δ 1.20 (m, 2H), 1.39-1.48 (m, 4H), 1.52 (s, 9H), 2.27 (t, J = 7.5 Hz, 2H), 2.40 (br s, 4H), 2.84 (t, J = 6.6 Hz, 2H), 3.07 (t, J = 7.6 Hz, 2H), 3.54 (m, 2H), 3.70 (t, J = 4.6 Hz, 4H), 4.34 (t, J = 5.5 Hz, 1H), 4.55 (s, 2H), 7.08 (br s, 1H), 7.15-7.17 (m, 2H), 7.19-7.25 (m, 3H), 7.26-7.30 (m, 2H), 7.60 (d, J = 7.0 Hz, 1H), 7.71 (m, 1H), 7.73 (dd, J = 8.1, 2.0 Hz, 1H), 8.22 (d, J = 8.1 Hz, 1H), 8.45 (d, J = 2.0 Hz, 1H), 10.15 (s, 1H)

N-(2-t-Butoxycarbonylaminophenyl)-5-
[3-(4-methoxyphenyl)-1-
[5-(morpholin-4-yl)pentyl]ureidomethyl]pyridine-
2-carboxylic acid amide
(Reference Compound No. 6-132)

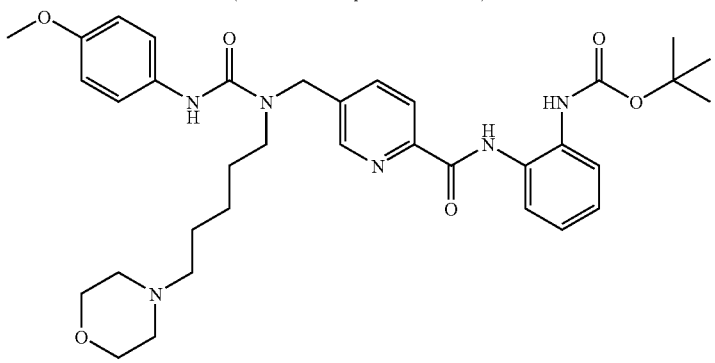

¹H-NMR (400 MHz, CDCl₃)
δ 1.38 (m, 2H), 1.52 (s, 9H), 1.55 (m, 2H), 1.68 (m, 2H), 2.32 (t, J = 7.4 Hz, 2H), 2.42 (t, J = 4.6 Hz, 4H), 3.30 (t, J = 7.7 Hz, 2H), 3.70 (t, J = 4.6 Hz, 4H), 3.79 (s, 3H), 4.68 (s, 2H), 6.24 (s, 1H), 6.85 (d, J = 9.0 Hz, 2H), 7.05 (br s, 1H), 7.19-7.22 (m, 2H), 7.25 (d, J = 9.0 Hz, 2H), 7.57 (d, J = 6.0 Hz, 1H), 7.72 (d, J = 6.6 Hz, 1H), 7.88 (dd, J = 8.0, 1.9 Hz, 1H), 8.28 (d, J = 8.0 Hz, 1H), 8.56 (d, J = 1.9 Hz, 1H), 10.17 (s, 1H)

| | |
|---|---|
| 5-[3-(4-Benzyloxyphenyl)-1-[5-(morpholin-4-yl)pentyl]ureidomethyl]-N-(2-t-butoxycarbonylaminophenyl)pyridine-2-carboxylic acid amide (Reference Compound No. 6-133) 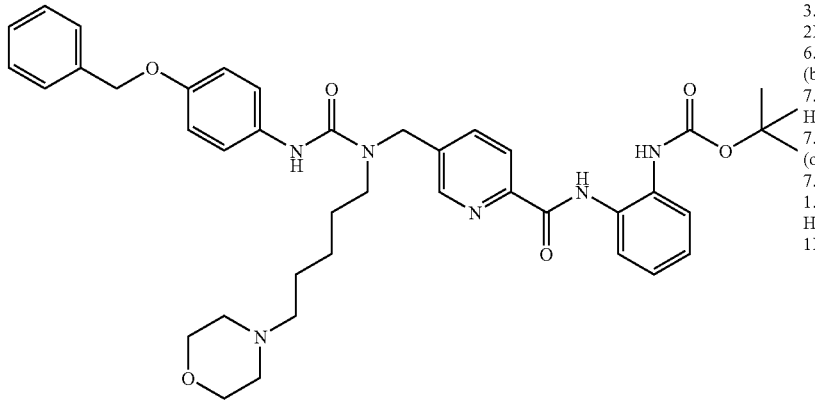 | $^1$H-NMR (500 MHz, CDCl$_3$) δ 1.38 (m, 2H), 1.52 (s, 9H), 1.57 (m, 2H), 1.68 (m, 2H), 2.32 (t, J = 7.5 Hz, 2H), 2.41 (s, 4H), 3.30 (t, J = 7.8 Hz, 2H), 3.70 (t, J = 4.6 Hz, 4H), 4.68 (s, 2H), 5.05 (s, 2H), 6.23 (s, 1H), 6.93 (d, J = 8.9 Hz, 2H), 7.05 (br s, 1H), 7.19-7.24 (m, 2H), 7.26 (m, 2H), 7.32 (d, J = 7.3 Hz, 1H), 7.36-7.40 (m, 2H), 7.42 (d, J = 7.3 Hz, 2H), 7.58 (d, J = 6.1 Hz, 1H), 7.73 (d, J = 7.9 Hz, 1H), 7.88 (d, J = 8.0, 1.9 Hz, 1H), 8.28 (d, J = 8.0 Hz, 1H), 8.56 (d, J = 1.9 Hz, 1H), 10.16 (s, 1H) |
| N-(2-t-Butoxycarbonylaminophenyl)-5-[3-(2-methoxyphenyl)-1-[5-(morpholin-4-yl)pentyl]ureidomethyl]pyridine-2-carboxylic acid amide (Reference Compound No. 6-134) 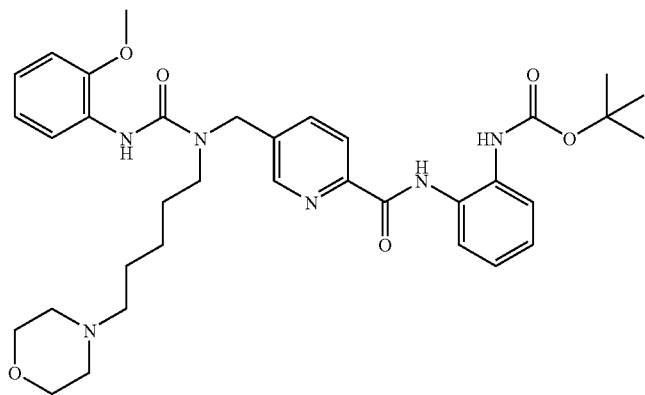 | $^1$H-NMR (500 MHz, CDCl$_3$) δ 1.39 (m, 2H), 1.51 (s, 9H), 1.54 (m, 2H), 1.71 (m, 2H), 2.33 (t, J = 7.6 Hz, 2H), 2.42 (m, 4H), 3.36 (t, J = 7.6 Hz, 2H), 3.70 (t, J = 4.7 Hz, 4H), 3.83 (s, 3H), 4.70 (s, 2H), 6.85 (m, 1H), 6.96-6.99 (m, 2H), 7.15 (s, 1H), 7.20-7.23 (m, 2H), 7.57 (d, J = 6.7 Hz, 1H), 7.73 (d, J = 6.4 Hz, 1H), 7.89 (dd, J = 7.9, 1.8 Hz, 1H), 8.17 (m, 1H), 8.28 (d, J = 7.9 Hz, 1H), 8.57 (d, J = 1.8 Hz, 1H), 10.17 (s, 1H) |
| N-(2-t-Butoxycarbonylaminophenyl)-5-[1-[3-(morpholin-4-yl)propyl]-3-(pyridin-3-yl)ureidomethyl]pyridine-2-carboxylic acid amide (Reference Compound No. 6-135) 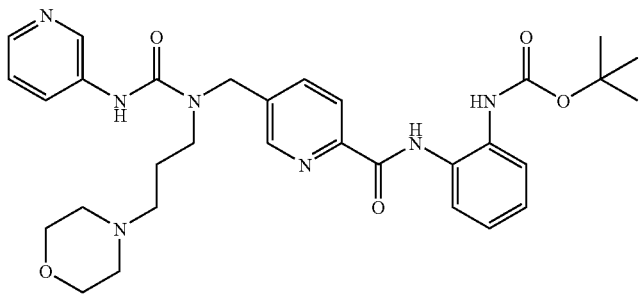 | $^1$H-NMR (500 MHz, CDCl$_3$) δ 1.51 (s, 9H), 1.82 (m, 2H), 2.48 (t, J = 4.5 Hz, 4H), 2.51 (t, J = 6.0 Hz, 2H), 3.42 (t, J = 5.5 Hz, 2H), 3.69 (t, J = 4.5 Hz, 4H), 4.65 (s, 2H), 7.04 (br s, 1H), 7.17-7.24 (m 2H), 7.29 (ddd, J = 8.0, 4.8, 0.9 Hz, 1H), 7.58 (d, J = 6.4 Hz, 1H), 7.71 (d, J = 6.1 Hz, 1H), 7.92 (dd, J = 7.9, 2.1 Hz, 1H), 8.04 (ddd, J = 8.0, 2.4, 1.2 Hz, 1H), 8.26 (dd, J = 7.9, 0.9 Hz, 1H), 8.34 (dd, J = 4.8, 1.2 Hz, 1H), 8.58 (dd, J = 2.1, 0.9 Hz, 1H), 8.58 (dd, J = 2.4, 0.9 Hz, 1H), 9.24 (s, 1H), 10.15 (s, 1H) |

| | |
|---|---|
| N-(2-t-Butoxycarbonylaminophenyl)-6-[1-(2-dimethylaminoethyl)-3-(3-methylphenyl)ureidomethyl]pyridine-3-carboxylic acid amide (Reference Compound No. 6-136) 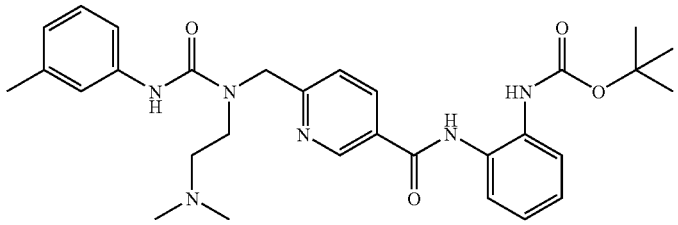 | $^1$H-NMR (400 MHz, CDCl$_3$) δ 1.51 (s, 9H), 2.32 (s, 3H), 2.39 (s, 6H), 2.58 (t, J = 4.4 Hz, 2H), 3.46 (t, J = 4.4 Hz, 2H), 4.73 (s, 2H), 6.78 (s, 1H), 6.80 (d, J = 7.8 Hz, 1H), 6.85 (d, J = 7.8 Hz, 1H), 7.06 (m, 1H), 7.10-7.25 (m, 4H), 7.54 (d, J = 7.8 Hz, 1H), 7.84 (d, J = 8.1 Hz, 1H), 8.21 (dd, J = 8.1, 2.0 Hz, 1H), 9.11 (d, J = 2.0 Hz, 1H), 9.48 (s, 1H), 10.91 (s, 1H) |
| N-(2-t-Butoxycarbonylaminophenyl)-6-[1-(2-dimethylaminoethyl)-3-(3-fluorophenyl)ureidomethyl]pyridine-3-carboxylic acid amide (Reference Compound No. 6-137) 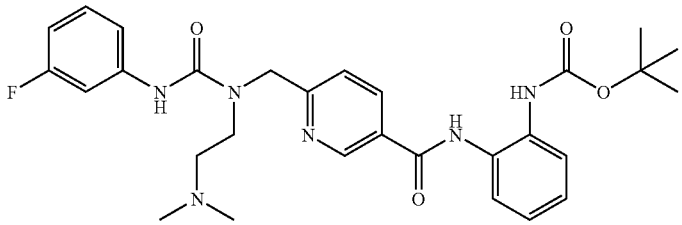 | $^1$H-NMR (400 MHz, CDCl$_3$) δ 1.51 (s, 9H), 2.40 (s, 6H), 2.61 (t, J = 4.3 Hz, 2H), 3.47 (t, J = 4.3 Hz, 2H), 4.72 (s, 2H), 6.64-6.71 (m, 2H), 6.77 (s, 1H), 6.97-7.00 (m, 2H), 7.17-7.22 (m, 3H), 7.53 (d, J = 7.6 Hz, 1H), 7.85 (d, J = 8.0 Hz, 1H), 8.22 (dd, J = 8.0, 1.9 Hz, 1H), 9.11 (d, J = 1.9 Hz, 1H), 9.50 (s, 1H), 11.30 (s, 1H) |
| N-(2-t-Butoxycarbonylaminophenyl)-6-[1-(2-dimethylaminoethyl)-3-(thiophen-3-yl)ureidomethyl]pyridine-3-carboxylic acid amide (Reference Compound No. 6-138) 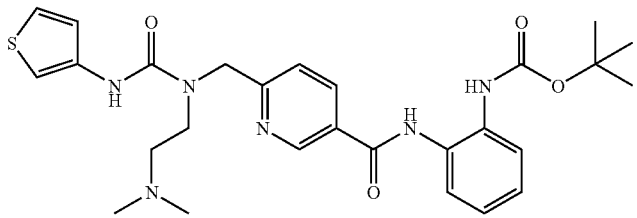 | $^1$H-NMR (400 MHz, CDCl$_3$) δ 1.51 (s, 9H), 2.39 (s, 6H), 2.58 (t, J = 4.3 Hz, 2H), 3.45 (t, J = 4.3 Hz, 2H), 4.74 (s, 2H), 6.80 (s, 1H), 6.86-6.89 (m, 2H), 7.19-7.24 (m, 3H), 7.28 (dd, J = 3.3, 1.3 Hz, 1H), 7.51 (d, J = 8.2 Hz, 1H), 7.84 (d, J = 8.2 Hz, 1H), 8.18 (dd, J = 8.2, 2.1 Hz, 1H), 9.09 (d, J = 2.1 Hz, 1H), 9.48 (s, 1H), 11.46 (s, 1H) |
| N-(2-t-Butoxycarbonylaminophenyl)-6-[3-(2,3-dihydrobenzo[1,4]dioxin-6-yl)-1-(2-dimethylaminoethyl)ureidomethyl]pyridine-3-carboxylic acid amide (Reference Compound No. 6-139) 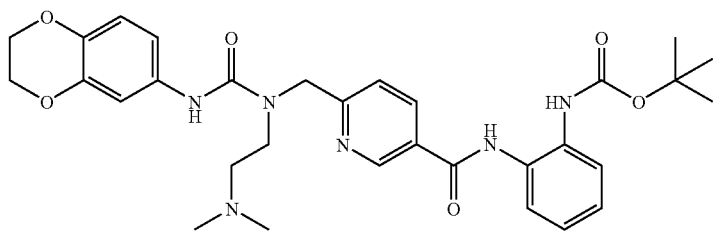 | $^1$H-NMR (400 MHz, CDCl$_3$) δ 1.51 (s, 9H), 2.37 (s, 6H), 2.56 (t, J = 4.2 Hz, 2H), 3.44 (t, J = 4.2 Hz, 2H), 4.20-4.24 (m, 4H), 4.71 (s, 2H), 6.72-6.83 (m, 4H), 6.92 (d, J = 2.2 Hz, 1H), 7.16-7.25 (m, 2H), 7.53 (d, J = 8.1 Hz, 1H), 7.83 (d, J = 7.6 Hz, 1H), 8.20 (dd, J = 8.1, 2.1 Hz, 1H), 9.10 (d, J = 2.1 Hz, 1H), 9.49 (s, 1H), 10.81 (s, 1H) |

N-(2-t-Butoxycarbonylaminophenyl)-6-
[1-(2-dimethylaminoethyl)-3-
(3-methoxyphenyl)ureidomethyl]pyridine-
3-carboxylic acid amide
(Reference Compound No. 6-140)

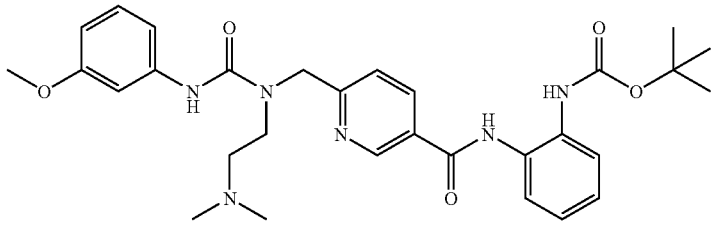

¹H-NMR (400 MHz, CDCl₃)
δ 1.51, (s, 9H), 2.39 (s, 6H),
2.58 (t, J = 4.4 Hz, 2H), 3.46 (t,
J = 4.4 Hz, 2H), 3.79 (s, 3H),
4.73 (s, 2H), 6.54 (ddd, J = 8.2,
2.2, 0.8 Hz, 1H), 6.79 (m, 1H),
6.80 (ddd, J = 8.2, 2.2, 1.0 Hz,
1H), 7.07 (t, J = 2.2 Hz, 1H),
7.13-7.24 (m, 3H), 7.16 (t, J =
8.3 Hz, 1H), 7.53 (d, J = 8.2
Hz, 1H), 7.84 (d, J = 8.2 Hz,
1H), 8.21 (dd, J = 8.2, 2.2 Hz,
1H), 9.11 (d, J = 2.2 Hz, 1H),
9.49 (s, 1H), 11.08 (s, 1H)

N-(2-t-Butoxycarbonylaminophenyl)-5-
[1-(4-dimethylaminonbutyl)-3-
(4-dimethylaminophenyl)ureidomethyl]pyridine-
2-carboxylic acid amide
(Reference Compound No. 6-141)

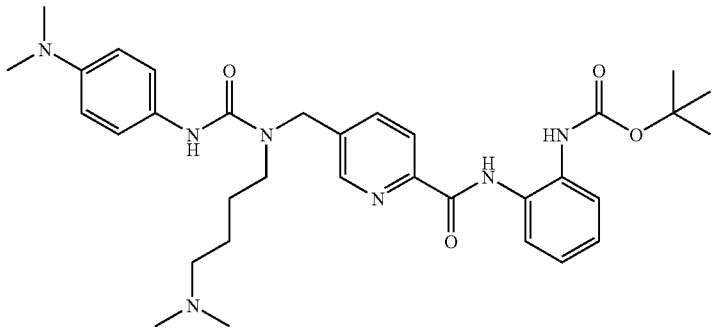

¹H-NMR (400 MHz, CDCl₃)
δ 1.52 (s, 9H), 1.53 (m, 2H),
1.71 (m, 2H), 2.19 (s, 6H), 2.34
(t, J = 6.5 Hz, 2H), 2.91 (s, 6H),
3.24 (t, J = 8.2 Hz, 2H), 4.69 (s,
2H), 6.72 (dd, J = 9.0 Hz, 2H),
7.11 (br s, 1H), 7.17-7.24 (m,
2H), 7.18 (d, J = 9.0 Hz, 2H),
7.60 (d, J = 6.4 Hz, 1H), 7.70
(d, J = 6.1 Hz, 1H), 7.84 (s,
1H), 7.91 (dd, J = 8.1, 2.1 Hz,
1H), 8.25 (dd, J = 8.1, 0.7 Hz,
1H), 8.57 (dd, J = 2.1, 0.7 Hz,
1H), 10.16 (s, 1H)

Reference Example 7

5-[3-(1,3-Benzothiazol-2-yl)-1-(3-dimethylamino-propyl)ureidomethyl]-N-(2-t-butoxycarbonylaminophenyl)pyridine-2-carboxylic acid amide (Reference Compound No. 7-1)

Under ice cooling, 2-amino-1,3-benzothiazole (100 mg, 0.60 mmol) was added to a solution of N,N'-carbonyldiimidazole (98 mg, 0.60 mmol) in THF (3.0 mL), and then the reaction mixture was stirred for 2 hours. N-(2-t-butoxycarbonylaminophenyl)-5-(3-dimethylaminopropylaminomethyl) pyridine-2-carboxylic acid amide (Reference Compound No. 5-1, 90 mg, 0.20 mmol) was added thereto, and then the reaction mixture was stirred at 60° C. for 3 hours. Water (30 mL) was added thereto, the whole was extracted with ethyl acetate (30 mL) twice, and then the organic layer was washed with water (30 mL) and brine (30 mL). After the organic layer was dried over anhydrous magnesium sulfate, the solvent was evaporated under reduced pressure to give 220 mg of a mixture containing the title reference compound as a white amorphous product.

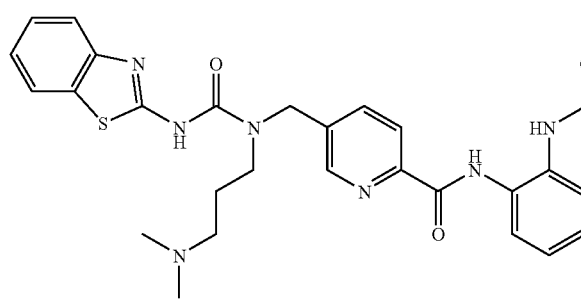

¹H-NMR (400 MHz, DMSO-d₆)
δ 1.45 (s, 9H), 1.74 (br s, 2H),
2.30 (br s, 6 H), 2.38 (br s, 2H),
3.43 (br s, 2H), 4.70 (s, 2H),
7.13-7.27 (m, 4H), 7.34 (m,
1H), 7.44 (br s, 1H), 7.58 (br s,
1H), 7.84 (br s, 1H), 8.00-8.01
(m, 2H), 8.15 (d, J = 8.1 Hz,
1H), ,8.60 (br s, 1H), 9.11 (br s,
1H), 10.47 (br s, 1H)

By using any compounds selected from Reference Compounds No. 5-1~5-20 and commercially available compounds, the following Reference Compounds No. 7-2~7-49 were obtained by a method similar to that of Reference Compound No. 7-1.

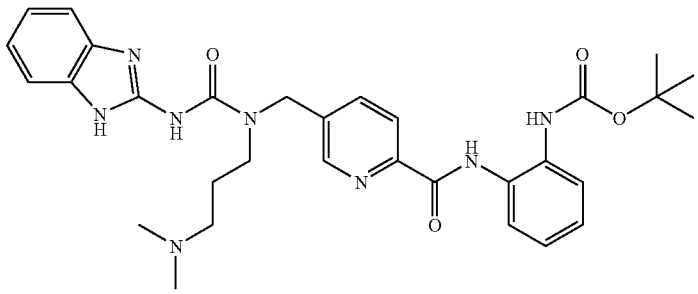

5-[3-(1H-Benzoimidazol-2-yl)-1-(3-dimethylaminopropyl)ureidomethyl]-N-(2-t-butoxycarbonylaminophenyl)pyridine-2-carboxylic acid amide (Reference Compound No. 7-2)

$^1$H-NMR (400 MHz, DMSO-d$_6$) δ 1.41 (s, 9 H), 1.71 (br s, 2H), 2.20 (br s, 8 H), 3.42 (br s, 2H), 4.72 (s, 2H), 7.01-7.03 (m, 2H), 7.14 (td, J = 7.6, 1.5 Hz, 1H), 7.22-7.29 (m, 4 H), 8.00-8.02 (m, 2H), 8.14 (d, J = 8.1 Hz, 1H), 8.59 (d, J = 1.2 Hz, 1H), 9.11 (br s, 1H), 10.47 (br s, 1H), 11.81 (br s, 2 H)

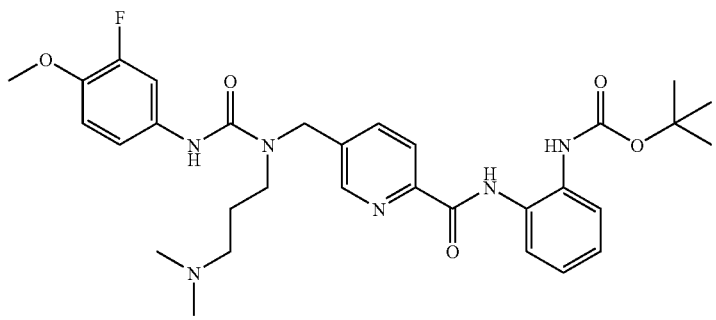

N-(2-t-Butoxycarbonylaminophenyl)-5-[1-(3-dimethylaminopropyl)-3-(3-fluoro-4-methoxyphenyl)ureido methyl]pyridine-2-carboxylic acid amide (Reference Compound No. 7-3)

$^1$H-NMR (400 MHz, CDCl$_3$) δ 1.51 (s, 9 H), 1.73 (m, 2H), 2.30 (s, 6 H), 2.40 (t, J = 6.0 Hz, 2H), 3.37 (t, J = 5.6 Hz, 2H), 3.86 (s, 3 H), 4.61 (s, 2H), 6.88 (t, J = 9.1 Hz, 1H), 7.06-7.09 (m, 2H), 7.17-7.24 (m, 2H), 7.32 (dd, J = 13.4, 2.4 Hz, 1H), 7.58 (m, 1H), 7.69 (m, 1H), 7.92 (dd, J = 7.9, 2.2 Hz, 1H), 8.25 (dd, J = 7.9, 0.6 Hz, 1H), 8.58 (d, J = 2.2 Hz, 1H), 10.16 (s, 1H), 10.17 (s, 1H)

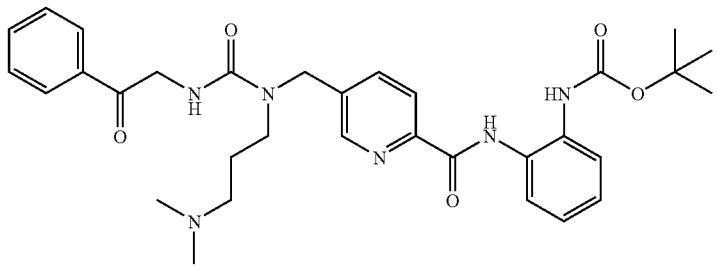

N-(2-t-Butoxycarbonylaminophenyl)-5-[1-(3-dimethylaminopropyl)-3-(phenylcarbonylmethyl)ureidomethyl]pyridine-2-carboxylic acid amide (Reference Compound No. 7-4)

$^1$H-NMR (400 MHz, CDCl$_3$) δ 1.51 (s, 9 H), 1.71 (m, 2H), 2.22 (s, 6 H), 2.40 (t, J = 6.1 Hz, 2H), 3.38 (t, J = 5.7 Hz, 2H), 4.61 (s, 2H), 4.71 (d, J = 4.4 Hz, 2H), 7.17-7.24 (m, 3 H), 7.45-7.49 (m, 2H), 7.59 (t, J = 8.0 Hz, 2H), 7.62 (s, 1H), 7.87 (dd, J = 8.1, 2.2 Hz, 1H), 7.99 (dd, J = 8.0, 1.2 Hz, 2H), 8.24 (d, J = 8.1 Hz, 1H), 8.34 (s, 1H), 8.53 (d, J = 2.2 Hz, 1H), 10.15 (s, 1H)

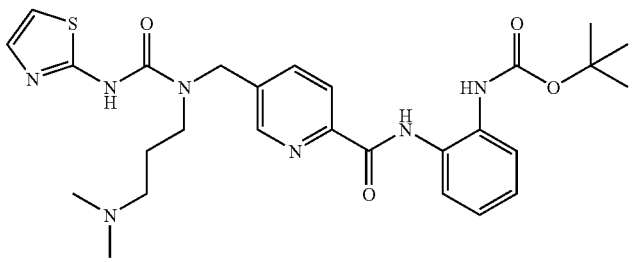

N-(2-t-Butoxycarbonylaminophenyl)-5-[1-(3-dimethylaminopropyl)-3-(1,3-thiazol-2-yl)ureidomethyl]pyridine-2-carboxylic acid amide (Reference Compound No. 7-5)

¹H-NMR (400 MHz, CDCl₃) δ 1.51 (s, 9 H), 1.73 (m, 2H), 2.35 (s, 6 H), 2.40 (t, J = 6.0 Hz, 2H), 3.40 (m, 2H), 4.66 (s, 2H), 6.85 (d, J = 3.7 Hz, 1H), 7.08 (br s, 1H), 7.17-7.24 (m, 2H), 7.37 (d, J = 3.7 Hz, 1H), 7.58 (br s, 1H), 7.72 (br s, 1H), 7.91 (dd, J = 8.1, 2.1 Hz, 1H), 8.26 (dd, J = 8.1, 0.5 Hz, 1H), 8.57 (dd, J = 2.1, 0.5 Hz, 1H), 10.17 (br s, 1H), 13.17 (br s, 1H)

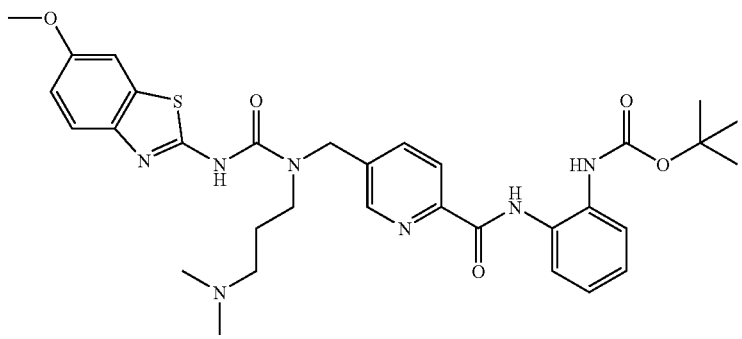

N-(2-t-Butoxycarbonylaminophenyl)-5-[1-(3-dimethylaminopropyl)-3-(6-methoxy-1,3-benzothiazol-2-yl)ureidomethyl]pyridine-2-carboxylic acid amide (Reference Compound No. 7-6)

¹H-NMR (400 MHz, DMSO-d₆) δ 1.46 (s, 9 H), 1.73 (m, 2H), 2.28 (s, 6 H), 2.33 (m, 2H), 3.41 (t, J = 5.1 Hz, 2H), 3.79 (s, 3 H), 4.71 (s, 2H), 6.94 (dd, J = 8.8, 2.3 Hz, 1H), 7.15 (td, J = 7.6, 1.2 Hz, 1H), 7.21-7.29 (m, 3 H), 7.45 (d, J = 2.3 Hz, 1H), 7.99-8.02 (m, 2H), 8.16 (d, J = 8.1 Hz, 1H), 8.61 (br s, 1H), 9.11 (br s, 1H), 10.47 (br s, 1H)

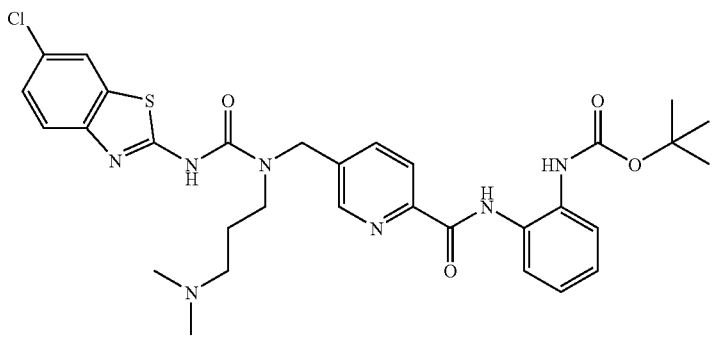

N-(2-t-Butoxycarbonylaminophenyl)-5-[3-(6-chloro-1,3-benzothiazol-2-yl)-1-(3-dimethylaminopropyl)ureidomethyl]pyridine-2-carboxylic acid amide (Reference Compound No. 7-7)

¹H-NMR (400 MHz, DMSO-d₆) δ 1.45 (s, 9 H), 1.75 (br s, 2H), 2.35 (br s, 8 H), 3.42 (t, J = 6.3 Hz, 2H), 4.70 (s, 2H), 7.15 (td, J = 7.6, 1.5 Hz, 1H), 7.22-7.27 (m, 2H), 7.29 (d, J = 8.5 Hz, 1H), 7.34 (dd, J = 8.5, 2.1 Hz, 1H), 7.77 (d, J = 2.1 Hz, 1H), 7.96-8.02 (m, 2H), 8.15 (d, J = 8.1 Hz, 1H), 8.61 (br s, 1H), 9.11 (br s, 1H), 10.47 (br s, 1H)

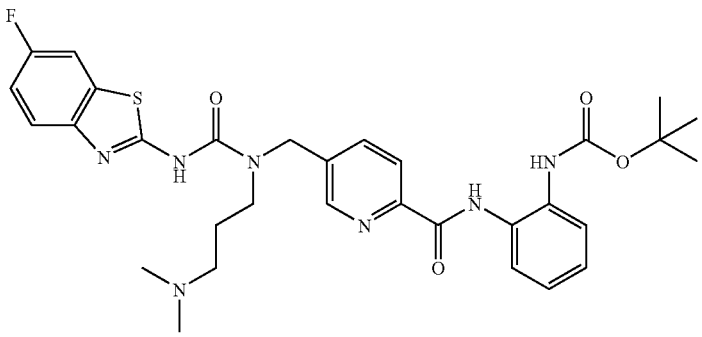

N-(2-t-Butoxycarbonylaminophenyl)-5-[1-(3-dimethylaminopropyl)-3-(6-fluoro-1,3-benzothiazol-2-yl)ureidomethyl]pyridine-2-carboxylic acid amide (Reference Compound No. 7-8)

$^1$H-NMR (400 MHz, DMSO-d$_6$) δ 1.45 (s, 9 H), 1.74 (m, 2H), 2.33 (br s, 6 H), 2.40 (br s, 2H), 3.42 (t, J = 5.5 Hz, 2H), 4.70 (s, 2H), 7.13-7.20 (m, 2H), 7.23-7.27 (m, 2H), 7.58 (m, 1H), 7.77 (dd, J = 8.9, 2.1 Hz, 1H), 7.99-8.02 (m, 2H), 8.15 (d, J = 8.1 Hz, 1H), 8.60 (br s, 1H), 9.12 (br s, 1H), 10.47 (br s, 1H)

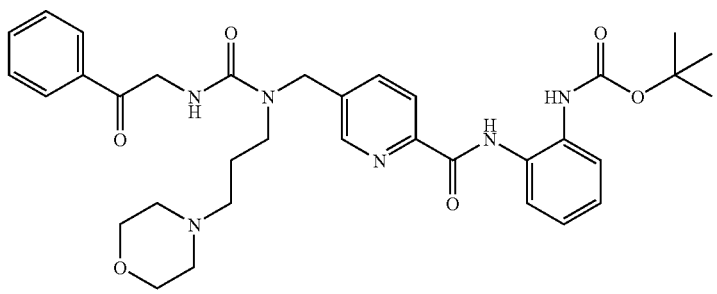

N-(2-t-Butoxycarbonylaminophenyl)-5-[1-[3-(morpholin-4-yl)propyl]-3-(phenylcarbonylmethyl)ureidomethyl]pyridine-2-carboxylic acid amide (Reference Compound No. 7-9)

$^1$H-NMR (400 MHz, CDCl$_3$) δ 1.52 (s, 9 H), 1.77 (m, 2H), 2.44-2.52 (m, 6 H), 3.39 (t, J = 6.0 Hz, 2H), 3.67 (t, J = 4.4 Hz, 4 H), 4.63 (s, 2H), 4.72 (d, J = 5.1 Hz, 2H), 7.16-7.24 (m, 2H), 7.30 (m, 1H), 7.39 (t, J = 7.9 Hz, 1H), 7.48-7.52 (m, 2H), 7.61-7.63 (m, 2H), 7.68 (s, 1H), 7.88 (dd, J = 8.1, 2.2 Hz, 1H), 8.00 (dd, J = 8.5, 1.5 Hz, 2H), 8.26 (d, J = 8.1 Hz, 1H), 8.54 (d, J = 2.2 Hz, 1H), 10.14 (s, 1H)

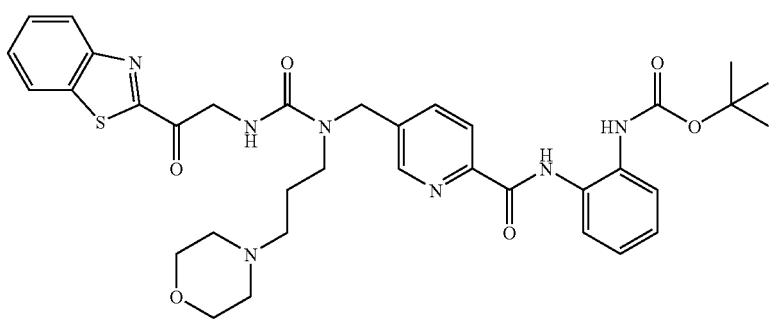

5-[3-(1,3-Benzothiazol-2-yl)-1-[3-(morpholin-4-yl)propyl]ureidomethyl]-N-(2-t-butoxycarbonylaminophenyl)pyridine-2-carboxylic acid amide (Reference Compound No. 7-10)

$^1$H-NMR (500 MHz, DMSO-d$_6$) δ 1.44 (s, 9 H), 1.75 (br s, 2H), 2.38 (br s, 6 H), 3.40-3.49 (m, 2H), 3.76 (br s, 4 H), 4.75 (br s, 2H), 7.15 (td, J = 7.6, 1.5 Hz, 1H), 7.23-7.27 (m, 3 H), 7.36 (t, J = 7.3 Hz, 1H), 7.60 (br s, 1H), 7.85 (br s, 1H), 7.98-8.01 (m, 2H), 8.15 (d, J = 8.2 Hz, 1H), 8.59 (s, 1H), 9.10 (br s, 1H), 10.47 (br s, 1H)

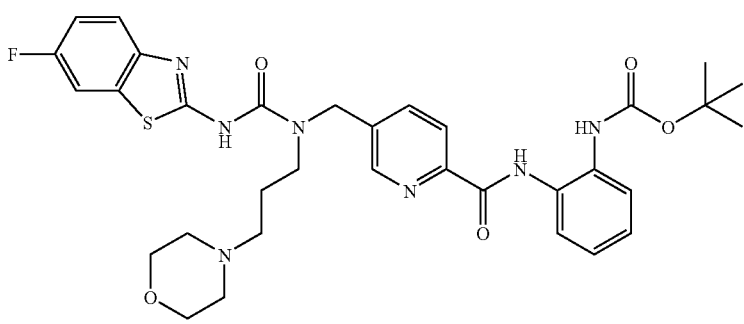

N-(2-t-Butoxycarbonylaminophenyl)-5-[3-(6-fluoro-1,3-benzothiazol-2-yl)-1-[3-(morpholin-4-yl)propyl]ureidomethyl]pyridine-2-carboxylic acid amide (Reference Compound No. 7-11)

$^1$H-NMR (400 MHz, CDCl$_3$) δ 1.51 (s, 9 H), 1.83 (m, 2H), 2.49 (t, J = 6.0 Hz, 2H), 2.55 (br s, 4 H), 3.43 (m, 2H), 4.11 (t, J = 7.2 Hz, 4 H), 4.69 (s, 2H), 7.03 (m, 1H), 7.10 (td, J = 9.0, 2.4 Hz, 1H), 7.18-7.24 (m, 2H), 7.46 (dd, J = 8.1, 2.4 Hz, 1H), 7.57 (d, J = 5.6 Hz, 1H), 7.64 (dd, J = 9.0, 4.6 Hz, 1H), 7.72 (d, J = 4.9 Hz, 1H), 7.92 (dd, J = 8.1, 2.2 Hz, 1H), 8.27 (dd, J = 8.1, 0.7 Hz, 1H), 8.59 (dd, J = 2.2, 0.7 Hz, 1H), 10.17 (br s, 1H)

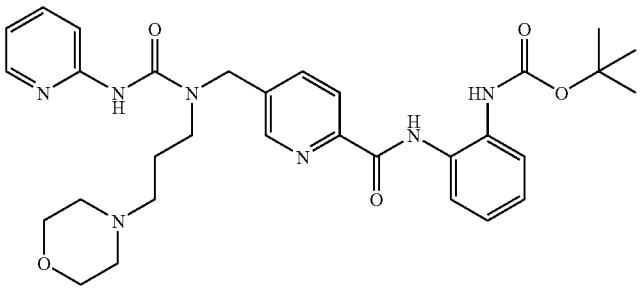

N-(2-t-Butoxycarbonylaminophenyl)-5-[1-[3-(morpholin-4-yl)propyl]-
3-(pyridine-2-yl)ureidomethyl]pyridine-2-carboxylic acid amide
(Reference Compound No. 7-12)

¹H-NMR (400 MHz, Solv. (CDCl₃) δ 1.51 (s, 9 H), 1.81 (m, 2H), 2.46 (t, J = 6.1 Hz, 2H), 2.51 (br s, 4 H), 3.44 (t, J = 5.6 Hz, 2H), 3.99 (t, J = 4.3 Hz, 4 H), 4.66 (s, 2H), 6.93 (ddd, J = 7.2, 4.9, 1.0 Hz, 1H), 7.05 (br s, 1H), 7.17-7.25 (m, 2H), 7.59 (d, J = 7.3 Hz, 1H), 7.63 (ddd, J = 8.6, 7.2, 2.0 Hz, 1H), 7.70 (d, J = 6.8 Hz, 1H), 7.92 (dd, J = 8.1, 2.2 Hz, 1H), 8.00 (dt, J = 8.6, 1.0 Hz, 1H), 8.22 (ddd, J = 4.9, 2.0, 1.0 Hz, 1H), 8.27 (dd, J = 2.2, 0.6 Hz, 1H), 9.83 (s, 1H), 10.16 (s, 1H)

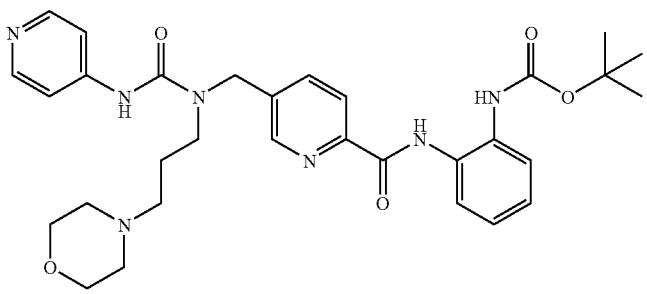

N-(2-t-Butoxycarbonylaminophenyl)-5-[1-[3-(morpholin-4-yl)propyl]-
3-(pyridin-4-yl)ureidomethyl]pyridine-2-carboxylic acid amide
(Reference Compound No. 7-13)

¹H-NMR (500 MHz, CDCl₃) δ 1.51 (s, 9 H), 1.83 (m, 2H), 2.44-2.56 (m, 6 H), 3.39 (t, J = 5.6 Hz, 2H), 3.80 (t, J = 4.6 Hz, 4 H), 4.65 (s, 2H), 7.02 (br s, 1H), 7.18-7.25 (m, 2H), 7.49 (d, J = 6.3 Hz, 2H), 7.57 (d, J = 6.3 Hz, 1H), 7.71 (d, J = 6.3 Hz, 1H), 7.91 (dd, J = 8.0, 2.2 Hz, 1H), 8.27 (dd, J = 8.0, 0.7 Hz, 1H), 8.47 (d, J = 6.3 Hz, 2H), 8.58 (dd, J = 2.2, 0.7 Hz, 1H), 9.10 (s, 1H), 10.17 (s, 1H)

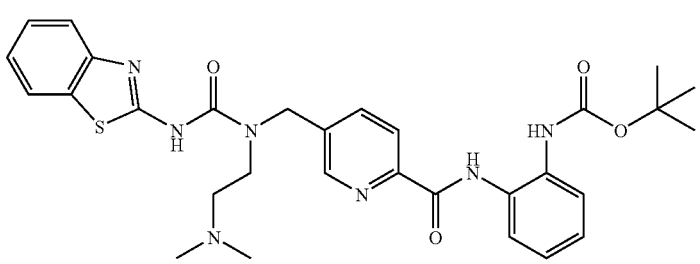

5-[3-(1,3-Benzothiazol-2-yl)-1-(2-dimethylaminoethyl)ureidomethyl]-
N-(2-t-butoxycarbonylaminophenyl)pyridine-2-carboxylic acid amide
(Reference Compound No. 7-14)

¹H-NMR (500 MHz, CDCl₃) δ 1.51 (s, 9 H), 2.50 (s, 6 H), 2.60 (t, J = 4.3 Hz, 2H), 3.39 (t, J = 4.3 Hz, 2H), 4.73 (s, 2H), 7.02 (br s, 1H), 7.19-7.24 (m, 3 H), 7.36 (m, 1H), 7.57 (d, J = 5.5 Hz, 1H), 7.70 (d, J = 8.7 Hz, 1H), 7.73 (m, 1H), 7.77 (d, J = 7.6 Hz, 1H), 7.92 (dd, J = 7.9, 2.1 Hz, 1H), 8.29 (d, J = 7.9 Hz, 1H), 8.58 (d, J = 2.1 Hz, 1H), 10.17 (s, 1H)

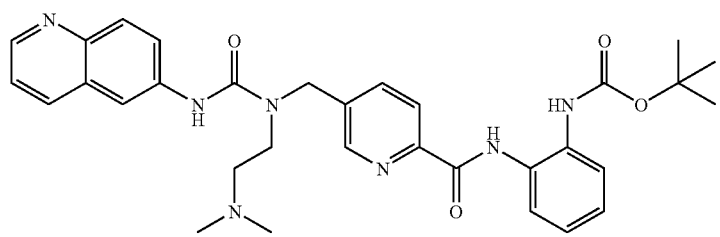

N-(2-t-Butoxycarbonylaminophenyl)-5-[1-(2-dimethylaminoethyl)-3-(quinolin-6-yl)
ureidomethyl]pyridine-2-carboxylic acid amide (Reference Compound No. 7-15)

¹H-NMR (500 MHz, CDCl₃) δ 1.51 (s, 9 H), 2.48 (s, 6 H), 2.61 (t, J = 4.3 Hz, 2H), 3.40 (t, J = 4.3 Hz, 2H), 4.71 (s, 2H), 7.05 (br s, 1H), 7.19-7.24 (m, 2H), 7.35 (dd, J = 8.2, 4.3 Hz, 1H), 7.39 (dd, J = 9.0, 2.4 Hz, 1H), 7.59 (d, J = 6.1 Hz, 1H), 7.72 (d, J = 6.1 Hz, 1H), 7.95 (dd, J = 7.9, 2.1 Hz, 1H), 8.01 (d, J = 9.0 Hz, 1H), 8.09 (d, J = 8.2 Hz, 1H), 8.18 (d, J = 2.4 Hz, 1H), 8.29 (d, J = 7.9 Hz, 1H), 8.61 (d, J = 2.1 Hz, 1H), 8.77 (d, J = 4.3 Hz, 1H), 10.17 (s, 1H), 11.50 (s, 1H)

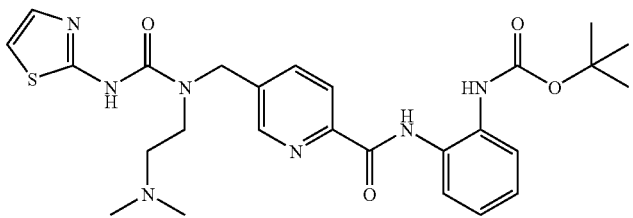

N-(2-t-Butoxycarbonylaminophenyl)-5-[1-(2-dimethylaminoethyl)-3-(1,3-thiazol-2-yl)ureidomethyl]pyridine-2-carboxylic acid amide (Reference Compound No. 7-16)

$^1$H-NMR (400 MHz, CDCl$_3$) δ 1.51 (s, 9 H), 2.45 (s, 6 H), 2.57 (t, J = 4.3 Hz, 2H), 3.35 (t, J = 4.3 Hz, 2H), 4.71 (s, 2H), 6.86 (d, J = 3.7 Hz, 1H), 7.02 (br s, 1H), 7.18-7.25 (m, 2H), 7.39 (d, J = 3.7 Hz, 1H), 7.58 (d, J = 6.3 Hz, 1H), 7.72 (d, J = 6.1 Hz, 1H), 7.90 (dd, J = 8.1 2.2 Hz, 1H), 8.28 (d , J = 8.1, Hz, 1H), 8.56 (d, J = 2.2 Hz, 1H), 10.16 (s, 1H)

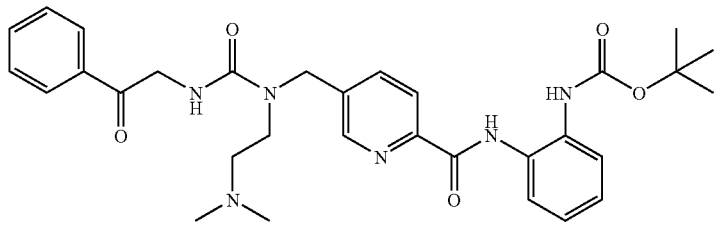

N-(2-t-Butoxycarbonylaminophenyl)-5-[1-(2-dimethylaminoethyl)-3-phenylcarbonylmethylureidomethyl]pyridine-2-carboxylic acid amide (Reference Compound No. 7-17)

$^1$H-NMR (400 MHz, CDCl$_3$) δ 1.51 (s, 9 H), 2.35 (s, 6 H), 2.51 (t, J = 5.0 Hz, 2H), 3.34 (t, J = 5.0 Hz, 2H), 4.66 (s, 2H), 4.79 (d, J = 3.7 Hz, 2H), 7.07 (br s, 1H), 7.17-7.25 (m, 2H), 7.47-7.52 (m, 2H), 7.58-7.63 (m, 2H), 7.69 (d, J = 8.1 Hz, 1H), 7.89 (dd, J = 8.1, 2.0 Hz, 1H), 7.99-8.01 (m, 2H), 8.27 (d, J = 8.1 Hz, 1H), 8.41 (br s, 1H), 8.54 (d, J = 2.0 Hz, 1H), 10.15 (s, 1H)

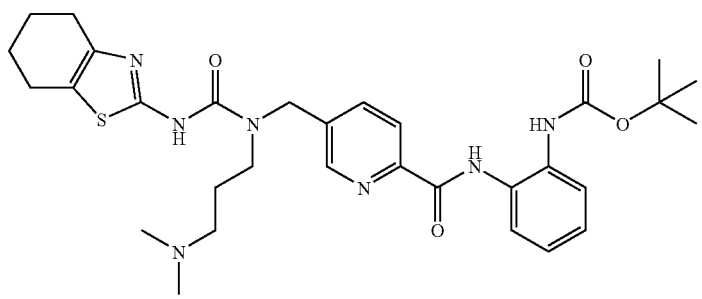

N-(2-t-Butoxycarbonylaminophenyl)-5-[1-(3-dimethylaminopropyl)-3-(4,5,6,7-tetrahydro-1,3-benzothiazol-2-yl)ureidomethyl]pyridine-2-carboxylic acid amide (Reference Compound No. 7-18)

$^1$H-NMR (400 MHz, DMSO-d$_6$) δ 1.46 (s, 9 H), 1.67 (m, 2H), 1.74 (br s, 4 H), 2.18 (s, 6 H), 2.25 (br s, 2H), 2.49-2.55 (m, 4 H), 3.34 (m, 2H), 4.66 (s, 2H), 7.15 (t, J = 7.4 Hz, 1H), 7.24 (d, J = 7.4 Hz, 1H), 7.25 (m, 1H), 7.94 (d, J = 8.1 Hz, 1H), 8.00 (d, J = 7.4 Hz, 1H), 8.14 (d, J = 8.1 Hz, 1H), 8.56 (s, 1H), 9.12 (br s, 1H), 10.47 (br s, 1H), 12.39 (br s, 1H)

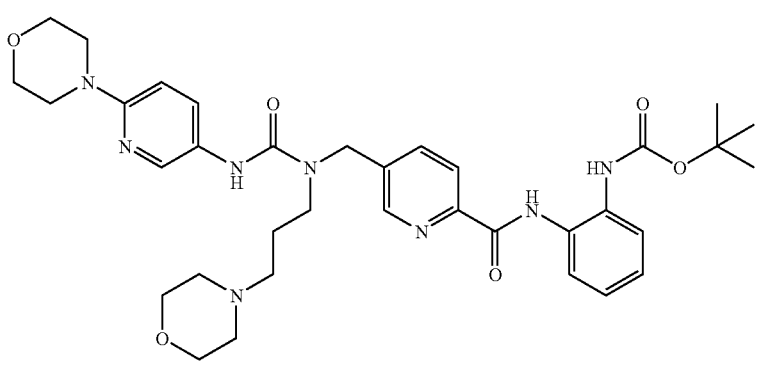

N-(2-t-Butoxycarbonylaminophenyl)-5-[1-[3-(morpholin-4-yl)propyl]-3-[2-(morpholin-4-yl)pyridin-5-yl]ureidomethyl]pyridine-2-carboxylic acid amide (Reference Compound No. 7-19)

$^1$H-NMR (400 MHz, CDCl$_3$) δ 1.51 (s, 9 H), 1.79 (m, 2H), 2.45 (br s, 4 H), 2.50 (t, J = 6.0 Hz, 2H), 3.39 (t, J = 5.4 Hz, 2H), 3.46 (t, J = 4.9 Hz, 4 H), 3.61 (t, J = 4.4 Hz, 4 H), 3.83 (t, J = 4.9 Hz, 4 H), 4.63 (s, 2H), 6.66 (d, J = 9.0 Hz, 1H), 7.05 (br s, 1H), 7.17-7.25 (m, 2H), 7.60 (d, J = 6.8 Hz, 1H), 7.70 (m, 1H), 7.70 (dd, J = 9.0, 2.8 Hz, 1H), 7.92 (dd, J = 7.9, 2.1 Hz, 1H), 8.11 (d, J = 2.8 Hz, 1H), 8.25 (dd, J = 7.9, 0.7 Hz, 1H), 8.57 (dd, J = 2.1, 0.7 Hz, 1H), 9.20 (s, 1H), 10.14 (s, 1H)

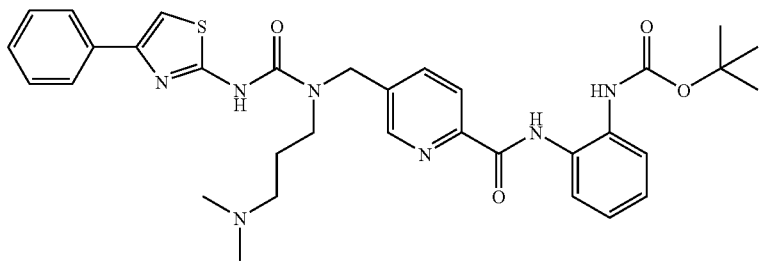

N-(2-t-Butoxycarbonylaminophenyl)-5-[1-(3-dimethylaminopropyl)-3-(4-phenyl-1,3-thiazol-2-yl)ureidomethyl]pyridine-2-carboxylic acid amide (Reference Compound No. 7-20)

$^1$H-NMR (400 MHz, DMSO-$d_6$) δ 1.47 (s, 9 H), 1.74 (m, 2H), 2.33 (s, 6 H), 2.37 (m, 2H), 3.41 (t, J = 5.6 Hz, 2H), 4.68 (s, 2H), 7.15 (t, J = 8.1 Hz, 1H), 7.23-7.27 (m, 2H), 7.29 (t, J = 7.7 Hz, 1H), 7.41 (t, J = 7.7 Hz, 2H), 7.48 (s, 1H), 7.89-7.91 (m, 2H), 8.01 (d, J = 7.7 Hz, 2H), 8.16 (d, J = 8.1 Hz, 1H), 8.61 (s, 1H), 9.12 (br s, 1H), 10.48 (br s, 1H), 13.44 (br s, 1H)

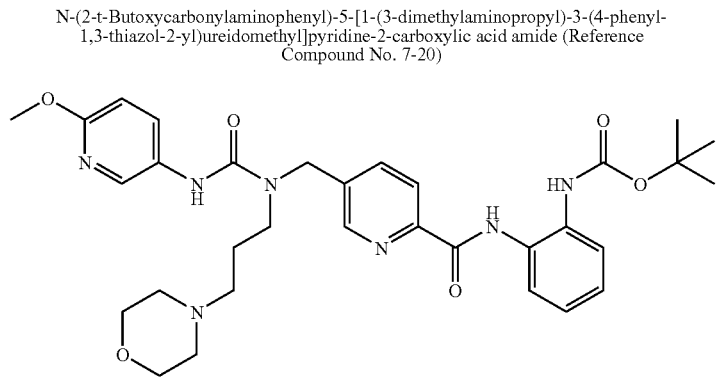

N-(2-t-Butoxycarbonylaminophenyl)-5-[3-(2-methoxypyridine-5-yl)-1-[3-(morpholin-4-yl)propyl]ureidomethyl]pyridine-2-carboxylic acid amide (Reference Compound No. 7-21)

$^1$H-NMR (400 MHz, CDCl$_3$) δ 1.51 (s, 9 H), 1.79 (m, 2H), 2.45 (br s, 4 H), 2.51 (t, J = 5.9 Hz, 2H), 3.40 (t, J = 5.2 Hz, 2H), 3.62 (t, J = 4.3 Hz, 4 H), 3.92 (s, 3 H), 4.64 (s, 2H), 6.75 (dd, J = 8.9, 0.6 Hz, 1H), 7.05 (br s, 1H), 7.17-7.25 (m, 2H), 7.60 (d, J = 7.3 Hz, 1H), 7.69 (d, J = 7.3 Hz, 1H), 7.78 (dt, J = 8.9, 2.6 Hz, 1H), 7.92 (dd, J = 8.1, 2.1 Hz, 1H), 8.06 (m, 1H), 8.26 (dd, J = 8.1, 0.7 Hz, 1H), 8.57 (dd, J = 2.1, 0.7 Hz, 1H), 9.27 (s, 1H), 10.15 (s, 1H)

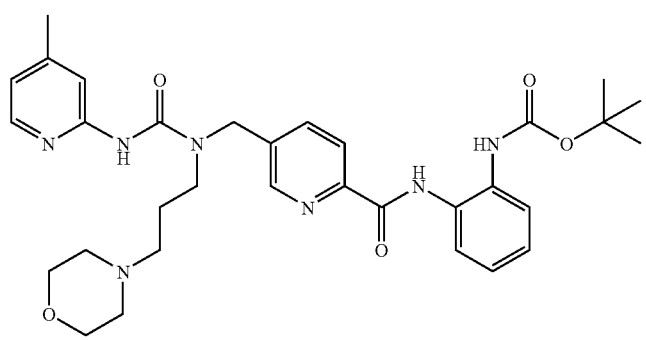

N-(2-t-Butoxycarbonylaminophenyl)-5-[3-(4-methylpyridine-2-yl)-1-[3-(morpholin-4-yl)propyl]ureidomethyl]pyridine-2-carboxylic acid amide (Reference Compound No. 7-22)

$^1$H-NMR (500 MHz, CDCl$_3$) δ 1.51 (s, 9 H), 1.80 (m, 2H), 2.34 (s, 3 H), 2.45 (t, J = 6.0 Hz, 2H), 2.50 (br s, 4 H), 3.44 (t, J = 5.7 Hz, 2H), 3.97 (br s, 4 H), 4.66 (s, 2H), 6.76 (d, J = 5.0 Hz, 1H), 7.06 (br s, 1H), 7.17-7.25 (m, 2H), 7.59 (d, J = 5.8 Hz, 1H), 7.70 (d, J = 5.5 Hz, 1H), 7.86 (s, 1H), 7.92 (dd, J = 7.9, 1.8 Hz, 1H), 8.08 (d, J = 5.0 Hz, 1H), 8.27 (d, J = 7.9 Hz, 1H), 8.59 (d, J = 1.8 Hz, 1H), 9.70 (s, 1H), 10.16 (s, 1H)

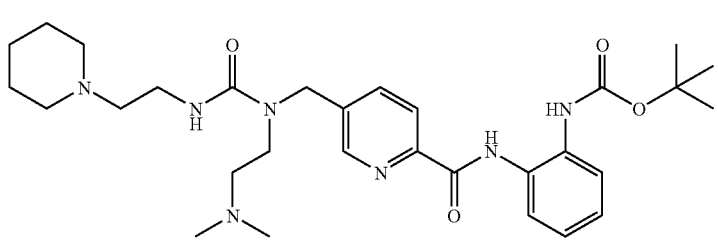

N-(2-t-Butoxycarbonylaminophenyl)-5-[1-(2-dimethylaminoethyl)-3-[2-(piperidin-1-yl)ethyl]ureidomethyl]pyridine-2-carboxylic acid amide (Reference Compound No. 7-23)

$^1$H-NMR (400 MHz, CDCl$_3$) δ 1.51 (s, 9 H), 1.55 (m, 4 H), 1.70 (m, 4 H), 2.26 (s, 6 H), 2.39 (s, 2H), 2.42 (t, J = 5.6 Hz, 2H), 2.44 (t, J = 6.8 Hz, 2H), 3.26 (t, J = 5.6 Hz, 2H), 3.33 (q, J = 6.8 Hz, 2H), 4.61 (s, 2H), 7.08 (br s, 1H), 7.13 (br s, 1H), 7.18-7.24 (m, 2H), 7.61 (d, J = 7.3 Hz, 1H), 7.68 (d, J = 7.6 Hz, 1H), 7.86 (dd, J = 7.9, 2.1 Hz, 1H), 8.25 (d, J = 8.0, 0.7 Hz, 1H), 8.52 (dd, J = 2.1, 0.7 Hz, 1H), 10.14 (s, 1H)

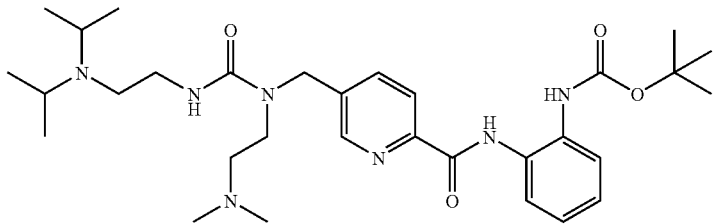

N-(2-t-Butoxycarbonylaminophenyl)-5-[3-(2-diisopropylaminoethyl)-1-(2-dimethylaminoethyl)ureidomethyl]pyridine-2-carboxylic acid amide (Reference Compound No. 7-24)

$^1$H-NMR (400 MHz, CDCl$_3$) δ 1.00 (d, J = 4.9 Hz,, 12H), 1.52 (s, 9 H), 2.25 (s, 6 H), 2.43 (t, J = 5.9 Hz, 2H), 2.58 (s, 2H), 3.00 (s, 2H), 3.22 (s, 2H), 3.27 (s, 2H), 4.63 (s, 2H), 6.62 (s, 1H), 7.06 (br s, 1H), 7.17-7.25 (m, 2H), 7.60 (d, J = 7.6 Hz, 1H), 7.69 (d, J = 6.8 Hz, 1H), 7.85 (dd, J = 8.0, 2.1 Hz, 1H), 8.25 (dd, J = 8.0, 0.7 Hz, 1H), 8.51 (dd, J = 2.1, 0.7 Hz, 1H), 10.14 (s, 1H)

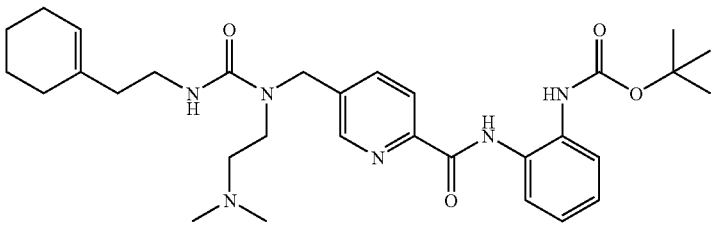

N-(2-t-Butoxycarbonylaminophenyl)-5-[3-[2-(cyclohexen-1-yl)ethyl]-1-(2-dimethylaminoethyl)ureidomethyl]pyridine-2-carboxylic acid amide (Reference Compound No. 7-25)

$^1$H-NMR (400 MHz, CDCl$_3$) δ 1.51 (s, 9 H), 1.55 (m, 2H), 1.62 (m, 2H), 1.92-1.97 (m, 4 H), 2.14 (t, J = 7.0 Hz, 2H), 2.24 (s, 6 H), 2.40 (t, J = 5.0 Hz, 2H), 3.20 (t, J = 5.0 Hz, 2H), 3.30 (td, J = 7.0, 5.1 Hz, 2H), 4.59 (s, 2H), 5.45 (m, 1H), 7.09 (br s, 1H), 7.17-7.24 (m, 2H), 7.33 (m, 1H), 7.60 (d, J = 6.8 Hz, 1H), 7.69 (d, J = 7.3 Hz, 1H), 7.84 (dd, J = 8.0, 2.2 Hz, 1H), 8.24 (dd, J = 8.0, 0.7 Hz, 1H), 8.50 (d, J = 2.2, 0.7 Hz, 1H), 10.15 (s, 1H)

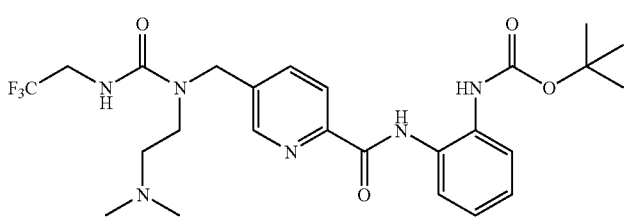

N-(2-t-Butoxycarbonylaminophenyl)-5-[1-(2-dimethylaminoethyl)-3-(2,2,2-trifluoroethyl)ureidomethyl]pyridine-2-carboxylic acid amide (Reference Compound No. 7-26)

$^1$H-NMR (400 MHz, CDCl$_3$) δ 1.52 (s, 9 H), 2.28 (s, 6 H), 2.45 (t, J = 4.3 Hz, 2H), 3.24 (t, J = 4.3 Hz, 2H), 3.87 (m, 2H), 4.61 (s, 2H), 7.09 (br s, 1H), 7.19-7.21 (m, 2H), 7.56 (d, J = 5.8 Hz, 1H), 7.73 (d, J = 5.5 Hz, 1H), 7.83 (dd, J = 7.9, 2.1 Hz, 1H), 8.25 (dd, J = 7.9, 0.6 Hz, 1H), 8.51 (dd, J = 2.1, 0.6 Hz, 1H), 9.48 (s, 1H), 10.18 (s, 1H)

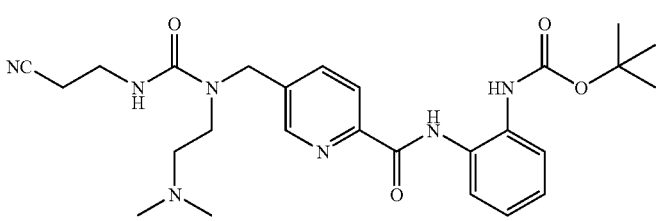

N-(2-t-Butoxycarbonylaminophenyl)-5-[3-(2-cyanoethyl)-1-(2-dimethylaminoethyl)ureidomethyl]pyridine-2-carboxylic acid amide (Reference Compound No. 7-27)

$^1$H-NMR (500 MHz, CDCl$_3$) δ 1.52 (s, 9 H), 2.32 (s, 6 H), 2.45 (t, J = 4.4 Hz, 2H), 2.59 (t, J = 6.3 Hz, 2H), 3.24 (t, J = 4.4 Hz, 2H), 3.45 (m, 2H), 4.60 (s, 2H), 7.10 (m, 1H), 7.19-7.25 (m, 2H), 7.58 (d, J = 6.7 Hz, 1H), 7.71 (d, J = 6.7 Hz, 1H), 7.84 (dd, J = 7.9, 2.1 Hz, 1H), 8.25 (dd, J = 7. 9, 0.6 Hz, 1H), 8.51 (dd, J = 2.1, 0.6 Hz, 1H), 9.06 (s, 1H), 10.17 (s, 1H)

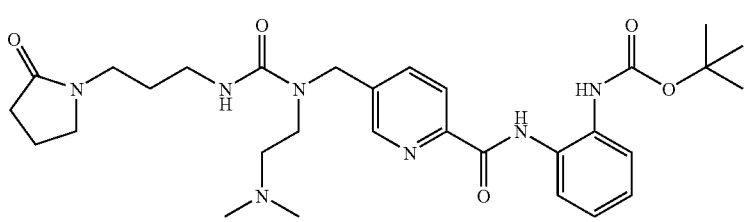

N-(2-t-Butoxycarbonylaminophenyl)-5-[1-(2-dimethylaminoethyl)-3-[3-(pyrrolidin-2-on-1-yl)propyl]ureidomethyl]pyridine-2-carboxylic acid amide (Reference Compound No. 7-28)

$^1$H-NMR (500 MHz, CDCl$_3$) δ 1.52 (s, 9 H), 1.71 (m, 2H), 2.04 (m, 2H), 2.27 (s, 6 H), 2.39 (t, J = 8.2 Hz, 2H), 2.46 (t, J = 5.5 Hz, 2H), 3.20 (m, 2H), 3.30-3.34 (m, 4 H), 3.40 (t, J = 7.2 Hz, 2H), 4.63 (s, 2H), 7.10 (br s, 1H), 7.17-7.24 (m, 2H), 7.38 (s, 1H), 7.60 (d, J = 7.0 Hz, 1H), 7.68 (m, 1H), 7.85 (dd, J = 7.9, 2.0 Hz, 1H), 8.24 (d, J = 7.9 Hz, 1H), 8.52 (d, J = 2.0 Hz, 1H), 10.14 (s, 1H)

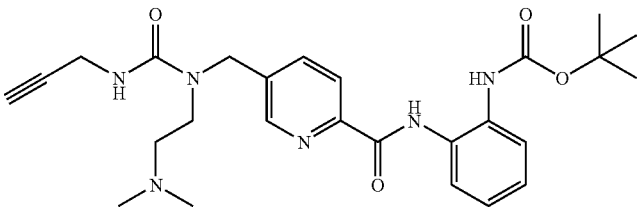

N-(2-t-Butoxycarbonylaminophenyl)-5-[3-propargyl-1-(2-dimethylamino-ethyl)ureidomethyl]pyridine-2-carboxylic acid amide (Reference Compound No. 7-29)

$^1$H-NMR (500 MHz, CDCl$_3$) δ 1.52 (s, 9 H), 2.20 (t, J = 2.5 Hz, 1H), 2.29 (s, 6 H), 2.44 (t, J = 4.4 Hz, 2H), 3.22 (t, J = 4.4 Hz, 2H), 3.99 (dd, J = 4.9, 2.5 Hz, 2H), 4.61 (s, 2H), 7.09 (m, 1H), 7.18-7.24 (m, 2H), 7.59 (d, J = 6.7 Hz, 1H), 7.70 (d, J = 6.4 Hz, 1H), 7.85 (dd, J = 7.8, 2.1 Hz, 1H) , 8.24 (dd, J = 7.8, 0.6 Hz, 1H), 8.51 (dd, J = 2.1, 0.6 Hz, 1H), 8.80 (s, 1H), 10.15 (s, 1H)

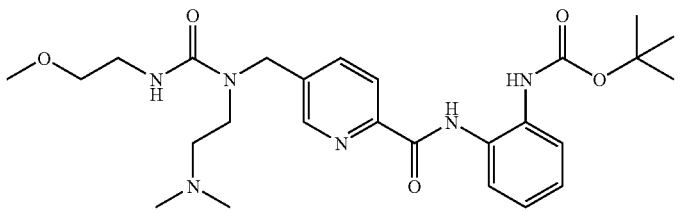

N-(2-t-Butoxycarbonylaminophenyl)-5-[1-(2-dimethylaminoethyl)-3-(2-methoxyethyl)ureidomethyl]pyridine-2-carboxylic acid amide (Reference Compound No. 7-30)

$^1$H-NMR (400 MHz, CDCl$_3$) δ 1.52 (s, 9 H), 2.26 (s, 6 H), 2.42 (t, J = 4.7 Hz, 2H), 3.22 (t, J = 4.7 Hz, 2H), 3.36 (s, 3 H), 3.41 (m, 2H), 3.49 (t, J = 4.9 Hz, 2H), 4.61 (s, 2H), 7.10 (br s, 1H), 7.17-7.25 (m, 2H), 7.60 (d, J = 7.3 Hz, 1H), 7.69 (m, 1H), 7.85 (dd, J = 8.0, 2.0 Hz, 1H), 8.10 (br s, 1H), 8.24 (d, J = 8.0 Hz, 1H), 8.51 (d, J = 2.0 Hz, 1H), 10.16 (s, 1H)

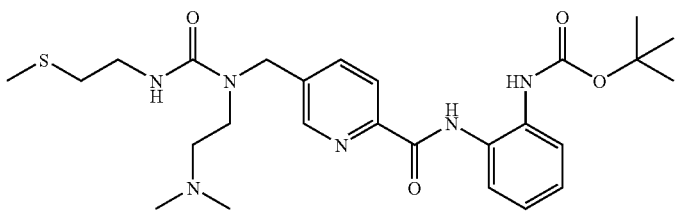

N-(2-t-Butoxycarbonylaminophenyl)-5-[1-(2-dimethylaminoethyl)-3-(2-methylthioethyl)ureidomethyl]pyridine-2-carboxylic acid amide (Reference Compound No. 7-31)

$^1$H-NMR (400 MHz, CDCl$_3$) δ 1.52 (s, 9 H), 2.13 (s, 3 H), 2.28 (s, 6 H), 2.43 (t, J = 4.7 Hz, 2H), 2.66 (t, J = 6.5 Hz, 2H), 3.23 (t, J = 4.7 Hz, 2H), 3.45 (m, 2H), 4.61 (s, 2H), 7.10 (br s, 1H), 7.17-7.24 (m, 2H), 7.59 (d, J = 7.1 Hz, 1H), 7.69 (m, 1H), 7.85 (dd, J = 8.0, 2.2 Hz, 1H), 8.11 (m, 1H), 8.24 ( dd, J = 8.0, 0.6 Hz, 1H), 8.51 (dd, J = 2.2, 0.6 Hz, 1H), 10.16 (s, 1H)

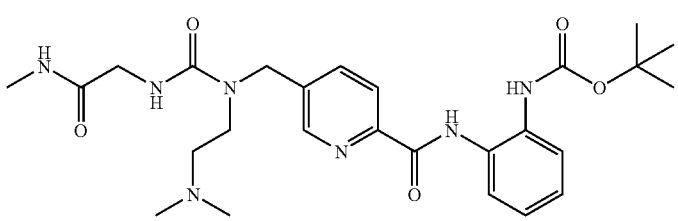

N-(2-t-Butoxycarbonylaminophenyl)-5-[1-(2-dimethylaminoethyl)-3-methylaminocarbonylmethylureidomethyl]pyridine-2-carboxylic acid amide (Reference Compound No. 7-32)

$^1$H-NMR (400 MHz, CDCl$_3$) δ 1.52 (s, 9 H), 2.46 (s, 6 H), 2.67 (t, J = 4.2 Hz, 2H), 2.83 (d, J = 4.9 Hz, 3 H), 3.44 (t, J = 4.2 Hz, 2H), 3.86 (d, J = 5.1 Hz, 2H), 4.65 (s, 2H), 6.76 (br s, 1H), 7.06 (br s, 1H), 7.18-7.23 (m, 2H), 7.54 (d, J = 6.8 Hz, 1H), 7.72 (m, 1H), 7.82 (dd, J = 1.9 Hz, 1H), 7.97 (br s, 1H), 8.25 (d, J = 7.9 Hz, 1H), 8.50 (d, J = 1.9 Hz, 1H), 10.16 (s, 1H)

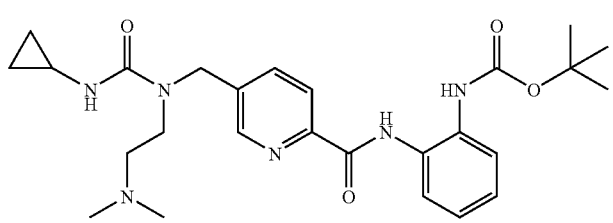

N-(2-t-Butoxycarbonylaminophenyl)-5-[3-cyclopropyl-1-(2-dimethyl-aminoethyl)ureidomethyl]pyridine-2-carboxylic acid amide (Reference Compound No. 7-33)

$^1$H-NMR (400 MHz, CDCl$_3$) δ 0.38 (m, 2H), 0.70 (td, J = 6.8, 5.2 Hz, 2H), 1.52 (s, 9 H), 2.24 (s, 6 H), 2.38 (t, J = 4.5 Hz, 2H), 2.69 (m, 1H), 3.15 (t, J = 4.5 Hz, 2H), 4.59 (s, 2H), 7.07 (br s, 1H), 7.17-7.24 (m, 2H), 7.56 (d, J = 7.1 Hz, 1H), 7.69 (m, 1H), 7.86 (dd, J = 8.0, 2.2 Hz, 1H), 8.24 (s, 1H), 8.51 (dd, J = 2.2, 0.7 Hz, 1H), 10.15 (s, 1H)

-continued

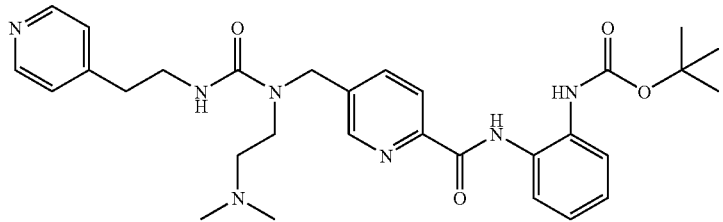

N-(2-t-Butoxycarbonylaminophenyl)-5-[1-(2-dimethylaminoethyl)-3-[2-(pyridin-4-yl)ethyl]ureidomethyl]pyridine-2-carboxylic acid amide (Reference Compound No. 7-34)

$^1$H-NMR (400 MHz, CDCl$_3$) δ 1.51 (s, 9 H), 2.06 (s, 6 H), 2.33 (t, J = 4.5 Hz, 2H), 2.85 (t, J = 6.8 Hz, 2H), 3.14 (t, J = 4.5 Hz, 2H), 3.53 (m, 2H), 4.57 (s, 2H), 7.06 (br s, 1H), 7.16 (d, J = 6.1 Hz, 2H), 7.18-7.23 (m, 2H), 7.60 (d, J = 6.8 Hz, 1H), 7.73 (d, J = 6.6 Hz, 1H), 7.81 (dd, J = 7.9, 2.2 Hz, 1H), 7.92 (s, 1H), 8.24 (dd, J = 7.9, 0.6 Hz, 1H), 8.46 (dd, J = 2.2, 0.6 Hz, 1H), 8.52 (d, J = 6.1 Hz, 2H), 10.16 (s, 1H)

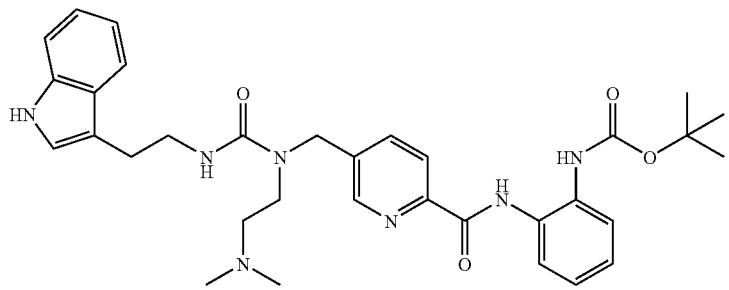

N-(2-t-Butoxycarbonylaminophenyl)-5-[1-(2-dimethylaminoethyl)-3-[2-(indol-3-yl)ethyl]ureidomethyl]pyridine-2-carboxylic acid amide (Reference Compound No. 7-35)

$^1$H-NMR (400 MHz, CDCl$_3$) δ 1.52 (s, 9 H), 1.97 (s, 6 H), 2.28 (t, J = 5.0 Hz, 2H), 2.99 (t, J = 6.7 Hz, 2H), 3.13 (t, J = 5.0 Hz, 2H), 3.60 (m, 2H), 4.58 (s, 2H), 7.02 (d, J = 2.2 Hz, 1H), 7.07 (br s, 1H), 7.08 (m, 1H), 7.18 (dd, J = 8.1, 1.1 Hz, 1H), 7.20-7.24 (m, 2H), 7.35 (dt, J = 8.1, 1.1 Hz, 1H), 7.52 (m, 1H), 7.57 (m, 1H), 7.62 (d, J = 8.1 Hz, 1H), 7.72 (m, 1H), 7.77 (dd, J = 8.0, 2.2 Hz, 1H), 8.20 (dd, J = 8.0, 0.6 Hz, 1H), 8.27 (s, 1H), 8.46 (dd, J = 2.2, 0.6 Hz, 1H), 10.19 (s, 1H)

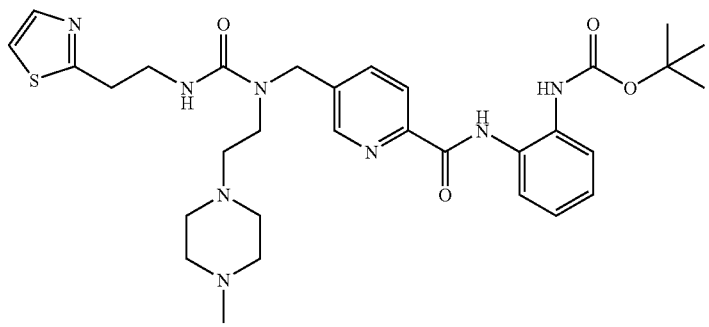

N-(2-t-Butoxycarbonylaminophenyl)-5-[1-[2-(4-methylpiperazin-1-yl)ethyl]-3-(1,3-thiazol-2-yl)ureidomethyl]pyridine-2-carboxylic acid amide (Reference Compound No. 7-36)

$^1$H-NMR (400 MHz, CDCl$_3$) δ 1.51 (s, 9 H), 2.38 (s, 3 H), 2.60 (t, J = 4.1 Hz, 2H), 2.71 (br s, 4 H), 2.76 (br s, 4 H), 3.38 (t, J = 4.1 Hz, 2H), 4.71 (s, 2H), 6.88 (d, J = 3.6 Hz, 1H), 7.10 (br s, 1H), 7.18-7.25 (m, 2H), 7.39 (d, J = 3.6 Hz, 1H), 7.56 (m, 1H), 7.73 (m, 1H), 7.89 (dd, J = 8.0, 2.2 Hz, 1H), 8.27 (d, J = 8.0 Hz, 1H), 8.56 (d, J = 2.2 Hz, 1H), 10.18 (s, 1H)

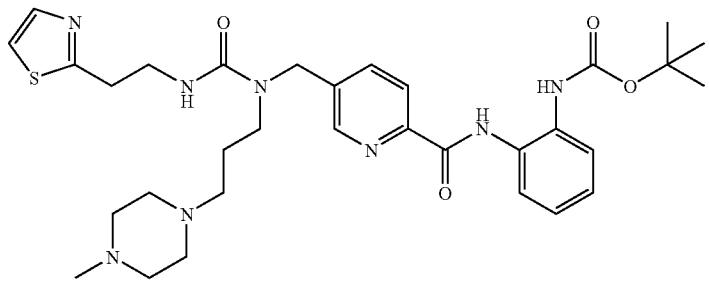

N-(2-t-Butoxycarbonylaminophenyl)-5-[1-[3-(4-methylpiperazin-1-yl)propyl]-3-(1,3-thiazol-2-yl)ureido methyl]pyridine-2-carboxylic acid amide (Reference Compound No. 7-37)

$^1$H-NMR (400 MHz, CDCl$_3$) δ 1.51 (s, 9 H), 1.80 (m, 2H), 2.40 (s, 3 H), 2.46 (t, J = 5.8 Hz, 2H), 2.56 (br s, 4 H), 2.77 (br s, 4 H), 3.39 (t, J = 5.8 Hz, 2H), 4.67 (s, 2H), 6.87 (d, J = 3.7 Hz, 1H), 7.11 (m, 1H), 7.18-7.25 (m, 2H), 7.37 (d, J = 3.7 Hz, 1H), 7.57 (d, J = 8.8 Hz, 1H), 7.72 (m, 1H), 7.90 (dd, J = 8.0, 2.2 Hz, 1H), 8.26 (d, J = 8.0 Hz, 1H), 8.57 (d, J = 2.2 Hz, 1H), 10.18 (s, 1H)

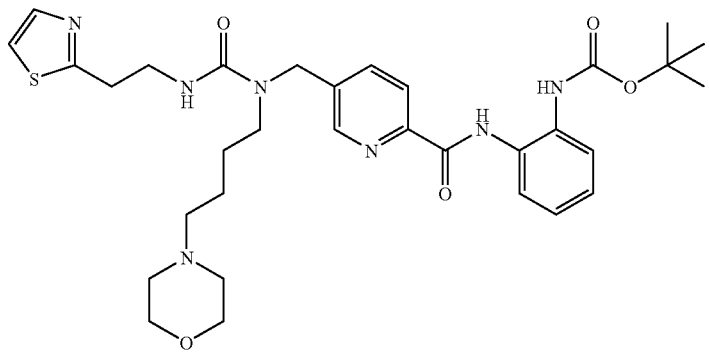

N-(2-t-Butoxycarbonylaminophenyl)-5-[1-[4-(morpholin-4-yl)butyl]-3-
(1,3-thiazol-2-yl)ureidomethyl]pyridine-2-carboxylic acid amide
(Reference Compound No. 7-38)

$^1$H-NMR (400 MHz, CDCl$_3$)
δ 1.51 (s, 9 H), 1.52 (m, 2H),
1.70 (m, 2H), 2.39 (t, J = 6.8
Hz, 2H), 2.47 (t, J = 4.8 Hz,
4 H), 3.36 (t, J = 8.0 Hz, 2H),
3.77 (t, J = 4.8 Hz, 4 H), 4.73 (s,
2H), 6.88 (d, J = 3.6 Hz, 1H),
7.08 (br s, 1H), 7.18-7.25 (m,
2H), 7.33 (d, J = 3.6 Hz, 1H),
7.58 (m, 1H), 7.73 (m, 1H),
7.86 (dd, J = 8.0, 2.2 Hz, 1H),
8.28 (d, J = 8.0 Hz, 1H), 8.54
(d, J = 2.2 Hz, 1H), 10.16 (s,
1H)

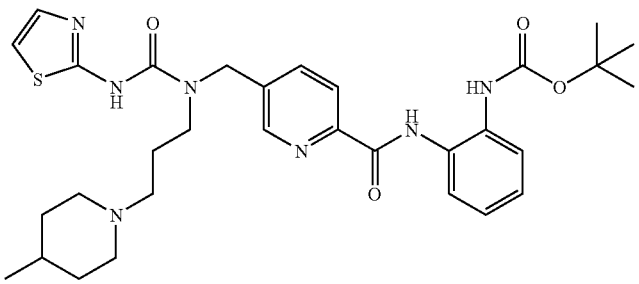

N-(2-t-Butoxycarbonylaminophenyl)-5-[3-[(4-methylpiperidin-1-yl)propyl]-3-
(1,3-thiazol-2-yl)ureido methyl]pyridine-2-carboxylic acid amide
(Reference Compound No. 7-39)

$^1$H-NMR (400 MHz, CDCl$_3$)
δ 1.01 (d, J = 6.6 Hz, 3 H), 1.44
(m, 1H), 1.51 (s, 9 H), 1.57 (m,
2H), 1.74-1.86 (m, 4 H), 2.01 (t,
J = 11.7 Hz, 2H), 2.40 (t, J =
6.0 Hz, 2H), 2.90 (d, J = 11.7
Hz, 2H), 3.39 (t, J = 5.6 Hz,
2H), 4.66 (s, 2H), 6.86 (d, J =
3.7 Hz, 1H), 7.03 (br s, 1H),
7.18-7.25 (m, 2H), 7.36 (d, J =
3.7 Hz, 1H), 7.59 (d, J = 7.3
Hz, 1H), 7.71 (d, J = 6.6 Hz,
1H), 7.91 (dd, J = 8.0, 2.0 Hz,
1H), 8.27 (d, J = 8.0 Hz, 1H),
8.57 (d, J = 2.0 Hz, 1H), 10.16
(s, 1H)

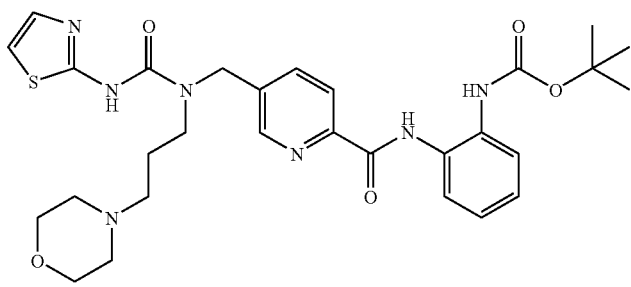

N-(2-t-Butoxycarbonylaminophenyl)-5-[1-[3-(morpholin-4-yl)propyl]-
3-(1,3-thiazol-2-yl)ureidomethyl]pyridine-2-carboxylic acid amide
(Reference Compound No. 7-40)

$^1$H-NMR (500 MHz, CDCl$_3$)
δ 1.51 (s, 9 H), 1.80 (m, 2H),
2.46 (t, J = 6.1 Hz, 2H), 2.51
(br s, 4 H), 3.40 (t, J = 5.7 Hz,
2H), 4.04 (br s, 4 H), 4.68 (s,
2H), 6.87 (d, J = 3.7 Hz, 1H),
7.01 (br s, 1H), 7.18-7.24 (m,
2H), 7.37 (d, J = 3.7 Hz, 1H),
7.58 (d, J = 6.1 Hz, 1H), 7.71
(d, J = 6.1 Hz, 1H), 7.91 (dd, J =
8.1, 2.2 Hz, 1H), 8.27 (dd, J =
8.1, 0.8 Hz, 1H), 8.58 (dd, J =
2.2, 0.8 Hz, 1H), 10.16 (s, 1H),
11.67 (br s, 1H)

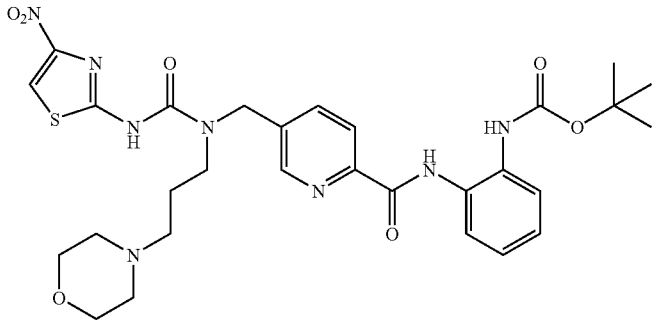

N-(2-t-Butoxycarbonylaminophenyl)-5-[1-[3-(morpholin-4-yl)propyl]-3-(5-nitro-1,3-thiazol-2-yl)ureidomethyl]pyridine-2-carboxylic acid amide (Reference Compound No. 7-41)

¹H-NMR (500 MHz, CDCl₃) δ 1.52 (s, 9 H), 1.85 (m, 2H), 2.49 (t, J = 6.1 Hz, 2H), 2.54 (br s, 4 H), 3.40 (t, J = 5.7 Hz, 2H), 4.01 (br s, 4 H), 4.66 (s, 2H), 6.96 (br s, 1H), 7.19-7.25 (m, 2H), 7.55 (br s, 1H), 7.75 (br s, 1H), 7.90 (dd, J = 7.9, 2.0 Hz, 1H), 8.26 (s, 1H), 8.29 (d, J = 7.9 Hz, 1H), 8.60 (d , J = 2.0 Hz, 1H), 10.19 (s, 1H)

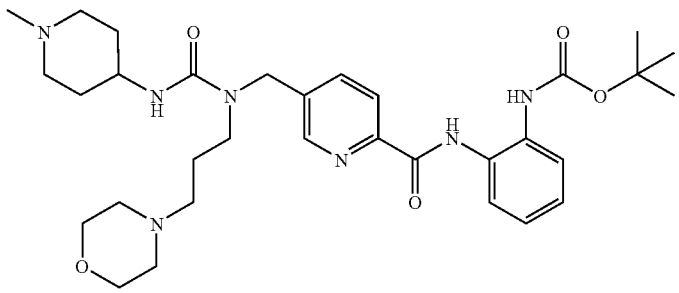

N-(2-t-Butoxycarbonylaminophenyl)-5-[3-(1-methylpiperidin-4-yl)-1-[3-(morpholin-4-yl)propyl]ureidomethyl]pyridine-2-carboxylic acid amide (Reference Compound No. 7-42)

¹H-NMR (400 MHz, CDCl₃) δ 1.42-1.55 (m, 2H), 1.52 (s, 9 H), 1.70 (m, 2H), 1.96 (d, J = 12.0 Hz, 2H), 2.03-2.12 (m, 2H), 2.27 (s, 3 H), 2.37 (t, J = 6.2 Hz, 2H), 2.44 (t, J = 4.5 Hz, 4 H), 2.84 (d, J = 12.0 Hz, 2H), 3.22 (t, J = 6.1 Hz, 2H), 3.66 (m, 1H), 3.75 (t, J = 4.5 Hz, 4 H), 4.57 (s, 2H), 5.84 (d, J = 7.6 Hz, 1H), 7.06 (br s, 1H), 7.17-7.26 (m, 2H), 7.60 (d, J = 7.3 Hz, 1H), 7.69 (d, J = 7.1 Hz, 1H), 7.85 (dd, J = 8.0, 2.1 Hz, 1H), 8.25 (dd, J = 8.0, 0.7 Hz, 1H), 8.52 (dd, J = 2.1, 0.7 Hz, 1H), 10.14 (s, 1H)

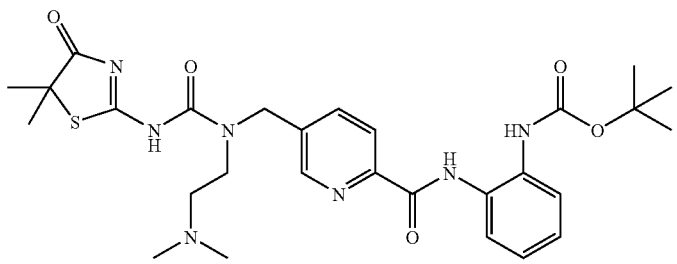

N-(2-t-Butoxycarbonylaminophenyl)-5-[1-(2-dimethylaminoethyl)-3-(5,5-dimethyl-4,5-dihydro-1,3-thiazol-4-on-2-yl)ureidomethyl]pyridine-2-carboxylic acid amide (Reference Compound No. 7-43)

¹H-NMR (400 MHz, CDCl₃) δ 1.52 (s, 9 H), 2.25 (s, 6 H), 2.29 (s, 6 H), 2.52 (t, J = 5.7 Hz, 2H), 3.49 (t, J = 5.7 Hz, 2H), 4.71 (s, 2H), 7.09 (br s, 1H), 7.19-7.24 (m, 2H), 7.57 (d, J = 7.1 Hz, 1H), 7.77 (m, 1H), 7.86 (dd, J = 8.0, 2.0 Hz, 1H), 8.19 (d, J = 8.0 Hz, 1H), 8.44 (s, 1H), 8.54 (d, J = 2.0 Hz, 1H), 10.19 (s, 1H)

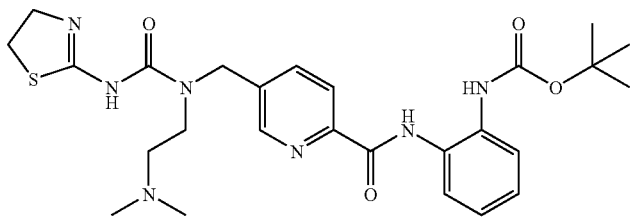

N-(2-t-Butoxycarbonylaminophenyl)-5-[3-(4,5-dihydro-1,3-thiazol-2-yl)-1-(2-dimethylaminoethyl)ureido methyl]pyridine-2-carboxylic acid amide (Reference Compound No. 7-44)

¹H-NMR (400 MHz, CDCl₃) δ 1.52 (s, 9 H), 2.24 (s, 6 H), 2.46 (m, 2H), 3.23 (t, J = 7.6 Hz, 2H), 3.44 (m, 1H), 3.58 (m, 1H), 3.75 (br s, 2H), 4.70 (br s, 1H), 4.88 (br s, 1H), 7.04 (br s, 1H), 7.17-7.25 (m, 2H), 7.59 (m, 1H), 7.69 (m, 1H), 7.81 (m, 1H), 8.22 (d, J = 7.8 Hz, 1H), 8.50 (m, 1H), 10.17 (m, 1H)

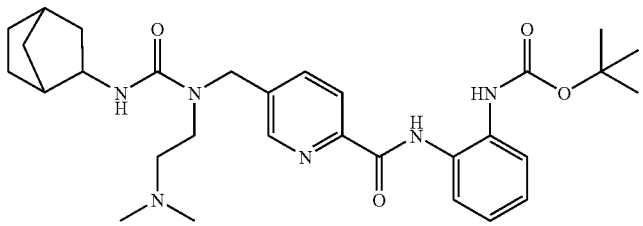

5-[3-(Bicyclo[2,2,1]heptan-2-yl)-1-(2-dimethylaminoethyl)ureidomethyl]-N-(2-t-butoxycarbonylaminophenyl)pyridine-2-carboxylic acid amide
(Reference Compound No. 7-45)

$^1$H-NMR (400 MHz, CDCl$_3$)
δ 0.69 (m, 1H), 1.16 (m, 1H), 1.32 (m, 1H), 1.44 (m, 2H), 1.52 (s, 9 H), 1.58 (m, 2H), 2.08 (m, 1H), 2.18 (m, 1H), 2.28 (s, 6 H), 2.41 (m, 1H), 2.45 (m, 2H), 3.20 (m, 2H), 4.02 (m, 1H), 4.43 (d, J = 15.6 Hz, 1H), 4.64 (d, J = 15.6 Hz, 1H), 7.06 (br s, 1H), 7.17-7.24 (m, 2H), 7.60 (d, J = 7.3 Hz, 1H), 7.68 (d, J = 6.9 Hz, 1H), 7.86 (dd, J = 8.0, 2.2 Hz, 1H), 8.05 (d, J = 7.1 Hz, 1H), 8.24 (dd, J = 8.0, 0.7 Hz, 1H), 8.51 (dd, J = 2.2, 0.7 Hz, 1H), 10.14 (s, 1H)

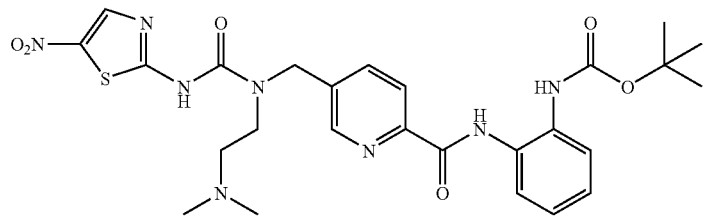

N-(2-t-Butoxycarbonylaminophenyl)-5-[1-(2-dimethylaminoethyl)-3-(5-nitro-1,3-thiazol-2-yl)ureidomethyl]pyridine-2-carboxylic acid amide
(Reference Compound No. 7-46)

$^1$H-NMR (400 MHz, CDCl$_3$)
δ 1.52 (s, 9 H), 2.48 (s, 6 H), 2.67 (t, J = 4.4 Hz, 2H), 3.39 (t, J = 4.4 Hz, 2H), 4.70 (s, 2H), 7.04 (s, 1H), 7.18-7.24 (m, 2H), 7.54 (m, 1H), 7.75 (m, 1H), 7.87 (dd, J = 8.0, 1.8 Hz, 1H), 8.26 (s, 1H), 8.28 (d, J = 8.0 Hz, 1H), 8.56 (d, J = 1.8 Hz, 1H), 10.19 (s, 1H)

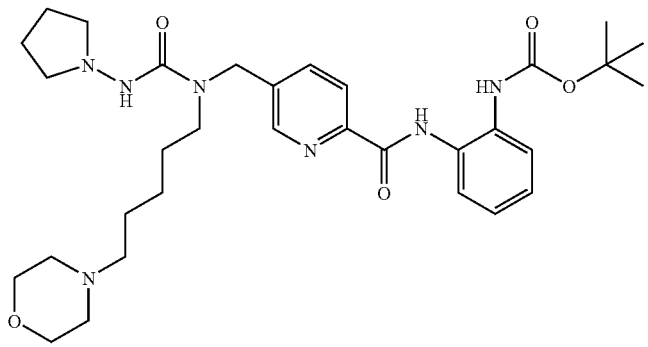

N-(2-t-Butoxycarbonylaminophenyl)-5-[1-[5-(morpholin-4-yl)pentyl]-3-(pyrrolidin-1-yl)ureidomethyl]pyridine-2-carboxylic acid amide
(Reference Compound No. 7-47)

$^1$H-NMR (400 MHz, CDCl$_3$)
δ 1.30 (m, 2H), 1.48 (m, 2H), 1.52 (s, 9 H), 1.67 (m, 2H), 1.76-1.81 (m, 4 H), 2.30 (t, J = 7.7 Hz, 2H), 2.41 (t, J = 4.4 Hz, 4 H), 2.80-2.85 (m, 4 H), 3.20 (t, J = 7.7 Hz, 2H), 3.71 (t, J = 4.4 Hz, 4 H), 4.61 (s, 2H), 7.06 (br s, 1H), 7.20-7.23 (m, 2H), 7.57 (d, J = 6.8 Hz, 1H), 7.73 (m, 1H), 7.83 (dd, J = 8.0, 2.1 Hz, 1H), 8.26 (dd, J = 8.0, 0.5 Hz, 1H), 8.51 (dd, J = 2.1, 0.5 Hz, 1H), 10.17 (s, 1H)

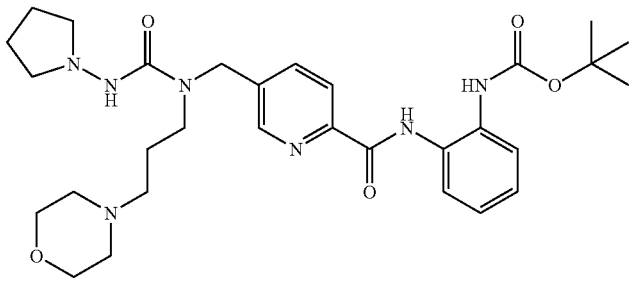

N-(2-t-Butoxycarbonylaminophenyl)-5-[1-[3-(morpholin-4-yl)propyl]-3-(pyrrolidin-1-yl)ureidomethyl]pyridine-2-carboxylic acid amide
(Reference Compound No. 7-48)

$^1$H-NMR (400 MHz, CDCl$_3$)
δ 1.52 (s, 9 H), 1.71 (m, 2H), 1.86 (br s, 4 H), 2.38 (t, J = 6.1 Hz, 2H), 2.48 (br s, 4 H), 2.99 (br s, 4 H), 3.20 (t, J = 6.0 Hz, 2H), 3.78 (t, J = 4.6 Hz, 4 H), 4.56 (s, 2H), 7.06 (br s, 1H), 7.17-7.26 (m, 2H), 7.60 (d, J = 6.8 Hz, 1H), 7.69 (d, J = 7.3 Hz, 1H), 7.73 (br s, 1H), 7.92 (dd, J = 8.0, 2.2 Hz, 1H), 8.25 (dd, J = 8.0, 0.7 Hz, 1H), 8.54 (dd, J = 2.2, 0.7 Hz, 1H), 10.14 (s, 1H)

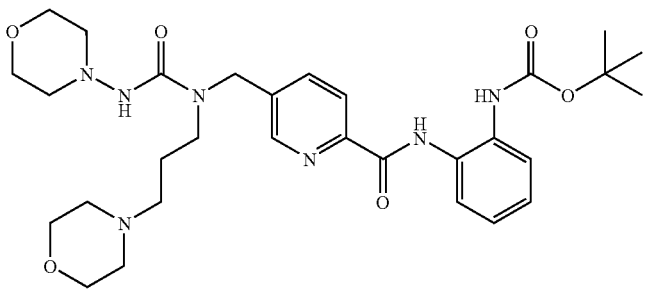

$^1$H-NMR (400 MHz, CDCl$_3$)
δ 1.52 (s, 9 H), 1.72 (m, 2H), 2.39 (t, J = 5.9 Hz, 2H), 2.49 (br s, 4 H), 2.97 (t, J = 4.8 Hz, 4 H), 3.21 (t, J = 5.7 Hz, 2H), 3.80 (t, J = 4.8 Hz, 4 H), 3.82 (t, J = 4.8 Hz, 4 H), 4.55 (s, 2H), 7.05 (br s, 1H), 7.17-7.25 (m, 2H), 7.60 (d, J = 7.3 Hz, 1H), 7.69 (d, J = 7.3 Hz, 1H), 7.91 (dd, J = 8.0, 2.0 Hz, 1H), 7.97 (s, 1H), 8.25 (dd, J = 8.0, 0.5 Hz, 1H), 8.54 (dd, J = 2.0, 0.5 Hz, 1H), 10.14 (s, 1H)

N-(2-t-Butoxycarbonylaminophenyl)-5-[3-(morpholin-4-yl)-1-[3-(morpholin-4-yl)propyl]ureidomethyl]pyridine-2-carboxylic acid amide
(Reference Compound No. 7-49)

Reference Example 8

6-Methylpyridine-3-carboxylic acid methyl ester N-oxide (Reference Compound No. 8-1)

30% Hydrogen peroxide in water (5.7 mL, 50 mmol) and sodium tungstate dihydrate (270 mg, 0.80 mmol) were added to 6-methylpyridine-3-carboxylic acid methyl ester (3.0 g, 20 mmol). The reaction mixture was stirred at 60° C. for 70 minutes and at 80° C. for 4.5 hours. Under ice cooling, methanol (10 mL) and manganese oxide (0.51 g, 6.0 mmol) were added thereto, and then the reaction mixture was stirred at room temperature for 16 hours. After the insoluble was filtered off with celite, the filtrate was concentrated to give 3.2 g of the title reference compound as a pale brown solid. (Yield 98%)

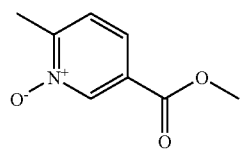

$^1$H-NMR (400 MHz, DMSO-d$_6$)
δ 2.42 (s, 3H), 3.88 (s, 3H), 7.64 (d, J = 8.2 Hz, 1H), 7.72 (dd, J = 8.2, 1.5 Hz, 1H), 8.58 (d, J = 1.5 Hz, 1H)

Reference Example 9

6-Acetoxymethylpyridine-3-carboxylic acid methyl ester (Reference Compound No. 9-1)

N,N-Diisopropylethylamine (2.2 mL, 13 mmol) and acetic anhydride (3.5 mL, 38 mmol) were added to a solution of 6-methylpyridine-3-carboxylic acid methyl ester N-oxide (Reference Compound No. 8-1, 2.1 g, 13 mmol) in acetic acid (14 mL), and then the reaction mixture was stirred at 120° C. for 135 minutes. After cooling, saturated aqueous sodium hydrogen carbonate solution (100 mL) was added thereto, and then sodium hydrogen carbonate was added until foam formation was ended. The whole was extracted with ethyl acetate (100 mL, 50 mL), the organic layer was dried over anhydrous magnesium sulfate, and then the solvent was evaporated under reduced pressure. The residue was purified by silica gel column chromatography (hexane-ethyl acetate), and then the resulting solid was collected by filtration with hexane and ethyl acetate to give 1.2 g of the title reference compound as a pale yellow solid. (Yield 48%)

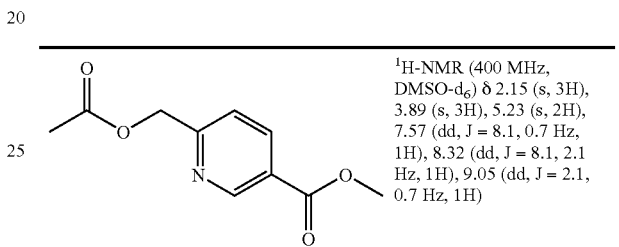

$^1$H-NMR (400 MHz, DMSO-d$_6$) δ 2.15 (s, 3H), 3.89 (s, 3H), 5.23 (s, 2H), 7.57 (dd, J = 8.1, 0.7 Hz, 1H), 8.32 (dd, J = 8.1, 2.1 Hz, 1H), 9.05 (dd, J = 2.1, 0.7 Hz, 1H)

Reference Example 10

6-Hydroxymethylpyridine-3-carboxylic acid (Reference Compound No. 10-1)

Under ice cooling, 2 M aqueous sodium hydroxide solution (3.0 mL) was added to a solution of 6-acetoxymethylpyridine-3-carboxylic acid methyl ester (Reference Compound No. 9-1, 0.60 g, 2.9 mmol) in methanol (6.0 mL). The reaction mixture was stirred under ice cooling for 40 minutes and at room temperature for 4 hours. Under ice cooling, 2 M hydrochloric acid (3.1 mL) was added thereto, and then the solvent was evaporated under reduced pressure to give the title reference compound as an orange solid.

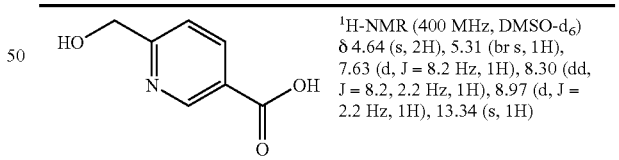

$^1$H-NMR (400 MHz, DMSO-d$_6$) δ 4.64 (s, 2H), 5.31 (br s, 1H), 7.63 (d, J = 8.2 Hz, 1H), 8.30 (dd, J = 8.2, 2.2 Hz, 1H), 8.97 (d, J = 2.2 Hz, 1H), 13.34 (s, 1H)

Reference Example 11

N-(2-t-Butoxycarbonylaminophenyl)-6-hydroxymethylpyridine-3-carboxylic acid amide (Reference Compound No. 11-1)

2-Aminophenyl carbamic acid t-butyl ester (Reference Compound No. 1-1, 0.60 g, 2.9 mmol), N,N-diisopropylethylamine (1.5 mL, 8.6 mmol), and HATU (1.1 g, 2.9 mmol) were added to a suspension of 6-hydroxymethylpyridine-3-carboxylic acid (Reference Compound No. 10-1) in DMF (10 mL), and then the reaction mixture was stirred at room temperature for 2 hours. Water (200 mL) was added thereto, the whole was extracted with ethyl acetate (100 mL, 50 mL), and then the organic layer was washed with brine (100 mL) twice. After the organic layer was dried over anhydrous magnesium sulfate, the solvent was evaporated under reduced pressure. The residue was purified by silica gel column chromatography (hexane-ethyl acetate) to give 0.66 g of the title reference compound as a brown oil. (Yield 67% in 2 steps)

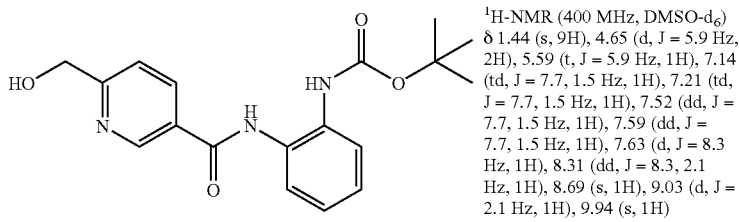

$^{1}$H-NMR (400 MHz, DMSO-$d_6$)
δ 1.44 (s, 9H), 4.65 (d, J = 5.9 Hz, 2H), 5.59 (t, J = 5.9 Hz, 1H), 7.14 (td, J = 7.7, 1.5 Hz, 1H), 7.21 (td, J = 7.7, 1.5 Hz, 1H), 7.52 (dd, J = 7.7, 1.5 Hz, 1H), 7.59 (dd, J = 7.7, 1.5 Hz, 1H), 7.63 (d, J = 8.3 Hz, 1H), 8.31 (dd, J = 8.3, 2.1 Hz, 1H), 8.69 (s, 1H), 9.03 (d, J = 2.1 Hz, 1H), 9.94 (s, 1H)

Example 1

N-(2-Aminophenyl)-5-[1-(3-dimethylaminopropyl)-3-phenethylureidomethyl]pyridine-2-carboxylic acid amide (Compound No. 1-1)

4.0 M hydrogen chloride-ethyl acetate solution (1.0 mL) was added to a solution of N-(2-t-butoxycarbonylaminophenyl)-5-[1-(3-dimethylaminopropyl)-3-phenethylureidomethyl]pyridine-2-carboxylic acid amide (Reference Compound No. 6-1, 31 mg, 0.060 mmol) in methanol (2.0 mL), and then the reaction mixture was stirred at room temperature for 4 hours. Saturated aqueous sodium hydrogen carbonate solution (30 mL) was added thereto, and then the whole was extracted with ethyl acetate (30 mL) three times. After the organic layer was dried over anhydrous magnesium sulfate, the solvent was evaporated under reduced pressure. The residue was purified by silica gel column chromatography (chloroform-methanol) to give 24 mg of the title compound as a yellow amorphous product. (Yield 84%)

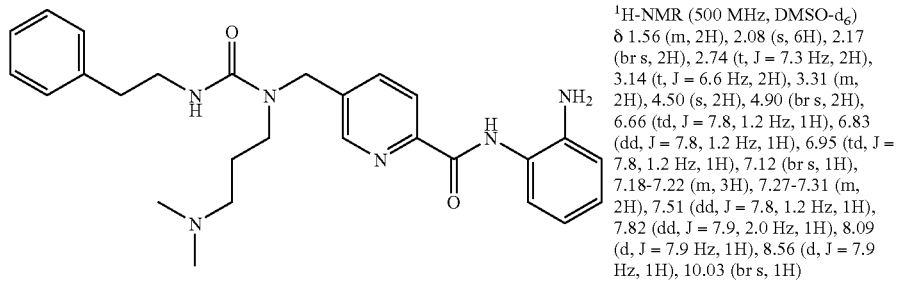

$^{1}$H-NMR (500 MHz, DMSO-$d_6$)
δ 1.56 (m, 2H), 2.08 (s, 6H), 2.17 (br s, 2H), 2.74 (t, J = 7.3 Hz, 2H), 3.14 (t, J = 6.6 Hz, 2H), 3.31 (m, 2H), 4.50 (s, 2H), 4.90 (br s, 2H), 6.66 (td, J = 7.8, 1.2 Hz, 1H), 6.83 (dd, J = 7.8, 1.2 Hz, 1H), 6.95 (td, J = 7.8, 1.2 Hz, 1H), 7.12 (br s, 1H), 7.18-7.22 (m, 3H), 7.27-7.31 (m, 2H), 7.51 (dd, J = 7.8, 1.2 Hz, 1H), 7.82 (dd, J = 7.9, 2.0 Hz, 1H), 8.09 (d, J = 7.9 Hz, 1H), 8.56 (d, J = 7.9 Hz, 1H), 10.03 (br s, 1H)

By using any compounds selected from Reference Compounds No. 6-2~6-141 and No. 7-1~7-49, the following Compounds No. 1-2~1-190 were obtained by a method similar to that of Compound No. 1-1.

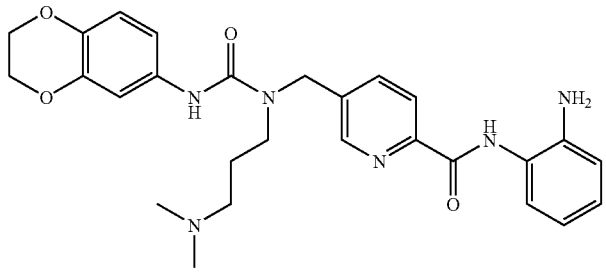

N-(2-Aminophenyl)-5-[3-(2,3-dihydrobenzo[1,4]dioxin-6-yl)-1-(3-dimethylaminopropyl)ureidomethyl]pyridine-2-carboxylic acid amide
(Compound No. 1-2)

$^1$H-NMR (500 MHz, DMSO-$d_6$)
δ 1.69 (m, 2H), 2.18 (s, 6H), 2.26 (t, J = 6.3 Hz, 2H), 3.34 (m, 2H), 4.16-4.21 (m, 4H), 4.61 (s, 2H), 4.89 (br s, 2H), 6.65 (td, J = 7.8, 1.2 Hz, 1H), 6.73 (d, J = 8.9 Hz, 1H), 6.78 (dd, J = 8.9, 2.4 Hz, 1H), 6.82 (dd, J = 7.8, 1.2 Hz, 1H), 6.95 (td, J = 7.8, 1.2 Hz, 1H), 7.07 (d, J = 2.4 Hz, 1H), 7.51 (dd, J = 7.8, 1.2 Hz, 1H), 7.94 (dd, J = 7.9, 2.1 Hz, 1H), 8.11 (d, J = 7.9 Hz, 1H), 8.65 (d, J = 2.1 Hz, 1H), 9.43 (br s, 1H), 10.02 (br s, 1H)

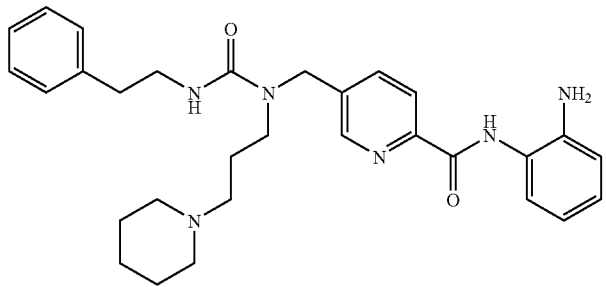

N-(2-Aminophenyl)-5-[1-[3-(morpholin-4-yl)propyl]-3-phenethylureidomethyl]pyridine-2-carboxylic acid amide
(Compound No. 1-3)

$^1$H-NMR (400 MHz, DMSO-$d_6$)
δ 1.59 (m, 2H), 2.21 (t, J = 6.6 Hz, 2H), 2.25 (br s, 4H), 2.75 (t, J = 7.2 Hz, 2H), 3.14 (t, J = 6.6 Hz, 2H), 3.34 (m, 2H), 3.50-3.52 (m, 4H), 4.56 (s, 2H), 4.89 (br s, 2H), 6.66 (td, J = 7.8, 1.2 Hz, 1H), 6.83 (dd, J = 7.8, 1.2 Hz, 1H), 6.90 (br s, 1H), 6.95 (td, J = 7.8, 1.2 Hz, 1H), 7.18-7.22 (m, 3H), 7.27-7.31 (m, 2H), 7.51 (dd, J = 7.8, 1.2 Hz, 1H), 7.82 (dd, J = 8.1, 2.0 Hz, 1H), 8.10 (d, J = 8.1 Hz, 1H), 8.57 (br s, 1H), 10.05 (br s, 1H)

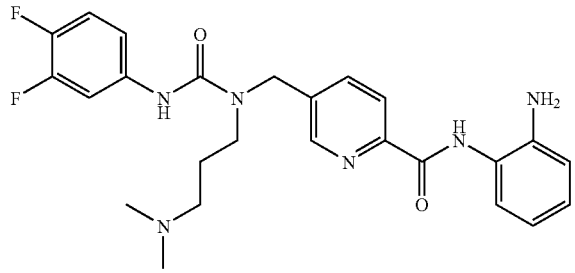

N-(2-Aminophenyl)-5-[3-(3,4-difluorophenyl)-1-(3-dimethylaminopropyl)ureidomethyl]pyridine-2-carboxylic acid amide
(Compound No. 1-4)

$^1$H-NMR (500 MHz, DMSO-$d_6$)
δ 1.71 (m, 2H), 2.19 (s, 6H), 2.27 (t, J = 6.4 Hz, 2H), 3.36 (t, J = 6.4 Hz, 2H), 4.63 (s, 2H), 4.89 (br s, 2H), 6.65 (td, J = 7.6, 1.4 Hz, 1H), 6.82 (d, J = 7.6 Hz, 1H), 6.95 (td, J = 7.6, 1.4 Hz, 1H), 7.09 (m, 1H), 7.31 (dd, J = 19.9, 9.2 Hz, 1H), 7.51 (d, J = 7.6 Hz, 1H), 7.68 (ddd, J = 13.7, 7.6, 2.4 Hz, 1H), 7.96 (dd, J = 7.9, 1.8 Hz, 1H), 8.10 (d, J = 7.9 Hz, 1H), 8.66 (d, J = 1.8 Hz, 1H), 9.93 (br s, 1H), 10.02 (br s, 1H)

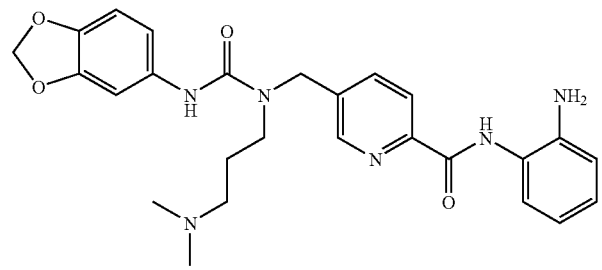

N-(2-Aminophenyl)-5-[3-(benzo[1,3]dioxol-5-yl)-1-(3-dimethylaminopropyl)ureidomethyl]pyridine-2-carboxylic acid amide
(Compound No. 1-5)

$^1$H-NMR (500 MHz, DMSO-$d_6$)
δ 1.70 (m, 2H), 2.18 (s, 6H), 2.27 (t, J = 6.3 Hz, 2H), 3.33 (m, 2H), 4.62 (s, 2H), 4.89 (br s, 2H), 5.95 (s, 2H), 6.65 (t, J = 7.6, Hz, 1H), 6.73 (dd, J = 8.6, 2.0 Hz, 1H), 6.80 (d, J = 8.6 Hz, 1H), 6.82 (d, J = 7.6 Hz, 1H), 6.95 (td, J = 7.6, 1.2 Hz, 1H), 7.19 (d, J = 2.0 Hz, 1H), 7.51 (d, J = 7.6 Hz, 1H), 7.95 (dd, J = 7.9, 2.1 Hz, 1H), 8.12 (d, J = 7.9 Hz, 1H), 8.65 (d, J = 2.1 Hz, 1H), 9.51 (br s, 1H), 10.02 (br s, 1H)

N-(2-Aminophenyl)-5-
[1-(3-dimethylaminopropyl)-3-
(4-methoxyphenyl)ureidomethyl]pyridine-
2-carboxylic acid amide
(Compound No. 1-6)

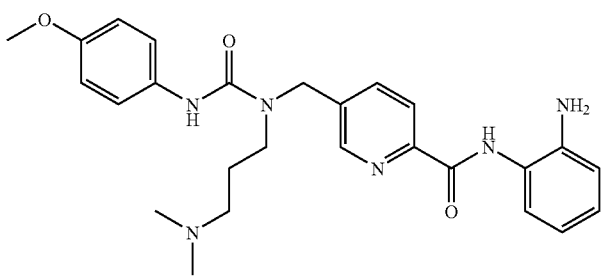

¹H-NMR (400 MHz, DMSO-d₆)
δ 1.70 (m, 2H), 2.18 (s, 6H), 2.27
(t, J = 6.3 Hz, 2H), 3.34 (m, 2H),
3.70 (s, 3H), 4.62 (s, 2H), 4.90
(br s, 2H), 6.65 (td, J = 7.6, 1.2
Hz, 1H), 6.83 (m, 1H), 6.84 (d, J =
9.0 Hz, 2H), 6.95 (td, J = 7.6,
1.2 Hz, 1H), 7.33 (d, J = 9.0 Hz,
2H), 7.51 (dd, J = 7.6, 1.2 Hz,
1H), 7.95 (dd, J = 8.1, 1.8 Hz,
1H), 8.11 (d, J = 8.1 Hz, 1H),
8.66 (d, J = 1.8 Hz, 1H), 9.43 (br
s, 1H), 10.03 (br s, 1H)

N-(2-Aminophenyl)-5-
[3-(benzo[1,3]dixol-5-yl)-1-
(3-dimethylaminopropyl)ureidomethyl]pyridine-
2-carboxylic acid amide
(Compound No. 1-7)

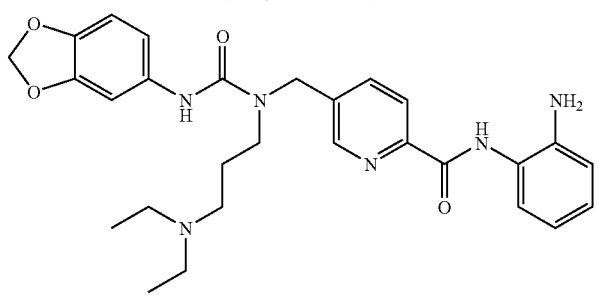

¹H-NMR (500 MHz, DMSO-d₆)
δ 0.93 (t, J = 7.2 Hz, 6H), 1.68
(m, 2H), 2.38 (m, 2H), 2.49 (m,
4H), 3.34 (m, 2H), 4.64 (s, 2H),
4.89 (br s, 2H), 5.95 (s, 2H), 6.65
(td, J = 7.6, 1.2 Hz, 1H), 6.75
(dd, J = 8.2, 2.1 Hz, 1H),
6.80-6.83 (m, 2H), 6.95 (td, J =
7.6, 1.2 Hz, 1H), 7.14 (d, J = 5 2.1
Hz, 1H), 7.50 (dd, J = 7.6, 1.2
Hz, 1H), 7.94 (dd, J = 8.1, 2.0
Hz, 1H), 8.11 (d, J = 8.1 Hz, 1H),
8.64 (d, J = 2.0 Hz, 1H), 8.98 (br
s, 1H), 10.03 (br s, 1H)

N-(2-Aminophenyl)-5-
[1-[3-(morpholin-4-yl)propyl]-3-
(pyridin-3-yl)ureidomethyl]pyridine-
2-carboxylic acid amide
(Compound No. 1-8)

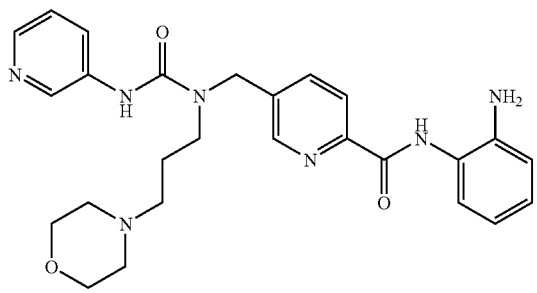

¹H-NMR (500 MHz, DMSO-d₆)
δ 1.72 (m, 2H), 2.29-2.32 (m,
6H), 3.41 (t, J = 7.0 Hz, 2H),
3.54-3.55 (m, 4H), 4.72 (s, 2H),
4.89 (br s, 2H), 6.65 (td, J = 7.9,
1.2 Hz, 1H), 6.82 (dd, J = 7.9,
1.2 Hz, 1H), 6.95 (td, J =7.9, 1.2
Hz, 1H), 7.30 (ddd, J = 8.2, 4.6,
0.6 Hz, 1H), 7.50 (dd, J = 7.9,
1.2 Hz, 1H), 7.91 (ddd, J = 8.2,
2.7, 1.5 Hz, 1H), 7.95 (dd, J =
7.9, 1.8 Hz, 1H), 8.13 (d, J = 7.9
Hz, 1H), 8.19 (dd, J = 4.6, 1.5
Hz, 1H), 8.65 (d, J = 1.8 Hz, 1H),
8.66 (d, J = 2.7 Hz, 1H), 8.81 (br
s, 1H), 10.03 (br s, 1H)

N-(2-Aminophenyl)-5-
[1-(3-dimethylaminopropyl)-3-
(2-fluorophenyl)ureidomethyl]pyridine-
2-carboxylic acid amide
(Compound No. 1-9)

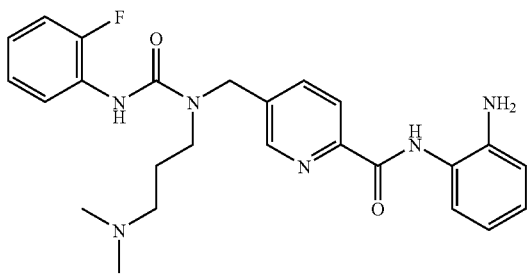

¹H-NMR (500 MHz, DMSO-d₆)
δ 1.75 (m, 2H), 2.16 (s, 6H), 2.28
(t, J = 6.1 Hz, 2H), 3.37 (t, J =
5.7 Hz, 2H), 4.62 (s, 2H), 4.90 (s,
2H), 6.65 (m, 1H), 6.82 (dd, J =
7.9, 1.2 Hz, 1H), 6.95 (m, 1H),
7.04 (ddd, J = 11.3, 5.6, 1.5 Hz,
1H), 7.11 (t, J = 7.9 Hz, 1H),
7.20 (ddd, J = 11.3, 7.9, 1.5 Hz,
1H), 7.51 (d, J = 7.9 Hz, 1H),
7.90 (t, J = 7.9 Hz, 1H), 7.97 (dd,
J = 7.9, 2.1 Hz, 1H), 8.12 (d, J =
7.9 Hz, 1H), 8.68 (d, J = 2.1 Hz,
1H), 9.90 (s, 1H), 10.03 (s, 1H)

N-(2-Aminophenyl)-5-
[1-(3-dimethylaminopropyl)-3-
(3-fluorophenyl)ureidomethyl]pyridine-
2-carboxylic acid amide
(Compound No. 1-10)

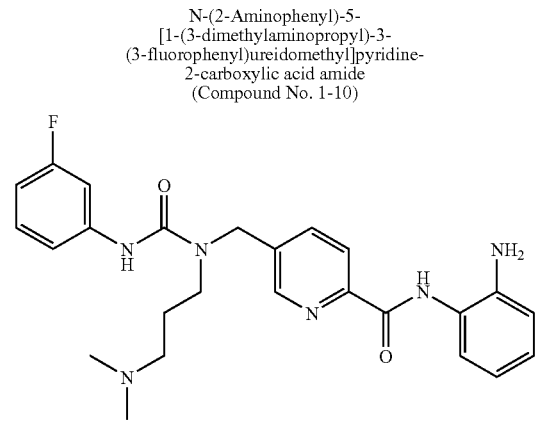

¹H-NMR (500 MHz, DMSO-d₆)
δ 1.72 (m, 2H), 2.21 (s, 6H), 2.29
(t, J = 6.3 Hz, 2H), 3.37 (t, J =
6.0 Hz, 2H), 4.63 (s, 2H), 4.89 (s,
2H), 6.65 (td, J = 7.9, 1.2 Hz,
1H), 6.75 (td, J = 8.3, 2.5 Hz,
1H), 6.82 (dd, J = 7.9, 1.2 Hz,
1H), 6.95 (td, J = 7.9, 1.2 Hz,
1H), 7.08 (dd, J = 8.3, 1.2 Hz,
1H), 7.27 (dd, J = 15.3, 8.3 Hz,
1H), 7.47-7.52 (m, 2H), 7.97 (dd,
J = 7.9, 1.8 Hz, 1H), 8.12 (d, J =
7.9 Hz, 1H), 8.67 (d, J = 1.8 Hz,
1H), 10.03 (s, 2H)

N-(2-Aminophenyl)-5-
[3-(2,5-difluorophenyl)-1-
(3-dimethylaminopropyl)ureidomethyl]pyridine-
2-carboxylic acid amide
(Compound No. 1-11)

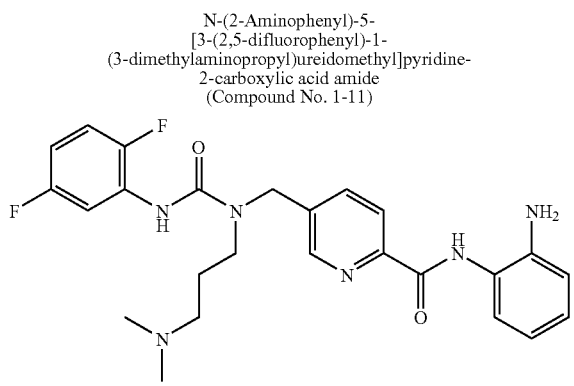

¹H-NMR (500 MHz, DMSO-d₆)
δ 1.75 (m, 2H), 2.17 (s, 6H), 2.28
(t, J = 6.1 Hz, 2H), 3.36 (t, J =
6.1 Hz, 2H), 4.62 (s, 2H), 4.89 (s,
2H), 6.65 (td, J = 8.2, 1.2 Hz,
1H), 6.79-6.83 (m, 2H), 6.95 (td,
J = 8.2, 1.2 Hz, 1H), 7.26 (m,
1H), 7.51 (dd, J = 8.2, 1.2 Hz,
1H), 7.95 (m, 1H), 7.98 (dd, J =
7.9, 2.4 Hz, 1H), 8.12 (d, J = 7.9
Hz, 1H), 8.69 (d, J = 2.4 Hz, 1H),
10.03 (s, 1H), 10.44 (s, 1H)

N-(2-Aminophenyl)-5-
[3-(3,5-difluorophenyl)-1-
(3-dimethylaminopropyl)ureidomethyl]pyridine-
2-carboxylic acid amide
(Compound No. 1-12)

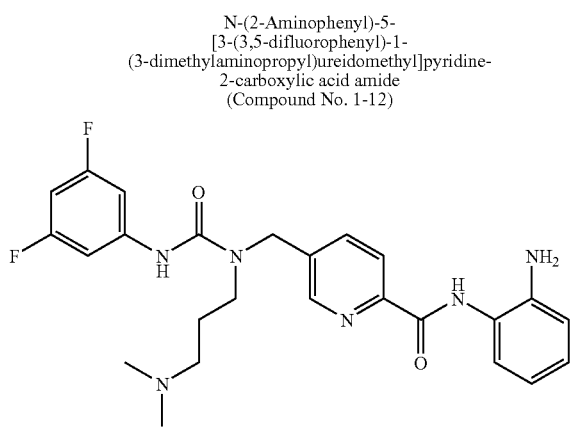

¹H-NMR (500 MHz, DMSO-d₆)
δ 1.72 (m, 2H), 2.20 (s, 6H), 2.28
(t, J = 6.3 Hz, 2H), 3.37 (t, J =
6.3 Hz, 2H), 4.64 (s, 2H), 4.88 (s,
2H), 6.65 (td, J = 8.1, 1.2 Hz,
1H), 6.76 (tt, J = 9.3, 2.4 Hz,
1H), 6.82 (dd, J = 8.1, 1.2 Hz,
1H), 6.95 (td, J = 8.1, 1.2 Hz,
1H), 7.16 (dd, J = 10.2, 2.4 Hz,
2H), 7.51 (dd, J = 8.1, 1.2 Hz,
1H), 7.96 (dd, J = 7.9, 2.1 Hz,
1H), 8.12 (d, J = 7.9 Hz, 1H),
8.67 (d, J = 2.1 Hz, 1H), 10.03 (s,
1H), 10.15 (s, 1H)

N-(2-Aminophenyl)-5-
[1-(3-dimethylaminpropyl)-3-
(3-fluoro-4-methylphenyl)ureidomethyl]pyridine-
2-carboxylic acid amide
(Compound No. 1-13)

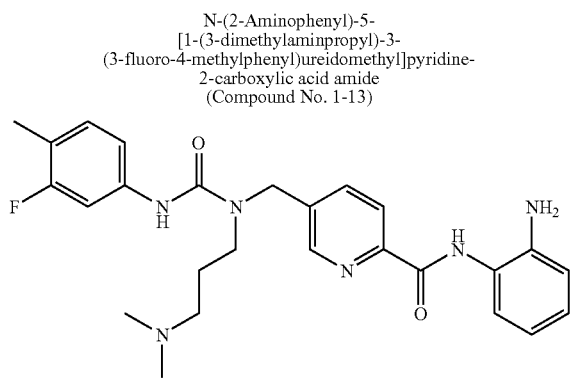

¹H-NMR (500 MHz, DMSO-d₆)
δ 1.71 (m, 2H), 2.15 (s, 3H), 2.20
(s, 6H), 2.28 (t, J = 6.3 Hz, 2H),
3.35 (t, J = 6.3 Hz, 2H), 4.62 (s,
2H), 4.89 (s, 2H), 6.65 (td, J =
7.9, 1.5 Hz, 1H), 6.82 (dd, J =
7.9, 1.5 Hz, 1H), 6.95 (td, J =
7.9, 1.5 Hz, 1H), 7.00 (dd, J =
8.4, 2.1 Hz, 1H), 7.13 (t, J = 8.4
Hz, 1H), 7.43 (dd, J = 12.8, 2.1
Hz, 1H), 7.50 (d, J = 7.9, 1.5 Hz,
1H), 7.96 (dd, J = 8.0, 2.1 Hz,
1H), 8.12 (d, J = 8.0 Hz, 1H),
8.66 (d, J = 2.1 Hz, 1H), 9.84 (s,
1H), 10.03 (s, 1H)

| Compound | NMR |
|---|---|
| N-(2-Aminophenyl)-5-[1-(3-dimethylaminpropyl)-3-(4-fluoro-3-methylphenyl)ureidomethyl]pyridine-2-carboxylic acid amide (Compound No. 1-14) 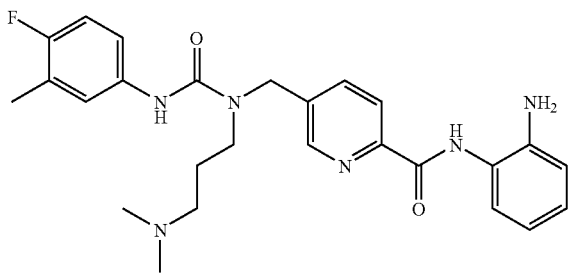 | ¹H-NMR (500 MHz, DMSO-d₆) δ 1.71 (m, 2H), 2.20 (s, 6H), 2.21 (s, 3H), 2.28 (t, J = 6.1 Hz, 2H), 3.35 (t, J = 6.1 Hz, 2H), 4.62 (s, 2H), 4.88 (s, 2H), 6.65 (td, J = 7.9, 1.5 Hz, 1H), 6.82 (dd, J = 7.9, 1.5 Hz, 1H), 6.95 (td, J = 7.9, 1.5 Hz, 1H), 7.01 (t, J = 9.2 Hz, 1H), 7.23 (m, 1H), 7.34 (dd, J = 7.0, 2.4 Hz, 1H), 7.51 (dd, J = 7.9, 1.5 Hz, 1H), 7.95 (dd, J = 8.1, 2.1 Hz, 1H), 8.12 (d, J = 8.1 Hz, 1H), 8.66 (d, J = 2.1 Hz, 1H), 9.57 (s, 1H), 10.03 (s, 1H) |
| N-(2-Aminophenyl)-5-[1-carboxymethyl-3-(4-dimethylaminophenyl)ureidomethyl]pyridine-2-carboxylic acid amide (Compound No. 1-15) 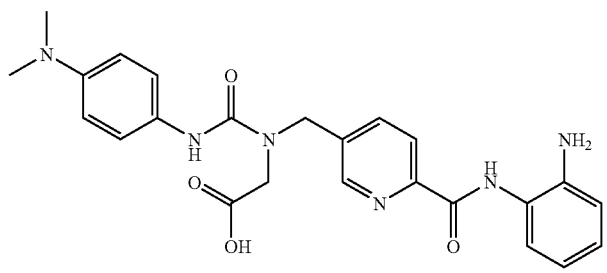 | ¹H-NMR (400 MHz, DMSO-d₆) δ 2.95 (s, 6H), 4.11 (s, 2H), 4.74 (s, 2H), 6.86 (br s, 2H), 7.15-7.27 (m, 5H), 7.59 (m, 2H), 8.08 (dd, J = 8.1, 1.8 Hz, 1H), 8.17 (dd, J = 8.1, 0.7 Hz, 1H), 8.76 (d, J = 1.8 Hz, 1H), 10.55 (br s, 1H) |
| N-(2-Aminophenyl)-5-[3-(benzo[1,3]dioxol-5-yl)-1-(2-carboxyethyl)ureidomethyl]pyridine-2-carboxylic acid amide (Compound No. 1-16) 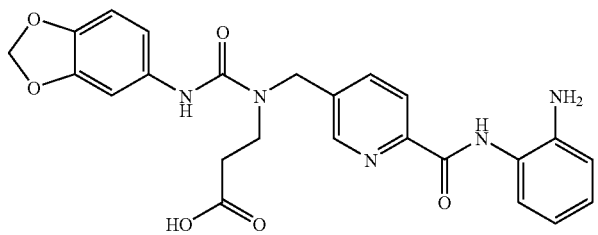 | ¹H-NMR (500 MHz, DMSO-d₆) δ 2.57 (t, J = 7.0 Hz, 2H), 3.55 (t, J = 7.0 Hz, 2H), 4.69 (s, 2H), 4.89 (br s, 2H), 5.95 (s, 2H), 6.65 (td, J = 7.6, 1.2 Hz, 1H), 6.79-6.84 (m, 3H), 6.95 (td, J = 7.6, 1.2 Hz, 1H), 7.13 (d, J = 1.8 Hz, 1H), 7.51 (dd, J = 7.6, 1.2 Hz, 1H), 7.92 (dd, J = 8.1, 1.8 Hz, 1H), 8.12 (d, J = 8.1 Hz, 1H), 8.54 (br s, 1H), 8.62 (d, J = 1.8 Hz, 1H), 10.03 (br s, 1H) |
| N-(2-Aminophenyl)-5-[1-(3-dimethylaminopropyl)-3-(indan-5-yl)ureidomethyl]pyridine-2-carboxylic acid amide (Compound No. 1-17) 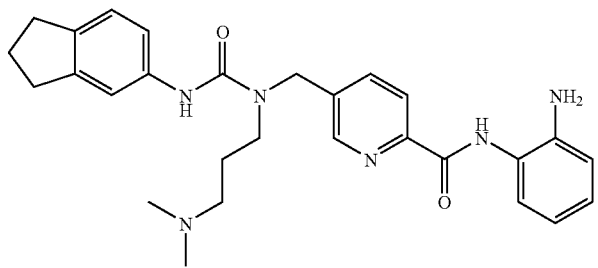 | ¹H-NMR (500 MHz, DMSO-d₆) δ 1.71 (m, 2H), 1.96-2.02 (m, 2H), 2.19 (s, 6H), 2.28 (t, J = 6.3 Hz, 2H), 2.76-2.83 (m, 4H), 3.35 (m, 2H), 4.62 (s, 2H), 4.89 (br s, 2H), 6.65 (t, J = 7.9 Hz, 1H), 6.82 (d, J = 7.9 Hz, 1H), 6.95 (td, J = 7.9, 1.4 Hz, 1H), 7.08 (d, J = 8.2 Hz, 1H), 7.10 (d, J = 8.2 Hz, 1H), 7.38 (s, 1H), 7.51 (d, J = 7.9 Hz, 1H), 7.96 (dd, J = 7.9, 2.1 Hz, 1H), 8.12 (d, J = 7.9 Hz, 1H), 8.66 (d, J = 2.1 Hz, 1H), 9.52 (br s, 1H), 10.03 (br s, 1H) |

N-(2-Aminophenyl)-5-
[3-(biphenyl-4-yl)-1-
(3-dimethylaminopropyl)ureidomethyl]pyridine-
2-carboxylic acid amide
(Compound No. 1-18)

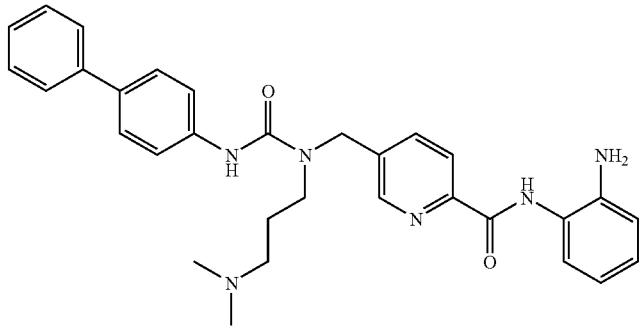

¹H-NMR (400 MHz, DMSO-$d_6$)
δ 1.74 (m, 2H), 2.23 (s, 6H), 2.31
(t, J = 6.3 Hz, 2H), 3.39 (t, J =
6.3 Hz, 2H), 4.65 (s, 2H), 4.90
(br s, 2H), 6.65 (t, J = 7.6 Hz,
1H), 6.82 (d, J = 7.6 Hz, 1H),
6.95 (td, J = 7.6, 1.3 Hz, 1H),
7.31 (t, J = 7.6 Hz, 1H), 7.43 (t,
J = 7.6 Hz, 2H), 7.50-7.64 (m,
7H), 7.98 (dd, J = 8.1, 2.0 Hz,
1H), 8.13 (dd, J = 8.1, 0.7 Hz,
1H), 8.69 (d, J = 2.0 Hz, 1H),
9.88 (br s, 1H), 10.04 (br s, 1H)

N-(2-Aminophenyl)-5-
[1-(3-dimethylaminopropyl)-3-
(4-trifluoromethylphenyl)ureidomethyl]pyridine-
2-carboxylic acid amide
(Compound No. 1-19)

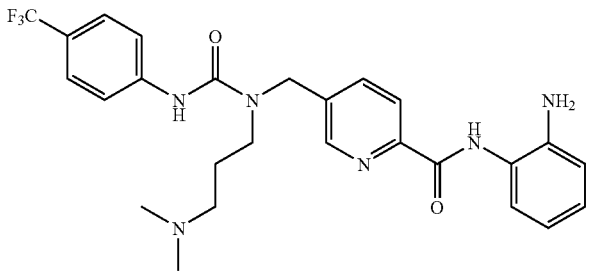

¹H-NMR (500 MHz, DMSO-$d_6$)
δ 1.72 (m, 2H), 2.06 (s, 6H), 2.28
(t, J = 6.3 Hz, 2H), 3.36 (t, J =
6.3 Hz, 2H), 4.64 (s, 2H), 4.89
(br s, 2H), 6.65 (t, J = 7.6 Hz,
1H), 6.82 (d, J = 7.6 Hz, 1H),
6.95 (td, J = 7.6, 1.4 Hz, 1H),
7.39 (m, 1H), 7.50 (m, 1H), 7.65
(m, 2H), 7.69 (d, J = 7.6 Hz, 1H),
7.93 (dd, J = 7.9, 1.8 Hz, 1H),
8.11 (d, J = 7.9 Hz, 1H), 8.63 (d,
J = 1.8 Hz, 1H), 9.61 (br s, 1H),
10.04 (br s, 1H)

N-(2-Aminophenyl)-5-
[3-(4-cyanophenyl)-1-
(3-dimethylaminopropyl)ureidomethyl]pyridine-
2-carboxylic acid amide
(Compound No. 1-20)

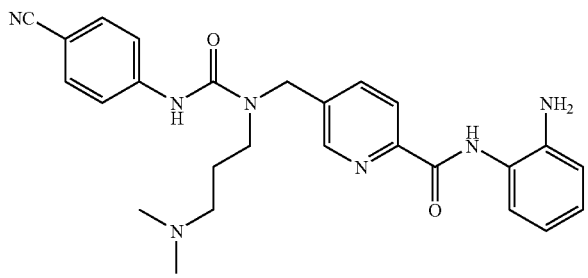

¹H-NMR (400 MHz, DMSO-$d_6$)
δ 1.74 (m, 2H), 2.20 (s, 6H), 2.29
(t, J = 6.0 Hz, 2H), 3.38 (t, J =
6.0 Hz, 2H), 4.64 (s, 2H), 4.90
(br s, 2H), 6.65 (td, J = 7.6, 1.5
Hz, 1H), 6.82 (dd, J = 7.6, 1.5
Hz, 1H), 6.95 (td, J = 7.6, 1.5
Hz, 1H), 7.50 (dd, J = 7.6, 1.5
Hz, 1H), 7.60 (d, J = 9.0 Hz, 2H),
7.70 (d, J = 9.0 Hz, 2H), 7.98
(dd, J = 8.1, 2.0 Hz, 1H), 8.12
(dd, J = 8.1, 0.5 Hz, 1H), 8.68 (d,
J = 2.0 Hz, 1H), 10.03 (br s, 1H),
10.46 (br s, 1H)

N-(2-Aminophenyl)-5-
[1-(3-dimethylaminopropyl)-3-
(4-trifluoromethylphenyl)ureidomethyl]pyridine-
2-carboxylic acid amide
(Compound No. 1-21)

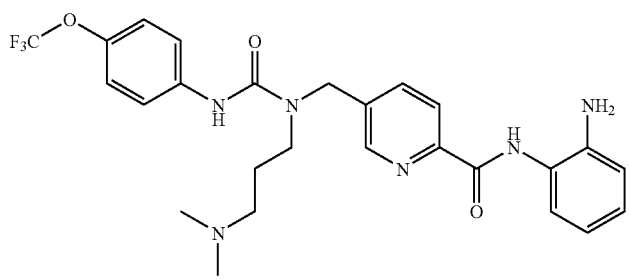

¹H-NMR (500 MHz, DMSO-$d_6$)
δ 1.72 (m, 2H), 2.21 (s, 6H), 2.28
(t, J = 6.3 Hz, 2H), 3.37 (t, J =
6.3 Hz, 2H), 4.63 (s, 2H), 4.89
(br s, 2H), 6.65 (td, J = 7.6, 1.2
Hz, 1H), 6.82 (dd, J = 7.6, 1.2
Hz, 1H), 6.95 (td, J = 7.6, 1.2
Hz, 1H), 7.25 (d, J = 8,7 Hz, 2H),
7.52 (m, 1H), 7.53 (d, J = 8.7 Hz,
2H), 7.96 (dd, J = 7.9, 2.0 Hz,
1H), 8.12 (d, J = 7.9 Hz, 1H),
8.67 (d, J = 2.0 Hz, 1H), 9.96 (br
s, 1H), 10.03 (br s, 1H)

| | |
|---|---|
| N-(2-Aminophenyl)-5-[3-(4-dimethylaminophenyl)-1-(3-hydroxypropyl)ureidomethyl]pyridine-2-carboxylic acid amide (Compound No. 1-22)<br />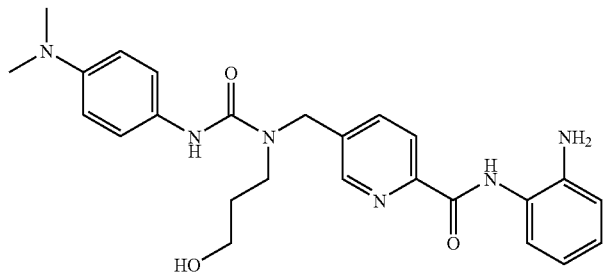 | $^1$H-NMR (400 MHz, DMSO-d$_6$) δ 1.69 (m, 2H), 2.82 (s, 6H), 3.40 (t, J = 6.7 Hz, 2H), 3.47 (m, 2H), 4.66 (s, 2H), 4.85 (br s, 1H), 4.90 (br s, 2H), 6.65 (m, 1H), 6.67 (d, J = 9.2 Hz, 2H), 6.83 (dd, J = 7.9, 1.5 Hz, 1H), 6.95 (td, J = 7.9, 1.5 Hz, 1H), 7.23 (d, J = 9.2 Hz, 2H), 7.51 (dd, J = 7.9, 1.5 Hz, 1H), 7.93 (dd, J = 8.1, 1.8 Hz, 1H), 8.12 (d, J = 8.1 Hz, 1H), 8.31 (br s, 1H), 8.64 (d, J = 1.8 Hz, 1H), 10.03 (br s, 1H) |
| N-(2-Aminophenyl)-5-[3-(2,3-dihydrobenzo[1,4]dixoin-6-yl)-1-(3-hydroxypropyl)ureidomethyl]pyridine-2-carboxylic acid amide (Compound No. 1-23)<br />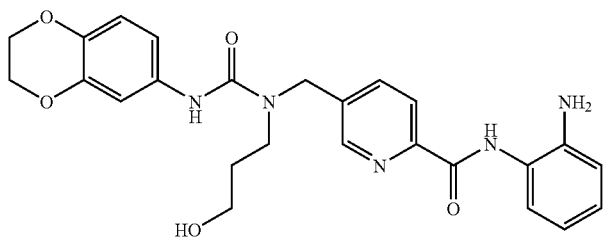 | $^1$H-NMR (500 MHz, DMSO-d$_6$) δ 1.68 (m, 2H), 3.40 (t, J = 6.6 Hz, 2H), 3.47 (m, 2H), 4.17-4.21 (m, 4H), 4.65 (s, 2H), 4.91 (br s, 3H), 6.65 (td, J = 7.8, 1.4 Hz, 1H), 6.72 (d, J = 8.7 Hz, 1H), 6.82 (dd, J = 7.8, 1.4 Hz, 1H), 6.85 (dd, J = 8.7, 2.6 Hz, 1H), 6.95 (td, J = 7.8, 1.4 Hz, 1H), 7.03 (d, J = 2.6 Hz, 1H), 7.51 (dd, J = 7.8, 1.4 Hz, 1H), 7.92 (dd, J = 8.1, 2.0 Hz, 1H), 8.12 (d, J = 8.1 Hz, 1H), 8.44 (br s, 1H), 8.63 (d, J = 2.0 Hz, 1H), 10.03 (br s, 1H) |
| N-(2-Aminophenyl)-5-[3-(4-cyanophenyl)-1-(3-hydroxypropyl)ureidomethyl]pyridine-2-carboxylic acid amide (Compound No. 1-24)<br />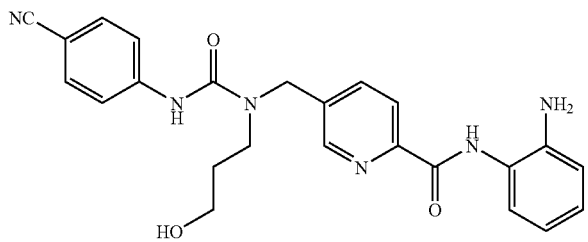 | $^1$H-NMR (500 MHz, DMSO-d$_6$) δ 1.71 (m, 2H), 3.45-3.49 (m, 4H), 4.70 (s, 2H), 4.89 (br s, 2H), 5.03 (br s, 1H), 6.65 (td, J = 7.8, 1.2 Hz, 1H), 6.82 (dd, J = 7.8, 1.2 Hz, 1H), 6.95 (td, J = 7.8, 1.2 Hz, 1H), 7.50 (dd, J = 7.8, 1.2 Hz, 1H), 7.65 (d, J = 9.0 Hz, 2H), 7.71 (d, J = 9.0 Hz, 2H), 7.92 (dd, J = 8.1, 1.8 Hz, 1H), 8.12 (d, J = 8.1 Hz, 1H), 8.66 (d, J = 1.8 Hz, 1H), 9.15 (br s, 1H), 10.03 (br s, 1H) |
| N-(2-Aminophenyl)-5-[3-(benzo[1,3]dioxol-5-yl)-1-(3-hydroxypropyl)ureidomethyl]pyridine-2-carboxylic acid amide (Compound No. 1-25)<br />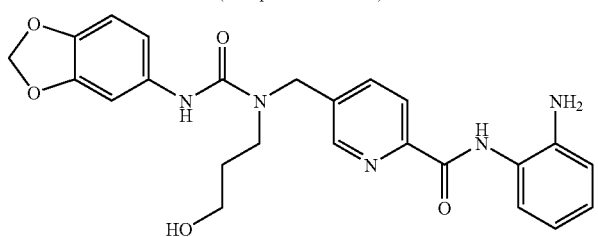 | $^1$H-NMR (500 MHz, DMSO-d$_6$) δ 1.69 (m, 2H), 3.40 (t, J = 6.9 Hz, 2H), 3.47 (m, 2H), 4.66 (s, 2H), 4.90 (br s, 2H), 4.92 (br s, 1H), 5.95 (s, 2H), 6.65 (td, J = 7.6, 1.2 Hz, 1H), 6.80 (m, 2H), 6.82 (dd, J = 7.6, 1.2 Hz, 1H), 6.95 (td, J = 7.6, 1.2 Hz, 1H), 7.13 (t, J = 1.2 Hz, 1H), 7.51 (d, J = 7.6 Hz, 1H), 7.93 (dd, J = 8.1, 2.0 Hz, 1H), 8.12 (d, J = 8.1 Hz, 1H), 8.53 (br s, 1H), 8.66 (d, J = 2.0 Hz, 1H), 10.03 (br s, 1H) |

| | |
|---|---|
| N-(2-Aminophenyl)-5-[1-(3-hydroxypropyl)-3-(4-methoxyphenyl)ureidomethyl]pyridine-2-carboxylic acid amide (Compound No. 1-26)<br>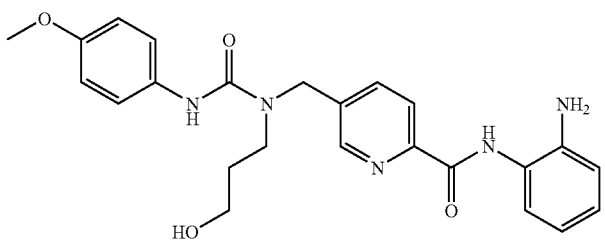 | $^1$H-NMR (500 MHz, DMSO-$d_6$) δ 1.69 (m, 2H), 3.41 (t, J = 6.6 Hz, 2H), 3.48 (m, 2H), 3.71 (s, 3H), 4.66 (s, 2H), 4.87-4.89 (m, 3H), 6.63 (td, J = 7.8, 1.4 Hz, 1H), 6.82 (m, 1H), 6.84 (d, J = 9.2 Hz, 2H), 6.95 (td, J = 7.8, 1.4 Hz, 1H), 7.33 (d, J = 9.2 Hz, 2H), 7.51 (dd, J = 7.8, 1.4 Hz, 1H), 7.94 (dd, J = 8.1, 1.8 Hz, 1H), 8.12 (dd, J = 8.1, 0.6 Hz, 1H), 8.46 (br s, 1H), 8.64 (d, J = 1.8 Hz, 1H), 10.03 (br s, 1H) |
| N-(2-Aminophenyl)-5-[3-(4-dimethylaminophenyl)-1-(2-ethoxycarbonylethyl)ureidomethyl]pyridine-2-carboxylic acid amide (Compound No. 1-27)<br>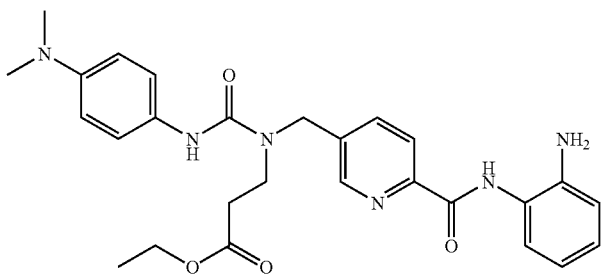 | $^1$H-NMR (400 MHz, DMSO-$d_6$) δ 1.17 (t, J = 7.1 Hz, 3H), 2.62 (t, J = 7.1 Hz, 2H), 2.82 (s, 6H), 3.59 (t, J = 7.1 Hz, 2H), 4.04 (q, J = 7.1 Hz, 2H), 4.70 (s, 2H), 4.90 (br s, 2H), 6.66 (d, J = 9.0 Hz, 2H), 6.67 (m, 1H), 6.82 (dd, J = 7.9, 1.2 Hz, 1H), 6.95 (m, 1H), 7.23 (d, J = 9.0 Hz, 2H), 7.50 (dd, J = 7.9, 1.2 Hz, 1H), 7.91 (dd, J = 8.1, 1.8 Hz, 1H), 8.12 (d, J = 8.1 Hz, 1H), 8.30 (br s, 1H), 8.62 (d, J = 1.8 Hz, 1H), 10.04 (br s, 1H) |
| N-(2-Aminophenyl)-5-[3-(benzo[1,3]dioxol-5-yl)-1-(2-ethoxycarbonylethyl)ureidomethyl]pyridine-2-carboxylic acid amide (Compound No. 1-28)<br>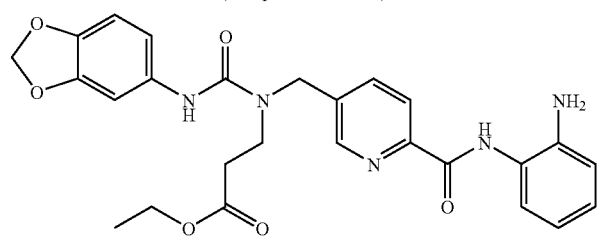 | $^1$H-NMR (400 MHz, DMSO-$d_6$) δ 1.17 (t, J = 7.1 Hz, 3H), 2.62 (t, J = 7.1 Hz, 2H), 3.59 (t, J = 7.1 Hz, 2H), 4.04 (q, J = 7.1 Hz, 2H), 4.70 (s, 2H), 4.90 (br s, 2H), 5.95 (s, 2H), 6.65 (t, J = 7.6 Hz, 1H), 6.79-6.84 (m, 3H), 6.95 (td, J = 7.6, 1.3 Hz, 1H), 7.13 (d, J = 2.0 Hz, 1H), 7.50 (dd, J = 7.6, 1.3 Hz, 1H), 7.91 (dd, J = 8.1, 1.8 Hz, 1H), 8.12 (d, J = 8.1 Hz, 1H), 8.48 (br s, 1H), 8.62 (d, J = 1.8 Hz, 1H), 10.04 (br s, 1H) |
| N-(2-Aminophenyl)-5-[1-(2-ethoxycarbonylethyl)-3-(4-methoxyphenyl)ureidomethyl]pyridine-2-carboxylic acid amide (Compound No. 1-29)<br>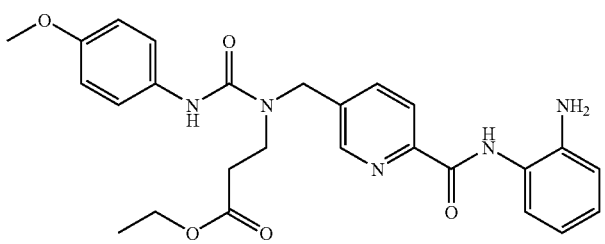 | $^1$H-NMR (400 MHz, DMSO-$d_6$) δ 1.17 (t, J = 7.1 Hz, 3H), 2.63 (t, J = 7.1 Hz, 2H), 3.60 (t, J = 7.1 Hz, 2H), 3.71 (s, 3H), 4.04 (q, J = 7.1 Hz, 2H), 4.71 (s, 2H), 4.90 (br s, 2H), 6.65 (td, J = 7.8, 1.2 Hz, 1H), 6.83 (m, 1H), 6.84 (d, J = 9.2 Hz, 2H), 6.95 (m, 1H), 7.34 (d, J = 9.2 Hz, 2H), 7.50 (d, J = 7.8 Hz, 1H), 7.91 (dd, J = 8.1, 1.8 Hz, 1H), 8.12 (d, J = 8.1 Hz, 1H), 8.44 (br s, 1H), 8.62 (d, J = 1.8 Hz, 1H), 10.04 (br s, 1H) |

| Compound | NMR |
|---|---|
| N-(2-Aminophenyl)-5-[3-(1,3-benzothiazol-2-yl)-1-(3-dimethylaminopropyl)ureidomethyl]pyridine-2-carboxylic acid amide (Compound No. 1-30)<br>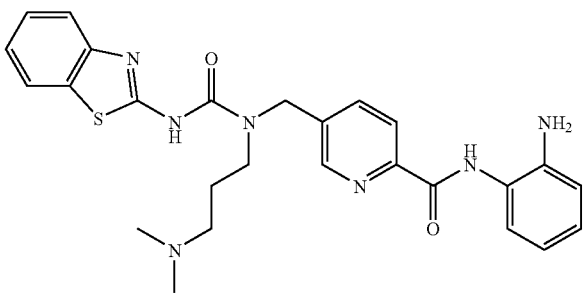 | $^1$H-NMR (500 MHz, DMSO-$d_6$) δ 1.76 (br s, 2H), 2.31 (br s, 6H), 2.38 (br s, 2H), 3.44 (br s, 2H), 4.71 (s, 2H), 4.90 (br s, 2H), 6.65 (td, J = 7.6, 1.4 Hz, 1H), 6.82 (dd, J = 7.6, 1.4 Hz, 1H), 6.95 (td, J = 7.6, 1.4 Hz, 1H), 7.19 (td, J = 8.1, 0.9 Hz, 1H), 7.34 (td, J = 8.1, 0.9 Hz, 1H), 7.51 (dd, J = 8.1, 0.9 Hz, 1H), 7.57 (br s, 1H), 7.83 (d, J = 7.6 Hz, 1H), 7.99 (dd, J = 7.9, 1.5 Hz, 1H), 8.13 (d, J = 7.9 Hz, 1H), 8.70 (d, J = 1.5 Hz, 1H), 10.03 (br s, 1H) |
| N-(2-Aminophenyl)-5-[3-(1H-benzoimidazol-2-yl)-1-(3-dimethylaminopropyl)ureidomethyl]pyridine-2-carboxylic acid amide (Compound No. 1-31)<br>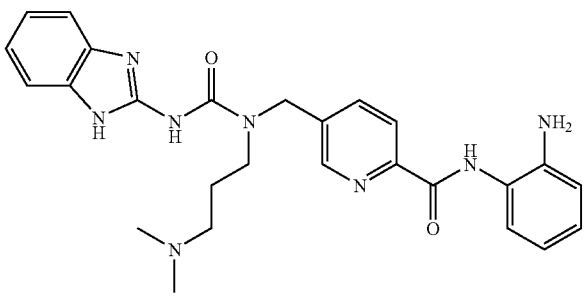 | $^1$H-NMR (500 MHz, DMSO-$d_6$) δ 1.74 (br s, 2H), 2.22 (br s, 8H), 3.44 (br s, 2H), 4.70 (s, 2H), 4.89 (br s, 2H), 6.65 (td, J = 7.6, 1.2 Hz, 1H), 6.82 (dd, J = 7.6, 1.2 Hz, 1H), 6.95 (td, J = 7.6, 1.2 Hz, 1H), 7.01-7.03 (m, 2H), 7.30 (br s, 2H), 7.51 (dd, J = 7.6, 1.2, Hz, 1H), 7.99 (d, J = 7.9 Hz, 1H), 8.12 (d, J = 7.9 Hz, 1H), 8.70 (br s, 1H), 10.03 (br s, 1H), 11.80 (br s, 1H) |
| N-(2-Aminophenyl)-5-[1-(3-dimethylaminopropyl)-3-(thiophen-2-yl)ureidomethyl]pyridine-2-carboxylic acid amide (Compound No. 1-32)<br>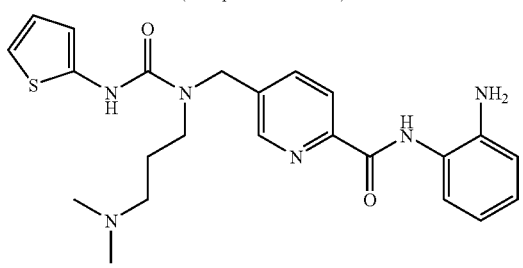 | $^1$H-NMR (400 MHz, DMSO-$d_6$) δ 1.71 (m, 2H), 2.22 (s, 6H), 2.29 (t, J = 6.1 Hz, 2H), 3.33 (m, 2H), 4.64 (s, 2H), 4.90 (br s, 2H), 6.53 (dd, J = 3.5, 1.6 Hz, 1H), 6.65 (td, J = 7.6, 1.2 Hz, 1H), 6.78-6.83 (m, 3H), 6.95 (td, J = 7.6, 1.2 Hz, 1H), 7.51 (dd, J = 7.6, 1.2 Hz, 1H), 7.94 (dd, J = 8.1, 1.8 Hz, 1H), 8.12 (d, J = 8.1 Hz, 1H), 8.66 (d, J = 1.8 Hz, 1H), 10.03 (br s, 1H), 11.10 (br s, 1H) |
| N-(2-Aminophenyl)-5-[1-(3-dimethylaminopropyl)-3-(thiophen-3-yl)ureidomethyl]pyridine-2-carboxylic acid amide (Compound No. 1-33)<br>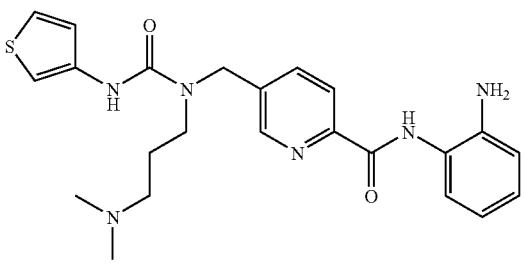 | $^1$H-NMR (500 MHz, DMSO-$d_6$) δ 1.69 (m, 2H), 2.19 (s, 6H), 2.27 (t, J = 6.4 Hz, 2H), 3.34 (m, 2H), 4.63 (s, 2H), 4.89 (br s, 2H), 6.65 (td, J = 7.6, 1.2 Hz, 1H), 6.82 (dd, J = 7.6, 1.2 Hz, 1H), 6.94 (td, J = 7.6, 1.2 Hz, 1H), 7.04 (dd, J = 5.0, 1.4 Hz, 1H), 7.28 (dd, J = 3.2, 1.4 Hz, 1H), 7.39 (dd, J = 5.0, 3.2 Hz, 1H), 7.51 (dd, J = 7.6, 1.2 Hz, 1H), 7.95 (dd, J = 8.1, 2.0 Hz, 1H), 8.11 (d, J = 8.1 Hz, 1H), 8.66 (d, J = 2.0 Hz, 1H), 10.03 (br s, 1H), 10.06 (br s, 1H) |

| Compound | NMR |
|---|---|
| N-(2-Aminophenyl)-5-[3-(2,3-dihydrobenzo[1,4]dioxin-6-yl)-1-[3-(morpholin-4-yl)propyl]ureidomethyl]pyridine-2-carboxylic acid amide (Compound No. 1-34)<br>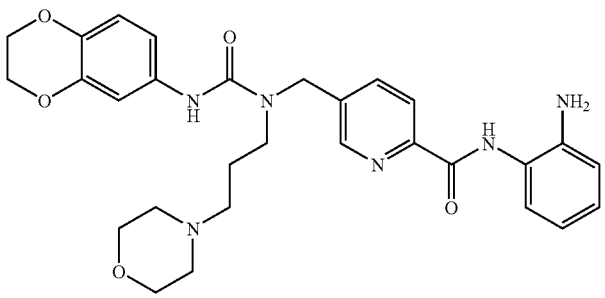 | $^1$H-NMR (500 MHz, DMSO-d$_6$) δ 1.69 (m, 2H), 2.27-2.31 (m, 6H), 3.35 (m, 2H), 3.53-3.55 (m, 4H), 4.17-4.21 (m, 4H), 4.67 (s, 2H), 4.89 (br s, 2H), 6.65 (td, J = 7.6, 1.2 Hz, 1H), 6.74 (d, J = 8.6 Hz, 1H), 6.82 (d, J = 7.6 Hz, 1H), 6.88 (dd, J = 8.6, 2.4 Hz, 1H), 6.95 (td, J = 7.6, 1.2 Hz, 1H), 7.05 (d, J = 2.4 Hz, 1H), 7.50 (d, J = 7.6 Hz, 1H), 7.92 (dd, J = 8.1, 2.0 Hz, 1H), 8.12 (d, J = 8.1 Hz, 1H), 8.48 (br s, 1H), 8.63 (d, J = 2.0 Hz, 1H), 10.03 (br s, 1H) |
| N-(2-Aminophenyl)-5-[3-(benzo[1,3]dioxin-5-yl)-1-[3-(morpholin-4-yl)propyl]ureidomethyl]pyridine-2-carboxylic acid amide (Compound No. 1-35)<br>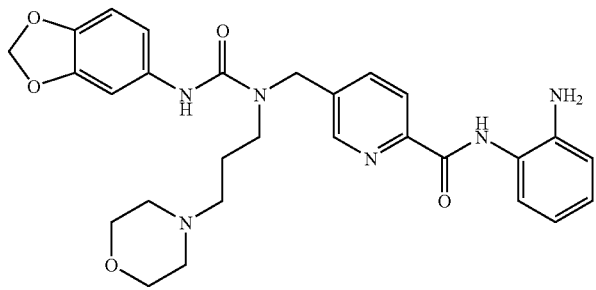 | $^1$H-NMR (400 MHz, DMSO-d$_6$) δ 1.70 (m, 2H), 2.27-2.31 (m, 6H), 3.36 (t, J = 6.6 Hz, 2H), 3.52-3.55 (m, 4H), 4.67 (s, 2H), 4.89 (br s, 2H), 5.96 (s, 2H), 6.65 (td, J = 7.6, 1.2 Hz, 1H), 6.80-6.83 (m, 3H), 6.93 (td, J = 7.6, 1.2 Hz, 1H), 7.15 (m, 1H), 7.50 (dd, J = 7.6, 1.2 Hz, 1H), 7.93 (dd, J = 8.1, 1.7 Hz, 1H), 8.12 (d, J = 8.1 Hz, 1H), 8.58 (br s, 1H), 8.64 (d, J = 1.7 Hz, 1H), 10.04 (br s, 1H) |
| N-(2-Aminophenyl)-5-[3-(4-methoxyphenyl)-1-[3-(morpholin-4-yl)propyl]ureidomethyl]pyridine-2-carboxylic acid amide (Compound No. 1-36)<br>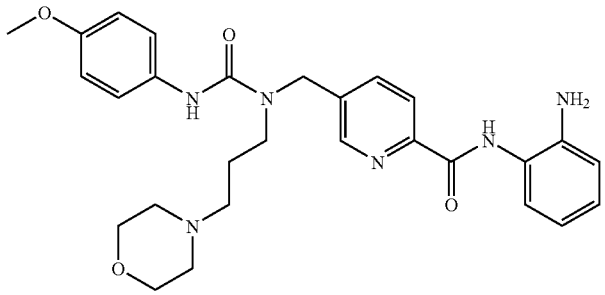 | $^1$H-NMR (400 MHz, DMSO-d$_6$) δ 1.71 (m, 2H), 2.27-2.32 (m, 6H), 3.36 (m, 2H), 3.52-3.54 (m, 4H), 3.71 (s, 3H), 4.67 (s, 2H), 4.90 (br s, 2H), 6.65 (td, J = 7.7, 1.2 Hz, 1H), 6.83 (m, 1H), 6.85 (d, J = 9.2 Hz, 2H), 6.95 (td, J = 7.7, 1.2 Hz, 1H), 7.34 (d, J = 9.2 Hz, 2H), 7.51 (dd, J = 7.7, 1.2 Hz, 1H), 7.93 (dd, J = 8.1, 1.8 Hz, 1H), 8.12 (d, J = 8.1 Hz, 1H), 8.55 (br s, 1H), 8.64 (d, J = 1.8 Hz, 1H), 10.04 (br s, 1H) |
| N-(2-Aminophenyl)-5-[3-(2,3-dihydro-1-benzofuran-5-yl)-1-(3-dimethylaminopropyl)ureidomethyl]pyridine-2-carboxylic acid amide (Compound No. 1-37)<br>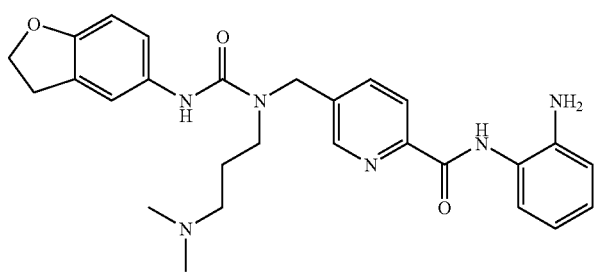 | $^1$H-NMR (400 MHz, DMSO-d$_6$) δ 1.70 (m, 2H), 2.17 (s, 6H), 2.27 (t, J = 6.3 Hz, 2H), 3.14 (t, J = 8.7 Hz, 2H), 3.33 (br s, 2H), 4.47 (t, J = 8.7 Hz, 2H), 4.62 (s, 2H), 4.90 (br s, 2H), 6.65 (d, J = 8.4 Hz, 1H), 6.65 (m, 1H), 6.82 (dd, J = 7.7, 1.2 Hz, 1H), 6.95 (td, J = 7.7, 1.2 Hz, 1H), 7.02 (dd, J = 8.4, 2.1 Hz, 1H), 7.36 (d, J = 2.1 Hz, 1H), 7.51 (dd, J = 7.7, 1.2 Hz, 1H), 7.95 (dd, J = 8.1, 2.0 Hz, 1H), 8.12 (d, J = 8.1 Hz, 1H), 8.66 (d, J = 2.0 Hz, 1H), 9.34 (br s, 1H), 10.03 (br s, 1H) |

N-(2-Aminophenyl)-5-
[3-(2,3-dihydro-1-benzofuran-5-yl)-1-
[3-(morpholin-4-yl)propyl)ureidomethyl]pyridine-
2-carboxylic acid amide
(Compound No. 1-38)

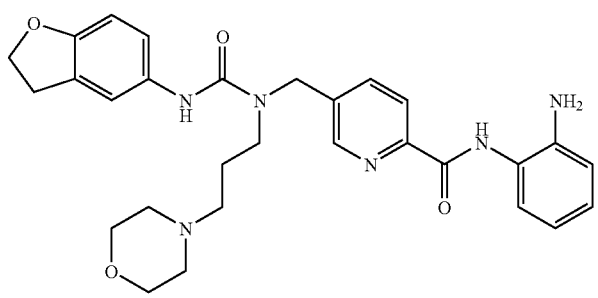

¹H-NMR (400 MHz, DMSO-d₆)
δ 1.71 (m, 2H), 2.27-2.32 (m, 6H), 3.14 (t, J = 8.5 Hz, 2H), 3.36 (m, 2H), 3.52-3.54 (m, 4H), 4.48 (t, J = 8.5 Hz, 2H), 4.67 (s, 2H), 4.90 (br s, 2H), 6.65 (d, J = 8.4 Hz, 1H), 6.65 (m, 1H), 6.82 (dd, J = 7.8, 1.2 Hz, 1H), 6.95 (td, J = 7.8, 1.2 Hz, 1H), 7.05 (dd, J = 8.4, 2.1 Hz, 1H), 7.33 (d, J = 2.1 Hz ,1H), 7.50 (dd, J = 7.8, 1.2 Hz, 1H), 7.93 (dd, J = 8.1, 1.7 Hz, 1H), 8.12 (dd, J = 8.1, 0.5 Hz, 1H), 8.51 (br s, 1H), 8.64 (d, J = 1.7 Hz, 1H), 10.04 (br s, 1H)

N-(2-Aminophenyl)-5-
[1-(3-dimethylaminopropyl)-3-
(3-fluoro-4-methoxyphenyl)ureidomethyl]pyridine-
2-carboxylic acid amide
(Compound No. 1-39)

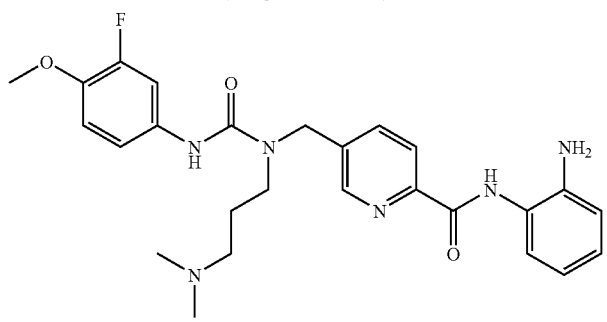

¹H-NMR (500 MHz, CDCl₃)
δ 1.74 (br s, 2H), 2.31 (s, 6H), 2.40 (br s, 2H), 3.38 (br s, 2H), 3.86 (s, 3H), 3.96 (s, 2H), 4.62 (s, 2H), 6.83-6.90 (m, 3H), 7.05-7.09 (m, 2H), 7.31 (dd, J = 13.6, 2.4 Hz, 1H), 7.49 (dd, J = 7.8, 1.4 Hz, 1H), 7.92 (dd, J = 7.9, 2.1 Hz, 1H), 8.24 (dd, J = 7.9, 0.6 Hz, 1H), 8.60 (d, J = 2.1 Hz, 1H), 9.83 (s, 1H), 10.16 (s, 1H)

N-(2-Aminophenyl)-5-
[1-(3-dimethylaminopropyl)-3-
(phenylcarbonylmethyl)ureidomethyl]pyridine-
2-carboxylic acid amide
(Compound No. 1-40)

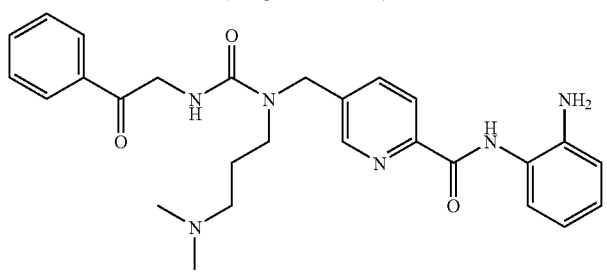

¹H-NMR (400 MHz, CDCl₃)
δ 1.72 (m, 2H), 2.30 (s, 6H), 2.43 (br s, 2H), 3.40 (t, J = 5.7 Hz, 2H), 3.97 (s, 2H), 4.63 (s, 2H), 4.73 (d, J = 4.2 Hz, 2H), 6.82-6.88 (m, 2H), 7.08 (td, J = 7.7, 1.5 Hz, 1H), 7.47-7.52 (m, 3H), 7.60 (tt, J = 7.7, 1.5 Hz, 1H), 7.87 (dd, J = 7.7, 2.1 Hz, 1H), 7.99-8.02 (m, 2H), 8.22 (s, 1H), 8.24 (dd, J = 8.1, 0.7 Hz, 1H), 8.56 (d, J = 1.5 Hz, 1H), 9.84 (s, 1H)

N-(2-Aminophenyl)-5-
[1-(3-dimethylaminopropyl)-3-
(1,3-thiazol-2-yl)ureidomethyl]pyridine-
2-carboxylic acid amide
(Compound No. 1-41)

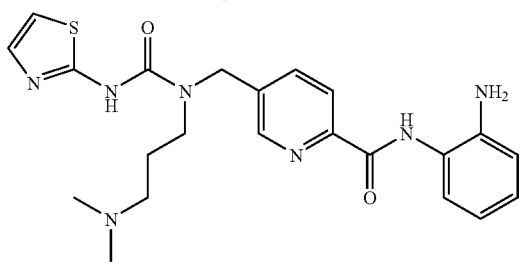

¹H-NMR (500 MHz, DMSO-d₆)
δ 1.73 (m, 2H), 2.24 (s, 6H), 2.32 (t, J = 6.0 Hz, 2H), 3.38 (t, J = 6.0 Hz, 2H), 4.66 (s, 2H), 4.90 (br s, 2H), 6.65 (td, J = 7.6, 1.5 Hz, 1H), 6.82 (dd, J = 7.6, 1.5 Hz, 1H), 6.95 (td, J = 7.6, 1.5 Hz, 1H), 7.02 (br s, 1H), 7.34 (d, J = 3.4 Hz, 1H), 7.50 (dd, J = 7.6, 1.5 Hz, 1H), 7.96 (dd, J = 7.9, 1.8 Hz, 1H), 8.11 (dd, J = 7.9, 0.6 Hz, 1H), 8.68 (d, J = 1.8 Hz, 1H), 10.03 (br s, 1H)

| | |
|---|---|
| N-(2-Aminophenyl)-5-[1-(3-dimethylaminopropyl)-3-(6-methoxy-1,3-benzothiazol-2-yl)ureidomethyl]pyridine-2-carboxylic acid amide (Compound No. 1-42)<br>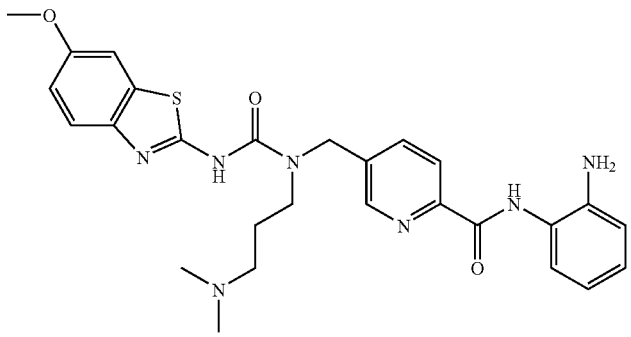 | $^1$H-NMR (500 MHz, DMSO-d$_6$) δ 1.75 (br s, 2H), 2.29 (s, 6H), 2.36 (br s, 2H), 3.42 (t, J = 5.7 Hz, 2H), 3.78 (s, 3H), 4.70 (s, 2H), 4.90 (br s, 2H), 6.65 (td, J = 7.8, 1.2 Hz, 1H), 6.82 (d, J = 7.8 Hz, 1H), 6.93-6.97 (m, 2H), 7.45 (d, J = 1.8 Hz, 1H), 7.48 (m, 1H), 7.50 (dd, J = 7.8, 1.2 Hz, 1H), 7.98 (dd, J = 7.9, 1.5 Hz, 1H), 8.13 (d, J = 7.9 Hz, 1H), 8.68 (d, J = 1.5 Hz, 1H), 10.03 (br s, 1H) |
| N-(2-Aminophenyl)-5-[3-(6-chloro-1,3-benzothiazol-2-yl)-1-(3-dimethylaminopropyl)ureidomethyl]pyridine-2-carboxylic acid amide (Compound No. 1-43)<br>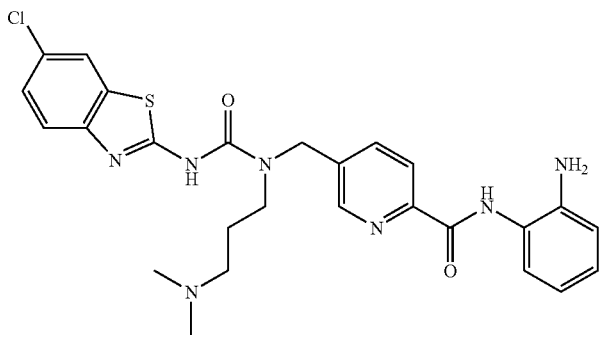 | $^1$H-NMR (500 MHz, DMSO-d$_6$) δ 1.77 (br s, 2H), 2.36 (s, 6H), 2.45 (br s, 2H), 3.43 (t, J = 5.2 Hz, 2H), 4.69 (s, 2H), 4.90 (br s, 2H), 6.65 (td, J = 7.9, 1.2 Hz, 1H), 6.82 (d, J = 7.9 Hz, 1H), 6.95 (td, J = 7.9, 1.2 Hz, 1H), 7.34 (dd, J = 8.6, 2.1 Hz, 1H), 7.51 (dd, J = 7.9, 1.2 Hz, 1H), 7.53 (br s, 1H), 7.95 (br s, 1H), 7.99 (dd, J = 8.1, 1.7 Hz, 1H), 8.13 (d, J = 8.1 Hz, 1H), 8.70 (d, J = 1.7 Hz, 1H), 10.03 (br s, 1H) |
| N-(2-Aminophenyl)-5-[1-(3-dimethylaminopropyl)-3-(6-fluoro-1,3-benzothiazol-2-yl)ureidomethyl]pyridine-2-carboxylic acid amide (Compound No. 1-44)<br>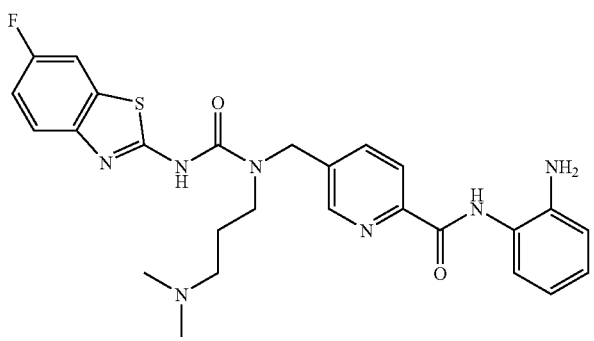 | $^1$H-NMR (500 MHz, DMSO-d$_6$) δ 1.76 (br s, 2H), 2.33 (s, 6H), 2.41 (br s, 2H), 3.43 (br s, 2H), 4.69 (s, 2H), 4.90 (br s, 2H), 6.65 (td, J = 7.8, 1.2 Hz, 1H), 6.82 (d, J = 7.8 Hz, 1H), 6.95 (td, J =7.8, 1.2 Hz, 1H), 7.17 (ddd, J = 9.2, 8.9, 2.3 Hz, 1H), 7.51 (dd, J = 7.8, 1.2 Hz, 1H), 7.57 (br s, 1H), 7.75 (dd, J = 8.1, 2.3 Hz, 1H), 7.98 (dd, J = 7.9, 1.5 Hz, 1H), 8.13 (d, J = 7.9 Hz, 1H), 8.70 (d, J = 1.5 Hz, 1H), 10.03 (br s, 1H) |

| | |
|---|---|
| N-(2-Aminophenyl)-5-[1-(3-diethylaminopropyl)-3-(4-fluorophenyl)ureidomethyl]pyridine-2-carboxylic acid amide (Compound No. 1-45)<br>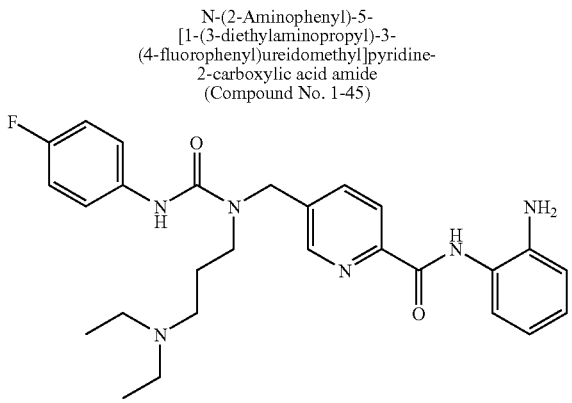 | $^1$H-NMR (500 MHz, DMSO-$d_6$) δ 0.93 (t, J = 7.0 Hz, 6H), 1.69 (m, 2H), 2.39 (t, J = 6.7 Hz, 2H), 2.48 (m, 4H), 3.36 (t, J = 6.7 Hz, 2H), 4.66 (s, 2H), 4.89 (br s, 2H), 6.65 (td, J = 7.6, 1.4 Hz, 1H), 6.82 (dd, J = 7.6, 1.4 Hz, 1H), 6.95 (td, J = 7.6, 1.4 Hz, 1H), 7.10 (t, J = 8.9 Hz, 2H), 7.43 (m, 2H), 7.50 (dd, J = 7.6, 1.4 Hz, 1H), 7.95 (dd, J = 8.2, 2.0 Hz, 1H), 8.12 (d, J = 8.2 Hz, 1H), 8.65 (d, J = 2.0 Hz, 1H), 9.13 (br s, 1H), 10.03 (br s, 1H) |
| N-(2-Aminophenyl)-5-[1-(3-diethylaminopropyl)-3-(3,4-difluorophenyl)ureidomethyl]pyridine-2-carboxylic acid amide (Compound No. 1-46)<br>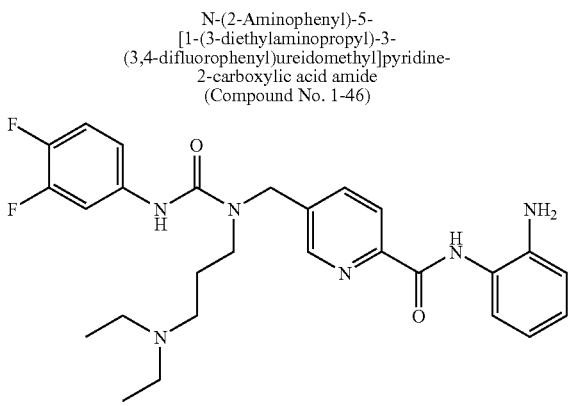 | $^1$H-NMR (500 MHz, DMSO-$d_6$) δ 0.93 (t, J = 7.2 Hz, 6H), 1.69 (m, 2H), 2.38 (t, J = 6.7 Hz, 2H), 2.48 (m, 4H), 3.36 (t, J = 6.7 Hz, 2H), 4.67 (s, 2H), 4.89 (br s, 2H), 6.65 (td, J = 7.6, 1.4 Hz, 1H), 6.82 (dd, J = 7.6, 1.4 Hz, 1H), 6.95 (td, J = 7.6, 1.4 Hz, 1H), 7.13 (m, 1H), 7.32 (dd, J = 19.7, 9.3 Hz, 1H), 7.50 (dd, J = 7.6, 1.4 Hz, 1H), 7.65 (ddd, J = 13.7, 7.6, 2.6 Hz, 1H), 7.95 (dd, J = 8.1, 1.8 Hz, 1H), 8.12 (d, J = 8.1 Hz, 1H), 8.65 (d, J = 1.8 Hz, 1H), 9.31 (br s, 1H), 10.03 (br s, 1H) |
| N-(2-Aminophenyl)-5-[1-(3-diethylaminopropyl)-3-(3,5-difluorophenyl)ureidomethyl]pyridine-2-carboxylic acid amide (Compound No. 1-47)<br>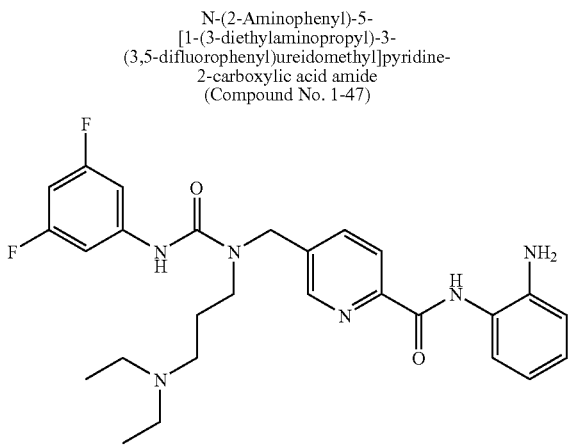 | $^1$H-NMR (500 MHz, DMSO-$d_6$) δ 0.94 (t, J = 7.2 Hz, 6H), 1.70 (m, 2H), 2.38 (t, J = 6.4 Hz, 2H), 2.49 (m, 4H), 3.38 (t, J = 6.4 Hz, 2H), 4.68 (s, 2H), 4.89 (br s, 2H), 6.65 (td, J = 7.8, 1.4 Hz, 1H), 6.77 (tt, J = 9.3, 2.4 Hz, 1H), 6.82 (dd, J = 7.8, 1.4 Hz, 1H), 6.95 (td, J = 7.8, 1.4 Hz, 1H), 7.20 (dd, J = 10.2, 2.4 Hz, 2H), 7.50 (dd, J = 7.8, 1.4 Hz, 1H), 7.95 (dd, J = 7.9, 1.8 Hz, 1H), 8.12 (d, J = 7.9 Hz, 1H), 8.66 (d, J = 1.8 Hz, 1H), 9.47 (br s, 1H), 10.03 (br s, 1H) |
| N-(2-Aminophenyl)-5-[3-(3-chloro-4-fluorophenyl)-1-(3-diethylaminopropyl)ureidomethyl]pyridine-2-carboxylic acid amide (Compound No. 1-48)<br>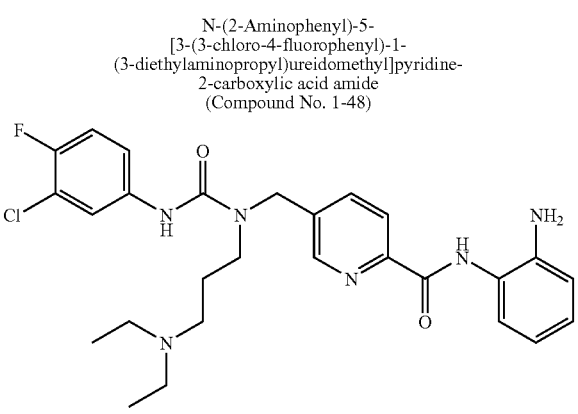 | $^1$H-NMR (500 MHz, DMSO-$d_6$) δ 0.93 (t, J = 7.0 Hz, 6H), 1.69 (m, 2H), 2.39 (t, J = 6.7 Hz, 2H), 2.48 (m, 4H), 3.37 (t, J = 6.7 Hz, 2H), 4.67 (s, 2H), 4.89 (br s, 2H), 6.65 (td, J = 7.8, 1.4 Hz, 1H), 6.82 (dd, J = 7.8, 1.4 Hz, 1H), 6.95 (td, J = 7.8, 1.4 Hz, 1H), 7.30-7.35 (m, 2H), 7.50 (dd, J = 7.8, 1.4 Hz, 1H), 7.75 (dd, J = 6.9, 2.3 Hz, 1H), 7.95 (dd, J = 7.9, 2.0 Hz, 1H), 8.12 (d, J = 7.9 Hz, 1H), 8.65 (d, J = 2.0 Hz, 1H), 9.26 (br s, 1H), 10.03 (br s, 1H) |

N-(2-Aminophenyl)-5-[1-(3-diethylaminopropyl)-3-(3-fluorophenyl)ureidomethyl]pyridine-2-carboxylic acid amide
(Compound No. 1-49)

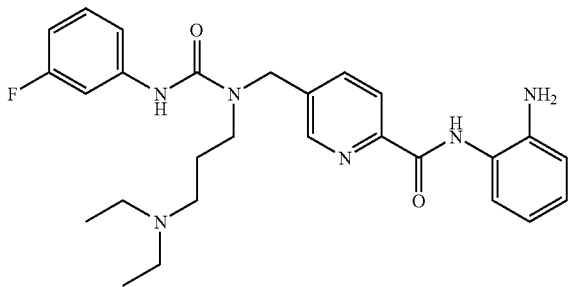

¹H-NMR (500 MHz, DMSO-d₆) δ 0.95 (t, J = 7.2 Hz, 6H), 1.71 (m, 2H), 2.39 (t, J = 6.6 Hz, 2H), 2.50 (m, 4H), 3.38 (t, J = 6.6 Hz, 2H), 4.67 (s, 2H), 4.89 (br s, 2H), 6.65 (td, J = 7.6, 1.2 Hz, 1H), 6.76 (td, J = 8.2, 2.3 Hz, 1H), 6.82 (dd, J = 7.6, 1.2 Hz, 1H), 6.95 (td, J = 7.6, 1.2 Hz, 1H), 7.15 (dd, J = 8.2, 2.3 Hz, 1H), 7.28 (dd, J = 15.3, 8.2 Hz, 1H), 7.46 (dt, J = 12.2, 2.3 Hz, 1H), 7.50 (dd, J = 7.6, 1.2 Hz, 1H), 7.95 (dd, J = 7.9, 1.8 Hz, 1H), 8.12 (d, J = 7.9 Hz, 1H), 8.66 (d, J = 1.8 Hz, 1H), 9.36 (br s, 1H), 10.03 (br s, 1H)

N-(2-Aminophenyl)-5-[1-(3-diethylaminopropyl)-3-(4-fluoro-3-methylphenyl)ureidomethyl]pyridine-2-carboxylic acid amide
(Compound No. 1-50)

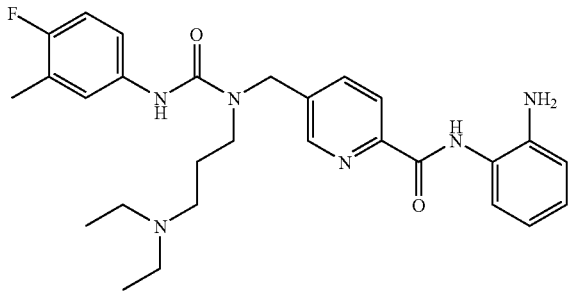

¹H-NMR (500 MHz, DMSO-d₆) δ 0.93 (t, J = 7.0 Hz, 6H), 1.69 (m, 2H), 2.19 (d, J = 1.5 Hz, 3H), 2.39 (t, J = 6.6 Hz, 2H), 2.49 (q, J = 7.0 Hz, 4H), 3.36 (t, J = 6.6 Hz, 2H), 4.65 (s, 2H), 4.89 (s, 2H), 6.65 (td, J = 7.7, 1.2 Hz, 1H), 6.82 (dd, J = 7.7, 1.2 Hz, 1H), 6.95 (td, J = 7.7, 1.2 Hz, 1H), 7.02 (t, J = 9.3 Hz, 1H), 7.23 (m, 1H), 7.34 (dd, J = 7.0, 2.4 Hz, 1H), 7.51 (dd, J = 7.7, 1.2 Hz, 1H), 7.94 (dd, J = 7.9, 2.1 Hz, 1H), 8.12 (d, J = 7.9 Hz, 1H), 8.65 (d, J = 2.1 Hz, 1H), 9.04 (s, 1H), 10.03 (s, 1H)

N-(2-Aminophenyl)-5-[1-(3-diethylaminopropyl)-3-(4-fluoro-3-nitrophenyl)ureidomethyl]pyridine-2-carboxylic acid amide
(Compound No. 1-51)

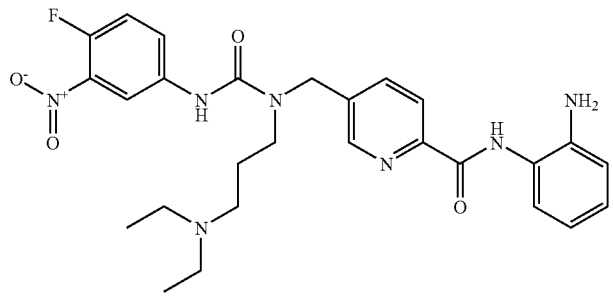

¹H-NMR (400 MHz, DMSO-d₆) δ 0.94 (t, J = 7.1 Hz, 6H), 1.71 (m, 2H), 2.40 (t, J = 6.7 Hz, 2H), 2.49 (q, J = 7.1 Hz, 4H), 3.40 (t, J = 6.7 Hz, 2H), 4.70 (s, 2H), 4.90 (s, 2H), 6.65 (td, J = 7.7, 1.1 Hz, 1H), 6.83 (dd, J = 7.7, 1.1 Hz, 1H), 6.95 (td, J = 7.7, 1.1 Hz, 1H), 7.48-7.53 (m, 2H), 7.81 (m, 1H), 7.96 (dd, J = 8.2, 2.1 Hz, 1H), 8.13 (d, J = 8.2 Hz, 1H), 8.37 (dd, J = 6.8, 2.7 Hz, 1H), 8.67 (d, J = 2.1 Hz, 1H), 9.53 (s, 1H), 10.04 (s, 1H)

N-(2-Aminophenyl)-5-[1-(3-diethylaminopropyl)-3-(3-ethoxyphenyl)ureidomethyl]pyridine-2-carboxylic acid amide
(Compound No. 1-52)

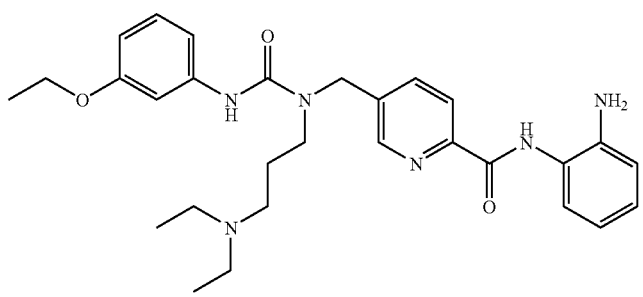

¹H-NMR (400 MHz, DMSO-d₆) δ 0.95 (t, J = 7.1 Hz, 6H), 1.31 (t, J = 6.9 Hz, 3H), 1.71 (m, 2H), 2.39 (t, J = 6.5 Hz, 2H), 2.50 (m, 4H), 3.36 (t, J = 6.5 Hz, 2H), 3.97 (q, J = 6.9 Hz, 2H), 4.66 (s, 2H), 4.90 (s, 2H), 6.51 (dd, J = 7.9, 2.1 Hz, 1H), 6.65 (td, J = 7.7, 1.1 Hz, 1H), 6.82 (dd, J = 7.7, 1.1 Hz, 1H), 6.93-6.97 (m, 2H), 7.11-7.15 (m, 2H), 7.51 (dd, J = 7.7, 1.1 Hz, 1H), 7.95 (dd, J = 7.9, 2.1 Hz, 1H), 8.13 (d, J = 7.9 Hz, 1H), 8.66 (d, J = 2.1 Hz, 1H), 9.15 (s, 1H), 10.04 (s, 1H)

N-(2-Aminophenyl)-5-
[3-(2,3-dihydrobenzo[1,4]dioxin-6-yl)-1-
(2-dimethylaminoethyl)ureidomethyl]pyridine-
2-carboxylic acid amide
(Compound No. 1-53)

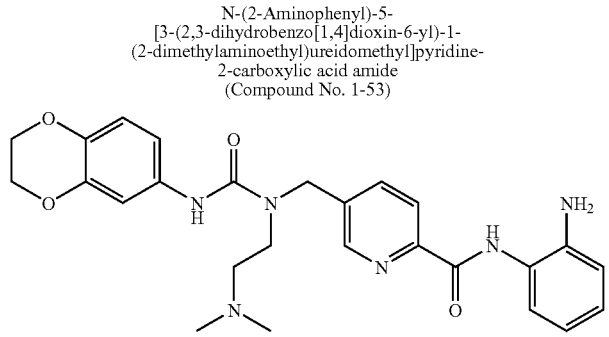

¹H-NMR (400 MHz, CDCl₃)
δ 2.38 (s, 6H), 2.51 (t, J = 4.3
Hz, 2H), 3.31 (t, J = 4.3 Hz, 2H),
3.96 (s, 2H), 4.21-4.24 (m, 4H),
4.65 (s, 2H), 6.77-6.88 (m, 4H),
6.93 (d, J = 2.2 Hz, 1H), 7.08 (td,
J = 7.7, 1.5 Hz, 1H), 7.48 (d, J =
7.7 Hz, 1H), 7.90 (dd, J = 8.1,
2.2 Hz, 1H), 8.24 (d, J = 8.1 Hz,
1H), 8.57 (d, J = 2.2 Hz, 1H),
9.83 (s, 1H), 10.84 (s, 1H)

N-(2-Aminophenyl)-5-
[1-(2-dimethylaminoethyl)-3-
(3-methoxyphenyl)ureidomethyl]pyridine-
2-carboxylic acid amide
(Compound No. 1-54)

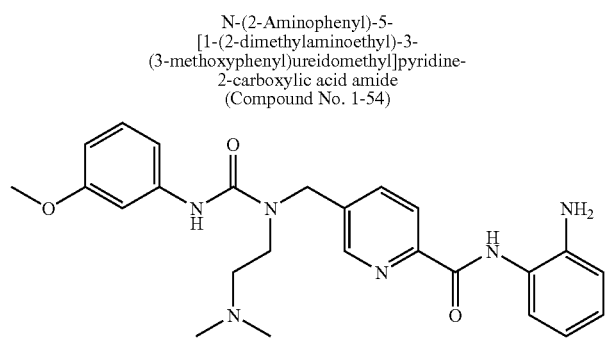

¹H-NMR (400 MHz, CDCl₃)
δ 2.40 (s, 6H), 2.53 (t, J = 4.3
Hz, 2H), 3.34 (t, J = 4.3 Hz, 2H),
3.82 (s, 3H), 3.96 (s, 2H), 4.67
(s, 2H), 6.57 (ddd, J = 7.8, 2.4,
0.7 Hz, 1H), 6.81-6.87 (m, 3H),
7.09 (td, J = 7.6, 1.5 Hz, 1H),
7.15 (t, J = 2.4 Hz, 1H), 7.17 (t,
J = 7.8 Hz, 1H), 7.48 (d, J = 7.8
Hz, 1H), 7.91 (dd, J = 8.1, 2.2
Hz, 1H), 8.26 (d, J = 8.1 Hz, 1H),
8.59 (d, J = 2.2 Hz, 1H), 9.83 (s,
1H), 11.11 (s, 1H)

N-(2-Aminophenyl)-5-
[1-(2-dimethylaminoethyl)-3-
(3-fluorophenyl)ureidomethyl]pyridine-
2-carboxylic acid amide
(Compound No. 1-55)

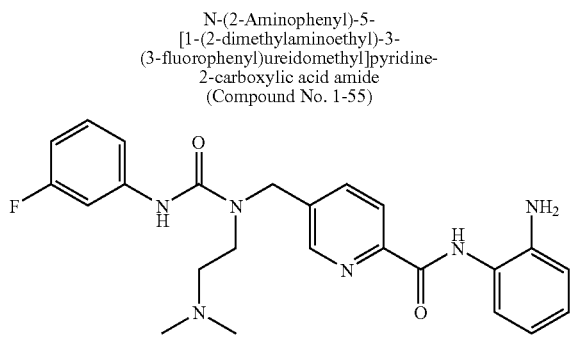

¹H-NMR (500 MHz, CDCl₃)
δ 2.41 (s, 6H), 2.54 (t, J = 4.3
Hz, 2H), 3.34 (t, J = 4.3 Hz, 2H),
3.96 (s, 2H), 4.66 (s, 2H), 6.68
(td, J = 8.1, 2.3 Hz, 1H),
6.83-6.88 (m, 2H), 7.01 (dd, J =
8.1, 1.5 Hz, 1H), 7.08 (m, 1H),
7.20 (m, 1H), 7.28 (m, 1H), 7.48
(d, J = 8.1 Hz, 1H), 7.91 (dd, J =
7.9, 2.1 Hz, 1H), 8.26 (d, J = 7.9
Hz, 1H), 8.59 (d, J = 2.1 Hz, 1H),
9.83 (s, 1H), 11.31 (s, 1H)

N-(2-Aminophenyl)-5-
[1-(2-dimethylaminoethyl)-3-
(thiophen-3-yl)ureidomethyl]pyridine-
2-carboxylic acid amide
(Compound No. 1-56)

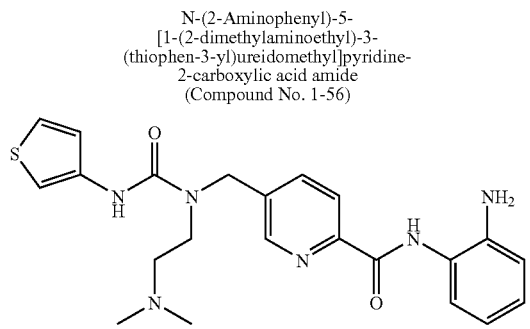

¹H-NMR (400 MHz, CDCl₃)
δ 2.39 (s, 6H), 2.52 (t, J = 4.4
Hz, 2H), 3.31 (d, J = 4.4 Hz, 2H),
3.96 (s, 2H), 4.67 (s, 2H),
6.83-6.87 (m, 3H), 7.08 (td, J =
7.8, 1.5 Hz, 1H), 7.21 (dd, J =
5.1, 3.3 Hz, 1H), 7.30 (dd, J =
3.3, 1.2 Hz, 1H), 7.48 (d, J = 7.8
Hz, 1H), 7.90 (dd, J = 8.1, 2.2
Hz, 1H), 8.25 (dd, J = 8.1, 0.7
Hz, 1H), 8.57 (d, J = 2.2 Hz, 1H),
9.83 (s, 1H), 11.48 (s, 1H)

N-(2-Aminophenyl)-5-
[3-(3,4-difluorophenyl)-1-
[3-pyrrolidin-1-yl)ureidomethyl]pyridine-
2-carboxylic acid amide
(Compound No. 1-57)

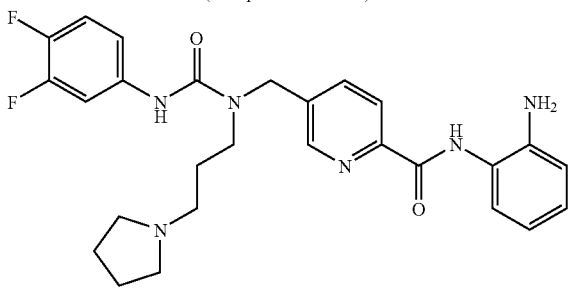

¹H-NMR (500 MHz, DMSO-d₆)
δ 1.70-1.73 (m, 6H), 2.41-2.45
(m, 6H), 3.40 (t, J = 6.3 Hz, 2H),
4.65 (s, 2H), 4.89 (br s, 2H), 6.65
(td, J = 7.6, 1.2 Hz, 1H), 6.82
(dd, J = 7.6, 1.2 Hz, 1H), 6.95
(td, J = 7.6, 1.2 Hz, 1H), 7.11 (m,
1H), 7.34 (dd, J = 19.9, 9.2 Hz,
1H), 7.51 (dd, J = 7.6, 1.2 Hz,
1H), 7.65 (ddd, J = 13.7, 7.6, 2.4
Hz, 1H), 7.95 (dd, J = 7.9, 1.8
Hz, 1H), 8.12 (d, J = 7.9 Hz, 1H),
8.66 (d, J = 1.8 Hz, 1H), 9.57 (br
s, 1H), 10.03 (br s, 1H)

N-(2-Aminophenyl)-5-
[3-(pyridin-3-yl)-1-
(3-pyrrolidin-1-yl)propyl]ureidomethyl]pyridine-
2-carboxylic acid amide
(Compound No. 1-58)

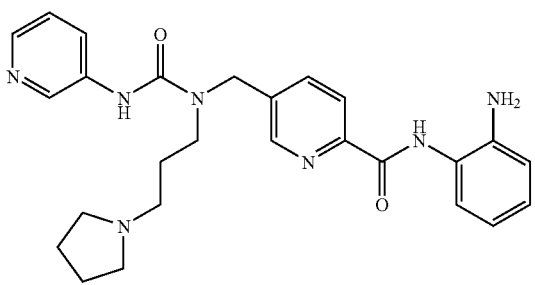

¹H-NMR (500 MHz, DMSO-d₆)
δ 1.73-1.75 (m, 6H), 2.43-2.46
(m, 6H), 3.43 (t, J = 6.3 Hz, 2H),
4.66 (s, 2H), 4.89 (br s, 2H), 6.65
(t, J = 7.6 Hz, 1H), 6.82 (dd, J =
7.6, 1.2 Hz, 1H), 6.95 (td, J =
7.6, 1.2 Hz, 1H), 7.30 (dd, J =
8.2, 4.6 Hz, 1H), 7.51 (dd, J =
7.6, 1.2 Hz, 1H), 7.90 (ddd, J =
8.2, 2.6, 1.5 Hz, 1H), 7.96 (dd, J =
7.9, 1.8 Hz, 1H), 8.12 (d, J =
7.9 Hz, 1H), 8.17 (dd, J = 4.6,
1.5 Hz, 1H), 8.56 (d, J = 2.6 Hz,
1H), 8.66 (d, J = 1.8 Hz, 1H),
9.59 (br s, 1H), 10.03 (br s, 1H)

N-(2-Aminophenyl)-5-
[1-[3-(morpholin-4-yl)propyl]-3-
(phenylcarbonylmethyl)ureidomethyl]pyridine-
2-carboxylic acid amide
(Compound No. 1-59)

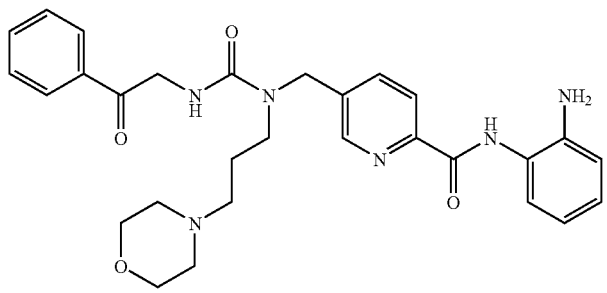

¹H-NMR (400 MHz, CDCl₃)
δ 1.75 (m, 2H), 2.42-2.52 (m,
6H), 3.39 (t, J = 6.0 Hz, 2H),
3.67 (t, J = 4.4 Hz, 4H), 3.96 (s,
2H), 4.63 (s, 2H), 4.72 (br s, 2H),
6.82-6.84 (m, 2H), 7.07 (dd, J =
7.6, 1.5 Hz, 1H), 7.47-7.52 (m,
3H), 7.61 (d, J = 7.6 Hz, 2H),
7.86 (dd, J = 8.0, 2.2 Hz, 1H),
7.97-8.01 (m, 2H), 8.23 (dd, J =
8.0, 0.7 Hz, 1H), 8.56 (d, J = 2.2
Hz, 1H), 9.83 (s, 1H)

N-(2-Aminophenyl)-5-
[3-(3-chlorophenyl)-1-
[3-(morpholin-4-yl)propyl]ureidomethyl]pyridine-
2-carboxylic acid amide
(Compound No. 1-60)

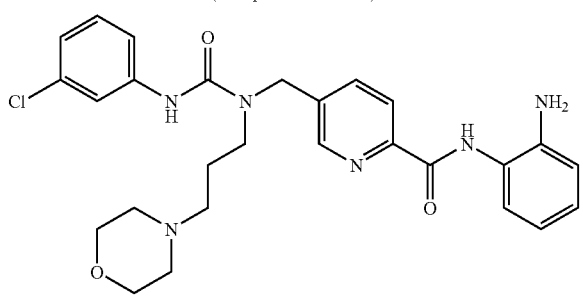

¹H-NMR (500 MHz, CDCl₃)
δ 1.80 (m, 2H), 2.43-2.49 (m,
6H), 3.39 (t, J = 5.7 Hz, 2H),
3.68-3.74 (m, 4H), 3.95 (s, 2H),
4.65 (s, 2H), 6.84-6.88 (m, 2H),
7.05-7.10 (m, 2H), 7.25 (m, 1H),
7.32 (dd, J = 8.3, 1.2 Hz, 1H),
7.48 (d, J = 7.9 Hz, 1H), 7.59 (m,
1H), 7.91 (dd, J = 7.9, 2.0 Hz,
1H), 8.25 (d, J = 7.9 Hz, 1H),
8.59 (d, J = 2.0 Hz, 1H), 9.05 (s,
1H), 9.82 (s, 1H)

N-(2-Aminophenyl)-5-
[3-(2-fluorophenethyl)-1-
[3-(morpholin-4-yl)propyl]ureidomethyl]pyridine-
2-carboxylic acid amide
(Compound No. 1-61)

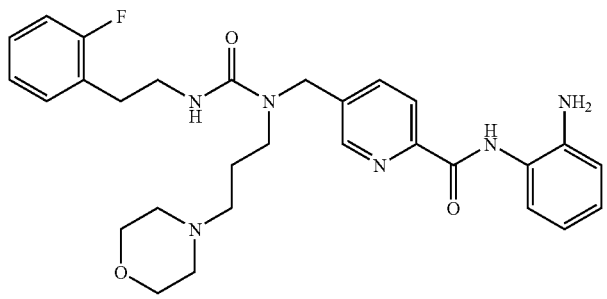

$^1$H-NMR (500 MHz, DMSO-d$_6$)
δ 1.58 (m, 2H), 2.21 (t, J = 6.8
Hz, 2H), 2.25 (br s, 4H), 2.80 (t,
J = 6.8 Hz, 2H), 3.13 (t, J = 6.8
Hz, 2H), 3.32 (m, 2H), 3.51 (br s,
4H), 4.55 (s, 2H), 4.90 (br s, 2H),
6.66 (t, J = 7.9 Hz, 1H), 6.83 (d,
J = 7.9 Hz, 1H), 6.93-7.01 (m,
2H), 7.10-7.18 (m, 2H),
7.23-7.30 (m, 2H), 7.52 (m, 1H),
7.80 (dd, J = 8.1, 1.8 Hz, 1H),
8.09 (d, J = 8.1 Hz, 1H), 8.55 (d,
J = 1.8 Hz, 1H), 10.04 (s, 1H)

N-(2-Aminophenyl)-5-
[3-(4-fluorophenethyl)-1-
[3-(morpholin-4-yl)propyl]ureidomethyl]pyridine-
2-carboxylic acid amide
(Compound No. 1-62)

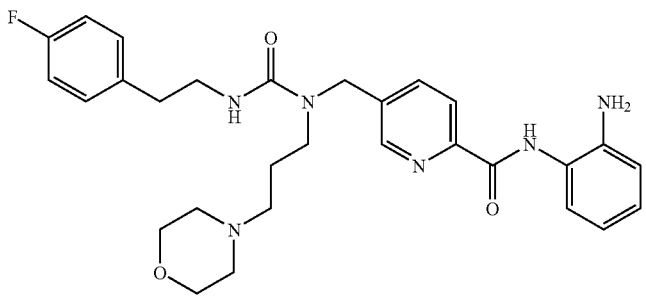

$^1$H-NMR (500 MHz, DMSO-d$_6$)
δ 1.58 (m, 2H), 2.20 (t, J = 6.8
Hz, 2H), 2.26 (br s, 4H), 2.74 (t,
J = 6.8 Hz, 2H), 3.14 (t, J = 6.8
Hz, 2H), 3.29 (m, 2H), 3.51 (t, J =
4.3 Hz, 4H), 4.55 (s, 2H), 4.89
(s, 2H), 6.66 (t, J = 7.7 Hz, 1H),
6.83 (d, J = 7.7 Hz, 1H), 6.86 (t,
J = 5.6 Hz, 1H), 6.96 (td, J = 7.7,
1.4 Hz, 1H), 7.10 (t, J = 8.9 Hz,
2H), 7.22 (dd, J = 8.9, 5.6 Hz,
2H), 7.51 (m, 1H), 7.80 (dd, J =
8.1, 1.8 Hz, 1H), 8.10 (d, J = 8.1
Hz, 1H), 8.55 (d, J = 1.8 Hz, 1H),
10.04 (s, 1H)

N-(2-Aminophenyl)-5-
[3-(3-fluorophenyl)-1-
[2-(4-methylpiperazin-1-yl)ethyl]ureidomethyl]pyridine-
2-carboxylic acid amide
(Compound No. 1-63)

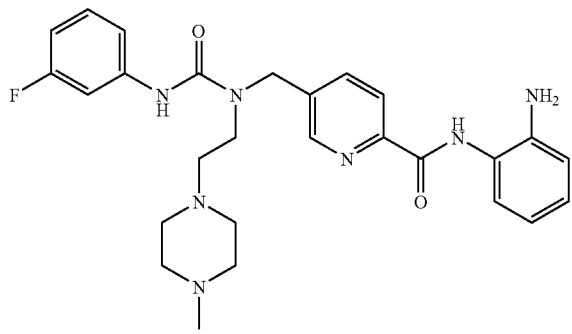

$^1$H-NMR (400 MHz, DMSO-d$_6$)
δ 2.13 (s, 3H), 2.30 (s, 4H), 2.46
(br s, 4H), 2.48 (m, 2H), 3.49 (t,
J = 5.4 Hz, 2H), 4.70 (s, 2H),
4.89 (s, 2H), 6.65 (t, J = 7.6 Hz,
1H), 6.77 (m, 1H), 6.83 (d, J =
8.1 Hz, 1H), 6.95 (td, J = 7.6, 1.3
Hz, 1H), 7.22-7.32 (m, 2H), 7.45
(d, J = 12.2 Hz, 1H), 7.51 (d, J =
7.6 Hz, 1H), 7.96 (dd, J = 8.1,
1.8 Hz, 1H), 8.12 (d, J = 8.1 Hz,
1H), 8.65 (d, J = 1.8 Hz, 1H),
9.37 (s, 1H), 10.04 (s, 1H)

| | |
|---|---|
| N-(2-Aminophenyl)-5-[3-(3,4-difluorophenyl)-1-[2-(4-methylpiperazin-1-yl)ethyl]ureidomethyl]pyridine-2-carboxylic acid amide (Compound No. 1-64) 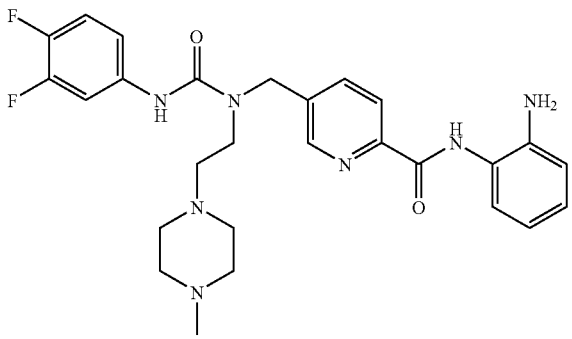 | $^1$H-NMR (500 MHz, DMSO-d$_6$) δ 2.12 (s, 3H), 2.28 (br s, 4H), 2.44 (br s, 4H), 2.48 (t, J = 5.7 Hz, 2H), 3.48 (t, J = 5.7 Hz, 2H), 4.70 (s, 2H), 4.89 (s, 2H), 6.65 (t, J = 7.9 Hz, 1H), 6.83 (d, J = 7.9 Hz, 1H) 6.95 (t, J = 7.9 Hz, 1H), 7.21 (d, J = 9.2 Hz, 1H), 7.33 (m, 9.2 Hz, 1H), 7.51 (d, J = 7.9 Hz, 1H), 7.63 (m, 1H), 7.95 (dd, J = 7.9, 1.5 Hz, 1H), 8.12 (d, J = 7.9 Hz, 1H), 8.64 (d, J = 1.5 Hz, 1H), 9.31 (s, 1H), 10.03 (s, 1H) |
| N-(2-Aminophenyl)-5-[3-(2,3-dihydrobenzo[1,4]dioxin-6-yl)-1-[2-(4-methylpiperazin-1-yl)ethyl]ureidomethyl]pyridine-2-carboxylic acid amide (Compound No. 1-65) 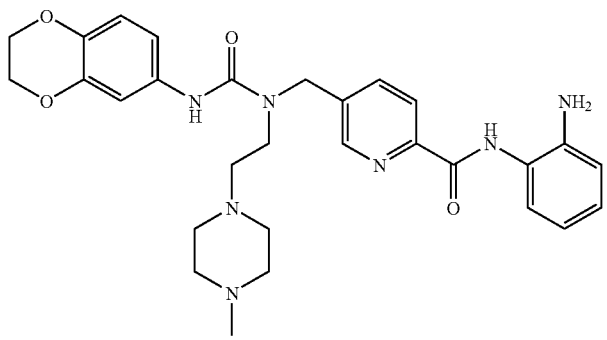 | $^1$H-NMR (400 MHz, DMSO-d$_6$) δ 2.13 (s, 3H), 2.30 (br s, 4H), 2.46 (br s, 4H), 2.47 (t, J = 4.6 Hz, 2H), 3.44 (t, J = 4.6 Hz, 2H), 4.17-4.21 (m, 4H), 4.67 (s, 2H), 4.89 (s, 2H), 6.65 (t, J = 7.4 Hz, 1H), 6.74 (d, J = 8.8 Hz, 1H), 6.81-6.87 (m, 2H), 6.95 (t, J = 7.4 Hz, 1H), 7.03 (d, J = 2.0 Hz, 1H), 7.51 (d, J = 7.8 Hz, 1H), 7.94 (d, J = 7.8 Hz, 1H), 8.11 (d, J = 7.8 Hz, 1H), 8.63 (s, 1H), 9.02 (s, 1H), 10.04 (s, 1H) |
| N-(2-Aminophenyl)-5-[3-(3-fluorophenyl)-1-[3-(4-methylpiperazin-1-yl)propyl]ureidomethyl]pyridine-2-carboxylic acid amide (Compound No. 1-66) 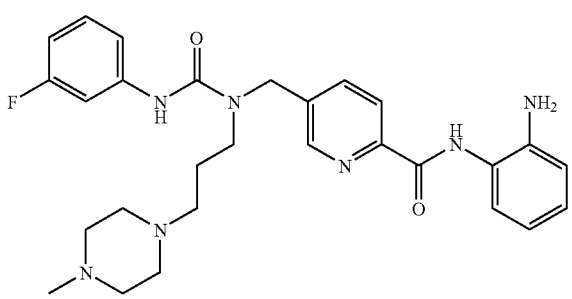 | $^1$H-NMR (400 MHz, DMSO-d$_6$) δ 1.71 (m, 2H), 2.13 (s, 3H), 2.28 (t, J = 6.4 Hz, 2H), 2.31 (br s, 8H), 3.38 (t, J = 6.4 Hz, 2H), 4.70 (s, 2H), 4.89 (s, 2H), 6.65 (t, J = 7.6 Hz, 1H), 6.76-6.83 (m, 2H), 6.95 (t, J = 7.6 Hz, 1H), 7.27-7.29 (m, 2H), 7.46-7.51 (m, 2H), 7.94 (d, J = 8.1 Hz, 1H), 8.12 (d, J = 8.1 Hz, 1H), 8.65 (s, 1H), 8.84 (s, 1H), 10.03 (s, 1H) |

| | |
|---|---|
| N-(2-Aminophenyl)-5-[3-(3,4-difluorophenyl)-1-[3-(4-methylpiperazin-1-yl)propyl]ureidomethyl]pyridine-2-carboxylic acid amide (Compound No. 1-67)<br>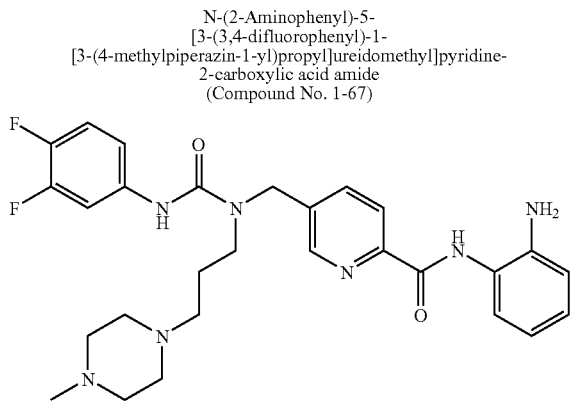 | $^1$H-NMR (400 MHz, DMSO-$d_6$) δ 1.70 (m, 2H), 2.12 (s, 3H), 2.28 (t, J = 6.7 Hz, 2H), 2.32 (br s, 8H), 3.37 (t, J = 6.7 Hz, 2H), 4.69 (s, 2H), 4.89 (s, 2H), 6.65 (t, J = 7.6 Hz, 1H), 6.82 (d, J = 7.6 Hz, 1H), 6.95 (t, J = 7.6 Hz, 1H), 7.25-7.33 (m, 2H), 7.50 (d, J = 7.6 Hz, 1H), 7.65 (m, 1H), 7.93 (dd, J = 8.1, 1.7 Hz, 1H), 8.12 (d, J = 8.1 Hz, 1H), 8.64 (d, J = 1.7 Hz, 1H), 8.86 (s, 1H), 10.03 (s, 1H) |
| N-(2-Aminophenyl)-5-[3-(2,3-dihydrobenzo[1,4]dioxin-6-yl)-1-[3-(4-methylpiperazin-1-yl)propyl]ureidomethyl]pyridine-2-carboxylic acid amide (Compound No. 1-68)<br>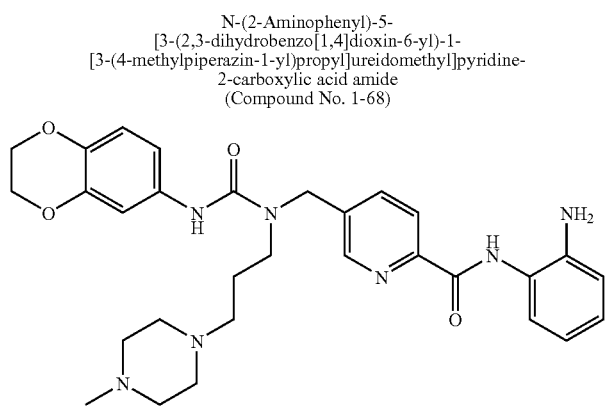 | $^1$H-NMR (400 MHz, DMSO-$d_6$) δ 1.69 (m, 2H), 2.12 (s, 3H), 2.28 (t, J = 6.6 Hz, 2H), 2.32 (br s, 8H), 3.33 (m, 2H), 4.17-4.21 (m, 4H), 4.65 (s, 2H), 4.89 (s, 2H), 6.65 (t, J = 7.6 Hz, 1H), 6.73 (d, J = 8.7 Hz, 1H), 6.82 (dd, J = 7.6, 1.4 Hz, 1H), 6.87 (dd, J = 8.7, 2.4 Hz, 1H), 6.95 (td, J = 7.6, 1.4 Hz, 1H), 7.05 (d, J = 2.4 Hz, 1H), 7.50 (d, J = 7.6 Hz, 1H), 7.92 (dd, J = 8.1, 2.0 Hz, 1H), 8.12 (d, J = 8.1 Hz, 1H), 8.55 (s, 1H), 8.63 (d, J = 2.0 Hz, 1H), 10.03 (s, 1H) |
| N-(2-Aminophenyl)-5-[3-(3-fluorophenyl)-1-[4-(pyrrolidin-1-yl)butyl]ureidomethyl]pyridine-2-carboxylic acid amide (Compound No. 1-69)<br>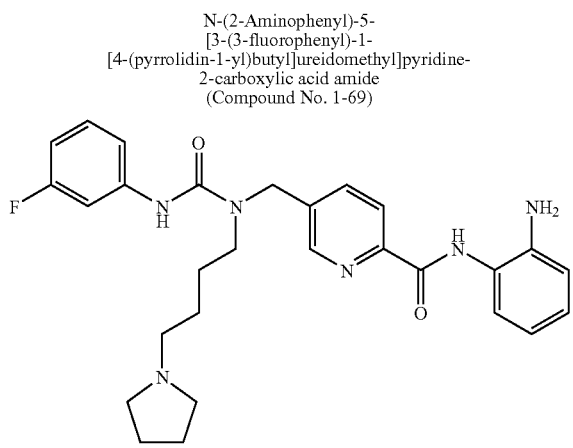 | $^1$H-NMR (400 MHz, DMSO-$d_6$) δ 1.41 (m, 2H), 1.55 (m, 2H), 1.63 (m, 4H), 2.32-2.36 (m, 6H), 3.40 (t, J = 7.3 Hz, 2H), 4.71 (s, 2H), 4.89 (s, 2H), 6.65 (t, J = 7.8 Hz, 1H), 6.76 (m, 1H), 6.82 (d, J = 7.8 Hz, 1H), 6.95 (t, J = 7.8 Hz, 1H), 7.23-7.29 (m, 2H), 7.44-7.53 (m, 2H), 7.93 (dd, J = 8.1, 1.8 Hz, 1H), 8.12 (d, J = 8.1 Hz, 1H), 8.62 (s, 1H), 8.64 (d, J = 1.8 Hz, 1H), 10.03 (s, 1H) |

| | |
|---|---|
| N-(2-Aminophenyl)-5-[3-(3,4-difluorophenyl)-1-[4-(pyrrolidin-1-yl)butyl]ureidomethyl]pyridine-2-carboxylic acid amide (Compound No. 1-70) 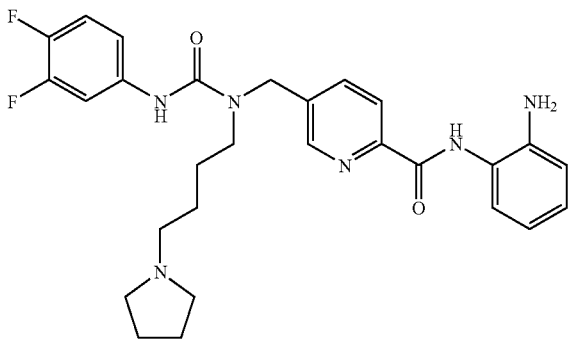 | $^1$H-NMR (500 MHz, DMSO-d$_6$) δ 1.41 (m, 2H), 1.54 (m, 2H), 1.63 (m, 4H), 2.33-2.36 (m, 6H), 3.39 (t, J = 7.3 Hz, 2H), 4.70 (s, 2H), 4.89 (s, 2H), 6.65 (t, J = 7.9 Hz, 1H), 6.83 (d, J = 7.9 Hz, 1H), 6.95 (t, J = 7.9 Hz, 1H), 7.26 (m, 1H), 7.31 (m, 1H), 7.50 (d, J = 7.9 Hz, 1H), 7.65 (m, 1H), 7.93 (dd, J = 8.1, 2.0 Hz, 1H), 8.12 (d, J = 8.1 Hz, 1H), 8.63 (s, 1H), 8.64 (d, J = 2.0 Hz, 1H), 10.03 (s, 1H) |
| N-(2-Aminophenyl)-5-[3-(2,3-dihydrobenzo[1,4]dioxin-6-yl)-1-[4-(pyrrolidin-1-yl)butyl]ureidomethyl]pyridine-2-carboxylic acid amide (Compound No. 1-71) 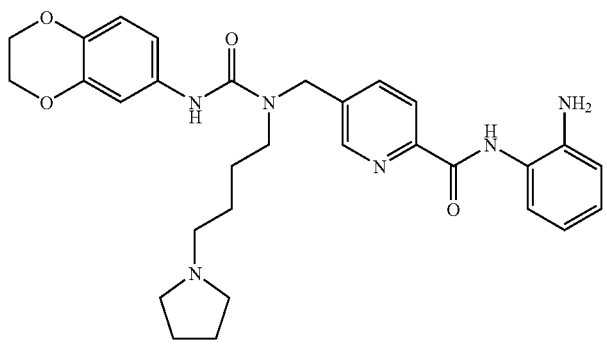 | $^1$H-NMR (500 MHz, DMSO-d$_6$) δ 1.40 (m, 2H), 1.53 (m, 2H), 1.63 (m, 4H), 2.32-2.36 (m, 6H), 3.35 (t, J = 7.5 Hz, 2H), 4.17-4.21 (m, 4H), 4.67 (s, 2H), 4.89 (s, 2H), 6.65 (t, J = 7.8 Hz, 1H), 6.72 (d, J = 8.6 Hz, 1H), 6.82 (d, J = 7.8 Hz, 1H), 6.87 (dd, J = 8.6, 2.4 Hz, 1H), 6.95 (t, J = 7.8 Hz, 1H), 7.04 (d, J = 2.4 Hz, 1H), 7.50 (d, J = 7.8 Hz, 1H), 7.91 (dd, J = 8.1, 2.0 Hz, 1H), 8.11 (d, J = 8.1 Hz, 1H), 8.23 (s, 1H), 8.62 (d, J = 2.0 Hz, 1H), 10.03 (s, 1H) |
| N-(2-Aminophenyl)-5-[1-(2-diethylaminoethyl)-3-(3-fluorophenyl)ureidomethyl]pyridine-2-carboxylic acid amide (Compound No. 1-72) 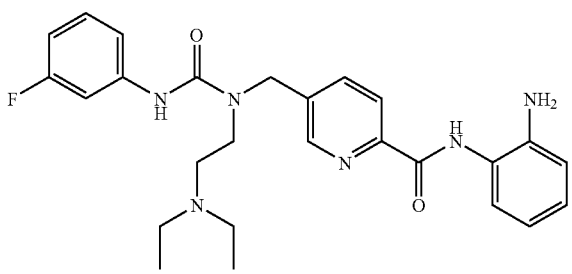 | $^1$H-NMR (400 MHz, DMSO-d$_6$) δ 0.99 (t, J = 7.1 Hz, 6H), 2.57-2.62 (m, 6H), 3.41 (t, J = 4.6 Hz, 2H), 4.67 (s, 2H), 4.90 (s, 2H), 6.66 (td, J = 7.7, 1.1 Hz, 1H), 6.76 (td, J = 8.1, 2.2 Hz, 1H), 6.83 (dd, J = 7.7, 1.1 Hz, 1H), 6.96 (td, J = 7.7, 1.1 Hz, 1H), 7.03 (dd, J = 8.1, 1.1 Hz, 1H), 7.29 (dd, J = 15.4, 8.1 Hz, 1H), 7.39 (dt, J = 12.1, 2.2 Hz, 1H), 7.52 (dd, J = 7.7, 1.1 Hz, 1H), 7.98 (dd, J = 8.1, 1.8 Hz, 1H), 8.13 (d, J = 8.1 Hz, 1H), 8.67 (d, J = 1.8 Hz, 1H), 10.05 (s, 1H), 10.72 (s, 1H) |
| N-(2-Aminophenyl)-5-[1-(2-diethylaminoethyl)-3-(3,4-difluorophenyl)ureidomethyl]pyridine-2-carboxylic acid amide (Compound No. 1-73) 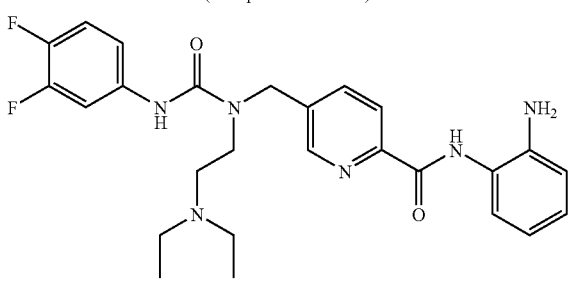 | $^1$H-NMR (400 MHz, DMSO-d$_6$) δ 0.98 (t, J = 7.1 Hz, 6H), 2.56-2.61 (m, 6H), 3.40 (t, J = 4.8 Hz, 2H), 4.67 (s, 2H), 4.90 (s, 2H), 6.66 (td, J = 7.7, 1.3 Hz, 1H), 6.83 (dd, J = 7.7, 1.3 Hz, 1H), 6.96 (td, J = 7.7, 1.3 Hz, 1H), 7.02 (d, J = 9.0 Hz, 1H), 7.32 (m, 1H), 7.52 (dd, J = 7.7, 1.3 Hz, 1H), 7.58 (m, 1H), 7.97 (dd, J = 8.1, 2.0 Hz, 1H), 8.13 (d, J = 8.1 Hz, 1H), 8.67 (d, J = 2.0 Hz, 1H), 10.04 (s, 1H), 10.61 (s, 1H) |

N-(2-Aminophenyl)-5-
[1-(2-diethylaminoethyl)-3-
(2,3-dihydrobenzo[1,4]dioxin-6-yl)ureidomethyl]pyridine-
2-carboxylic acid amide
(Compound No. 1-74)

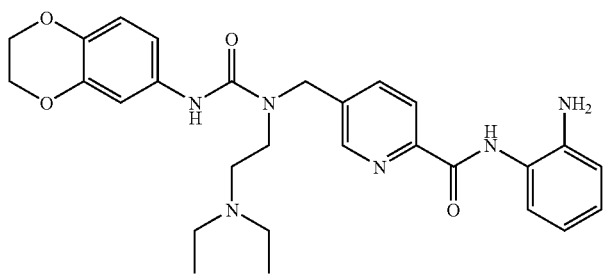

$^1$H-NMR (500 MHz, DMSO-$d_6$)
δ 0.98 (t, J = 7.2 Hz, 6H),
2.54-2.58 (m, 6H), 3.36 (t, J =
4.7 Hz, 2H), 4.17-4.21 (m, 4H),
4.64 (s, 2H), 4.90 (s, 2H), 6.65
(td, J = 7.9, 1.2 Hz, 1H),
6.73-6.74 (m, 2H), 6.83 (dd, J =
7.9, 1.2 Hz, 1H), 6.94-6.97 (m,
2H), 7.51 (dd, J = 7.9, 1.2 Hz,
1H), 7.95 (dd, J = 8.1, 2.0 Hz,
1H), 8.12 (d, J = 8.1 Hz, 1H),
8.65 (d, J = 2.0 Hz, 1H), 10.04 (s,
1H), 10.15 (s, 1H)

N-(2-Aminophenyl)-5-
[3-(2,3-dihydrobenzo[1,4]dioxin-6-yl)-1-
(4-dimethylaminobutyl)ureidomethyl]pyridine-
2-carboxylic acid amide
(Compound No. 1-75)

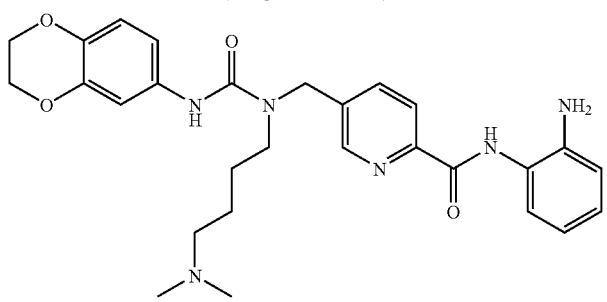

$^1$H-NMR (500 MHz, CDCl$_3$)
δ 1.53 (m, 2H), 1.69 (m, 2H),
2.21 (s, 6H), 2.36 (t, J = 6.4 Hz,
2H), 3.24 (t, J = 8.4 Hz, 2H),
3.96 (s, 2H), 4.23 (s, 4H), 4.68
(s, 2H), 6.78-6.80 (m, 2H), 6.85
(dd, J = 7.8, 1.5 Hz, 1H), 6.86
(td, J = 7.8, 1.5 Hz, 1H), 6.91
(dd, J = 1.8, 0.9 Hz, 1H), 7.09
(td, J = 7.8, 1.5 Hz, 1H), 7.49
(dd, J = 7.8, 1.5 Hz, 1H), 7.87 (s,
1H), 7.89 (dd, J = 8.0, 2.1 Hz,
1H), 8.24 (d, J = 8.0 Hz, 1H),
8.58 (d, J = 2.1 Hz, 1H), 9.83 (s,
1H)

N-(2-Aminophenyl)-5-
[1-(4-dimethylaminobutyl)-3-
(4-dimethylaminophenyl)ureidomethyl]pyridine-
2-carboxylic acid amide
(Compound No. 1-76)

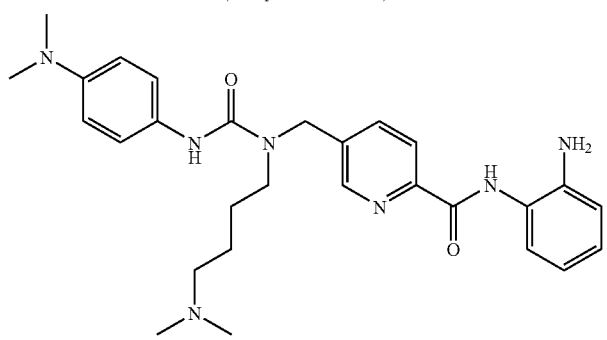

$^1$H-NMR (400 MHz, CDCl$_3$)
δ 1.53 (m, 2H), 1.68 (m, 2H),
2.22 (s, 6H), 2.37 (t, J = 6.6 Hz,
2H), 2.91 (s, 6H), 3.26 (t, J = 8.2
Hz, 2H), 3.96 (s, 2H), 4.69 (s,
2H), 6.72 (d, J = 9.0 Hz, 2H),
6.85 (dd, J = 7.8, 1.5 Hz, 1H),
6.86 (td, J = 7.8, 1.5 Hz, 1H),
7.09 (td, J = 7.8, 1.5 Hz, 1H),
7.18 (d, J = 9.0 Hz, 2H), 7.48
(dd, J = 7.8, 1.5 Hz, 1H), 7.79 (s,
1H), 7.90 (dd, J = 8.0, 2.1 Hz,
1H), 8.24 (dd, J = 8.0, 0.7 Hz,
1H), 8.58 (d, J = 2.1 Hz, 1H),
9.84 (s, 1H)

N-(2-Aminophenyl)-5-
[1-(4-dimethylaminobutyl)-3-
(3-fluorophenyl)ureidomethyl]pyridine-
2-carboxylic acid amide
(Compound No. 1-77)

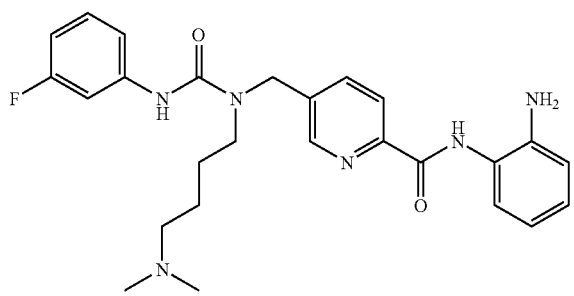

$^1$H-NMR (500 MHz, CDCl$_3$)
δ 1.56 (m, 2H), 1.72 (m, 2H),
2.25 (s, 6H), 2.38 (t, J = 6.4 Hz,
2H), 3.27 (t, J = 8.4 Hz, 2H),
3.96 (s, 2H), 4.70 (s, 2H), 6.76
(tdd, J = 8.2, 2.4, 0.9 Hz, 1H),
6.85 (dd, J = 7.8 Hz, 1H), 6.86
(td, J = 7.8, 1.5 Hz, 1H),
7.06-7.10 (m, 2H), 7.22-7.27 (m,
2H), 7.49 (dd, J = 7.8, 1.5 Hz,
1H), 7.89 (dd, J = 7.9, 2.3 Hz,
1H), 7.96 (s, 1H), 8.26 (d, J = 7.9
Hz, 1H), 8.59 (d, J = 2.3 Hz, 1H),
9.83 (s, 1H)

N-(2-Aminophenyl)-5-
[3-(1,3-benzothiazol-2-yl)-1-
[3-(morpholin-4-yl)propyl]ureidomethyl]pyridine-
2-carboxylic acid amide
(Compound No. 1-78)

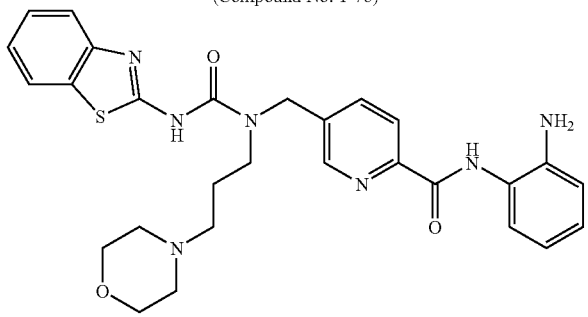

$^1$H-NMR (500 MHz, DMSO-d$_6$)
δ 1.77 (br s, 2H), 2.39 (br s, 6H),
3.46 (br s, 2H), 3.79 (br s, 4H),
4.74 (br s, 2H), 4.89 (br s, 2H),
6.65 (t, J = 7.7 Hz, 1H), 6.82 (d,
J = 7.7 Hz, 1H), 6.95 (t, J = 7.7
Hz, 1H), 7.22 (t, J = 7.0 Hz, 1H),
7.36 (t, J = 7.0 Hz, 1H), 7.50 (d,
J = 7.7 Hz, 1H), 7.60 (br s, 1H),
7.87 (br s, 1H), 7.97 (d, J = 7.8
Hz, 1H), 8.13 (d, J = 7.8 Hz, 1H),
8.69 (s, 1H), 10.03 (br s, 1H)

N-(2-Aminophenyl)-5-
[1-(2-dimethylaminoethyl)-3-
(3-methylphenyl)ureidomethyl]pyridine-
2-carboxylic acid amide
(Compound No. 1-79)

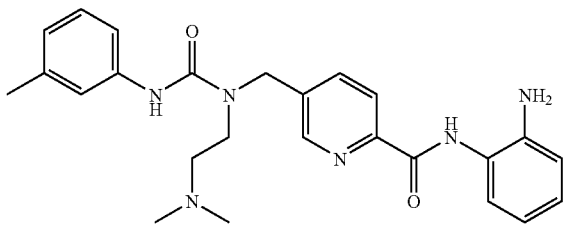

$^1$H-NMR (500 MHz, DMSO-d$_6$)
δ 2.26 (s, 3H), 2.28 (s, 6H), 2.49
(m, 2H), 3.42 (t, J = 4.9 Hz, 2H),
4.66 (s, 2H), 4.90 (s, 2H), 6.65 (t,
J = 7.6 Hz, 1H), 6.75 (d, J = 6.4
Hz, 1H), 6.83 (d, J = 7.6 Hz, 1H),
6.95 (t, J = 7.6 Hz, 1H),
7.11-7.15 (m, 2H), 7.24 (s, 1H),
7.52 (d, J = 7.6 Hz, 1H), 7.96
(dd, J = 7.9, 1.8 Hz, 1H), 8.12 (d,
J = 7.9 Hz, 1H), 8.66 (d, J = 1.8
Hz, 1H), 10.04 (s, 1H), 10.17 (s,
1H)

N-(2-Aminophenyl)-5-
[3-(3-chlorophenyl)-1-
(2-dimethylaminoethyl)ureidomethyl]pyridine-
2-carboxylic acid amide
(Compound No. 1-80)

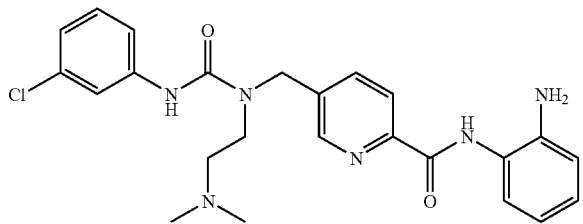

$^1$H-NMR (500 MHz, DMSO-d$_6$)
δ 2.28 (s, 6H), 2.50 (m, 2H), 3.44
(m, 2H), 4.67 (s, 2H), 4.90 (s,
2H), 6.65 (t, J = 7.6 Hz, 1H),
6.83 (d, J = 7.9 Hz, 1H),
6.94-6.99 (m, 2H), 7.19 (d, J =
7.6 Hz, 1H), 7.27 (t, J = 7.6 Hz,
1H), 7.51 (d, J = 7.6 Hz, 1H),
7.66 (s, 1H), 7.97 (d, J = 7.9 Hz,
1H), 8.12 (d, J = 7.9 Hz, 1H),
8.66 (s, 1H), 10.04 (s, 1H), 10.52
(s, 1H)

N-(2-Aminophenyl)-5-
[1-(2-dimethylaminoethyl)-3-
(pyridin-3-yl)ureidomethyl]pyridine-
2-carboxylic acid amide
(Compound No. 1-81)

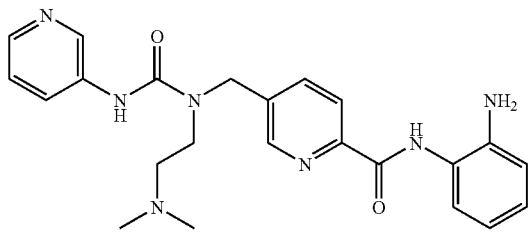

$^1$H-NMR (400 MHz, DMSO-d$_6$)
δ 2.29 (s, 6H), 2.51 (m, 2H), 3.46
(t, J = 4.9 Hz, 2H), 4.69 (s, 2H),
4.90 (s, 2H), 6.65 (t, J = 7.6 Hz,
1H), 6.83 (d, J = 7.6 Hz, 1H),
6.95 (t, J = 7.6 Hz, 1H), 7.29 (dd,
J = 8.3, 4.6 Hz, 1H), 7.51 (d, J =
7.6 Hz, 1H), 7.86 (d, J = 8.3 Hz,
1H), 7.98 (dd, J = 8.1, 2.0 Hz,
1H), 8.13 (d, J = 8.1 Hz, 1H),
8.16 (dd, J = 4.6, 1.2 Hz, 1H),
8.53 (d, J = 2.0 Hz, 1H), 8.67 (d,
J = 1.2 Hz, 1H), 10.04 (s, 1H),
10.56 (s, 1H)

N-(2-Aminophenyl)-5-
[3-(6-fluoro-1,3-benzothiazol-2-yl)-1-
[3-(morpholin-4-yl)propyl]ureidomethyl]pyridine-
2-carboxylic acid amide
(Compound No. 1-82)

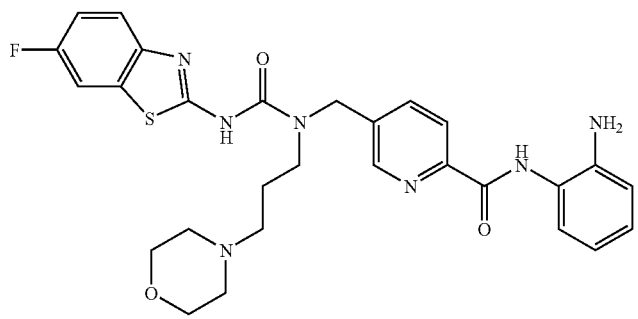

¹H-NMR (500 MHz, DMSO-d₆)
δ 1.77 (br s, 2H), 2.18 (t, J = 7.5 Hz, 2H), 2.40 (br s, 4H), 3.45 (br s, 2H), 3.78 (br s, 4H), 4.74 (s, 2H), 4.89 (br s, 2H), 6.65 (t, J = 7.8 Hz, 1H), 6.82 (dd, J = 7.8, 1.2 Hz, 1H), 6.95 (td, J = 7.8, 1.2 Hz, 1H), 7.21 (t, J = 7.9 Hz, 1H), 7.50 (d, J = 7.8 Hz, 1H), 7.60 (br s, 1H), 7.79 (br s, 1H), 7.97 (d, J = 8.1 Hz, 1H), 8.13 (d, J = 8.1 Hz, 1H), 8.68 (s, 1H), 10.03 (br s, 1H), 11.94 (br s, 1H)

N-(2-Aminophenyl)-5-
[3-(3-chlorophenyl)-1-
(3-dimethylaminopropyl)ureidomethyl]pyridine-
2-carboxylic acid amide
(Compound No. 1-83)

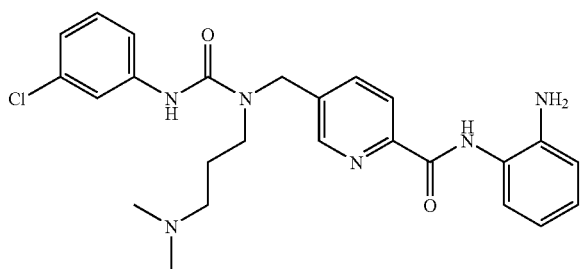

¹H-NMR (400 MHz, DMSO-d₆)
δ 1.72 (m, 2H), 2.20 (s, 6H), 2.28 (t, J = 6.2 Hz, 2H), 3.37 (t, J = 6.1 Hz, 2H), 4.63 (s, 2H), 4.90 (br s, 2H), 6.65 (t, J = 7.8 Hz, 1H), 6.82 (d, J = 7.8 Hz, 1H), 6.95 (t, J = 7.8 Hz, 1H), 6.98 (m, 1H), 7.22 (d, J = 8.4 Hz, 1H), 7.28 (t, J = 8.4 Hz, 1H), 7.51 (d, J = 7.8 Hz, 1H), 7.72 (t, J = 2.0 Hz, 1H), 7.97 (dd, J = 8.1, 1.7 Hz, 1H), 8.12 (d, J = 8.1 Hz, 1H), 8.67 (d, J = 1.7 Hz, 1H), 9.96 (br s, 1H), 10.03 (br s, 1H)

N-(2-Aminophenyl)-5-
[1-(3-dimethylaminopropyl)-3-
(3-methylphenyl)ureidomethyl]pyridine-
2-carboxylic acid amide
(Compound No. 1-84)

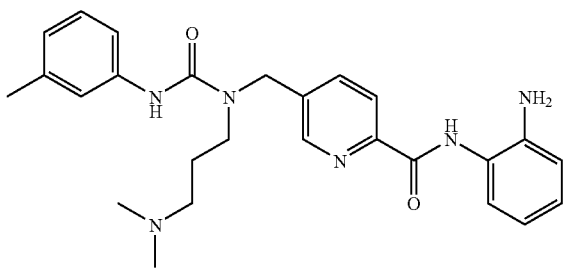

¹H-NMR (400 MHz, DMSO-d₆)
δ 1.72 (m, 2H), 2.21 (s, 6H), 2.26 (s, 3H), 2.29 (m, 2H), 3.36 (t, J = 6.2 Hz, 2H), 4.62 (s, 2H), 4.90 (br s, 2H), 6.65 (t, J = 7.7 Hz, 1H), 6.75 (d, J = 7.7 Hz, 1H), 6.82 (d, J = 7.7 Hz, 1H), 6.95 (t, J = 7.7 Hz, 1H), 7.13 (t, J = 7.7 Hz, 1H) 7.20 (d, J = 7.7 Hz, 1H), 7.28 (s, 1H), 7.51 (d, J = 7.7 Hz, 1H), 7.96 (dd, J = 7.9, 2.0 Hz, 1H), 8.12 (d, J = 7.9 Hz, 1H), 8.67 (d, J = 2.0 Hz, 1H), 9.62 (br s, 1H), 10.03 (br s, 1H)

N-(2-Aminophenyl)-5-
[1-[3-(morpholin-4-yl)propyl]-3-
(pyridin-2-yl)ureidomethyl]pyridine-
2-carboxylic acid amide
(Compound No. 1-85)

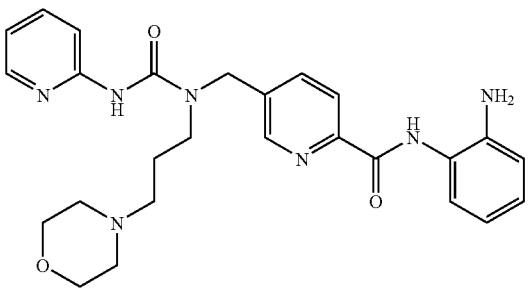

¹H-NMR (400 MHz, CDCl₃)
δ 1.80 (m, 2H), 2.46 (t, J = 6.0 Hz, 2H), 2.51 (br s, 4H), 3.44 (t, J = 5.7 Hz, 2H), 3.59 (br s, 2H), 3.98 (t, J = 4.5 Hz, 4H), 4.66 (s, 2H), 6.83-6.88 (m, 2H), 6.93 (ddd, J = 7.3, 4.9, 1.0 Hz, 1H), 7.09 (td, J = 7.9, 1.5 Hz, 1H), 7.48 (d, J = 7.9 Hz, 1H), 7.63 (ddd, J = 8.5, 7.3, 2.0 Hz, 1H), 7.92 (dd, J = 8.1, 2.2 Hz, 1H), 8.00 (dt, J = 8.5, 1.0 Hz, 1H), 8.22 (ddd, J = 4.9, 2.0, 1.0 Hz, 1H), 8.26 (dd, J = 8.1, 0.5 Hz, 1H), 8.61 (dd, J = 2.2, 0.5 Hz, 1H), 9.83 (s, 2H)

| Compound | NMR |
|---|---|
| N-(2-Aminophenyl)-5-[1-[3-(morpholin-4-yl)propyl]-3-(pyridin-4-yl)ureidomethyl]pyridine-2-carboxylic acid amide (Compound No. 1-86)<br>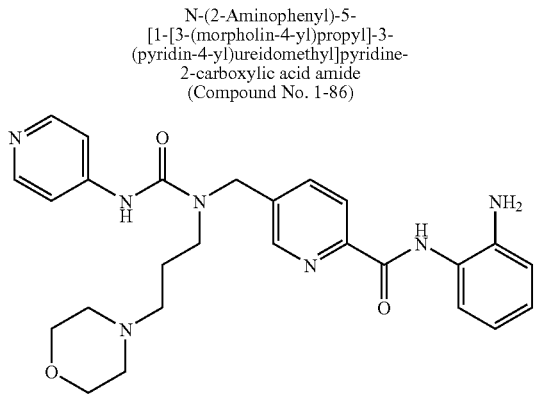 | $^1$H-NMR (400 MHz, CDCl$_3$) δ 1.82 (m, 2H), 2.45-2.55 (m, 6H), 3.40 (t, J = 5.7 Hz, 2H), 3.79 (t, J = 4.8 Hz, 4H), 3.95 (br s, 2H), 4.65 (s, 2H), 6.83-6.89 (m, 2H), 7.09 (td, J = 7.7, 1.5 Hz, 1H), 7.48 (m 1H) 7.49 (d, J = 6.3 Hz, 2H), 7.90 (dd, J = 8.0, 2.2 Hz, 1H), 8.26 (dd, J = 8.0, 0.7 Hz, 1H), 8.47 (d, J = 6.3 Hz, 2H), 8.60 (dd, J = 2.2, 0.7 Hz, 1H), 9.10 (s, 1H), 9.82 (s, 1H) |
| N-(2-Aminophenyl)-5-[3-(4-dimethylaminophenyl)-1-[4-(morpholin-4-yl)butyl]ureidomethyl]pyridine-2-carboxylic acid amide (Compound No. 1-87)<br>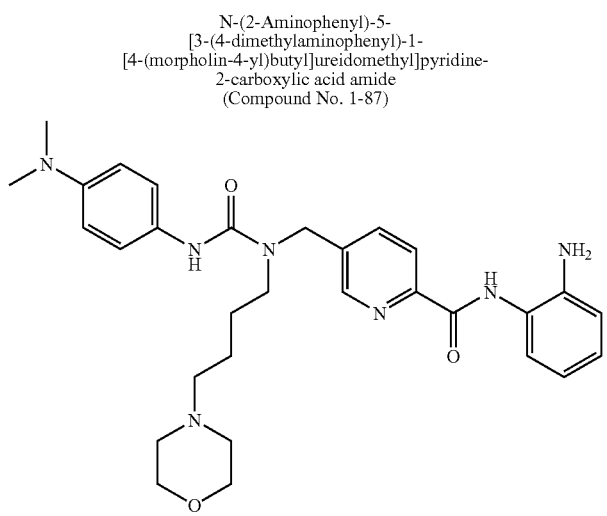 | $^1$H-NMR (500 MHz, CDCl$_3$) δ 1.54 (m, 2H), 1.71 (m, 2H), 2.39 (t, J = 7.0 Hz, 2H), 2.41 (m, 4H), 2.92 (s, 6H), 3.30 (t, J = 7.9 Hz, 2H), 3.63 (t, J = 4.6 Hz, 4H), 3.96 (s, 2H), 4.68 (s, 2H), 6.60 (s, 1H), 6.71 (d, J = 8.9 Hz, 2H), 6.85 (dd, J = 7.9, 1.5 Hz, 1H), 6.86 (td, J = 7.9, 1.5 Hz, 1H), 7.09 (td, J = 7.9, 1.5 Hz, 1H), 7.17 (d, J = 8.9 Hz, 2H), 7.49 (dd, J = 7.9, 1.5 Hz, 1H), 7.89 (dd, J = 8.1, 1.8 Hz, 1H), 8.25 (d, J = 8.1 Hz, 1H), 8.58 (d, J = 1.8 Hz, 1H), 9.83 (s, 1H) |
| N-(2-Aminophenyl)-5-[3-(3-fluorophenyl)-1-[4-(morpholin-4-yl)butyl]ureidomethyl]pyridine-2-carboxylic acid amide (Compound No. 1-88)<br>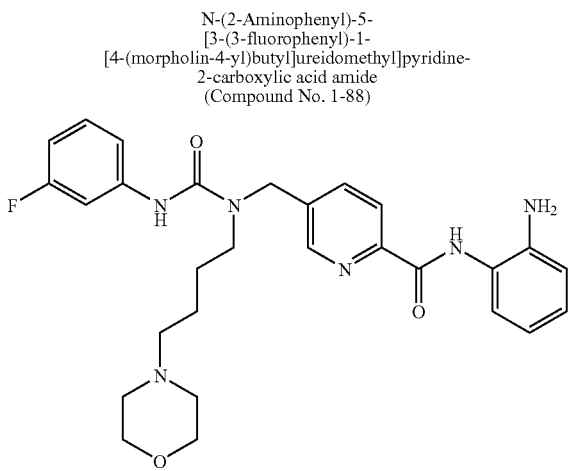 | $^1$H-NMR (400 MHz, CDCl$_3$) δ 1.54 (m, 2H), 1.72 (m, 2H), 2.39 (t, J = 7.0 Hz, 2H), 2.43 (t, J = 4.5 Hz, 4H), 3.34 (t, J = 7.9 Hz, 2H), 3.68 (t, J = 4.5 Hz, 4H) 3.95 (s, 2H), 4.69 (s, 2H), 6.65 (2, 1H), 6.78 (tdd, J = 8.3, 2.3 0.9 Hz, 1H), 6.85 (dd, J = 7.8, 1.5 Hz, 1H), 6.86 (td, J = 7.8, 1.5 Hz, 1H), 7.01 (ddd, J = 8.3, 2.3, 0.9 Hz, 1H), 7.09 (td, J = 7.8, 1.5 Hz, 1H), 7.23 (td, J = 8.3, 6.6 Hz, 1H), 7.32 (dt, J = 11.0, 2.3 Hz, 1H), 7.50 (dd, J = 7.8, 1.5 Hz, 1H), 7.88 (dd, J = 8.0, 1.8 Hz, 1H), 8.27 (d, J = 8.0 Hz, 1H), 8.59 (d, J = 1.8 Hz, 1H), 9.82 (s, 1H) |

| | |
|---|---|
| N-(2-Aminophenyl)-5-[1-[4-(morpholin-4-yl)butyl]-3-(thiophen-3-yl)ureidomethyl]pyridine-2-carboxylic acid amide (Compound No. 1-89) 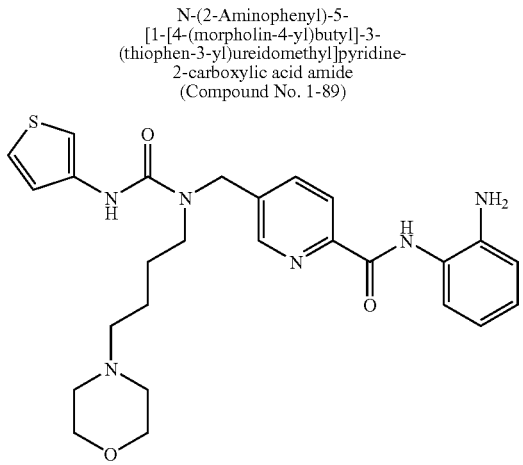 | $^1$H-NMR (400 MHz, CDCl$_3$) δ 1.54 (m, 2H), 1.70 (m, 2H), 2.38 (t, J = 7.0 Hz, 2H), 2.42 (t, J = 4.5 Hz, 4H), 3.31 (t, J = 7.9 Hz, 2H), 3.67 (t, J = 4.5 Hz, 4H), 3.95 (s, 2H), 4.69 (s, 2H), 6.84 (s, 1H), 6.85 (dd, J = 7.8, 1.4 1H), 6.86 (td, J = 7.8, 1.4 Hz, 1H), 6.97(dd, J = 5.1, 1.4 Hz, 1H), 7.09 (td, J = 7.8, 1.4 Hz, 1H), 7.24 (dd, J = 5.1, 3.3 Hz, 1H), 7.28(dd, J = 3.3, 1.4 Hz, 1H), 7.49 (dd, J = 7.8, 1.4 Hz, 1H), 7.87 (dd, J = 8.0, 1.8 Hz, 1H), 8.26 (d, J = 8.0 Hz, 1H), 8.58 (d, J = 1.8 Hz, 1H), 9.82 (s, 1H) |
| N-(2-Aminophenyl)-5-[3-(2,3-dihydrobenzo[1,4]dioxin-6-yl)-1-[4-(morpholin-4-yl)butyl]ureidomethyl]pyridine-2-carboxylic acid amide (Compound No. 1-90) 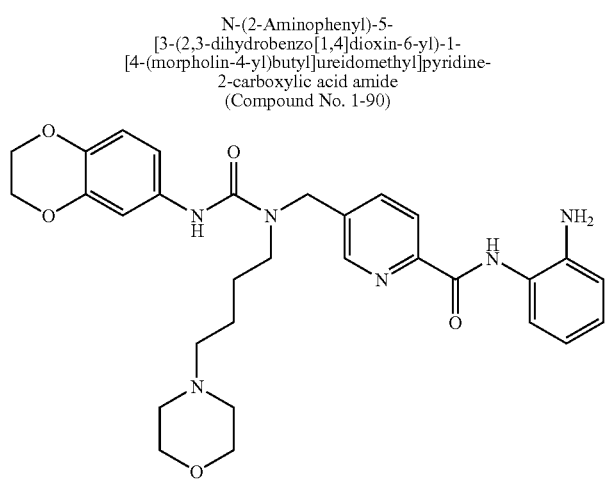 | $^1$H-NMR (400 MHz, CDCl$_3$) δ 1.54 (m, 2H), 1.70 (m, 2H), 2.39 (t, J = 6.8 Hz, 2H), 2.42 (t, J = 4.5 Hz, 4H), 3.30 (t, J = 7.9 Hz, 2H), 3.64 (t, J = 4.5 Hz, 4H), 3.96 (s, 2H), 4.24 (s, 4H), 4.68 (s, 2H), 6.60 (s, 1H), 6.75 (dd, J = 8.5, 2.3 Hz, 1H), 6.80 (d, J = 8.5 Hz, 1H), 6.85 (dd, J = 7.8, 1.5 Hz, 1H), 6.86 (td, J = 7.8, 1.5 Hz, 1H), 6.92 (d, J = 2.3 Hz, 1H), 7.09 (td, J = 7.8, 1.5 Hz, 1H), 7.50 (dd, J = 7.8, 1.5 Hz, 1H), 7.88 (dd, J = 8.0, 1.8 Hz, 1H), 8.26 (d, J = 8.0 Hz, 1H), 8.58 (d, J = 1.8 Hz, 1H), 9.83 (s, 1H) |
| N-(2-Aminophenyl)-5-[1-[4-(morpholin-4-yl)butyl]-3-(pyridin-3-yl)ureidomethyl]pyridine-2-carboxylic acid amide (Compound No. 1-91) 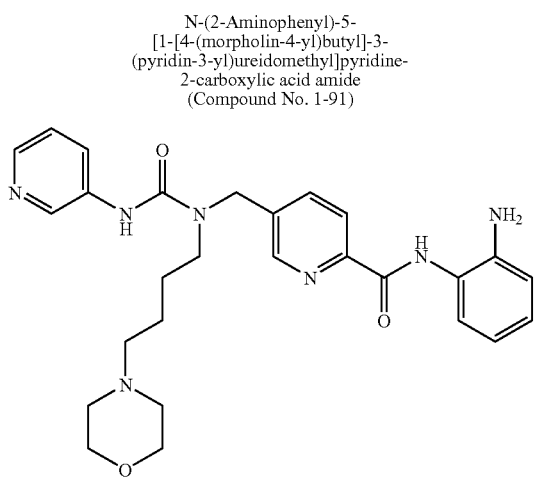 | $^1$H-NMR (500 MHz, CDCl$_3$) δ 1.55 (m, 2H), 1.70 (m, 2H), 2.41 (t, J = 6.9 Hz, 2H), 2.43 (t, J = 4.5 Hz, 4H), 3.36 (t, J = 8.1 Hz, 2H), 3.66 (t, J = 4.5 Hz, 4H), 3.95 (s, 2H), 4.71 (s, 2H), 6.75 (s, 1H), 6.85 (dd, J = 7.8, 1.5 Hz, 1H), 6.86 (td, J = 7.8, 1.5 Hz, 1H), 7.09 (td, J = 7.8, 1.5 Hz, 1H), 7.28 (dd, J = 8.2, 4.2 Hz, 1H), 7.49 (dd, J = 7.8, 1.5 Hz, 1H), 7.88 (dd, J = 7.9, 1.8 Hz, 1H), 7.99 (ddd, J = 8.2, 2.7, 1.5 Hz, 1H), 8.27 (dd, J = 7.9, 0.6 Hz, 1H), 8.34 (dd, J = 4.2, 1.5 Hz, 1H), 8.43 (d, J = 2.7 Hz, 1H), 8.59 (dd, J = 1.8, 0.6 Hz, 1H), 9.82 (s, 1H) |

| | |
|---|---|
| N-(2-Aminophenyl)-5-[1-[4-(morpholin-4-yl)butyl]-3-phenethylureidomethyl]pyridine-2-carboxylic acid amide (Compound No. 1-92) 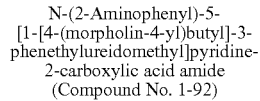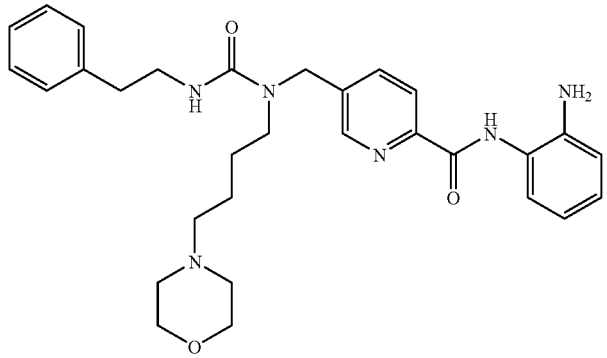 | $^1$H-NMR (400 MHz, CDCl$_3$) δ 1.39 (m, 2H), 1.48 (m, 2H), 2.25 (t, J = 7.0 Hz, 2H), 2.32 (t, J = 4.5 Hz, 4H), 2.86 (t, J = 6.6 Hz, 2H), 3.09 (t, J = 7.8 Hz, 2H), 3.55 (td, J = 6.6, 5.6 Hz, 2H), 3.65 (t, J = 4.5 Hz, 4H), 3.96 (s, 2H), 4.58 (s, 2H), 4.76 (t, J = 5.6 Hz, 1H), 6.86 (dd, J = 7.8, 1.5 Hz, 1H), 6.87 (td, J = 7.8, 1.5 Hz, 1H), 7.09 (td, J = 7.8, 1.5 Hz, 1H), 7.15-7.25 (m, 3H), 7.27-7.32 (m, 2H), 7.50 (dd, J = 7.8, 1.5 Hz, 1H), 7.76 (dd, J = 8.0, 2.0 Hz, 1H), 8.23 (dd, J = 8.0, 0.7 Hz, 1H), 8.49 (dd, J = 2.0, 0.7 Hz, 1H), 9.83 (s, 1H) |
| N-(2-Aminophenyl)-5-[3-(3-methoxyphenyl)-1-[4-(morpholin-4-yl)butyl]ureidomethyl]pyridine-2-carboxylic acid amide (Compound No. 1-93) 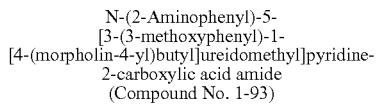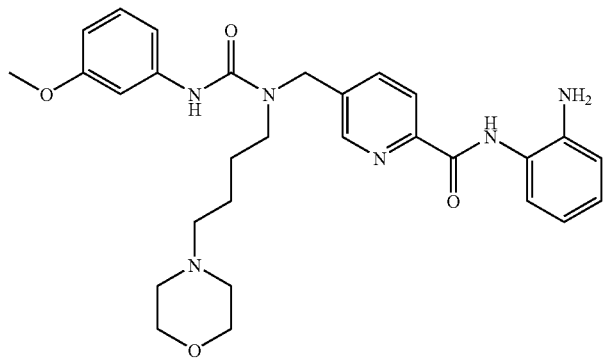 | $^1$H-NMR (400 MHz, CDCl$_3$) δ 1.55 (m, 2H), 1.71 (m, 2H), 2.38 (t, J = 7.1 Hz, 2H), 2.42 (t, J = 4.5 Hz, 4H), 3.33 (t, J = 7.8 Hz, 2H), 3.67 (t, J = 4.5 Hz, 4H), 3.81 (s, 3H), 3.95 (s, 2H), 4.70 (s, 2H), 6.59 (s, 1H), 6.64 (ddd, J = 8.3, 2.6, 0.9 Hz, 1H), 6.84 (m, 1H), 6.85 (d, J = 7.8 Hz, 1H), 6.86 (t, J = 7.8 Hz, 1H), 7.08 (t, J = 7.8 Hz, 1H ), 7.11 (m, 1H), 7.20 (t, J = 8.2 Hz, 1H), 7.50 (d, J = 7.8 Hz, 1H), 7.88 (dd, J = 8.0, 2.2 Hz, 1H), 8.27 (dd, J = 8.0, 0.7 Hz, 1H), 8.58 (dd, J = 2.2, 0.7 Hz, 1H), 9.82 (s, 1H) |
| N-(2-Aminophenyl)-5-[3-(1,3-benzothiazol-2-yl)-1-(2-dimethylaminoethyl)ureidomethyl]pyridine-2-carboxylic acid amide (Compound No. 1-94) 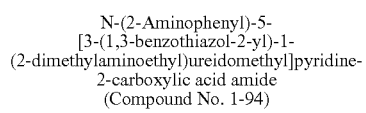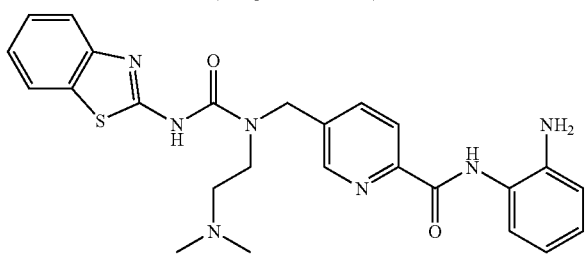 | $^1$H-NMR (500 MHz, CDCl$_3$) δ 2.48 (s, 6H), 2.58 (t, J = 3.8 Hz, 2H), 3.38 (t, J = 3.8 Hz, 2H), 3.97 (br s, 2H), 4.72 (s, 2H), 6.83-6.87 (m, 2H), 7.08 (t, J = 7.5 Hz, 1H), 7.22 (t, J = 7.5 Hz, 1H), 7.36 (t, J = 7.5 Hz, 1H), 7.49 (d, J = 7.5 Hz, 1H), 7.70 (d, J = 7.5 Hz, 1H), 7.76 (d, J = 7.5 Hz, 1H), 7.90 (d, J = 7.9 Hz, 1H), 8.26 (d, J = 7.9 Hz, 1H), 8.58 (s, 1H), 9.82 (s, 1H) |
| N-(2-Aminophenyl)-5-[1-(2-dimethylaminoethyl)-3-(quinolin-6-yl)ureidomethyl]pyridine-2-carboxylic acid amide (Compound No. 1-95) 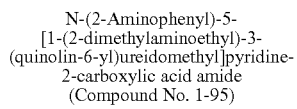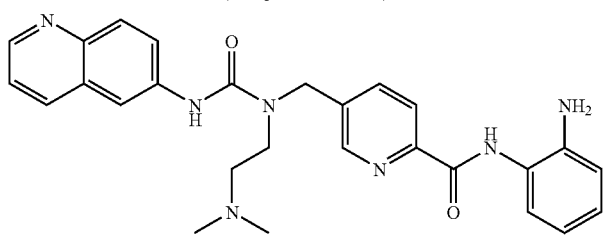 | $^1$H-NMR (500 MHz, CDCl$_3$) δ 2.46 (s, 6H), 2.59 (t, J = 4.1 Hz, 2H), 3.39 (t, J = 4.1 Hz, 2H), 3.97 (br s, 2H), 4.70 (s, 2H), 6.83-6.87 (m, 2H), 7.08 (m, 1H), 7.34 (dd, J = 7.9, 4.3 Hz, 1H), 7.39 (dd, J = 9.0, 2.4 Hz, 1H), 7.50 (d, J = 7.0 Hz, 1H), 7.93 (dd, J = 7.9, 1.8 Hz, 1H), 8.01 (d, J = 9.0 Hz, 1H), 8.09 (d, J = 7.9 Hz, 1H), 8.18 (d, J = 2.4 Hz, 1H), 8.27 (d, J = 7.9 Hz, 1H), 8.61 (d, J = 1.8 Hz, 1H), 8.77 (d, J = 4.3 Hz, 1H), 9.84 (s, 1H), 11.50 (s, 1H) |

| Compound | ¹H-NMR |
|---|---|
| N-(2-Aminophenyl)-5-[1-(2-dimethylaminoethyl)-3-(1,3-thiazol-2-yl)ureidomethyl]pyridine-2-carboxylic acid amide (Compound No. 1-96) 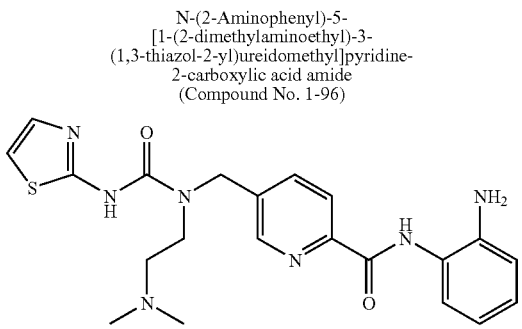 | ¹H-NMR (500 MHz, CDCl₃) δ 2.45 (s, 6H), 2.56 (t, J = 4.3 Hz, 2H), 3.36 (t, J = 4.3 Hz, 2H), 3.96 (s, 2H), 4.71 (s, 2H), 6.84-6.88 (m, 3H), 7.09 (m, 1H), 7.39 (d, J = 3.7 Hz, 1H), 7.49 (d, J = 7.9 Hz, 1H), 7.89 (dd, J = 8.1, 1.8 Hz, 1H), 8.26 (d, J = 8.1 Hz, 1H), 8.58 (d, J = 1.8 Hz, 1H), 9.82 (s, 1H) |
| N-(2-Aminophenyl)-5-[1-(2-dimethylaminoethyl)-3-phenylcarbonylmethylureidomethyl]pyridine-2-carboxylic acid amide (Compound No. 1-97) 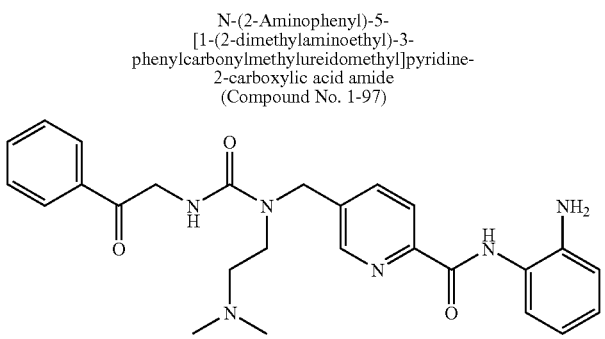 | ¹H-NMR (500 MHz, CDCl₃) δ 2.34 (s, 6H), 2.50 (t, J = 5.0 Hz, 2H), 3.35 (t, J = 5.0 Hz, 2H), 3.96 (br s, 2H), 4.66 (s, 2H), 4.79 (s, 2H), 6.84-6.87 (m, 2H), 7.08 (td, J = 7.6, 1.2 Hz, 1H), 7.47-7.51 (m, 3H) 7.60 (t, J = 7.6 Hz, 1H), 7.87 (dd, J = 8.1, 2.0 Hz, 1H), 7.99-8.01 (m, 2H), 8.25 (d, J = 8.1 Hz, 1H), 8.36 (br s, 1H), 8.56 (d, J = 2.0 Hz, 1H), 9.83 (s, 1H) |
| N-(2-Aminophenyl)-5-[3-(2,3-dihydrobenzo[1,4]dioxin-6-yl)-1-(5-dimethylaminopentyl)ureidomethyl]pyridine-2-carboxylic acid amide (Compound No. 1-98) 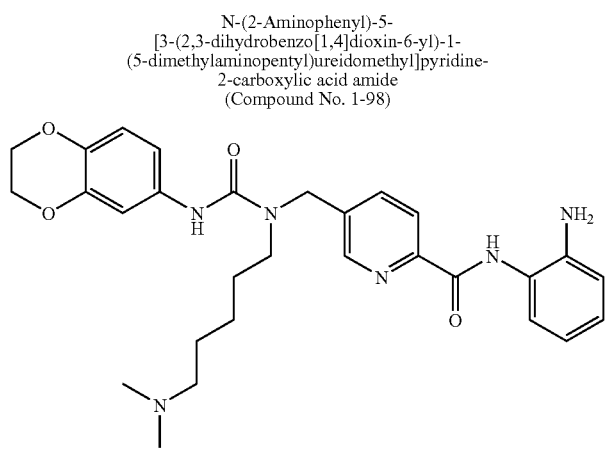 | ¹H-NMR (500 MHz, DMSO-d₆) 1.26 (m, 2H), 1.49-1.58 (m, 4H), 2.09 (s, 6H), 2.54 (m, 2H), 3.35 (t, J = 7.3 Hz, 2H), 4.17-4.20 (m, 4H), 4.69 (s, 2H), 4.89 (s, 2H), 6.65 (t, J = 7.8 Hz, 1H), 6.72 (d, J = 8.8 Hz, 1H), 6.83 (d, J = 7.8 Hz, 1H), 6.89 (dd, J = 8.8, 2.4 Hz, 1H), 6.95 (t, J = 7.8 Hz, 1H), 7.06 (d, J = 2.4 Hz, 1H), 7.50 (d, J = 7.8 Hz, 1H), 7.91 (dd, J = 8.1, 1.8 Hz, 1H), 8.12 (d, J = 8.1 Hz, 1H), 8.30 (s, 1H), 8.63 (d, J = 1.8 Hz, 1H), 10.03 (s, 1H) |
| N-(2-Aminophenyl)-5-[1-(5-dimethylaminopentyl)-3-(3-fluorophenyl)ureidomethyl]pyridine-2-carboxylic acid amide (Compound No. 1-99) 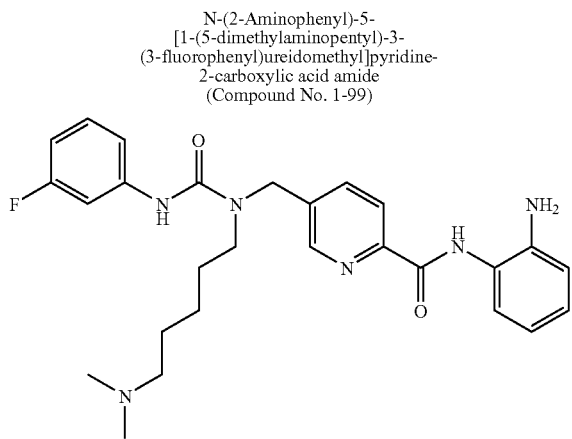 | ¹H-NMR (400 MHz, CDCl₃) 1.39 (m, 2H), 1.52 (m, 2H), 1.68 (m, 2H), 2.21 (s, 6H), 2.27 (t, J = 7.1 Hz, 2H), 3.31 (t, J = 7.8 Hz, 2H), 3.96 (s, 2H), 4.69 (s, 2H), 6.73 (s, 1H), 6.76 (tdd, J = 8.3, 2.4, 0.9 Hz, 1H), 6.85 (dd, J = 7.7, 1.5 Hz, 1H), 6.86 (td, J = 7.7, 1.5 Hz, 1H), 7.04 (ddd, J = 8.3, 2.4, 0.9 Hz, 1H), 7.09 (td, J = 7.7, 1.5 Hz, 1H), 7.23 (td, J = 8.3, 6.5 Hz, 1H), 7.35 (dt, J = 11.1, 2.4 Hz, 1H), 7.50 (dd, J = 7.7, 1.5 Hz, 1H), 7.87 (dd, J = 8.1, 2.2 Hz, 1H), 8.26 (dd, J = 8.1, 0.7 Hz, 1H), 8.58 (dd, J = 2.2, 0.7 Hz, 1H), 9.82 (s, 1H) |

N-(2-Aminophenyl)-5-
[1-(3-dimethylaminopropyl)-3-
(4,5,6,7-tetrahydro-1,3-benzothiazol-2-yl)ureidomethyl]pyridine-
2-carboxylic acid amide
(Compound No. 1-100)

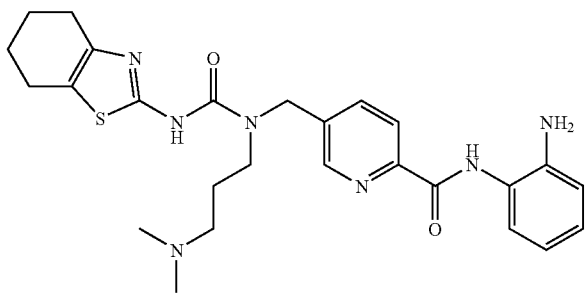

¹H-NMR (400 MHz, DMSO-d₆)
δ 1.70 (m, 2H), 1.74 (br s, 4H),
2.21 (s, 6H), 2.29 (br s, 4H), 2.55
(br s, 2H), 3.35 (m, 2H), 4.66 (s,
2H), 4.90 (br s, 2H), 6.65 (td, J =
7.7, 1.3 Hz, 1H), 6.82 (dd, J =
7.7, 1.3 Hz, 1H), 6.95 (td, J =
7.7, 1.3 Hz, 1H), 7.50 (dd, J =
7.7, 1.3 Hz, 1H), 7.93 (dd, J =
8.0, 2.1 Hz, 1H), 8.11 (d, J = 8.0
Hz, 1H), 8.65 (d, J = 2.1 Hz, 1H),
10.03 (br s, 1H), 12.36 (br s, 1H)

N-(2-Aminophenyl)-5-
[1-(3-dimethylaminopropyl)-3-
(pyridin-3-yl)ureidomethyl]pyridine-
2-carboxylic acid amide
(Compound No. 1-101)

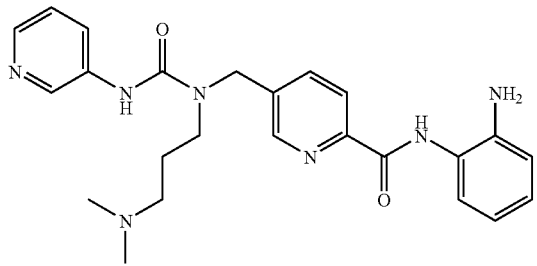

¹H-NMR (500 MHz, DMSO-d₆)
δ 1.75 (m, 2H), 2.26 (s, 6H), 2.36
(m, 2H), 3.39 (t, J = 6.3 Hz, 2H),
4.66 (s, 2H), 4.89 (br s, 2H), 6.65
(td, J = 7.8, 1.2 Hz, 1H), 6.82
(dd, J = 7.8, 1.2 Hz, 1H), 6.95
(td, J = 7.8, 1.2 Hz, 1H), 7.29
(dd, J = 8.4, 4.6 Hz, 1H), 7.51
(dd, J = 7.8, 1.2 Hz, 1H), 7.91
(ddd, J = 8.4, 2.4, 1.5 Hz, 1H),
7.98 (dd, J = 7.9, 2.0 Hz, 1H),
8.13 (d, J = 7.9 Hz, 1H), 8.16
(dd, J = 4.6, 1.5 Hz, 1H), 8.59 (d,
J = 2.4 Hz, 1H), 8.67 (d, J = 2.0
Hz, 1H), 9.86 (br s, 1H), 10.03
(br s, 1H)

N-(2-Aminophenyl)-5-
[1-(3-dimethylaminopropyl)-3-
(3-nitrophenyl)ureidomethyl]pyridine-
2-carboxylic acid amide
(Compound No. 1-102)

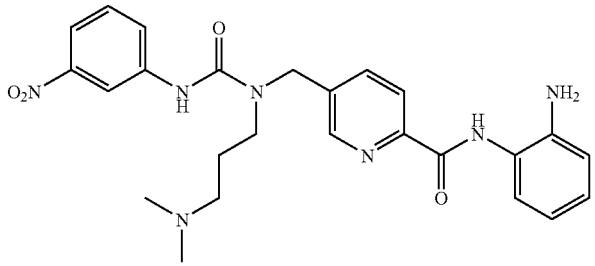

¹H-NMR (400 MHz, DMSO-d₆)
δ 1.74 (m, 2H), 2.22 (s, 6H), 2.30
(t, J = 6.2 Hz, 2H), 3.41 (t, J =
6.2 Hz, 2H), 4.67 (s, 2H), 4.90
(br s, 2H), 6.65 (t, J = 7.7 Hz,
1H), 6.82 (d, J = 7.7 Hz, 1H),
6.95 (t, J = 7.7 Hz, 1H), 7.50 (d,
J = 7.7 Hz, 1H), 7.55 (t, J = 8.2
Hz, 1H), 7.72 (m, 1H), 7.80 (m,
1H), 7.98 (dd, J = 8.1, 1.8 Hz,
1H), 8.13 (d, J = 8.1 Hz, 1H),
8.55 (t, J = 2.2 Hz, 1H), 8.69 (d,
J = 1.8 Hz, 1H), 10.04 (br s, 1H),
10.28 (br s, 1H)

5-[3-(3-Acetylphenyl)-1-
(3-dimethylaminopropyl)ureidomethyl]-
N-(2-aminophenyl)pyridine-
2-carboxylic acid amide
(Compound No. 1-103)

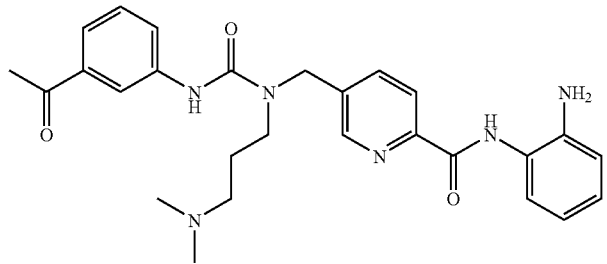

¹H-NMR (500 MHz, DMSO-d₆)
δ 1.73 (m, 2H), 2.21 (s, 6H), 2.30
(t, J = 6.3 Hz, 2H), 2.56 (s, 3H),
3.39 (t, J = 6.3 Hz, 2H), 4.66 (s,
2H), 4.89 (br s, 2H), 6.65 (t, J =
7.8 Hz, 1H), 6.82 (d, J = 7.8 Hz,
1H), 6.95 (t, J = 7.8 Hz, 1H),
7.41 (t, J = 7.7 Hz, 1H), 7.51 (d,
J = 7.8 Hz, 1H), 7.56 (d, J = 7.7
Hz, 1H), 7.70 (d, J = 7.7 Hz, 1H),
7.97 (dd, J = 8.0, 2.0 Hz, 1H),
8.03 (s, 1H), 8.12 (d, J = 8.0 Hz,
1H), 8.68 (d, J = 2.0 Hz, 1H),
9.90 (br s, 1H), 10.03 (br s, 1H)

N-(2-Aminophenyl)-5-
[1-(3-dimethylaminopropyl)-3-
(3-methylthiophenyl)ureidomethyl]pyridine-
2-carboxylic acid amide
(Compound No. 1-104)

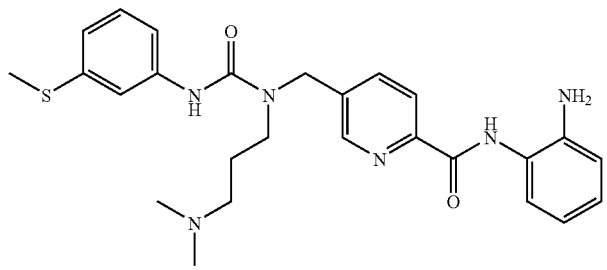

¹H-NMR (400 MHz, DMSO-$d_6$)
δ 1.72 (m, 2H), 2.20 (s, 6H), 2.28 (t, J = 6.1 Hz, 2H), 2.45 (s, 3H), 3.36 (t, J = 6.0 Hz, 2H), 4.63 (s, 2H), 4.90 (br s, 2H), 6.65 (t, J = 7.9 Hz, 1H), 6.81-6.84 (m, 2H), 6.95 (t, J = 7.9 Hz, 1H), 7.15 (d, J = 8.1 Hz, 1H), 7.20 (t, J = 8.1 Hz, 1H), 7.45 (s, 1H), 7.51 (d, J = 7.9 Hz, 1H), 7.96 (dd, J = 8.1, 1.7 Hz, 1H), 8.12 (d, J = 8.1 Hz, 1H), 8.67 (s, 1H), 9.77 (br s, 1H), 10.03 (br s, 1H)

N-(2-Aminophenyl)-5-
[1-[3-(morpholin-4-yl)propyl]-3-
[6-(morpholin-4-yl)pyridin-3-yl]ureidomethyl]pyridine-
2-carboxylic acid amide
(Compound No. 1-105)

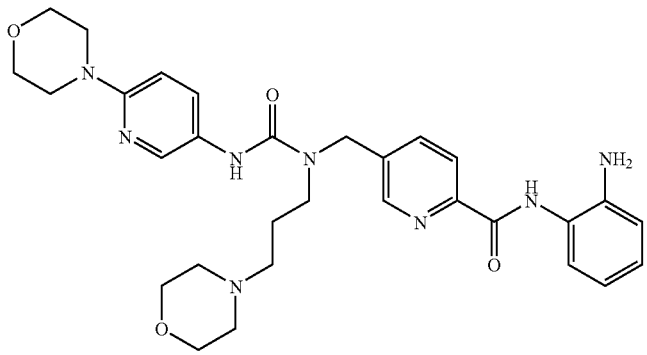

¹H-NMR (500 MHz, CDCl₃)
δ 1.77 (m, 2H), 2.44 (br s, 4H), 2.49 (t, J = 6.0 Hz, 2H), 3.39 (t, J = 5.5 Hz, 2H), 3.45 (t, J = 4.9 Hz, 4H), 3.60 (t, J = 4.3 Hz, 4H), 3.83 (t, J = 4.9 Hz, 4H), 3.92 (br s, 2H), 4.62 (s, 2H), 6.65 (d, J = 8.9 Hz, 1H), 6.82-6.87 (m, 2H), 7.07 (td, J = 7.7, 1.3 Hz, 1H), 7.48 (dd, J = 7.7, 1.3 Hz, 1H), 7.70 (dd, J = 8.9, 2.6 Hz, 1H), 7.90 (dd, J = 7.9, 2.1 Hz, 1H), 8.11 (d, J = 2.6 Hz, 1H), 8.22 (dd, J = 7.9, 0.6 Hz, 1H), 8.57 (dd, J = 2.1, 0.6 Hz, 1H), 9.18 (s, 1H), 9.82 (s, 1H)

N-(2-Aminophenyl)-5-
[3-(3-fluorophenyl)-1-
[3-(morpholin-4-yl)propyl]ureidomethyl]pyridine-
2-carboxylic acid amide
(Compound No. 1-106)

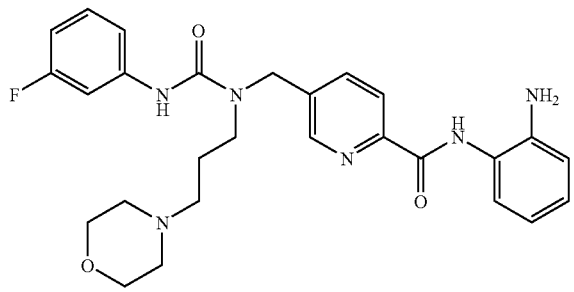

¹H-NMR (400 MHz, CDCl₃)
δ 1.80 (m, 2H), 2.44-2.52 (m, 6H), 3.39 (t, J = 5.7 Hz, 2H), 3.71 (t, J = 4.8 Hz, 4H), 3.96 (br s, 2H), 4.65 (s, 2H), 6.78 (tdd, J = 8.3, 2.6, 0.9 Hz, 1H), 6.83-6.88 (m, 2H), 7.09 (td, J = 7.8, 1.5 Hz, 1H), 7.13 (ddd, J = 8.3, 2.2, 1.0 Hz, 1H), 7.26 (m, 1H), 7.41 (dt, J = 11.1, 2.2 Hz, 1H), 7.48 (d, J = 7.8 Hz, 1H), 7.91 (dd, J = 8.1, 2.2 Hz, 1H), 8.24 (dd, J = 8.1, 0.6 Hz, 1H), 8.59 (dd, J = 2.2, 0.6 Hz, 1H), 9.04 (s, 1H), 9.82 (s, 1H)

N-(2-Aminophenyl)-5-
[3-(3-fluoro-4-methylphenyl)-1-
[3-(morpholin-4-yl)propyl]ureidomethyl]pyridine-
2-carboxylic acid amide
(Compound No. 1-107)

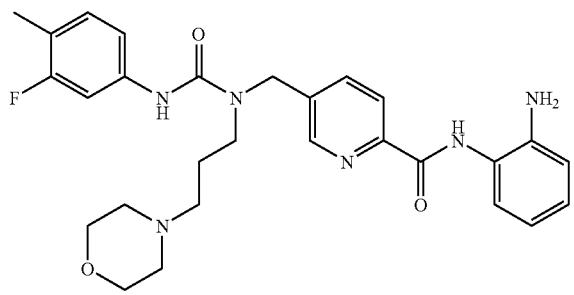

¹H-NMR (400 MHz, CDCl₃)
δ 1.78 (m, 2H), 2.23 (d, J = 1.7 Hz, 3H), 2.43-2.50 (m, 6H), 3.38 (t, J = 5.6 Hz, 2H), 3.69 (t, J = 4.6 Hz, 4H), 3.95 (br s, 2H), 4.64 (s, 2H), 6.83-6.89 (m, 2H), 7.02 (dd, J = 8.2, 2.1 Hz, 1H), 7.06-7.13 (m, 2H), 7.31 (dd, J = 11.5, 2.1 Hz, 1H), 7.48 (d, J = 7.8 Hz, 1H), 7.91 (dd, J = 8.0, 2.1 Hz, 1H), 8.24 (dd, J = 8.0, 0.7 Hz, 1H), 8.59 (dd, J = 2.1, 0.7 Hz, 1H), 9.01 (s, 1H), 9.83 (s, 1H)

N-(2-Aminophenyl)-5-
[1-[3-(morpholin-4-yl)propyl]-3-
(thiophen-3-yl)ureidomethyl]pyridine-
2-carboxylic acid amide
(Compound No. 1-108)

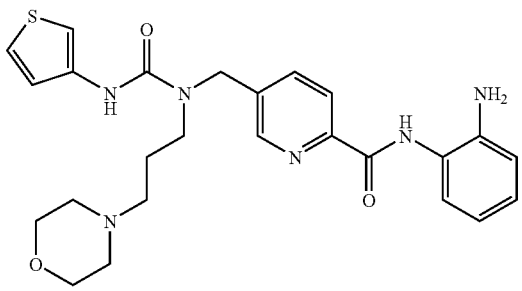

$^1$H-NMR (400 MHz, CDCl$_3$)
δ 1.78 (m, 2H), 2.42-2.51 (m,
6H), 3.37 (t, J = 5.6 Hz, 2H),
3.72 (t, J = 4.6 Hz, 4H), 3.95 (br
s, 2H), 4.65 (s, 2H), 6.83-6.88
(m, 2H), 7.09 (td, J = 7.8, 1.5 Hz,
1H), 7.10 (dd, J = 5.2, 1.5 Hz,
1H), 7.25 (dd, J = 5.2, 3.2 Hz,
1H), 7.31 (dd, J = 3.2, 1.5 Hz,
1H), 7.48 (d, J = 7.8 Hz, 1H),
7.91 (dd, J = 8.0, 2.1 Hz, 1H),
8.24 (dd, J = 8.0, 0.5 Hz, 1H),
8.58 (dd, J = 2.1, 0.5 Hz, 1H),
9.25 (s, 1H), 9.83 (s, 1H)

N-(2-Aminophenyl)-5-
[3-(4-methoxyphenyl)-1-
[4-(morpholin-4-yl)butyl]ureidomethyl]pyridine-
2-carboxylic acid amide
(Compound No. 1-109)

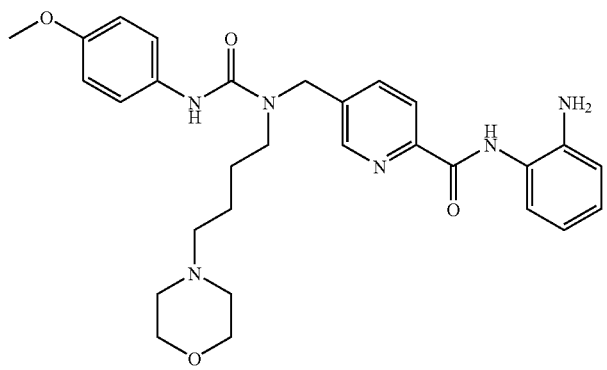

$^1$H-NMR (400 MHz, CDCl$_3$)
δ 1.55 (m, 2H), 1.71 (m, 2H),
2.39 (t, J = 6.8 Hz, 2H), 2.41 (t,
J = 4.6 Hz, 4H), 3.32 (t, J = 8.1
Hz, 2H), 3.63 (t, J = 4.6 Hz, 4H),
3.80 (s, 3H), 3.96 (s, 2H), 4.69
(s, 2H), 6.67 (s, 1H), 6.86 (t, J =
7.6 Hz, 1H), 6.87 (m, 1H), 6.87
(d, J = 9.0 Hz, 2H), 7.09 (td, J =
7.6, 1.3 Hz, 1H), 7.24 (d, J = 9.0
Hz, 2H), 7.49 (dd, J = 7.6, 1.3
Hz, 1H), 7.89 (dd, J = 8.0, 2.1
Hz, 1H), 8.26 (dd, J = 8.0, 0.7
Hz, 1H), 8.58 (dd, J = 2.1, 0.7
Hz, 1H), 9.83 (s, 1H)

N-(2-Aminophenyl)-5-
[3-(4-methylphenyl)-1-
[4-(morpholin-4-yl)butyl]ureidomethyl]pyridine-
2-carboxylic acid amide
(Compound No. 1-110)

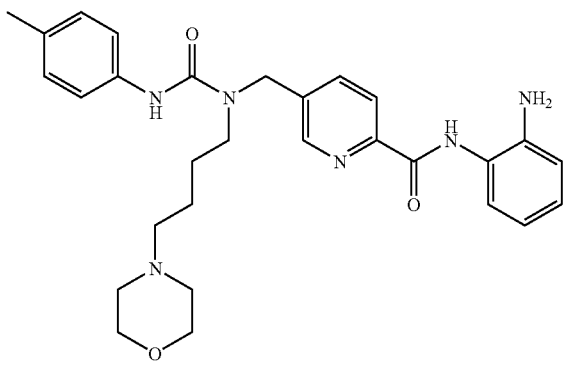

$^1$H-NMR (400 MHz, CDCl$_3$)
δ 1.55 (m, 2H), 1.71 (m, 2H),
2.31 (s, 3H), 2.39 (t, J = 6.0 Hz,
2H), 2.42 (t, J = 4.6 Hz, 4H),
3.32 (t, J = 7.9 Hz, 2H), 3.65 (t,
J = 4.6 Hz, 4H), 3.96 (s, 2H),
4.69 (s, 2H), 6.60 (s, 1H), 6.86
(d, J = 7.7 Hz, 1H), 6.87 (t, J =
7.7 Hz, 1H), 7.09 (t, J = 7.7 Hz,
1H), 7.12 (d, J = 8.4 Hz, 2H),
7.23 (d, J = 8.4 Hz, 2H), 7.50 (d,
J = 7.7 Hz, 1H), 7.89 (dd, J =
8.1, 2.2 Hz, 1H), 8.26 (dd, J =
8.1, 0.7 Hz, 1H), 8.58 (dd, J =
2.2, 0.7 Hz, 1H), 9.83 (s, 1H)

N-(2-Aminophenyl)-5-
[3-(3,4-dimethoxyphenyl)-1-
[4-(morpholin-4-yl)butyl]ureidomethyl]pyridine-
2-carboxylic acid amide
(Compound No. 1-111)

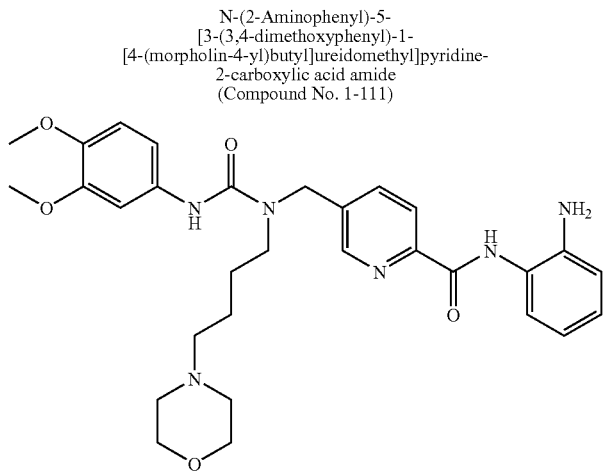

$^1$H-NMR (500 MHz, CDCl$_3$)
δ 1.54 (m, 2H), 1.72 (m, 2H),
2.39 (t, J = 7.0 Hz, 2H), 2.42 (t,
J = 4.6 Hz, 4H), 3.32 (t, J = 8.1
Hz, 2H), 3.64 (t, J = 4.6 Hz, 4H),
3.86 (s, 3H), 3.90 (s, 3H), 3.95
(s, 2H), 4.70 (s, 2H), 6.64 (s,
1H), 6.71 (dd, J = 8.6, 2.4 Hz,
1H), 6.80 (d, J = 8.6 Hz, 1H),
6.85 (dd, J = 7.8, 1.2 Hz, 1H),
6.88 (td, J = 7.8, 1.2 Hz, 1H),
7.09 (td, J = 7.8, 1.2 Hz, 1H),
7.14 (d, J = 2.4 Hz, 1H), 7.48
(dd, J = 7.8, 1.2 Hz, 1H), 7.89
(dd, J = 8.1, 1.9 Hz, 1H), 8.27 (d,
J = 8.1 Hz, 1H), 8.59 (d, J = 1.9
Hz, 1H), 9.82 (s, 1H)

N-(2-Aminophenyl)-5-
[3-(3-ethoxyphenyl)-1-
[4-(morpholin-4-yl)butyl]ureidomethyl]pyridine-
2-carboxylic acid amide
(Compound No. 1-112)

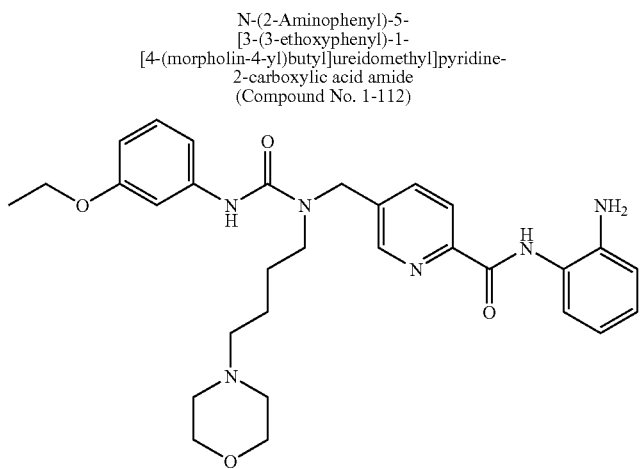

$^1$H-NMR (500 MHz, CDCl$_3$)
δ 1.39 (t, J = 7.0 Hz, 3H), 1.54
(m, 2H), 1.71 (m, 2H), 2.38 (t, J =
7.0 Hz, 2H), 2.42 (m, 4H), 3.33
(t, J = 7.8 Hz, 2H), 3.68 (t, J =
4.6 Hz, 4H), 3.95 (s, 2H), 4.04
(q, J = 7.0 Hz, 2H), 4.70 (s, 2H),
6.57 (s, 1H), 6.63 (dd, J = 8.2,
2.4 Hz, 1H), 6.81-6.88 (m, 3H),
7.07-7.10 (m, 2H), 7.19 (t, J =
7.8 Hz, 1H), 7.49 (d, J = 7.8 Hz,
1H), 7.88 (dd, J = 7.9, 2.1 Hz,
1H), 8.27 (d, J = 7.9 Hz, 1H),
8.59 (d, J = 2.1 Hz, 1H), 9.82 (s,
1H)

N-(2-Aminophenyl)-5-
[3-(3-methoxyphenyl)-1-
[4-(morpholin-4-yl)butyl]ureidomethyl]pyridine-
2-carboxylic acid amide
(Compound No. 1-113)

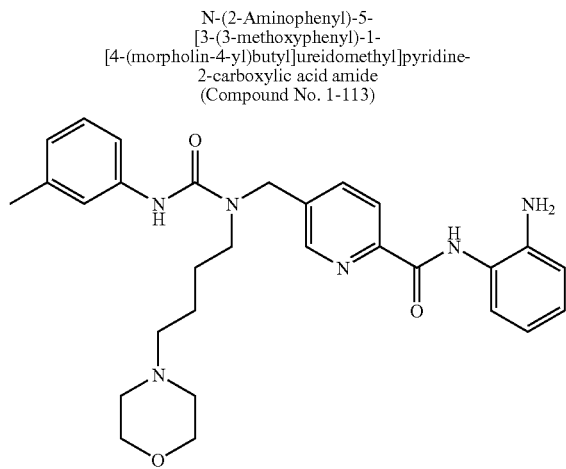

$^1$H-NMR (500 MHz, CDCl$_3$)
δ 1.55 (m, 2H), 1.72 (m, 2H),
2.34 (s, 3H), 2.39 (t, J = 7.2 Hz,
2H), 2.53 (m, 4H), 3.33 (t, J =
7.9 Hz, 2H), 3.67 (t, J = 4.6 Hz,
4H), 3.96 (s, 2H), 4.70 (s, 2H),
6.57 (s, 1H), 6.84-6.88 (m, 2H),
6.91 (d, J = 7.0 Hz, 1H), 7.09 (td,
J = 7.7, 1.3 Hz, 1H), 7.11 (d, J =
7.0 Hz, 1H), 7.20 (t, J = 7.7 Hz,
1H), 7.23 (s, 1H), 7.48 (d, J = 7.7
Hz, 1H), 7.89 (dd, J = 8.0, 2.1
Hz, 1H), 8.27 (d, J = 8.0 Hz, 1H),
8.59 (d, J = 2.1 Hz, 1H), 9.82 (s,
14H)

| | |
|---|---|
| 5-[3-(3-Acetylphenyl)-1-[4-(morpholin-4-yl)butyl]ureidomethyl]-N-(2-aminophenyl)pyridine-2-carboxylic acid amide (Compound No. 1-114) 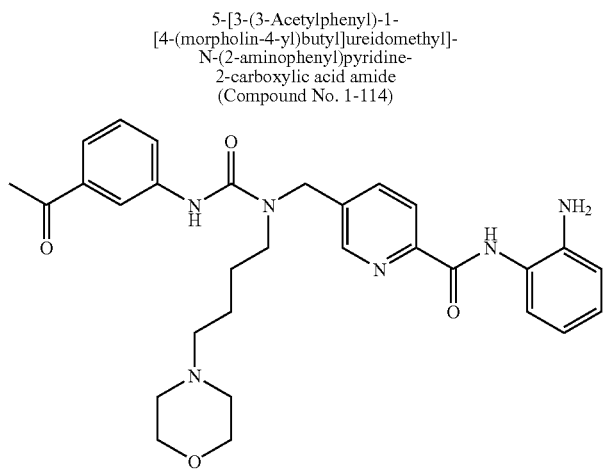 | $^1$H-NMR (500 MHz, CDCl$_3$) δ 1.56 (m, 2H), 1.74 (m, 2H), 2.40 (t, J = 7.0 Hz, 2H), 2.44 (t, J = 4.7 Hz, 4H), 2.61 (s, 3H), 3.35 (t, J = 7.9 Hz, 2H), 3.67 (t, J = 4.7 Hz, 4H), 3.95 (s, 2H), 4.71 (s, 2H), 6.81 (s, 1H), 6.85 (dd, J = 7.8, 1.3 Hz, 1H), 6.86 (td, J = 7.8, 1.3 Hz, 1H), 7.09 (td, J = 7.8, 1.3 Hz, 1H), 7.43 (t, J = 7.9 Hz, 1H), 7.49 (dd, J = 7.8, 1.3 Hz, 1H), 7.66 (ddd, J = 7.9, 2.2, 1.1 Hz, 1H), 7.78 (ddd, J = 7.9, 2.2, 1.1 Hz, 1H), 7.82 (t, J = 2.2 Hz, 1H), 7.89 (dd, J = 7.9, 2.1 Hz, 1H), 8.27 (d, J = 7.9 Hz, 1H), 8.59 (d, J = 2.1 Hz, 1H), 9.82 (s, 1H) |
| N-(2-Aminophenyl)-5-[3-(2-methoxyphenyl)-1-[4-(morpholin-4-yl)butyl]ureidomethyl]pyridine-2-carboxylic acid amide (Compound No. 1-115) 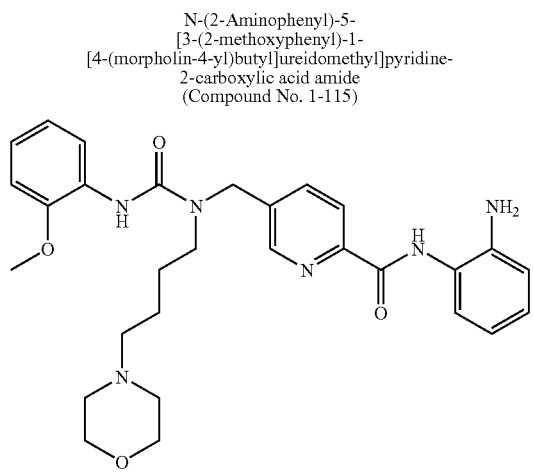 | $^1$H-NMR (400 MHz, CDCl$_3$) δ 1.56 (m, 2H), 1.73 (m, 2H), 2.37 (t, J = 7.3 Hz, 2H), 2.42 (t, J = 4.6 Hz, 4H), 3.39 (t, J = 7.5 Hz, 2H), 3.69 (t, J = 4.6 Hz, 4H), 3.83 (s, 3H), 3.95 (s, 2H), 4.70 (s, 2H), 6.85 (d, J = 7.7 Hz, 1H), 6.86 (m, 1H), 6.86 (td, J = 7.7, 1.4 Hz, 1H), 6.98-7.00 (m, 2H), 7.09 (td, J = 7.7, 1.4 Hz, 1H), 7.15 (s, 1H), 7.49 (dd, J = 7.7, 1.4 Hz, 1H), 7.89 (dd, J = 8.0, 2.2 Hz, 1H), 8.14 (m, 1H), 8.27 (dd, J = 8.0, 0.7 Hz, 1H), 8.60 (dd, J = 2.2, 0.7 Hz, 1H), 9.83 (s, 1H) |
| N-(2-Aminophenyl)-5-[3-(3-methylphenyl)-1-[3-(4-methylpiperidin-1-yl)propyl]ureidomethyl]pyridine-2-carboxylic acid amide (Compound No. 1-116) 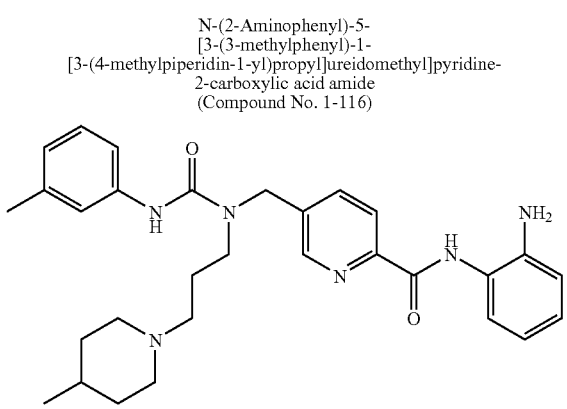 | $^1$H-NMR (400 MHz, DMSO-d$_6$) δ 0.86 (d, J = 6.6 Hz, 3H), 1.11 (m, 2H), 1.30 (m, 1H), 1.54 (d, J = 11.5 Hz, 2H), 1.71 (m, 2H), 1.81 (t, J = 11.1 Hz, 2H), 2.26 (s, 3H), 2.27 (t, J = 6.8 Hz, 2H), 2.79 (d, J = 11.1 Hz, 2H), 3.36 (t, J = 6.3 Hz, 2H), 4.66 (s, 2H), 4.89 (s, 2H), 6.65 (t, J = 7.7 Hz, 1H), 6.79-6.83 (m, 2H), 6.95 (m, 1H), 7.13 (t, J = 7.7 Hz, 1H), 7.28-7.32 (m, 2H), 7.50 (d, J = 7.7 Hz, 1H), 7.93 (dd, J = 8.2, 2.1 Hz, 1H), 8.12 (d, J = 8.2 Hz, 1H), 8.64 (d, J = 2.1 Hz, 1H), 8.79 (s, 1H), 10.03 (s, 1H) |

| | |
|---|---|
| N-(2-Aminophenyl)-5-[3-(3,4-difluorophenyl)-1-[3-(4-methylpiperidin-1-yl)propyl]ureidomethyl]pyridine-2-carboxylic acid amide (Compound No. 1-117)<br>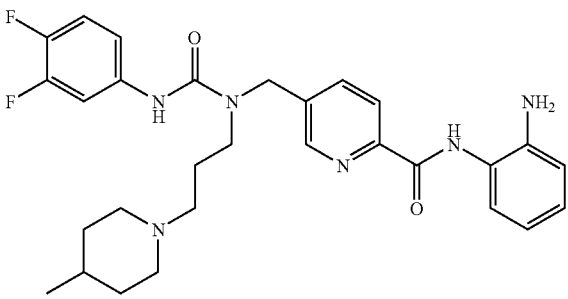 | ¹H-NMR (400 MHz, DMSO-d₆) δ 0.86 (d, J = 6.3 Hz, 3H), 1.07 (m, 2H), 1.29 (m, 1H), 1.53 (d, J = 11.0 Hz, 2H), 1.70 (m, 2H), 1.80 (t, J = 11.0 Hz, 2H), 2.26 (t, J = 6.5 Hz, 2H), 2.77 (d, J = 11.0 Hz, 2H), 3.37 (t, J = 7.0 Hz, 2H), 4.68 (s, 2H), 4.89 (s, 2H), 6.65 (t, J = 7.8 Hz, 1H), 6.82 (d, J = 8.3 Hz, 1H), 6.95 (m, 1H), 7.24 (m, 1H), 7.33 (m, 1H), 7.50 (d, J = 7.8 Hz, 1H), 7.65 (m, 1H), 7.93 (dd, J = 8.1, 2.0 Hz, 1H), 8.12 (d, J = 8.1 Hz, 1H), 8.64 (d, J = 2.0 Hz, 1H), 9.00 (s, 1H), 10.03 (s, 1H) |
| N-(2-Aminophenyl)-5-[3-(2,3-dihydrobenzo[1,4]dioxin-6-yl)-1-[3-(4-methylpiperidin-1-yl)propyl]ureidomethyl]pyridine-2-carboxylic acid amide (Compound No. 1-118)<br>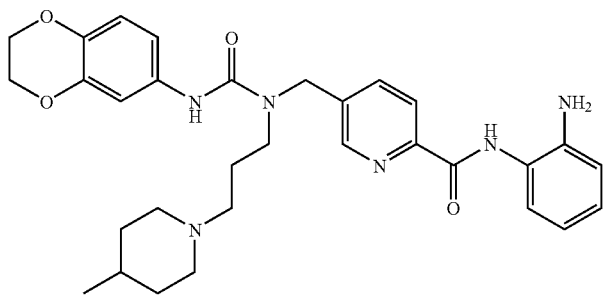 | ¹H-NMR (400 MHz, DMSO-d₆) δ 0.85 (d, J = 6.3 Hz, 3H), 1.08 (m, 2H), 1.29 (m, 1H), 1.53 (d, J = 11.2 Hz, 2H), 1.69 (m, 2H), 1.80 (t, J = 11.2 Hz, 2H), 2.26 (t, J = 6.3 Hz, 2H), 2.78 (d, J = 11.2 Hz, 2H), 3.32 (m, 2H), 4.17-4.21 (m, 4H), 4.64 (s, 2H), 4.90 (s, 2H), 6.65 (m, 1H), 6.74 (d, J = 8.7 Hz, 1H), 6.82 (dd, J = 8.1, 1.3 Hz, 1H), 6.86 (dd, J = 8.7, 2.4 Hz, 1H), 6.95 (m, 1H), 7.04 (d, J = 2.4 Hz, 1H), 7.50 (d, J = 8.1 Hz, 1H), 7.92 (dd, J = 8.1, 2.0 Hz, 1H), 8.11 (d, J = 8.1 Hz, 1H), 8.63 (d, J = 2.0 Hz, 1H), 8.72 (s, 1H), 10.03 (s, 1H) |
| N-(2-Aminophenyl)-5-[3-(4-fluorophenyl)-1-[3-(morpholin-4-yl)propyl]ureidomethyl]pyridine-2-carboxylic acid amide (Compound No. 1-119)<br>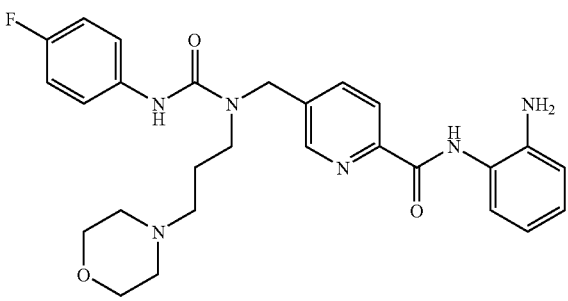 | ¹H-NMR (500 MHz, CDCl₃) δ 1.79 (m, 2H), 2.45 (br s, 4H), 2.49 (t, J = 6.0 Hz, 2H), 3.39 (t, J = 5.7 Hz, 2H), 3.63 (t, J = 4.4 Hz, 4H), 3.96 (br s, 2H), 4.64 (s, 2H), 6.83-6.88 (m, 2H), 7.03 (t, J = 8.9 Hz, 2H), 7.09 (td, J = 7.7, 1.1 Hz, 1H), 7.38 (dd, J = 8.9, 4.9 Hz, 2H), 7.48 (dd, J = 7.7, 1.1 Hz, 1H), 7.91 (dd, J = 8.0, 1.9 Hz, 1H), 8.24 (d, J = 8.0 Hz, 1H), 8.59 (d, J = 1.9 Hz, 1H), 9.08 (s, 1H), 9.82 (s, 1H) |
| N-(2-Aminophenyl)-5-[3-(4-fluoro-3-methylphenyl)-1-[3-(morpholin-4-yl)propyl]ureidomethyl]pyridine-2-carboxylic acid amide (Compound No. 1-120)<br>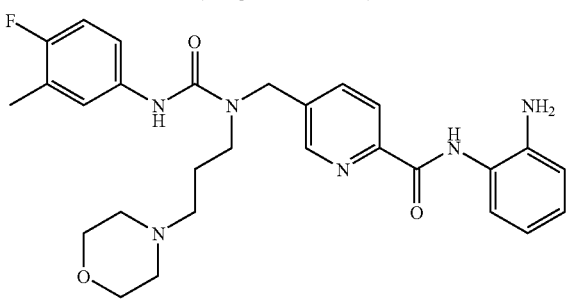 | ¹H-NMR (500 MHz, CDCl₃) δ 1.78 (m, 2H), 2.27 (d, J = 2.1 Hz, 3H), 2.45 (br s, 4H), 2.48 (t, J = 6.0 Hz, 2H), 3.38 (t, J = 5.7 Hz, 2H), 3.64 (t, J = 4.6 Hz, 4H), 3.95 (br s, 2H), 4.64 (s, 2H), 6.83-6.88 (m, 2H), 6.95 (t, J = 8.7 Hz, 1H), 7.09 (td, J = 7.7, 1.3 Hz, 1H), 7.13 (ddd, J = 8.7, 4.3, 2.7 Hz, 1H), 7.30 (dd, J = 6.9, 2.7 Hz, 1H), 7.48 (dd, J = 7.7, 1.3 Hz, 1H), 7.91 (dd, J = 7.9, 2.0 Hz, 1H), 8.24 (d, J = 7.9 Hz, 1H), 8.59 (d, J = 2.0 Hz, 1H), 8.99 (s, 1H), 9.82 (s, 1H) |

N-(2-Aminophenyl)-5-
[3-(3,4-diflurophenyl)-1-
[3-(morpholin-4-yl)propyl]ureidomethyl]pyridine-
2-carboxylic acid amide
(Compound No. 1-121)

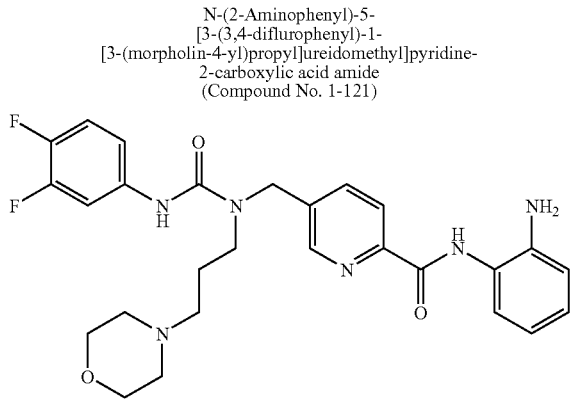

$^1$H-NMR (400 MHz, CDCl$_3$)
δ 1.79 (m, 2H), 2.43-2.52 (m, 6H), 3.38 (t, J = 5.6 Hz, 2H), 3.67 (t, J = 4.8 Hz, 4H), 3.96 (br s, 2H), 4.64 (s, 2H), 6.85 (d, J = 7.6 Hz, 1H), 6.86 (m, 1H), 7.01-7.14 (m, 3H), 7.46-7.53 (m, 2H), 7.90 (dd, J = 8.1, 2.2 Hz, 1H), 8.24 (dd, J = 8.1, 0.7 Hz, 1H), 8.58 (dd, J = 2.2, 0.7 Hz, 1H), 9.16 (s, 1H), 9.82 (s, 1H)

N-(2-Aminophenyl)-5-
[3-(3-methylphenyl)-1-
[3-(morpholin-4-yl)propyl]ureidomethyl]pyridine-
2-carboxylic acid amide
(Compound No. 1-122)

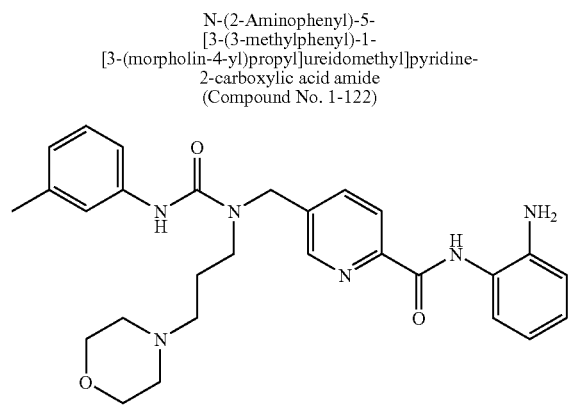

$^1$H-NMR (400 MHz, CDCl$_3$)
δ 1.79 (m, 2H), 2.35 (s, 3H), 2.43-2.52 (m, 6H), 3.39 (t, J = 5.7 Hz, 2H), 3.70 (t, J = 4.6 Hz, 4H), 3.96 (br s, 2H), 4.65 (s, 2H), 6.85 (d, J = 7.6 Hz, 1H), 6.86 (m, 1H), 6.91 (m, 1H), 7.09 (td, J = 7.6, 1.4 Hz, 1H), 7.19-7.22 (m, 2H), 7.34 (s, 1H), 7.48 (dd, J = 7.6, 1.4 Hz, 1H), 7.92 (dd, J = 8.1, 2.2 Hz, 1H), 8.24 (dd, J = 8.1, 0.7 Hz, 1H), 8.59 (dd, J = 2.2, 0.7 Hz, 1H), 8.87 (s, 1H), 9.83 (s, 1H)

N-[3-(3-Acetylphenyl)-1-
[3-(morpholin-4-yl)propyl]ureidomethyl]-
N-(2-aminophenyl)pyridine-
2-carboxylic acid amide
(Compound No. 1-123)

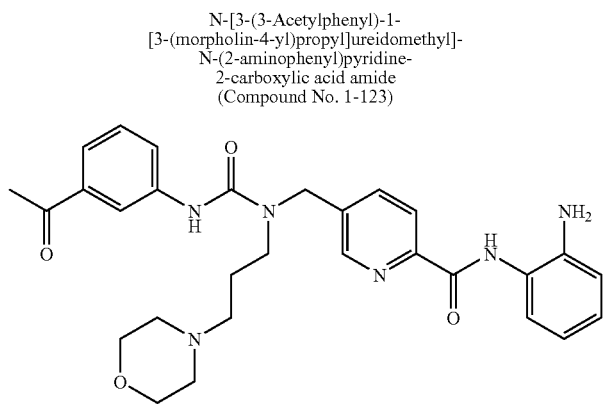

$^1$H-NMR (400 MHz, CDCl$_3$)
δ 1.81 (m, 2H), 2.45-2.53 (m, 6H), 2.62 (s, 3H), 3.42 (t, J = 5.6 Hz, 2H), 3.72 (t, J = 4.6 Hz, 4H), 3.96 (br s, 2H), 4.66 (s, 2H), 6.85 (d, J = 7.8 Hz, 1H), 6.86 (m, 1H), 7.09 (td, J = 7.8, 1.5 Hz, 1H), 7.44 (t, J = 7.9 Hz, 1H), 7.48 (d, J = 7.8 Hz, 1H), 7.67 (ddd, J = 7.9, 1.8, 1.0 Hz, 1H), 7.81 (ddd, J = 7.9, 1.8, 1.0 Hz, 1H), 7.92 (dd, J = 8.1, 2.2 Hz, 1H), 8.00 (t, J = 1.8 Hz, 1H), 8.25 (dd, J = 8.1, 0.7 Hz, 1H), 8.60 (dd, J = 2.2, 0.7 Hz, 1H), 9.22 (s, 1H), 9.83 (s, 1H)

| | |
|---|---|
| N-(2-Aminophenyl)-5-[3-(3-methylphenyl)-1-[5-(morpholin-4-yl)pentyl]ureidomethyl]pyridine-2-carboxylic acid amide (Compound No. 1-124) 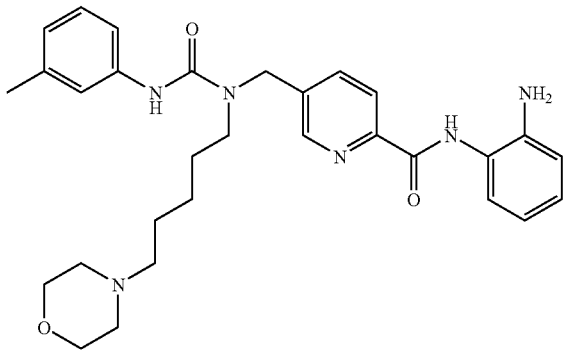 | $^1$H-NMR (400 MHz, CDCl$_3$) δ 1.37 (m, 2H), 1.53 (m, 2H), 1.67 (m, 2H), 2.32 (m, 2H), 2.33 (s, 3H), 2.42 (br s, 4H), 3.31 (t, J = 7.4 Hz, 2H), 3.70 (br s, 4H), 3.95 (br s, 2H), 4.68 (s, 2H), 6.37 (s, 1H), 6.83-6.89 (m, 3H), 7.07-7.20 (m, 3H), 7.25 (s, 1H), 7.49 (d, J = 7.6 Hz, 1H), 7.86 (d, J = 8.1 Hz, 1H), 8.25 (d, J = 8.1 Hz, 1H), 8.57 (s, 1H), 9.82 (s, 1H) |
| N-(2-Aminophenyl)-5-[3-(3,4-difluorophenyl)-1-[5-(morpholin-4-yl)pentyl]ureidomethyl]pyridine-2-carboxylic acid amide (Compound No. 1-125) 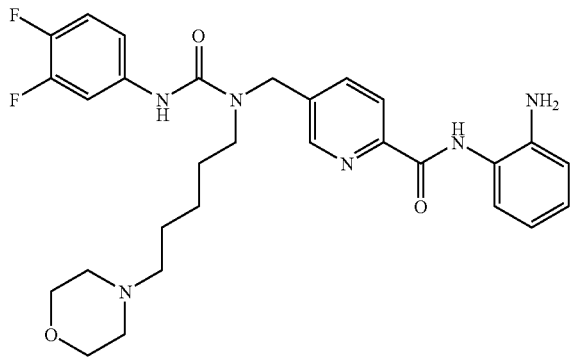 | $^1$H-NMR (500 MHz, CDCl$_3$) δ 1.35 (m, 2H), 1.52 (m, 2H), 1.65 (m, 2H), 2.32 (t, J = 7.5 Hz, 2H), 2.42 (br s, 4H), 3.29 (t, J = 7.8 Hz, 2H), 3.70 (t, J = 4.6 Hz, 4H), 3.94 (s, 2H), 4.65 (s, 2H), 6.69 (s, 1H), 6.83-6.87 (m, 2H), 6.97 (d, J = 8.9 Hz, 1H), 7.02-7.10 (m, 2H), 7.45 (m, 1H), 7.48 (d, J = 7.9 Hz, 1H), 7.80 (dd, J = 7.9, 1.8 Hz, 1H), 8.18 (d, J = 7.9 Hz, 1H), 8.53 (d, J = 1.8 Hz, 1H), 9.81 (s, 1H) |
| N-(2-Aminophenyl)-5-[3-(2,3-dihydrobenzo[1,4]dioxin-6-yl)-1-[5-(morpholin-4-yl)pentyl]ureidomethyl]pyridine-2-carboxylic acid amide (Compound No. 1-126) 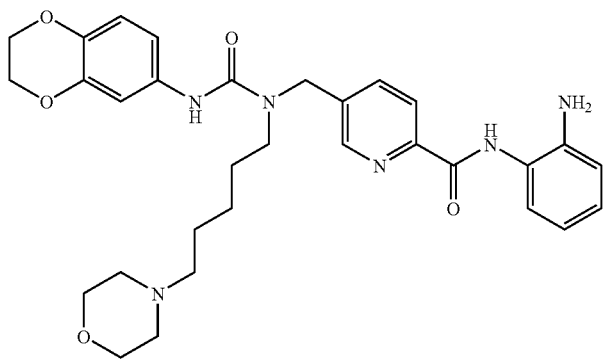 | $^1$H-NMR (400 MHz, CDCl$_3$) δ 1.35 (m, 2H), 1.52 (m, 2H), 1.65 (m, 2H), 2.31 (t, J = 7.7 Hz, 2H), 2.41 (br s, 4H), 3.28 (t, J = 7.7 Hz, 2H), 3.70 (t, J = 4.5 Hz, 4H), 3.96 (s, 2H), 4.20-4.24 (m, 4H), 4.65 (s, 2H), 6.32 (s, 1H), 6.75-6.79 (m, 2H), 6.83-6.88 (m, 2H), 6.95 (m, 1H), 7.08 (td, J = 7.7, 1.4 Hz, 1H), 7.49 (d, J = 7.7 Hz, 1H), 7.84 (dd, J = 8.1, 2.0 Hz, 1H), 8.23 (d, J = 8.1 Hz, 1H), 8.55 (d, J = 2.0 Hz, 1H), 9.82 (s, 1H) |

N-(2-Aminophenyl)-5-
[1-(3-dimethyaminopropyl)-3-
(4-phenyl-1,3-thiazol-2-yl)ureidomethyl]pyridine-
2-carboxylic acid amide
(Compound No. 1-127)

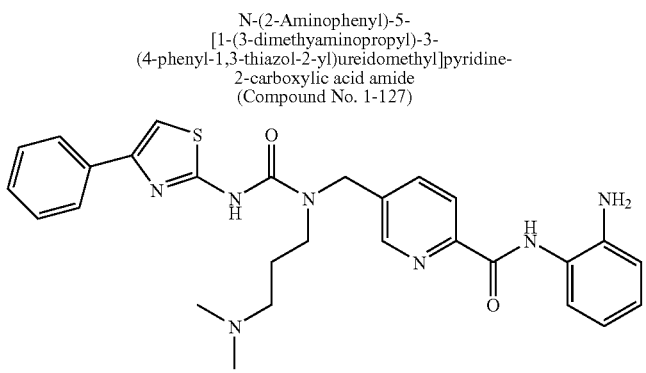

$^1$H-NMR (400 MHz, DMSO-d$_6$)
δ 1.76 (m, 2H), 2.34 (s, 6H), 2.37 (t, J = 5.7 Hz, 2H), 3.42 (t, J = 5.5 Hz, 2H), 4.68 (s, 2H), 4.91 (br s, 2H), 6.65 (t, J = 7.8 Hz, 1H), 6.82 (d, J = 7.8 Hz, 1H), 6.95 (t, J = 7.8 Hz, 1H), 7.29 (t, J = 7.8 Hz, 1H), 7.41 (t, J = 7.8 Hz, 2H), 7.48 (s, 1H), 7.51 (d, J = 7.8 Hz, 1H), 7.90 (d, J = 7.8 Hz, 2H), 7.99 (dd, J = 8.1, 1.7 Hz, 1H), 8.13 (d, J = 8.1 Hz, 1H), 8.70 (d, J = 1.7 Hz, 1H), 10.04 (br s, 1H), 13.45 (br s, 1H)

N-(2-Aminophenyl)-5-
[3-(6-methoxypyridin-3-yl)-1-
[3-(morpholin-4-yl)propyl]ureidomethyl]pyridine-
2-carboxylic acid amide
(Compound No. 1-128)

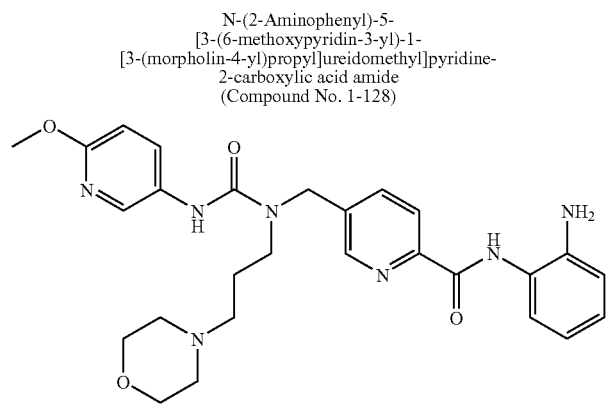

$^1$H-NMR (500 MHz, CDCl$_3$)
δ 1.79 (m, 2H), 2.45 (br s, 4H), 2.50 (t, J = 6.0 Hz, 2H), 3.41 (t, J = 5.5 Hz, 2H), 3.61 (t, J = 4.3 Hz, 4H), 3.92 (s, 3H), 3.98 (br s, 2H), 4.64 (s, 2H), 6.75 (d, J = 8.9 Hz, 1H), 6.84-6.88 (m, 2H), 7.09 (td, J = 7.7, 1.5 Hz, 1H), 7.48 (dd, J = 7.7, 1.5 Hz, 1H), 7.78 (dd, J = 8.9, 2.6 Hz, 1H), 7.91 (dd, J = 7.9, 2.1 Hz, 1H), 8.06 (d, J = 2.6 Hz, 1H), 8.24 (dd, J = 7.9, 0.6 Hz, 1H), 8.59 (dd, J = 2.1, 0.6 Hz, 1H), 9.26 (s, 1H), 9.82 (s, 1H)

N-(2-Aminophenyl)-5-
[3-(4-methylpyridin-2-yl)-1-
[3-(morpholin-4-yl)propyl]ureidomethyl]pyridine-
2-carboxylic acid amide
(Compound No. 1-129)

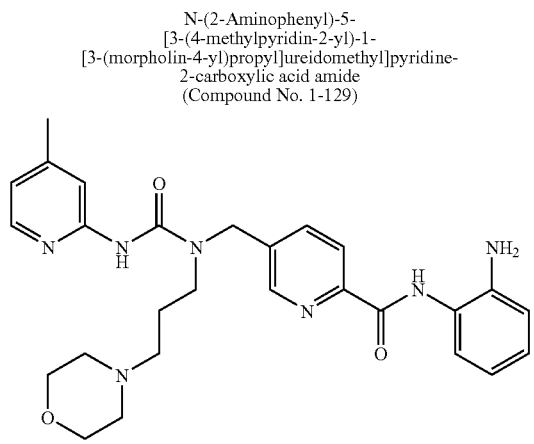

$^1$H-NMR (400 MHz, CDCl$_3$)
δ 1.80 (m, 2H), 2.34 (s, 3H), 2.45 (t, J = 5.9 Hz, 2H), 2.50 (br s, 4H), 3.44 (t, J = 5.6 Hz, 2H), 3.54 (br s, 2H), 3.97 (t, J = 4.3 Hz, 4H), 4.66 (s, 2H), 6.76 (d, J = 4.9 Hz, 1H), 6.83-6.89 (m, 2H), 7.09 (td, J = 7.8, 1.4 Hz, 1H), 7.48 (dd, J = 7.8, 1.4 Hz, 1H), 7.86 (s, 1H), 7.91 (dd, J = 8.0, 2.1 Hz, 1H), 8.08 (d, J = 4.9 Hz, 1H), 8.26 (dd, J = 8.0, 0.5 Hz, 1H), 8.60 (dd, J = 2.1, 0.5 Hz, 1H), 9.71 (s, 1H), 9.83 (s, 1H)

N-(2-Aminophenyl)-5-
[1-[3-(morpholin-4-yl)propyl]-3-
(1,3-thiazol-2-yl)ureidomethyl]pyridine-
2-carboxylic acid amide
(Compound No. 1-130)

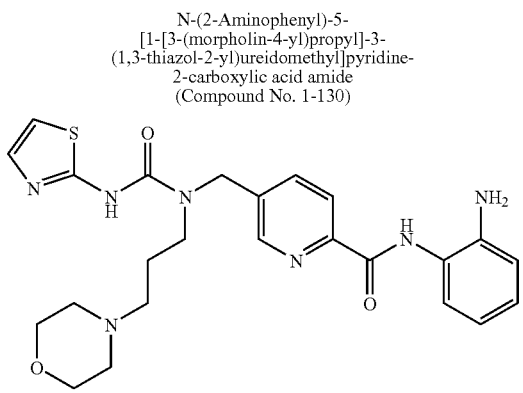

$^1$H-NMR (500 MHz, CDCl$_3$)
δ 1.79 (m, 2H), 2.46 (t, J = 6.0 Hz, 2H), 2.51 (br s, 4H), 3.40 (t, J = 5.7 Hz, 2H), 3.95 (br s, 2H), 4.03 (br s, 4H), 4.68 (s, 2H), 6.83-6.88 (m, 2H), 6.87 (d, J = 3.5 Hz, 1H), 7.09 (td, J = 7.7, 1.5 Hz, 1H), 7.37 (d, J = 3.5 Hz, 1H), 7.48 (dd, J = 7.7, 1.5 Hz, 1H), 7.91 (dd, J = 7.9, 2.1 Hz, 1H), 8.26 (dd, J = 7.9, 0.6 Hz, 1H), 8.60 (dd, J = 2.1, 0.6 Hz, 1H), 9.82 (s, 1H), 11.67 (br s, 1H)

N-(2-Aminophenyl)-5-
[1-[3-(morpholin-4-yl)propyl]-3-
(5-nitro-1,3-thiazol-2-yl)ureidomethyl]pyridine-
2-carboxylic acid amide
(Compound No. 1-131)

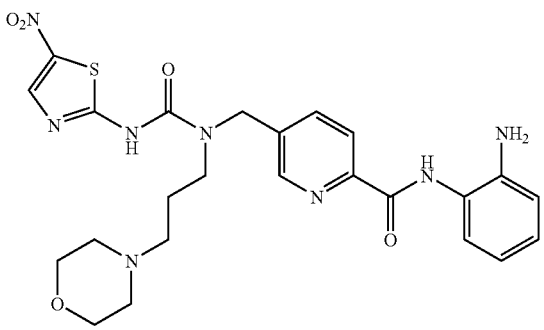

$^1$H-NMR (500 MHz, CDCl$_3$)
δ 1.84 (m, 2H), 2.48 (t, J = 6.0 Hz, 2H), 2.54 (br s, 4H), 3.41 (t, J = 5.7 Hz, 2H), 3.93 (br s, 2H), 4.01 (br s, 4H), 4.67 (s, 2H), 6.84-6.89 (m, 2H), 7.10 (td, J = 7.8, 1.2 Hz, 1H), 7.49 (dd, J = 7.8, 1.2 Hz, 1H), 7.90 (dd, J = 8.0, 2.1 Hz, 1H), 8.26 (s, 1H), 8.28 (d, J = 8.0 Hz, 1H), 8.61 (d, J = 2.1 Hz, 1H), 9.81 (s, 1H)

N-(2-Aminophenyl)-5-
[3-cylcopentyl-1-
[3-(morpholin-4-yl)propyl]ureidomethyl]pyridine-
2-carboxylic acid amide
(Compound No. 1-132)

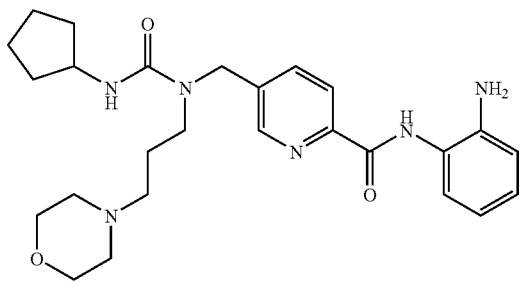

$^1$H-NMR (400 MHz, CDCl$_3$)
δ 1.35 (m, 2H), 1.58-1.70 (m, 6H), 2.07 (m, 2H), 2.37 (t, J = 6.1 Hz, 2H), 2.45 (t, J = 4.4 Hz, 4H), 3.21 (t, J = 6.1 Hz, 2H), 3.74 (t, J = 4.5 Hz, 4H), 3.96 (s, 2H), 4.11 (m, 1H), 4.58 (s, 2H), 5.91 (d, J = 6.8 Hz, 1H), 6.85 (dd, J = 7.7, 1.5 Hz, 1H), 6.87 (td, J = 7.7, 1.5 Hz, 1H), 7.08 (td, J = 7.7, 1.5 Hz, 1H), 7.48 (dd, J = 7.7, 1.5 Hz, 1H), 7.84 (dd, J = 8.0, 2.2 Hz, 1H), 8.23 (dd, J = 8.0, 0.6 Hz, 1H), 8.53 (dd, J = 2.2, 0.6 Hz, 1H), 9.82 (s, 1H)

N-(2-Aminophenyl)-5-
[3-[2-(benzo[1,3]dioxol-5-yl)ethyl]-1-
[3-(morpholin-4-yl)propyl]ureidomethyl]pyridine-
2-carboxylic acid amide
(Compound No. 1-133)

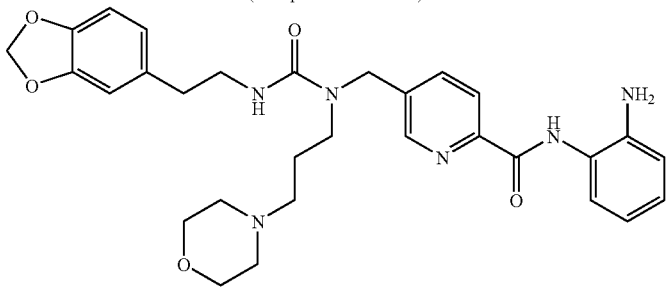

$^1$H-NMR (500 MHz, CDCl$_3$)
δ 1.63 (m, 2H), 2.33 (t, J = 5.8 Hz, 2H), 2.33 (s, 4H), 2.78 (t, J = 6.9 Hz, 2H), 3.17 (t, J = 5.8 Hz, 2H), 3.44 (q, J = 6.9 Hz, 2H), 3.60 (s, 4H), 3.97 (s, 2H), 4.57 (s, 2H), 5.92 (s, 2H), 6.64 (dd, J = 8.2, 1.7 Hz, 1H), 6.70 (d, J = 1.7 Hz, 1H), 6.75 (d, J = 8.2 Hz, 1H), 6.85 (dd, J = 7.8, 1.3 Hz, 1H), 6.86 (td, J = 7.8, 1.3 Hz, 1H), 7.06 (br s, 1H), 7.09 (td, J = 7.8, 1.3 Hz, 1H), 7.49 (dd, J = 7.8, 1.3 Hz, 1H), 7.80 (dd, J = 7.9, 2.1Hz, 1H), 8.23 (dd, J = 7.9, 0.9 Hz, 1H), 8.48 (dd, J = 2.1, 0.9 Hz, 1H), 9.84 (s, 1H)

N-(2-Aminophenyl)-5-
[3-isopropyl-1-
[3-(morpholin-4-yl)propyl]ureidomethyl]pyridine-
2-carboxylic acid amide
(Compound No. 1-134)

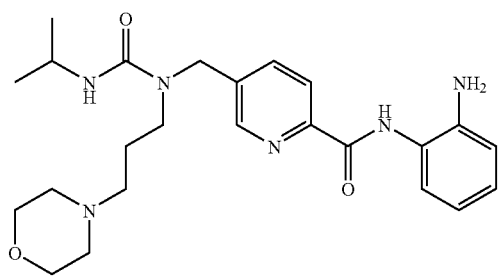

$^1$H-NMR (400 MHz, CDCl$_3$)
δ 1.20 (d, J = 6.6 Hz, 6H), 1.68 (m, 2H), 2.37 (t, J = 6.2 Hz, 2H), 2.45 (t, J = 4.5 Hz, 4H), 3.21 (t, J = 6.2 Hz, 2H), 3.76 (t, J = 4.5 Hz, 4H), 3.96 (s, 2H), 4.01 (m, 1H), 4.58 (s, 2H), 5.88 (d, J = 8.1 Hz, 1H), 6.85 (dd, J = 7.6, 1.5 Hz, 1H), 6.86 (td, J = 7.6, 1.5 Hz, 1H), 7.09 (td, J = 7.6, 1.5 Hz, 1H), 7.49 (dd, J = 7.6, 1.5 Hz, 1H), 7.84 (dd, J = 8.1, 2.2 Hz, 1H), 8.23 (dd, J = 8.1, 0.9 Hz, 1H), 8.53 (dd, J = 2.2, 0.9 Hz, 1H), 9.82 (s, 1H)

| Compound | <sup>1</sup>H-NMR |
|---|---|
| N-(2-Aminophenyl)-5-[1-[3-(morpholin-4-yl)propyl]-3-propylureidomethyl]pyridine-2-carboxylic acid amide (Compound No. 1-135) 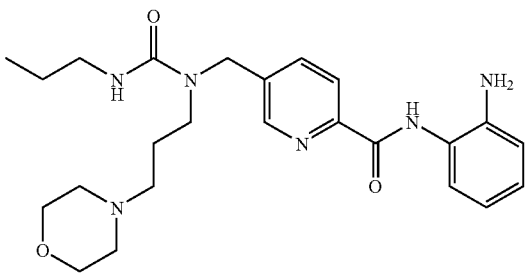 | <sup>1</sup>H-NMR (500 MHz, CDCl$_3$) δ 0.95 (t, J = 7.5 Hz, 3H), 1.55 (m, 2H), 1.67 (m, 2H), 2.38 (t, J = 6.0 Hz, 2H), 2.44 (s, 4H), 3.20 (m, 2H), 3.24 (t, J = 5.8 Hz, 2H), 3.73 (t, J = 4.4 Hz, 4H), 3.96 (s, 2H), 4.58 (s, 2H), 6.85 (dd, J = 7.6, 1.2 Hz, 1H), 6.86 (td, J = 7.6, 1.2 Hz, 1H), 7.01 (t, J = 5.7 Hz, 1H), 7.08 (td, J = 7.6, 1.2 Hz, 1H), 7.48 (dd, J = 7.6, 1.2 Hz, 1H), 7.85 (dd, J = 7.9, 2.0 Hz, 1H), 8.23 (d, J = 7.9 Hz, 1H), 8.53 (d, J = 2.0 Hz, 1H), 9.82 (s, 1H) |
| N-(2-Aminophenyl)-5-[1-[4-(morpholin-4-yl)butyl]-3-propylureidomethyl]pyridine-2-carboxylic acid amide (Compound No. 1-136) 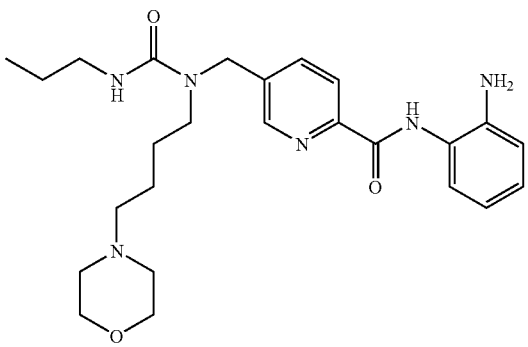 | <sup>1</sup>H-NMR (500 MHz, CDCl$_3$) δ 0.92 (t, J = 7.5 Hz, 3H), 1.46-1.63 (m, 6H), 2.35 (t, J = 7.0 Hz, 2H), 2.41 (br s, 4H), 3.18 (t, J = 7.9 Hz, 2H), 3.25 (m, 2H), 3.71 (t, J = 4.6 Hz, 4H), 3.96 (br s, 2H), 4.61 (s, 2H), 4.78 (t, J = 5.5 Hz, 1H), 6.84-6.88 (m, 2H), 7.09 (td, J = 7.6, 1.5 Hz, 1H), 7.48 (d, J = 7.6 Hz, 1H), 7.81 (dd, J = 7.9, 2.0 Hz, 1H), 8.24 (d, J = 7.9 Hz, 1H), 8.52 (d, J = 2.0 Hz, 1H), 9.82 (s, 1H) |
| N-(2-Aminophenyl)-5-[3-isopropyl-1-[4-(morpholin-4-yl)butyl]ureidomethyl]pyridine-2-carboxylic acid amide (Compound No. 1-137) 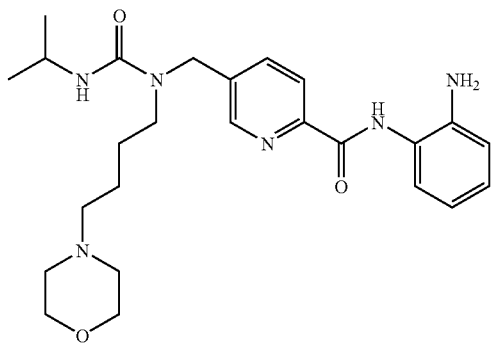 | <sup>1</sup>H-NMR (500 MHz, CDCl$_3$) δ 1.17 (d, J = 6.4 Hz, 6H), 1.48 (m, 2H), 1.59 (m, 2H), 2.33 (t, J = 7.2 Hz, 2H), 2.41 (br s, 4H), 3.17 (t, J = 7.6 Hz, 2H), 3.71 (t, J = 4.4 Hz, 4H), 3.96 (br s, 2H), 4.03 (m, 1H), 4.26 (d, J = 7.6 Hz, 1H), 4.59 (s, 2H), 6.84-6.89 (m, 2H), 7.08 (t, J = 7.6 Hz, 1H), 7.49 (d, J = 7.6 Hz, 1H), 7.80 (d, J = 7.9 Hz, 1H), 8.24 (d, J = 7.9 Hz, 1H), 8.51 (s, 1H), 9.82 (s, 1H) |

| | |
|---|---|
| N-(2-Aminophenyl)-5-[3-cyclopentyl-1-[4-(morpholin-4-yl)butyl]ureidomethyl]pyridine-2-carboxylic acid amide (Compound No. 1-138) 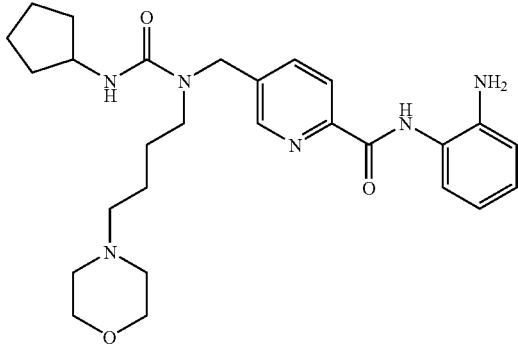 | $^1$H-NMR (500 MHz, CDCl$_3$) δ 1.34 (m, 2H), 1.48 (m, 2H), 1.55-1.66 (m, 6H), 2.01 (m, 2H), 2.33 (t, J = 7.2 Hz, 2H), 2.40 (br s, 4H), 3.18 (t, J = 7.6 Hz, 2H), 3.70 (t, J = 4.6 Hz, 4H), 3.96 (br s, 2H), 4.15 (m, 1H), 4.37 (d, J = 6.7 Hz, 1H), 4.59 (s, 2H), 6.84-6.87 (m, 2H), 7.08 (td, J = 7.6, 1.2 Hz, 1H), 7.49 (d, J = 7.6 Hz, 1H), 7.81 (dd, J = 7.9, 2.1 Hz, 1H), 8.24 (d, J = 7.9 Hz, 1H), 8.51 (d, J = 2.1 Hz, 1H), 9.82 (s, 1H) |
| N-(2-Aminophenyl)-5-[1-[5-(morpholin-4-yl)pentyl]-3-propylureidomethyl]pyridine-2-carboxylic acid amide (Compound No. 1-139) 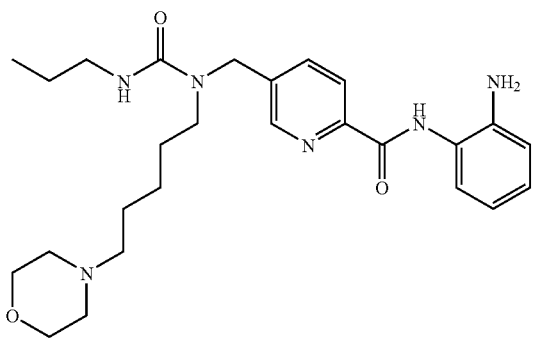 | $^1$H-NMR (400 MHz, CDCl$_3$) δ 0.91 (t, J = 7.4 Hz, 3H), 1.31 (m, 2H), 1.46-1.62 (m, 6H), 2.30 (t, J = 7.6 Hz, 2H), 2.41 (br s, 4H), 3.17 (t, J = 7.7 Hz, 2H), 3.23 (m, 2H), 3.70 (t, J = 4.6 Hz, 4H), 3.96 (br s, 2H), 4.46 (t, J = 5.5 Hz, 1H), 4.60 (s, 2H), 6.84-6.88 (m, 2H), 7.08 (td, J = 7.7, 1.4 Hz, 1H), 7.48 (d, J = 7.7 Hz, 1H), 7.80 (dd, J = 7.9, 2.1 Hz, 1H), 8.23 (d, J = 7.9 Hz, 1H), 8.51 (d, J = 2.1 Hz, 1H), 9.82 (s, 1H) |
| N-(2-Aminophenyl)-5-[3-isopropyl-1-[5-(morpholin-4-yl)pentyl]ureidomethyl]pyridine-2-carboxylic acid amide (Compound No. 1-140) 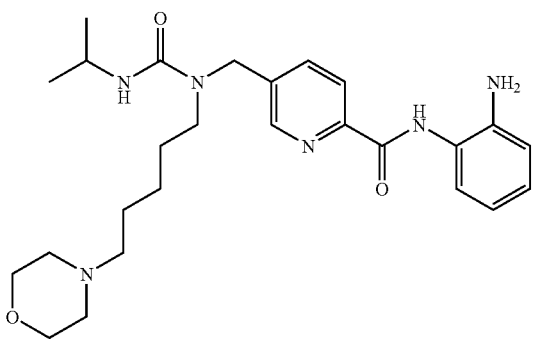 | $^1$H-NMR (500 MHz, CDCl$_3$) δ 1.16 (d, J = 6.7 Hz, 6H), 1.31 (m, 2H), 1.46-1.59 (m, 4H), 2.30 (t, J = 7.5 Hz, 2H), 2.41 (br s, 4H), 3.15 (t, J = 7.6 Hz, 2H), 3.70 (t, J = 4.7 Hz, 4H), 3.97 (br s, 2H), 4.01 (m, 1H), 4.20 (d, J = 7.3 Hz, 1H), 4.59 (s, 2H), 6.84-6.87 (m, 2H), 7.08 (td, J = 7.6, 1.5 Hz, 1H), 7.49 (d, J = 7.6 Hz, 1H), 7.79 (dd, J = 8.1, 2.0 Hz, 1H), 8.23 (d, J = 8.1 Hz, 1H), 8.51 (d, J = 2.0 Hz, 1H), 9.82 (s, 1H) |

| | |
|---|---|
| N-(2-Aminophenyl)-5-[3-cyclopentyl-1-[5-(morpholin-4-yl)pentyl]ureidomethyl]pyridine-2-carboxylic acid amide (Compound No. 1-141) 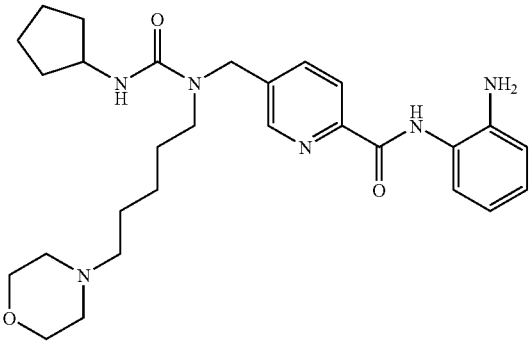 | $^1$H-NMR (500 MHz, CDCl$_3$) δ 1.27-1.37 (m, 4H), 1.46-1.66 (m, 8H), 2.00 (m, 2H), 2.30 (t, J = 7.5 Hz, 2H), 2.41 (br s, 4H), 3.15 (t, J = 7.6 Hz, 2H), 3.70 (t, J = 4.6 Hz, 4H), 3.97 (br s, 2H), 4.14 (m, 1H), 4.33 (d, J = 7.0 Hz, 1H), 4.58 (s, 2H), 6.84-6.87 (m, 2H), 7.08 (td, J = 7.7, 1.2 Hz, 1H), 7.49 (d, J = 7.7 Hz, 1H), 7.80 (dd, J = 8.2, 1.8 Hz, 1H), 8.23 (d, J = 8.2 Hz, 1H), 8.51 (d, J = 1.8 Hz, 1H), 9.82 (s, 1H) |
| N-(2-Aminophenyl)-5-[1-(2-dimethylaminoethyl)-3-[2-(piperidin-1-yl)ethyl]ureidomethyl]pyridine-2-carboxylic acid amide (Compound No. 1-142) 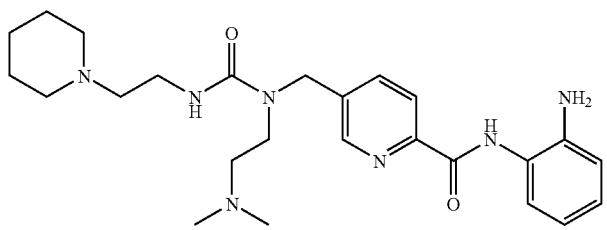 | $^1$H-NMR (500 MHz, CDCl$_3$) δ 1.44 (m, 2H), 1.54 (m, 4H), 2.26 (s, 6H), 2.39 (m, 4H), 2.41-2.46 (m, 4H), 3.26 (t, J = 5.5 Hz, 2H), 3.33 (m, 2H), 3.96 (s, 2H), 4.61 (s, 2H), 6.85 (dd, J = 7.8, 1.4 Hz, 1H), 6.86 (td, J = 7.8, 1.4 Hz, 1H), 7.09 (td, J = 7.8, 1.4 Hz, 1H), 7.10 (br s, 1H), 7.48 (dd, J = 7.8, 1.4 Hz, 1H), 7.85 (dd, J = 8.1, 2.1 Hz, 1H), 8.23 (dd, J = 8.1, 0.6 Hz, 1H), 8.54 (dd, J = 2.1, 0.6 Hz, 1H), 9.83 (s, 1H) |
| N-(2-Aminophenyl)-5-[3-(2-diisopropylaminoethyl)-1-(2-dimethylaminoethyl)ureidomethyl]pyridine-2-carboxylic acid amide (Compound No. 1-143) 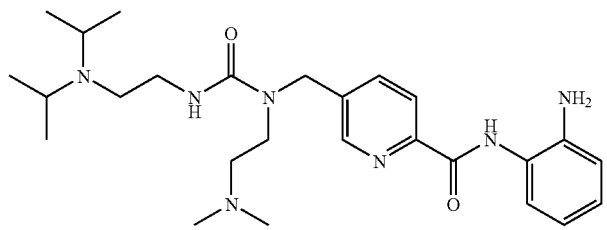 | $^1$H-NMR (500 MHz, CDCl$_3$) δ 1.38 (m, 12H), 2.30 (s, 6H), 2.55 (m, 2H), 3.07 (m, 2H), 3.42-3.50 (m, 4H), 3.60 (m, 2H), 3.96 (s, 2H), 4.71 (s, 2H), 6.85 (dd, J = 7.6, 1.3 Hz, 1H), 6.86 (td, J = 7.6, 1.3 Hz, 1H), 7.08 (td, J = 7.6, 1.3 Hz, 1H), 7.49 (dd, J = 7.6, 1.3 Hz, 1H), 7.85 (dd, J = 8.0, 2.0 Hz, 1H), 8.22 (d, J = 8.0 Hz, 1H), 8.57 (m, 1H), 9.82 (s, 1H) |
| N-(2-Aminophenyl)-5-[3-[2-(cyclohexen-1-yl)ethyl]-1-(2-dimethylaminoethyl)ureidomethyl]pyridine-2-carboxylic acid amide (Compound No. 1-144) 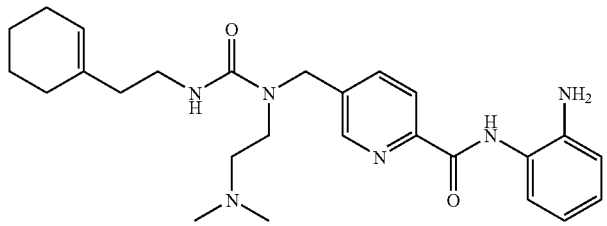 | $^1$H-NMR (500 MHz, CDCl$_3$) δ 1.54-1.62 (m, 4H), 1.95-2.02 (m, 4H), 2.14 (t, J = 7.0 Hz, 2H), 2.24 (m, 1H), 2.24 (s, 6H), 2.40 (m, 2H), 3.22 (m, 2H), 3.31 (m, 1H), 3.46 (m, 1H), 3.96 (s, 2H), 4.60 (s, 2H), 5.45 (m, 1H), 6.85 (dd, J = 7.8, 1.3 Hz, 1H), 6.86 (td, J = 7.8, 1.3 Hz, 1H), 7.08 (td, J = 7.8, 1.3 Hz, 1H), 7.11 (m, 1H), 7.48 (dd, J = 7.8, 1.3 Hz, 1H), 7.84 (dd, J = 7.9, 2.1 Hz, 1H), 8.23 (dd, J = 7.9, 0.9 Hz, 1H), 8.52 (dd, J = 2.1, 0.9 Hz, 1H), 9.82 (s, 1H) |

| | |
|---|---|
| N-(2-Aminophenyl)-5-[1-(2-dimethylaminoethyl)-3-propylureidomethyl]pyridine-2-carboxylic acid amide (Compound No. 1-145) 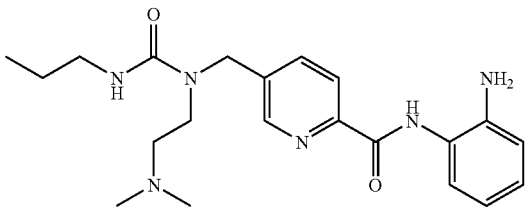 | ¹H-NMR (400 MHz, CDCl₃) δ 0.95 (t, J = 7.5 Hz, 3H), 1.53 (m, 2H), 2.26 (s, 6H), 2.39 (t, J = 4.6 Hz, 2H), 3.18 (m, 2H), 3.21 (t, J = 4.6 Hz, 2H), 3.96 (s, 2H), 4.60 (s, 2H), 6.85 (dd, J = 7.6, 1.2 Hz, 1H), 6.86 (td, J = 7.6, 1.2 Hz, 1H), 7.08 (td, J = 7.6, 1.2 Hz, 1H), 7.48 (dd, J = 7.6, 1.2 Hz, 1H), 7.78 (t, J = 5.2 Hz, 1H), 7.85 (dd, J = 7.9, 1.8 Hz, 1H), 8.23 (d, J = 7.9 Hz, 1H), 8.53 (d, J = 1.8 Hz, 1H), 9.83 (s, 1H) |
| N-(2-Aminophenyl)-5-[1-(2-dimethylaminoethyl)-3-isopropylureidomethyl]pyridine-2-carboxylic acid amide (Compound No. 1-146) 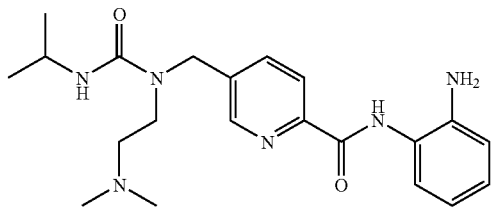 | ¹H-NMR (400 MHz, CDCl₃) δ 1.15 (d, J = 6.4 Hz, 6H), 2.27 (s, 6H), 2.41 (s, 2H), 3.20 (s, 2H), 3.90 (m, 1H), 3.96 (s, 2H), 4.60 (s, 2H), 6.85 (dd, J = 7.8, 1.4 Hz, 1H), 6.86 (td, J = 7.8, 1.4 Hz, 1H), 7.09 (td, J = 7.8, 1.4 Hz, 1H), 7.48 (dd, J = 7.8, 1.4 Hz, 1H), 7.84 (dd, J = 7.9, 2.1 Hz, 1H), 7.91 (s, 1H), 8.23 (dd, J = 7.9, 0.6 Hz, 1H), 8.53 (dd, J = 2.1, 0.6 Hz, 1H), 9.83 (s, 1H) |
| N-(2-Aminophenyl)-5-[3-sec-butyl-1-(2-dimethylaminoethyl)ureidomethyl]pyridine-2-carboxylic acid amide (Compound No. 1-147) 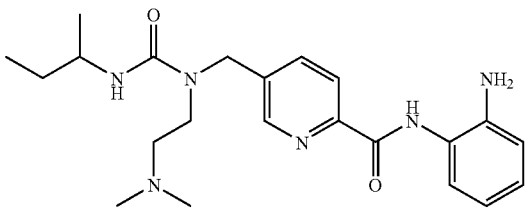 | ¹H-NMR (400 MHz, CDCl₃) δ 0.93 (t, J = 7.3 Hz, 3H), 1.12 (d, J = 6.4 Hz, 3H), 1.48 (m, 2H), 2.26 (s, 6H), 2.40 (t, J = 4.4 Hz, 2H), 3.20 (m, 2H), 3.75 (m, 1H), 3.96 (s, 2H), 4.60 (d, J = 15.9 Hz, 1H), 4.60 (d, J = 15.9 Hz, 1H), 6.84 (dd, J = 7.6, 0.8 Hz, 1H), 6.85 (td, J = 7.6, 0.8 Hz, 1H), 7.07 (td, J = 7.6, 0.8 Hz, 1H), 7.48 (dd, J = 7.6, 0.8 Hz, 1H), 7.80 (s, 1H), 7.84 (dd, J = 7.9, 1.8 Hz, 1H), 8.23 (d, J = 7.9 Hz, 1H), 8.53 (d, J = 1.8 Hz, 1H), 9.82 (s, 1H) |
| N-(2-Aminophenyl)-5-[3-cyclopentyl-1-(2-dimethylaminoethyl)ureidomethyl]pyridine-2-carboxylic acid amide (Compound No. 1-148) 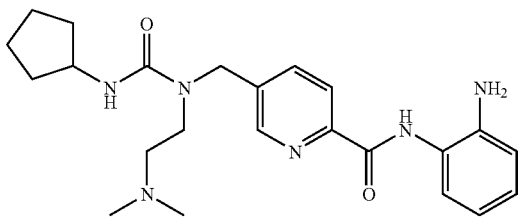 | ¹H-NMR (400 MHz, CDCl₃) δ 1.40 (m, 2H), 1.62-1.69 (m, 4H), 1.97 (m, 2H), 2.26 (s, 6H), 2.40 (t, J = 4.4 Hz, 2H), 3.18 (t, J = 4.4 Hz, 2H), 3.96 (s, 2H), 4.07 (m, 1H), 4.59 (s, 2H), 6.85 (dd, J = 7.8, 1.5 Hz, 1H), 6.86 (td, J = 7.8, 1.5 Hz, 1H), 7.08 (td, J = 7.8, 1.5 Hz, 1H), 7.48 (dd, J = 7.8, 1.5 Hz, 1H), 7.85 (dd, J = 8.0, 1.9 Hz, 1H), 8.02 (s, 1H), 8.23 (d, J = 8.0 Hz, 1H), 8.53 (d, J = 1.9 Hz, 1H), 9.83 (s, 1H) |
| N-(2-Aminophenyl)-5-[1-(2-dimethylaminoethyl)-3-hexylureidomethyl]pyridine-2-carboxylic acid amide (Compound No. 1-149) 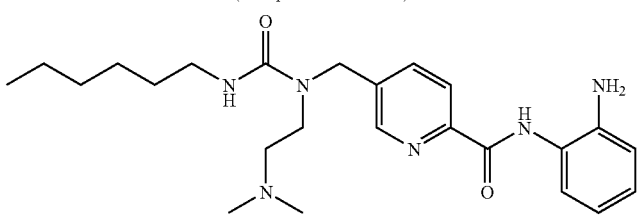 | ¹H-NMR (500 MHz, CDCl₃) δ 0.89 (t, J = 7.0 Hz, 3H), 1.28-1.36 (m, 6H), 1.50 (m, 2H), 2.38 (s, 6H), 2.56 (m, 2H), 3.21 (m, 2H), 3.35 (s, 2H), 3.96 (s, 2H), 4.62 (s, 2H), 6.85 (dd, J = 7.7, 1.3 Hz, 1H), 6.86 (td, J = 7.7, 1.3 Hz, 1H), 7.08 (td, J = 7.7, 1.3 Hz, 1H), 7.48 (dd, J = 7.7, 1.3 Hz, 1H), 7.84 (dd, J = 7.9, 2.1 Hz, 1H), 8.22 (dd, J = 7.9, 0.6 Hz, 1H), 8.52 (dd, J = 2.1, 0.6 Hz, 1H), 9.82 (s, 1H) |

| | |
|---|---|
| N-(2-Aminophenyl)-5-[3-cyclohexyl-1-(2-dimethylaminoethyl)ureidomethyl]pyridine-2-carboxylic acid amide (Compound No. 1-150)<br>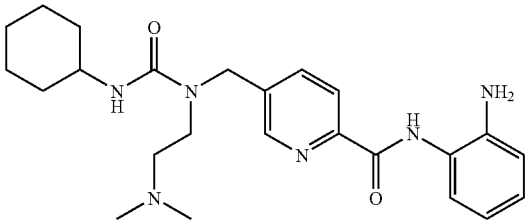 | $^1$H-NMR (400 MHz, CDCl$_3$) δ 1.11 (m, 2H), 1.39 (m, 2H), 1.60 (m, 2H), 1.71 (m, 2H), 1.96 (m, 2H), 2.25 (s, 6H), 2.40 (t, J = 4.5 Hz, 2H), 3.19 (t, J = 4.5 Hz, 2H), 3.59 (m, 1H), 3.96 (s, 2H), 4.59 (s, 2H), 6.85 (dd, J = 7.7, 1.5 Hz, 1H), 6.86 (td, J = 7.7, 1.5 Hz, 1H), 7.08 (td, J = 7.7, 1.5 Hz, 1H), 7.49 (dd, J = 7.7, 1.5 Hz, 1H), 7.85 (dd, J = 8.0, 2.2 Hz, 1H), 7.89 (d, J = 6.6 Hz, 1H), 8.23 (dd, J = 8.0, 0.7 Hz, 1H), 8.53 (dd, J = 2.2, 0.7 Hz, 1H), 9.83 (s, 1H) |
| N-(2-Aminophenyl)-5-[1-(2-dimethylaminoethyl)-3-phenethylureidomethyl]pyridine-2-carboxylic acid amide (Compound No. 1-151)<br>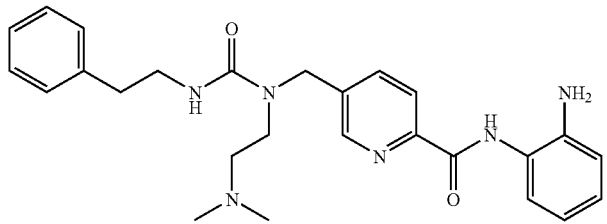 | $^1$H-NMR (400 MHz, CDCl$_3$) δ 2.04 (s, 6H), 2.30 (t, J = 4.8 Hz, 2H), 2.85 (t, J = 6.9 Hz, 2H), 3.12 (t, J = 4.8 Hz, 2H), 3.53 (m, 2H), 3.96 (s, 2H), 4.59 (s, 2H), 6.85 (dd, J = 7.8, 1.5 Hz, 1H), 6.86 (td, J = 7.8, 1.5 Hz, 1H), 7.09 (td, J = 7.8, 1.5 Hz, 1H), 7.19-7.24 (m, 3H), 7.28-7.32 (m, 2H), 7.48 (dd, J = 7.8, 1.5 Hz, 1H), 7.70 (t, J = 4.9 Hz, 1H), 7.81 (dd, J = 7.9, 2.1 Hz, 1H), 8.23 (dd, J = 7.9, 0.6 Hz, 1H), 8.51 (dd, J = 2.1, 0.6 Hz, 1H), 9.83 (s, 1H) |
| N-(2-Aminophenyl)-5-[1-(2-dimethylaminoethyl)-3-[2-(thiophen-2-yl)ethyl]ureidomethyl]pyridine-2-carboxylic acid amide (Compound No. 1-152)<br>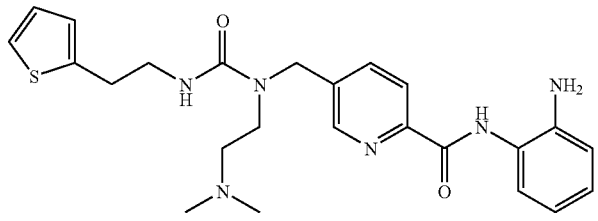 | $^1$H-NMR (400 MHz, CDCl$_3$) δ 2.10 (s, 6H), 2.34 (t, J = 4.7 Hz, 2H), 3.06 (t, J = 6.3 Hz, 2H), 3.17 (t, J = 4.7 Hz, 2H), 3.64 (m, 2H), 3.96 (s, 2H), 4.60 (s, 2H), 6.85 (dd, J = 3.4, 1.2 Hz, 1H), 6.85 (dd, J = 7.8, 1.5 Hz, 1H), 6.86 (td, J = 7.8, 1.5 Hz, 1H), 6.94 (dd, J = 5.1, 3.4 Hz, 1H), 7.09 (td, J = 7.7, 1.5 Hz, 1H), 7.14 (dd, J = 5.1, 1.2 Hz, 1H), 7.50 (dd, J = 7.7, 1.5 Hz, 1H), 7.82 (dd, J = 8.0, 2.1 Hz, 1H), 7.89 (s, 1H), 8.23 (dd, J = 8.0, 0.6 Hz, 1H), 8.51 (dd, J = 2.1, 0.6 Hz, 1H), 9.83 (s, 1H) |
| N-(2-Aminophenyl)-5-[1-(2-dimethylaminoethyl)-3-(2,2,2-trifluoroethyl)ureidomethyl]pyridine-2-carboxylic acid amide (Compound No. 1-153)<br>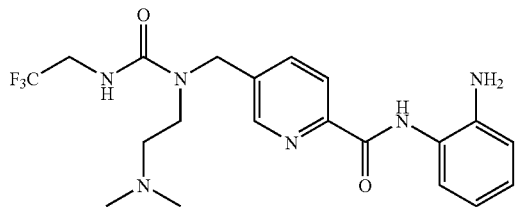 | $^1$H-NMR (400 MHz, CDCl$_3$) δ 2.28 (s, 6H), 2.44 (t, J = 4.3 Hz, 2H), 3.25 (t, J = 4.3 Hz, 2H), 3.88 (m, 2H), 3.96 (s, 2H), 4.62 (s, 2H), 6.85 (dd, J = 7.7, 1.5 Hz, 1H), 6.86 (td, J = 7.7, 1.5 Hz, 1H), 7.09 (td, J = 7.7, 1.5 Hz, 1H), 7.50 (dd, J = 7.7, 1.5 Hz, 1H), 7.83 (dd, J = 8.0, 2.2 Hz, 1H), 8.23 (dd, J = 8.0, 0.6 Hz, 1H), 8.53 (dd, J = 2.2, 0.6 Hz, 1H), 9.45 (m, 1H), 9.82 (s, 1H) |

N-(2-Aminophenyl)-5-
[3-(2-cyanoethyl)-1-
(2-dimethylaminoethyl)ureidomethyl]pyridine-
2-carboxylic acid amide
(Compound No. 1-154)

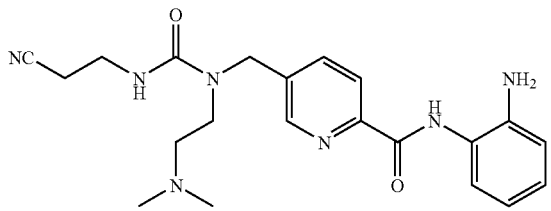

¹H-NMR (500 MHz, CDCl₃)
δ 2.26 (s, 6H), 2.41 (t, J = 4.9 Hz, 2H), 2.57 (t, J = 6.3 Hz, 2H), 3.21 (t, J = 4.9 Hz, 2H), 3.50 (m, 2H), 3.69 (s, 2H), 4.59 (s, 2H), 6.85 (dd, J = 7.7, 1.5 Hz, 1H), 6.87 (td, J = 7.7, 1.5 Hz, 1H), 7.08 (td, J = 7.7, 1.5 Hz, 1H), 7.48 (dd, J = 7.7, 1.5 Hz, 1H), 7.83 (dd, J = 7.9, 2.1 Hz, 1H), 7.92 (s, 1H), 8.23 (d, J = 7.9 Hz, 1H), 8.52 (d, J = 1.8 Hz, 1H), 9.82 (s, 1H)

N-(2-Aminophenyl)-5-
[1-(2-dimethylaminoethyl)-3-
[3-(pyrrolidin-2-on-1-yl)propyl]ureidomethyl]pyridine-
2-carboxylic acid amide
(Compound No. 1-155)

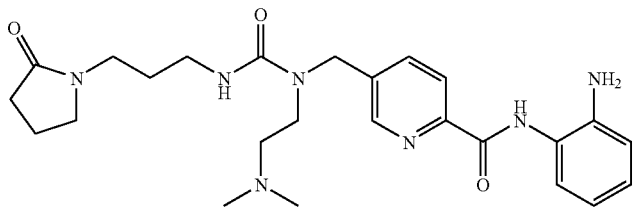

¹H-NMR (400 MHz, CDCl₃)
δ 1.70 (m, 2H), 2.04 (m, 2H), 2.27 (s, 6H), 2.39 (t, J = 8.2 Hz, 2H), 2.45 (t, J = 5.6 Hz, 2H), 3.20 (m, 2H), 3.30 (t, J = 5.6 Hz, 2H), 3.33 (t, J = 6.6 Hz, 2H), 3.40 (t, J = 7.1 Hz, 2H), 3.97 (s, 2H), 4.63 (s, 2H), 6.84 (dd, J = 7.7, 1.5 Hz, 1H), 6.85 (td, J = 7.7, 1.5 Hz, 1H), 7.08 (td, J = 7.7, 1.5 Hz, 1H), 7.36 (s, 1H), 7.48 (dd, J = 7.7, 1.5 Hz, 1H), 7.84 (dd, J = 8.0, 1.9 Hz, 1H), 8.23 (d, J = 8.0 Hz, 1H), 8.53 (d, J = 1.9 Hz, 1H), 9.83 (s, 1H)

N-(2-Aminophenyl)-5-
[3-propargyl-1-
(2-dimethylaminoethyl)ureidomethyl]pyridine-
2-carboxylic acid amide
(Compound No. 1-156)

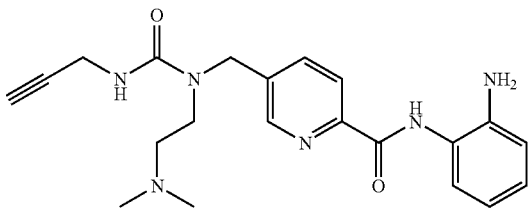

¹H-NMR (500 MHz, CDCl₃)
δ 2.20 (t, J = 2.5 Hz, 1H), 2.29 (s, 6H), 2.43 (t, J = 4.4 Hz, 2H), 3.22 (t, J = 4.4 Hz, 2H), 3.95 (s, 2H), 3.99 (dd, J = 4.7, 2.5 Hz, 2H), 4.61 (s, 2H), 6.84 (dd, J = 7.8, 1.6 Hz, 1H), 6.85 (td, J = 7.8, 1.6 Hz, 1H), 7.08 (td, J = 7.8, 1.6 Hz, 1H), 7.47 (dd, J = 7.8, 1.6 Hz, 1H), 7.84 (dd, J = 7.9, 2.1 Hz, 1H), 8.23 (dd, J = 7.9, 0.6 Hz, 1H), 8.52 (dd, J = 2.1, 0.6 Hz, 1H), 8.78 (s, 1H), 9.82 (s, 1H)

N-(2-Aminophenyl)-5-
[1-(2-dimethylaminoethyl)-3-
(2-methoxyethyl)ureidomethyl]pyridine-
2-carboxylic acid amide
(Compound No. 1-157)

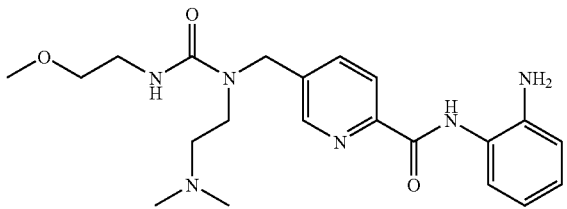

¹H-NMR (400 MHz, CDCl₃)
δ 2.26 (s, 6H), 2.41 (t, J = 4.8 Hz, 2H), 3.22 (t, J = 4.8 Hz, 2H), 3.36 (s, 3H), 3.42 (m, 2H), 3.49 (t, J = 4.8 Hz, 2H), 3.96 (s, 2H), 4.61 (s, 2H), 6.84 (dd, J = 7.7, 1.5 Hz, 1H), 6.86 (td, J = 7.7, 1.5 Hz, 1H), 7.09 (td, J = 7.7, 1.5 Hz, 1H), 7.48 (dd, J = 7.7, 1.5 Hz, 1H), 7.85 (dd, J = 8.0, 2.2 Hz, 1H), 8.05 (s, 1H), 8.23 (dd, J = 8.0, 0.5 Hz, 1H), 8.53 (dd, J = 2.2, 0.5 Hz, 1H), 9.83 (s, 1H)

N-(2-Aminophenyl)-5-
[1-(2-dimethylaminoethyl)-3-
(2-methylthioethyl)ureidomethyl]pyridine-
2-carboxylic acid amide
(Compound No. 1-158)

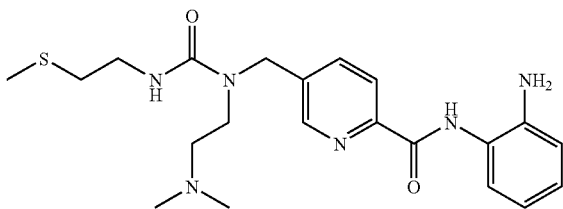

¹H-NMR (400 MHz, CDCl₃)
δ 2.13 (s, 3H), 2.28 (s, 6H), 2.42 (t, J = 4.8 Hz, 2H), 2.66 (t, J = 6.5 Hz, 2H), 3.23 (t, J = 4.6 Hz, 2H), 3.44 (m, 2H), 3.96 (s, 2H), 4.61 (s, 2H), 6.84 (dd, J = 7.7, 1.5 Hz, 1H), 6.86 (td, J = 7.7, 1.5 Hz, 1H), 7.08 (td, J = 7.7, 1.5 Hz, 1H), 7.48 (dd, J = 7.7, 1.5 Hz, 1H), 7.85 (dd, J = 8.0, 2.2 Hz, 1H), 8.08 (m, 1H), 8.23 (dd, J = 8.0, 0.7 Hz, 1H), 8.53 (dd, J = 2.2, 0.7 Hz, 1H), 9.82 (s, 1H)

| | |
|---|---|
| N-(2-Aminophenyl)-5-[1-(2-dimethylaminoethyl)-3-methylaminocarbonylmethylureidomethyl]pyridine-2-carboxylic acid amide (Compound No. 1-159) 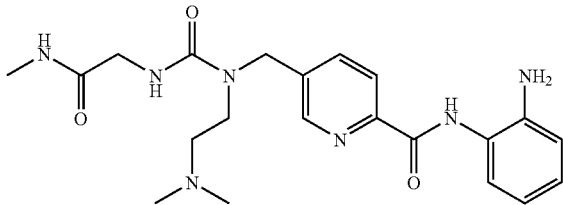 | ¹H-NMR (400 MHz, CDCl₃) δ 2.30 (s, 6H), 2.47 (br s, 2H), 2.84 (d, J = 4.9 Hz, 3H), 3.28 (br s, 2H), 3.86 (d, J = 5.6 Hz, 2H), 3.96 (s, 2H), 4.63 (s, 2H), 6.52 (s, 1H), 6.85 (dd, J = 7.7, 1.5 Hz, 1H), 6.86 (td, J = 7.7, 1.5 Hz, 1H), 7.09 (td, J = 7.7, 1.5 Hz, 1H), 7.50 (dd, J = 7.7, 1.5 Hz, 1H), 7.83 (dd, J = 8.0, 2.0 Hz, 1H), 8.24 (d, J = 8.0 Hz, 1H), 8.53 (d, J = 2.0 Hz, 1H), 8.63 (s, 1H), 9.82 (s, 1H) |
| N-(2-Aminophenyl)-5-[3-cyclopropyl-1-(2-dimethylaminoethyl)ureidomethyl]pyridine-2-carboxylic acid amide (Compound No. 1-160) 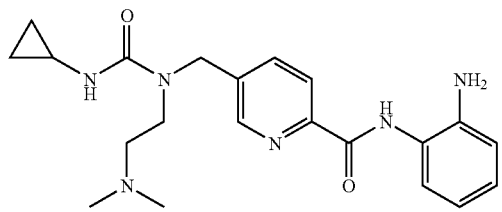 | ¹H-NMR (400 MHz, CDCl₃) δ 0.39 (m, 2H), 0.71 (m, 2H), 2.24 (s, 6H), 2.38 (t, J = 4.5 Hz, 2H), 2.70 (m, 1H), 3.15 (t, J = 4.5 Hz, 2H), 3.96 (s, 2H), 4.60 (s, 2H), 6.84 (dd, J = 7.7, 1.5 Hz, 1H), 6.86 (td, J = 7.7, 1.5 Hz, 1H), 7.09 (td, J = 7.7, 1.5 Hz, 1H), 7.49 (dd, J = 7.7, 1.5 Hz, 1H), 7.86 (dd, J = 8.0, 2.2 Hz, 1H), 8.23 (dd, J = 8.0, 0.7 Hz, 1H), 8.24 (s, 1H), 8.53 (dd, J = 2.2, 0.7 Hz, 1H), 9.83 (s, 1H) |
| N-(2-Aminophenyl)-5-[1-(2-dimethylaminoethyl)-3-[2-(pyridin-4-yl)ethyl]ureidomethyl]pyridine-2-carboxylic acid amide (Compound No. 1-161) 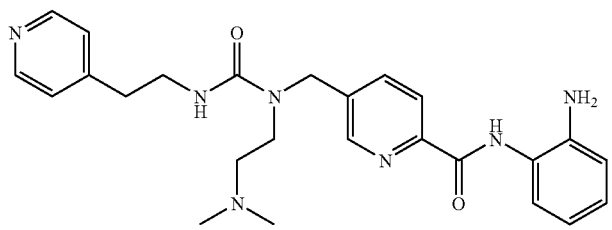 | ¹H-NMR (400 MHz, CDCl₃) δ 2.05 (s, 6H), 2.32 (t, J = 4.5 Hz, 2H), 2.86 (t, J = 6.8 Hz, 2H), 3.13 (t, J = 4.5 Hz, 2H), 3.54 (m, 2H), 3.99 (s, 2H), 4.58 (s, 2H), 6.85 (dd, J = 7.7, 1.4 Hz, 1H), 6.87 (td, J = 7.7, 1.4 Hz, 1H), 7.08 (td, J = 7.7, 1.4 Hz, 1H), 7.17 (d, J = 6.1 Hz, 2H), 7.50 (dd, J = 7.7, 1.4 Hz, 1H), 7.82 (dd, J = 7.9, 2.1 Hz, 1H), 7.97 (s, 1H), 8.23 (dd, J = 7.9, 0.6 Hz, 1H), 8.49 (dd, J = 2.1, 0.6 Hz, 1H), 8.54 (d, J = 6.1 Hz, 2H), 9.83 (s, 1H) |
| N-(2-Aminophenyl)-5-[1-(2-dimethylaminoethyl)-3-[2-(indol-3-yl)ethyl]ureidomethyl]pyridine-2-carboxylic acid amide (Compound No. 1-162) 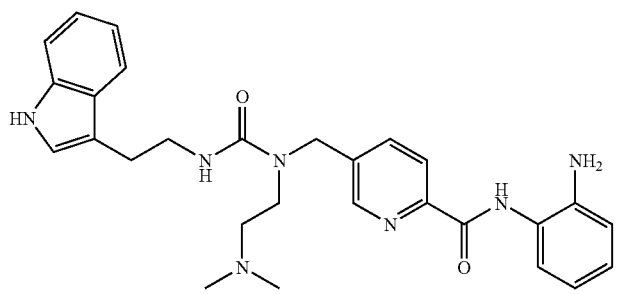 | ¹H-NMR (400 MHz, CDCl₃) δ 1.97 (s, 6H), 2.27 (t, J = 4.9 Hz, 2H), 3.00 (t, J = 6.7 Hz, 2H), 3.13 (t, J = 4.9 Hz, 2H), 3.61 (m, 2H), 3.97 (s, 2H), 4.59 (s, 2H), 6.85 (dd, J = 7.7, 1.5 Hz, 1H), 6.87 (td, J = 7.7, 1.5 Hz, 1H), 7.03 (d, J = 2.2 Hz, 1H), 7.09 (td, J = 7.7, 1.5 Hz, 1H), 7.11 (t, J = 7.5 Hz, 1H), 7.19 (t, J = 7.5 Hz, 1H), 7.35 (d, J = 7.5 Hz, 1H), 7.49 (dd, J = 7.7, 1.5 Hz, 1H), 7.54 (s, 1H), 7.63 (d, J = 7.5 Hz, 1H), 7.79 (dd, J = 8.0, 2.2 Hz, 1H), 8.03 (s, 1H), 8.21 (dd, J = 8.0, 0.6 Hz, 1H), 8.50 (dd, J = 2.2, 0.6 Hz, 1H), 9.84 (s, 1H) |

| | |
|---|---|
| N-(2-Aminophenyl)-5-[3-isopropyl-1-[2-(4-methylpiperazin-1-yl)ethyl]ureidomethyl]pyridine-2-carboxylic acid amide (Compound No. 1-163) 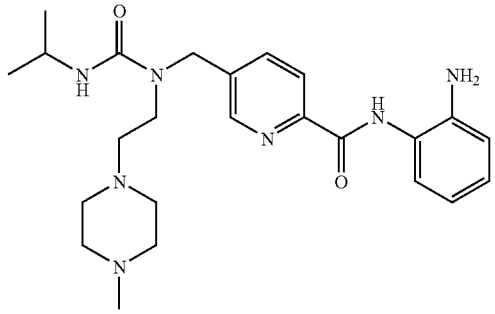 | $^1$H-NMR (400 MHz, CDCl$_3$) δ 1.22 (d, J = 6.6 Hz, 6H), 2.30 (s, 3H), 2.45 (t, J = 4.5 Hz, 2H), 2.47 (br s, 4H), 2.55 (br s, 4H), 3.21 (t, J = 4.5 Hz, 2H), 3.96 (br s, 2H), 3.98 (m, 1H), 4.59 (s, 2H), 6.84-6.88 (m, 2H), 7.04 (d, J = 7.7Hz, 1H), 7.09 (t, J = 7.7 Hz, 1H), 7.48 (d, J = 7.7 Hz, 1H), 7.84 (dd, J = 8.0, 2.0 Hz, 1H), 8.23 (d, J = 8.0 Hz, 1H), 8.52 (d, J = 2.0 Hz, 1H), 9.82 (s, 1H) |
| N-(2-Aminophenyl)-5-[1-[2-(4-methylpiperazin-1-yl)ethyl]-3-phenethylureidomethyl]pyridine-2-carboxylic acid amide (Compound No. 1-164) 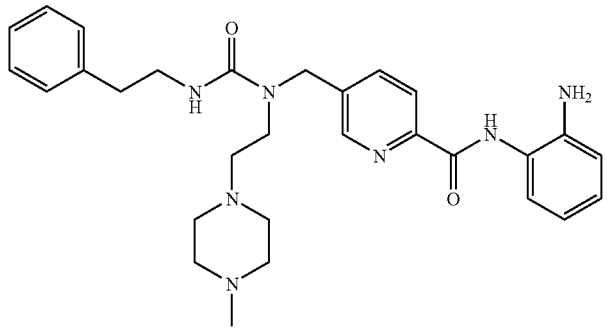 | $^1$H-NMR (400 MHz, CDCl$_3$) δ 2.21 (br s, 4H), 2.24 (s, 3H), 2.36 (br s, 4H), 2.39 (t, J = 4.5 Hz, 2H), 2.88 (t, J = 6.8 Hz, 2H), 3.16 (t, J = 4.5 Hz, 2H), 3.49 (m, 2H), 3.97 (br s, 2H), 4.60 (s, 2H), 6.84-6.89 (m, 2H), 7.09 (td, J = 7.6, 1.5 Hz, 1H), 7.20-7.32 (m, 5H), 7.49 (d, J = 7.6 Hz, 1H), 7.74 (br s, 1H), 7.82 (dd, J = 8.0, 2.1 Hz, 1H), 8.24 (d, J =8.0 Hz, 1H), 8.52 (d, J = 2.1 Hz, 1H), 9.83 (s, 1H) |
| N-(2-Aminophenyl)-5-[3-(4-methylphenyl)-1-[2-(4-methylpiperazin-1-yl)ethyl]ureidomethyl]pyridine-2-carboxylic acid amide (Compound No. 1-165) 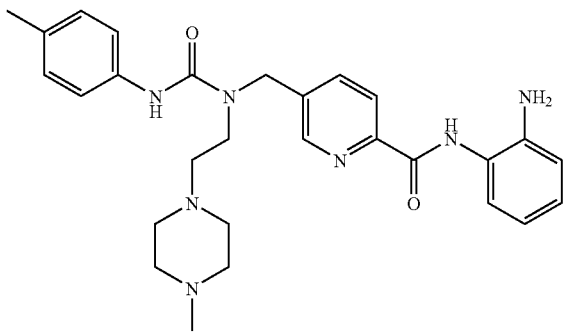 | $^1$H-NMR (400 MHz, CDCl$_3$) δ 2.31 (s, 3H), 2.32 (s, 3H), 2.53 (br s, 4H), 2.57 (t, J = 4.3 Hz, 2H), 2.65 (br s, 4H), 3.37 (t, J = 4.3 Hz, 2H), 3.95 (br s, 2H), 4.66 (s, 2H), 6.84-6.88 (m, 2H), 7.09 (td, J = 7.8, 1.5 Hz, 1H), 7.13 (d, J = 8.3 Hz, 2H), 7.35 (d, J = 8.3 Hz, 2H), 7.49 (d, J = 7.8 Hz, 1H), 7.92 (dd, J = 8.0, 2.2 Hz, 1H), 8.25 (d, J = 8.0 Hz, 1H), 8.59 (d, J = 2.2 Hz, 1H), 9.83 (s, 1H), 9.88 (s, 1H) |

N-(2-Aminophenyl)-5-
[3-isopropyl-1-
[3-(4-methylpiperazin-1-yl)propyl]ureidomethyl]pyridine-
2-carboxylic acid amide
(Compound No. 1-166)

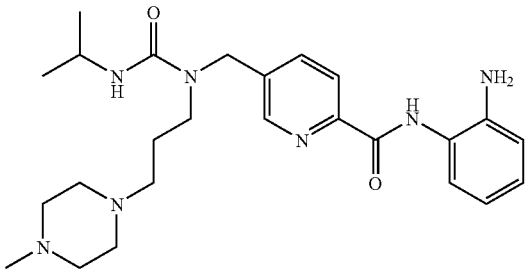

$^1$H-NMR (400 MHz, CDCl$_3$)
δ 1.21 (d, J = 6.6 Hz, 6H), 1.67
(m, 2H), 2.31 (s, 3H), 2.36 (t, J =
6.1 Hz, 2H), 2.48 (br s, 8H), 3.19
(t, J = 5.9 Hz, 2H), 3.96 (br s,
2H), 4.01 (m, 1H), 4.56 (s, 2H),
6.04 (d, J = 8.0 Hz, 1H),
6.83-6.87 (m, 2H), 7.08 (td, J =
7.8, 1.5 Hz, 1H), 7.48 (d, J = 7.8
Hz, 1H), 7.84 (dd, J = 8.0, 2.2
Hz, 1H), 8.22 (d, J = 8.0 Hz, 1H),
8.53 (d, J = 2.2 Hz, 1H), 9.82 (s,
1H)

N-(2-Aminophenyl)-5-
[1-[3-(4-methylpiperazin-1-yl)propyl]-3-
phenethylureidomethyl]pyridine-
2-carboxylic acid amide
(Compound No. 1-167)

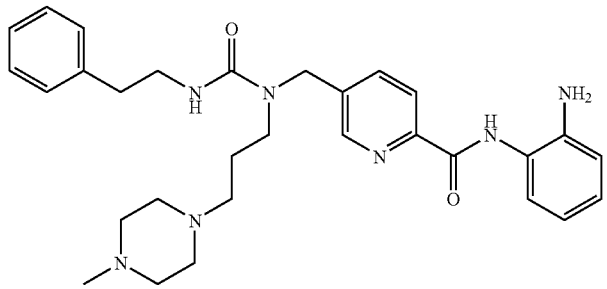

$^1$H-NMR (400 MHz, CDCl$_3$)
δ 1.60 (m, 2H), 2.26 (s, 3H), 2.31
(t, J = 6.0 Hz, 2H), 2.33 (br s,
8H), 2.87 (t, J = 7.0 Hz, 2H),
3.14 (t, J = 5.7 Hz, 2H), 3.49 (m,
2H), 3.96 (br s, 2H), 4.58 (s, 2H),
6.84-6.88 (m, 2H), 7.08 (td, J =
7.6, 1.4 Hz, 1H), 7.20-7.35 (m,
6H), 7.49 (d, J = 7.6 Hz, 1H),
7.79 (dd, J = 8.0, 2.2 Hz, 1H),
8.23 (d, J = 8.0 Hz, 1H), 8.52 (d,
J = 2.2 Hz, 1H), 9.84 (s, 1H)

N-(2-Aminophenyl)-5-
[3-(4-methylphenyl)-1-
[3-(4-methylpiperazin-1-yl)propyl]ureidomethyl]pyridine-
2-carboxylic acid amide
(Compound No. 1-168)

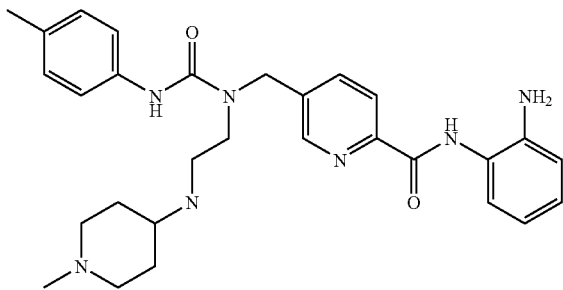

$^1$H-NMR (400 MHz, CDCl$_3$)
δ 1.77 (m, 2H), 2.25 (s, 3H), 2.32
(s, 3H), 2.42 (br s, 4H), 2.48 (t, J =
5.9 Hz, 2H), 2.49 (br s, 4H),
3.37 (t, J = 5.6 Hz, 2H), 3.95 (br
s, 2H), 4.64 (s, 2H), 6.83-6.88
(m, 2H), 7.08 (td, J = 7.8, 1.5 Hz,
1H), 7.12 (d, J = 8.3 Hz, 2H),
7.33 (d, J = 8.3 Hz, 2H), 7.48 (d,
J = 7.8 Hz, 1H), 7.92 (dd, J =
8.0, 2.2 Hz, 1H), 8.23 (d, J = 8.0
Hz, 1H), 8.59 (d, J = 2.2 Hz, 1H),
8.99 (s, 1H), 9.83 (s, 1H)

N-(2-Aminophenyl)-5-
[1-[2-(4-methylpiperazin-1-yl)ethyl]-3-
(1,3-thiazol-2-yl)ureidomethyl]pyridine-
2-carboxylic acid amide
(Compound No. 1-169)

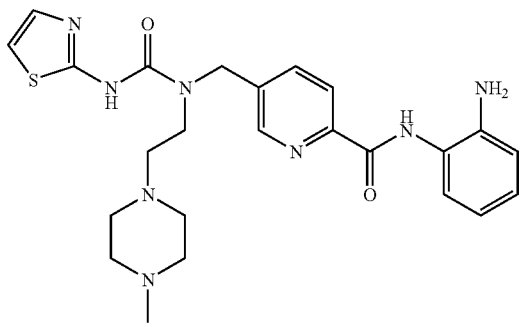

$^1$H-NMR (500 MHz, CDCl$_3$)
δ 2.37 (s, 3H), 2.58 (t, J = 4.3
Hz, 2H), 2.69 (br s, 4H), 2.75 (br
s, 4H), 3.37 (t, J = 4.3 Hz, 2H),
3.96 (br s, 2H), 4.70 (s, 2H),
6.83-6.86 (m, 2H), 6.87 (d, J =
3.7 Hz, 1H), 7.08 (td, J = 7.9, 1.2
Hz, 1H), 7.38 (d, J = 3.7 Hz, 1H),
7.48 (d, J = 7.9 Hz, 1H), 7.88
(dd, J = 8.1, 2.0 Hz, 1H), 8.25 (d,
J = 8.1 Hz, 1H), 8.57 (d, J = 2.0
Hz, 1H), 9.81 (s, 1H), 13.17 (br
s, 1H)

| | |
|---|---|
| N-(2-Aminophenyl)-5-[1-[3-(4-methylpiperazin-1-yl)propyl]-3-(1,3-thiazol-2-yl)ureidomethyl]pyridine-2-carboxylic acid amide (Compound No. 1-170) 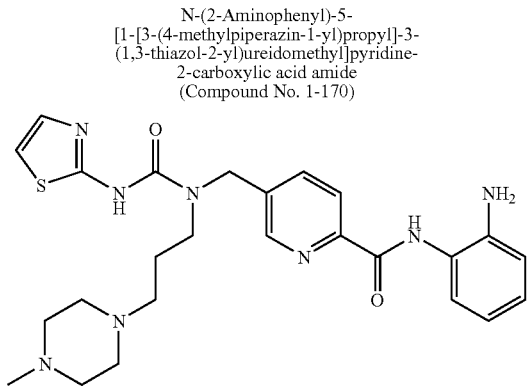 | ¹H-NMR (500 MHz, CDCl₃) δ 1.79 (m, 2H), 2.39 (s, 3H), 2.45 (t, J = 6.1 Hz, 2H), 2.56 (br s, 4H), 2.76 (br s, 4H), 3.40 (t, J = 5.7 Hz, 2H), 3.95 (br s, 2H), 4.67 (s, 2H), 6.84-6.86 (m, 2H), 6.87 (d, J = 3.7 Hz, 1H), 7.09 (m, 1H), 7.37 (d, J = 3.7 Hz, 1H), 7.48 (d, J = 7.9 Hz, 1H), 7.90 (dd, J = 8.1, 2.0 Hz, 1H), 8.25 (d, J = 8.1 Hz, 1H), 8.59 (d, J = 1.8 Hz, 1H), 9.82 (s, 1H), 11.65 (br s, 1H) |
| N-(2-Aminophenyl)-5-[1-[4-(morpholin-4-yl)butyl]-3-(1,3-thiazol-2-yl)ureidomethyl]pyridine-2-carboxylic acid amide (Compound No. 1-171) 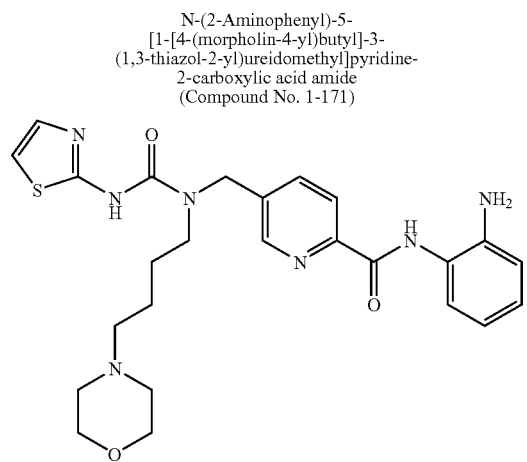 | ¹H-NMR (500 MHz, CDCl₃) δ 1.49 (m, 2H), 1.67 (m, 2H), 2.37 (t, J = 6.9 Hz, 2H), 2.45 (br s, 4H), 3.35 (t, J = 8.1 Hz, 2H), 3.75 (t, J = 4.6 Hz, 4H), 3.97 (br s, 2H), 4.71 (s, 2H), 6.83-6.88 (m, 3H), 7.08 (td, J = 7.7, 1.5 Hz, 1H), 7.32 (d, J = 3.7 Hz, 1H), 7.50 (dd, J = 7.7, 1.5 Hz, 1H), 7.83 (dd, J = 8.1, 2.0 Hz, 1H), 8.25 (d, J = 8.1 Hz, 1H), 8.52 (d, J = 2.0 Hz, 1H), 9.03 (br s, 1H), 9.80 (s, 1H) |
| N-(2-Aminophenyl)-5-[1-[3-(4-methylpiperazin-1-yl)propyl]-3-phenethylureidomethyl]pyridine-2-carboxylic acid amide (Compound No. 1-172) 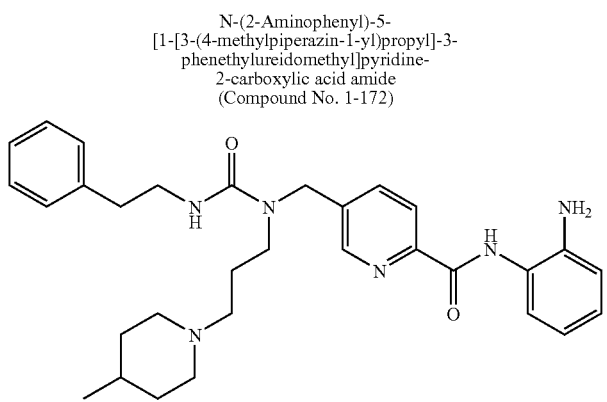 | ¹H-NMR (500 MHz, CDCl₃) δ 0.92 (d, J = 6.4 Hz, 3H), 1.00 (m, 2H), 1.36 (m, 1H), 1.57-1.63 (m, 4H), 1.83 (t, J = 11.6 Hz, 2H), 2.27 (t, J = 6.0 Hz, 2H), 2.70 (d, J = 11.6 Hz, 2H), 2.85 (t, J = 7.0 Hz, 2H), 3.14 (t, J = 5.7 Hz, 2H), 3.47 (m, 2H), 3.97 (br s, 2H), 4.57 (s, 2H), 6.84-6.87 (m, 2H), 7.08 (td, J = 7.7, 1.2 Hz, 1H), 7.20-7.23 (m, 3H), 7.26-7.31 (m, 2H), 7.49 (d, J = 7.7 Hz, 1H), 7.67 (br s, 1H), 7.78 (dd, J = 8.2, 1.8 Hz, 1H), 8.22 (d, J = 8.2 Hz, 1H), 8.51 (d, J = 1.8 Hz, 1H), 9.84 (s, 1H) |

N-(2-Aminophenyl)-5-[1-[5-(morpholin-4-yl)pentyl]-3-phenethylureidomethyl]pyridine-2-carboxylic acid amide
(Compound No. 1-173)

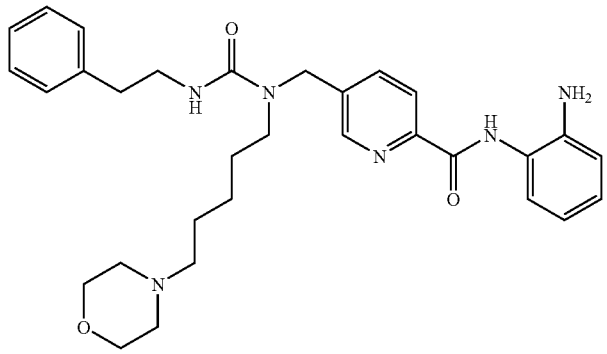

$^1$H-NMR (500 MHz, CDCl$_3$)
δ 1.20 (m, 2H), 1.39-1.47 (m, 4H), 2.26 (t, J = 7.5 Hz, 2H), 2.40 (br s, 4H), 2.84 (t, J = 6.7 Hz, 2H), 3.07 (t, J = 7.6 Hz, 2H), 3.54 (m, 2H), 3.70 (t, J = 4.6 Hz, 4H), 3.97 (br s, 2H), 4.38 (t, J = 5.5 Hz, 1H), 4.55 (s, 2H), 6.84-6.88 (m, 2H), 7.09 (t, J = 7.7 Hz, 1H), 7.17 (d, J = 7.3 Hz, 2H), 7.22 (t, J = 7.3 Hz, 1H), 7.29 (t, J = 7.3 Hz, 2H), 7.49 (d, J = 7.7 Hz, 1H), 7.72 (dd, J = 7.9, 1.8 Hz, 1H), 8.21 (d, J = 7.9 Hz, 1H), 8.46 (d, J = 1.8 Hz, 1H), 9.82 (s, 1H)

N-(2-Aminophenyl)-5-[1-[3-(4-methylpiperidin-1-yl)propyl]-3-(1,3-thiazol-2-yl)ureidomethyl]pyridine-2-carboxylic acid amide
(Compound No. 1-174)

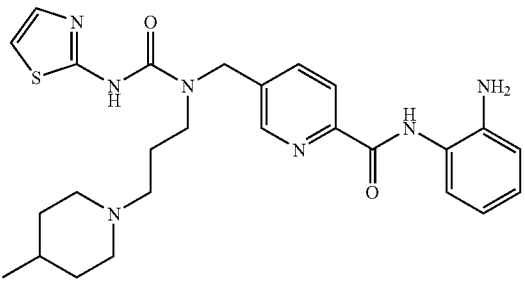

$^1$H-NMR (400 MHz, CDCl$_3$)
δ 1.00 (d, J = 6.6 Hz, 3H), 1.44 (m, 1H), 1.57 (m, 2H), 1.75-1.85 (m, 4H), 2.00 (t, J = 11.7 Hz, 2H), 2.39 (t, J = 6.1 Hz, 2H), 2.90 (d, J = 11.7 Hz, 2H), 3.39 (t, J = 5.6 Hz, 2H), 3.95 (br s, 2H), 4.66 (s, 2H), 6.83-6.88 (m, 3H), 7.08 (td, J = 7.7, 1.5 Hz, 1H), 7.36 (d, J = 3.7 Hz, 1H), 7.48 (d, J = 7.7 Hz, 1H), 7.90 (dd, J = 8.0, 2.2 Hz, 1H), 8.25 (d, J = 8.0 Hz, 1H), 8.59 (d, J = 2.2 Hz, 1H), 9.82 (s, 1H)

N-(2-Aminophenyl)-6-[1-(2-dimethylaminoethyl)-3-(3-methoxyphenyl)ureidomethyl]pyridine-3-carboxylic acid amide
(Compound No. 1-175)

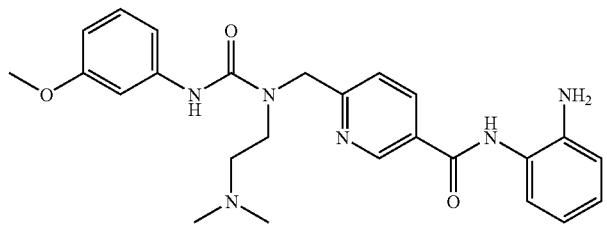

$^1$H-NMR (500 MHz, CDCl$_3$)
δ 2.40 (s, 6H), 2.59 (t, J = 4.2 Hz, 2H), 3.46 (t, J = 4.2 Hz, 2H), 3.79 (s, 3H), 3.85 (s, 2H), 4.72 (s, 2H), 6.54 (dd, J = 8.1, 1.9 Hz, 1H), 6.83 (dd, J = 8.1, 1.9 Hz, 1H), 6.86 (t, J = 7.6 Hz, 1H), 6.87 (m, 1H), 7.10 (dd, J = 7.6, 1.2 Hz, 1H), 7.13 (t, J = 1.9 Hz, 1H), 7.16 (t, J = 8.1 Hz, 1H), 7.37 (d, J = 7.6 Hz, 1H), 7.55 (d, J = 7.9 Hz, 1H), 8.02 (s, 1H), 8.17 (d, J = 7.9 Hz, 1H), 9.04 (s, 1H), 11.08 (s, 1H)

N-(2-Aminophenyl)-5-[1-(2-dimethylaminoethyl)-3-(5,5-dimethyl-4,5-dihydro-1,3-thiazol-4-on-2-yl)ureidomethyl]pyridine-2-carboxylic acid amide
(Compound No. 1-176)

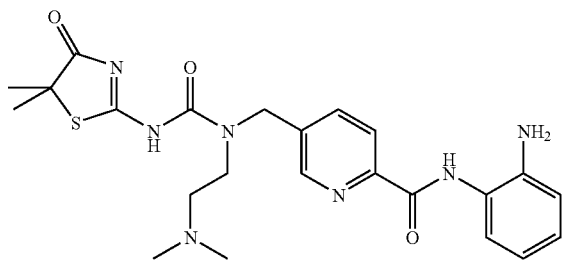

$^1$H-NMR (500 MHz, CDCl$_3$)
δ 2.16 (s, 6H), 2.32 (s, 6H), 2.50 (m, 2H), 3.47 (m, 2H), 3.92 (br s, 2H), 4.70 (s, 2H), 6.84 (dd, J = 7.7, 1.4 Hz, 1H), 6.85 (td, J = 7.7, 1.4 Hz, 1H), 7.08 (td, J = 7.7, 1.4 Hz, 1H), 7.47 (dd, J = 7.7, 1.4 Hz, 1H), 7.75 (s, 1H), 7.85 (dd, J = 7.9, 1.7 Hz, 1H), 8.24 (d, J = 8.1 Hz, 1H), 8.54 (d, J = 1.7 Hz, 1H), 9.80 (s, 1H)

N-(2-Aminophenyl)-5-
[3-(4,5-dihydro-1,3-thiazol-2-yl)-1-
(2-dimethylaminoethyl)ureidomethyl]pyridine-
2-carboxylic acid amide
(Compound No. 1-177)

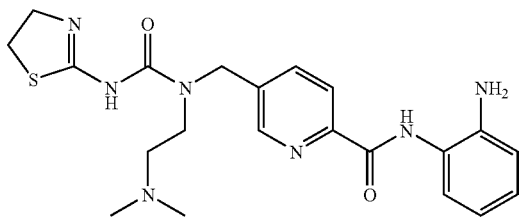

¹H-NMR (400 MHz, CDCl₃)
δ 2.24 (s, 6H), 2.46 (m, 2H), 3.24 (t, J = 7.4 Hz, 2H), 3.44 (m, 1H), 3.58 (m, 1H), 3.76 (m, 2H), 3.96 (s, 2H), 4.70 (m, 1H), 4.89 (m, 1H), 6.84 (m, 1H), 6.86 (td, J = 7.6, 1.4 Hz, 1H), 7.09 (td, J = 7.6, 1.4 Hz, 1H), 7.50 (dd, J = 7.6, 1.4 Hz, 1H), 7.83 (m, 1H), 8.22 (dd, J = 7.9, 0.6 Hz, 1H), 8.53 (m, 1H), 9.84 (s, 1H)

N-(2-Aminophenyl)-5-
[3-(bicyclo[2.2.1]heptan-2-yl)-1-
(2-dimethylaminoethyl)ureidomethyl]pyridine-
2-carboxylic acid amide
(Compound No. 1-178)

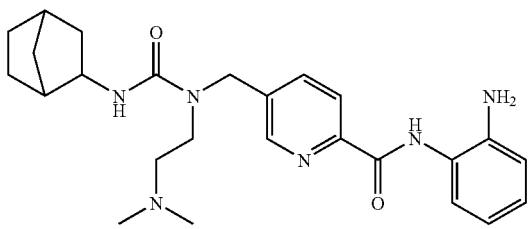

¹H-NMR (500 MHz, CDCl₃)
δ 0.69 (m, 1H), 1.16 (m, 1H), 1.32 (m, 1H), 1.40-1.47 (m, 2H), 1.58-1.61 (m, 2H), 2.07 (m, 1H), 2.20 (t, J = 4.1 Hz, 1H), 2.28 (s, 6H), 2.39 (m, 1H), 2.45 (t, J = 4.4 Hz, 2H), 3.21 (m, 2H), 3.96 (s, 2H), 4.02 (m, 1H), 4.53 (d, J = 15.6 Hz, 1H), 4.65 (d, J = 15.6 Hz, 1H), 6.84 (dd, J = 7.7, 1.4 Hz, 1H), 6.86 (td, J = 7.7, 1.4 Hz, 1H), 7.08 (td, J = 7.7, 1.4 Hz, 1H), 7.48 (dd, J = 7.7, 1.4 Hz, 1H), 7.85 (dd, J = 7.9, 1.8 Hz, 1H), 8.04 (d, J = 6.1 Hz, 1H), 8.23 (d, J = 7.9 Hz, 1H), 8.53 (d, J = 1.8 Hz, 1H), 9.83 (s, 1H)

N-(2-Aminophenyl)-5-
[1-(2-dimethylaminoethyl)-3-
(5-nitro-1,3-thiazol-2-yl)ureidomethyl]pyridine-
2-carboxylic acid amide
(Compound No. 1-179)

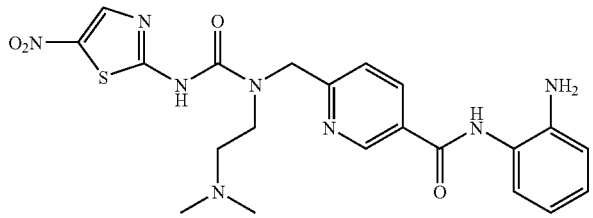

¹H-NMR (400 MHz, DMSO-d₆)
δ 2.79 (s, 6H), 3.17 (s, 2H), 3.70 (s, 2H), 4.69 (s, 2H), 4.88 (s, 2H), 6.65 (td, J = 7.8, 1.3 Hz, 1H), 6.82 (dd, J = 7.8, 1.3 Hz, 1H), 6.95 (td, J = 7.8, 1.3 Hz, 1H), 7.51 (dd, J = 7.8, 1.3 Hz, 1H), 7.70 (s, 1H), 7.94 (dd, J = 8.0, 1.9 Hz, 1H), 8.11 (dd, J = 8.0, 0.6 Hz, 1H), 8.40 (br s, 1H), 8.66 (dd, J = 1.9, 0.6 Hz, 1H), 10.03 (s, 1H)

N-(2-Aminophenyl)-5-
[1-[5-(morpholin-4-yl)pentyl]-3-
(pyrrolidin-1-yl)ureidomethyl]pyridine-
2-carboxylic acid amide
(Compound No. 1-180)

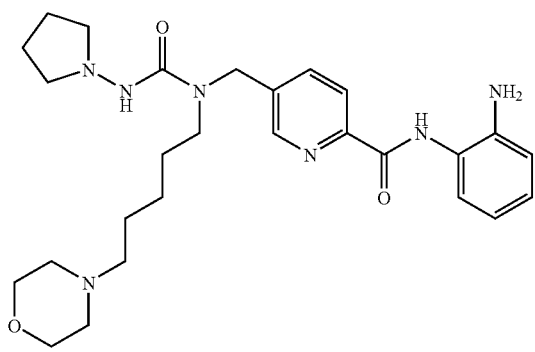

¹H-NMR (500 MHz, CDCl₃)
δ 1.30 (m, 2H), 1.50 (m, 2H), 1.60 (m, 2H), 1.78 (m, 4H), 2.31 (t, J = 7.6 Hz, 2H), 2.42 (m, 4H), 2.83 (m, 4H), 3.21 (t, J = 7.6 Hz, 2H), 3.71 (t, J = 4.6 Hz, 4H), 3.96 (s, 2H), 4.61 (s, 2H), 5.07 (s, 1H), 6.85 (dd, J = 7.7, 1.4 Hz, 1H), 6.87 (td, J = 7.7, 1.4 Hz, 1H), 7.09 (td, J = 7.7, 1.4 Hz, 1H), 7.48 (dd, J = 7.7, 1.4 Hz, 1H), 7.83 (dd, J = 7.9, 2.0 Hz, 1H), 8.24 (d, J = 7.9 Hz, 1H), 8.52 (d, J = 2.0 Hz, 1H), 9.82 (s, 1H)

N-(2-Aminophenyl)-5-
[3-(4-methoxyphenyl)-1-
[5-(morpholin-4-yl)pentyl]ureidomethyl]pyridine-
2-carboxylic acid amide
(Compound No. 1-181)

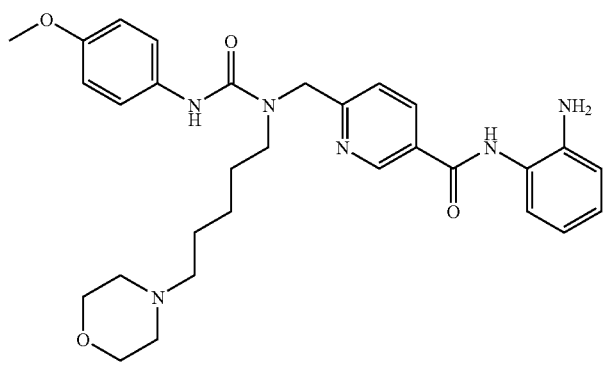

¹H-NMR (500 MHz, CDCl₃)
δ 1.36 (m, 2H), 1.53 (m, 2H),
1.68 (m, 2H), 2.32 (t, J = 7.6 Hz,
2H), 2.42 (s, 4H), 3.31 (t, J = 7.6
Hz, 2H), 3.68 (t, J = 4.7 Hz, 4H),
3.79 (s, 3H), 3.96 (s, 2H), 4.68
(s, 2H), 6.26 (s, 1H), 6.85 (d, J =
8.9 Hz, 2H), 6.84-6.88 (m, 2H),
7.09 (td, J = 7.8, 1.4 Hz, 1H),
7.26 (d, J = 8.9 Hz, 2H), 7.49
(dd, J = 7.8, 1.4 Hz, 1H), 7.87
(dd, J = 8.1, 2.0 Hz, 1H), 8.26 (d,
J = 8.1 Hz, 1H), 8.58 (d, J = 2.0
Hz, 1H), 9.82 (s, 1H)

N-(2-Aminophenyl)-5-
[3-(4-benzyloxyphenyl)-1-
[5-(morpholin-4-yl)pentyl]ureidomethyl]pyridine-
2-carboxylic acid amide
(Compound No. 1-182)

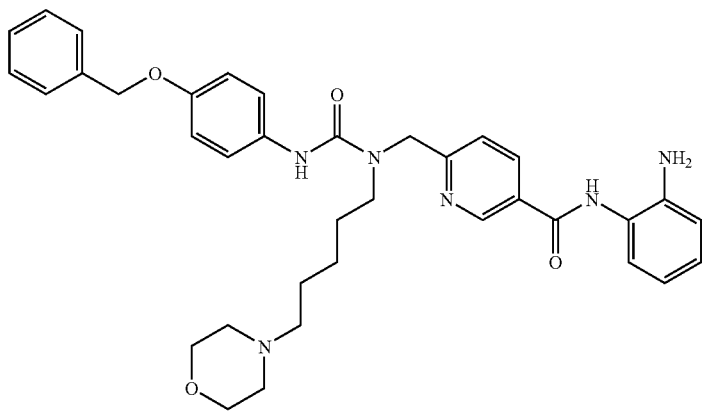

¹H-NMR (500 MHz, CDCl₃)
δ 1.38 (m, 2H), 1.53 (m, 2H),
1.68 (m, 2H), 2.32 (t, J = 7.6 Hz,
2H), 2.42 (m, 4H), 3.31 (t, J =
7.6 Hz, 2H), 3.70 (t, J = 4.6 Hz,
4H), 3.95 (s, 2H), 4.68 (s, 2H),
5.05 (s, 2H), 6.24 (s, 1H), 6.85
(dd, J = 7.8, 1.4 Hz, 1H), 6.86
(td, J = 7.8, 1.4 Hz, 1H), 6.93 (d,
J = 8.9 Hz, 2H), 7.09 (td, J = 7.8,
1.4 Hz, 1H), 7.25 (d, J = 8.9 Hz,
2H), 7.32 (m, 1H), 7.38 (d, J =
7.0 Hz, 2H), 7.42 (d, J = 7.0 Hz,
2H), 7.49 (dd, J = 7.8, 1.4 Hz,
1H), 7.87 (dd, J = 8.1, 2.0 Hz,
1H), 8.26 (d, J = 8.1 Hz, 1H),
8.58 (d, J = 2.0 Hz, 1H), 9.82 (s,
1H)

N-(2-Aminophenyl)-5-
[3-(2-methoxyphenyl)-1-
[5-(morpholin-4-yl)pentyl]ureidomethyl]pyridine-
2-carboxylic acid amide
(Compound No. 1-183)

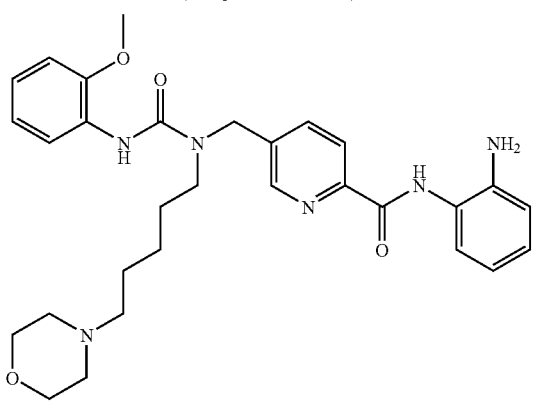

¹H-NMR (400 MHz, CDCl₃)
δ 1.40 (m, 2H), 1.55 (m, 2H),
1.71 (m, 2H), 2.33 (t, J = 7.6 Hz,
2H), 2.42 (m, 4H), 3.36 (t, J =
7.6 Hz, 2H), 3.71 (t, J = 4.6 Hz,
4H), 3.83 (s, 3H), 3.96 (s, 2H),
4.70 (s, 2H), 6.85 (dd, J = 7.7,
1.4 Hz, 1H), 6.85 (m, 1H), 6.87
(td, J = 7.7, 1.4 Hz, 1H),
6.95-7.00 (m, 2H), 7.09 (td, J =
7.7, 1.4 Hz, 1H), 7.16 (s, 1H),
7.49 (dd, J = 7.7, 1.4 Hz, 1H),
7.89 (dd, J = 8.0, 2.2 Hz, 1H),
8.17 (m, 1H), 8.27 (d, J = 8.0, 0.7
Hz, 1H), 8.60 (dd, J = 2.2, 0.7
Hz, 1H), 9.83 (s, 1H)

| | |
|---|---|
| N-(2-Aminophenyl)-5-[1-[3-(morpholin-4-yl)propyl]-3-(pyrrolidin-1-yl)ureidomethyl]pyridine-2-carboxylic acid amide (Compound No. 1-184)<br>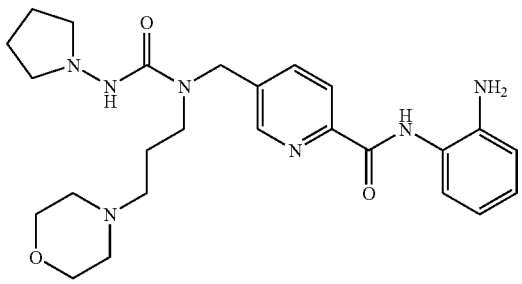 | ¹H-NMR (500 MHz, CDCl₃) δ 1.70 (m, 2H), 1.83-1.88 (m, 4H), 2.38 (t, J = 6.1 Hz, 2H), 2.47 (br s, 4H), 2.98 (br s, 4H), 3.21 (t, J = 6.0 Hz, 2H), 3.78 (t, J = 4.6 Hz, 4H), 3.96 (br s, 2H), 4.56 (s, 2H), 6.83-6.88 (m, 2H), 7.09 (td, J = 7.8, 1.4 Hz, 1H), 7.48 (dd, J = 7.8, 1.4 Hz, 1H), 7.71 (s, 1H), 7.91 (dd, J = 7.9, 2.0 Hz, 1H), 8.23 (d, J = 7.9 Hz, 1H), 8.55 (d, J = 2.0 Hz, 1H), 9.83 (s, 1H) |
| N-(2-Aminophenyl)-5-[3-(morpholin-4-yl)-1-[3-(morpholin-4-yl)propyl]ureidomethyl]pyridine-2-carboxylic acid amide (Compound No. 1-185)<br>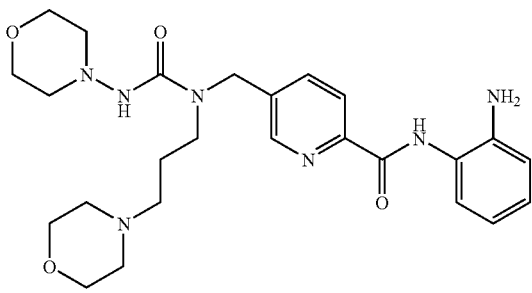 | ¹H-NMR (500 MHz, CDCl₃) δ 1.72 (m, 2H), 2.39 (t, J = 6.0 Hz, 2H), 2.49 (br s, 4H), 2.97 (t, J = 4.6 Hz, 4H), 3.21 (t, J = 6.0 Hz, 2H), 3.77-3.84 (m, 8H), 3.96 (br s, 2H), 4.55 (s, 2H), 6.83-6.88 (m, 2H), 7.09 (td, J = 7.8, 1.5 Hz, 1H), 7.48 (dd, J = 7.8, 1.5 Hz, 1H), 7.90 (dd, J = 7.9, 2.0 Hz, 1H), 7.94 (br s, 1H), 8.23 (d, J = 7.9 Hz, 1H), 8.55 (d, J = 2.0 Hz, 1H), 9.82 (s, 1H) |
| N-(2-Aminophenyl)-5-[3-(1-methylpiperidin-4-yl)-1-[3-(morpholin-4-yl)propyl]ureidomethyl]pyridine-2-carboxylic acid amide (Compound No. 1-186)<br>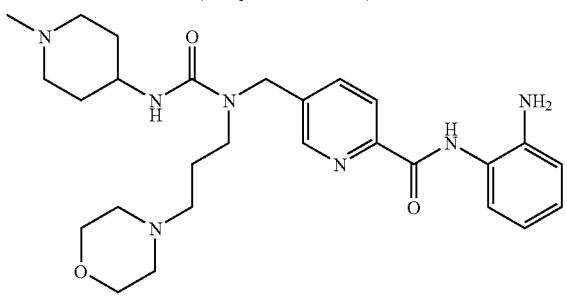 | ¹H-NMR (500 MHz, CDCl₃) δ 1.48 (qd, J = 11.9, 3.7 Hz, 2H), 1.71 (m, 2H), 1.96 (d, J = 11.9 Hz, 2H), 2.04-2.11 (m, 2H), 2.27 (s, 3H), 2.37 (t, J = 6.3 Hz, 2H), 2.44 (br s, 4H), 2.84 (d, J = 11.9 Hz, 2H), 3.22 (t, J = 6.1 Hz, 2H), 3.66 (m, 1H), 3.75 (t, J = 4.7 Hz, 4H), 3.95 (br s, 2H), 4.57 (s, 2H), 5.82 (d, J = 7.6 Hz, 1H), 6.83-6.88 (m, 2H), 7.09 (td, J = 7.7, 1.5 Hz, 1H), 7.48 (dd, J = 7.7, 1.5 Hz, 1H), 7.84 (dd, J = 8.1, 2.1 Hz, 1H), 8.23 (dd, J = 8.1, 0.6 Hz, 1H), 8.53 (dd, J = 2.1, 0.6 Hz, 1H), 9.82 (s, 1H) |
| N-(2-Aminophenyl)-6-[1-(2-dimethylaminoethyl)-3-(3-fluorophenyl)ureidomethyl]pyridine-3-carboxylic acid amide (Compound No. 1-187)<br>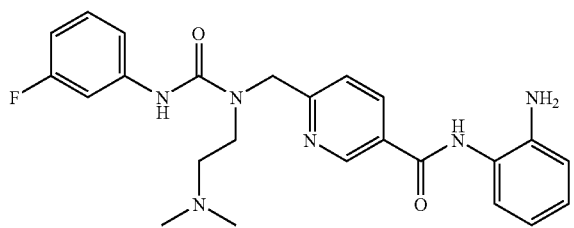 | ¹H-NMR (400 MHz, CDCl₃) δ 2.41 (s, 6H), 2.62 (t, J = 4.2 Hz, 2H), 3.48 (t, J = 4.2 Hz, 2H), 3.84 (s, 2H), 4.72 (s, 2H), 6.66 (td, J = 7.8, 1.5 Hz, 1H), 6.87 (d, J = 7.8 Hz, 1H), 6.89 (m, 1H), 6.99 (m, 1H), 7.12 (td, J = 7.8, 1.5 Hz, 1H), 7.19 (td, J = 8.3, 6.6 Hz, 1H), 7.27 (m, 1H), 7.38 (d, J = 7.8 Hz, 1H), 7.57 (d, J = 8.2 Hz, 1H), 7.92 (s, 1H), 8.18 (d, J = 8.2 Hz, 1H), 9.05 (s, 1H), 11.30 (s, 1H) |

N-(2-Aminophenyl)-6-
[1-(2-dimethylaminoethyl)-3-
(thiophen-3-yl)ureidomethyl]pyridine-
3-carboxylic acid amide
(Compound No. 1-188)

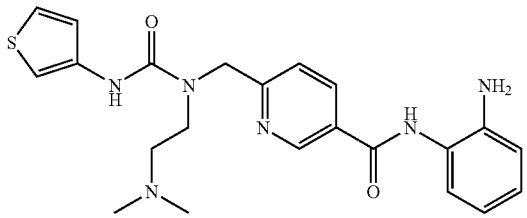

¹H-NMR (400 MHz, CDCl₃)
δ 2.39 (s, 6H), 2.59 (t, J = 4.3
Hz, 2H), 3.45 (t, J = 4.3 Hz, 2H),
3.84 (s, 2H), 4.74 (s, 2H),
6.85-6.90 (m, 2H), 6.87 (dd, J =
5.1, 1.4 Hz, 1H), 7.12 (td, J =
7.8, 1.4 Hz, 1H), 7.20 (dd, J =
5.1, 3.2 Hz, 1H), 7.28 (dd, J =
3.2, 1.4 Hz, 1H), 7.38 (d, J = 7.8
Hz, 1H), 7.56 (d, J = 7.8 Hz, 1H),
7.90 (s, 1H), 8.17 (d, J = 7.8 Hz,
1H), 9.04 (s, 1H), 11.45 (s, 1H)

N-(2-Aminophenyl)-6-
[3-(2,3-dihydrobenzo[1,4]dioxin-6-yl)-1-
(2-dimethylaminoethyl)ureidomethyl]pyridine-
3-carboxylic acid amide
(Compound No. 1-189)

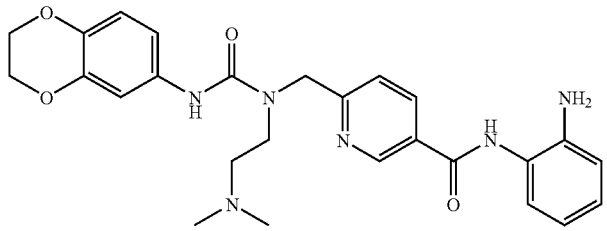

¹H-NMR (500 MHz, CDCl₃)
δ 2.38 (s, 6H), 2.57 (t, J = 4.1
Hz, 2H), 3.44 (t, J = 4.1 Hz, 2H),
3.84 (s, 2H), 4.20-4.25 (m, 4H),
4.71 (s, 2H), 6.76 (d, J = 8.8 Hz,
1H), 6.81 (dd, J = 8.8, 2.4 Hz,
1H), 6.85-6.90 (m, 2H), 6.88 (m,
1H), 6.92 (d, J = 2.4 Hz, 1H),
7.12 (td, J = 7.6, 1.5 Hz, 1H),
7.38 (d, J = 7.6 Hz, 1H), 7.58 (d,
J = 7.9 Hz, 1H), 7.92 (s, 1H),
8.17 (d, J = 7.9 Hz, 1H), 9.04 (s,
1H), 10.80 (s, 1H)

N-(2-Aminophenyl)-6-
[1-(2-dimethylaminoethyl)-3-
(3-methylphenyl)ureidomethyl]pyridine-
3-carboxylic acid amide
(Compound No. 1-190)

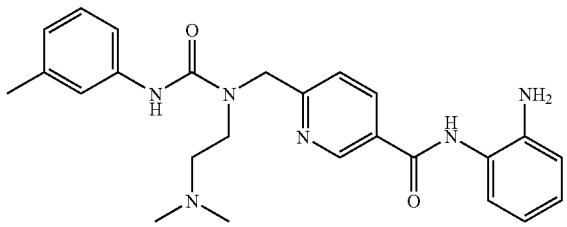

¹H-NMR (500 MHz, CDCl₃)
δ 2.32 (s, 3H), 2.40 (s, 6H), 2.60
(t, J = 4.0 Hz, 2H), 3.47 (t, J =
4.0 Hz, 2H), 3.84 (s, 2H), 4.72 (s,
2H), 6.80 (d, J = 8.0 Hz, 1H),
6.86 (d, J = 7.8 Hz, 1H), 6.87 (m,
1H, 7.05 (d, J = 8.0 Hz, 1H),
7.11 (t, J = 7.8 Hz, 1H), 7.15 (t,
J = 8.0 Hz, 1H), 7.28 (s, 1H), 7.37
(d, J = 7.8 Hz, 1H), 7.57 (d, J =
7.8 Hz, 1H), 7.97 (s, 1H), 8.18
(d, J = 7.8 Hz, 1H), 9.05 (s, 1H),
10.91 (s, 1H)

Example 2

N-(2-Aminophenyl)-5-[3-(4-dimethylaminophenyl)-
1-[3-(morpholin-4-yl)propyl]ureidomethyl]pyridine-
2-carboxylic acid amide (Compound No. 2-1)

4-Dimethylaminophenylisocyanate (23 mg 0.14 mmol) was added to a solution of N-(2-t-butoxycarbonylaminophenyl)-5-[3-(morpholin-4-yl)propylaminomethyl)]pyridine-2-carboxylic acid amide (Reference Compound No. 5-10, 25 mg, 0.053 mmol) in dichloromethane (1.0 mL), and then the mixture was stirred at room temperature for 2 hours. The reaction mixture was purified by silica gel column chromatography (NH-modified silica gel, hexane-ethyl acetate) to give a colorless compound. The obtained compound was dissolved in methanol (0.5 mL), 4.0 M hydrogen chloride-ethyl acetate solution (1.0 mL) was added thereto, and then the reaction mixture was stirred at room temperature for 4 hours. Saturated aqueous sodium hydrogen carbonate solution (30 mL) was added thereto, and then the whole was extracted with ethyl acetate (30 mL). The organic layer was dried over anhydrous magnesium sulfate, and then the solvent was evaporated under reduced pressure to give 27 mg of the title compound as a colorless amorphous product. (Yield 77%)

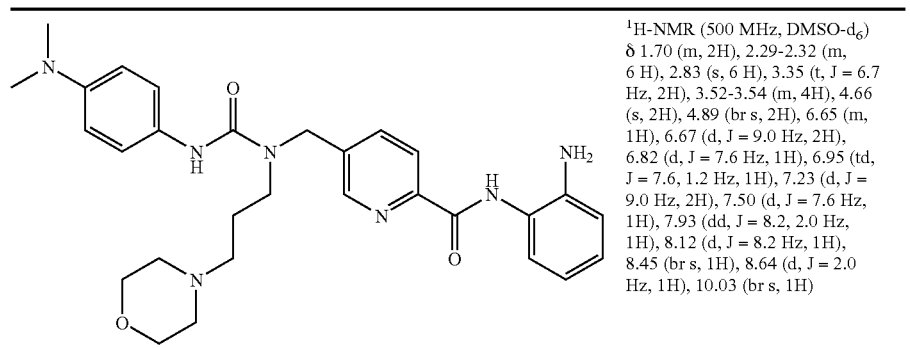

¹H-NMR (500 MHz, DMSO-d₆)
δ 1.70 (m, 2H), 2.29-2.32 (m, 6 H), 2.83 (s, 6 H), 3.35 (t, J = 6.7 Hz, 2H), 3.52-3.54 (m, 4H), 4.66 (s, 2H), 4.89 (br s, 2H), 6.65 (m, 1H), 6.67 (d, J = 9.0 Hz, 2H), 6.82 (d, J = 7.6 Hz, 1H), 6.95 (td, J = 7.6, 1.2 Hz, 1H), 7.23 (d, J = 9.0 Hz, 2H), 7.50 (d, J = 7.6 Hz, 1H), 7.93 (dd, J = 8.2, 2.0 Hz, 1H), 8.12 (d, J = 8.2 Hz, 1H), 8.45 (br s, 1H), 8.64 (d, J = 2.0 Hz, 1H), 10.03 (br s, 1H)

By using any compounds selected from Reference Compounds No. 5-1, 5-2, 5-6, 5-7, 5-9, and 5-10, the following Compounds No. 2-2~2-15 were obtained by a method similar to that of Compound No. 2-1.

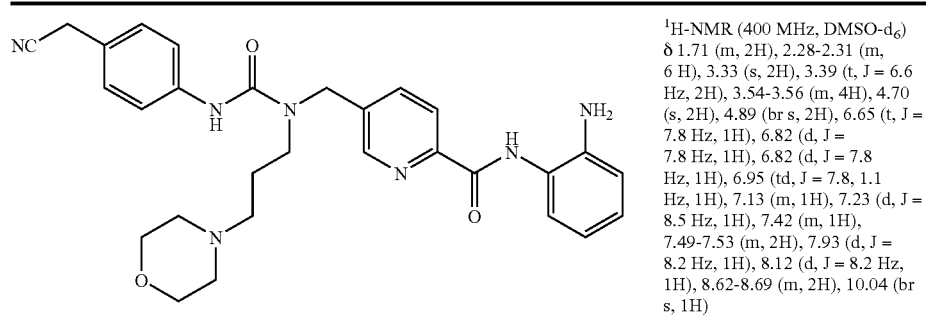

¹H-NMR (400 MHz, DMSO-d₆)
δ 1.71 (m, 2H), 2.28-2.31 (m, 6 H), 3.33 (s, 2H), 3.39 (t, J = 6.6 Hz, 2H), 3.54-3.56 (m, 4H), 4.70 (s, 2H), 4.89 (br s, 2H), 6.65 (t, J = 7.8 Hz, 1H), 6.82 (d, J = 7.8 Hz, 1H), 6.82 (d, J = 7.8 Hz, 1H), 6.95 (td, J = 7.8, 1.1 Hz, 1H), 7.13 (m, 1H), 7.23 (d, J = 8.5 Hz, 1H), 7.42 (m, 1H), 7.49-7.53 (m, 2H), 7.93 (d, J = 8.2 Hz, 1H), 8.12 (d, J = 8.2 Hz, 1H), 8.62-8.69 (m, 2H), 10.04 (br s, 1H)

N-(2-Aminophenyl)-5-[3-(4-cyano methylphenyl)-1-[3-morpholin-4-yl) propyl]ureidomethyl]pyridine-2-carboxylic acid amide
(Compound No. 2-2)

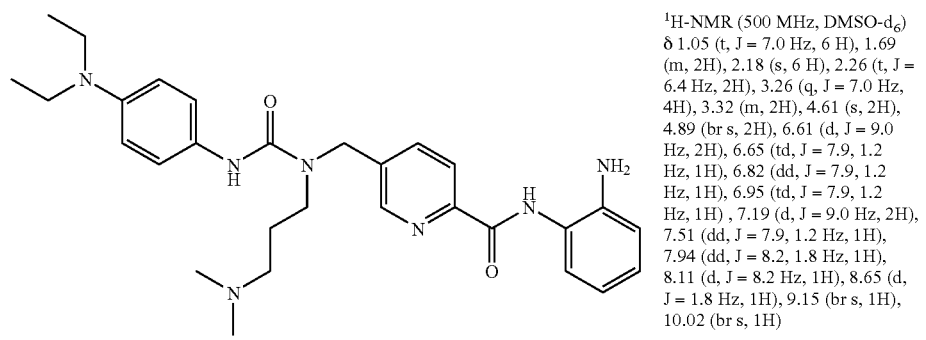

¹H-NMR (500 MHz, DMSO-d₆)
δ 1.05 (t, J = 7.0 Hz, 6 H), 1.69 (m, 2H), 2.18 (s, 6 H), 2.26 (t, J = 6.4 Hz, 2H), 3.26 (q, J = 7.0 Hz, 4H), 3.32 (m, 2H), 4.61 (s, 2H), 4.89 (br s, 2H), 6.61 (d, J = 9.0 Hz, 2H), 6.65 (td, J = 7.9, 1.2 Hz, 1H), 6.82 (dd, J = 7.9, 1.2 Hz, 1H), 6.95 (td, J = 7.9, 1.2 Hz, 1H), 7.19 (d, J = 9.0 Hz, 2H), 7.51 (dd, J = 7.9, 1.2 Hz, 1H), 7.94 (dd, J = 8.2, 1.8 Hz, 1H), 8.11 (d, J = 8.2 Hz, 1H), 8.65 (d, J = 1.8 Hz, 1H), 9.15 (br s, 1H), 10.02 (br s, 1H)

N-(2-Aminophenyl)-5-[3-(4-diethylaminophenyl)-1-(3-dimethylaminopropyl) ureidomethyl]pyridine-2-carboxylic acid amide
(Compound No. 2-3)

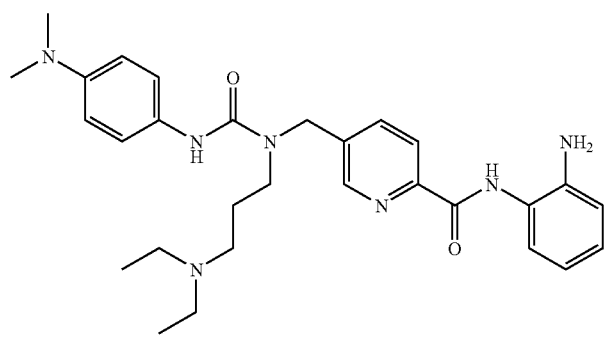

N-(2-Aminophenyl)-5-[1-(3-diethylaminopropyl)-3-(4-dimethylamino-
phenyl)ureidomethyl]pyridine-2-carboxylic acid amide
(Compound No. 2-4)

$^1$H-NMR (400 MHz, DMSO-$d_6$) δ 0.93 (t, J = 7.1 Hz, 6 H), 1.68 (m, 2H), 2.39 (br s, 2H), 2.50 (m, 4H), 2.82 (s, 6 H), 3.33 (m, 2H), 4.64 (s, 2H), 4.89 (br s, 2H), 6.63-6.69 (m, 3H), 6.82 (dd, J = 7.8, 1.2 Hz, 1H), 6.95 (td, J = 7.8, 1.2 Hz, 1H), 7.22 (d, J = 9.0 Hz, 2H), 7.50 (dd, J = 7.8, 1.2 Hz, 1H), 7.94 (dd, J = 8.1, 1.8 Hz, 1H), 8.12 (d, J = 8.1 Hz, 1H), 8.65 (d, J = 1.8 Hz, 1H), 8.78 (br s, 1H), 10.03 (br s, 1H)

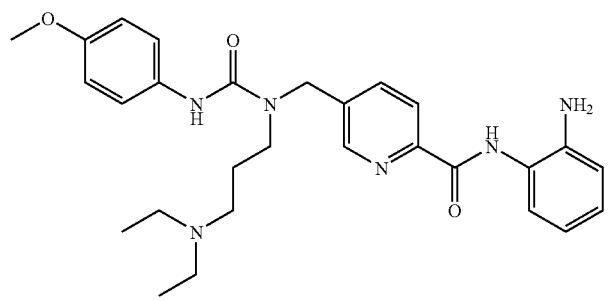

N-(2-Aminophenyl)-5-[1-(3-diethylaminopropyl)-3-(4-methoxyphenyl)
ureidomethyl]pyridine-2-carboxylic acid amide
(Compound No. 2-5)

$^1$H-NMR (400 MHz, DMSO-$d_6$) δ 0.93 (t, J = 7.1 Hz, 6 H), 1.69 (m, 2H), 2.39 (t, J = 6.6 Hz, 2H), 2.49 (m, 4H), 3.35 (m, 2H), 3.71 (s, 3H), 4.65 (s, 2H), 4.89 (br s, 2H), 6.65 (td, J = 7.8, 1.3 Hz, 1H), 6.81-6.86 (m, 3H), 6.95 (td, J = 7.8, 1.3 Hz, 1H), 7.32 (d, J = 9.0 Hz, 2H), 7.50 (dd, J = 7.8, 1.3 Hz, 1H), 7.94 (dd, J = 8.1, 1.8 Hz, 1H), 8.12 (d, J = 8.1 Hz, 1H), 8.65 (d, J = 1.8 Hz, 1H), 8.93 (br s, 1H), 10.03 (br s, 1H)

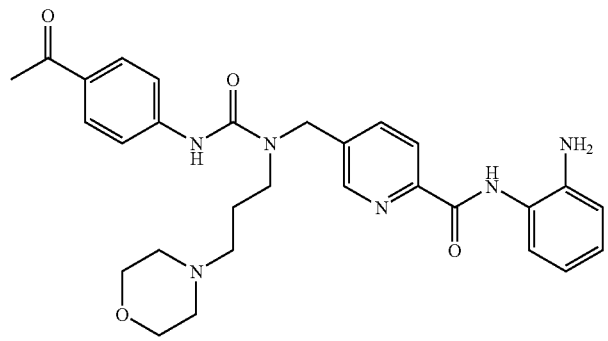

5-[3-(4-Acetylphenyl)-1-[3-(morpholin-4-yl)propyl]ureidomethyl]-
N-(2-aminophenyl)pyridine-2-carboxylic acid amide
(Compound No. 2-6)

$^1$H-NMR (500 MHz, DMSO-$d_6$) δ 1.73 (m, 2H), 2.28-2.32 (m, 6 H), 2.51 (s, 3H), 3.43 (t, J = 6.7 Hz, 2H), 3.54-3.57 (m, 4H), 4.74 (s, 2H), 4.89 (br s, 2H), 6.65 (td, J = 7.6, 1.2 Hz, 1H), 6.82 (dd, J = 7.6, 1.2 Hz, 1H), 6.95 (td, J = 7.6, 1.2 Hz, 1H), 7.51 (d, J = 7.6 Hz, 1H), 7.66 (d, J = 9.0 Hz, 2H), 7.88 (d, J = 9.0 Hz, 2H), 7.95 (dd, J = 8.1, 1.8 Hz, 1H), 8.13 (d, J = 8.1 Hz, 1H), 8.66 (d, J = 1.8 Hz, 1H), 8.93 (br s, 1H), 10.03 (br s, 1H)

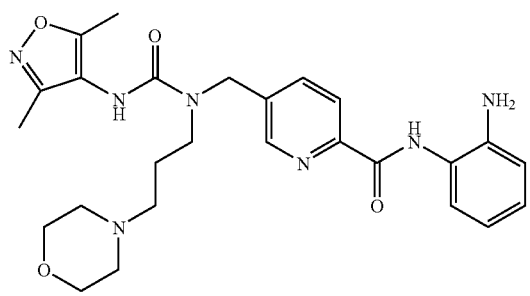

N-(2-Aminophenyl)-5-[3-(3,5-dimethylisoxazol-4-yl)-1-[3-(morpholin-4-yl)propyl]ureidomethyl]pyridine-2-carboxylic acid amide (Compound No. 2-7)

$^1$H-NMR (500 MHz, DMSO-$d_6$) δ 1.71 (m, 2H), 2.08 (s, 3H), 2.25 (s, 3H), 2.30-2.33 (m, 6 H), 3.35 (t, J = 6.7 Hz, 2H), 3.49-3.50 (m, 4H), 4.66 (s, 2H), 4.89 (br s, 2H), 6.65 (td, J = 7.6, 1.2 Hz, 1H), 6.82 (dd, J = 7.6, 1.2 Hz, 1H), 6.96 (td, J = 7.6, 1.2 Hz, 1H), 7.49 (dd, J = 7.6, 1.2 Hz, 1H), 7.92 (dd, J = 8.1, 2.0 Hz, 1H), 8.13 (d, J = 8.1 Hz, 1H), 8.36 (br s, 1H), 8.63 (d, J = 2.0 Hz, 1H), 10.04 (br s, 1H)

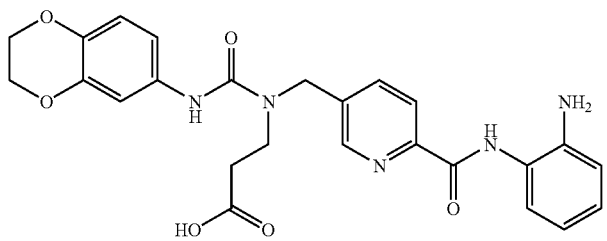

N-(2-Aminophenyl)-5-[1-(2-carboxyethyl)-3-(2,3-dihydrobenzo[1,4]dioxin-6-yl)ureidomethyl]pyridine-2-carboxylic acid amide (Compound No. 2-8)

$^1$H-NMR (500 MHz, DMSO-$d_6$) δ 2.56 (t, J = 7.2 Hz, 2H), 3.54 (m, 2H), 4.17-4.26 (m, 4H), 4.67-4.72 (m, 4H), 6.65 (m, 1H), 6.73 (d, J = 8.7 Hz, 1H), 6.82 (dd, J = 7.9, 1.2 Hz, 1H), 6.87 (dd, J = 8.7, 2.6 Hz, 1H), 6.95 (td, J = 7.9, 1.2 Hz, 1H), 7.04 (d, J = 2.6 Hz, 1H), 7.51 (dd, J = 7.9, 1.2 Hz, 1H), 7.91 (dd, J = 7.9, 1.8 Hz, 1H), 8.12 (d, J = 7.9 Hz, 1H), 8.46 (br s, 1H), 8.62 (d, J = 1.8 Hz, 1H), 10.03 (br s, 1H)

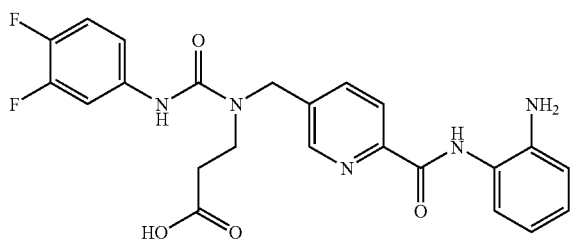

N-(2-Aminophenyl)-5-[1-(2-carboxyethyl)-3-(3,4-difluorophenyl)ureidomethyl]pyridine-2-carboxylic acid amide (Compound No.2-9)

$^1$H-NMR (500 MHz, DMSO-$d_6$) δ 2.55 (t, J = 7.0 Hz, 2H), 3.56 (t, J = 7.0 Hz, 2H), 4.70 (s, 2H), 4.90 (br s, 2H), 6.65 (td, J = 7.6, 1.4 Hz, 1H), 6.82 (dd, J = 7.6, 1.4 Hz, 1H), 6.95 (td, J = 7.6, 1.4 Hz, 1H), 7.24 (m, 1H), 7.31 (dd, J = 19.7, 9.3 Hz, 1H), 7.51 (dd, J = 7.6, 1.4 Hz, 1H), 7.64 (ddd, J = 13.7, 7.6, 2.4 Hz, 1H), 7.93 (dd, J = 7.9, 2.0 Hz, 1H), 8.12 (d, J = 7.9 Hz, 1H), 8.63 (d, J = 2.0 Hz, 1H), 9.13 (br s, 1H), 10.16 (br s, 1H)

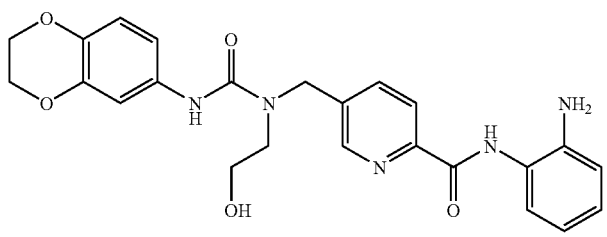

N-(2-Aminophenyl)-5-[3-(2,3-dihydrobenzo[1,4]dioxin-6-yl)-1-(2-hydroxyethyl)ureidomethyl]pyridine-2-carboxylic acid amide (Compound No. 2-10)

$^1$H-NMR (400 MHz, DMSO-$d_6$) δ 3.43 (t, J = 5.1 Hz, 2H), 3.58 (t, J = 5.1 Hz, 2H), 4.16-4.21 (m, 4H), 4.69 (s, 2H), 4.90 (br s, 2H), 5.28 (br s, 1H), 6.65 (td, J = 7.7, 1.2 Hz, 1H), 6.72 (d, J = 8.8 Hz, 1H), 6.80 (dd, J = 8.8, 2.4 Hz, 1H), 6.83 (m, 1H), 6.95 (td, J = 7.7, 1.2 Hz, 1H), 7.02 (d, J = 2.4 Hz, 1H), 7.50 (dd, J = 7.7, 1.2 Hz, 1H), 7.93 (dd, J = 8.1, 1.8 Hz, 1H), 8.11 (dd, J = 8.1, 0.5 Hz, 1H), 8.55 (br s, 1H), 8.64 (d, J = 1.8 Hz, 1H), 10.03 (br s, 1H)

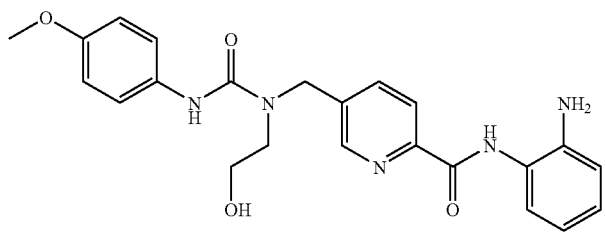

N-(2-Aminophenyl)-5-[1-(2-hydroxyethyl)-3-(4-methoxyphenyl)ureido-methyl]pyridine-2-carboxylic acid amide (Compound No. 2-11)

¹H-NMR (400 MHz, DMSO-d$_6$) δ 3.44 (t, J = 5.1 Hz, 2H), 3.59 (m, 2H), 3.70 (s, 3H), 4.71 (s, 2H), 4.90 (br s, 2H), 5.27 (br s, 1H), 6.65 (td, J = 7.6, 1.2 Hz, 1H), 6.83 (m, 1H), 6.84 (d, J = 9.0 Hz, 2H), 6.95 (td, J = 7.6, 1.2 Hz, 1H), 7.30 (d, J = 9.0 Hz, 2H), 7.51 (dd, J = 7.6, 1.2 Hz, 1H), 7.94 (dd, J = 8.1, 1.8 Hz, 1H), 8.11 (d, J = 8.1 Hz, 1H), 8.57 (br s, 1H), 8.65 (d, J = 1.8 Hz, 1H), 10.03 (br s, 1H)

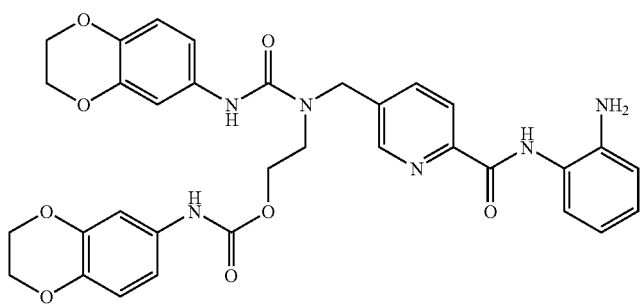

N-(2-Aminophenyl)-5-[3-(2,3-dihydrobenzo[1,4]dioxin-6-yl)-1-[2-(2,3-dihydrobenzo[1,4]dioxin-6-yl aminocarbonyloxy)ethyl]ureidom ethyl]pyridine-2-carboxylic acid amide (Compound No. 2-12)

¹H-NMR (400 MHz, DMSO-d$_6$) δ 3.65 (t, J = 5.5 Hz, 2H), 4.16-4.22 (m, 10 H), 4.77 (s, 2H), 4.89 (br s, 2H), 6.65 (td, J = 7.6, 1.2 Hz, 1H), 6.71 (d, J = 8.5 Hz, 1H), 6.74 (d, J = 8.5 Hz, 1H), 6.82 (d, J = 7.6 Hz, 1H), 6.86 (m, 1H), 6.87 (dd, J = 8.5, 2.6 Hz, 1H), 6.95 (td, J = 7.6, 1.2 Hz, 1H), 7.01 (m, 1H), 7.04 (d, J = 2.6 Hz, 1H), 7.49 (dd, J = 7.6, 1.2 Hz, 1H), 7.92 (dd, J = 8.2, 1.6 Hz, 1H), 8.11 (d, J = 8.2 Hz, 1H), 8.36 (br s, 1H), 8.62 (d, J = 1.6 Hz, 1H), 9.43 (br s, 1H), 10.01 (br s, 1H)

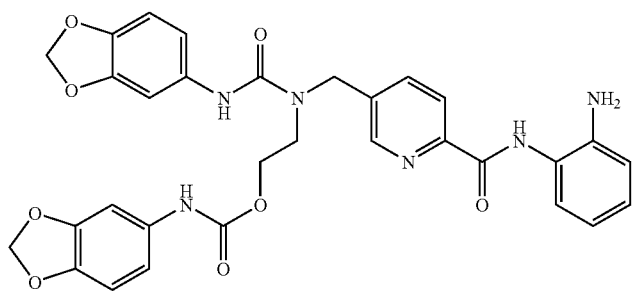

N-(2-Aminophenyl)-5-[3-(benzo[1,3]dioxol-5-yl)-1-[2-(benzo[1,3]dioxol-5-ylaminocarbonyloxy)ethyl]ureidomethyl]pyridine-2-carboxylic acid amide (Compound No. 2-13)

¹H-NMR (500 MHz, DMSO-d$_6$) δ 3.66 (t, J = 5.8 Hz, 2H), 4.22 (t, J = 5.8 Hz, 2H), 4.77 (s, 2H), 4.88 (br s, 2H), 5.94 (s, 2H), 5.95 (s, 2H), 6.65 (td, J = 7.8, 1.2 Hz, 1H), 6.78 (d, J = 8.2 Hz, 1H), 6.81-6.84 (m, 4H), 6.95 (td, J = 7.8, 1.2 Hz, 1H), 7.08 (br s, 1H), 7.12 (d, J = 1.8 Hz, 1H), 7.50 (dd, J = 7.8, 1.2 Hz, 1H), 7.93 (dd, J = 8.0, 1.5 Hz, 1H), 8.11 (d, J = 8.0 Hz, 1H), 8.44 (br s, 1H), 8.63 (d, J = 1.5 Hz, 1H), 9.51 (br s, 1H), 10.01 (br s, 1H)

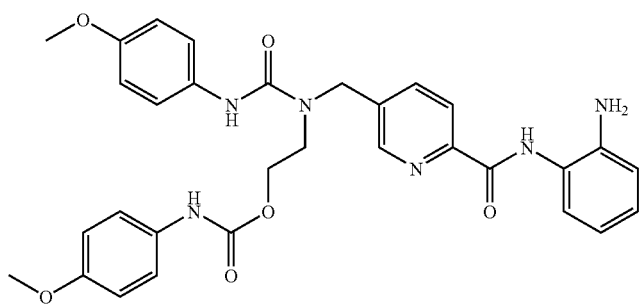

N-(2-Aminophenyl)-5-[3-(4-methoxyphenyl)-1-[2-(4-methoxyphenyl-aminocarbonyloxy)ethyl]ureido methyl]pyridine-2-carboxylic acid amide (Compound No. 2-14)

¹H-NMR (400 MHz, DMSO-d$_6$) δ 3.67 (m, 2H), 3.69 (s, 3H), 3.70 (s, 3H), 4.22 (t, J = 5.5 Hz, 2H), 4.79 (s, 2H), 4.89 (br s, 2H), 6.65 (td, J = 7.8, 1.3 Hz, 1H), 6.81-6.86 (m, 5 H), 6.95 (td, J = 7.8, 1.3 Hz, 1H), 7.32-7.36 (m, 4H), 7.50 (dd, J = 7.8, 1.3 Hz, 1H), 7.94 (d, J = 7.8 Hz, 1H), 8.12 (d, J = 7.8 Hz, 1H), 8.42 (br s, 1H), 8.64 (d, J = 1.2 Hz, 1H), 9.45 (br s, 1H), 10.02 (br s, 1H)

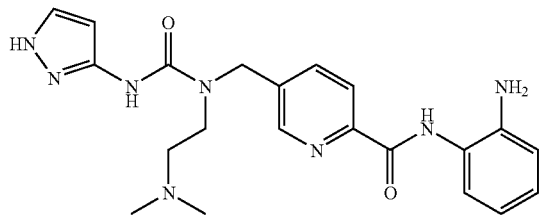

N-(2-Aminophenyl)-5-[1-(2-dimethylaminoethyl)-3-(1H-pyrazol-3-yl)ureidomethyl]pyridine-2-carboxylic acid amide
(Compound No. 2-15)

$^1$H-NMR (500 MHz, CDCl$_3$)
δ 2.40 (s, 6 H), 2.54 (t, J = 4.4 Hz, 2H), 3.34 (t, J = 4.4 Hz, 2H), 3.95 (s, 2H), 4.67 (s, 2H), 6.01 (s, 1H), 6.84 (dd, J = 7.7, 1.4 Hz, 1H), 6.86 (td, J = 7.7, 1.4 Hz, 1H), 7.09 (td, J = 7.7, 1.4 Hz, 1H), 7.43 (d, J = 2.1 Hz, 1H), 7.49 (dd, J = 7.7, 1.4 Hz, 1H), 7.89 (dd, J = 7.9, 2.0 Hz, 1H), 8.26 (d, J = 7.9 Hz, 1H), 8.57 (d, J = 2.0 Hz, 1H), 9.82 (s, 1H), 12.18 (s, 1H)

Example 3

N-(2-Aminophenyl)-5-[3-(4-hydroxyphenyl)-1-[5-(morpholin-4-yl)pentyl]ureidomethyl]pyridine-2-carboxylic acid amide (Compound No. 3-1)

Under a nitrogen atmosphere, 10% palladium on carbon (30 mg) was added to a solution of N-(2-aminophenyl)-5-[3-(4-benzyloxyphenyl)-1-[5-(morpholin-4-yl)pentyl]ureidomethyl]pyridine-2-carboxylic acid amide (Compound No. 1-182, 45 mg, 0.072 mmol) in a mixed solvent (ethyl acetate (2.0 mL) and methanol (3.0 mL)), and then the reaction mixture was stirred under a hydrogen atmosphere at room temperature for 2 hours. After the insoluble was filtered off with celite, the filtrate was concentrated. The residue was purified by silica gel column chromatography (chloroform-methanol) to give 32 mg of the title compound as a yellow oil. (Yield 84%)

| 1) Tablet (in 150 mg) | |
|---|---|
| Calcium carboxymethyl cellulose | 4.5 mg |
| Hydroxypropyl cellulose | 4 mg |
| Magnesium stearate | 0.5 mg |

A tablet of the above-mentioned formulation is coated using 3 mg of a coating agent (for example, a conventional coating agent such as hydroxypropylmethyl cellulose, macrogol or a silicone resin), whereby a desired tablet can be obtained. In addition, a desired tablet can be obtained by appropriately changing the kinds and/or amounts of the present compound and additives.

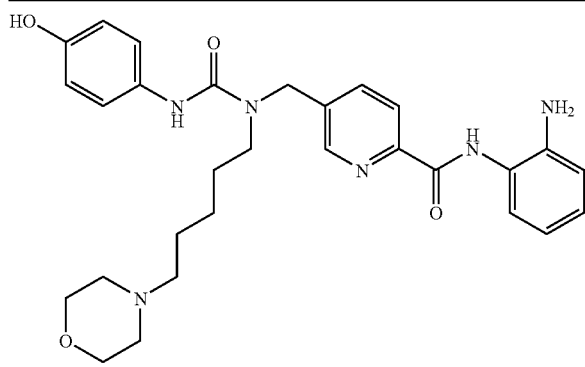

$^1$H-NMR (500 MHz, CDCl$_3$)
δ 1.34 (m, 2H), 1.52 (m, 2H), 1.63 (m, 2H), 2.33 (t, J = 7.6 Hz, 2H), 2.44 (m, 4H), 3.28 (t, J = 7.6 Hz, 2H), 3.71 (t, J = 4.7 Hz, 4H), 3.98 (s, 2H), 4.62 (s, 2H), 6.40 (s, 1H), 6.69 (d, J = 8.9 Hz, 2H), 6.84 (dd, J = 7.8, 1.4 Hz, 1H), 6.86 (td, J = 7.8, 1.4 Hz, 1H), 7.09 (td, J = 7.8, 1.4 Hz, 1H), 7.10 (d, J = 8.9 Hz, 2H), 7.49 (dd, J = 7.8, 1.4 Hz, 1H), 7.80 (dd, J = 8.0, 2.0 Hz, 1H), 8.21 (d, J = 8.0 Hz, 1H), 8.52 (d, J = 2.0 Hz, 1H), 9.82 (s, 1H)

Preparation Examples

Hereinafter, typical preparation examples of the present compound will be shown.

| 1) Tablet (in 150 mg) | |
|---|---|
| The Present compound | 1 mg |
| Lactose | 100 mg |
| Cornstarch | 40 mg |

| 2) Capsule (in 150 mg) | |
|---|---|
| The Present compound | 5 mg |
| Lactose | 135 mg |
| Calcium carboxymethyl cellulose | 4.5 mg |
| Hydroxypropyl cellulose | 4 mg |
| Magnesium stearate | 1.5 mg |

A desired capsule can be obtained by appropriately changing the kinds and/or amounts of the present compound and additives.

| 3) Eye drop (in 100 mL) | |
|---|---|
| The Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kinds and/or amounts of the present compound and additives.

[Pharmacological Test]

1. Test for Evaluation of HDAC Inhibitory Activity

Using HDAC Fluorimetric Assay/Drug Discovery Kit (manufactured by Biomol), HDAC inhibitory activity of the present compounds was measured according to the protocol included with the kit. The kit contains Buffer, HeLa nuclear extract (includes HDAC), Substrate, Developer and Trichostatin A (an HDAC inhibitor).

(Preparation of Test Compound Solution)

A test compound was dissolved in dimethyl sulfoxide, whereby a 2 mg/mL solution was prepared. Then, the resulting solution was diluted with Buffer containing 5% dimethyl sulfoxide, whereby a 150 µM test compound solution was prepared.

(Test Method and Measurement Method)

1) To a 384-well culture plate, the test compound solution was added in an amount of 2 µL per well.

2) HeLa nuclear extract was diluted 30-fold with Buffer. The resulting solution was added in an amount of 3 µL per well and then, incubation was performed at 37° C. for 2 hours.

3) Substrate was diluted 500-fold with Buffer. The resulting solution was added in an amount of 5 µL per well (the final concentration of the test compound was 30 µM) and then, incubation was performed at 37° C. for 10 minutes.

4) Developer was diluted 20-fold with Buffer and Trichostatin A (2 µM) was added to it. The resulting solution was added in an amount of 10 µL per well and then, incubation was performed at room temperature for 15 minutes.

5) The fluorescence intensity of each well was measured using multilabel counter ARVO (manufactured by Wallac) with excitation at 360 nm and emission at 460 nm.

6) A control data was obtained from the same experiment except that Buffer containing 5% DMSO was added instead of the test compound solution as the above-mentioned procedure from 1) to 5).

7) A blank data was obtained from the same experiment except that Buffer containing 5% DMSO was added instead of the test compound solution and that Buffer was added instead of Hela nuclear extract as the above-mentioned procedure from 1) to 5).

(Calculation Equation for Enzyme Inhibitory Rate)

Enzyme inhibitory rate (%) was calculated using the following equation.

(Enzyme Inhibitory Rate(%))=100×[1−{(Fluorescence Intensity of Test Compound Solution)−(Florescence Intensity of Blank)}/{(Florescence Intensity of Control)−(Florescence Intensity of Blank)}]

(Test Results)

As an example of the test results, the enzyme inhibitory rate of the respective test compound (Compound 1-2, Compound 1-3, Compound 1-4, Compound 1-6, Compound 1-8, Compound 1-10, Compound 1-13, Compound 1-14, Compound 1-20, Compound 1-21, Compound 1-24, Compound 1-25, Compound 1-27, Compound 1-30, Compound 1-31, Compound 1-38, Compound 1-40, Compound 1-41, Compound 1-42, Compound 1-44, Compound 1-46, Compound 1-51, Compound 1-53, Compound 1-55, Compound 1-56, Compound 1-58, Compound 1-63, Compound 1-68, Compound 1-79, Compound 1-90, Compound 1-96, Compound 1-115, Compound 1-116, Compound 1-141, Compound 2-1, Compound 2-3, Compound 2-10) are shown in Table I.

TABLE I

| Test Compound | Enzyme Inhibitory Rate (%) |
|---|---|
| Compound 1-2 | 100 |
| Compound 1-3 | 100 |
| Compound 1-4 | 100 |
| Compound 1-6 | 100 |
| Compound 1-8 | 96 |
| Compound 1-10 | 98 |
| Compound 1-13 | 100 |
| Compound 1-14 | 100 |
| Compound 1-20 | 99 |
| Compound 1-21 | 98 |
| Compound 1-24 | 96 |
| Compound 1-25 | 97 |
| Compound 1-27 | 97 |
| Compound 1-30 | 100 |
| Compound 1-31 | 99 |
| Compound 1-38 | 97 |
| Compound 1-40 | 97 |
| Compound 1-41 | 96 |
| Compound 1-42 | 98 |
| Compound 1-44 | 98 |
| Compound 1-46 | 98 |
| Compound 1-51 | 98 |
| Compound 1-53 | 98 |
| Compound 1-55 | 98 |
| Compound 1-56 | 97 |
| Compound 1-58 | 98 |
| Compound 1-63 | 97 |
| Compound 1-68 | 99 |
| Compound 1-79 | 98 |
| Compound 1-90 | 98 |
| Compound 1-96 | 98 |
| Compound 1-115 | 97 |
| Compound 1-116 | 100 |
| Compound 1-141 | 91 |
| Compound 2-1 | 98 |
| Compound 2-3 | 100 |
| Compound 2-10 | 99 |

If the enzyme inhibitory rate was more than 100%, the value is shown to be 100% in Table I.

2. Test for Evaluation of Effect of Morphological Change on Trabecular Meshwork Cells As a method for evaluating a cellular morphological change, an evaluation system using the cell shape index (hereinafter referred to as "CSI") as an index has been reported in The Journal of Clinical Investigation, 103, 1141-1150 (1999). Therefore, according to the method described in the above document, an effect of morphological change of the present compounds on trabecular meshwork cells was evaluated.

(Used Cells)

A human trabecular meshwork cell line (hereinafter referred to as "TM-1 cells") reported in Investigative Opthalmology & Visual Science, 43, 151-161 (2002) was used.

(Preparation of Reagents)

Culture medium 1: A reagent was prepared by adding fetal bovine serum (10%), L-glutamine (2 mM), amphotericin B (2.5 µg/mL), and gentamicin (25 µg/mL) to Dulbecco's Modified Eagle Medium (hereinafter referred to as "D-MEM").

Culture medium 2: Fetal bovine serum (3%), L-glutamine (2 mM), amphotericin B (2.5 µg/mL), and gentamicin (25 µg/mL) were added to D-MEM.

Cell staining liquid: A mixed liquid of Calcein-AM (16 µM) and Hoechst 33342 (40 µM) was prepared by diluting a Calcein-AM solution (cytoplasmic staining reagent, manufactured by Dojindo Laboratories) and a Hoechst 33342 solution (nuclear staining reagent, manufactured by Dojindo Laboratories) with D-MEM containing L-glutamine (2 mM), amphotericin B (2.5 µg/mL), and gentamicin (25 µg/mL).

(Preparation of Cells)

TM-1 cells subcultured at 37° C. in a 8% carbon dioxide gas atmosphere were treated with a trypsin/EDTA solution (0.05% trypsin and 0.53 mM tetrasodium ethylenediaminetetraacetate) at 24 hours before performing a drug treatment mentioned below and seeded on a 96-well culture plate. The culture medium 1 was used for the subculture of the cells. The culture medium 2 was used for the cell culture after seeding the cells on the plate.

(Preparation of Test Compound Solution)

A test compound was dissolved in dimethyl sulfoxide, whereby a 5 mM solution was prepared. Then, the resulting solution was diluted with the culture medium 2, whereby a 200 µM test compound solution was prepared.

(Preparation of Positive Control Compound Solution)

It has been reported that Y-27632 which is a Rho kinase inhibitor induces a morphological change in trabecular meshwork cells in Investigative Opthalmology & Visual Science, 42, 137-144 (2001). Therefore, Y-27632 (produced according to the method described in WO 90/05723) was used as a positive control, and dissolved in dimethyl sulfoxide in the same manner as the test compound, whereby a 5 mM solution was prepared, and then, the resulting solution was diluted with the culture medium 2, whereby a 200 µM positive control compound solution was prepared.

(Test Method and Measurement Method)

1) To a 96-well culture plate, a solution of TM-1 cells adjusted to a cell density of $1.6 \times 10^4$ cells/mL was added in an amount of 95 µL ($1.5 \times 10^4$ cells) per well.

2) Incubation was performed at 37° C. in a 8% carbon dioxide gas atmosphere for 24 hours.

3) The test compound solution or positive control compound solution was added in an amount of 5 µL per well (the final concentration of the test compound or positive control compound was 10 µM). As a control, the culture medium 2 containing dimethyl sulfoxide (4%) was added in an amount of 5 µL per well.

4) Incubation was performed at 37° C. in a 8% carbon dioxide gas atmosphere for 24 hours.

5) The cell staining liquid was added in an amount of 10 µL per well.

6) Incubation was performed at 37° C. in a 8% carbon dioxide gas atmosphere for 1 hour to stain the cells.

7) A 37% formaldehyde solution was added in an amount of 10 µL per well.

8) Incubation was performed at room temperature for 1 hour to fix the cells.

9) Washing with phosphate-buffered saline was performed.

10) Using Array Scan Vti HCS reader (manufactured by Cellomics), images of stained cells magnified with a 20-fold objective lens were captured in 80 fields (10 fields×8 wells) per test compound addition group.

11) CSI was calculated for each cell and an average value was obtained for each test compound addition group.

(Calculation Equation for CSI)

CSI was calculated using the following equation.

$$CSI = 4\pi \times (\text{Cell Area})/(\text{Cell Perimeter})^2$$

(Test Results)

As an example of the test results, the CSI values of the respective test compound (Compound 1-2, Compound 1-3, Compound 1-4, Compound 1-6, Compound 1-8, Compound 1-10, Compound 1-13, Compound 1-14, Compound 1-20, Compound 1-21, Compound 1-24, Compound 1-25, Compound 1-27, Compound 1-30, Compound 1-31, Compound 1-38, Compound 1-40, Compound 1-41, Compound 1-42, Compound 1-44, Compound 1-46, Compound 1-51, Compound 1-53, Compound 1-55, Compound 1-56, Compound 1-58, Compound 1-63, Compound 1-68, Compound 1-79, Compound 1-90, Compound 1-96, Compound 1-115, Compound 1-116, Compound 1-141, Compound 2-1, Compound 2-3, Compound 2-10) addition groups and Y-27632 addition group are shown in Table II.

TABLE II

| Test Compound | CSI |
| --- | --- |
| Control | 0.679 |
| Compound 1-2 | 0.516 |
| Compound 1-3 | 0.569 |
| Compound 1-4 | 0.556 |
| Compound 1-6 | 0.549 |
| Compound 1-8 | 0.538 |
| Compound 1-10 | 0.528 |
| Compound 1-13 | 0.545 |
| Compound 1-14 | 0.520 |
| Compound 1-20 | 0.516 |
| Compound 1-21 | 0.575 |
| Compound 1-24 | 0.597 |
| Compound 1-25 | 0.571 |
| Compound 1-27 | 0.624 |
| Compound 1-30 | 0.564 |
| Compound 1-31 | 0.551 |
| Compound 1-38 | 0.575 |
| Compound 1-40 | 0.572 |
| Compound 1-41 | 0.499 |
| Compound 1-42 | 0.536 |
| Compound 1-44 | 0.554 |
| Compound 1-46 | 0.547 |
| Compound 1-51 | 0.518 |
| Compound 1-53 | 0.502 |
| Compound 1-55 | 0.525 |
| Compound 1-56 | 0.526 |
| Compound 1-58 | 0.518 |
| Compound 1-63 | 0.521 |
| Compound 1-68 | 0.502 |
| Compound 1-79 | 0.497 |
| Compound 1-90 | 0.480 |
| Compound 1-96 | 0.489 |
| Compound 1-115 | 0.467 |
| Compound 1-116 | 0.455 |
| Compound 1-141 | 0.515 |
| Compound 2-1 | 0.574 |
| Compound 2-3 | 0.550 |
| Compound 2-10 | 0.582 |
| Y-27632 | 0.543 |

3. Test for Evaluation of Intraocular Pressure-Lowering Effect

In order to evaluate an intraocular pressure-lowering effect of the present compounds, a test for evaluation of intraocular pressure-lowering effect of intracameral administration of a drug using male Japanese White rabbits was performed.

(Preparation of Test Compound Administration Liquid)

A test compound was dissolved or suspended in physiological saline containing 0.5% dimethyl sulfoxide, whereby a 1 mM test compound administration liquid was prepared.

(Test Method and Measurement Method)

One drop of 0.4% oxybuprocaine hydrochloride eye drop was instilled into both eyes of each male Japanese White rabbit to achieve local anesthesia, and thereafter, the intraocular pressure was measured using an applanation tonometer. Then, by using a syringe fitted with a 30-gauge needle, the test compound administration liquid (20 µL) was intracamerally administered to one eye. As a control, 20 µL of the vehicle (physiological saline containing 0.5% dimethyl sulfoxide) for the test compound was intracamerally administered. After the lapse of a certain period of time from the administration of the test compound or vehicle, one drop of 0.4% oxybuprocaine hydrochloride eye drop was instilled into the administered eye to achieve local anesthesia, and thereafter, the intraocular pressure was measured using an applanation tonometer.

(Calculation Equation for Intraocular Pressure Reduction Rate)

The intraocular pressure-lowering effect of each test compound was evaluated by calculating an intraocular pressure reduction rate. The intraocular pressure reduction rate (%) was calculated using the following equation.

(Intraocular Pressure Reduction Rate(%))=100×{(Average Value of Intraocular Pressure of Control Group)−(Average Value of Intraocular Pressure of Each Test Compound Administration Group)}/(Average Value of Intraocular Pressure of Control Group)

(Test Results and Discussion)

As an example of the test results, the intraocular pressure reduction rate of the test compound administration group at 9 hours after administering the test compound (Compound 1-96) is shown in Table III (one group consisting of 6 cases).

TABLE III

| Test Compound | Intraocular Pressure Reduction Rate (%) |
| --- | --- |
| Compound 1-96 | 18 |

As shown in Table I, the present compounds have an excellent HDAC inhibitory activity and are expected to be useful as a preventive and/or therapeutic agent for diseases which an HDAC inhibitor is considered to be useful in treating, for example cancer, autoimmune diseases, inflammatory diseases, neurodegenerative diseases, infectious disease, hematopoietic disorders, fibrosis, cardiovascular disorders, diseases associated with angiogenesis, etc. Additionally, as shown in Table II, the present compounds have an excellent effect of cellular morphological change on trabecular meshwork cells equal to or greater than that of Y-27632 used as the positive control (lower CSI indicates greater morphological changes in Table II). Further, as shown in Table III, the present compounds have an excellent intraocular pressure-lowering effect also in the test using actual animal models. Accordingly, the present compounds can be used as an intraocular pressure-lowering agent and are expected to be useful as a preventive and/or therapeutic agent for diseases associated with aqueous humor circulation and/or intraocular pressure, particularly as a preventive and/or therapeutic agent for glaucoma, ocular hypertension, etc.

INDUSTRIAL APPLICABILITY

The present compound has an HDAC inhibitory activity and therefore is useful as a preventive and/or therapeutic agent for a disease against which an HDAC inhibitor is considered to be effective, and is particularly useful as a preventive and/or therapeutic agent for cancer, an autoimmune disease, an inflammatory disease, a neurodegenerative disease, an infectious disease, hematopoietic disorder, fibrosis, a cardiovascular disease, a disease considered to be associated with angiogenesis. Further, the present compound has an effect of morphological change on trabecular meshwork cells and an effect of intraocular pressure reduction and therefore is useful as a preventive and/or therapeutic agent for a disease considered to be associated with circulation of aqueous humor and/or intraocular pressure such as glaucoma or ocular hypertension.

The invention claimed is:

1. A compound represented by the following general formula (1) or a salt thereof:

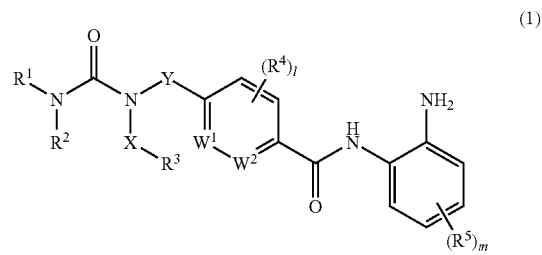

wherein $R^1$ and $R^2$ are the same or different and represent a hydrogen atom, a lower alkyl group which may have a substituent, a lower alkenyl group which may have a substituent, a lower alkynyl group which may have a substituent or a group represented by the following general formula (2);

$R^3$ represents a hydroxy group, a lower alkoxy group which may have a substituent, a lower cycloalkyloxy group which may have a substituent, an aryloxy group which may have a substituent, a carboxy group, a lower alkoxycarbonyl group which may have a substituent, —OCONR$^a$R$^b$, —NR$^c$R$^d$ or a group represented by the following general formula (3);

$R^4$ and $R^5$ are the same or different and represent a halogen atom, a lower alkyl group which may have a substituent, a hydroxy group, or a lower alkoxy group which may have a substituent;

$R^6$ represents a halogen atom, a lower alkyl group which may have a substituent, a lower cycloalkyl group which may have a substituent, an aryl group which may have a substituent, a heterocyclic group which may have a substituent, a hydroxy group, a lower alkoxy group which may have a substituent, a lower cycloalkyloxy group which may have a substituent, an aryloxy group which may have a substituent, a mercapto group, a lower alkylthio group which may have a substituent, a lower cycloalkylthio group which may have a substituent, an arylthio group which may have a substituent, a formyl group, a lower alkylcarbonyl group which may have a substituent, a carboxy group, a lower alkoxycarbonyl group which may have a substituent, a nitro group, a cyano group or —NR$^e$R$^f$;

R$^7$ represents a lower alkyl group which may have a substituent, a lower cycloalkyl group which may have a substituent, an aryl group which may have a substituent, a hydroxy group, a lower alkoxy group which may have a substituent, a lower cycloalkyloxy group which may have a substituent or an aryloxy group which may have a substituent;

R$^a$ and R$^b$ are the same or different and represent a hydrogen atom, a lower alkyl group which may have a substituent, a lower cycloalkyl group which may have a substituent, an aryl group which may have a substituent or a heterocyclic group which may have a substituent;

R$^c$, R$^d$, R$^e$ and R$^f$ are the same or different and represent a hydrogen atom, a lower alkyl group which may have a substituent, a lower cycloalkyl group which may have a substituent or an aryl group which may have a substituent;

the ring A represents a cyclic hydrocarbon or a heterocyclic ring;

the ring B represents a heterocyclic ring having one or plural heteroatoms selected from the group consisting of a nitrogen atom and an oxygen atom in the ring;

X represents a lower alkylene group which may have a substituent;

Y and Z are the same or different and represent a single bond or a lower alkylene group which may have a substituent;

W$^1$-W$^2$ represents N—C or C—N; and l, m, n and o are the same or different and represent 0, 1, 2 or 3.

2. The compound or a salt thereof according to claim 1, wherein, in the general formula (1), R$^1$ and R$^2$ are the same or different and represent a hydrogen atom, a lower alkyl group, a lower alkyl group having a halogen atom as a substituent, a lower alkyl group having a methoxy group as a substituent, a lower alkyl group having a methylthio group as a substituent, a lower alkyl group having a cyano group as a substituent, a lower alkyl group having a methylaminocarbonyl group as a substituent, a lower alkyl group having a diisopropylamino group as a substituent, a lower alkenyl group, a lower alkynyl group or a group represented by the following general formula (2);

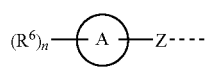

(2)

R$^3$ represents a hydroxy group, a lower alkoxy group, a lower cycloalkyloxy group, an aryloxy group, a carboxy group, a lower alkoxycarbonyl group, —OCONR$^a$R$^b$, —NR$^c$R$^d$ or a group represented by the following general formula (3);

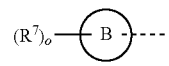

(3)

R$^4$ and R$^5$ are the same or different and represent a halogen atom, a lower alkyl group, a hydroxy group or a lower alkoxy group;

R$^6$ represents a halogen atom, a lower alkyl group, a lower alkyl group having a halogen atom as a substituent, a lower alkyl group having a cyano group as a substituent, a lower cycloalkyl group, an aryl group, a heterocyclic group, a hydroxy group, a lower alkoxy group, a lower alkoxy group having a halogen atom as a substituent, a lower alkoxy group having an aryl group as a substituent, a lower cycloalkyloxy group, an aryloxy group, a mercapto group, a lower alkylthio group, a lower cycloalkylthio group, an arylthio group, a formyl group, a lower alkylcarbonyl group, a carboxy group, a lower alkoxycarbonyl group, a nitro group, a cyano group or —NR$^e$R$^f$;

R$^7$ represents a lower alkyl group, a lower cycloalkyl group, an aryl group, a hydroxy group, a lower alkoxy group, a lower cycloalkyloxy group or an aryloxy group;

R$^a$ and R$^b$ are the same or different and represent a hydrogen atom, a lower alkyl group, a lower cycloalkyl group, an aryl group or a heterocyclic group;

R$^c$, R$^d$, R$^e$ and R$^f$ are the same or different and represent a hydrogen atom, a lower alkyl group, a lower cycloalkyl group or an aryl group;

the ring A represents a cyclic hydrocarbon or a heterocyclic ring;

the ring B represents a heterocyclic ring having one or plural heteroatoms selected from the group consisting of a nitrogen atom and an oxygen atom in the ring;

X represents a lower alkylene group;

Y and Z are the same or different and represent a single bond, a lower alkylene group or a lower alkylene group having an oxo group as a substituent;

W$^1$-W$^2$ represents N—C or C—N; and l, m, n and o are the same or different and represent 0, 1, 2 or 3.

3. The compound or a salt thereof according to claim 1, wherein, in the general formula (1), R$^1$ represents a lower alkyl group, a lower alkyl group having a halogen atom as a substituent, a lower alkyl group having a methoxy group as a substituent, a lower alkyl group having a methylthio group as a substituent, a lower alkyl group having a cyano group as a substituent, a lower alkyl group having a methylaminocarbonyl group as a substituent, a lower alkyl group having a diisopropylamino group as a substituent, a lower alkynyl group or a group represented by the following general formula (2);

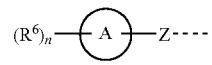

(2)

$R^2$ represents a hydrogen atom;

$R^3$ represents a hydroxy group, a carboxy group, a lower alkoxycarbonyl group, —OCONR$^a$R$^b$, —NR$^c$R$^d$ or a group represented by the following general formula (3);

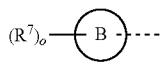  (3)

$R^6$ represents a halogen atom, a lower alkyl group, a lower alkyl group having a halogen atom as a substituent, a lower alkyl group having a cyano group as a substituent, an aryl group, a morpholino group, a hydroxy group, a lower alkoxy group, a lower alkoxy group having a halogen atom as a substituent, a lower alkoxy group having an aryl group as a substituent, a lower alkylthio group, a lower alkylcarbonyl group, a nitro group, a cyano group or —NR$^e$R$^f$;

$R^7$ represents a lower alkyl group or a lower alkoxy group;

$R^a$ and $R^b$ are the same or different and represent a hydrogen atom or a heterocyclic group;

$R^c$, $R^d$, $R^e$ and $R^f$ represent a lower alkyl group;

the ring A represents a cyclic hydrocarbon or a heterocyclic ring;

the ring B represents a heterocyclic ring having plural heteroatoms selected from the group consisting of a nitrogen atom and an oxygen atom in the ring;

X and Y represent a lower alkylene group;

Z represents a single bond, a lower alkylene group or a lower alkylene group substituted with an oxo group;

$W^1$-$W^2$ represents C—N or N—C;

l and m represent 0;

o represents 0 or 1; and n represents 0, 1 or 2.

4. The compound or a salt thereof according to claim 1, wherein, in the general formula (1), the ring A represents benzene, indan, thiophene, benzo[1,3]dioxole, 2,3-dihydrobenzofuran, 1H-benzimidazole, isoxazole, thiazole, benzothiazole, 2,3-dihydrobenzo[1,4]dioxin or pyridine.

5. The compound or a salt thereof according to claim 1, wherein, in the general formula (1), the ring B represents pyrrolidine or morpholine.

6. A compound or a salt thereof selected from the group consisting of

N-(2-Aminophenyl)-5-[3-(2,3-dihydrobenzo[1,4]dioxin-6-yl)-1-(3-dimethylaminopropyl)ureidomethyl]pyridine-2-carboxylic acid amide, N-(2-Aminophenyl)-5-[3-(4-dimethylaminophenyl)-1-(3-(morpholin-4-yl)propyl)ureidomethyl]pyridine-2-carboxylic acid amide, N-(2-Aminophenyl)-5-[1-(3-(morpholin-4-yl)propyl)-3-phenethylureidomethyl]pyridine-2-carboxylic acid amide, N-(2-Aminophenyl)-5-[3-(3,4-difluorophenyl)-1-(3-dimethylaminopropyl)ureidomethyl]pyridine-2-carboxylic acid amide, N-(2-Aminophenyl)-5-[1-(3-dimethylaminopropyl)-3-(4-methoxyphenyl)ureidomethyl]pyridine-2-carboxylic acid amide, N-(2-Aminophenyl)-5-[3-(4-diethylaminophenyl)-1-(3-dimethylaminopropyl)ureidomethyl]pyridine-2-carboxylic acid amide, N-(2-Aminophenyl)-5-[1-(3-dimethylaminopropyl)-3-(3-fluorophenyl)ureidomethyl]pyridine-2-carboxylic acid amide, N-(2-Aminophenyl)-5-[1-(3-dimethylaminopropyl)-3-(3-fluoro-4-methylphenyl)ureidomethyl]pyridine-2-carboxylic acid amide, N-(2-Aminophenyl)-5-[1-(3-dimethylaminopropyl)-3-(4-fluoro-3-methylphenyl)ureidomethyl]pyridine-2-carboxylic acid amide, N-(2-Aminophenyl)-5-[3-(4-cyanophenyl)-1-(3-dimethylaminopropyl)ureidomethyl]pyridine-2-carboxylic acid amide, N-(2-Aminophenyl)-5-[1-(3-dimethylaminopropyl)-3-(4-trifluoromethoxyphenyl)ureidomethyl]pyridine-2-carboxylic acid amide, N-(2-Aminophenyl)-5-[3-(benzo[1,3]dioxol-5-yl)-1-(3-hydroxypropyl)ureidomethyl]pyridine-2-carboxylic acid amide, N-(2-Aminophenyl)-5-[3-(4-dimethylaminophenyl)-1-(2-ethoxycarbonylethyl)ureidomethyl]pyridine-2-carboxylic acid amide, N-(2-Aminophenyl)-5-[3-(1,3-benzothiazol-2-yl)-1-(3-dimethylaminopropyl)ureidomethyl]pyridine-2-carboxylic acid amide, N-(2-Aminophenyl)-5-[3-(1H-benzoimidazol-2-yl)-1-(3-dimethylaminopropyl)ureidomethyl]pyridine-2-carboxylic acid amide, N-(2-Aminophenyl)-5-[3-(2,3-dihydro-1-benzofuran-5-yl)-1-(3-(morpholin-4-yl)propyl)ureidomethyl]pyridine-2-carboxylic acid amide, N-(2-Aminophenyl)-5-[3-(2,3-dihydrobenzo[1,4]dioxin-6-yl)-1-(2-hydroxyethyl)ureidomethyl]pyridine-2-carboxylic acid amide, N-(2-Aminophenyl)-5-[1-(3-dimethylaminopropyl)-3-(phenylcarbonylmethyl)ureidomethyl]pyridine-2-carboxylic acid amide, N-(2-Aminophenyl)-5-[1-(3-dimethylaminopropyl)-3-(1,3-thiazol-2-yl)ureidomethyl]pyridine-2-carboxylic acid amide, N-(2-Aminophenyl)-5-[1-(3-dimethylaminopropyl)-3-(6-methoxy-1,3-benzothiazol-2-yl)ureidomethyl]pyridine-2-carboxylic acid amide, N-(2-Aminophenyl)-5-[1-(3-dimethylaminopropyl)-3-(6-fluoro-1,3-benzothiazol-2-yl)ureidomethyl]pyridine-2-carboxylic acid amide, N-(2-Aminophenyl)-5-[1-(3-diethylaminopropyl)-3-(3,4-difluorophenyl)ureidomethyl]pyridine-2-carboxylic acid amide, N-(2-Aminophenyl)-5-[1-(3-(morpholin-4-yl)propyl)-3-(pyridin-3-yl)ureidomethyl]pyridine-2-carboxylic acid amide, N-(2-Aminophenyl)-5-[1-(3-dimethylaminopropyl)-3-(thiophen-3-yl)ureidomethyl]pyridine-2-carboxylic acid amide, N-(2-Aminophenyl)-5-[1-(3-dimethylaminopropyl)-3-(3-fluoro-4-methoxyphenyl)ureidomethyl]pyridine-2-carboxylic acid amide, N-(2-Aminophenyl)-5-[3-(3-chloro-4-fluorophenyl)-1-(3-diethylaminopropyl)ureidomethyl]pyridine-2-carboxylic acid amide, N-(2-Aminophenyl)-5-[1-(3-diethylaminopropyl)-3-(4-fluoro-3-nitrophenyl)ureidomethyl]pyridine-2-carboxylic acid amide, N-(2-Aminophenyl)-5-[3-(2,3-dihydrobenzo[1,4]dioxin-6-yl)-1-(2-dimethylaminoethyl)ureidomethyl]pyridine-2-carboxylic acid amide, N-(2-Aminophenyl)-5-[1-(2-dimethylaminoethyl)-3-(3-methoxyphenyl)ureidomethyl]pyridine-2-carboxylic acid amide, N-(2-Aminophenyl)-5-[1-(2-dimethylaminoethyl)-3-(3-fluorophenyl)ureidomethyl]pyridine-2-carboxylic acid amide, N-(2-Aminophenyl)-5-[1-(2-dimethylaminoethyl)-3-(thiophen-3-yl)ureidomethyl]pyridine-2-carboxylic acid amide, N-(2-Aminophenyl)-5-[3-(pyridin-3-yl)-1-[3-(pyrrolidin-1-yl)propyl]ureidomethyl]pyridine-2-carboxylic acid amide, N-(2-Aminophenyl)-5-[1-(3-(morpholin-4-yl)propyl)-3-(phenylcarbonylmethyl)ureidomethyl]pyridine-2-carboxylic acid amide, N-(2-Aminophenyl)-5-[3-(3-chlorophenyl)-1-(3-(morpholin-4-yl)propyl)ureidomethyl]pyridine-2-carboxylic acid amide, N-(2-Aminophenyl)-5-[3-(4-fluorophenethyl)-1-(3-(morpholin-4-yl)propyl)ureidomethyl]pyridine-2-carboxylic acid amide, N-(2-Aminophenyl)-5-[3-(4-cyanophenyl)-1-(3-hydroxypropyl)ureidomethyl]pyridine-2-carboxylic acid amide, N-(2-Aminophenyl)-5-[3-(3-fluorophenyl)-1-[2-(4-methylpiperazin-1-yl)ethyl]ureidomethyl]pyridine-2-carboxylic acid amide, N-(2-Aminophenyl)-5-[3-(2,3-dihydrobenzo[1,4]dioxin-6-yl)-1-[3-(4-methylpiperazin-1-yl)propyl]ureidomethyl]pyridine-2-carboxylic acid amide, N-(2-Aminophenyl)-5-[1-(2-dimethylaminoethyl)-3-(3-methylphenyl)ureidomethyl]pyridine-2-carboxylic acid amide, N-(2-Aminophenyl)-5-[3-(2,3-dihydrobenzo[1,4]dioxin-6-yl)-1-[4-(morpholin-4-yl)butyl]ureidomethyl]pyridine-2-carboxylic acid amide, N-(2-Aminophenyl)-5-[1-(2-dimethylaminoethyl)-3-(1,3-thiazol-2-yl)ureidomethyl]pyridine-2-carboxylic acid amide, N-(2-Aminophenyl)-5-[3-(2-methoxyphenyl)-1-[4-(morpholin-4-yl)butyl]ureidomethyl]pyridine-2-carboxylic acid amide, N-(2-Aminophenyl)-5-[3-(3-methylphenyl)-1-[3-(4-methylpiperidin-1-yl)propyl]ureidomethyl]pyridine-2-carboxylic acid amide; and N-(2-Aminophenyl)-5-[3-cyclopentyl-1-[5-(morpholin-4-yl)pentyl]ureidomethyl]pyridine-2-carboxylic acid amide.

7. A pharmaceutical composition comprising at least one member selected from the group consisting of the compound and a salt thereof according to any one of claims 1 to 6 and a pharmaceutical carrier.

8. A histone deacetylase inhibitor comprising at least one member selected from the group consisting of the compound and a salt thereof according to claim 1 as an active ingredient.

9. A therapeutic agent for treating glaucoma or ocular hypertension comprising at least one member selected from the group consisting of the compound and a salt thereof according to claim 1 as an active ingredient.

10. A method for inhibiting histone deacetylase comprising administering to a patient an effective amount of at least one member selected from the group consisting of the compound and a salt thereof according to any one of claims 1 to 6.

11. A method for treating glaucoma or ocular hypetension comprising administering to a patient an effective amount of at least one member selected from the group consisting of the compound and a salt thereof according to any one of claims 1 to 6.

* * * * *